United States Patent
Ignatovich et al.

(10) Patent No.: US 7,696,320 B2
(45) Date of Patent: Apr. 13, 2010

(54) LIGANDS THAT HAVE BINDING SPECIFICITY FOR VEGF AND/OR EGFR AND METHODS OF USE THEREFOR

(75) Inventors: Olga Ignatovich, Cambridge (GB); Steve Holmes, Cambridge (GB); Roland Beckmann, Geneva (CH); Rudolf M. T. de Wildt, Cambridge (GB)

(73) Assignee: Domantis Limited (GB)

( * ) Notice: Subject to any disclaimer, the term of this patent is extended or adjusted under 35 U.S.C. 154(b) by 195 days.

(21) Appl. No.: 11/331,415

(22) Filed: Jan. 11, 2006

(65) Prior Publication Data

US 2007/0003549 A1    Jan. 4, 2007

Related U.S. Application Data

(63) Continuation-in-part of application No. 11/098,758, filed on Apr. 4, 2005, which is a continuation-in-part of application No. 10/925,366, filed on Aug. 24, 2004.

(51) Int. Cl.
    C12P 21/08    (2006.01)
(52) U.S. Cl. .................. 530/387.1; 424/130.1
(58) Field of Classification Search .................. None
    See application file for complete search history.

(56) References Cited

U.S. PATENT DOCUMENTS

| | | | |
|---|---|---|---|
| 5,459,061 A | 10/1995 | Sato et al. |
| 5,558,864 A | 9/1996 | Bendig et al. |
| 5,726,152 A | 3/1998 | Bayne et al. |
| 5,770,195 A | 6/1998 | Hudziak et al. |
| 5,824,782 A | 10/1998 | Hölzer et al. |
| 5,837,243 A | 11/1998 | Deo et al. |
| 5,840,693 A | 11/1998 | Eriksson et al. |
| 5,891,996 A | 4/1999 | Mateo de Acosta del Rio et al. |
| 5,906,820 A | 5/1999 | Bacha |
| 5,922,845 A | 7/1999 | Deo et al. |
| 5,928,939 A | 7/1999 | Eriksson et al. |
| 6,013,780 A | 1/2000 | Neufeld et al. |
| 6,020,473 A | 2/2000 | Keyt et al. |
| 6,057,428 A | 5/2000 | Keyt et al. |
| 6,121,230 A | 9/2000 | Charnock-Jones et al. |
| 6,193,966 B1 | 2/2001 | Deo et al. |
| 6,214,974 B1 | 4/2001 | Rosenblum et al. |
| 6,217,866 B1 | 4/2001 | Schlessinger et al. |
| 6,270,765 B1 | 8/2001 | Deo et al. |
| 6,303,755 B1 | 10/2001 | Deo et al. |
| 6,331,301 B1 | 12/2001 | Eriksson et al. |
| 6,342,219 B1 | 1/2002 | Thorpe et al. |
| 6,342,221 B1 | 1/2002 | Thorpe et al. |
| 6,395,272 B1 | 5/2002 | Deo et al. |
| 6,416,758 B1 | 7/2002 | Thorpe et al. |
| 6,475,796 B1 | 11/2002 | Pollitt et al. |
| 6,485,942 B1 | 11/2002 | Zioncheck et al. |
| 6,583,276 B1 | 6/2003 | Neufeld et al. |
| 6,676,941 B2 | 1/2004 | Thorpe et al. |
| 6,699,473 B2 | 3/2004 | Raisch et al. |
| 6,703,020 B1 | 3/2004 | Thorpe et al. |
| 6,750,044 B1 | 6/2004 | Keyt et al. |
| 6,777,534 B1 | 8/2004 | Klagsbrun et al. |
| 6,965,010 B2 | 11/2005 | Alitalo et al. |
| 2001/0014328 A1 | 8/2001 | Deo et al. |
| 2001/0053539 A1 | 12/2001 | Lauffer et al. |
| 2002/0004587 A1 | 1/2002 | Miller et al. |
| 2002/0012663 A1 | 1/2002 | Waksal |
| 2002/0032315 A1 | 3/2002 | Baca et al. |
| 2002/0103345 A1 | 8/2002 | Zhu |
| 2002/0173629 A1 | 11/2002 | Jakobovits et al. |
| 2002/0192211 A1 | 12/2002 | Hudziak et al. |
| 2002/0192634 A1 | 12/2002 | Ferrara et al. |
| 2003/0023046 A1 | 1/2003 | Ferrara et al. |
| 2003/0032145 A1 | 2/2003 | Zioncheck et al. |
| 2003/0091561 A1 | 5/2003 | van de Winkel et al. |
| 2003/0096373 A1 | 5/2003 | Majumdar et al. |
| 2003/0148409 A1 | 8/2003 | Rossi et al. |
| 2003/0157104 A1 | 8/2003 | Waksal |
| 2003/0165467 A1 | 9/2003 | Neufeld et al. |
| 2003/0170253 A1 | 9/2003 | Eriksson et al. |
| 2003/0175271 A1 | 9/2003 | Shitara et al. |
| 2003/0175276 A1 | 9/2003 | Thorpe et al. |
| 2003/0185832 A1 | 10/2003 | Thorpe et al. |
| 2003/0190317 A1 | 10/2003 | Baca et al. |

(Continued)

FOREIGN PATENT DOCUMENTS

CA    2 008 735 C    3/2000

(Continued)

OTHER PUBLICATIONS

Smith-Gill et al. (J. Immunol. 139:4135-4144 (1987)).*

(Continued)

*Primary Examiner*—Larry R. Helms
*Assistant Examiner*—Meera Natarajan
(74) *Attorney, Agent, or Firm*—Jason C. Fedon; William T. Han

(57) ABSTRACT

Disclosed are ligands that have binding specificity for vascular endothelial growth factor (VEGF), for epidermal growth factor receptor (EGFR), or for VEGF and EGFR. Also disclosed are methods of using these ligands. In particular, the use of these ligands for cancer therapy is described.

65 Claims, 68 Drawing Sheets

U.S. PATENT DOCUMENTS

| | | |
|---|---|---|
| 2003/0203409 A1 | 10/2003 | Kim et al. |
| 2003/0224001 A1 | 12/2003 | Goldstein et al. |
| 2003/0226155 A1 | 12/2003 | Sadeghi et al. |
| 2004/0006212 A1 | 1/2004 | Goldstein et al. |
| 2004/0018557 A1 | 1/2004 | Qu et al. |
| 2004/0057950 A1 | 3/2004 | Waksal et al. |
| 2004/0082039 A1 | 4/2004 | Gillies et al. |
| 2004/0106605 A1 | 6/2004 | Carboni et al. |
| 2004/0131611 A1 | 7/2004 | Oliver et al. |
| 2004/0133357 A1 | 7/2004 | Zhong et al. |
| 2004/0152636 A1 | 8/2004 | Keyt et al. |
| 2004/0157214 A1 | 8/2004 | McCafferty et al. |
| 2004/0248196 A1 | 12/2004 | Adams et al. |
| 2004/0259156 A1 | 12/2004 | Zhu |
| 2004/0265309 A1 | 12/2004 | Kandel et al. |
| 2005/0019826 A1 | 1/2005 | Tournaire et al. |
| 2005/0032130 A1* | 2/2005 | Beresini et al. .......... 435/7.2 |
| 2005/0032699 A1 | 2/2005 | Holash et al. |
| 2005/0043233 A1 | 2/2005 | Stefanic et al. |
| 2005/0053599 A1 | 3/2005 | Van Bruggen et al. |
| 2005/0053608 A1 | 3/2005 | Weber et al. |
| 2005/0059087 A1 | 3/2005 | Weber et al. |
| 2005/0064522 A1 | 3/2005 | Ferrara et al. |
| 2005/0079184 A1 | 4/2005 | Hsing-Chang et al. |
| 2005/0100546 A1 | 5/2005 | Jakobovits et al. |
| 2005/0123537 A1 | 6/2005 | Thorpe et al. |
| 2005/0158829 A1 | 7/2005 | Fandl et al. |
| 2005/0186208 A1 | 8/2005 | Fyfe et al. |
| 2005/0196340 A1 | 9/2005 | Holash et al. |
| 2005/0202028 A1 | 9/2005 | Ledbetter et al. |
| 2005/0202534 A1 | 9/2005 | Ledbetter et al. |
| 2005/0220786 A1 | 10/2005 | Mahler et al. |
| 2005/0244405 A1 | 11/2005 | Van Bruggen et al. |
| 2005/0255555 A1 | 11/2005 | Johns et al. |
| 2005/0271663 A1 | 12/2005 | Ignatovich et al. |

FOREIGN PATENT DOCUMENTS

| | | | |
|---|---|---|---|
| EP | 0 453 082 | A1 | 10/1991 |
| EP | 0 368 684 | B1 | 3/1994 |
| EP | 0 739 984 | A1 | 10/1996 |
| EP | 0 927 758 | A2 | 7/1999 |
| EP | 0 586 002 | B1 | 1/2000 |
| EP | 0 476 983 | B1 | 3/2000 |
| EP | 1 026 239 | A2 | 8/2000 |
| EP | 0 672 142 | B1 | 2/2001 |
| EP | 0 667 165 | B1 | 3/2002 |
| EP | 0 666 868 | B1 | 4/2002 |
| EP | 1 238 986 | A2 | 9/2002 |
| EP | 0 814 827 | B1 | 7/2003 |
| EP | 1 325 932 | B1 | 7/2003 |
| EP | 0 931 092 | B1 | 1/2004 |
| EP | 1 382 679 | A2 | 1/2004 |
| EP | 1 179 541 | B1 | 6/2004 |
| EP | 1 454 917 | A2 | 9/2004 |
| WO | WO 89/06692 | A1 | 7/1989 |
| WO | WO 90/05144 | A1 | 5/1990 |
| WO | WO 90/14430 | A1 | 11/1990 |
| WO | WO 91/16350 | A1 | 10/1991 |
| WO | WO 92/01047 | A1 | 1/1992 |
| WO | WO 92/20791 | A1 | 11/1992 |
| WO | WO 93/11236 | A1 | 6/1993 |
| WO | WO 94/13804 | A1 | 6/1994 |
| WO | WO 96/40210 | A1 | 12/1996 |
| WO | WO 98/45331 | A2 | 10/1998 |
| WO | WO 99/23221 | A2 | 5/1999 |
| WO | WO 99/48523 | A2 | 9/1999 |
| WO | WO 00/29004 | A1 | 5/2000 |
| WO | WO 00/34337 | A1 | 6/2000 |
| WO | WO 00/47228 | A1 | 8/2000 |
| WO | WO 00/59525 | A2 | 10/2000 |
| WO | WO 00/61186 | A1 | 10/2000 |
| WO | WO 00/63380 | A1 | 10/2000 |
| WO | WO 00/69459 | A1 | 11/2000 |
| WO | WO 01/07084 | A1 | 2/2001 |
| WO | WO 01/09186 | A2 | 2/2001 |
| WO | WO 01/77342 | A1 | 10/2001 |
| WO | WO 01/90192 | A2 | 11/2001 |
| WO | WO 02/02120 | A1 | 1/2002 |
| WO | WO 02/02773 | A2 | 1/2002 |
| WO | WO 02/11677 | A2 | 2/2002 |
| WO | WO 02/12328 | A2 | 2/2002 |
| WO | WO 02/45653 | A2 | 6/2002 |
| WO | WO 02/060955 | A2 | 8/2002 |
| WO | WO 02/070008 | A1 | 9/2002 |
| WO | WO 02/096948 | A2 | 12/2002 |
| WO | WO 02/100348 | A2 | 12/2002 |
| WO | WO 03/030835 | A2 | 4/2003 |
| WO | WO 03/030910 | A1 | 4/2003 |
| WO | WO 03/050531 | A2 | 6/2003 |
| WO | WO 03/075841 | A2 | 9/2003 |
| WO | WO 03/075947 | A1 | 9/2003 |
| WO | WO 03/080569 | A2 | 10/2003 |
| WO | WO 03/097086 | A2 | 11/2003 |
| WO | WO 03/106487 | A1 | 12/2003 |
| WO | WO 2004/030625 | A2 | 4/2004 |
| WO | WO 2004/032961 | A1 | 4/2004 |
| WO | WO 2004/041867 | A2 | 5/2004 |
| WO | WO 2004/056847 | A2 | 7/2004 |
| WO | WO 2004/085474 | A2 | 10/2004 |
| WO | WO 2004/087207 | A2 | 10/2004 |
| WO | WO 2004/110490 | A2 | 12/2004 |
| WO | WO 2005/000900 | A1 | 1/2005 |
| WO | WO 2005/004809 | A2 | 1/2005 |
| WO | WO 2005/010151 | A2 | 2/2005 |
| WO | WO 2005/011734 | A2 | 2/2005 |
| WO | WO 2005/012359 | A2 | 2/2005 |
| WO | WO 2005/012479 | A2 | 2/2005 |
| WO | WO 2005/014618 | A2 | 2/2005 |
| WO | WO 2005/016369 | A1 | 2/2005 |
| WO | WO 2005/027972 | A2 | 3/2005 |
| WO | WO 2005/027973 | A2 | 3/2005 |
| WO | WO 2005/044853 | A2 | 5/2005 |
| WO | WO 2005/044858 | A1 | 5/2005 |
| WO | WO 2005/054273 | A2 | 6/2005 |
| WO | WO 2005/056606 | A2 | 6/2005 |
| WO | WO 2005/076972 | A2 | 8/2005 |
| WO | WO 2005/087812 | A1 | 9/2005 |
| WO | WO 2006/003388 | A2 | 1/2006 |
| WO | WO 2007/066106 | A1 | 6/2007 |

OTHER PUBLICATIONS

Kumar et al. (J. Biol. Chem. 275:35129-35136 (2000)).*
Song et al. (Biochem Biophys Res Comm 268:390-394 (2000)).*
De Genst et al. (Devel. & Compar. Immunol. 30:187-198 (2006)).*
Ibragimova and Eade (Biophysical Journal, Oct. 1999, vol. 77, pp. 2191-2198).*
MacCallum et al. (J. Mol. Biol. (1996) 262:732-745).*
Pascalis et al. The Journal of Immunology (2002) 169, 3076-3084.*
Casset et al. (2003) BBRC 307, 198-205.*
Vajdos et al. (2002) J. Mol. Biol. 320, 415-428.*
Holm et al (2007) Mol. Immunol. 44: 1075-1084.*
Chen et al. J. Mol. Bio. (1999) 293, 865-881.*
Wu et al. J. Mol. Biol. (1999) 294, 151-162.*
Brummell et al. (Biochemistry 32:1180-1187 (1993)).*
Kobayashi et al. (Protein Engineering 12:879-844 (1999)).*
Burks et al. (PNAS 94:412-417 (1997)).*
Jang et al. (Molec. Immunol. 35:1207-1217 (1998)).*
Brorson et al. (J. Immunol. 163:6694-6701 (1999)).*
Coleman (Research in Immunol. 145:33-36 (1994)).*
Seaver (1994; Genetic Engineering vol. 14(14): pp. 10 and 21).*
McCarron et al. (Molecular Interventions 5(6): 368-380 (2005)).*
Stein (Pharmacology and Therapeutics 85: 231-236, 2000).*

Stein (J. Clinical Investigation 108(5): 641-644, 2001).*

Caplen (Gene Therapy 11(16): 1241-1248, 2004).*

Conrath, K.E., et al., "Camel Single-domain Antibodies as Modular Building Units in Bispecific and Bivalent Antibody Constructs," *J. Biol. Chem.*, 276(10):7346-7350 (2001).

Hoogenboom, H.R., "Mix and Match: Building Manifold Binding Sites," *Nature Biotechnol.*, 15:125-126 (1997).

Lu, J., et al., "Vascular Endothelial Growth Factor Expression and Regulation of Murine Collagen-Induced Arthritis", *J. Immunol.*, 164: 5922-5927 (2000).

Zhu, Z., et al., "Remodeling Domain Interfaces to Enhance Heterodimer Formation," *Prot. Sci.* 6: 781-788 (1997).

Hu, S., et al., "Minibody: A Novel Engineered Anti-Carcinoembryonic Antigen Antibody Fragment (Single-Chain Fv-$C_H3$) Which Exhibits Rapid, High-Level Targeting of Xenografts", *Cancer Res.*, 56:3055-3061 (1996).

Atwell, J.L., et al., "Design and Expression of a Stable Bispecific scFv Dimer with Affinity for Both Glycophorin and N9 Neuraminidase." *Mol. Immunol.*, 33(17/18) 1301-1312 (1996).

Milstein, C., et al., "Hybrid Hybridomas and Their Use in Immunohistochemistry," *Nature*, 305: 537-540 (1983).

Holliger, P., et al., "Diabodies": Small Bivalent and Bispecific Antibody Fragments, *Proc. Natl. Acad. Sci. USA*, 90: 6444-6448 (1993).

Knarr, G., et al., "BiP Binding Sequences in Antibodies," *J. Biol. Chem.*, 270(46): 27589-27594 (1995).

Wörn, A., et al., "Mutual Stabilization of $V_L$ and $V_H$ in Single-Chain Antibody Fragments, Investigated with Mutants Engineered for Stability," *Biochemistry*, 37: 13120-13127 (1998).

Neri, D., et al., "High-Affinity Antigen Binding by Chelating Recombinant Antibodies (CRAbs)," *J. Mol. Biol.*, 246: 367-373 (1995).

Hamers-Casterman, C., et al., "Naturally Occuring Antibodies Devoid of Light Chains," *Nature*, 363: 446-448 (1993).

Davies, J., et al., "Antibody VH Domains as Small Recognition Units," *Biotechnol.*, 13: 475-479 (1995).

Griffiths, A.D., et al., "Isolation of High Affinity Human Antibodies Directly From Large Synthetic Repertoires," *EMBO Journal*, 13(14): 3245-3260 (1994).

Sone, H., et al., "Neutralization of Vascular Endothelial Growth Factor Prevents Collagen-Induced Arthritis and Ameliorates Established Disease in Mice," *Biochem. Biophys. Res. Comm.*. 281: 562-568 (2001).

Saklatvala, J., et al., "Purification of Two Immunologically Different Leukocyte Proteins that Cause Cartilage Resorption, Lymphocyte Activation, and Fever," *J. Exp. Med.*, 162: 1208-1222 (1985).

Nagashima, M., et al., "Role of Vascular Endothelial Growth Factor in Angiogenesis of Rheumatoid Arthirits," *J. Rheum.*, 22(9): 1624-1630 (1995).

Fava, R.A., et al., "Vascular Permeability Factor/Endothelial Growth Factor (VPF/VEGF): Accumulation and Expression in Human Synovial Fluids and Rheumatoid Synovial Tissue," *J. Exp. Med.*, 180: 341-346 (1994).

Ghahroudi, M.A., et al., "Selection and Identification of Single Domain Antibody Fragments from Camel Heavy-Chain Antibodies," *FEBS Letters*, 414, 521-526 (1997).

Davies, J., et al., "'Camelising' Human Antibody Fragments: NMR Studies on VH Domains," *FEBS Letters*., 339: 285-290 (1994).

Dayer, J.-M., et al., "Human Recombinant Interleukin 1 Stimulates Collagenase and Prostaglandin $E_2$ Production by Human Synovial Cells," *J. Clin. Invest.*, 77: 645-648 (1986).

Dayer, J.-M., et al., "Cachectin/Tumor Necrosis Factor Stimulates Collagenase and Prostaglandin $E_2$ Production by Human Synovial Cells and Dermal Fibroblasts," *J.J. Exp. Med.*, 162: 2163-2168 (1985).

U.S. National Institute of Health: "Bevacizumab and Cetuximab With or Without Irinotecan in Treating Patients with Irinotecan-Refractory Metastatic Colorectal Cancer" (2004) [online], [retrieved on Mar. 13, 2007]. Retrieved from the Internet <URL:http://clinicaltrials.gov/ct/show/NCTO>.

Hoang, et al., "Tumor Response Augmentation with Combination Cetuximab (Erbitux®) and Bevacizumab (Avastin®)," *Lung Cancer*, 49(PD144):S108-S109 (2005).

* cited by examiner

>TAR15-1 (SEQ ID NO:1)
GACATCCAGA TGACCCAGTC TCCATCCTCC CTGTCTGCAT CTGTAGGAGA CCGTGTCACC
ATCACTTGCC GGGCAAGTCA GTGGATTGGT CCTGAGTTAA GTTGGTACCA GCAGAAACCA
GGGAAAGCCC CTAAGCTCCT GATCTATCAT GGTTCCATTT TGCAAAGTGG GGTCCCATCA
CGTTTCAGTG GCAGTGGATC TGGGACAGAT TTCACTCTCA CCATCAGCAG TCTGCAACCT
GAAGATTTTG CTACGTACTA CTGTCAACAG CGTATGTATC GGCCTGCTAC GTTCGGCCAA
GGGACCAAGG TGGAAATCAA ACGG
>TAR15-10 (SEQ ID NO:5)
GACATCCAGA TGACCCAGTC TCCATCCTCC CTGTCTGCAT CTGTAGGAGA CCGTGTCACC
ATCACTTGCC GGGCAAGTCA GTGGATTGGT CCGGAGTTAA GTTGGTACCA GCAGAAACCA
GGGAAAGCCC CTAAGCTCCT GATCTATCAT ACGTCCATTT TGCAAAGTGG GGTCCCATCA
CGTTTCAGTG GCAGTGGATC TGGGACAGAT TTCACTCTCA CCATCAGCAG TCTGCAACCT
GAAGATTTTG CTACGTACTA CTGTCAACAG TATATGTTTC AGCCTAGGAC GTTCGGCCAA
GGGACCAAGG TGGAAATCAG ACGG
>TAR15-11 (SEQ ID NO:6)
GACATCCAGA TGATCCAGTC TCCATCCTCC CTGTCCGCAT CTGTAGGAGA CCGTGTCACC
ATCACTTGCC GGGCAAGTCA GTTTATTGGT AATGAGTTAA GTTGGTATCA GCAGAAACCA
GGGAAAGCCC CTAAGCTCCT GATCTATCAT GCTTCCAGTT TGCAAAGTGG GGTCCCATCA
CGTTTCAGTG GCAGTGGATC TGGGACAGAT TTCACTCTCA CCATCAGCAG TCTGCAACCT
GAAGATTTTG CTACGTACTA CTGTCAACAG GTTCTGGGTT ATCCTTATAC GTTCGGCCAA
GGGACCAAGG TGGAAATCAA ACGG
>TAR15-12 (SEQ ID NO:7)
GACATCCAGA TGACCCAGTC TCCATCCTCC CTGTCTGCAT CTGTAGGAGA CCGTGTCACC
ATCACTTGCC GGGCAAGTCA GTGGATTGGT CCTGAGTTAA GTTGGTACCA GCAGAAACCA
GGGAAAGCCC CTAAGCTCCT GATCTATCAT GGTTCCATTT TGCAAAGTGG GGTCCCATCA
CGTTTCAGTG GCAGTGGATC TGGGACAGAT TTCACTCTCA CCATCAGCAG TCTGCAACCT
GAAGATTTTG CTACGTACTA CTGTCAACAG GTTCTGTATA GTCCTTTGAC GTTCGGCCAA
GGGACCAAGG TGGAAATCAA ACGG
>TAR15-13 (SEQ ID NO:8)
GACATCCAGA TGACCCAGTC TCCATCCTCC CTGTCTGCAT CTGTAGGAGA CCGTGTCACC
ATCACTTGCC GGGCAAGTCA GTGGATTGGG AATGAGTTAA AGTGGTATCA GCAGAAACCA
GGGAAAGCCC CTAAGCTCCT GATCTATATG TCTTCCCTTT TGCAAAGTGG GGTCCCATCA
CGTTTCAGTG GCAGTGGATC TGGGACAGAT TTCACTCTCA CCATCAGCAG TCTGCAACCT
GAAGATTTAG CTACGTACTA CTGTCAACAG ACGCTTTTGC TTCCTTTTAC GTTCGGCCAA
GGGACCAAGG TGGAAATCAA ACGG
>TAR15-14 (SEQ ID NO:9)
GACATCCAGA TGACCCAGTC TCCATCCTCC CTGTCTGCAT CTGTAGGAGA CCGTGTCACC
ATCACTTGCC GGGCAAGTCA GTGGATTGGT CCTGAGTTAA GTTGGTACCA GCAGAAACCA
GGGAAAGCCC CTAAGCTCCT GATCTATCAT GGTTCCATTT TGCAAAGTGG GGTCCCATCA
CGTTTCAGTG GCAGTGGATC TGGGACAGAT TTCACTCTCA CCATCAGCAG TCTGCAACCT
GAAGATTTTG CTACGTACTA CTGTCAACAG CGTCTGTATT ATCCTGGTAC GTTCGGCCAA
GGGACCAAGG TGGAAATCAA ACGG
>TAR15-15 (SEQ ID NO:10)
GACATCCAGA TGACCCAGTC TCCATCCTCC CTGTCTGCAT CTGTAGGAGA CCGTGTCACC
ATCACTTGCC GGGCAAGTCA GTCTATTGGG CGTGAGTTAA GTTGGTACCA GCAGAAACCA
GGGAAAGCCC CTATGCTCCT GATCTATCAT AGTTCCAATT TGCAAAGTGG GGTCCCATCA
CGTTTCAGTG GCAGTGGATC TGGGACAGAT TTCACTCTCA CCATCAGCAG TCTGCAACCT
GAAGATTTTG CTACGTACTA CTGTCAACAG GGGATGTATT GGCCTTATAC GTTCGGCCAA
GGGACCAAGG TGGAAATCAA ACGG

FIG. 1A

>TAR15-16 (SEQ ID NO:11)
GACATCCAGA TGACCCAGTC TCCATCCTCC CTGTCTGCAT CTGTAGGAGA CCGTGTCACC
ATCACTTGCC GGGCAAGTCA GTGGATTAAG CCGGCCTTAC ATTGGTACCA GCAGAAACCA
GGGAAAGCCC CTAAGCTCCT GATCTATCAT GGTTCCATTT TGCAAAGTGG GGTCCCATCA
CGTTTCAGTG GCAGTGGATC TGGGACAGAT TTCACTCTCA CCATTAGCAG TCTGCAACCT
GAAGATTTTG CTACGTACTA CTGTCAACAG ACTCTTTTTA TGCCTTATAC GTTCGGCCAA
GGGACCAAGG TGGAAATCAA ACGG
>TAR15-17 (SEQ ID NO:12)
GACATCCAGA TGACCCAGTC TCCATCCTCC CTGTCTGCAT CTGTAGGAGA CCGTGTCACC
ATCACTTGCC GGGCAAGTCA GTCTATTAGT ACTGCGTTAC TGTGGTATCA GCAGAAACCA
GGGAAAGCCC CTAAGCTCCT GATCTATAAT GGTTCCATGT TGCCAAATGG GGTCCCATCA
CGTTTCAGTG GCAGTGGATC TGGGACAGAT TTCACTCTCA CCATCAGCAG TCTGCAACCT
GAAGATTTTG CTACGTACTA CTGTCAACAG ACTTGGGATA CTCCTATGAC GTTCGGCCAA
GGGACCAAGG TGGAAATCAA ACGG
>TAR15-18 (SEQ ID NO:13)
GACATCCAGA TGACCCAGTC TCCATCCTCC CTGTCTGCAT CTGTAGGAGA CCGTGTCACC
ATCACTTGCC GGGCAAGTCA GTGGATTGGG CATGATTTAT CGTGGTACCA GCAGAAACCA
GGGAAAGCCC CTAAGCTCCT GATCTATCAT TCGTCCTCTT TGCAAAGTGG GGTCCCATCA
CGTTTCAGTG GCAGTGGATC TGGGACAGAT TTCACTCTCA CCATCAGCAG TCTGCAACCT
GAAGATGTTG CTACGTACTA CTGTCAACAG CTTATGGGTT ATCCTTTTAC GTTCGGCCAA
GGGACCAAGG TGGAAATCAA ACGG
>TAR15-21 (SEQ ID NO:535)
GACATCCAGA TGACCCAGTC TCCATCCTCC CTGTCTGCAT CTGTAGGAGA CCGTGTCACC
ATCACTTGCC GGGCAAGTCA GTGGATTGGT CCTGAGTTAA GTTGGTACCA GCAGAAACCA
GGGAAAGCCC CTAAGCTCCT GATCTATCAT GGTTCCATTT TGCAAAGTGG GGTCCCATCA
CGTTTCAGTG GCAGTGGATC TGGGACAGAT TTCACTCTCA CCATCAGCAG TCTGCAACCT
GAAGATTTTG CTACGTACTA CTGTCAACAG TATATGACGT ATCCTCCGAC GTTCGGCCAA
GGGACCAAGG TGGAAATCAA ACGG
>TAR15-2 (SEQ ID NO:536)
GACATCCAGA TGACCCAGTC TCCATCCTCC CTGTCTGCAT CCGTAGGAGA CCGTGTCACC
ATCACTTGCC GGGCAAGTCA GTTTATTGGG AAGGAGTTAC GTTGGTATCA GCAGAAACCA
GGGAAAGCCC CTAAGCTCCT GATCTATCAT CAGTCCTTGT TGCAAAGTGG GGTCCCATCA
CGTTTCAGTG GCAGTGGATC TGGGACAGAT TCATTCTCA CCATCAGCAG TCTGCAACCT
GAAGATTTTG CTACGTACTA CTGTCAACAG CATATGTATA GGCCTTTTAC GTTCGGCCAA
GGGACCAAGG TGGAAATCAA ACGA
>TAR15-4 (SEQ ID NO:3)
GACATCCAGA TGACCCAGTC TCCATCCTCC CTGTCTGCAT CTGTAGGAGA CCGTGTCACC
ATCACTTGCC GGGCAAGTCA GGATATTGCG AATGATTTAA TGTGGTACCA GCAGAAACCA
GGGAAAGCCC CTAAGCTCCT GATCTATCGT AATTCCCGTT TGCAAGGTGG GGTCCCATCA
CGTTTCAGTG GCAGTGGATC TGGGACAGAT TTCACTCTCA CCATCAGCAG TCTGCAACCT
GAAGATTTTG CTACGTACTA CTGTCAACAG CTTGTTCATC GCCCTTATAC GATCGGCCAA
GGGACCAAGG TGGAAATCAA ACGG
>TAR15-19 (SEQ ID NO:14)
GACATCCAGA TGACCCAGTC TCCATCCTCC CTGTCTGCAT CTGTAGGAGA CCGTGTCACC
ATCACTTGCC GGGCAAGTCA GGATATTGGG GGTTTGTTAG TGTGGTATCA GCAGAAACCA
GGGAAAGCCC CTAAGCTCCT GATCTACCGG AGTTCCTATT TGCAAAGTGG GGTCCCATCA
CGTTTCAGTG GCAGTGGATC TGGGACAGAT TTCACTCTCA CCATCAGCAG TCTGCAACCT
GAAGATTTCG CTACGTACTA CTGTCAACAG ACGTGGGGTA TTCCTCATAC GTTCGGCCAA

FIG. 1B

GGGACCAAGG TGGAAATCAA ACGG
>TAR15-20 (SEQ ID NO:15)
GACATCCAGA TGACCCAGTC TCCATCCTCC CTGTCTGCAT CTGTAGGAGA CCGTGTCACC
ATCACTTGCC GGGCAAGTCA GAAGATTTTT AATGGTTTAA GTTGGTATCA GCAGAAACCA
GGGAAAGCCC CTAAGCTCCT GATCTATCAT AGTTCCACGT TGCAAAGTGG GGTCCCATCA
CGTTTCAGTG GCAGTGGATC TGGGACAGAT TTCACTCTCA CCATCAGCAG TCTGCAACCT
GAAGATTTTG CTACGTACTA CTGTCAACAG GTTCTTCTGT ATCCTTATAC GTTCGGCCAA
GGGACCAAGG TGGAAATCAA ACGG
>TAR15-22 (SEQ ID NO:16)
GACATCCAGA TGACCCAGTC TCCATCCTCC CTGTCTGCAT CTGTAGGAGA CCGTGTCACC
ATCACTTGCC GGGCAAGTCA GAGTATTGGG ACTAATTTAT CTTGGTACCA GCAGAAACCT
GGGAAAGCCC CTAGGCTCCT GATCTATCGG ACGTCCATGT TGCAAAGTGG GGTCCCATCA
CGTTTCAGTG GCAGTGGATC TGGGACAGAT TTCACTCTCA CCATCAGCAG TCTGCAACCT
GAAGATTTTG CTACGTACTA CTGTCAACAG CAGTTTTTTT GGCCTCATAC GTTCGGCCAA
GGGACCAAGG TGGAAATCAA ACGG
>TAR15-3 (SEQ ID NO:2)
GACATCCAGA TGACCCAGTC TCCATCCTCC CTGTCTGCAT CTGTAGGAGA CCGTGTCACC
ATCACTTGCC GGGCAAGTCA GTGGATTGGT AGGGAGTTAA AGTGGTATCA GCAGAAACCA
GGGAAAGCCC CTAGGCTCCT GATCTATCAT GGTTCCGTGT TGCAAAGTGG GGTCCCATCA
CGTTTCAGTG GCAGTGGATC TGGGACAGAT TTCACTCTCA CCATCAGCAG TCTGCAACCT
GAAGATTTTG CTACGTACTA CTGTCAACAG GATTTTTTG TTCCTGATAC GTTCGGCCAA
GGGACCAAGG TGGAAATCAA ACGG
>TAR15-9 (SEQ ID NO:4)
GACATCCAGA TGACCCAGTC TCCATCCTCC CTGTCTGCAT CTGTAGGAGA CCGTGTCACC
ATCACTTGCC GGGCAAGTCA GTTTATTGGG CCGCATTTAA CGTGGTATCA GCAGAAACCA
GGGAAAGCCC CTAAGCTCCT GATCTATCAT TCTTCCTTGT TGCAAAGTGG GGTCCCATCA
CGTTTCAGTG GCAGTGGATC TGGGACAGAT TTCACTCTCA CCATCAGCAG TCTGCAGCCT
GAAGATTTCG CTACGTACTA CTGTCAACAG TATATGTATT ATCCTTCTAC GTTCGGCCAA
GGGACCAAGG TGAAAATCAA GCGG
>TAR15-23 (SEQ ID NO:21)
GAGGTGCAGC TGTTGGAGTC TGGGGGAGGC TTGGTACAGC CTGGGGGGTC CCTGCGTCTC
TCCTGTGCAG CCTCCGGATT CACCTTTAAG CTTATGAGA TGGGTTGGGT CCGCCAGGCT
CCAGGGAAGG GTCTGGAGTG GGTCTCAGGT ATTTCTCCTA ATGGTGGTTG GACATACTAC
GCAGACTCCG TGAAGGGCCG GTTCACCATC TCCCGCGACA ATTCCAAGAA CACGCTGTAT
CTGCAAATGA ACAGCCTGCG TGCCGAGGAT ACCGCGGTAT ATTACTGTGC GAAAGAGTCG
ATTAGTCCTA CTCCGTTGGG GTTTGACTAC TGGGGTCAGG GAACCCTGGT CACCGTCTCG
AGC
>TAR15-24 (SEQ ID NO:22)
GAGGTGCAGC TGTTGGAGTC TGGGGGAGGC TTGGTACAGC CTGGGGGGTC CCTGCGTCTC
TCCTGTGCAG CCTCCGGATT CACCTTTACT GGGTATGAGA TGGGGTGGGT CCGCCAGGCT
CCAGGGAAGG GTCTAGAGTG GGTCTCATAT ATTTCTAGGG GTGGTCGGTG GACATACTAC
GCAGACTCCG TGAAGGGCCG GTTCACCATC TCCCGCGACA ATTCCAAGAA CACGCTGTAT
CTGCAAATGA ACAGCCTGCG TGCCGAGGAC ACCGCGGTAT ATTACTGTGC GAAATCGGAT
ACTATGTTTG ACTACTGGGG TCAGGGAACC CTGGTCACCG TCTCGAGC
>TAR15-25 (SEQ ID NO:23)
GAGGTGCAGC TGTTGGAGTC TGGGGGAGGC TTGGTACAGC CTGGGGGGTC CCTGCGTCTC
TCCTGTGCAG CCTCCGGATT CACCTTTAGT GCTTATGAGA TGGGTTGGGT CCGCCAGGCT
CCAGGGAAGG GTCTAGAGTG GGTCTCATTT ATTTCTGGGG GGGTCGGTG GACATACTAC
GCAGACTCCG TGAAGGGCCG GTTCACCATC TCCCGCGACA ATTCCAAGAA CACGCTGTAT

FIG. 1C

CTGCAAATGA ACAGCCTGCG TGCCGAGGAC ACCGCGGTAT ATTACTGTGC GAAATATTCG
GAGGATTTTG ACTACTGGGG TCAGGAACC CTGGTCACCG TCTCGAGC
>TAR15-26 (SEQ ID NO:24)
GAGGTGCAGC TGTTGGAGTC TGGGGGAGGC TTGGTACAGC CTGGGGGGTC CCTGCGTCTC
TCCTGTGCAG CCTCCGGATT CACCTTTGGG GCTTATCCGA TGATGTGGGT CCGCCAGGCT
CCAGGGAAGG GTCTAGAGTG GGTCTCAGAG ATTTCGCCTT CGGGTTCTTA TACATACTAC
GCAGACTCCG TGAAGGGCCG GTTCACCATC TCCCGCGACA ATTCCAAGAA CACGCTGTAT
CTGCAAATGA ACAGCCTGCG TGCCGAGGAC ACCGCGGTAT ATTACTGTGC GAAAGATCCT
CGGAAGTTTG ACTACTGGGG TCAGGGAACC CTGGTCACCG TCTCGAGC
>TAR15-27 (SEQ ID NO:25)
GAGGTGCAGC TGTTGGAGTC TGGGGGAGGC TTGGTACAGC CTGGGGGGTC CCTGCGTCTC
TCCTGTGCAG CCTCCGGATT CACCTTTCAG TTTTATAAGA TGGGTTGGGT CCGCCAGGCT
CCGGGGAAGG GTCTAGAGTG GGTCTCATCT ATTAGTAGTG TGGGTGATGC GACATACTAC
GCAGACTCCG TGAAGGGCCG GTTCACCATC TCCCGCGACA ATTCCAAGAA CACGCTGTAT
CTGCAAATGA ACAGCCTGCG TGCCGAGGAC ACCGCGGTAT ATTACTGTGC GAAAATGGGG
GGGGGGCCTC CTACGTATGT TGTGTATTTT GACTACTGGG GTCAGGGAAC CCTGGTCACC
GTCTCGAGC
>TAR15-29 (SEQ ID NO:26)
GAGGTGCAGC TGTTGGAGTC TGGGGGAGGC TTGGTACAGC CTGGGGGGTC CCTGCGTCTC
TCCTGTGCAG CCTCCGGATT CACCTTTGGG GAGTATGGGA TGTATTGGGT CCGCCAGGCT
CCAGGGAAGG GTCTAGAGTG GGTCTCATCT ATTAGTGAGC GTGGTCGGTT GACATACTAC
GCAGACTCCG TGAAGGGCCG GTTCACCATC TCCCGCGACA ATTCCAAGAA CACGCTGTAT
CTGCAAATGA ACAACCTGCG TGCCGAGGAT ACCGCGGTAT ATTACTGTGC GAAATCGGCG
CTTTCGTCTG AGGGTTTTTC GCGTTCTTTT GACTACTGGG GTCAGGGAAC CCTGGTCACC
GTCTCGAGC
>TAR15-30 (SEQ ID NO:27)
GAGGTGCAGC TGTTGGAGTC TGGGGGAGGC TTGGTACAGC CTGGGGGGTC CCTGCGTCTC
TCCTGTGCAG CCTCCGGATT CACCTTTAGT GATTATGCGA TGTATTGGGT CCGCCAGGCT
CCAGGGAAGG GTCTAGAGTG GGTCTCATCG ATTACGGCTA GGGGTTTTAT TACATACTAC
GCAGACTCCG TGAAGGGCCG GTTCACCATC TCCCGCGACA ATTCCAAGAA CACGCTGTAT
CTGCAAATGA ACAGCCTGCG TGCCGAGGAC ACCGCGGTAT ATTACTGTGC GAAATCGGGT
TTTCCGCATA AGTCGGGTTC GAATTATTTT GACTACTGGG GTCAGGGAAC CCTGGTCACC
GTCTCGAGC
>TAR15-5 (SEQ ID NO:17)
GAGGTGCAGC TGTTGGAGTC TGGGGGAGGC TTGGTACAGC CTGGGGGGTC CCTGCGTCTC
TCCTGTGCAG CCTCCGGATT CACCTTTAGG TTGTATGATA TGGTTTGGGT CCGCCAGGCT
CCAGGGAAGG GTCTGGAGTG GGTCTCATAT ATTAGTTCTG GGGGTTCTGG TACATACTAC
GCAGACTCCG TGAAGGGCCG GTTCACCATC TCCCGCGACA ATTCCAAGAA CACGCTGTAT
CTGCAAATGA ACAGCCTGCG TGCCGAGGAC ACCGCGGTAT ATTACTGTGC GAAAGCGGGG
GGGCGGGCTA GTTTTGACTA CTGGGGTCAG GAACCCTGG TCACCGTCTC GAGC
>TAR15-6 (SEQ ID NO:18)
GAGGTGCAGC TGTTGGAGTC TGGGGGAGGC TTGGTACAGC CTGGGGGGTC CCTGCGTCTC
TCCTGTGCAG CCTCCGGATT CACCTTTCAT CTTTATGATA TGATGTGGGT CCGCCAGGCT
CCAGGGAAGG GTCTAGAGTG GGTCTCATTT ATTGGGGGGG ATGGTCTTAA TACATACTAC
GCAGACTCCG TGAAGGGCCG GTTCACCATC TCCCGCGACA ATTCCAAGAA CACGCTGTAT
CTGCAAATGA ACAGCCTGCG TGCCGAGGAC ACCGCGGTAT ATTACTGTGC GAAAGCGGGG
ACTCAGTTTG ACTACTGGGG TCAGGAACC CTGGTCACCG TCTCGAGC
>TAR15-7 (SEQ ID NO:19)
GAGGTGCAGC TGTTGGAGTC TGGGGGAGGC TTGGTACAGC CTGGGGGGTC CCTGCGTCTC

FIG. 1D

```
TCCTGTGCAG CCTCCGGATT CACCTTTAAT AAGTATCCTA TGATGTGGGT CCGCCAGGCT
CCAGGGAAGG GTCTAGAGTG GGTCTCAGAG ATTTCTCCGT CTGGTCAGGA TACATACTAC
GCAGACTCCG TGAAGGGCCG GTTCACCATC TCCCGCGACA ATTCCAAGAA CACGCTGTAT
CTGCAAATGA ACAGCCTGCG TGCCGAGGAC ACCGCGGTAT ATTACTGTGC GAAAAATCCT
CAGATTCTGT CTAATTTTGA CTACTGGGGT CAGGGAACCC TGGTCACCGT CTCGAGC
>TAR15-8 (SEQ ID NO:20)
GAGGTGCAGC TGTTGGAGTC TGGGGGAGGC TTGGTACAGC CTGGGGGGTC CCTGCGTCTC
TCCTGTGCGG CCTCCGGATT CACCTTTCAG TGGTATCCTA TGTGGTGGGT CCGCCAGGCT
CCAGGGAAGG GTCTTGAGTG GGTCTCACTG ATTGAGGGGC AGGGTGATAG ACATACTAC
GCAGACTCCG TGAAGGGCCG GTTCACCATC TCCCGCGACA ATTCCAAGAA CACGCTGTAT
CTGCAAATGA ACAGCCTGCG TGCCGAGGAC ACCGCGGTAT ATTACTGTGC GAAAGCGGGG
GATCGTACGG CTGGGTCTAG GGGTAATTCT TTTGACTACT GGGGTCAGGG AACCCTGGTC
ACCGTCTCGA GC
```

FIG. 1E

```
TAR15-6      GAGGTGCAGC TGTTGGAGTC TGGGGGAGGC TTGGTACAGC CTGGGGGGTC CCTGCGTCTC
TAR15-6-500  GAGGTGCAGC TGTTGGAGTC TGGGGGAGGC TTGGTACAGC CTGGGGGGTC CCTGCGTCTC
TAR15-6-501  GAGGTGCAGC TGTTGGAGTC TGGGGGAGGC TTGGTACAGC CTGGGGGGTC CCTGCGTCTC
TAR15-6-502  GAGGTGCAGC TGTTGGAGTC TGGGGGAGGC TTGGTACAGC CTGGGGGGTC CCTGCGTCTC
TAR15-6-503  GAGGTGCAGC TGTTGGAGTC TGGGGGAGGC TTGGTACAGC CTGGGGGGTC CCTGCGTCTC
TAR15-6-504  GAGGTGCAGC TGTTGGAGTC TGGGGGAGGC TTGGTACAGC CTGGGGGGTC CCTGCGTCTC
TAR15-6-505  GAGGTGCAGC TGTTGGAGTC TGGGGGAGGC TTGGTACAGC CTGGGGGGTC CCTGCGTCTC
TAR15-6-506  GAGGTGCAGC TGTTGGAGTC TGGGGGAGGC TTGGTACAGC CTGGGGGGTC CCTGCGTCTC
TAR15-6-507  GAGGTGCAGC TGTTGGAGTC TGGGGGAGGC TTGGTACAGC CTGGGGGGTC CCTGCGTCTC
TAR15-6-508  GAGGTGCAGC TGTTGGAGTC TGGGGGAGGC TTGGTACAGC CTGGGGGGTC CCTGCGTCTC
TAR15-6-509  GAGGTGCAGC TGTTGGAGTC TGGGGGAGGC TTGGTACAGC CTGGGGGGTC CCTGCGTCTC
TAR15-6-510  GAGGTGCAGC TGTTGGAGTC TGGGGGAGGC TTGGTACAGC CTGGGGGGTC CCTGCGTCTC

TAR15-6      TCCTGTGCAG CCTCCGGATT CACCTTTCAT CTTTATGATA TGATGTGGGT CCGCCAGGCT
TAR15-6-500  TCCTGTGCAG CCTCCGGATT CACCTTTAGG TTGTACGATA TGATGTGGGT CCGCCAGGCT
TAR15-6-501  TCCTGTGCAG CCTCCGGATT CACCTTTTCC TTCTTCGATA TGATGTGGGT CCGCCAGGCT
TAR15-6-502  TCCTGTGCAG CCTCCGGATT CACCTTTATG CTCTTCGATA TGATGTGGGT CCGCCAGGCT
TAR15-6-503  TCCTGTGCAG CCTCCGGATT CACCTTTCCG TTGTACGATA TGATGTGGGT CCGCCAGGCT
TAR15-6-504  TCCTGTGCAG CCTCCGGATT CACCTTTCCC CTCTACGATA TGATGTGGGT CCGCCAGGCT
TAR15-6-505  TCCTGTGCAG CCTCCGGATT CACCTTTCAG TACTTCGATA TGATGTGGGT CCGCCAGGCT
TAR15-6-506  TCCTGTGCAG CCTCCGGATT CACCTTTCAT CTTTATGATA TGATGTGGGT CCGCCAGGCT
TAR15-6-507  TCCTGTGCAG CCTCCGGATT CACCTTTCAT CTTTATGATA TGATGTGGGT CCGCCAGGCT
TAR15-6-508  TCCTGTGCAG CCTCCGGATT CACCTTTCAT CTTTATGATA TGATGTGGGT CCGCCAGGCT
TAR15-6-509  TCCTGTGCAG CCTCCGGATT CACCTTTCAT CTTTATGATA TGATGTGGGT CCGCCAGGCT
TAR15-6-510  TCCTGTGCAG CCTCCGGATT CACCTTTCAT CTTTATGATA TGATGTGGGT CCGCCAGGCT
```

FIG. 2A

| | 125 | 135 | 145 | 155 | 165 | 175 |
|---|---|---|---|---|---|---|
| TAR15-6     | CCAGGGAAGG | GTCTAGAGTG | GGTCTCATTT | ATTGGGGGGG | ATGGTCTTAA | TACATACTAC |
| TAR15-6-500 | CCAGGGAAGG | GTCTAGAGTG | GGTCTCATTT | ATTGGGGGGG | ATGGTCTTAA | TACATACTAC |
| TAR15-6-501 | CCAGGGAAGG | GTCTAGAGTG | GGTCTCATTT | ATTGGGGGGG | ATGGTCTTAA | TACATACTAC |
| TAR15-6-502 | CCAGGGAAGG | GTCTAGAGTG | GGTCTCATTT | ATTGGGGGGG | ATGGTCTTAA | TACATACTAC |
| TAR15-6-503 | CCAGGGAAGG | GTCTAGAGTG | GGTCTCATTT | ATTGGGGGGG | ATGGTCTTAA | TACATACTAC |
| TAR15-6-504 | CCAGGGAAGG | GTCTAGAGTG | GGTCTCATTT | ATTGGGGGGG | ATGGTCTTAA | TACATACTAC |
| TAR15-6-505 | CCAGGGAAGG | GTCTAGAGTG | GGTCTCATTT | ATTGGGGGGG | ATGGTCTTAA | TACATACTAC |
| TAR15-6-506 | CCAGGGAAGG | GTCTAGAGTG | GGTCTCATTT | ATTGGGGGGG | ATGGTCTTAA | TACATACTAC |
| TAR15-6-507 | CCAGGGAAGG | GTCTAGAGTG | GGTCTCATTT | ATTGGGGGGG | ATGGTCTTAA | TACATACTAC |
| TAR15-6-508 | CCAGGGAAGG | GTCTAGAGTG | GGTCTCATTT | ATTGGGGGGG | ATGGTCTTAA | TACATACTAC |
| TAR15-6-509 | CCAGGGAAGG | GTCTAGAGTG | GGTCTCATTT | ATTGGGGGGG | ATGGTCTTAA | TACATACTAC |
| TAR15-6-510 | CCAGGGAAGG | GTCTAGAGTG | GGTCTCATTT | ATTGGGGGGG | ATGGTCTTAA | TACATACTAC |

| | 185 | 195 | 205 | 215 | 225 | 235 |
|---|---|---|---|---|---|---|
| TAR15-6     | GCAGACTCCG | TGAAGGGCCG | GTTCACCATC | TCCCGCGACA | ATTCCAAGAA | CACGCTGTAT |
| TAR15-6-500 | GCAGACTCCG | TGAAGGGCCG | GTTCACCATC | TCCCGCGACA | ATTCCAAGAA | CACGCTGTAT |
| TAR15-6-501 | GCAGACTCCG | TGAAGGGCCG | GTTCACCATC | TCCCGCGACA | ATTCCAAGAA | CACGCTGTAT |
| TAR15-6-502 | GCAGACTCCG | TGAAGGGCCG | GTTCACCATC | TCCCGCGACA | ATTCCAAGAA | CACGCTGTAT |
| TAR15-6-503 | GCAGACTCCG | TGAAGGGCCG | GTTCACCATC | TCCCGCGACA | ATTCCAAGAA | CACGCTGTAT |
| TAR15-6-504 | GCAGACTCCG | TGAAGGGCCG | GTTCACCATC | TCCCGCGACA | ATTCCAAGAA | CACGCTGTAT |
| TAR15-6-505 | GCAGACTCCG | TGAAGGGCCG | GTTCACCATC | TCCCGCGACA | ATTCCAAGAA | CACGCTGTAT |
| TAR15-6-506 | GCAGACTCCG | TGAAGGGCCG | GTTCACCATC | TCCCGCGACA | ATTCCAAGAA | CACGCTGTAT |
| TAR15-6-507 | GCAGACTCCG | TGAAGGGCCG | GTTCACCATC | TCCCGCGACA | ATTCCAAGAA | CACGCTGTAT |
| TAR15-6-508 | GCAGACTCCG | TGAAGGGCCG | GTTCACCATC | TCCCGCGACA | ATTCCAAGAA | CACGCTGTAT |
| TAR15-6-509 | GCAGACTCCG | TGAAGGGCCG | GTTCACCATC | TCCCGCGACA | ATTCCAAGAA | CACGCTGTAT |
| TAR15-6-510 | GCAGACTCCG | TGAAGGGCCG | GTTCACCATC | TCCCGCGACA | ATTCCAAGAA | CACGCTGTAT |

FIG. 2B

| | 245 | 255 | 265 | 275 | 285 | 295 |
|---|---|---|---|---|---|---|
| TAR15-6 | CTGCAAATGA | ACAGCCTGCG | TGCCGAGGAC | ACCGCGGTAT | ATTACTGTGC | GAAAGCGGGG |
| TAR15-6-500 | CTGCAAATGA | ACAGCCTGCG | TGCCGAGGAC | ACCGCGGTAT | ATTACTGTGC | GAAAGATCCT |
| TAR15-6-501 | CTGCAAATGA | ACAGCCTGCG | TGCCGAGGAC | ACCGCGGTAT | ATTACTGTGC | GAAAGCGGGG |
| TAR15-6-502 | CTGCAAATGA | ACAGCCTGCG | TGCCGAGGAC | ACCGCGGTAT | ATTACTGTGC | GAAAGCGGGG |
| TAR15-6-503 | CTGCAAATGA | ACAGCCTGCG | TGCCGAGGAC | ACCGCGGTAT | ATTACTGTGC | GAAAGCGGGG |
| TAR15-6-504 | CTGCAAATGA | ACAGCCTGCG | TGCCGAGGAC | ACCGCGGTAT | ATTACTGTGC | GAAAGCGGGG |
| TAR15-6-505 | CTGCAAATGA | ACAGCCTGCG | TGCCGAGGAC | ACCGCGGTAT | ATTACTGTGC | GAAAGCGGGG |
| TAR15-6-506 | CTGCAAATGA | ACAGCCTGCG | TGCCGAGGAC | ACCGCGGTAT | ATTACTGTGC | GAAATCCCCC |
| TAR15-6-507 | CTGCAAATGA | ACAGCCTGCG | TGCCGAGGAC | ACCGCGGTAT | ATTACTGTGC | GAAAACCCCC |
| TAR15-6-508 | CTGCAAATGA | ACAGCCTGCG | TGCCGAGGAC | ACCGCGGTAT | ATTACTGTGC | GAAAAGTCG |
| TAR15-6-509 | CTGCAAATGA | ACAGCCTGCG | TGCCGAGGAC | ACCGCGGTAT | ATTACTGTGC | GAAATCCCCC |
| TAR15-6-510 | CTGCAAATGA | ACAGCCTGCG | TGCCGAGGAC | ACCGCGGTAT | ATTACTGTGC | GAAAGATCCT |

| | 305 | 315 | 325 | 335 | 345 | |
|---|---|---|---|---|---|---|
| TAR15-6 | ACTCAGTTTG | ACTACTGGGG | TCAGGGAACC | CTGGTCACCG | TCTCGAGC | |
| TAR15-6-500 | CGGAAGTTTG | ACTACTGGGG | TCAGGGAACC | CTGGTCACCG | TCTCGAGC | |
| TAR15-6-501 | ACTCAGTTTG | ACTACTGGGG | TCAGGGAACC | CTGGTCACCG | TCTCGAGC | |
| TAR15-6-502 | ACTCAGTTTG | ACTACTGGGG | TCAGGGAACC | CTGGTCACCG | TCTCGAGC | |
| TAR15-6-503 | ACTCAGTTTG | ACTACTGGGG | TCAGGGAACC | CTGGTCACCG | TCTCGAGC | |
| TAR15-6-504 | ACTCAGTTTG | ACTACTGGGG | TCAGGGAACC | CTGGTCACCG | TCTCGAGC | |
| TAR15-6-505 | ACTCAGTTTG | ACTACTGGGG | TCAGGGAACC | CTGGTCACCG | TCTCGAGC | |
| TAR15-6-506 | CGCCAGTTTG | ACTACTGGGG | TCAGGGAACC | CTGGTCACCG | TCTCGAGC | |
| TAR15-6-507 | AGGCAGTTTG | ACTACTGGGG | TCAGGGAACC | CTGGTCACCG | TCTCGAGC | |
| TAR15-6-508 | ATGCAGTTTG | ACTACTGGGG | TCAGGGAACC | CTGGTCACCG | TCTCGAGC | |
| TAR15-6-509 | CGCAAGTTTG | ACTACTGGGG | TCAGGGAACC | CTGGTCACCG | TCTCGAGC | |
| TAR15-6-510 | CGGAAGTTTG | ACTACTGGGG | TCAGGGAACC | CTGGTCACCG | TCTCGAGC | |

FIG. 2C

```
                       ....|....|    ....|....|    ....|....|    ....|....|    ....|....|    ....|....|
                                5             15            25            35            45            55
TAR15-8        GAGGTGCAGC    TGTTGGAGTC    TGGGGGAGGC    TTGGTACAGC    CTGGGGGGTC    CCTGCGTCTC
TAR15-8-500    GAGGTGCAGC    TGTTGGAGTC    TGGGGGAGGC    TTGGTACAGC    CTGGGGGGTC    CCTGCGTCTC
TAR15-8-501    GAGGTGCAGC    TGTTGGAGTC    TGGGGGAGGC    TTGGTACAGC    CTGGGGGGTC    CCTGCGTCTC
TAR15-8-502    GAGGTGCAGC    TGTTGGAGTC    TGGGGGAGGC    TTGGTACAGC    CTGGGGGGTC    CCTGCGTCTC
TAR15-8-503    GAGGTGCAGC    TGTTGGAGTC    TGGGGGAGGC    TTGGTACAGC    CTGGGGGGTC    CCTGCGTCTC
TAR15-8-505    GAGGTGCAGC    TGTTGGAGTC    TGGGGGAGGC    TTGGTACAGC    CTGGGGGGTC    CCTGCGTCTC
TAR15-8-506    GAGGTGCAGC    TGTTGGAGTC    TGGGGGAGGC    TTGGTACAGC    CTGGGGGGTC    CCTGCGTCTC
TAR15-8-507    GAGGTGCAGC    TGTTGGAGTC    TGGGGGAGGC    TTGGTACAGC    CTGGGGGGTC    CCTGCGTCTC
TAR15-8-508    GAGGTGCAGC    TGTTGGAGTC    TGGGGGAGGC    TTGGTACAGC    CTGGGGGGTC    CCTGCGTCTC
TAR15-8-509    GAGGTGCAGC    TGTTGGAGTC    TGGGGGAGGC    TTGGTACAGC    CTGGGGGGTC    CCTGCGTCTC
TAR15-8-510    GAGGTGCAGC    TGTTGGAGTC    TGGGGGAGGC    TTGGTACAGC    CTGGGGGGTC    CCTGCGTCTC
TAR15-8-511    GAGGTGCAGC    TGTTGGAGTC    TGGGGGAGGC    TTGGTACAGC    CTGGGGGGTC    CCTGCGTCTC

....|....|    ....|....|    ....|....|    ....|....|    ....|....|    ....|....|
                               65            75            85            95           105           115
TAR15-8        TCCTGTGCGG    CCTCCGGATT    CACCTTTCAG    TGGTATCCTA    TGTGGTGGGT    CCGCCAGGCT
TAR15-8-500    TCCTGTGCGG    CCTCCGGATA    C---------    -----CCTA    TGTGGTGGGT    CCGCCAGGCT
TAR15-8-501    TCCTGTGCGG    CCTCCGGATT    CACCTTTCAG    TGGGCCCCCA    TGCCCTGGGT    CCGCCAGGCT
TAR15-8-502    TCCTGTGCGG    CCTCCGGATT    CACCTTTCAG    TGGCCCCACA    TGCCCTGGGT    CCGCCAGGCT
TAR15-8-503    TCCTGTGCGG    CCTCCGGATT    CACCTTTNAN    TGGCCCCACA    TGCACTGGGT    CCGCCAGGCT
TAR15-8-505    TCCTGTGCGG    CCTCCGGATT    CACCTTTCAG    TGGTATCCTA    TGTGGTGGGT    CCGCCAGGCT
TAR15-8-506    TCCTGTGCGG    CCTCCGGATT    CACCTTTCAG    TGGTATCCTA    TGTGGTGGGT    CCGCCAGGCT
TAR15-8-507    TCCTGTGCGG    CCTCCGGATT    CACCTTTCAG    TGGTATCCTA    TGTGGTGGGT    CCGCCAGGCT
TAR15-8-508    TCCTGTGCGG    CCTCCGGATT    CACCTTTCAG    TGGTATCCTA    TGTGGTGGGT    CCGCCAGGCT
TAR15-8-509    TCCTGTGCGG    CCTCCGGATT    CACCTTTCAG    TGGTATCCTA    TGTGGTGGGT    CCGCCAGGCT
TAR15-8-510    TCCTGTGCGG    CCTCCGGATT    CACCTTTCAG    TGGTATCCTA    TGTGGTGGGT    CCGCCAGGCT
TAR15-8-511    TCCTGTGCGG    CCTCCGGATT    CACCTTTCAG    TGGTATCCTA    TGTGGTGGGT    CCGCCAGGCT
```

FIG. 3A

|              | 125        | 135        | 145        | 155        | 165        | 175        |
|--------------|------------|------------|------------|------------|------------|------------|
| TAR15-8      | CCAGGGAAGG | GTCTTGAGTG | GGTCTCACTG | ATTGAGGGGC | AGGGTGATAG | GACATACTAC |
| TAR15-8-500  | CCAGGGAAGG | GTCCTGAGTG | GGTCTCACTG | ATTGAGGGGC | AGGGTGATAG | GACATACTAC |
| TAR15-8-501  | CCAGGGAAGG | GTCTTGAGTG | GGTCTCACTG | ATTGAGGGGC | AGGGTGATAG | GACATACTAC |
| TAR15-8-502  | CCAGGGAAGG | GTCTTGAGTG | GGTCTCACTG | ATTGAGGGGC | AGGGTGATAG | GACATACTAC |
| TAR15-8-503  | CCAGGGAAGG | GTCTTGAGTG | GGTCTCACTG | ATTGAGGGGC | AGGGTGATAG | GACATACTAC |
| TAR15-8-505  | CCAGGGAAGG | GTCTTGAGTG | GGTCTCACTG | ATTGAGGGGC | AGGGTGATAG | GACATACTAC |
| TAR15-8-506  | CCAGGGAAGG | GTCTTGAGTG | GGTCTCACTG | ATTGAGGGGC | AGGGTGATAG | GACATACTAC |
| TAR15-8-507  | CCAGGGAAGG | GTCTTGAGTG | GGTCTCACTG | ATTGAGGGGC | AGGGTGATAG | GACATACTAC |
| TAR15-8-508  | CCAGGGAAGG | GTCTTGAGTG | GGTCTCACTG | ATTGAGGTGC | AGGGTGATAG | GACATACTAC |
| TAR15-8-509  | CCAGGGAAGG | GTCTTGAGTG | GGTCTCACTG | ATTGAGGGGC | AGGGTGATAG | GACATACTAC |
| TAR15-8-510  | CCAGGGAAGG | GTCTTGAGTG | GGTCTCACTG | ATTGAGGGGC | AGGGTGATAG | GACATACTAC |
| TAR15-8-511  | CCAGGGAAGG | GTCTTGAGTG | GGTCTCACTG | ATTGAGGGGC | AGGGTGATAG | GACATACTAC |

|              | 185        | 195        | 205        | 215        | 225        | 235        |
|--------------|------------|------------|------------|------------|------------|------------|
| TAR15-8      | GCAGACTCCG | TGAAGGGCCG | GTTCACCATC | TCCCGCGACA | ATTCCAAGAA | CACGCTGTAT |
| TAR15-8-500  | GCAGACTCCG | TGAAGGGCCG | GTTCACCATC | TCCCGCGACA | ATTCCAAGAA | CACGCTGTAT |
| TAR15-8-501  | GCAGACTCCG | TGAAGGGCCG | GTTCACCATC | TCCCGCGACA | ATTCCAAGAA | CACGCTGTAT |
| TAR15-8-502  | GCAGACTCCG | TGAAGGGCCG | GTTCACCATC | TCCCGCGACA | ATTCCAAGAA | CACGCTGTAT |
| TAR15-8-503  | GCAGACTCCG | TGAAGGGCCG | GTTCACCATC | TCCCGCGACA | ATTCCAAGAA | CACGCTGTAT |
| TAR15-8-505  | GCAGACTCCG | TGAAGGGCCG | GTTCACCATC | TCCCGCGACA | ATTCCAAGAA | CACGCTGTAT |
| TAR15-8-506  | GCAGACTCCG | TGAAGGGCCG | GTTCACCATC | TCCCGCGACA | ATTCCAAGAA | CACGCTGTAT |
| TAR15-8-507  | GCAGACTCCG | TGAAGGGCCG | GTTCACCATC | TCCCGCGACA | ATTCCAAGAA | CACGCTGTAT |
| TAR15-8-508  | GCAGACTCCG | TGAAGGGCCG | GTTCACCATC | TCCCGCGACA | ATTCCAAGAA | CACGCTGTAT |
| TAR15-8-509  | GCAGACTCCG | TGAAGGGCCG | GTTCACCATC | TCCCGCGACA | ATTCCAAGAA | CACGCTGTAT |
| TAR15-8-510  | GCAGACTCCG | TGAAGGGCCG | GTTCACCATC | TCCCGCGACA | ATTCCAAGAA | CACGCTGTAT |
| TAR15-8-511  | GCAGACTCCG | TGAAGGGCCG | GTTCACCATC | TCCCGCGACA | ATTCCAAGAA | CACGCTGTAT |

FIG. 3B

| | 245 | 255 | 265 | 275 | 285 | 295 |
|---|---|---|---|---|---|---|
| TAR15-8 | CTGCAAATGA | ACAGCCTGCG | TGCCGAGGAC | ACCGCGGTAT | ATTACTGTGC | GAAAGCGGGG |
| TAR15-8-500 | CTGCAAATGA | ACAGCCTGCC | CGCCGAGGAC | ACCGCGGTAT | ATTACTGTGC | GAAAGCGGGG |
| TAR15-8-501 | CTGCAAATGA | ACAGCCTGCG | TGCCGAGGAC | ACCGCGGTAT | ATTACTGTGC | GAAAGCGGGG |
| TAR15-8-502 | CTGCAAATGA | ACAGCCTGCG | TGCCGAGGAC | ACCGCGGTAT | ATTACTGTGC | GAAAGCGGGG |
| TAR15-8-503 | CTGCAAATGA | ACAGCCTGCG | TGCCGAGGAC | ACCGCGGTAT | ATTACTGTGC | GAAAGCGGGG |
| TAR15-8-505 | CTGCAAATGA | ACAGCCTGCG | TGCCGAGGAC | ACCGCGGTAT | ATTACTGTGC | GAAAGCGGGG |
| TAR15-8-506 | CTGCAAATGA | ACAGCCTGCG | TGCCGAGGAC | ACCGCGGTAT | ATTACTGTGC | GAAAGCGGGG |
| TAR15-8-507 | CTGCAAATGA | ACAGCCTGCG | TGCCGAGGAC | ACCGCGGTAT | ATTACTGTGC | GAAAGCGGGG |
| TAR15-8-508 | CTGCAAATGA | ACAGCCTGCG | TGCCGAGGAC | ACCGCGGTAT | ATTACTGTGC | GAAAGCGGGG |
| TAR15-8-509 | CTGCAAATGA | ACAGCCTGCG | TGCCGAGGAC | ACCGCGGTAT | ATTACTGTGC | GAAAGCGGGG |
| TAR15-8-510 | CTGCAAATGA | ACAGCCTGCG | TGCCGAGGAC | ACCGCGGTAT | ATTACTGTGC | GAAAGCGGGG |
| TAR15-8-511 | CTGCAAATGA | ACAGCCTGCG | TGCCGAGGAC | ACCGCGGTAT | ATTACTGTGC | GAAAGCGGGG |

| | 305 | 315 | 325 | 335 | 345 | 355 |
|---|---|---|---|---|---|---|
| TAR15-8 | GATCGTACGG | CTGGGTCTAG | GGGTAATTCT | TTTGACTACT | GGGGTCAGGG | AACCCTGGTC |
| TAR15-8-500 | GATCGTACGG | CTGGGTCTAG | GGGTAATTCT | TTTGACTACT | GGGGTCAGGG | AACCCTGGTC |
| TAR15-8-501 | GATCGTACGG | CTGGGTCTAG | GGGTAATTCT | TTTGACTACT | GGGGTCAGGG | AACCCTGGTC |
| TAR15-8-502 | GATCGTACGG | CTGGGTCTAG | GGGTAATTCT | TTTGACTACT | GGGGTCAGGG | AACCCTGGTC |
| TAR15-8-503 | GATCGTACGG | CTGGGTCTAG | GGGTAATTCT | TTTGACTACT | GGGGTCAGGG | AACCCTGGTC |
| TAR15-8-505 | GATCGTACGG | TGTTGTCTAG | GGGTAATTCT | TTTGACTACT | GGGGTCAGGG | AACCCTGGTC |
| TAR15-8-506 | GATCGTCGCT | TCCTCTCTAG | GGGTAATTCT | TTTGACTACT | GGGGTCAGGG | AACCCTGGTC |
| TAR15-8-507 | GATCGTCACA | GGACCTCTAG | GGGTAATTCT | TTTGACTACT | GGGGTCAGGG | AACCCTGGTC |
| TAR15-8-508 | CCCCCCTTCG | CTGGGTCTAG | CGGTAATTCT | TTTGACTACT | GGGGTCGGGG | AACCCTGGTC |
| TAR15-8-509 | ACCAACAACG | CTCAGAACAG | GGGTAATTCT | TTTGACTACT | GGGGTCAGGG | AACCCTGGTC |
| TAR15-8-510 | GATCGTACGG | CTGGGTCTAG | GGGTAATTCT | TTTGACTACT | GGGGTCAGGG | AACCCTGGTC |
| TAR15-8-511 | AACAGCAACG | CTGGGTCTAG | GGGTAATTCT | TTTGACTACT | GGGGTCAGGG | AACCCTGGTC |

FIG. 3C

| | | |
|---|---|---|
| | ....\|.... : | |
| | 365 | |
| TAR15-8 | ACCGTCTCGA | GC |
| TAR15-8-500 | ACCGTCTCGA | GC |
| TAR15-8-501 | ACCGTCTCGA | GC |
| TAR15-8-502 | ACCGTCTCGA | GC |
| TAR15-8-503 | ACCGTCTCGA | GC |
| TAR15-8-505 | ACCGTCTCGA | GC |
| TAR15-8-506 | ACCGTCTCGA | GC |
| TAR15-8-507 | ACCGTCTCGA | GC |
| TAR15-8-508 | ACCGTCTCGA | GC |
| TAR15-8-509 | ACCGTCTCGA | GC |
| TAR15-8-510 | ACCGTCTCGA | GC |
| TAR15-8-511 | ACCGTCTCGA | GC |

FIG. 3D

| | 5 | 15 | 25 | 35 | 45 | 55 |
|---|---|---|---|---|---|---|
| TAR15-26 | GAGGTGCAGC | TGTTGGAGTC | TGGGGGAGGC | TTGGTACAGC | CTGGGGGGTC | CCTGCGTCTC |
| TAR15-26-500 | GAGGTGCAGC | TGTTGGAGTC | TGGGGGAGGC | TTGGTACAGC | CTGGGGGGTC | CCTGCGTCTC |
| TAR15-26-501 | GAGGTGCAGC | TGTTGGAGTC | TGGGGGAGGC | TTGGTACAGC | CTGGGGGGTC | CCTGCGTCTC |
| TAR15-26-502 | GAGGTGCAGC | TGTTGGAGTC | TGGGGGAGGC | TTGGTACAGC | CTGGGGGGTC | CCTGCGTCTC |
| TAR15-26-503 | GAGGTGCAGC | TGTTGGAGTC | TGGGGGAGGC | TTGGTACAGC | CTGGGGGGTC | CCTGCGTCTC |
| TAR15-26-504 | GAGGTGCAGC | TGTTGGAGTC | TGGGGGAGGC | TTGGTACAGC | CTGGGGGGTC | CCTGCGTCTC |
| TAR15-26-505 | GAGGTGCAGC | TGTTGGAGTC | TGGGGGAGGC | TTGGTACAGC | CTGGGGGGTC | CCTGCGTCTC |
| TAR15-26-506 | GAGGTGCAGC | TGTTGGAGTC | TGGGGGAGGC | TTGGTACAGC | CTGGGGGGTC | CCTGCGTCTC |
| TAR15-26-507 | GAGGTGCAGC | TGTTGGAGTC | TGGGGGAGGC | TTGGTACAGC | CTGGGGGGTC | CCTGCGTCTC |
| TAR15-26-508 | GAGGTGCAGC | TGTTGGAGTC | TGGGGGAGGC | TTGGTACAGC | CTGGGGGGTC | CCTGCGTCTC |
| TAR15-26-509 | GAGGTGCAGC | TGTTGGAGTC | TGGGGGAGGC | TTGGTACAGC | CTGGGGGGTC | CCTGCGTCTC |
| TAR15-26-510 | GAGGTGCAGC | TGTTGGAGTC | TGGGGGAGGC | TTGGTACAGC | CTGGGGGGTC | CCTGCGTCTC |
| TAR15-26-511 | GAGGTGCAGC | TGTTGGAGTC | CGGGGGAGGC | TTGGTACAGC | CTGGGGGGTC | CCTGCGTCTC |
| TAR15-26-512 | GAGGTGCAGC | TGTTGGAGTC | TGGGGGAGGC | TTGGTACAGC | CTGGGGGGTC | CCTGCGTCTC |
| TAR15-26-513 | GAGGTGCAGC | TGTTGGAGTC | TGGGGGAGGC | TTGGTACAGC | CTGGGGGGTC | CCTGCGTCTC |
| TAR15-26-514 | GAGGTGCAGC | TGTTGGAGTC | TGGGGGAGGC | TTGGTACAGC | CTGGGGGGTC | CCTGCGTCTC |
| TAR15-26-515 | GAGGTGCAGC | TGTTGGAGTC | TGGGGGAGGC | TTGGTACAGC | CTGGGGGGTC | CCTGCGTCTC |
| TAR15-26-516 | GAGGTGCAGC | TGTTGGAGTC | TGGGGGAGGC | TTGGTACAGC | CTGGGGGGTC | CCTGCGTCTC |
| TAR15-26-517 | GAGGTGCAGC | TGTTGGAGTC | TGGGGGAGGC | TTGGTACAGC | CTGGGGGGTC | CCTGCGTCTC |
| TAR15-26-518 | GAGGTGCAGC | TGTTGGAGTC | TGGGGGAGGC | TTGGTACAGC | CTGGGGGGTC | CCTGCGTCTC |
| TAR15-26-519 | GAGGTGCAGC | AGTTGGAGTC | TGGGGGAGGC | TTGGTACAGC | CTGGGGGGTC | CCTGCGTCTC |
| TAR15-26-520 | GAGGTGCAGC | TGTTGGAGTC | TGGGGGAGGC | TTGGTACAGC | CTGGGGGGTC | CCTGCGTCTC |
| TAR15-26-521 | GAGGTGCAGC | TGTTGGAGTC | TGGGGGAGGC | TTGGTACAGC | CTGGGGGGTC | CCTGCGCCTC |
| TAR15-26-522 | GAGGTGCAGC | TGTTGGAGTC | TGGGGGAGGC | TTGGTACAGC | CTGGGGGGTC | CCTGCGTCTC |
| TAR15-26-523 | GAGGTGCAGC | TGTTGGAGTC | TGGGGGAGGT | TTGGTACAGC | CTGGGGGGTC | CCTGCGTCTC |
| TAR15-26-524 | GAGGTGCAGC | TGTTGGAGTC | TGGGGGAGGC | TTGGTACAGC | CTGGGGGGTC | CCTGCGTCTC |
| TAR15-26-525 | GAGGTGCAGC | TGTTGGAGTC | TGGGGGAGGC | TTGGTACAGC | CTGGGGGGTC | CCTGCGTCTC |
| TAR15-26-526 | GAGGTGCAGC | TGTTGGAGTC | TGGGGGAGGC | TTGGTACAGC | CTGGGGGGTC | CCTGCGTCTC |
| TAR15-26-527 | GAGGTGCAGC | TGTTGGAGTC | TGGGGGAGGC | TTGGTACAGC | CTGGGGGGTC | CCTGCGTCTC |
| TAR15-26-528 | GAGGTGCAGC | TGTTGGAGTC | TGGGGGAGGC | TTGGTACAGC | CTGGGGGGTC | CCTGCGTCTC |
| TAR15-26-529 | GAGGTGCAGC | TGTTGGAGTC | TGGGGGAGGC | TTGGTACAGC | CTGGGGGGTC | CCTGCGTCTC |
| TAR15-26-530 | GAGGTGCAGC | TGTTGGAGTC | TGGGGGAGGC | TTGGTACAGC | CTGGGGGGTC | CCTGCGTCTC |
| TAR15-26-531 | GAGGTGCAGC | TGTTGGAGTC | TGGGGGAGGC | TTGGTACAGC | CTGGGGGGTC | CCTGCGTCTC |
| TAR15-26-532 | GAGGTGCAGC | TGTTGGAGTC | TGGGGGAGGC | TTGGTACAGC | CTGGGGGGTC | CCTGCGTCTC |

FIG. 4A

| | | | | | | | |
|---|---|---|---|---|---|---|---|
| TAR15-26-533 | GAGGTGCAGC | TGTTGGAGTC | TGGGGGAGGC | TTGGTACAGC | CTGGGGGGTC | CCTGCGTCTC |
| TAR15-26-534 | GAGGTGCAGC | TGTTGGAGTC | TGGGGGAGGC | TTGGTACAGC | CTGGGGGGTC | CCTGCGTCTC |
| TAR15-26-535 | GAGGTGCAGC | TGTTGGAGTC | TGGGGGAGGC | TTGGTACAGC | CTGGGGGGTC | CCTGCGTCTC |
| TAR15-26-536 | GAGGTGCAGC | TGTTGGAGTC | TGGGGGAGGC | TTGGTACAGC | CTGGGGGGTC | CCTGCGTCTC |
| TAR15-26-537 | GAGGTGCAGC | TGTTGGAGTC | TGGGGGAGGC | TTGGTACAGC | CTGGGGGGTC | CCTGCGTCTC |
| TAR15-26-538 | GAGGTGCAGC | TGTTGGAGTC | TGGGGGAGGC | TTGGTACAGC | CTGGGGGGTC | CCTGCGTCTC |
| TAR15-26-539 | GAGGTGCAGC | TGTTGGAGTC | TGGGGGAGGC | TTGGTACAGC | CTGGGGGGTC | CCTGCGTCTC |
| TAR15-26-540 | GAGGTGCAGC | TGTTGGAGTC | TGGGGGAGGC | TTGGTACAGC | CTGGGGGGTC | CCTGCGTCTC |
| TAR15-26-541 | GAGGTGCAGC | TGTTGGAGTC | TGGGGGAGGC | TTGGTACAGC | CTGGGGGGTC | CCTGCGTCTC |
| TAR15-26-542 | GAGGTGCAGC | TGTTGGAGTC | TGGGGGAGGC | TTGGTACAGC | CTGGGGGGTC | CCTGCGTCTC |
| TAR15-26-543 | GAGGTGCAGC | TGTTGGAGTC | TGGGGGAGGC | TTGGTACAGC | CTGGGGGGTC | CCTGCGTCTC |
| TAR15-26-544 | GAGGTGCAGC | TGTTGGAGTC | TGGGGGAGGC | TTGGTACAGC | CTGGGGGGTC | CCTGCGTCTC |
| TAR15-26-545 | GAGGTGCAGC | TGTTGGAGTC | TGGGGGAGGC | TTGGTACAGC | CTGGGGGGTC | CCTGCGTCTC |
| TAR15-26-546 | GAGGTGCAGC | TGTTGGAGTC | TGGGGGAGGC | TTGGTACAGC | CTGGGGGGTC | CCTGCGTCTC |
| TAR15-26-547 | GAGGTGCAGC | TGTTGGAGTC | TGGGGGAGGC | TTGGTACAGC | CTGGGGGGTC | CCTGCGTCTC |
| TAR15-26-548 | GAGGTGCAGC | TGTTGGAGTC | TGGGGGAGGC | TTGGTACAGC | CTGGGGGGTC | CCTGCGTCTC |
| TAR15-26-549 | GAGGTGCAGC | TGTTGGAGTC | TGGGGGAGGC | TTGGTACAGC | CTGGGGGGTC | CCTGCGTCTC |
| TAR15-26-550 | GAGGTGCAGC | TGTTGGAGTC | TGGGGGAGGC | TTGGTACAGC | CTGGGGGGTC | CCTGCGTCTC |
| TAR15-26-551 | GAGGTGCAGC | TGTTGGAGTC | TGGGGGAGGC | TTGGTACAGC | CTGGGGGGTC | CCTGCGTCTC |
| | ....\|....65 | ....\|....75 | ....\|....85 | ....\|....95 | ....\|....105 | ....\|....115 |
| TAR15-26 | TCCTGTGCAG | CCTCCGGATT | CACCTTTGGG | GCTTATCCGA | TGATGTGGGT | CCGCCAGGCT |
| TAR15-26-500 | TCCTGTGCAG | CCTCCGGATT | CACCTTTCCC | GCTTATCCGA | TGATGTGGGT | CCGCCAGGCT |
| TAR15-26-501 | TCCTGTGCAG | CCTCCGGATT | CACCTTTAAG | GCTTATCCGA | TAATGTGGGT | CCGCCAGGCT |
| TAR15-26-502 | TCCTGTGCAG | CCTCCGGATT | CACCTTTACG | GCTTATCCGA | TGATGTGGGT | CCGCCAGGCT |
| TAR15-26-503 | TCCTGTGCAG | CCTCCGGATT | CACCTTTGGG | TGTATCCGA | TGATGTGGGT | CCGCCAGGCT |
| TAR15-26-504 | TCCTGTGCAG | CCTCCGGATT | CACCTTTGGG | CTCTATCCGA | TGATGTGGGT | CCGCCAGGCT |
| TAR15-26-505 | TCCTGTGCAG | CCTCCGGATT | CACCTTTCTG | GCTTATCCGA | TGATGTGGGT | CCGCCAGGCT |
| TAR15-26-506 | TCCTGTGCAG | CCTCCGGATT | CACCTTTGGG | AGTATCCGA | TGATGTGGGT | CCGCCAGGCT |
| TAR15-26-507 | TCCTGTGCAG | CCTCCGGATT | CACCTTTGGG | GCTTTCCCGA | TGTTGTGGGT | CCGCCAGGCT |
| TAR15-26-508 | TCCTGTGCAG | CCTCCGGATT | CACCTTTCC | GCTTATCCGA | TGATGTGGGT | CCGCCAGGCT |
| TAR15-26-509 | TCCTGTGCAG | CCTCCGGATT | CACCTTTTTC | CTCTCCCCGA | TGATGTGGGT | CCGCCAGGCT |
| TAR15-26-510 | TCCTGTGCAG | CCTCCGGATT | CACCTTTTTT | TTGTTCCCGA | TGATGTGGGT | CCGCCAGGCT |
| TAR15-26-511 | TCCTGTGCAG | CCTCCGGATT | CACCTTTTCG | TACTTCCCGA | TGATGTGGGT | CCGCCAGGCT |
| TAR15-26-512 | TCCTGTGCAG | CCTCCGGATT | CACCTTTGCC | TTCGCCCCGA | TGATGTGGGT | CCGCCAGGCT |
| TAR15-26-513 | TCCTGTGCAG | CCTCCGGATT | CACCTTTGCC | CCCTACCCGA | TGATGTGGGT | CCGCCAGGCT |

FIG. 4B

| | | | | | | |
|---|---|---|---|---|---|---|
| TAR15-26-514 | TCCTGTGCAG | CCTCCGGATT | CACCTTTACC | TCCCACCCGA | TGATGTGGGT | CCGCCAGGCT |
| TAR15-26-515 | TCCTGTGCAG | CCTCCGGATT | CACCTTTACG | AGCCACCCGA | TGATGTGGGT | CCGCCAGGCT |
| TAR15-26-516 | TCCTGTGCAG | CCTCCGGATT | CACCTTTCAC | GCTTATCCGA | TGATGTGGGT | CCGCCAGGCT |
| TAR15-26-517 | TCCTGTGCAG | CCTCCGGATT | CACCTTTAGG | GCTTATCCGA | TGATGTGGGT | CCGCCAGGCT |
| TAR15-26-518 | TCCTGTGCAG | CCTCCGGATT | CACCTTTTTG | GCTTATCCGA | TGATGTGGGT | CCGCCAGGCT |
| TAR15-26-519 | TCCTGTGCAG | CCTCCGGATT | CACCTTTTTG | GCTTATCCGA | TGATGTGGGT | CCGCCAGGCT |
| TAR15-26-520 | TCCTGTGCAG | CCTCCGGATT | CACCTTTTGG | GCTTATCCGA | TGATGTGGGT | CCGCCAGGCT |
| TAR15-26-521 | TCCTGTGCAG | CCTCCGGATT | CACCTTTCAG | GCTTATCCGA | TGATGTGGGT | CCGCCAGGCT |
| TAR15-26-522 | TCCTGTGCAG | CCTCCGGATT | CACCTTTGGG | CACTATCCGA | TGATGTGGGT | CCGCCAGGCT |
| TAR15-26-523 | TCCTGTGCAG | CCTCCGGATT | CACCTTTGGG | TTGTATCCGA | TGATGTGGGT | CCGCCAGGCT |
| TAR15-26-524 | TCCTGTGCAG | CCTCCGGATT | CACCTTTGGG | TGGTATCCGA | TGATGTGGGT | CCGCCAGGCT |
| TAR15-26-525 | TCCTGTGCAG | CCTCCGGATT | CACCTTTGGG | GCTTTCCCGA | TGATGTGGGT | CCGCCAGGCT |
| TAR15-26-526 | TCCTGTGCAG | CCTCCGGATT | CACCTTTAAG | GCTTATCCGA | TAATGTGGGT | CCGCCAGGCT |
| TAR15-26-527 | TCCTGTGCAG | CCTCCGGATT | CACCTTTAAG | GCTTATCCGA | TAATGTGGGT | CCGCCAGGCT |
| TAR15-26-528 | TCCTGTGCAG | CCTCCGGATT | CACCTTTAAG | GCTTATCCGA | TAATGTGGGT | CCGCCAGGCT |
| TAR15-26-529 | TCCTGTGCAG | CCTCCGGATT | CACCTTTAAG | GCTTATCCGA | TAATGTGGGT | CCGCCAGGCT |
| TAR15-26-530 | TCCTGTGCAG | CCTCCGGATT | CACCTTTAAG | GCTTATCCGA | TAATGTGGGT | CCGCCAGGCT |
| TAR15-26-531 | TCCTGTGCAG | CCTCCGGATT | CACCTTTAAG | GCTTATCCGA | TAATGTGGGT | CCGCCAGGCT |
| TAR15-26-532 | TCCTGTGCAG | CCTCCGGATT | CACCTTTAAG | GCTTATCCGA | TAATGTGGGT | CCGCCAGGCT |
| TAR15-26-533 | TCCTGTGCAG | CCTCCGGATT | CACCTTTAAG | GCTTATCCGA | TAATGTGGGT | CCGCCAGGCT |
| TAR15-26-534 | TCCTGTGCAG | CCTCCGGATT | CACCTTTAAG | GCTTATCCGA | TATTGTGGGT | CCGCCAGGCT |
| TAR15-26-535 | TCCTGTGCAG | CCTCCGGATT | CACCTTTAAG | GCTTATCCGA | TAATGTGGGT | CCGCCAGGCT |
| TAR15-26-536 | TCCTGTGCAG | CCTCCGGATT | CACCTTTAAG | GCTTATCCGA | TAATGTGGGT | CCGCCAGGCC |
| TAR15-26-537 | TCCTGTGCAG | CCTCCGGATT | CACCTTTAAG | GCTTATCCGA | TAATGTGGGT | CCGCCAGGCT |
| TAR15-26-538 | TCCTGTGCAG | CCTCCGGATT | CACCTTTAAG | GCTTATCCGA | TAATGTGGGT | CCGCCAGGCT |
| TAR15-26-539 | TCCTGTGCAG | CCTCCGGATT | CACCTTTAAG | GCTTATCCGA | TAATGTGGGT | CCGCCAGGCT |
| TAR15-26-540 | TCCTGTGCAG | CCTCCGGATT | CACCTTTAAG | GCTTATCCGA | TAATGTGGGT | CCGCCAGGCT |
| TAR15-26-541 | TCCTGTGCAG | CCTCCGGATT | CACCTTTAAG | GCTTATCCGA | TAATGTGGGT | CCGCCAGGCT |
| TAR15-26-542 | TCCTGTGCAG | CCTCCGGATT | CACCTTTAAG | GCTTATCCGA | TAATGTGGGT | CCGCCAGGCT |
| TAR15-26-543 | TCCTGTGCAG | CCTCCGGATT | CACCTTTAGG | GCTTATCCGA | TAATGTGGGT | CCGCCAGGCT |
| TAR15-26-544 | TCCTGTGCAG | CCTCCGGATT | CACCTTTAAG | GCTTATCCGA | TAATGTGGGT | CCGCCAGGCT |
| TAR15-26-545 | TCCTGTGCAG | CCTCCGGATT | CACCTTTAAG | GCTTATCCGA | TAATGTGGGT | CCGCCAGGCT |
| TAR15-26-546 | TCCTGTGCAG | CCTCCGGATT | CACCTTTAAG | GCTTATCCGA | TAATGTGGGT | CCGCCAGGCT |
| TAR15-26-547 | TCCTGTGCAG | CCTCCGGATT | CACCTTTAAG | GCTTATCCGA | TAATGTGGGT | CCGCCAGGCT |
| TAR15-26-548 | TCCTGTGCAG | CCTCCGGATT | CACCTTTAAG | GCTTATCCGA | TAATGTGGGT | CCGCCAGGCT |
| TAR15-26-549 | TCCTGTGCAG | CCTCCGGATT | CACCTTTAAG | GCTTATCCGA | TAATGTGGGT | CCGCCAGGCT |

| | | | | | | |
|---|---|---|---|---|---|---|
| TAR15-26-530 | CCAGGGAAGG | GTCTAGAGTG | GGTCTCAGAG | ATTTCGCCTT | CGGGTTCTTA | TACATACTAC |
| TAR15-26-531 | CCAGGGAAGG | GTCTAGAGTG | GGTCTCAGAG | ATTTCGCCTT | CGGGTTCTTA | TACATACTAC |
| TAR15-26-532 | CCAGGGAAGG | GTCTAGAGTG | GGTCTCAGAG | ATTTCGCCTT | CGGGTTCTTA | TACATACTAC |
| TAR15-26-533 | CCAGGGAAGG | GTCTAGAGTG | GGTCTCAGAG | ATTTCGCCTT | CGGGTTCTCA | TACATACTAC |
| TAR15-26-534 | CCAGGGAAGG | GTCTAGAGTG | GGTCTCAGAG | ATTTCGCCTT | CGGGTTCTTA | TACATACTAC |
| TAR15-26-535 | CCAGGGAAGG | GTCTAGAGTG | GGTCTCAGAG | ATTTCGCCTT | CGGGCAAGAT | GAAGTACTAC |
| TAR15-26-536 | CCAGGGAAGG | GTCTAGAGTG | GGTCTCAGAG | ATTTCGCCCA | CCGGTTCTTA | TACATACTAC |
| TAR15-26-537 | CCAGGGAAGG | GTCTAGAGTG | GGTCTCAGAG | ATTTCGCCTT | CGGGTTCTTA | TACATACTAC |
| TAR15-26-538 | CCAGGGAAGG | GTCTAGAGTG | GGTCTCAGAG | ATTTCGCCCT | CCGGTTCTTA | TACATACTAC |
| TAR15-26-539 | CCAGGGAAGG | GTCTAGAGTG | GGTCTCAGAG | ATTTCGCCTT | CGGGTCAGAT | GAGGTACTAC |
| TAR15-26-540 | CCAGGGAAGG | GTCTAGAGTG | GGTCTCAGAG | ATTTCGCCTT | CGGGTAGGTC | GCGGTACTAC |
| TAR15-26-541 | CCAGGGAAGG | GTCTAGAGTG | GGTCTCAGAG | ATTTCGCCTT | CGGGTAGGTA | CAGCTACTAC |
| TAR15-26-542 | CCAGGGAAGG | GTCTAGAGTG | GGTCTCAGAG | ATTTCGCCTT | CGGGTGAGGC | GAGGTACTAC |
| TAR15-26-543 | CCAGGGAAGG | GTCTAGAGTG | GGTCTCAGAG | ATTTCGCCTT | CGGGTGAGAA | GCGGTACTAC |
| TAR15-26-544 | CCAGGGAAGG | GTCTAGAGTG | GGTCTCAGAG | ATTTCGCCTT | CGGGTGAGGA | GGAGTACTAC |
| TAR15-26-545 | CCAGGGAAGG | GTCTAGAGTG | GGTCTCAGAG | ATTTCGCCTT | CGGGTAAGAA | GACGTACTAC |
| TAR15-26-546 | CCAGGGAAGG | GTCTAGAGTG | GGTCTCAGAG | ATTTCGCCTT | CGGGTAAGAA | GAAGTACTAC |
| TAR15-26-547 | CCAGGGAAGG | GTCTAGAGTG | GGTCTCAGAG | ATTTCGCCTT | CGGGTGGGTA | TACATACTAC |
| TAR15-26-548 | CCAGGGAAGG | GTCTAGAGTG | GGTCTCAGAG | ATTTCGCCTT | CGGGTTCTTA | TACATACTAC |
| TAR15-26-549 | CCAGGGAAGG | GTCTAGAGTG | GGTCTCAGAG | ATTTCGCCTT | CGGGTCACAA | CAAGTACTAC |
| TAR15-26-550 | CCAGGGAAGG | GTCTAGAGTG | GGTCTCAGAG | ATTTCGCCTT | CGGGTTCTGA | GACATACTAC |
| TAR15-26-551 | CCAGGGAAGG | GTCTAGAGTG | GGTCTCAGAG | ATTTCGCCTT | CGGGTTCTCG | GACATACTAC |

| | ....\|....\| 185 | ....\|....\| 195 | ....\|....\| 205 | ....\|....\| 215 | ....\|....\| 225 | ....\|....\| 235 |
|---|---|---|---|---|---|---|
| TAR15-26 | GCAGACTCCG | TGAAGGGCCG | GTTCACCATC | TCCCGCGACA | ATTCCAAGAA | CACGCTGTAT |
| TAR15-26-500 | GCAGACTCCG | TGAAGGGCCG | GTTCACCATC | TCCCGCGACA | ATTCCAAGAA | CACGCTGTAT |
| TAR15-26-501 | GCAGACTCCG | TGAAGGGCCG | GTTCACCATC | TCCCGCGACA | ATTCCAAGAA | CACGCTGTAT |
| TAR15-26-502 | GCAGACTCCG | TGAAGGGCCG | GTTCACCATC | TCCCGCGACA | ATTCCAAGAA | CACGCTGTAT |
| TAR15-26-503 | GCAGACTCCG | TGAAGGGCCG | GTTCACCATC | TCCCGCGACA | ATTCCAAGAA | CACGCTGTAT |
| TAR15-26-504 | GCAGACTCCG | TGAAGGGCCG | GTTCACCATC | TCCCGCGACA | ATTCCAAGAA | CACGCTGTAT |
| TAR15-26-505 | GCAGACTCCG | TGAAGGGCCG | GTTCACCATC | TCCCGCGACA | ATTCCAAGAA | CACGCTGTAT |
| TAR15-26-506 | GCAGACTCCG | TGAAGGGCCG | GTTCACCATC | TCCCGCGACA | ATTCCAAGAA | CACGCTATAT |
| TAR15-26-507 | GCAGACTCCG | TGAAGGGCCG | GTTCACCATC | TCCCGCGACA | ATTCCAAGAA | CACGCTGTAT |
| TAR15-26-508 | GCAGACTCCG | TGAAGGGCCG | GTTCACCATC | TCCCGCGACA | ATTCCAAGAA | CACGCTGTAT |
| TAR15-26-509 | GCAGACTCCG | TGAAGGGCCG | GTTCACCATC | TCCCGCGACA | ATTCCAAGAA | CACGCTGTAT |

FIG. 4E

| | | | | | | |
|---|---|---|---|---|---|---|
| TAR15-26-510 | GCAGACTCCG | TGAAGGGCCG | GTTCACCATC | TCCCGCGACA | ATTCCAAGAA | CACGCTGTAT |
| TAR15-26-511 | GCAGACTCCG | TGAAGGGCCG | GTTCACCATC | TCCCGCGACA | ATTCCAAGAA | CACGCTGTAT |
| TAR15-26-512 | GCAGÀCTCCG | TGAAGGGCCG | GTTCACCATC | TCCCGCGACA | ATTCCAAGAA | CACGCTGTAT |
| TAR15-26-513 | GCAGACTCCG | TGAAGGGCCG | GTTCACCATC | TCCCGCGACA | ATTCCAAGAA | CACGCTGTAT |
| TAR15-26-514 | GCAGACTCCG | TGAAGGGCCG | GTTCACCATC | TCCCGCGACA | ATTCCAAGAA | CACGCTGTAT |
| TAR15-26-515 | GCAGACTCCG | TGAAGGGCCG | GTTCACCATC | TCCCGCGACA | ATTCCAAGAA | CGCGCTGTAT |
| TAR15-26-516 | GCAGACTCCG | TGAAGGGCCG | GTTCACCATC | TCCCGCGACA | ATTCCAAGAA | CACGCTGTAT |
| TAR15-26-517 | GCAGACTCCG | TGAAGGGCCG | GTTCACCATC | TCCCGCGACA | ATTCCAAGAA | CACGCTGTAT |
| TAR15-26-518 | GCAGACTCCG | TGAAGGGCCG | GTTCACCATC | TCCCGCGACA | ATTCCAAGAA | CACGCTGTAT |
| TAR15-26-519 | GCAGACTCCG | TGAAGGGCCG | GTTCACCATC | TCCCGCGACA | ATTCCAAGAA | CACGCTGTAT |
| TAR15-26-520 | GCAGACTCCG | TGAAGGGCCG | GTTCACCATC | TCCCGCGACA | ATTCCAAGAA | CACGCTGTAT |
| TAR15-26-521 | GCAGACTCCG | TGAAGGGCCG | GTTCACCATC | TCCCGCGACA | ATTCCAAGAA | CACGCTGTAT |
| TAR15-26-522 | GCAGACTCCG | TGAAGGGCCG | GTTCACCATC | TCCCGCGACA | ATTCCAAGAA | CACGCTGTAT |
| TAR15-26-523 | GCAGACTCCG | TGAAGGGCCG | GTTCACCATC | TCCCGCGACA | ATTCCAAGAA | CACGCTGTAT |
| TAR15-26-524 | GCAGACTCCG | TGAAGGGCCG | GTTCACCATC | TCCCGCGACA | ATTCCAAGAA | CACGCTGTAT |
| TAR15-26-525 | GCAGACTCCG | TGAAGGGCCG | GTTCACCATC | TCCCGCGACA | ATTCCAAGAA | CACGCTGTAT |
| TAR15-26-526 | GCAGACTCCG | TGAAGGGCCG | GTTCACCATC | TCCCGCGACA | ATTCCAAGAA | CACGCTGTAT |
| TAR15-26-527 | GCAGACTCCG | TGAAGGGCCG | GTTCACCATC | TCCCGCGACA | ATTCCAAGAA | CACGCTGTAT |
| TAR15-26-528 | GCAGACTCCG | TGAAGGGCCG | GTTCACCATC | TCCCGCGACA | ACTCCAAGAA | CACGCTGTAT |
| TAR15-26-529 | GCAGACTCCG | TGAAGGGCCG | GTTCACCATC | TCCCGCGACA | ATTCCAAGAA | CACGCTGTAT |
| TAR15-26-530 | GCAGACTCCG | TGAAGGGCCG | GTTCACCATC | TCCCGCGACA | ATTCCAAGAA | CACGCTGTAT |
| TAR15-26-531 | GCAGACTCCG | TGAAGGGCCG | GTTCACCATC | TCCCGCGACA | ATTCCAAGAA | CACGCTGTAT |
| TAR15-26-532 | GCAGACTCCG | TGAAGGGCCG | GTTCACCATC | TCCCGCGACA | ATTCCAAGAA | CACGCTGTAT |
| TAR15-26-533 | GCAGACTCCG | TGAAGGGCCG | GTTCACCATC | TCCCGCGACA | ATTCCAAGAA | CACGCTGTAT |
| TAR15-26-534 | GCAGACTCCG | TGAAGGGCCG | GTTCACCATC | TCCCGCGACA | ATTCCAAGAA | CACGCTGTAT |
| TAR15-26-535 | GCAAACTCCG | TGAAGGGCCG | GTTCACCATC | TCCCGCGACA | ATTCCAAGAA | CACGCTGTAT |
| TAR15-26-536 | GCAGACTCCG | TGAAGGGCCG | GTTCACCATC | TCCCGCGACA | ATTCCAAGAA | CACGCTGTAT |
| TAR15-26-537 | GCAGACTCCG | TGAAGGGCCG | GTTCACCATC | TCCCGCGACA | ATTCCAAGAA | CACGCTGTAT |
| TAR15-26-538 | GCAGACTCCG | TGAAGGGCCG | GTTCACCATC | TCCCGCGACA | ATTCCAAGAA | CACGCTGTAT |
| TAR15-26-539 | GCAGACTCCG | TGAAGGGCCG | GTTCACCATC | TCCCGCGACA | ATTCCAAGAA | CACGCTGTAT |
| TAR15-26-540 | GCAGACTCCG | TGAAGGGCCG | GTTCACCATC | TCCCGCGACA | ATTCCAAGAA | CACGCTGTAT |
| TAR15-26-541 | GCAGACTCCG | TGAAGGGCCG | GTTCACCATC | TCCCGCGACA | ATTCCAAGAA | CACGCTGTAT |
| TAR15-26-542 | GCAGACTCCG | TGAAGGGCCG | GTTCACCATC | TCCCGCGACA | ATTCCAAGAA | CACGCTGTAT |
| TAR15-26-543 | GCAGACTCCG | TGAAGGGCCG | GTTCACCATC | TCCCGCGACA | ATTCCAAGAA | CACGCTGTAT |
| TAR15-26-544 | GCAGACTCCG | TGCAGGGCCG | GTTCACCATC | TCCCGCGACA | ATTCCAAGAA | CACGCTGTAT |
| TAR15-26-545 | GCAGACTCCG | TGCAGGGCCG | GTTCACCATC | TCCCGCGACA | ATTCCAAGAA | CACGCTGTAT |

FIG. 4F

```
TAR15-26-546    GCAGACTCCG  TGAAGGGCCG  GTTCACCATC  TCCCGCGACA  ATTCCAAGAA  CACGCTGTAT
TAR15-26-547    GCAGACTCCG  TGAAGGGCCG  GTTCACCATC  TCCCGCGACA  ATTCCAAGAA  CACGCTGTAT
TAR15-26-548    GCAGACGAGG  TGAAGGGCCG  GTTCACCATC  TCCCGCGACA  ATTCCAAGAA  CACGCTGTAT
TAR15-26-549    GCAGACTCCG  TGAAGGGCCG  GTTCACCATC  TCCCGCGACA  ATTCCAAGAA  CACGCTGTAT
TAR15-26-550    GCAGACTCCG  TGAAGGGCCG  GTTCACCATC  TCCCGCGACA  ATTCCAAGAA  CACGCTGTAT
TAR15-26-551    GCAGACTCTG  TGAAGGGCCG  GTTCACCATC  TCCCGCGACA  ATTCCAAGAA  CACGCTGTAT

....|....|  ....|....|  ....|....|  ....|....|  ....|....|  ....|....|
                    245         255         265         275         285         295
TAR15-26        CTGCAAATGA  ACAGCCTGCG  TGCCGAGGAC  ACCGCGGTAT  ATTACTGTGC  GAAAGATCCT
TAR15-26-500    CTGCAAATGA  ACAGCCTGCG  TGCCGAGGAC  ACCGCGGTAT  ATTACTGTGC  GAAAGATCCT
TAR15-26-501    CTGCAAATGA  ACAGCCTGCG  TGCCGAGGAC  ACCGCGGTAT  ATTACTGTGC  GAAAGATCCT
TAR15-26-502    CTGCAAATGA  ACAGCCTGCG  TGCCGAGGAC  ACCGCGGTAT  ATTACTGTGC  GAAAGATCCT
TAR15-26-503    CTGCAAATGA  ACAGCCTGCG  TGCCGAGGAC  ACCGCGGTAT  ATTACTGTGC  GAAAGATCCT
TAR15-26-504    CTGCAAATGA  ACAGCCTGCG  TGCCGAGGAC  ACCGCGGTAT  ATTACTGTGC  GAAAGATCCT
TAR15-26-505    CTGCAAATGA  ACAGCCTGCG  TGCCGAGGAC  ACCGCGGTAT  ATTACTGTGC  GAAAGATCCT
TAR15-26-506    CTGCAAATGA  ACAGCCTGCG  TGCCGAGGAC  ACCGCGGTAT  ATTACTGTGC  GAAAGATCCT
TAR15-26-507    CTGCAAATGA  ACAGCCTGCG  TGCCGAGGAC  ACCGCGGTAT  ATTACTGTGC  GAAAGATCCT
TAR15-26-508    CTGCAAATGA  ACAGCCTGCG  TGCCGAGGAC  ACCGCGGTAT  ATTACTGTGC  GAAAGATCCT
TAR15-26-509    CTGCAAATGA  ACAGCCTGCG  TGCCGAGGAC  ACCGCGGTAT  ATTACTGTGC  GAAAGATCCT
TAR15-26-510    CTGCAAATGA  ACAGCCTGCG  TGCCGAGGAC  ACCGCGGTAT  ATTACTGTGC  GAAAGATCCT
TAR15-26-511    CTGCAAATGA  ACAGCCTGCG  TGCCGAGGAC  ACCGCGGTAT  ATTACTGTGC  GAAAGATCCT
TAR15-26-512    CTGCAAATGA  ACAGCCTGCG  TGCCGAGGAC  ACCGCGGTAT  ATTACTGTGC  GAAAGATCCT
TAR15-26-513    CTGCAAATGA  ACAGCCTGCG  TGCCGAGGAC  ACCGCGGTAT  ATTACTGTGC  GAAAGATCCT
TAR15-26-514    CTGCAAATGA  ACAGCCTGCG  TGCCGAGGAC  ACCGCGGTAT  ATTACTGTGC  GAAAGATCCT
TAR15-26-515    CTGCAAATGA  ACAGCCTGCG  TGCCGAGGAC  ACCGCGGTAT  ATTACTGTGC  GAAAGATCCT
TAR15-26-516    CTGCAAATGA  ACAGCCTGCG  TGCCGAGGAC  ACCGCGGTAT  ATTACTGTGC  GAAAGATCCT
TAR15-26-517    CTGCAAATGA  ACAGCCTGCG  TGCCGAGGAC  ACCGCGGTAT  ATTACTGTGC  GAAAGATCCT
TAR15-26-518    CTGCAAATGA  ACAGCCTGCG  TGCCGAGGAC  ACCGCGGTAT  ATTACTGTGC  GAAAGATCCT
TAR15-26-519    CTGCAAATGA  ACAGCCTGCG  TGCCGAGGAC  ACCGCGGTAT  ATTACTGTGC  GAAAGATCCT
TAR15-26-520    CTGCAAATGA  ACAGCCTGCG  TGCCGAGGAC  ACCGCGGTAT  ATTACTGTGC  GAAAGATCCT
TAR15-26-521    CTGCAAATGA  ACAGCCTGCG  TGCCGAGGAC  ACCGCGGTAT  ATTACTGTGC  GAAAGATCCT
TAR15-26-522    CTGCAAATGA  ACAGCCTGCG  TGCCGAGGAC  ACCGCGGTAT  ATTACTGTGC  GAAAGATCCT
TAR15-26-523    CTGCAAATGA  ACAGCCTGCG  TGCCGAGGAC  ACCGCGGTAT  ATTACTGTGC  GAAAGATCCT
TAR15-26-524    CTGCAAATGA  ACAGCCTGCG  TGCCGAGGAC  ACCGCGGTAT  ATTACTGTGC  GAAAGATCCT
TAR15-26-525    CTGCAAATGA  ACAGCCTGCG  TGCCGAGGAC  ACCGCGGTAT  ATTACTGTGC  GAAAGATCCT
```

FIG. 4G

| | | | | | | |
|---|---|---|---|---|---|---|
| TAR15-26-526 | CTGCAAATGA | ACAGCCTGCG | TGCCGAGGAC | ACCGCGGTAT | ATTACTGTGC | GAAAGATCCC |
| TAR15-26-527 | CTGCAAATGA | ACAGCCTGCG | TGCCGAGGAC | ACCGCGGTAT | ATTACTGTGC | GAAATCCCCC |
| TAR15-26-528 | CTGCAAATGA | ACAGCCTGCG | TGCCGAGGAC | ACCGCGGTAT | ATTACTGTGC | GAAAACCCCC |
| TAR15-26-529 | CTGCAAATGA | ACAGCCTGCG | TGCCGAGGAC | ACCGCGGTAT | ATTACTGTGC | GAAAGATCCT |
| TAR15-26-530 | CTGCAAATGA | ACAGCCTGCG | TGCCGAGGAC | ACCGCGGTAT | ATTACTGTGC | GAAAGATCCC |
| TAR15-26-531 | CTGCAAATGA | ACAGCCTGCG | TGCCGAGGAC | ACCGCGGTAT | ATTACTGTGC | GAAAGATCCC |
| TAR15-26-532 | CTGCAAATGA | ACAGCCTGCG | TGCCGAGGAC | ACCGCGGTAT | ATTACTGTGC | GAAAACCCCC |
| TAR15-26-533 | CTGCAAATGA | ACAGCCTGCG | TGCCGAGGAC | ACCGCGGTAT | ATTACTGTGC | GAAAGATTTC |
| TAR15-26-534 | CTGCAAATGA | ACAGCCTGCG | TGCCGAGGAC | ACCGCGGTAT | ATTACTGTGC | GAAAGATCCT |
| TAR15-26-535 | CTGCAAATGA | ACAGCCTGCG | TGCCGAGGAC | ACCGCGGTAT | ATTACTGTGC | GAAAACCCCC |
| TAR15-26-536 | CTGCAAATGA | ACAGCCTGCG | TGCCGAGGAC | ACCGCGGTAT | ATTACTGTGC | GAAATCCCCC |
| TAR15-26-537 | CTGCAAATGA | ACAGCCTGCG | TGCCGAGGAC | ACCGCGGTAT | ATTACTGTGC | GAAAGATCCC |
| TAR15-26-538 | CTGCAAATGA | ACAGCCTGCG | TGCCGAGGAC | ACCGCGGTAT | ATTACTGTGC | GAAAACCCCC |
| TAR15-26-539 | CTGCAAATGA | ACAGCCTGCG | TGCCGAGGAC | ACCGCGGTAT | ATTACTGTGC | GAAAGATCCT |
| TAR15-26-540 | CTGCAAATGA | ACAGCCTGCG | TGCCGAGGAC | ACCGCGGTAT | ATTACTGTGC | GAAAGATCCT |
| TAR15-26-541 | CTGCAAATGA | ACAGCCTGCG | TGCCGAGGAC | ACCGCGGTAT | ATTACTGTGC | GAAAGATCCC |
| TAR15-26-542 | CTGCAAATGA | ACAGCCTGCG | TGCCGAGGAC | ACCGCGGTAT | ATTACTGTGC | GAAAGATCCC |
| TAR15-26-543 | CTGCAAATGA | ACAGCCTGCG | TGCCGAGGAC | ACCGCGGTAT | ATTACTGTGC | GAAAGATCCC |
| TAR15-26-544 | CTGCAAATGA | ACAGCCTGCG | TGCCGAGGAC | ACCGCGGTAT | ATTACTGTGC | GAAAGATCCC |
| TAR15-26-545 | CTGCAAATGA | ACAGCCTGCG | TGCCGAGGAC | ACCGCGGTAT | ATTACTGTGC | GAAAGATCCC |
| TAR15-26-546 | CTGCAAATGA | ACAGCCTGCG | TGCCGAGGAC | ACCGCGGTAT | ATTACTGTGC | GAAAGATCCC |
| TAR15-26-547 | CTGCAAATGA | ACAGCCTGCG | TGCCGAGGAC | ACCGCGGTAT | ATTACTGTGC | GAAAGATCCT |
| TAR15-26-548 | CTGCAAATGA | ACAGCCTGCG | TGCCGAGGAC | ACCGCGGTAT | ATTACTGTGC | GAAAGATCCT |
| TAR15-26-549 | CTGCAAATGA | ACAGCCTGCG | TGCCGAGGAC | ACCGCGGTAT | ATTACTGTGC | GAAAGATCCC |
| TAR15-26-550 | CTGCAAATGA | ACAGCCTGCG | TGCCGAGGAC | ACCGCGGTAT | ATTACTGTGC | GAAAGATCCT |
| TAR15-26-551 | CTGCAAATGA | ACAGCCTGCG | TGCCGAGGAC | ACCGCGGTAT | ATTACTGTGC | GAAAGATCCT |

```
              ....|....|....|....|....|....|....|....|....|
                 305        315        325        335        345
TAR15-26      CGGAAGTTTG ACTACTGGGG TCAGGGAACC CTGGTCACCG TCTCGAGC
TAR15-26-500  CGGAAGTTTG ACTACTGGGG TCAGGGAACC CTGGTCACCG TCTCGAGC
TAR15-26-501  CGGAAGTTTG ACTACTGGGG TCAGGGAACC CTGGTCACCG TCTCGAGC
TAR15-26-502  CGGAAGTTTG ACTACTGGGG TCAGGGAACC CTGGTCACCG TCTCGAGC
TAR15-26-503  CGGAAGTTTG ACTACTGGGG TCAGGGAACC CTGGTCACCG TCTAAAGC
TAR15-26-504  CGGAAGTTTG ACTACTGGGG TCAGGGAACC CTGGTCACCG TCTAGAGC
TAR15-26-505  CGGAAGTTTG ACTACTGGGG TCAGGGAACC CTGGTCACCG TCTCGAGC
```

FIG. 4H

| | | | | | |
|---|---|---|---|---|---|
| TAR15-26-506 | CGGAAGTTTG | ACTACTGGGG | TCAGGGAACC | CTGGTCACCG | TCTCGAGC |
| TAR15-26-507 | CGGAAGTTTG | ACTACTGGGG | TCAGGGAACC | CTGGTCACCG | TCTCGAGC |
| TAR15-26-508 | CGGAAGTTTG | ACTACTGGGG | TCAGGGAACC | CTGGTCACCG | TCTCGAGC |
| TAR15-26-509 | CGGAAGTTTG | ACTACTGGGG | TCAGGGAACC | CTGGTCACCG | TCTCGAGC |
| TAR15-26-510 | CGGAAGTTTG | ACTACTGGGG | TCAGGGAACC | CTGGTCACCG | TCTCGAGC |
| TAR15-26-511 | CGGAAGTTTG | ACTACTGGGG | TCAGGGAACC | CTGGTCACCG | TCTCGAGC |
| TAR15-26-512 | CGGAAGTTTG | ACTACTGGGG | TCAGGGAACC | CTGGTCACCG | TCTCAAGC |
| TAR15-26-513 | CGGAAGTTTG | ACTACTGGGG | TCAGGGAACC | CTGGTCACCG | TCTCAAGC |
| TAR15-26-514 | CGGAAGTTTG | ACTACTGGGG | TCAGGGAACC | CTGGTCACCG | TCTCGAGC |
| TAR15-26-515 | CGGAAGTTTG | ACTACTGGGG | TCAGGGAACC | CTGGTCACCG | TCTCGAGC |
| TAR15-26-516 | CGGAAGTTTG | ACTACTGGGG | TCAGGGAACC | CTGGTCACCG | TCTCGAGC |
| TAR15-26-517 | CGGAAGTTTG | ACTACTGGGG | TCAGGGAACC | CTGGTCACCG | TCTCGAGC |
| TAR15-26-518 | CGGAAGTTTG | ACTACTGGGG | TCAGGGAACC | CTGGTCACCG | TCTCGAGC |
| TAR15-26-519 | CGGAAGTTTG | ACTACTGGGG | TCAGGGAACC | CTGGTCACCG | TCTCGAGC |
| TAR15-26-520 | CGGAAGTTTG | ACTACTGGGG | TCAGGGAACC | CTGGTCACCG | TCTAGAGC |
| TAR15-26-521 | CGGAAGTTTG | ACTACTGGGG | TCAGGGAACC | CTGGTCACCG | TCTCGAGC |
| TAR15-26-522 | CGGAAGTTTG | ACTACTGGGG | TCAGGGAACC | CTGGTCACCG | TCTCGAGC |
| TAR15-26-523 | CGGAAGTTTG | ACTACTGGGG | TCAGGGAACC | CTGGTCACCG | TCTCGAGC |
| TAR15-26-524 | CGGAAGTTTG | ACTACTGGGG | TCAGGGAACC | CTGGTCACCG | TCTCGAGC |
| TAR15-26-525 | CGGCCTTTG  | ACTACTGGGG | TCAGGGAACC | CTGGTCACCG | TCTCGAGC |
| TAR15-26-526 | CGCGCTTTG  | ACTACTGGGG | TCGGGGAACC | CTGGTCACCG | TCTCCAGC |
| TAR15-26-527 | CGCAAGTTTG | ACTACTGGGG | TCAGGGAACC | CTGGTCACCG | TCTCGAGC |
| TAR15-26-528 | CGCAAGTTTG | ACTACTGGGG | TCAGGGAACC | CTGGTCACCG | TCTCGAGC |
| TAR15-26-529 | CGGGAGTTTG | ACTACTGGGG | TCAGGGAACC | CTGGTCACCG | TCTCGAGC |
| TAR15-26-530 | CGGCGCTTTG | ACTACTGGGG | TCAGGGAACC | CTGGTCACCG | TCTCGAGC |
| TAR15-26-531 | CGCTTCTTTG | ACTACTGGGG | TCAGGGAACC | CTGGTCACCG | TCTCGAGC |
| TAR15-26-532 | ATCGAGTTTG | ACTACTGGGG | TCAGGGAACC | CTGGTCACCG | TCTCGAGC |
| TAR15-26-533 | TCGCAGTTTG | ACTACTGGGG | TCAGGGAACC | CTGGTCACCG | TCTCGAGC |
| TAR15-26-534 | CGGAAGTTTG | ACTACTGGGG | TCAGGGAACC | CTGGTCACCG | TCTCGAGC |
| TAR15-26-535 | CGCAAGTTTG | ACTACTGGGG | TCGGGGAACC | CTGGTCACCG | TCTCCAGC |
| TAR15-26-536 | CGCAAGTTTG | ACTACTGGGG | TCAGGGAACC | CTGGTCACCG | TCTCGAGC |
| TAR15-26-537 | CGCGCCTTTG | ACTACTGGGG | TCAGGGAACC | CTGGTCACCG | TCTCGAGC |
| TAR15-26-538 | CGCAAGTTTG | ACTACTGGGG | TCAGGGAACC | CTGGTCACCG | TCTCGAGC |
| TAR15-26-539 | CGGGAGTTTG | ACTACTGGGG | TCAGGGAACC | CTGGTCACCG | TCTCGAGC |
| TAR15-26-540 | CGGGCTTTG  | ACTACTGGGG | TCAGGGAACC | CTGGTCACCG | TCTCGAGC |
| TAR15-26-541 | CGGCGCTTTG | ACTACTGGGG | TCAGGGAACC | CTGGTCACCG | TCTCGAGC |

FIG. 4I

| | | | | |
|---|---|---|---|---|
| TAR15-26-542 | CGCGCCTTTG | ACTACTGGGG | TCAGGGAACC | CTGGTCACCG | TCTCGAGC |
| TAR15-26-543 | CGCGCCTTTG | ACTACTGGGG | TCAGGGAACC | CTGGTCACCG | TCTCGAGC |
| TAR15-26-544 | CGCGCCTTTG | ACTACTGGGG | TCAGGGAACC | CTGGTCACCG | TCTCGAGC |
| TAR15-26-545 | CGCGCCTTTG | ACTACTGGGG | TCAGGGAACC | CTGGTCACCG | TCTCGAGC |
| TAR15-26-546 | CGCGCCTTTG | ACTACTGGGG | TCAGGGAACC | CTGGTCACCG | TCTCGAGC |
| TAR15-26-547 | CGGAAGTTTG | ACTACTGGGG | TCAGGGAACC | CTGGTCACCG | TCTCGAGC |
| TAR15-26-548 | CGGAAGTTTG | ACTACTGGGG | TCAGGGAACC | CTGGTCACCG | TCTCGAGC |
| TAR15-26-549 | CGGAGTTTG | ACTACTGGGG | TCAGGGAACC | CTGGTCACCG | TCTCGAGC |
| TAR15-26-550 | CGGAAGTTTG | ACTACTGGGG | TCAGGGAACC | CTGGTCACCG | TCTCGAGC |
| TAR15-26-551 | CGGAAGTTTG | ACTACTGGGG | TCAGGGAACC | CTGGTCACCG | TCTCGAGC |

FIG. 4J

TAR15-1 (SEQ ID NO:100)
DIQMTQSPSSLSASVGDRVTITCRASQWIGPELSWYQQKPGKAPKLLIYHGSILQSG
V
PSRFSGSGSGTDFTLTISSLQPEDFATYYCQQRMYRPATFGQGTKVEIKR

TAR15-3 (SEQ ID NO:101)
DIQMTQSPSSLSASVGDRVTITCRASQWIGRELKWYQQKPGKAPRLLIYHGSVLQSG
VPSRFSGSGSGTDFTLTISSLQPEDFATYYCQQDFFVPDTFGQGTKVEIKR

TAR15-4 (SEQ ID NO:102)
DIQMTQSPSSLSASVGDRVTITCRASQDIANDLMWYQQKPGKAPKLLIYRNSRLQGG
VPSRFSGSGSGTDFTLTISSLQPEDFATYYCQQLVHRPYTIGQGTKVEIKR

TAR15-9 (SEQ ID NO:103)
DIQMTQSPSSLSASVGDRVTITCRASQFIGPHLTWYQQKPGKAPKLLIYHSSLLQSG
V
PSRFSGSGSGTDFTLTISSLQPEDFATYYCQQYMYYPSTFGQGTKVKIKR

TAR15-10 (SEQ ID NO:104)
DIQMTQSPSSLSASVGDRVTITCRASQWIGPELSWYQQKPGKAPKLLIYHTSILQSG
VP
SRFSGSGSGTDFTLTISSLQPEDFATYYCQQYMFQPRTFGQGTKVEIRR

TAR15-11 (SEQ ID NO:105)
DIQMIQSPSSLSASVGDRVTITCRASQFIGNELSWYQQKPGKAPKLLIYHASSLQSG
V
PSRFSGSGSGTDFTLTISSLQPEDFATYYCQQVLGYPYTFGQGTKVEIKR

TAR15-12 (SEQ ID NO:106)
DIQMTQSPSSLSASVGDRVTITCRASQWIGPELSWYQQKPGKAPKLLIYHGSILQSG
VPSRFSGSGSGTDFTLTISSLQPEDFATYYCQQVLYSPLTFGQGTKVEIKR

TAR15-13 (SEQ ID NO:107)
DIQMTQSPSSLSASVGDRVTITCRASQWIGNELKWYQQKPGKAPKLLIYMSSLLQSG
VPSRFSGSGSGTDFTLTISSLQPEDLATYYCQQTLLLPFTFGQGTKVEIKR

TAR15-14 (SEQ ID NO:108)
DIQMTQSPSSLSASVGDRVTITCRASQWIGPELSWYQQKPGKAPKLLIYHGSILQSG
VPSRFSGSGSGTDFTLTISSLQPEDFATYYCQQRLYYPGTFGQGTKVEIKR

TAR15-15 (SEQ ID NO:109)
DIQMTQSPSSLSASVGDRVTITCRASQSIGRELSWYQQKPGKAPMLLIYHSSNLQSG
VPSRFSGSGSGTDFTLTISSLQPEDFATYYCQQGMYWPYTFGQGTKVEIKR

TAR15-16 (SEQ ID NO:110)
DIQMTQSPSSLSASVGDRVTITCRASQWIKPALHWYQQKPGKAPKLLIYHGSILQSG
V
PSRFSGSGSGTDFTLTISSLQPEDFATYYCQQTLFMPYTFGQGTKVEIKR

FIG. 5A

TAR15-17 (SEQ ID NO:111)
DIQMTQSPSSLSASVGDRVTITCRASQSISTALLWYQQKPGKAPKLLIYNGSMLPNGVP
SRFSGSGSGTDFTLTISSLQPEDFATYYCQQTWDTPMTFGQGTKVEIKR

TAR15-18 (SEQ ID NO:112)
DIQMTQSPSSLSASVGDRVTITCRASQWIGHDLSWYQQKPGKAPKLLIYHSSSLQSGV
PSRFSGSGSGTDFTLTISSLQPEDVATYYCQQLMGYPFTFGQGTKVEIKR

TAR15-19 (SEQ ID NO:113)
DIQMTQSPSSLSASVGDRVTITCRASQDIGGLLVWYQQKPGKAPKLLIYRSSYLQSGV
PSRFSGSGSGTDFTLTISSLQPEDFATYYCQQTWGIPHTFGQGTKVEIKR

TAR15-20 (SEQ ID NO:114)
DIQMTQSPSSLSASVGDRVTITCRASQKIFNGLSWYQQKPGKAPKLLIYHSSTLQSGVP
SRFSGSGSGTDFTLTISSLQPEDFATYYCQQVLLYPYTFGQGTKVEIKR

TAR 15-22 (SEQ ID NO:115)
DIQMTQSPSSLSASVGDRVTITCRASQSIGTNLSWYQQKPGKAPRLLIYRTSMLQSG
VPSRFSGSGSGTDFTLTISSLQPEDFATYYCQQQFFWPHTFGQGTKVEIKR

TAR15-5 (SEQ ID NO:116)
EVQLLESGGGLVQPGGSLRLSCAASGFTFRLYDMVWVRQAPGKGLEWVSYISSGGSG
TYYADSVKGRFTISRDNSKNTLYLQMNSLRAEDTAVYYCAKAGGRASFDYWGQGTLV
TVSS

TAR15-6_ (SEQ ID NO:117)
EVQLLESGGGLVQPGGSLRLSCAASGFTFHLYDMMWVRQAPGKGLEWVSFIGGDGLN
TYYADSVKGRFTISRDNSKNTLYLQMNSLRAEDTAVYYCAKAGTQFDYWGQGTLVTV
SS

TAR15-7 (SEQ ID NO:118)
EVQLLESGGGLVQPGGSLRLSCAASGFTFNKYPMMWVRQAPGKGLEWVSEISPSGQD
TYYADSVKGRFTISRDNSKNTLYLQMNSLRAEDTAVYYCAKNPQILSNFDYWGQGTL
VTVSS

TAR15-8 (SEQ ID NO:119)
EVQLLESGGGLVQPGGSLRLSCAASGFTFQWYPMWWVRQAPGKGLEWVSLIEGQGDR
TYYADSVKGRFTISRDNSKNTLYLQMNSLRAEDTAVYYCAKAGDRTAGSRGNSFDYW
GQGTLVTVSS

TAR15-23 (SEQ ID NO:120)
EVQLLESGGGLVQPGGSLRLSCAASGFTFKAYEMGWVRQAPGKGLEWVSGISPNGGW
TYYADSVKGRFTISRDNSKNTLYLQMNSLRAEDTAVYYCAKESISPTPLGFDYWGQG
TLVTVSS

FIG. 5B

TAR15-24 (SEQ ID NO:121)
EVQLLESGGGLVQPGGSLRLSCAASGFTFTGYEMGWVRQAPGKGLEWVSYISRGGRW
TYYADSVKGRFTISRDNSKNTLYLQMNSLRAEDTAVYYCAKSDTMFDYWGQGTLVTV
SS

TAR15-25 (SEQ ID NO:122)
EVQLLESGGGLVQPGGSLRLSCAASGFTFSAYEMGWVRQAPGKGLEWVSFISGGGRW
TYYADSVKGRFTISRDNSKNTLYLQMNSLRAEDTAVYYCAKYSEDFDYWGQGTLVTV
SS

TAR15-26 (SEQ ID NO:123)
EVQLLESGGGLVQPGGSLRLSCAASGFTFGAYPMMWVRQAPGKGLEWVSEISPSGSY
TYYADSVKGRFTISRDNSKNTLYLQMNSLRAEDTAVYYCAKDPRKFDYWGQGTLVTV
SS

TAR15-27 (SEQ ID NO:124)
EVQLLESGGGLVQPGGSLRLSCAASGFTFQFYKMGWVRQAPGKGLEWVSSISSVGDA
TYYADSVKGRFTISRDNSKNTLYLQMNSLRAEDTAVYYCAKMGGGPPTYVVYFDYWG
QGTLVTVSS

TAR15-29 (SEQ ID NO:125)
EVQLLESGGGLVQPGGSLRLSCAASGFTFGEYGMYWVRQAPGKGLEWVSSISERGRL
TYYADSVKGRFTISRDNSKNTLYLQMNNLRAEDTAVYYCAKSALSSEGFSRSFDYWG
QGTLVTVSS

TAR15-30 (SEQ ID NO:126)
EVQLLESGGGLVQPGGSLRLSCAASGFTFSDYAMYWVRQAPGKGLEWVSSITARGFI
TYYADSVKGRFTISRDNSKNTLYLQMNSLRAEDTAVYYCAKSGFPHKSGSNYFDYWG
QGTLVTVSS

FIG. 5C

| | | | | | | |
|---|---|---|---|---|---|---|
| TAR15-6     | EVQLLESGGG | LVQPGGSLRL | SCAASGFTFH | LYDMMWVRQA | PGKGLEWVSF | IGGDGLNTYY |
| TAR15-6-500 | EVQLLESGGG | LVQPGGSLRL | SCAASGFTFR | LYDMMWVRQA | PGKGLEWVSF | IGGDGLNTYY |
| TAR15-6-501 | EVQLLESGGG | LVQPGGSLRL | SCAASGFTFS | FFDMMWVRQA | PGKGLEWVSF | IGGDGLNTYY |
| TAR15-6-502 | EVQLLESGGG | LVQPGGSLRL | SCAASGFTFM | LFDMMWVRQA | PGKGLEWVSF | IGGDGLNTYY |
| TAR15-6-503 | EVQLLESGGG | LVQPGGSLRL | SCAASGFTFP | LYDMMWVRQA | PGKGLEWVSF | IGGDGLNTYY |
| TAR15-6-504 | EVQLLESGGG | LVQPGGSLRL | SCAASGFTFP | LYDMMWVRQA | PGKGLEWVSF | IGGDGLNTYY |
| TAR15-6-505 | EVQLLESGGG | LVQPGGSLRL | SCAASGFTFQ | YFDMMWVRQA | PGKGLEWVSF | IGGDGLNTYY |
| TAR15-6-506 | EVQLLESGGG | LVQPGGSLRL | SCAASGFTFH | LYDMMWVRQA | PGKGLEWVSF | IGGDGLNTYY |
| TAR15-6-507 | EVQLLESGGG | LVQPGGSLRL | SCAASGFTFH | LYDMMWVRQA | PGKGLEWVSF | IGGDGLNTYY |
| TAR15-6-508 | EVQLLESGGG | LVQPGGSLRL | SCAASGFTFH | LYDMMWVRQA | PGKGLEWVSF | IGGDGLNTYY |
| TAR15-6-509 | EVQLLESGGG | LVQPGGSLRL | SCAASGFTFH | LYDMMWVRQA | PGKGLEWVSF | IGGDGLNTYY |
| TAR15-6-510 | EVQLLESGGG | LVQPGGSLRL | SCAASGFTFH | LYDMMWVRQA | PGKGLEWVSF | IGGDGLNTYY |

| | | | | | | |
|---|---|---|---|---|---|---|
| TAR15-6     | ADSVKGRFTI | SRDNSKNTLY | LQMNSLRAED | TAVYYCAKAG | TQFDYWGQGT | LVTVSS |
| TAR15-6-500 | ADSVKGRFTI | SRDNSKNTLY | LQMNSLRAED | TAVYYCAKDP | RKFDYWGQGT | LVTVSS |
| TAR15-6-501 | ADSVKGRFTI | SRDNSKNTLY | LQMNSLRAED | TAVYYCAKAG | TQFDYWGQGT | LVTVSS |
| TAR15-6-502 | ADSVKGRFTI | SRDNSKNTLY | LQMNSLRAED | TAVYYCAKAG | TQFDYWGQGT | LVTVSS |
| TAR15-6-503 | ADSVKGRFTI | SRDNSKNTLY | LQMNSLRAED | TAVYYCAKAG | TQFDYWGQGT | LVTVSS |
| TAR15-6-504 | ADSVKGRFTI | SRDNSKNTLY | LQMNSLRAED | TAVYYCAKAG | TQFDYWGQGT | LVTVSS |
| TAR15-6-505 | ADSVKGRFTI | SRDNSKNTLY | LQMNSLRAED | TAVYYCAKAG | TQFDYWGQGT | LVTVSS |
| TAR15-6-506 | ADSVKGRFTI | SRDNSKNTLY | LQMNSLRAED | TAVYYCAKSP | RQFDYWGQGT | LVTVSS |
| TAR15-6-507 | ADSVKGRFTI | SRDNSKNTLY | LQMNSLRAED | TAVYYCAKNP | RQFDYWGQGT | LVTVSS |
| TAR15-6-508 | ADSVKGRFTI | SRDNSKNTLY | LQMNSLRAED | TAVYYCAKAG | MQFDYWGQGT | LVTVSS |
| TAR15-6-509 | ADSVKGRFTI | SRDNSKNTLY | LQMNSLRAED | TAVYYCAKKS | RKFDYWGQGT | LVTVSS |
| TAR15-6-510 | ADSVKGRFTI | SRDNSKNTLY | LQMNSLRAED | TAVYYCAKDP | RKFDYWGQGT | LVTVSS |

FIG. 6

| | | | | | | |
|---|---|---|---|---|---|---|
| | ....\|....\| | ....\|....\| | ....\|....\| | ....\|....\| | ....\|....\| | ....\| |
| | 5 | 15 | 25 | 35 | 45 | 55 |
| TAR15-8     | EVQLLESGGG | LVQPGGSLRL | SCAASGFTFQ | WYPMWWVRQA | PGKGLEWVSL | IEGQGDRTYY |
| TAR15-8-500 | EVQLLESGGG | LVQPGGSLRL | SCAASGY~~  | ~~PMWWVRQA | PGKGPEWVSL | IEGQGDRTYY |
| TAR15-8-501 | EVQLLESGGG | LVQPGGSLRL | SCAASGFTFQ | WAPMPWVRQA | PGKGLEWVSL | IEGQGDRTYY |
| TAR15-8-502 | EVQLLESGGG | LVQPGGSLRL | SCAASGFTFQ | WPHMPWVRQA | PGKGLEWVSL | IEGQGDRTYY |
| TAR15-8-503 | EVQLLESGGG | LVQPGGSLRL | SCAASGFTFX | WPHMHWVRQA | PGKGLEWVSL | IEGQGDRTYY |
| TAR15-8-505 | EVQLLESGGG | LVQPGGSLRL | SCAASGFTFQ | WYPMWWVRQA | PGKGLEWVSL | IEGQGDRTYY |
| TAR15-8-506 | EVQLLESGGG | LVQPGGSLRL | SCAASGFTFQ | WYPMWWVRQA | PGKGLEWVSL | IEGQGDRTYY |
| TAR15-8-507 | EVQLLESGGG | LVQPGGSLRL | SCAASGFTFQ | WYPMWWVRQA | PGKGLEWVSL | IEGQGDRTYY |
| TAR15-8-508 | EVQLLESGGG | LVQPGGSLRL | SCAASGFTFQ | WYPMWWVRQA | PGKGLEWVSL | IEVQGDRTYY |
| TAR15-8-509 | EVQLLESGGG | LVQPGGSLRL | SCAASGFTFQ | WYPMWWVRQA | PGKGLEWVSL | IEGQGDRTYY |
| TAR15-8-510 | EVQLLESGGG | LVQPGGSLRL | SCAASGFTFQ | WYPMWWVRQA | PGKGLEWVSL | IEGQGDRTYY |
| TAR15-8-511 | EVQLLESGGG | LVQPGGSLRL | SCAASGFTFQ | WYPMWWVRQA | PGKGLEWVSL | IEGQGDRTYY |

| | | | | | | |
|---|---|---|---|---|---|---|
| | ....\|....\| | ....\|....\| | ....\|....\| | ....\|....\| | ....\|....\| | ....\| |
| | 65 | 75 | 85 | 95 | 105 | 115 |
| TAR15-8     | ADSVKGRFTI | SRDNSKNTLY | LQMNSLRAED | TAVYYCAKAG | DRTAGSRGNS | FDYWGQGTLV |
| TAR15-8-500 | ADSVKGRFTI | SRDNSKNTLY | LQMNSLRAED | TAVYYCAKAG | DRTAGSRGNS | FDYWGQGTLV |
| TAR15-8-501 | ADSVKGRFTI | SRDNSKNTLY | LQMNSLRAED | TAVYYCAKAG | DRTAGSRGNS | FDYWGQGTLV |
| TAR15-8-502 | ADSVKGRFTI | SRDNSKNTLY | LQMNSLRAED | TAVYYCAKAG | DRTAGSRGNS | FDYWGQGTLV |
| TAR15-8-503 | ADSVKGRFTI | SRDNSKNTLY | LQMNSLRAED | TAVYYCAKAG | DRTAGSRGNS | FDYWGQGTLV |
| TAR15-8-505 | ADSVKGRFTI | SRDNSKNTLY | LQMNSLRAED | TAVYYCAKAG | DRWLSRGNS  | FDYWGQGTLV |
| TAR15-8-506 | ADSVKGRFTI | SRDNSKNTLY | LQMNSLRAED | TAVYYCAKAG | DRRFLSRGNS | FDYWGQGTLV |
| TAR15-8-507 | ADSVKGRFTI | SRDNSKNTLY | LQMNSLRAED | TAVYYCAKAG | DRHRTSRGNS | FDYWGQGTLV |
| TAR15-8-508 | ADSVKGRFTI | SRDNSKNTLY | LQMNSLRAED | TAVYYCAKAG | PPFAGSRGNS | FDYWGQGTLV |
| TAR15-8-509 | ADSVKGRFTI | SRDNSKNTLY | LQMNSLRAED | TAVYYCAKAG | TNNAGSRGNS | FDYWGQGTLV |
| TAR15-8-510 | ADSVKGRFTI | SRDNSKNTLY | LQMNSLRAED | TAVYYCAKAG | DRTAQNSGNS | FDYWGRGTLV |
| TAR15-8-511 | ADSVKGRFTI | SRDNSKNTLY | LQMNSLRAED | TAVYYCAKAG | NSNAGSRGNS | FDYWGQGTLV |

| | |
|---|---|
| TAR15-8 | ⋮ |
| TAR15-8-500 | TVSS |
| TAR15-8-501 | TVSS |
| TAR15-8-502 | TVSS |
| TAR15-8-503 | TVSS |
| TAR15-8-505 | TVSS |
| TAR15-8-506 | TVSS |
| TAR15-8-507 | TVSS |
| TAR15-8-508 | TVSS |
| TAR15-8-509 | TVSS |
| TAR15-8-510 | TVSS |
| TAR15-8-511 | TVSS |

```
            |....|....|....|....|....|....|....|....|....|....|....|....|
                 5         15        25        35        45        55
TAR15-26     EVQLLESGGG LVQPGGSLRL SCAASGFTFG AYPMMWVRQA PGKGLEWVSE ISPSGSYTYY
TAR15-26-500 EVQLLESGGG LVQPGGSLRL SCAASGFTFP AYPMMWVRQA PGKGLEWVSE ISPSGSYTYY
TAR15-26-501 EVQLLESGGG LVQPGGSLRL SCAASGFTFK AYPIMWVRQA PGKGLEWVSE ISPSGSYTYY
TAR15-26-502 EVQLLESGGG LVQPGGSLRL SCAASGFTFT AYPMMWVRQA PGKGLEWVSE ISPSGSYTYY
TAR15-26-503 EVQLLESGGG LVQPGGSLRL SCAASGFTFG WYPMMWVRQA PGKGLEWVSE ISPSGSYTYY
TAR15-26-504 EVQLLESGGG LVQPGGSLRL SCAASGFTFG LYPMMWVRQA PGKGLEWVSE ISPSGSYTYY
TAR15-26-505 EVQLLESGGG LVQPGGSLRL SCAASGFTFL AYPMMWVRQA PGKGLEWVSE ISPSGSYTYY
TAR15-26-506 EVQLLESGGG LVQPGGSLRL SCAASGFTFG RYPMMWVRQA PGKGLEWVSE ISPSGSYTYY
TAR15-26-507 EVQLLESGGG LVQPGGSLRL SCAASGFTFG AFPMMWVRQA PGKGLEWVSE ISPSGSYTYY
TAR15-26-508 EVQLLESGGG LVQPGGSLRL SCAASGFTFG AYPMLWVRQA PGKGLEWVSE ISPSGSYTYY
TAR15-26-509 EVQLLESGGG LVQPGGSLRL SCAASGFTFS LFPMMWVRQA PGKGLEWVSE ISPSGSYTYY
TAR15-26-510 EVQLLESGGG LVQPGGSLRL SCAASGFTFF LFPMMWVRQA PGKGLEWVSE ISPSGSYTYY
TAR15-26-511 EVQLLESGGG LVQPGGSLRL SCAASGFTFS YFPMMWVRQA PGKGLEWVSE ISPSGSYTYY
TAR15-26-512 EVQLLESGGG LVQPGGSLRL SCAASGFTFA FAPMMWVRQA PGKGLEWVSE ISPSGSYTYY
TAR15-26-513 EVQLLESGGG LVQPGGSLRL SCAASGFTFA PYPMMWVRQA PGKGLEWVSE ISPSGSYTYY
TAR15-26-514 EVQLLESGGG LVQPGGSLRL SCAASGFTFT SHPMMWVRQA PGKGLEWVSE ISPSGSYTYY
TAR15-26-515 EVQLLESGGG LVQPGGSLRL SCAASGFTFT SHPMMWVRQA PGKGLEWVSE ISPSGSYTYY
TAR15-26-516 EVQLLESGGG LVQPGGSLRL SCAASGFTFH AYPMMWVRQA PGKGLEWVSE ISPSGSYTYY
TAR15-26-517 EVQLLESGGG LVQPGGSLRL SCAASGFTFR AYPMMWVRQA PGKGLEWVSE ISPSGSYTYY
TAR15-26-518 EVQLLESGGG LVQPGGSLRL SCAASGFTFL AYPMMWVRQA PGKGLEWVSE ISPSGSYTYY
TAR15-26-519 EVQLLESGGG LVQPGGSLRL SCAASGFTFL AYPMMWVRQA PGKGLEWVSE ISPSGSYTYY
TAR15-26-520 EVQLLESGGG LVQPGGSLRL SCAASGFTFW AYPMMWVRQA PGKGLEWVSE ISPSGSYTYY
TAR15-26-521 EVQQLESGGG LVQPGGSLRL SCAASGFTFQ AYPMMWVRQA PGKGLEWVSE ISPSGSYTYY
TAR15-26-522 EVQLLESGGG LVQPGGSLRL SCAASGFTFG HYPMMWVRQA PGKGLEWVSE ISPSGSYTYY
TAR15-26-523 EVQLLESGGG LVQPGGSLRL SCAASGFTFG LYPMMWVRQA PGKGLEWVSE ISPSGSYTYY
TAR15-26-524 EVQLLESGGG LVQPGGSLRL SCAASGFTFG WYPMMWVRQA PGKGLEWVSE ISPSGSYTYY
TAR15-26-525 EVQLLESGGG LVQPGGSLRL SCAASGFTFG AFPMMWVRQA PGKGLEWVSE ISPSGSYTYY
```

FIG. 8A

| | | | | | | |
|---|---|---|---|---|---|---|
| TAR15-26-526 | EVQLLESGGG | LVQPGGSLRL | SCAASGFTFK | AYPIMWVRQA | PGKGLEWVSE | ISPSGSYTYY |
| TAR15-26-527 | EVQLLESGGG | LVQPGGSLRL | SCAASGFTFK | AYPIMWVRQA | PGKGLEWVSE | ISPSGSYTYY |
| TAR15-26-528 | EVQLLESGGG | LVQPGGSLRL | SCAASGFTFK | AYPIMWVRQA | PGKGLEWVSE | ISPSGSYTYY |
| TAR15-26-529 | EVQLLESGGG | LVQPGGSLRL | SCAASGFTFK | AYPIMWVRQA | PGKGLEWVSE | ISPSGSYTYY |
| TAR15-26-530 | EVQLLESGGG | LVQPGGSLRL | SCAASGFTFK | AYPIMWVRQA | PGKGLEWVSE | ISPSGSYTYY |
| TAR15-26-531 | EVQLLESGGG | LVQPGGSLRL | SCAASGFTFK | AYPIMWVRQA | PGKGLEWVSE | ISPSGSYTYY |
| TAR15-26-532 | EVQLLESGGG | LVQPGGSLRL | SCAASGFTFK | AYPIMWVRQA | PGKGLEWVSE | ISPSGSYTYY |
| TAR15-26-533 | EVQLLESGGG | LVQPGGSLRL | SCAASGFTFK | AYPIMWVRQA | PGKGLEWVSE | ISPSGSHTYY |
| TAR15-26-534 | EVQLLESGGG | LVQPGGSLRL | SCAASGFTFK | AYPILWVRQA | PGKGLEWVSE | ISPSGSYTYY |
| TAR15-26-535 | EVQLLESGGG | LVQPGGSLRL | SCAASGFTFK | AYPIMWVRQA | PGKGLEWVSE | ISPSGKMKYY |
| TAR15-26-536 | EVQLLESGGG | LVQPGGSLRL | SCAASGFTFK | AYPIMWVRQA | PGKGLEWVSE | ISPTGSYTYY |
| TAR15-26-537 | EVQLLESGGG | LVQPGGSLRL | SCAASGFTFK | AYPIMWVRQA | PGKGLEWVSE | ISPSGSYTYY |
| TAR15-26-538 | EVQLLESGGG | LVQPGGSLRL | SCAASGFTFK | AYPIMWVRQA | PGKGLEWVSE | ISPSGQMRYY |
| TAR15-26-539 | EVQLLESGGG | LVQPGGSLRL | SCAASGFTFK | AYPIMWVRQA | PGKGLEWVSE | ISPSGRSRYY |
| TAR15-26-540 | EVQLLESGGG | LVQPGGSLRL | SCAASGFTFK | AYPIMWVRQA | PGKGLEWVSE | ISPSGRYSYY |
| TAR15-26-541 | EVQLLESGGG | LVQPGGSLRL | SCAASGFTFK | AYPIMWVRQA | PGKGLEWVSE | ISPSGEARYY |
| TAR15-26-542 | EVQLLESGGG | LVQPGGSLRL | SCAASGFTFR | AYPIMWVRQA | PGKGLEWVSE | ISPSGEKRYY |
| TAR15-26-543 | EVQLLESGGG | LVQPGGSLRL | SCAASGFTFK | AYPIMWVRQA | PGKGLEWVSE | ISPSGEEEYY |
| TAR15-26-544 | EVQLLESGGG | LVQPGGSLRL | SCAASGFTFK | AYPIMWVRQA | PGKGLEWVSE | ISPSGKKTYY |
| TAR15-26-545 | EVQLLESGGG | LVQPGGSLRL | SCAASGFTFK | AYPIMWVRQA | PGKGLEWVSE | ISPSGKKKYY |
| TAR15-26-546 | EVQLLESGGG | LVQPGGSLRL | SCAASGFTFK | AYPIMWVRQA | PGKGLEWVSE | ISPSGGYTYY |
| TAR15-26-547 | EVQLLESGGG | LVQPGGSLRL | SCAASGFTFK | AYPIMWVRQA | PGKGLEWVSE | ISPSGSYTYY |
| TAR15-26-548 | EVQLLESGGG | LVQPGGSLRL | SCAASGFTFK | AYPIMWVRQA | PGKGLEWVSE | ISPSGHNKYY |
| TAR15-26-549 | EVQLLESGGG | LVQPGGSLRL | SCAASGFTFK | AYPIMWVRQA | PGKGLEWVSE | ISPSGHNKYY |
| TAR15-26-550 | EVQLLESGGG | LVQPGGSLRL | SCAASGFTFK | AYPIMWVRQA | PGKGLEWVSE | ISPSGSETYY |
| TAR15-26-551 | EVQLLESGGG | LVQPGGSLRL | SCAASGFTFK | AYPIMWVRQA | PGKGLEWVSE | ISPSGSRTYY |

FIG. 8B

| | 65 | 75 | 85 | 95 | 105 | 115 |
|---|---|---|---|---|---|---|
| TAR15-26 | ADSVKGRFTI | SRDNSKNTLY | LQMNSLRAED | TAVYYCAKDP | RKFDYWGQGT | LVTVSS |
| TAR15-26-500 | ADSVKGRFTI | SRDNSKNTLY | LQMNSLRAED | TAVYYCAKDP | RKFDYWGQGT | LVTVSS |
| TAR15-26-501 | ADSVKGRFTI | SRDNSKNTLY | LQMNSLRAED | TAVYYCAKDP | RKFDYWGQGT | LVTVSS |
| TAR15-26-502 | ADSVKGRFTI | SRDNSKNTLY | LQMNSLRAED | TAVYYCAKDP | RKFDYWGQGT | LVTV |
| TAR15-26-503 | ADSVKGRFTI | SRDNSKNTLY | LQMNSLRAED | TAVYYCAKDP | RKFDYWGQGT | LVTVSS |
| TAR15-26-504 | ADSVKGRFTI | SRDNSKNTLY | LQMNSLRAED | TAVYYCAKDP | RKFDYWGQGT | LVTV |
| TAR15-26-505 | ADSVKGRFTI | SRDNSKNTLY | LQMNSLRAED | TAVYYCAKDP | RKFDYWGQGT | LVTVSS |
| TAR15-26-506 | ADSVKGRFTI | SRDNSKNTLY | LQMNSLRAED | TAVYYCAKDP | RKFDYWGQGT | LVTVSS |
| TAR15-26-507 | ADSVKGRFTI | SRDNSKNTLY | LQMNSLRAED | TAVYYCAKDP | RKFDYWGQGT | LVTVSS |
| TAR15-26-508 | ADSVKGRFTI | SRDNSKNTLY | LQMNSLRAED | TAVYYCAKDP | RKFDYWGQGT | LVTVSS |
| TAR15-26-509 | ADSVKGRFTI | SRDNSKNTLY | LQMNSLRAED | TAVYYCAKDP | RKFDYWGQGT | LVTVSS |
| TAR15-26-510 | ADSVKGRFTI | SRDNSKNTLY | LQMNSLRAED | TAVYYCAKDP | RKFDYWGQGT | LVTVSS |
| TAR15-26-511 | ADSVKGRFTI | SRDNSKNTLY | LQMNSLRAED | TAVYYCAKDP | RKFDYWGQGT | LVTVSS |
| TAR15-26-512 | ADSVKGRFTI | SRDNSKNTLY | LQMNSLRAED | TAVYYCAKDP | RKFDYWGQGT | LVTVSS |
| TAR15-26-513 | ADSVKGRFTI | SRDNSKNTLY | LQMNSLRAED | TAVYYCAKDP | RKFDYWGQGT | LVTVSS |
| TAR15-26-514 | ADSVKGRFTI | SRDNSKNTLY | LQMNSLRAED | TAVYYCAKDP | RKFDYWGQGT | LVTVSS |
| TAR15-26-515 | ADSVKGRFTI | SRDNSKNALY | LQMNSLRAED | TAVYYCAKDP | RKFDYWGQGT | LVTVSS |
| TAR15-26-516 | ADSVKGRFTI | SRDNSKNTLY | LQMNSLRAED | TAVYYCAKDP | RKFDYWGQGT | LVTVSS |
| TAR15-26-517 | ADSVKGRFTI | SRDNSKNTLY | LQMNSLRAED | TAVYYCAKDP | RKFDYWGQGT | LVTVSS |
| TAR15-26-518 | ADSVKGRFTI | SRDNSKNTLY | LQMNSLRAED | TAVYYCAKDP | RKFDYWGQGT | LVTVSS |
| TAR15-26-519 | ADSVKGRFTI | SRDNSKNTLY | LQMNSLRAED | TAVYYCAKDP | RKFDYWGQGT | LVTVSS |
| TAR15-26-520 | ADSVKGRFTI | SRDNSKNTLY | LQMNSLRAED | TAVYYCAKDP | RKFDYWGQGT | LVTVSS |
| TAR15-26-521 | ADSVKGRFTI | SRDNSKNTLY | LQMNSLRAED | TAVYYCAKDP | RKFDYWGQGT | LVTV |
| TAR15-26-522 | ADSVKGRFTI | SRDNSKNTLY | LQMNSLRAED | TAVYYCAKDP | RKFDYWGQGT | LVTVSS |
| TAR15-26-523 | ADSVKGRFTI | SRDNSKNTLY | LQMNSLRAED | TAVYYCAKDP | RKFDYWGQGT | LVTVSS |
| TAR15-26-524 | ADSVKGRFTI | SRDNSKNTLY | LQMNSLRAED | TAVYYCAKDP | RKFDYWGQGT | LVTVSS |
| TAR15-26-525 | ADSVKGRFTI | SRDNSKNTLY | LQMNSLRAED | TAVYYCAKDP | RKFDYWGQGT | LVTVSS |

FIG. 8C

| | | | | | | |
|---|---|---|---|---|---|---|
| TAR15-26-526 | ADSVKGRFTI | SRDNSKNTLY | LQMNSLRAED | TAVYYCAKDP | RAFDYWGQGT | LVTVSS |
| TAR15-26-527 | ADSVKGRFTI | SRDNSKNTLY | LQMNSLRAED | TAVYYCAKSP | RKFDYWGQGT | LVTVSS |
| TAR15-26-528 | ADSVKGRFTI | SRDNSKNTLY | LQMNSLRAED | TAVYYCAKTP | RKFDYWGRGT | LVTVSS |
| TAR15-26-529 | ADSVKGRFTI | SRDNSKNTLY | LQMNSLRAED | TAVYYCAKDP | REFDYWGQGT | LVTVSS |
| TAR15-26-530 | ADSVKGRFTI | SRDNSKNTLY | LQMNSLRAED | TAVYYCAKDP | RRFDYWGQGT | LVTVSS |
| TAR15-26-531 | ADSVKGRFTI | SRDNSKNTLY | LQMNSLRAED | TAVYYCAKDP | RFFDYWGQGT | LVTVSS |
| TAR15-26-532 | ADSVKGRFTI | SRDNSKNTLY | LQMNSLRAED | TAVYYCAKTP | IKFDYWGQGT | LVTVSS |
| TAR15-26-533 | ADSVKGRFTI | SRDNSKNTLY | LQMNSLRAED | TAVYYCAKDF | SQFDYWGQGT | LVTVSS |
| TAR15-26-534 | ADSVKGRFTI | SRDNSKNTLY | LQMNSLRAED | TAVYYCAKDP | RKFDYWGQGT | LVTVSS |
| TAR15-26-535 | ADSVKGRFTI | SRDNSKNTLY | LQMNSLRAED | TAVYYCAKTP | RKFDYWGQGT | LVTVSS |
| TAR15-26-536 | ADSVKGRFTI | SRDNSKNTLY | LQMNSLRAED | TAVYYCAKSP | RKFDYWGQGT | LVTVSS |
| TAR15-26-537 | ANSVKGRFTI | SRDNSKNTLY | LQMNSLRAED | TAVYYCAKDP | RAFDYWGQGT | LVTVSS |
| TAR15-26-538 | ADSVKGRFTI | SRDNSKNTLY | LQMNSLRAED | TAVYYCAKTP | RKFDYWGQGT | LVTVSS |
| TAR15-26-539 | ADSVKGRFTI | SRDNSKNTLY | LQMNSLRAED | TAVYYCAKDP | REFDYWGQGT | LVTVSS |
| TAR15-26-540 | ADSVKGRFTI | SRDNSKNTLY | LQMNSLRAED | TAVYYCAKDP | REFDYWGQGT | LVTVSS |
| TAR15-26-541 | ADSVKGRFTI | SRDNSKNTLY | LQMNSLRAED | TAVYYCAKDP | RRFDYWGQGT | LVTVSS |
| TAR15-26-542 | ADSVKGRFTI | SRDNSKNTLY | LQMNSLRAED | TAVYYCAKDP | RAFDYWGQGT | LVTVSS |
| TAR15-26-543 | ADSVKGRFTI | SRDNSKNTLY | LQMNSLRAED | TAVYYCAKDP | RAFDYWGQGT | LVTVSS |
| TAR15-26-544 | ADSVQGRFTI | SRDNSKNTLY | LQMNSLRAED | TAVYYCAKDP | RAFDYWGQGT | LVTVSS |
| TAR15-26-545 | ADSVKGRFTI | SRDNSKNTLY | LQMNSLRAED | TAVYYCAKDP | RAFDYWGQGT | LVTVSS |
| TAR15-26-546 | ADSVKGRFTI | SRDNSKNTLY | LQMNSLRAED | TAVYYCAKDP | RKFDYWGQGT | LVTVSS |
| TAR15-26-547 | ADSVKGRFTI | SRDNSKNTLY | LQMNSLRAED | TAVYYCAKDP | RKFDYWGQGT | LVTVSS |
| TAR15-26-548 | ADEVKGRFTI | SRDNSKNTLY | LQMNSLRAED | TAVYYCAKDP | RRFDYWGQGT | LVTVSS |
| TAR15-26-549 | ADSVKGRFTI | SRDNSKNTLY | LQMNSLRAED | TAVYYCAKDP | RKFDYWGQGT | LVTVSS |
| TAR15-26-550 | ADSVKGRFTI | SRDNSKNTLY | LQMNSLRAED | TAVYYCAKDP | RKFDYWGQGT | LVTVSS |
| TAR15-26-551 | ADSVKGRFTI | SRDNSKNTLY | LQMNSLRAED | TAVYYCAKDP | RKFDYWGQGT | LVTVSS |

FIG. 8D

>DOM16-17 (SEQ ID NO:199)
GACATCCAGATGACCCAGTCTCCATCCTCCCTGTCTGCATCTGTAGGAGACCGTGTCACC
ATCACTTGCCGGGCAAGTCAGTATATTGGTGCGGAGTTATCCTGGTACCAGCAGAAACCA
GGGAAAGCCCCTAAGCTCCTGATCTATTGGATTTCCGAGTTGCAAAGTGGGGTCCCATCA
CGTTTCAGTGGCAGTGGATCTGGGACAGATTTCACTCTCACCATCAGCAGTCTGCAACCT
GAAGATTTTGCTACGTACTACTGTCAACAGTCTAGTAATACTCCTTATACGTTCGGCCAA
GGGACCAAGGTGGAGATCAAACGGGC
>DOM16-18 (SEQ ID NO:200)
GACATCCAGATGACCCAGTCTCCATCCTCCCTGTCTGCATCTGTAGGAGACCGTGTCACC
ATCACTTGCCGGGCAAGTCAGTATATTGGTATTAATTTAATTTGGTACCAGCAGAAACCA
GGGAAAGCCCCTAAGCTCCTGATCTATTGGGCTTCCGTTTTGCAAAGTGGGGTCCCATCA
CGTTTCAGTGGCAGTGGATCTGGGACAGATTTCACTCTCACCATCAGCAGTCTGCAACCT
GAAGATTTTGCTACGTACTACTGTCAACAGTCGGTGTATGATCCTCCTACGTACGGCCAA
GGGACCAAGGTGGAAATCAAACGGGC
>DOM16-19 (SEQ ID NO:201)
GACATCCAGATGACCCAGTCTCCATCCTCCCTGTCTGCATCTGTAGGAGACCGTGTCACC
ATCACTTGCCGGGCAAGTCAGGATATTTTTGGTTGTTATCTTGGTACCAGCAGAAACCA
GGGAAAGCCCCTACGCTCCTGATCTATTCTACTTCCATTTTGCAAAGTGGGGTCCCATCA
CGTTTCAGTGGCAGTGGATCTGGGACAGATTTCACTCTCACCATCAGCAGTCTGCAACCT
GAAGATTTTGCTACGTACTACTGTCAACAGTATTATCTTGATCCTCCTACGTTCAGCCAA
GGGACCAAGGTGGAAATCAAACGGGC
>DOM16-20 (SEQ ID NO:202)
GACATCCAGATGACCCAGTCTCCATCCTCCCTGTCTGCATCTGTAGGAGACCGTGTCACC
ATCACTTGCCGGGCAAGTCAGTTTATTGGTGTTAATTTAAATTGGTACCAGCAGAAACCA
GGGAAAGCCCCTAGGCTCCTGATCTATTTGTCGTCCATTCTGCAAAGTGGGGTCCCATCA
CGTTTCAGTGGCAGTGGATCTGGGACAGATTTCACTCTCACCATCAGCAGTCTGCAACCT
GAAGATTTTGCTACGTACTACTGTCAACAGACTTATGATATTCCTACTACGTTCGGCCAA
GGGACCAAGGTGGAAATCAAACGGGC
>DOM16-21 (SEQ ID NO:203)
GACATCCAGATGACCCAGTCTCCATCCTCCCTGTCTGCATCTGTAGGAGACCGTGTCACC
ATCACTTGCCGGGCAAGTCAGAACATTGGTATTAATTTGCAGTGGTATCAGCAGAAACCA
AGGAAAGCCCCTAAGCTCCTGATCTATTATGCTTCCATTTTGCAAAGTGGGGTCCCATCA
CGTTTCAGTGGCAGTGGATCTGGGACAGATTTCACTCTCACCATCAGCAGTCTGCAACCT
GAAGATTTTGCTACGTACTACTGTCAACAGGATTATGATACTCCTTTTACGTTCGGCCAA
GGGACCAAGGTGGAAATCAAACGGGC
>DOM16-22 (SEQ ID NO:204)
GACATCCAGATGACCCAGTTTCCATCCTCCCTGTCTGCATCTGTAGGAGACCGTGTCACC
ATCACTTGCCGGGCGAGTCAGCATATTGAGAGGTGGTTAAATTGGTATCAGCAGAAACCA
GGGAAAGCCCCTAAGCTCCTGATCTATCGTTCGTCCTATTTGCAAAGTGGGGTCCCATCA
CGTTTCAGTGGCAGTGGATCTGGGACAGATTTCACTCTCACCATCAGCAGTCTGCAACCT
GAAGATTTTGCTACGTACTACTGTCAACAGGATGCTATTCTTCCTCATACGTTCGGCCAA
GGGACCAAGGTGGAAATCAAACGGGC
>DOM16-23 (SEQ ID NO:205)
GACATCCAGATGACCCAGTCTCCATCCTCCCTGTCTGCATCTGTAGGAGACCGTGTCACC
ATCACTTGCCGGGCAAGTCAGGGGATTGGGGTGAATTTACAGTGGTACCAGCAGAAACCA
GGGAAAGCCCCTAAGCTCCTGATCTATTTTAGTTCCGTGTTGCAAAGTGGGGTCCCATCA
CGTTTCAGTGGCAGTGGATCTGGGACAGATTTCACTCTCACCATCAGCAGTCTGCAACCT
GAAGATTTTGCTACGTACTACTGTCAACAGGATTTTGATTTTCCTCAGACGTTCGGCCAA
GGGACCAAGGTGGAAATCAAACGGGC
>DOM16-24 (SEQ ID NO:206)
GACATCCAGATGACCCAGTCTCCATCCTCCCTGTCTGCATCTGTAGGAGACCGTGTCACC
ATCACTTGCCGGGCAAGTCAGAATATTGGTATTAATTTGCAGTGGTATCAGCAGAAACCA
AGGAAAGCCCCTAAGCTCCTGATCTATTATGCTTCCATTTTGCAAAGTGGGGTCCCATCA
CGTTTCAGTGGCAGTGGATCTGGGACAGATTTCACTCTCACCATCAGCAGTCTGCAACCT
GAAGATTTTGCTACGTACTACTGTCAACAGGAGTATGATTATCCTAATACGTTCGGCCAA
GGGACCAAGGTGGAAATCAAACGGGC
>DOM16-25 (SEQ ID NO:207)
GACATCCAGATGACCCAGTCTCCATCCTCCCTGTCTGCATCTGTAGGAGACCGTGTCACC
ATCACTTGCCGGGCAAGTAGTAGTATTGGGTCGGGGTTAGAGTGGTACCAGCAGAAACCA
GGGAAAGCCCCTAAGCTCCTGATCGTTGGGTGGTCCGGGTTGCAAAGTGGGGTCCCATCA

FIG. 9A

CGTTTCAGTGGCAGTGGATCTGGGACAGATTTCACTCTCACCATCAGCAGTCTGCAACCT
GAAGATTTTGCTACGTACTACTGTCGGCAGTGTGTGGGTTTGCCTTGTACGTTCGGCCAA
GGGACCAAGGTGGAAATCAAACGGGC
>DOM16-26 (SEQ ID NO:208)
GACATCCAGATGACCCAGTCTCCATCCTCCCTGTCTGCATCTGTAGGAGACCGTGTCACC
ATCACTTGCCGGGCAAGTCAGTGGATTGGGGTGGAGTTAAGTTGGTATCAGCAGAAACCA
GGGAAAGCCCCTAAGCTCCTGATCTATTGGGGTTCCGAGTTGCAAAGTGGGGTCCCATCA
CGTTTCAGTGGCAGTGGATCTGGGACAGATTTCACTCTCACCATCAGCAGTCTGCAACCT
GAAGATTTTGCTACGTACTACTGTCAACAGTTGGCGTTACCTCCTTTTACGTTCGGCCAA
GGGACCAAGGTGGAAATCAAACGGGC
>DOM16-27 (SEQ ID NO:209)
GACATCCAGATGACCCAGTCTCCATCCTCCCTGTCTGCATCTGTAGGAGACCGTGTCACC
ATCACTTGCCGGGCAAGTCATGATATTGGGGTGAGTTTAGATTGGTACCAGCAGAAACCA
GGGAAAGCCCCTAAGCTCCTGATCGTGTGGGCGTCCGTGTTGCAAAGTGGGGTCCCATCA
CGTTTCAGTGGCAGTGGATCTGGGACAGATTTCACTCTCACCATCAGCAGTCTGCAACCT
GAAGATTTTGCTACGTACTACTGTCTGCAGGTGGGTGCTGGGCCTATGACGTTCGGCCAA
GGGACCAAGGTGGAAATCAAACGGGC
>DOM16-28 (SEQ ID NO:210)
GACATCCAGATGACCCAGTCTCCATCCTCCCTGTCTGCATCTGTAGGAGACGGTGTCACC
ATCACTTGCCGGGCAAGTCAGTATATTGGTATTGATTTAGCGTGGTACCAGCGGAAACCA
GGGAAAGCCCCTAGGCTCCTGATCTATAAGGCTTCCGCTTTGCAAAGTGGGGTCCCATCA
CGTTTCAGTGGCAGTGGATCTGGGACAGATTTCACTCTCACCATCAGCAGTCTGCAACCT
GAAGATTTTGCTACGTACTACTGTCAACAGTATGCGGATTATCCTGCTACGTTCGGCCAA
GGGACCAAGGTGGAAATCAAACGGGC
>DOM16-29 (SEQ ID NO:211)
GACATCCAGATGACCCAGTCTCCATCCTCCCTGTCTGCATCTGTAGGAGACCGTGTCACC
ATCACTTGCCGGGCAAGTCAGGAGATTGAGCATTATTTATCTTGGTACCAGCAGAAACCA
GGGAAAGCCCCTAAGCTCCTGATCTATCTTTCGTCCCGTTTGCAAAGTGGGGTCCCATCA
CGTTTCAGTGGCAGTGGATCTGGGACAGATTTCACTCTCACCATCAGCAGTCTGCAACCC
GAAGATTTTGCTACGTACTACTGTCAACAGAATGTGCAGCTGCCTATTACGTTCGGCCAA
GGGACCAAGGTGGAAATCAAACGGGC
>DOM16-30 (SEQ ID NO:212)
GACATCCAGATGACCCAGTCTCCATCCTCCCTGTCTGCATCTGTAGGAGACCGTGTCACC
ATCACTTGCCGGGCAAGTCAGGAGATTGGTGTTAGTTTATCGTGGTACCAGCAGAAACCA
GGGAAAGCCCCTAAGCTCCTGATCTATTGGGGTTCCGAGTTGCAAAGTGGGGTCCCATCA
CGTTTCAGTGGCAGTGGATCTGGGACAGATTTCACTCTCACCATCAGCAGTCTGCAACCT
GAAGATTTTGCTACGTACTACTGTCAACAGGATCATAATTGGCCTATGACGTTCGGCCAA
GGGACCAAGGTGGAAATCAAACGGGC
>DOM16-31 (SEQ ID NO:213)
GACATCCAGATGACCCAGTCTCCATCCTCCCTGTCTGCATCTGTAGGAGACCGTGTCACC
ATCACTTGCCGGGCAAGTGCTCTTATTATGGGGATTTAGATTGGTACCAGCAGAAACCA
GGGAAAGCCCCTAAGCTCCTGATCGCGGGTGTGTCCTTTTTGCAAAGTGGGGTCCCATCA
CGTTTCAGTGGCAGTGGATCTGGGACAGATTTCACTCTCACCATCAGCAGTCTGCAACCT
GAAGATTTTGCTACGTACTACTGTGCTCAGTCTAGGTCGTGGCCTTATACGTTCGGCCAA
GGGACCAAGGTGGAAATCAAACGGGC
>DOM16-32 (SEQ ID NO:214)
GACATCCAGATGACCCAGTCTCCATCCTCCCTGTCTGCATCTGTAGGAGACCGTGTCACC
ATCACTTGCCGGGCAAGTAAGATGATTGATGAGAATTTAGCTTGGTACCAGCAGAAACCA
GGGAAAGCCCCTAAGCTCCTGATCCTTCGGAGTTCCGGGTTGCAAAGTGGGGTCCCATCA
CGTTTCAGTGGCAGTGGATCTGGGACAGATTTCACTCTCACCATCAGCAGTCTGCAACCT
GAAGATTTTGCTACGTACTACTGTCATCAGGGTCATTCTGCTCCTGGTACGTTCGGCCAA
GGGACCAAGGTGGAAATCAAACGGGC
>DOM16-33 (SEQ ID NO:215)
GACATCCAGATGACCCAGTCTCCATCCTCCCTGTCTGCATCTGTAGGAGACCGTGTCACC
ATCACTTGCCGGGCAAGTCGGTATATTGGGGTGTCTTTAGATTGGTACCAGCAGAAACCA
GGGAAAGCCCCTAAGCTCCTGATCATGTGGGGTTCCGCGTTGCAAAGTGGGGTCCCATCA
CGTTTCAGTGGCAGTGGATCTGGGACAGATTTCACTCTCACCATCAGCAGTCTGCAACCT
GAAGATTTTGCTACGTACTACTGTTTGCAGTCTGCGGCGCCGCCTGCGACGTTCGGCCAA
GGGACCAAGGTGGAAATCAAACGGGC
>DOM16-35 (SEQ ID NO:216)
GACATCCAGATGACCCAGTCTCCATCCTCCCTGTCTGCATCTGTAGGAGACCGTGTCACC

FIG. 9B

>DOM16-37 (SEQ ID NO:217)
GACATCCAGATGACCCAGTCTCCATCCTCCCTGTCTGCATCTGTAGGAGACCGTGTCACC
ATCACTTGCCGGGCAAGTCAGGAGATTGCTAGTGATTTACTTTGGTATCAGCAGAAACCA
GGGAAAGCCCCTAAGCTCCTGATCTATAATGGGTCCTCGTTGCAAAGTGGGGTCCCATCA
CGTTTCAGTGGCAGTGGATCTGGGACAGATTTCACTCTCACCATCAGCAGACTGCAACCT
GAAGATTTTGCTACGTACTACTGTCAATGGTTGTGGAGTGAGCCTTTGACGTTCGGCCAA
GGGACCAAGGTGGAAATCAAACGGGC
>DOM16-38 (SEQ ID NO:218)
GACATCCAGATGACCCAGTCTCCATCCTCCCTGTCTGCATCTGTAGGAGACCGTGTCACC
ATCACTTGCCGGGCAAGTCAGCATATTGGTGATGCGTTATGGTGGTATCAGCAGAAACCA
GGGAAAGCCCCTAAGCTCCTGATCTATTGGACTTCCAATTTGCAAAGTGGGGTCCCATCA
CGTTTCAGTGGCAGTGGATCTGGGACAGATTTCACTCTCACCATCAGCAGTCTGCAACCT
GAAGATTTTGCTACGTACTACTGTCAACAGACTATTCGTCGGCCTTATACGTTCGGCCAA
GGGACCAAGGTGAAAATCAAACGGGC
>DOM16-39 (SEQ ID NO:219)
GACATCCAGATGACCCAGTCTCCATCCTCCCTGTCTGCATCTGTAGGAGACCGTGTCACC
ATCACTTGCCGGGCAAGTCAGTGGATTGGTATTTTGTTAGATTGGTACCAGCAGAAACCA
GGGGAAGCCCCTAAGCTCCTGATCTATTATGCTTCCTTTTTGCAAAGTGGGGTCCCATCA
CGTTTCAGTGGCAGTGGATCTGGGACAGATTTCACTCTCACCATCAGCAGTCTGCAACCT
GAAGATTTTGCTACGTACTACTGTCAACAGGCTAATCCGGCGCCTCTGACGTTCGGCCAA
GGGACCAAGGTGGAAATCAAACGGGC
>DOM16-40 (SEQ ID NO:220)
GACATCCAGATGACCCAGTCTCCATCCTCCCTGTCTGCATCTGTAGGAGACCGTGTCACC
ATCACTTGCCGGGCAAGTCAGAATATTGGTATTAATTTGCAGTGGTATCAGCAGAAACCA
AGGAAAGCCCCTAAGCTCCTGATCTATTATGCTTCCATTTTGCAAAGTGGGGTCCCATCA
CGTTTCAGTGGCAGTGGATCTGGGACAGATTTCACTCTCACCATCAGCAGTCTGCAACCT
GAAGATTTTGCTACGTACTACTGTCAACAGTCTTATGATTTGCCTAAGACGTTCGGCCAA
GGGACCAAGGTGGAAATCAAACGGGC
>DOM16-41 (SEQ ID NO:221)
GACATCCAGATGATCCAGTCTCCATCCTCCCTGTCTGCATCTGTAGGAGACCGTGTCACC
ATCACTTGCCGGGCAAGTCAGGAGATTGGTGTTAGTTTATCGTGGTACCAGCAGAAACCA
GGGAAAGCCCCTAAGCTCCTGATCTATTGGGGTTCCGAGTTGCAAAGTGGGGTCCCATCA
CGTTTCAGTGGCAGTGGATCTGGGACAGATTTCACTCTCACCATCAGCAGTCTGCAACCT
GAAGATTTTGCTACGTACTACTGTCAACAGTGGTATGGTTGGCCTGATACGTTCGGCCAA
GGGACCAAGGTAGGAATCAAACGGGC
>DOM16-42 (SEQ ID NO:222)
GACATCCAGATGACCCAGTCTCCATCTTCCCTGTCTGCATCTGTAGGAGACCGTGTCACC
ATCACTTGCCGGGCAAGTCAGCATATTGGGATTGAGTTAAATTGGTATCAGCAGAAACCA
GGGAAAGCCCCTAAGCTCCTGATCTATTGGGCTTCCGTTTTGCAAAGTGGGGTCCCATCA
CGTTTCAGTGGCAGTGGATCTGGGACAGATTTCACTCTCACCATCAGCAGTCTGCAACCT
GAAGATTTCGCTACGTACTACTGTCAACAGAGTGTTTATGTTCCTACTACGTTCGGCCAA
GGGACCAAGGTGGAAATCAAACGGGC
>DOM16-43 (SEQ ID NO:223)
GACATCCAGATGACCCAGTCTCCATCCTCCCTGTCTGCATCTGTAGGAGACCGTGTCACC
ATCACTTGCCGGGCAAGTCAGTGGATTGGTGCGGAGTTAGTGTGGTATCAGCAGAAACCA
GGGAAAGCCCCTAAGCTCCTGATCTATTGGAGTTCCGTTTTGCAAAGTGGGGTCCCATCA
CGTTTCAGTGGCAGTGGATCTGGGACAGATTTCACTCTCACCATCAGCAGTCTGCAACCT
GAAGATTTTGCTACGTACTACTGTCAGCAGGCTGCTCATAGTCCTCCTACGTTCGGCCAA
GGGACCAAGGTGGAAATCAAACGGGC
>DOM16-44 (SEQ ID NO:224)
GACATCCAGATGACCCAGTCTCCATCCTCCCTGTCTGCATCTGTAGGAGACCGTGTCACC
ATCACTTGCCGGGCAAGTCAGGATATTAGTCGTAGTTTAGCTTGGTACCAGCGGAAACCA
GGGAAAGCCCCTAGGCTTCTGATCTATATGTCTTCCACTTTGCAAAGTGGGGTCCCATCA
CGTTTCAGTGGCAGTGGATCTGGGACAGATTTCACTCTCACCATCAGCAGTCTGCAACCT
GAAGATTTTGCTACGTACTACTGTCAACAGTATGATTCTTATCCTTCGACGTTCGGCCAA
GGGACCAAGGTGGAAATCAAACGGGC

FIG. 9C

>DOM16-45 (SEQ ID NO:225)
GACATCCAGATGACCCAGTCTCCATCCTCCCTGTCTGCATCTGTAGGAGACCGTGTCACC
ATCACTTGCCGGGCAAGTAGGATGATTGGGGGTATGTTACTTTGGTACCAGCAGAAACCA
GGGAAAGCCCCTAAGCTCCTGATCACGTATGGGTCCGTGTTGCAAAGTGGGGTCCCATCA
CGTTTCAGTGGCAGTGGATCTGGGACAGATTTCACTCTCACCATCAGCAGTCTGCAACCT
GAAGATTTTGCTACGTACTACTGTGCTCAGGAGTTTTGGTGGCCTCATACGTTCGGCCAA
GGGACCAAGGTGGAAATCAAACGGGC
>DOM16-46 (SEQ ID NO:226)
GACATCCAGATGACCCAGTCTCCATCCTCCCTGTCTGCATCTGTAGGAGACCGTGTCACC
ATCACTTGCCGGGCAAGTCGGCCTATTGGGGATAGGTTAACGTGGTACCAGCAGAAACCA
GGGAAAGCCCCTAAGCTCCTGATCTCGTGGGTTTCCGTTTTGCAAAGTGGGGTCCCATCA
CGTTTCAGTGGCAGTGGATCTGGGACAGATTTCACTCTCACCATCAGCAGTCTGCAACCT
GAAGATTTTGCTACGTACTACTGTCGTCAGCTTGGGGGTGGGCCTTTTACGTTCGGCCAA
GGGACCAAGGTGGAAATCAAACGGGC
>DOM16-47 (SEQ ID NO:227)
GACATCCAGATGACCCAGTCTCCATCCTCCCTGTCTGCATCTGTAGGAGACCGTGTCACC
ATCACTTGCCGGGCAAGTCAGTATATTGGGGTGTCGTTAAGTTGGTACCAGCAGAAACCA
GGGAAAGCCCCTAAGCTCCTGATCTATTTTGCTTCCGCGTTGCAAAGTGGGGTCCCATCA
CGTTTCAGTGGCAGTGGATCTGGGACAGATTTCACTCTCACCATCAGCAGTCTGCAACCT
GAAGATTTTGCTACGTACTACTGTCAACAGGATCGTGATTGGCCTGCGACGTTCGGCCAA
GGGACCAAGGTGGAAATCAAACGGGC
>DOM16-48 (SEQ ID NO:228)
GACATCCAGATGACCCAGTCTCCATCCTCCCTGTCTGCATCTGTAGGAGACCGTGTCACC
ATCACTTGCCGGGCAAGTGGTGCTATTGGGGATCGTTTAAAGTGGTACCAGCAGAAACCA
GGGAAAGCCCCTAAGCTCCTGATCTCTTGGGCGTCCGTTTTGCAAAGTGGGGTCCCATCA
CGTTTCAGTGGCAGTGGATCTGGGACAGATTTCACTCTCACCATCAGCAGTCTGCAACCT
GAAGATTTTGCTACGTACTACTGTGTGCAGGGGCCGGGGTGCCTCTGACGTTCGGCCAA
GGGACCAAGGTGGAAATCAAACGGGC
>DOM16-49 (SEQ ID NO:229)
GACATCCAGATGACTCAGTCTCCATCCTCCCTGTCCGCATCTGTAGGAGACCGTGTCACC
ATCACTTGCCGGGCAAGTCAGCCGATTGCTCGTTGGTTAGCTTGGTACCAGCAGAAACCA
GGGAAAGCCCCTAAGCTCCTGATCTATGGTTCTTCCGTTTTGCAAAGTGGGGTCCCATCA
CGTTTCAGTGGCAGTGGATCTGGGACAGATTTCACTCTCACCATCAGCAGTCTGCAACCT
GAAGATTTTGCTACGTACTACTGTCAACAGGATTTGAGGTTGCCTCCGACGTTCGGCCAA
GGGACCAAGGTGGAAATCAAACGGGC
>DOM16-50 (SEQ ID NO:230)
GACATCCAGATGACCCAGTCTCCATCCTCCCTGTCTGCATCTGTAGGAGACCGTGTCACC
ATCACTTGCCGGGCAAGTCAGAATATTGGTGTGTCGTTATCGTGGTACCAGCAGAAACCA
GGGAAAGCCCCTAGGCTCCTGATCTATTATGGGTCCAATTTGCTAAGTGGGGTCCCATCA
CGTTTCAGTGGCAGTGGATCTGGGACAGATTTCACTCTCACCATCAGCAGTCTGCAACCT
GAAGATTTTGCTACGTACTACTGTCAACAGGAGTTTTCGTGGCCTGTGACGTTCGGCCAA
GGGACCAAGGTGGAAATCAAACGGGC
>DOM16-59 (SEQ ID NO:231)
GACATCCAGATGACCCAGTCTCCATCCTCCCTGTCTGCATCTGTAGGAGACCGTGTCACC
ATCACTTGCCGGGCAAGTCTTCCGATTGATGATGGTTTAGGTTGGTACCAGCAGAAACCA
GGGAAAGCCCCTAAGCTCCTGATCTGTGGGGTGTCCGGTTTGCAAAGTGGGGTCCCATTA
CGTTTCAGTGGCAGTGGATCTGGGACAGATTTCACTCTCACCATCAGCAGTCTGCAACCT
GAAGATTTTGCTACGTACTACTGTGGTCAGGGGCAGGTTCAGCCTAGTACGTTCGGCCAA
GGGACCAAGGTGGAAATCAAACGGGC
>DOM16-60 (SEQ ID NO:232)
GACATCCAGATGACCCAGTCTCCATCCTCCCTGTCTGCATCTGTAGGAGACCGTGTCACC
ATCACTTGCCGGGCAAGTCAGAATATTGGTATTAATTTGCAGTGGTATCAGCAGAAACCA
AGGAAAGCCCCTAAGCTCCTGATCTATTATGCTTCCATTTTGCAAAGTGGGGTCCCATCA
CGTTTCAGTGGCAGTGGATCTGGGACAGATTTCACTCTCACCATCAGCAGTCTGCAACCT
GAAGATTTTGCTACGTACTACTGTCAACAGTCGTATGATGCGCCTACTACGTTCGGCCAA
GGGACCAAGGTGGAAATCAAACGGGC
>DOM16-61 (SEQ ID NO:233)
GACATCCAGATGACCCAGTCTCCATCCTCCCTGTCTGCATCTGTAGGAGACCGTGTCACC
ATCACTTGCCGGGCAAGTCAGTCTATTGGGGTTAATTTAATGTGGTACCAGCAGAAACCA
GGGAAAGCCCCTAAGCTCCTGATCTATTTTGCTTCCATTTTGCAAAGTGGGGTCCCATCA
CGTTTCAGTGGCAGTGGATCTGGGACAGATTTCACTCTCACCATCAGCAGTCTGCAACCT

FIG. 9D

GAAGACTTTGCTACGTACTACTGTCAACAGAATTATGATATTCCTAAGACGTTCGGCCAA
GGGACCAAGGTGGAAATCAAACGGGC
>DOM16-62 (SEQ ID NO:234)
GACATCCAGATGACCCAGTCTCCATCCTCCCTGTCTGCATCTGTAGGAGACCGTGTCACC
ATCACTTGCCGGGCAAGTCAGTGGATTGGTATTTCTTTATCTTGGTATCAGCAGAAACCA
GGGAAAGCCCCTAAGCTCCTAATCTATTATGGGTCCGTGTTGCAAAGTGGGGTCCCATCC
CGTTTCAGTGGCAGTGGATCTGGGACAGATTTCACTCTCACCATCAGCAGTCTGCAACCT
GAAGATTTTGCTACGTACTACTGTCAACAGTCTCATGATCTTCCTGTGACGTTTGGCCAA
GGGACCAAGGTGGAAATCAAACGGGC
>DOM16-63 (SEQ ID NO:235)
GACATCCAGATGACCCAGTCTCCATCCTCCCTGTCTGCATCTGTAGGAGACCGTGTCACC
ATCACTTGCCGGGCAAGTCAGTGGATTGGTGTTAGTTTATCTTGGTATCAGCAGAAACCA
GGGAAAGCCCCTAAGCTCCTGATCTATTATGCGTCCATTTTGCAAAGTGGGGTCCCATCA
CGTTTCAGTGGCAGTGGATCTGGGACAGATTTCACTCTCACCATCAGCAGTCTGCAACCT
GAAGATTTTGCTACGTACTACTGTCAACAGGAGATGTCGTATCCTCCTACGTTCGGCCAA
GGGACCAAGGTGGAAATCAAACGGGC
>DOM16-64 (SEQ ID NO:236)
GACATCCAGATGACCCAGTCTCCATCCTCCCTGTCTGCATCTGTAGGAGACCGTGTCACC
ATCACTTGCCGGGCAAGCCAGGATATTGGTGTTAGTTTAGAGTGGTATCAGCAGAAACCA
GGGAAAGCCCCTAAGCTCCTGATCTATTGGAGTTCCGCTTTGCAAAGTGGGGTCCCATCA
CGTTTCAGTGGCAGTGGATCTGGGACAGATTTCACTCTCACCATCAGCAGTCTGCAACCT
GAAGATTTGGCTACGTACTACTGTCAACAGGGGCATACGTATCCTAGTACGTTCGGCCAA
GGGACCAAGGTGGAAATCAAACGGGC
>DOM16-65 (SEQ ID NO:237)
GACATCCAGATGACCCAGTCTCCATCCTCCCTGTCTGCATCTGTAGGAGACCGTGTCACC
ATCACTTGCCGGGCAAGTCAGTATATTGGTGTTTATTTAAGTTGGTATCAGCAGAAACCA
GGGAAAGCCCCTAAGCTCCTGATCTATTGGGCGTCCCTTTTGCAAAGTGGGGTCCCATCA
CGTTTCAGTGGCAGTGGATCTGGGACAGATTTCACTCTCACCATCAGCAGTCTGCAACCT
GAAGATTTTGCTACGTACTACTGTCAACAGACTGTTAGGGATCCTATTACGTTCGGCCAA
GGGACCAAGGTGGAAATCAAACGGGC
>DOM16-66 (SEQ ID NO:238)
GACATCCAGATGACCCAGTCTCCATCCTTCCTGTCTGCATCTGTAGGAGACCGTGTCACC
ATCACTTGCCGGGCAAGTCAGTCTATTTATACTATGTTAAATTGGTATCAGCAGAAACCA
GGGAAAGCCCCTAAGCTCCTGATCTATCGTGCTTCCTATTTGCAAAGTGGGGTCCCATCA
CGTTTCAGTGGCAGTGGATCTGGGACAGATTTCACTCTCACCATCAGCAGTCTGCTACCT
GAAGATTCTGCTACGTACTACTGTCAACAGGATTTTTCGTATCCTAGTACGTTCGGCCAA
GGGACCAAGGTGGAAATCAAACGGGC
>DOM16-67 (SEQ ID NO:239)
GACATCCAGATGACCCAGTCTCCATCCTCCCTGTCTGCATCTGTAGGAGACCGTGTCACC
ATCACTTGCCGGGCAAGTCAGTATATTGGGGCGAATTTAAGTTGGTATCAGCAGAAACCA
GGGAAAGCCCCTAAGCTCCTGATCTATTATATTTCCGTTTTGCAAAGTGGGGTCCCATCA
CGTTTCAGTGGCAGTGGATCTGGGACAGATTTCACTCTCACCATCAGCAGTCTGCAACCT
GAAGATTTTGCTACGTACTACTGTCAACAGGAGCTTTATACTCCTCATACGTTCGGCCAA
GGGACCAAGGTGGAAATCAAACGGGC
>DOM16-68 (SEQ ID NO:240)
GACATCCAGTTGACCCAGTCTCCATCCTCCCTGTCTGCATCTGTAGGAGACCGTGTCACC
ATCACTTGCCGGGCAAGTCAGTATATTGGTGTGACTTTAATGTGGTATCAGCAGAAACCA
GGGAAAGCCCCTAAGCTCCTGATCTATTATGCTTCCCAGTTGCAAAGTGGGGTCCCATCA
CGTTTCAGTGGCAGTGGATCTGGGACAGATTTCACTCTCACCATCAGCAGTCTGCAACCT
GAAGATTTTGCTACGTACTACTGTCAACAGGAGGTTAGTTATCCTTATACGTTCGGCCAA
GGGACCAAGGTGGAAATCAAACGGGC
>DOM16-69 (SEQ ID NO:241)
GACATCCAGATGACCCAGTCTCCATCCTCTCTGTCTGCATCTGTAGGAGACCGTGTCACC
ATCACTTGCCGGGCAAGTCAGCATATTGGTGTGAGTTTAACTTGGTACCAGCAGAAACCA
GGGAAAGCCCCTAAGCTCCTGATCTATTTGCTTCCATTTTGCAAAGTGGGGTCCCATCA
CGTTTCAGTGGCAGTGGATCTGGGACAGATTTCACTCTCACCATCAGCAGTCTGCAACCT
GAAGATTATGCTACGTACTACTGTCAACAGGATATGTCTTATCCTCCTACGTTCGGCCAA
GGGACCAAGGTGGGAATCAAACGGGC
>DOM16-70 (SEQ ID NO:242)
GACATCCAGATGACCCAGTCTCCATCCTCCCTGTCTGCATCTGTAGGAGACCGTGTCACC
ATCACTTGCCGGGCAAGTCAGGATATTGGTATCAGTTTAGAGTGGTATCAGCAGAAACCA

FIG. 9E

```
GGGAAAGCCCCTAAGCTCCTGATCTATTTTGCTTCCCAGTTGCAAAGTGGGGTCCCATCA
CGTTTCAGTGGCAGTGGATCTGGGACAGATTTCACTCTCACCATCAGCAGTCTGCAACCT
GAAGATTTTGCTACGTACTACTGTCAACAGGTGTATGATTTTCCTAATACGTTCGGCCAA
GGGACCAAGGTGGAAATCAAACGGGC
>DOM16-71 (SEQ ID NO:243)
GACATCCAGATGACCCAGTCTCCATCCTCCCTGTCTGCATCTGTAGGAGACCGTGTCACC
ATCACTTGCCGGGCAAGTCAGCATATTGGTGTGAGTTTAAATTGGTATCAGCAGAAACCA
GGGAAAGTCCCTAAGCTCCTGATCTATTGGGCTTCCATTTTGCAAAGTGGGGTCCCATCA
CGTTTCAGTGGCAGTGGATCTGGGACAGATTTCACTCTCACCATCAGCAGTCTGCAACCT
GAAGATTTTGCTACGTACTACTGTCAACAGGAGCATACTATTCCTTCTACGTTCGGCCAA
GGGACCAAGGTGGAAATCAAACGGGC
>DOM16-72 (SEQ ID NO:244)
GACATCCAGATGACCCAGTCTCCATCCTCCCTGTCTGCATCTGTAGGAGACCGTGTCACC
ATCACTTGCCGGGCAAGTCAGCATATTGGGGTTTCGTTAGATTGGTACCAGCAGAAACCA
GGGAAAGCCCCTAAGCTCCTGATCTATTATGGTTCCGAGTTGCAAAGTGGGGTCCCATCA
CGTTTCAGTGGCAGTGGATCTGGGACAGATTTCACTCTCACCATCAGCAGTCTGCAACCT
GAAGATTTTGCTACGTACTACTGTCAACAGTATGTTACTCATCCTACGACGTTCGGCCAA
GGGACCAAGGTGGAAATCAAACGGGC
>DOM16-73 (SEQ ID NO:245)
GACATCCAGATGACCCAGTCTCCATCCTCCCTGTCTGCATCTGTAGGAGACCGTGTCACC
ATCACTTGCCGGGCAAGTCAGAGGATTGGTATGATGTTAGATTGGTATCAGCAGAAACCA
GGGAAAGCCCCTAAGCTCCTGATCTATGGGGGTTCCAAGTTGCAAAGTGGGGTCCCATCA
CGTTTCAGTGGCAGTGGATCTGGGACAGATTTCACTCTCACCATCAGCAGTCTGCAACCT
GAAGATTTTGCTACGTACTACTGTCAACACCGGGGTTGGTATCCTCTGACGTTCGGCCAA
GGGACCAAGGTGGAAATCAAACGGGC
>DOM16-74 (SEQ ID NO:246)
GACATCCAGATGACCCAGTCTCCATCCTCCCTGTCTGCATCTGTAGGAGACCGTGTCACC
ATCACTTGCCGGGCAAGTCAGCCTATTGGTGATCGTTTAAGTTGGTACCAGCAGAAACCA
GGGAAAGCCCCTAAGCTCCTGATCTATTTTTCTTCCGTTTTGCAAAGTGGGGTCCCATCA
CGTTTCAGTGGCAGTGGATCTGGGACAGATTTCACTCTCACCATCAGCAGTCTGCAACCT
GAAGATTTTGCTACGTACTACTGTCAACAGCATGGTTTGCGGCCTGATACGTTCGGCCAA
GGGACCAAGGTGGAAATCAAACGGGC
>DOM16-75 (SEQ ID NO:247)
GACATCCAGATGACCCAGTCTCCATCCTCCCTGTCTGCATCAGTAGGAGACCGTGTCACC
ATCACTTGCCGGGCAAGTCAGTGGATTGGTAGTAGTTTAATGTGGTATCAGCAGAAACCA
GGGAAAGCCCCTAAGCTCCTGATCTATTGGGCTTCCGAGTTGCAAAGTGGGGTCCCATCG
CGTTTCAGTGGCAGTGGATCTGGGACAGATTTCACTCTCACCATCAGCAGTCTGCAACCT
GAAGATTTTGCTACGTACTACTGTCAACAGGAGTATAGTTATCCTAGTACGTTCGGCCAA
GGGACCAAAGTGGAAATCAAACGGGC
>DOM16-76 (SEQ ID NO:248)
GACATCCAGATGACCCAGTCTCCATCCTCCCTGTCTGCATCTGTAGGAGACCGTGTCACC
ATCACTTGCCGGGCAAGTCAGGATATTGGTGTTTCGTTAGCTTGGTACCAGCAGAAACCG
GGGAAAGCCCCTAAGCTCCTGATCTATTTTGGTTCCGTGTCGCTAAGTGGGGTCCCATCA
CGTTTCAGTGGCAGTGGATCTGGGACAGATTTCACTCTCACCATCAGCAGTCTGCAACCT
GAAGATTTTGCTACGTACTACTGTCAACAGTCTCATCTTCCTCCTACTACGTTCGGCCAA
GGGACCAAGGTGGAAATCAAACGGGC
>DOM16-77 (SEQ ID NO:249)
GACATCCAGATGACCCAGTCTCCATCCTCCCTGTCTGCATCTGTAGGAGACCGTGTCACC
ATCACTTGCCGGGCAAGTCAGTGGATTGGGGTGGAGTTAAATTGGTATCAGCAGAAACCA
GGGAAAGCCCCTAAGCTCCTGATCTATTGGACGTCCATTTTGCAAAGTGGGGTCCCATCA
CGTTTCAGTGGCAGTGGATCTGGGACAGATTTCACTCTCACCATCAGCAGTCTGCAACCT
GAAGATTTTGCTACGTACTACTGTCAACAGGTTATTAATAGTCCCTATACGTTCGGCCAA
GGGACCAAGGTGGAAATCAAACGGGC
>dom16-78 (SEQ ID NO:250)
GACATCCAGATGACCCAGTCTCCATCCTCCCTGTCTGCATCTGTAGGAGACCGTGTCACC
ATCACTTGCCGGGCAAGTCAGGATATTGGTAAGTGGTTAGAGTGGTACCAGCAGAAACCA
GGGAAAGCCCCTAAGCTCCTGATCGGGGCGACGTCCTGGTTGCAAAGTGGGGTCCCATCA
CGTTTCAGTGGCAGTGGATCTGGGACAGATTTCACTCTCACCATCAGCAGTCTGCAACCT
GAAGATTTTGCTACGTACTACTGTGTTCAGCAGGGGAGGCGTCCTGGGACGTTCGGCCAA
GGGACCAAGGTGGAAATCAAACGGGC
>DOM16-79 (SEQ ID NO:251)
```

FIG. 9F

GACATCCAGATGACCCAGTCTCCATCCTCCCTGTCTGCATCTGTAGGAGACCGTGTCACC
ATCACTTGCCGGGCAAGTCAGTGGATTGGTATTTTGTTAGATTGGTACCAGCAGAAACCA
GGGGAAGCCCCTAAGCTCCTGATCTATTATGCTTCCTTTTTGCAAAGTGGGGTCCCATCA
CGTTTCAGTGGCAGTGGATCTGGGACAGATTTCACTCTCACCATCAGCAGTCTGCAACCT
GAAGATTTTGCTACGTACTACTGTCAACGGTCGGATCTGTCTCCTCTGACGTTCGGCCAA
GGGACCAAGGTGGAAATCAAACGGGC
>DOM16-80 (SEQ ID NO:252)
GACATCCAGATGACCCAGTCTCCATCCTCCCTGTCTGCATCTGTAGGAGACCGTGTCACC
ATCACTTGCCGGGCAAGTCAGAATATTTATATGAATTTAGAGTGGTACCAGCAGAAACCA
GGGAAAGCCCCTAAGCTCCTGATCGTTTTTGGTTCCTGGTTGCAAAGTGGGGTCCCATCA
CGTTTCAGTGGCAGTGGATCTGGGACAGATTTCACTCTCACCATCAGCAGTCTGCAACCT
GAAGATTTTGCTACGTACTACTGTCGGCAGACTGAGGCGCCGCCTTCTACGTTCGGCCAA
GGGACCAAGGTGGAAATCAAACGGGC
>DOM16-81 (SEQ ID NO:253)
GACATCCGGATGACCCAGTCTCCATCCTCCCTGTCTGCATCTGTAGGAGACCGTGTCACC
ATCACTTGCCGGGCAAGTCAGCATATTGGGTCGTCGTTATCTTGGTACCAGCAGAAACCA
GGGAAAGCCCCTAAGCTCCTGATCTATTATGCCTCCGTTTTGCAAAGTGGGGTCCCATCA
CGTTTCAGTGGCAGTGGATCTGGGACAGATTTCACTCTCACCATCAGCAGTCTGCAACCT
GAAGATTTTGCTACGTACTACTGTCAACAGGAGTATTCTTGGCCTCCTACGCTCGGCCAA
GGGACCAAGGTGGAAATCAAACGGGC
>DOM16-82 (SEQ ID NO:254)
GACATCCAGATGACCCAGTCTCCATCCTCCCTGTCTGCATCTGTAGGAGACCGTGTCACC
ATCACTTGCCGGGCAAGTCAGGATATTCGGACGCTGTTACGGTGGTACCAGCAGAAACCA
GGGAAAGCCCCTAAGCTCCTGATCTATTGGTCTTCCGAGTTGCAAAGTGGGGTCCCATCA
CGTTTCAGTGGCAGTGGATCTGGGACAGATTTCACTCTCACCATCAGCAGTCTGCAACCT
GAAGATTTTGCTACGTACTACTGTCAACAGACGTTTCATGCGCCTAATACGTTCGGCCAA
GGGACCAAGGTGGAAATCAAACGGGC
>DOM16-83 (SEQ ID NO:255)
GACATCCGGATGACCCAGTCTCCATCCTCCCTGTCTGCATCTGTAGGAGACCGTGTCACC
ATCACTTGCCGGGCAAGTCAGTATATTGGGAAGTATTTAAGTTGGTACCAGCAGAAACCA
GGGAAAGCCCCTAAGCTCCTGATCTATTTGTCGTCCACGTTGCAAAGTGGGGTCCCATCA
CGTTTCAGTGGCAGTGGATCTGGGACAGATTTCACTCTCACCATCAGCAGTCTGCAACCT
GAAGATTTTGCTACGTACTACTGTCAACAGAATGATCGTTTACCTCTTACGCTCGGCCAA
GGGACCAAGGTGGAAATCAAACGGGC
>DOM16-84 (SEQ ID NO:256)
GACATCCAGATGACCCAGTCTCCATCCTCCCTGTCTGCATCTGTAGGAGACCGTGTCACC
ATCACTTGCCAGGCAAGTCAGCTGATTGGGAATATGTTATCTTGGTACCAGCAGAAACCA
GGGAAAGCCCCTACGCTCCTGATCTATATTGGTTCCTCTTTGCAAAGTGGGGTCCCATCA
CGTTTCAGTGGCAGTGGATCTGGGACAGATTTCACTCTCACCATCAGCAGTCTGCAACCT
GAAGATTTTGCTACGTACTACTGTCAACAGACGTATTTTGATCCTCCTACGTTCGGCCAA
GGGACCAAGGTGGAAATCAAACGGGC
>DOM16-85 (SEQ ID NO:257)
GACATCCAGATGACCCAGTCTCCATCCTCCCTGTCTGCATCTGTAGGAGACCGTGTCACC
ATCACTTGCCGGGCAAGTCAGTATATTGGTATTAATTTAAGGTGGTACCAGCAGAAACCA
GGGAAAGCCCCTAAGCTCCTGATCTATTATAGTTCCACTTTGCTAAGTGGGGTCCCATCA
CGTTTCAGTGGCAGTGGATCTGGGACAGATTTCACTCTCACCATCAGCAGTCTGCAACCT
GAAGATTTTGCTACGTACTACTGTCAACAGTCTTATGATTCTCCTGTTACGTTCGGCCAA
GGGACCAAGGTGGAAATCAAACGGGC
>DOM16-87 (SEQ ID NO:258)
GACATCCAGATGACCCAGTCTCCATCCTCCCTGTCTGCATCTGTAGGAGACCGTGTCACC
ATCACTTGCCGGGCAAGTTGGGCTATTGGTGATCGTTTAGAGTGGTACCAGCAGAAACCA
GGGAAAGCCCCTAAGCTCCTGATCGCGTGGGGGTCCGTGTTGCAAAGTGGGGTCCCATCA
CGTTTCAGTGGCAGTGGATCTGGGACAGATTTCACTCTCACCATCAGCAGTCTGCAACCT
GAAGATTTTGCTACGTACTACTGTTCTCAGCTGGGTTCGCGGCCTCGTACGTTCGGCCAA
GGGACCAAGGTGGAAATCAAACGGGC
>DOM16-88 (SEQ ID NO:259)
GACATCCAGATGACCCAGTCTCCATCCTCCCTGTCTGCATCTGTAGGAGACCGTGTCACC
ATCACTTGCCGGGCAAGTCAGTCGATTGATAATTGGTTAGCGTGGTACCAGCAGAAACCA
GGGGAAGCCCCTAAGCTCCTGATCTATGGTACGTCCCGGTTGCAAAGTGGGGTCCCATCG
CGTTTCAGTGGCAGTGGATCTGGGACAGATTTTACTCTCACCATCAGCAGTCTGCAACCT
GAAGATTTTGCTACGTACTACTGTCAACAGTATAATTTTTTCCTTCTACGTTCGGCCAA

FIG. 9G

```
GGGACCAAGGTGGAAATCAAACGGGC
>DOM16-89 (SEQ ID NO:260)
GACATCCAGATGACCCAGTCTCCATCCTCCCTGTCTGCATCTGTAGGAGACCGTGTCACC
ATCACTTGCCGGGCAAGTACTTTTATTGGTAATGTGTTAAATTGGTACCAGCAGAAACCA
GGGAAAGCCCCTAAGCTCCTGATCTCTTATGTGTCCATGTTGCAAAGTGGGGTCCCATCA
CGTTTCAGTGGCAGTGGATCTGGGACAGATTTCACTCTCACCATCAGCAGTCTGCAACCT
GAAGATTTTGCTACGTACTACTGTTGTCAGTCGTATGATGTGCCTTTTACGTTCGGCCAA
GGGACCCAGGTGGAAATCAAACGGGC
>DOM16-90 (SEQ ID NO:261)
GACATCCAGATGACCCAGTCTCCATCCTCCCTGTCTGCATCTGTAGGAGACCGTGTCACC
ATCACTTGCCGGGCAAGTCAGTGGATTGGGGTTAGTTTAGTTTGGTATCAGCAGAAACCA
GGGAAAGCCCCTAAGCTCCTGATCTATTGGGCTTCCGTTTTGCAAAGTGGAGTCCCATCA
CGTTTCAGTGGCAGTGGATCTGGGACAGATTTCACTCTCACCATCAGCAGTCTGCAACCT
GAGGATTTTGCTACGTACTACTGTCAACAGACGCATGCAGGGCCTCATACGTTCGGCCAA
GGGACCAAGGTGGAAATCAAACGGGC
>DOM16-91 (SEQ ID NO:262)
GACATCCAGATGACCCAGTCTCCATCCTCCCTGTCTGCATCTGTAGGAGACCGTGTCACC
ATCACTTGCCGGGCAAGTCAGTGGATTGGTATTTTGTTAGATTGGTACCAGCAGAAACCA
GGGGAAGCCCCTAAGCTCCTGATCTATTATGCTTCCTTTTTGCAAAGTGGGGTCCCATCA
CGTTTCAGTGGCAGTGGATCTGGGACAGATTTCACTCTCACCATCAGCAGTCTGCAACCT
GAAGATTTTGCTACGTACTACTGTCAACAGTCTTCTGTGGATCCTCTTACGTTCGGCCAA
GGGACCAAGGTGGAAATCAAACGGGC
>DOM16-92 (SEQ ID NO:263)
GACATCCAGATGACCCAGTCTCCATCCTCCCTGTCTGCATCTGTAGGAGACCGTGTCACC
ATCACTTGCCGGGCAAGTCAGGATATTGGTGTGTCGTTAAGGTGGTATCAGCAGAAACCA
GGGAAAGCCCCTAAGCTCCTGATCTATTGGGCTTCCGAGTTGCAAAGTGGGGTCCCATCA
CGTTTCAGTGGCAGTGGATCTGGGACAGATTTCACTCTCACCATCAGCAGTCTGCAACCT
GAAGATTTTGCTACGTACTACTGTCAACAGCTTTATGATTATCCTCCGACGTTCGGCCAA
GGGACCAAGGTGGAAATCAAACGGGC
>DOM16-94 (SEQ ID NO:264)
GACATCCAGATGACCCAGTCTCCATCCTCCCTGTCTGCATCTGTAGGAGACCGTGTCACC
ATCACTTGCCGGGCAAGTCGTTTTATTGCTTCTGGTTTAGATTGGTACCAGCAGAAACCA
GGGAAAGCCCCTAAGCTCCTGATCTCGCGGTTTTCCGGGTTGCAAAGTGGGGTCCCATCA
CGTTTCAGTGGCAGTGGATCTGGGACAGATTTCACTCTCACCATCAGCAGTCTGCAACCT
GAAGATTTTGCTACGTACTACTGTAAGCAGGGGTTTGGGGCTCCTGCGACGTTCGGCCAA
GGGACCAAGGTGGAAATCAAACGGGC
>DOM16-95 (SEQ ID NO:265)
GACATCCAGATGACCCAGTCTCCATCCTCCCTGTCTGCATCTGTAGGAGACCGTGTCACC
ATCACTTGCCGGGCAAGTCAGTATATTTCTACGGAGTTAGAGTGGTATCAGCAGAAACCA
GGGAAAGCCCCTAAGCTCCTGATCTATTCGAGTTCCATGTTGCAAAGTGGGGTCCCATCA
CGTTTCAGTGGCAGTGGATCTGGGACAGATTTCACTCTCACCATCAGCAGTCTGCAACCT
GAAGATTTTGCTACGTACTACTGTCAACAGAGTGCTTCGGCGCTTCCTCTGACGTTCGGC
CAAGGGACCAAGGTGGAAATCAAACGGGC
>DOM16-96 (SEQ ID NO:266)
GACATCCAGATGACCCAGTCTCCATCCTCCCTGTCTGCATCTGTAGGAGACCGTGTCACC
ATCACTTGCCGGGCAAGTCAGTGGATTGGTGCGTCTTTACAGTGGTACCAGCAGAAACCA
GGGCAAGCCCCTAAGCTCCTGATCTATTATATGTCCGTGTTGCAAAGTGGGGTCCCATCA
CGTTTCAGTGGCAGTGGATCTGGGACAGATTTCACTCTCACCATCAGCAGTCTGCAACCT
GAAGATTTTGCTACGTACTACTGTCAACAGACGGCTTTGACTCCTGCTACGTTCGGCCAA
GGGACCAAGGTGGAAATCAAACGGGC
>DOM16-97 (SEQ ID NO:267)
GACATCCAGATGACCCAGTCTCCATCCTCCCTGTCTGCATCTGTAGGAGACCGTGTCACC
ATCACTTGCCGGGCAAGTCAGGTTATTGGGGATTATTTATCTTGGTACCAGCAGAAACCA
GGGAAAGCCCCTAAGCTCCTGATCTATTTCGTTCCGTTTTGCAAAGTGGGGTCCCATCA
CGTTTCAGTGGCAGTGGATCTGGGACAGATTTCACTCTCACCATCAGCAGTCTGCAACCT
GAAGATTTTGCTACGTACTACTGTCAACAGAATTGGAATTTGCCTGTTACGTTCGGCCAA
GGGACCAAGGTGGAAATCAAACGGGC
>DOM16-98 (SEQ ID NO:268)
GACATCCAGATGACCCAGTCTCCATCCTCCCTGTCTGCATCTGTAGGAGACCGTGTCACC
ATCACTTGCCGGGCAAGTCAGTATATTGGTGTGAATTTATCGTGGTACCAGCAGAAACCA
GGGAAAGCCCCTAAGCTCCTGATCTATTATGTTTCCGTTTTGCAAAGTGGGGTCCCATCA
```

FIG. 9H

CGTTTCAGTGGCAGTGGATCTGGGACAGATTTCACTCTCACCATCAGCAGTCTGCAACCT
GAAGATTTTGCTACGTACTACTGTCAACAGACTTATGATATTCCTTCTACGTTCGGCCAA
GGGACCAAGGTGGAAATTAAACGGGC
>DOM16-99 (SEQ ID NO:269)
GACATCCAGATGACCCAGTCTCCATCCACCCTGTCTGCATCTGTAGGAGACCGTGTCACC
ATCACTTGCCGGGCAAGTCAGTGGATTGGTGTGTCTTTATCGTGGTACCAGCAGAAACCA
GGGAAAGCCCCTAAGCTCCTGATCTATTATACGTCCTATTTGCAAAGTGGGGTCCCATCA
CGTTTCAGTGGCAGTGGATCTGGGACAGATTTCACTCTCACCATCAGCAGTCTGCAACCT
GAAGATTTTGCTACATACTACTGTCAACAGGAGACGACGTGGCCTTATACGTTCGGCCAA
GGGACCAAGGTGGAAATCAAACGGGC
>DOM16-100 (SEQ ID NO:270)
GACATCCAGATGACCCAGTCTCCATCCTCCTTGTCTGCATCTGTAGGAGACCGTGTCACC
ATCACTTGCCGGGCAAGTCAGTATATTGGGGCGGAGTTAAATTGGTACCAGCAGAAACCA
GGGAAAGCCCCTAAGCTCCTGATCTATTGGACTTCCGTGTTGCAAAGTGGGGTCCCATCA
CGTTTCAGTGGCAGTGGATCTGGGACAGATTTCACTCTCACCATCAGCAGTCTGCAACCT
GAAGATTTTGCTACGTACTACTGTCAACAGGCGATTCTGGCGCCTCTTACGTTCGGCCAA
GGGACCAAGGTGGAAATCAAACGGGC
>DOM16-101 (SEQ ID NO:271)
GACATCCAGATGACCCAGTCTCCATCCTCCCTGTCTGCATCTGTAGGAGACCGTGTCACC
ATCACTTGCCGGGCAAGTCAGTGGATTGGTGTTAGTTTAAATTGGTATCAGCAGAAACCA
GGGAAAGCCCCTAAGCTCCTGATCTACTTTGCGTCCGTGTTGCAGAGTGGGGTCCCATCA
CGTTTCAGTGGCAGTGGATCTGGGACAGATTTCACTCTCACCATCAGCAGTCTGCAACCT
GAAGATTTTGCTACGTACTACTGTCAACAGAATGCGTTTTATCCTGATACGTTCGGCCAA
GGGACCAAGGTGGAAATCAAACGGGC
>DOM16-102(SEQ ID NO:272)
GACATCCAGATGACCCAGTCTCCATCCTCCCTGTCTGCATCTGTAGGAGACCGTGTCACC
ATCACTTGCCGGGCAAGTCAGTGGATTGGTGCGGAGTTAAATTGGTATCAGCAGAAACCA
GGGAAAGCCCCTAAGCTCCTGATCTATTGGATGTCCGTGTTGCAAAGTGGGGTCCCATCA
CGTTTCAGTGGCAGTGGATCTGGGACAGATTTCACTCTCACCATCAGCAGTCTGCAACCT
GAAGATTTTGCTACGTACTACTGTCAACAGACTTCTTTTTTTCCTATTACGTTCGGCCAA
GGGACCAAGGTGGAAATCAAACGGGC
>DOM16-103 (SEQ ID NO:273)
GACATCCAGATGACCCAGTCTCCATCCTCCCTGTCTGCCTCTGTAGGAGACCGTGTCGCC
ATCACTTGCCGGGCAAGTCAGGATATTCGGACGCTTTTAGCTTGGTACCAGCAGAAACCA
GGGAAAGCCCCTATGCTCCTGATCTATTGGGCTTCCGAGTTGCAAAGTGGGGTCCCATCA
CGTTTCAGTGGCAGTGGATCTGGGACAGATTTCACTCTCACCATCAGCAGTCTGCAACCT
GAAGATTTTGCTACGTACTACTGTCAACAGTCTCTTTCTTGGCCTTCGACGTTCGGCCAA
GGGACCAAGGTGGAAATCAAACGGGC
>DOM16-104 (SEQ ID NO:274)
ACATCCAGATGACCCAGTCTCCATCCTCCCTGTCTGCATCTGTAGGAGACCGTGTCACC
ATCACTTGCCGGGCAAGTCAGTATATTGGGGTGAGTTTAGATTGGTACCAGCAGAAACCA
GGGAAAGCCCCTAAGCTCCTGATCTATTATAGTTCCATGTTGCAAAGTGGGGTCCCATCA
CGTTTCAGTGGCAGTGGATCTGGGACAGATTTCACTCTCACCATCAGCAGTCTGCAACCT
GAAGATTTTGCTACGTACTACTGTCAACAGTATTATACTGTTCCTGATACGTTCGGCCAA
GGGACCAAGGTGGAAATCAAACGGGC
>DOM16-105 (SEQ ID NO:275)
GACATCCAGATGACCCAGTCTCCATCCTCCCTGTCTGCATCTGTAGGAGACCGTGTCACC
ATCACTTGCCGGGCAAGTTGGCCGATTGGTGATCGTTTAAATTGGTACCAGCAGAAACCA
GGGAAAGCCCCTAAGCTCCTGATCGCTTGGGTTTCCGTTTTGCAAAGTGGGGTCCCATCA
CGTTTCAGTGGCAGTGGATCTGGGACAGATTTCACTCTCACCATCAGCAGTCTGCAACCT
GAAGATTTTGCTACGTACTACTGTGGGCAGTTGGGGGGTGGGCCTCGGACGTTCGGCCAA
GGGACCAAGGTGGAAATCAAACGGGC
>DOM16-106 (SEQ ID NO:276)
GACATCCAGATGACCCAGTCTCCATCCTCCCTGTCTGCATCTGTAGGAGACCGTGTCTCC
ATCACTTGCCGGGCAAGTCAGTTTATTGGGTGGGAGTTAGCTTGGTACCAGCAGAAACCA
GGGAAAGCCCCTATGCTCCTGATCTATCCGTATTCCACGTTGCAAAGTGGGGTCCCATCA
CGTTTCAGTGGCAGTGGATCTGGGACAGATTTCACTCTCACCATCAGCAGTCTGCAACCT
GAAGATTTTGCTACGTACTACTGTCAACAGCTGGCTGGTTTTCCTTATACGTTCGGCCAA
GGGACCAAGGTGGAAATCAAACGGGC
>DOM16-107(SEQ ID NO:277)
GACATCCAGATGACCCAGTCTCCATCCTCCCTGTCTGCATCTGTAGGAGACCGTGTCACC

FIG. 9I

ATCACTTGCCGGGCAAGTCAGCCTATTGGTGATCGTTTATCTTGGTACCAGCAGAAACCA
GGGAAAGCCCCTAAGCTCCTGATCTATTTTGTGTCCCAGTTGCAAAGTGGGGTCCCATCA
CGTTTCAGTGGCAGTGGATCTGGGACAGATTTCACTCTCACCATCAGCAGTCTGCAACCT
GAAGATTTTGCTACGTACTACTGTCAACAGAGTCATCCTAATCCTAAGACGTTTGGCCAA
GGGACCAAGGTGGAAATCAAACGGGC
>DOM16-108 (SEQ ID NO:278)
GACATCCAGATGACCCAGTCTCCATCCTCCCTGTCTGCATCTGTAGGAGACGGTGTCACC
ATCACTTGCCGGGCAAGTCAGTGGATTGGGGTGGAGTTAAGTTGGTATCAGCAGAAACCA
GGGAAAGCCCCTAAGCTCCTGATCTATTGGGGTTCCGAGTTGCAAAGTGGGGTCCCATCA
CGTTTCAGTGGCAGTGGATCTGGGACAGATTTCACTCTCACCATCAGCAGTCTGCAACCT
GAAGATTTTGCTACGTACTACTGTCAACAGTTGGCGTTACCTCCTTTTACGTTCGGCCAA
GGGACCAAGGTGGAAATCAAACGGGC
>DOM16-109 (SEQ ID NO:279)
GACATCCAGATGACCCAGTCTCCATCCTCCCTGTCTGCATCTGTAGGAGACCGTGTCACC
ATCACTTGCCGGGCAAGTCAGGAGATCGGGGCTAGTTTAGAGTGGTACCAGCAGAAACCA
GGGAAAGCCCCTAAGCTCCTGATCTATTGGGCTTCCGTGTTGCAAAGTGGGGTCCCATCA
CGTTTCAGTGGCAGTGGATCTGGGACAGATTTCACTCTCACCATCAGCAGTCTGCAACCT
GAAGATTTTGCTACGTACTACTGTCAACAGATGCATCATACTCCTTTTACGTTCGGCCAA
GGGACCAAGGTGGAAATCAAACGGGC
>DOM16-110 (SEQ ID NO:280)
GACATCCAGATGACCCAATCTCCATCCTCCCTGTCCGCATCTGTAGGAGACCGTGTCACC
ATCACTTGCCGGGCAAGTCAGCATATTGGGCAGTTTTTAAGTTGGTACCAGCAGAAGCCA
GGGAAAGCCCCTAAGCTCCTGATCTATTTGGCTTCCAGGTTGCAAAGTGGGGTCCCATCA
CGTTTCAGTGGTAGTGGATCTGGGACAGATTTCACTCTCACCATCAGCAGTCTGCAACCT
GAAGATTTTGCTACGTACTACTGTCAACAGGTTGATAGGATTCCTGTTACGTTCGGCCAA
GGGACCAAGGTGGAAATCAAACGGGC
>DOM16-111 (SEQ ID NO:281)
GACATCCAGATGACCCAGTCTCCATCCTCCCTGTCTGCATCTGTAGGAGACCGTGTCACC
ATCACTTGCCGGGCAAGTCAGGGGATTGATCATTTTTATCGTGGTACCAGCAGAAACCA
GGGAAAGCCCCTAAGCTCCTGATCTATTTGCGTCCACGTTGCAAAGTGGGGTCCCATCA
CGTTTCAGTGGCAGTGGATCTGGGACAGATTTCACTCTCACCATCAGCAGTCTGCAACCT
GAAGATTTTGCTACGTACTACTGTCAACAGAATGCGAGTATTCCTATTACGTTCGGCCAA
GGGACCAAGGTGGAAATCAAACGGGC
>DOM16-112 (SEQ ID NO:282)
GACATCCAGATGACCCAGTCTCCATCCTCCCTGTCTGCATCTGTAGGAGACCGTGTCACC
ATCACTTGCCGGGCAAGTCAGAATATTGGTACTAATTTAAAGTGGTATCAGCAGAAACCA
GAGAAAGCCCCTAAGCTCCTGATCTATTATGGGTCCCTTTTGCAAAGTGGGGTCCCATCA
CGTTTCAGTGGCAGTGGATCTGGGACAGATTTCACTCTCACCATCAGCAGTCTGCAACCT
GAAGATTTTGCTACGTACTACTGTCAACAGGATTATGATTTTCCTTATACGTTCGGCCAA
GGGACCAAGGTGGAAATCAAACGGGC
>DOM16-113 (SEQ ID NO:283)
GACATCCAGATGACCCAGTCTCCATCTTCCCTGTCTGCATCTGTAGGAGACCGTGTCTCC
ATCACTTGCCGGGCAAGTCAGTGGATTGGGGAGAGTTAAATTGGTACCAGCAGAAACCA
GGGAAAGCCCCTAAGCTCCTGATCTATTGGGTTCCACGTTGCAAAGTGGGGTCCCATCA
CGTTTCAGTGGCAGTGGATCTGGGACAGATTTCACTCTCACCATCAGCAGTCTGCAACCA
GAAGATTTTGCTACGTACTACTGTCAACAGATTGCGCGGTATCCTGCGACGTTCGGCCAA
GGGACCAAGGTGGAAATCAAACGGGC
>DOM16-114 (SEQ ID NO:284)
GACATCCAGATGACCCAGTCTCCATCCTCCCTGTCTGCATCTGTAGGAGACCGTGTCACC
ATCACTTGCCGGGCAAGTCAGAATATTGGTGTGAATTTAATTTGGTACCAGCAGAAACCA
GGGAAAGCCCCTAGGCTCCTGATCTATTTTTCTTCCCTTTTGCAAAGTGGGGTCCCATCA
CGTTTCAGTGGCAGTGGATCTGGGACAGATTTCACTCTCACCATCAGCAGTCTGCAACCT
GAAGATTTTGCTACGTACTACTGTCAACAGGATTATGATGTTCCTCAGACGTTCGGCCAA
GGGACCAAGGTGGAAATCAAACGGGC
>DOM16-115 (SEQ ID NO:285)
GACATCCAGATGACCCAGTCTCCATCCTCCCTGTCTGCATCTGTAGGAGACCGTGTCACC
ATCACTTGCCGGGCAAGTCAGAATATTGGGAGTGGGTTACATTGGTACCAGCAGAAACCA
GGGAAAGCCCCTAAGCTCCTGATCGTTTCTTGGTCCGGTTTGCAAAGTGGGGTCCCATCA
CGTTTCAGTGGCAGTGGATCTGGGACAGATTTCACTCTCACCATCAGCAGTCTGCAACCT
GAAGATTTTGCTACGTACTACTGTGGTCAGGATGTGTTGGGTCCTCCTACGTTCGGCCAA
GGGACCAAGGTGGAAATCAAACGGGC

FIG. 9J

>DOM16-116 (SEQ ID NO:286)
GACATCCAGATGACCCAGTCTCCATCCTCCCTGTCTGCATCTGTAGGAGACCGTGTCACC
ATCACTTGCCGGGCAAGTCAGTGGATTGGGGCGTCGTTAGCTTGCAAAGTGGGGTCCCATCA
GGGAAAGCCCCTAAGCTCCTGATCTATTTTATGTCCGAGTTGCAAAGTGGGGTCCCATCA
CGTTTTAGTGGCAGTGGATCTGGGACAGATTTCACTCTCACCATCAGCAGTCTGCAACCT
GAAGATTTTGCTACGTACTACTGTCAACAGGATTATGGTTATCCTACTACGTTCGGCCAA
GGGACCAAGGTGGAAATCAAACGGGC
>DOM16-117 (SEQ ID NO:287)
GACATCCAGATGACCCAGTCTCCATCCTCCCTGTCTGCATCTGTAGGAGACCGTGTCACC
ATCACTTGCCGGGCAAGTCAGTGGATTGGTGTTAATTTATTGTGGTACCAGCAGAAACCA
GGGAAAGCCCCTAAGCTCCTGATCTATTATGGTTCCATTTTGCAAAGTGGGGTCCCATCA
CGTTTCAGTGGCAGTGGATCTGGGACAGATTTCACTCTCACCATCAGCAGTCTGCAACCT
GAAGATTTTGCTACGTACTACTGTCAACAGGATTATCATGGGCCTTATACGTTCGGCCAA
GGGACCAAGGTGGAAATCAAACGGGC
>DOM16-118 (SEQ ID NO:288)
GACATCCAGATGACCCAGTCTCCATCCTCCCTGTCTGCATCTGTAGGAGACCGTGTCACC
ATCACTTGCCGGACAAGTCAGGATATTGGGTCTCTGTTATCGTGGTACCAGCAGAAACCA
GGGAAAGCCCCTAAGCTCCTGATCTATATGGTTTCCATGTTGCAAAGTGGGGTCCCATCA
CGTTTCAGTGGCAGTGGATCTGGGACAGATTTCACTCTCACCATCAGCAGTCTGCAACCT
GAAGATTTTGCTACGTACTACTGTCAACATAATTCGTGGTATCCTATTACGTTCGGCCAA
GGGACCAAGGTGGAAATCAAACGGGC
>DOM16-119 (SEQ ID NO:289)
ACATCCAGATGACCCAGTCTCCATCCTCCCTGTCTGCATCTGTAGGAGACCGTGTCACC
ATCACTTGCCGGGCAAGTCAGTTTATTTATACTATGTTAAATTGGTACCAGCAGAAACCA
GGGAAAGCCCCTAAGCTCCTGATCTATAGGACGTCCTGGTTGCAAAGTGGGGTCCCATCA
CGTTTCAGTGGCAGTGGATCTGGGACAGATTTCACTCTCACCATCAGCAGTCTGCAACCT
GAAGATTTTGCTACGTACTACTGTCAACAGGATTATGCGTCGCCTTTTACGTTCGGCCAA
GGGACCAAGGTGGAAATCAAACGGGC
>DOM16-39-6 (SEQ ID NO:290)
GACATCCAGATGACCCAGTCTCCATCCTCCCTGTCTGCATCTGTTGGAGACCGTGTCACC
ATCACTTGCCGGGCAAGTCAGTGGATTGGTATTTTGTTAGATTGGTACCAGCAGAAACCA
GGGGAAGCCCCTAAGCTCCTGATCTATTATGCTTCCTTTTTGCAAAGCGGGGTCCCATCA
CGTTTCAGTGGCAGTGGATTTGGGACAGATTTCACTCTCACCATCAGCAGTCTGCAACCT
GAAGATTTTGCTACGTACTACTGTCAACAGGCTAATCCGGCGCCTCTGACGTTCGGCCAA
GGGACCAAGGTGGAAATCAAACGGGC
>DOM16-39-8 (SEQ ID NO:291)
GACATCCAGATGACCCAGTCTCCATCCTCCCTGTCTGCATCTGTAGGAGACCGTGTCACC
ATCACTTGCCGGGCAAGTCAGTGGATTGGTATTTTGATAGATTGGTACCAGCAGAAACCA
GGGGAAGCCCCTAAGCTCCTGATCTATTATGCTTCCTTTTTGCAAAGTGGGGTCCCATCA
CGTTTCAGTGGCAGTGGATCTGGGACAGATTTCACTCTCACCATCAGCAGTCTGCAACCT
GAAGATTCTGCTACGTACTACTGTCAACAGGCTAATCCGGCGCCTCTGACGTTCGGCCAA
GGGACCAAGGTGGAAATCAAACGGGC
>DOM16-39-34 (SEQ ID NO:292)
GACATCCAGTTGACCCAGTCTCCATCCTCCCTGTCTGCATCTGTAGGAGACCGAGTCACC
ATCACTTGCCGGGCAAGTCAGTGGATTGGTATTTTGTTAGATTGGTACCAGCAGAAACCA
GGGGAAGCCCCTAAGCTCCTGATCTATTATGCTTCCTTTTTGCAAAGTGGGGTCCCATCA
CGTTTCAGTGGCAGTGGATCTGGGACAGATTTCACTCTCACCATCAACAGTCTGCAACCT
GAAGATTTTGCTACGTACTACTGTCAACAGGCTAATCCGGCGCCTCTGACGTTCGGCCAA
GGGACCAAGGTGGAAATCAAACGGGC
>DOM16-39-48 (SEQ ID NO:293)
GACATCCAGATGACCCAGTCTCCATCCTTCCTGTCTGCATCTGTAGGAGACCGTGTCACC
ATCACTTGCCGGGCAAGTCAGTGGATTGGTATTTTGTTAGATTGGTACCAGCAGAAACCA
GGGGAAGCCCCTAAGCTCCTGATCTATTATGCTTCCTTTTTGCAAAGTGGGGTCCCATCA
CGTTTCAGTGGCAGTGGATCTGGGACAGATTTCACTCTCACCATCAGCAGTCTGCAACCT
GAAGATTTTGCTACGTACTACTGTCAACAGGCTAATCCGGCGCCTCTGACGTTAGGCCAA
GGGACCAAGGTGGAAATCAAACGGGC
>DOM16-39-87 (SEQ ID NO:294)
GACATCCAGATGACCCAGTCTCCATCCTCCCTGTCTGCATCTGTAGGAGACCGTGTCACC
ATCACTTGCCGGGCAAGTCAGTGGATTGGTATTTTGGTAGATTGGTACCAGCAGAAACCA
GGGGAAGCCCCTAAGCTCCTGATCTATTATGCTTCCTTTTTGCAAAGTGGGGTCCCATCA
CGTTTCAGTGGCAGTGGATCTGGGACAGATTTCACTCTCACCATCAGCAGTCTGCAACCT

FIG. 9K

GAAGATTTTGCTACGTACTACTGTCAACAGGCTAATCCGGCGCCTCTGAGGTTCGGCCAA
GGGACCAAGGTGGAAATCAAACGGGC
>DOM16-39-90 (SEQ ID NO:295)
GACATCCAGATGACCCAGTCTCCATCCTCCCTGTCTGCATCTGTAGGAGACCGTGTCACC
ATCACTTGCCGGGCAAGTCAGTGGATTGGTATTTTGTTAGATTGGTACCAGCAGAAACCA
GGGGAAGCCCCTAAGCTCCTGATCTATTATGCTTCCTTTTTGCAAAATGGGGTCCCATCA
CGTTTCAGTGGCAGTGGATCTGGGACAGATTTCACTCTCACCATCAGCAGTCTGCAACCT
GAAGATTTTGCTACGTACTACTGTCAACAGGCTAATCCGGCGCCTCTGACGTTCGGCCAA
GGGACCAAGGTGGAAATCAAACGGGC
>DOM16-39-96 (SEQ ID NO:296)
GACATCCAGATGATCCAGTCTCCATCCTCCCTGTCTGCATCTGTAGGAGACCGTGTCACC
ATCACTTGCCGGGCAAGTCAGTGGATTGGTATTTTGTTAGATTGGTACCAGCAGAAACCA
GGGGAAGCCCCTAAGCTCCTGATCTATTATGCTTCCTTTTTGCAAAGTGGGGTCCCATCA
CGTTTCAGTGGCAGTGGATCTGGGACAGATTTCACTCTCACCATCAGTAATCTGCAACCT
GAAGATTTTGCTACGTACTACTGTCAACAGGCTAATCCGGCGCCTCTGACGTTCGGCCAA
GGGACCAAGGTGGAAATCAAACGGGC
>DOM16-39-100 (SEQ ID NO:297)
GACATCCAGATGACCCAGTCTCCATCCTCCCTGTCTGCATCTGTGGGAGACCGTGTCACC
ATCACTTGCCGGGCAAGTCAGTGGATTGGTATTTTGGTAGATTGGTACCAGCAGAAACCA
GGGGAAGCCCCTAAGCTCCTGATCTATTATGCTTCCTTTTTGCAAAGTGGGGTCCCATCA
CGTTTCAGCGGCAGTGGATTTGGGACAGATTTCACTCTCACCATCAGCAGTCTGCATCCT
GAAGATTTTGCTACGTACTACTGTCAACAGGCTAATCCGGCGCCTCTGACGTTCGGCCAA
GGGACCAAGGTGGAAATCAAACGGGC
>DOM16-39-101 (SEQ ID NO:298)
GACATCCAGATGACCCAGTCTCCATCCTCCCTGTCTGCATCTGTAGGAGACCGTGTCACC
ATCACTTGCCGGGCAAGTCAGTGGATTGGTATTTTGTTAGATTGGTACCAGCAGAAACCA
GGGGAAGCCCCTAAGCTCCTGATCTATTATGCTTCCTTTTTGCAAAGTGGGGTCCCATCA
CGTTTCAGTGGCAGTGGATCTGGGACAGATTTCACTCTCACCATCAGCAATCTGCAACCT
GAAGATTTTGCTACGTACTACTGTCAACAGGCTGATCCGGCGCCTCTGACGTTCGGCCAA
GGGACCAAGGTGGAAATCAAACGGGC
>DOM16-39-102 (SEQ ID NO:299)
GACATCCAGATGACCCAGTCTCCATCTTCCCTGTCTGCATCTGTAGGAGACAGTGTCACC
ATCACTTGCCGGGCAAGTCAGTGGATTGGTATTTTGTTAGATTGGTACCAGCAGAAACCA
GGGGAAGCCCCTAAGCTCCTGATCTATTATGCTTCCTTTTTGCAAAGTGGGGTCCCATCA
CGTTTCAGTGGCAGTGGATCTGGGACAGATTTCACTCTCACCATCAGCAGTCTGCAACCT
GAAGATTTTGCTACGTACTACTGTCAACAGGCTAATCCGGCGCCTCTGACGTTCGGCCAA
GGGACAAAGGTGGAAATCAAACGGGC
>DOM16-39-103 (SEQ ID NO:300)
GACATCCAGATGACCCAGTATCCATCCTCCCTGTCTGCATCTGTAGGAGACCGTGTCACC
ATCACTTGCCGGGCAAGTCAGTGGATTGGTATTTTGTTAGATTGGTACCAGCAGAAACCA
GGGGAAGCCCCTAAGCTCCTGATCTATTATGCCTCCTTTTTGCAGAGTGGGGTCCCATCA
CGTTTCAGTGGCAGTGGATCTGGGACAGATTTCACTCTCACCATCAGCAGTCTGCAACCT
GAAGATTTTGGTACGTACTACTGTCAACAGGCTAATCCGGCGCCTCTGACGTTCGGCCAA
GGGACCAAGGTGGAAATCAAACGGGC
>DOM16-39-104 (SEQ ID NO:301)
GACATCCAGATGACCCAGTCTCCATCCTCCCTGTATGCATCTGTAGGAGACCGTGTCACC
ATCACTTGCCGGGCAAGTCAGTGGATTGGTATTTTGTTAGATTGGTACCAGCAGAAACCA
GGGGAAGCCCCTAAGCTCCTGATCTATTATGCTTCCTTTTTGCAAAGTGGGGTCCCATCA
CGTTTCAGTGGCAGTGGATCTGGGACAGATTTCACTCTCACCATCAGCAGTCTGCAACCT
GAAGATTTTGCTACGTACTACTGTCAACAGGCTAATCCGGCGCCTCTGACGTTCGGCCAA
GGGACCAAGGTGGAAATCAAACGGGC
>DOM16-39-105 (SEQ ID NO:302)
GACATCCAGATGACCCAGTCTCCATCCTCCCTGTCTGCATCTGTAGGAGACCGTGTCACC
ATCACTTGCCGGGCAAGTCAGTGGATTGGTATTTTGTTAGATTGGTACCAGCAGAAACCA
GGGGAAGCCCCTAAGCTCCTGATCTATTATGCTTCCTTTTTGCAAAGTGGGGTCCCATCA
CGTTTCAGTGGCAGTGGATCTGGGACAGATTTCACTCTCACCATCAGCAGTCTGCAACCT
GAAGATTTTGCTACGTACTACTGTCAACCGGCTAATCCGGCACCTCTGACGTTCGGCCAA
GGGACCAAGGTGGAAATCAAACGGGC
>DOM16-39-106 (SEQ ID NO:303)
GACATCCAGATGACCCAGTCTCCATCCTCCCTGTCTGCATCTGTAGGAGACCGTGTCACC
ATCACTTGCCGGTCAAGTCGGTGGATTGGTATTTTGTTAGATTGGTACCAGCAGAAACCA

FIG. 9L

GGGGAAGCCCCTAAGCTCCTGATCTATTATGCTTCCTTTTTGCAAAGTGGGGTCCCCTCA
CGTTTCAGTGGCAGTGGGTCTGGGACAGATTTCACTCTCACCATCAGCAGTCTGCAACCT
GAAGATGTTGCTACGTACTACTGTCAACAGGCTAATCCGGCGCCTCTGACGTTCGGCCAA
GGGACCAAGGTGGAAATCAAACGGGC
>DOM16-39-107 (SEQ ID NO:304)
GACATCCAGATGACCCAGTCTCCATCCTCCCTGTCTGCATCTGTAGGAGACCGTGTCACC
ATCACTTGCCGGGCAAGTCAGTGGATCGGTATTTTGGTAGATTGGTACCAGCAGAAACCA
GGGGAAGCCCCTAAGCTCCTGATCTATTATGCTTCCTTTTTGCAAAGTGGGGTCCCATCA
CGTTTCAGTGGCAGTGGATCAGGGACAGATTTCACTCTCACCATCAGCAGTCTGCAACCT
GAAGATTTTGCTACGTACTACTGTCAACAGGCTAATCCGGCGCCTCTGACGTTCGGCCAA
GGGACCAAGGTGGAAATCAAACGGGC
>DOM16-39-108 (SEQ ID NO:305)
GACATCCAGTTGACCCAGTCTCCATCCTCCCTGTCTGCATCTGTAGGAGACCGTGTCACC
ATCACTTGCCGGGCAAGTCAGTGGATTGGTATTTTGTTAGATTGGTACCAGCAGAAACCA
GGGGAAGCCCCTAAGCTCCTGATCTATTATGCTTCCTTTTTGCAAAGTGGGGTCCCATCA
CGTTTCAGTGGCAGTGGATCTGGGACAGATTTCACTCTCACCATCAGCAGTCTGCAACCT
GAAGATTTTGCTACGTACTATTGTCAACAGGCTAATCCGGCGCCTCTGACGTTCGGCCAA
GGGACCAAGGTGGAAATCAAACGGGC
>DOM16-39-109 (SEQ ID NO:306)
GACATCCAGATGACCCAGTCTCCAACCTCCCTGTCTGCATCTGTAGGAGACCGTGTCACC
ATCACTTGCCGGGCAAGTCAGTGGATTGGTAATTTGTTAGATTGGTACCAGCAGAAACCA
GGGGAAGCCCCTAAGCTCCTGATCTATTATGCTTCCTTTTTGCAAAGTGGGGTCCCATCA
CGTTTCAGTGGCGGTGGATTTGGGACAGATTTCACTCTCACCATCAGCAGTCTGCAACCT
GAAGATTTTGCTACGTACTACTGTCAACAGGCTAATCCGGCGCCTCTGACGTTCGGCCAA
GGGACCAAGGTGGAAATCAAACGGGC
>DOM16-39-110 (SEQ ID NO:307)
GACATCCAGATGACCCAGTCTCCATCCTCCCTGTCTGCATCTGTAGGAGACCGTGTCACC
ATCACTTGCCGGGCAAGTCAGTGGATTGGTATTTTGTTAGATTGGTACCAGCAGAAACCA
GGGGAAGCCCCTAAGCTCCTGATCTATTATGCTTCCTTTTTGCAAAGTGGGGTCCCATCA
CGTTTCAGTGGCAGTGGATCTGGGACAGATTTCACTCTCACCATCAGCAGTCTGCAACCT
GAAGATTTTGCTACGTACTACTGTCAACAGGCTAATCCGGCGCCTCCGACGTTCGGCCAA
GGGACCAAGGTGGAAATCAAACGGGC
>DOM16-39-111 (SEQ ID NO:308)
GACATCCAGATGACCCAGTCTCCATCCTCCCTGTCTGCATCTGTAGGAGACCGTGTCACC
ATCACTTGCCGGGCAAGTCAGTGGATTGGTATTTTGTTAGATTGGTACCAGCAGAAACCA
GGGGAAGACCCTAAGCTCCTGATCTATTATGCTTCCTTTTTGCAAAGTGGGGTCCCATCA
CGTTTCAGTGGCAGTGGATCTGGGACAGATTTCACTCTCACCATCAGCAGTCTGCAACCT
GAAGATTTTGCTACGTACTACTGCCAACAGGCTAATCCGGCGCCTCTGACGTTCGGCCAA
GGGACCAAGGTGGAAATCAAACGGGC
>DOM16-39-112 (SEQ ID NO:309)
GACATCCAGATGACCCAGTCTCCAACCTCCCTGTCTGCATCTGTAGGAGACCGTGTCACC
ATCACTGCAGGGCAAGTCAGTGGATTGGTATTTTGTTAGATTGGTACCAGCAGAAACCA
GGGGAAGCCCCTAAGCTCCTGATCTATTATGCTTCCTTTTTGCAAAGTGGGGTCCCATCA
CGTTTCAGTGGCAGTGGATCTGGGACAGATTTCACTCTCACCATCAGCAGTCTGCAACCT
GAAGATTTTGCTACGTACTACTGTCAACAGGCTAATCCGGCGCCTCTGACGTTCGGCCAA
GGGACCAAGGTGGAAATCAAACGGGC
>DOM16-39-113 (SEQ ID NO:310)
GACATCCAGATGACCCAGTCTCCATCCTCCCTGTCTGCATCTGTAGGAGACCGTGTCACC
ATCACTTGCCGGGCAAGTCAGTGGATTGGTATTTTGGTAGATTGGTACCAGCAGAAACCA
GGGGAAGCCCCTAAGCTCCTGATCTATTATGGTTCCTTTTTGCAAAGTGGGGTCCCATCA
CGTTTCAGTGGCAGTGGATCTGGGACAGATTTCACTCTCACCATCAGCAGTCTGCAACCT
GAAGATTTTGCTACGTACTACTGTCAACAGGCTAATCCGGCGCCTCTGACGTTCGGCCAA
GGGACCAAGGTGGAAATCAAACGGGC
>DOM16-39-114 (SEQ ID NO:311)
GACATCCAGATGACCCAGTCTCCATCCTCCCTGTCTGCATCTGTAGGAGACCGTGTCACC
ATCACTTGCCGGGCAAGTCAGTGGATTGGTATTTTGTTAGATTGGTACCAGCAGAAACCA
GGGGAAGCCCCTAAGCTCCTGATCTATTATGCTTCCTTTTTGCAAAGTGGGGTCCCATCA
CGTTTCAGTGGCAGTGGATCTGGGACAGATTTCACTCTCACCATCAGCAGTCTGCAACCT
GAAGATTTTGCTACGTACTACTGTCAACAGGCTAATCCGGCGCCTCTGACGTTCGGCCAA
GGGACCAAGGTGGAAATCAGACGGGC
>DOM16-39-115 (SEQ ID NO:312)

FIG. 9M

GACATCCAGATGACCCAGTCTCCATCCTCCCTGTCTGCATCTGTAGGAGACCGTGTCACC
ATCACTTGCCGGGCAAGTCAGTGGATTGGTATTTTGTTAGATTGGTACCAGCAGAAACCA
GGGGAAGCCCCTAAGCTCCTGATCTATTATGCTTCCTTTTTGCAAAGTGGGGTCCCATCA
CGTTTCAGTGGCAGTGGATATGGGACAGATTTCACTCTCACCATCAGCAGTTTGCAACCT
GAAGATTTTGCTACGTACTACTGCCAACAGGCTAATCCGGCGCCTCTGACGTTCGGCCAA
GGGACCAAGGTGGAAATCAAACGGGC
>DOM16-39-116 (SEQ ID NO:313)
GACATCCAGATGACCCAGTCTCCATCCTCCCTGTCTGCATCTGTAGGAGACCGTGTCACC
ATCACTTGCCGGGCAAGTCAGTGGATTGGTATTTTGTTAGATTGGTATCAGCAGAAACCA
GGGGAAGCCCCTAAGCTCCTGATCTATTATGCTTCCTTTTTGCAAAGTGGGGTCCCATCA
CGTTTCAGTGGCAGTGGATCTGGGACAGATTTCACTCTCACCATCAGCAGTCTGCAACCT
GAAGATTTTGCTACGTACTACTGTCAACAGGCTAATCCGGCGCCTCTGACGTTCGGCCAA
GGGACCAAGGTGGAAATGAAACGGGC
>DOM16-39-117 (SEQ ID NO:314)
GACATCCAGATGACCCAGTCTCCATCCTCCCTGTCTGCATCTGTAGGAGACCGTGTCACC
ATCACTTGCCGGGCAAGTCAGTGGATTGGTATTTTGTTAGATTGGTACCAGCAGAAACCA
GGGGAAGACCCTAAGCTCCTGATCTATTATGCTTCCTTTTTGCAAAGTGGGGTCCCATCA
CGTTTCAGTGGCAGCGGATCTGGGACAGATTTCACTCTCACCATCAGCAGTCTGCAACCT
GAAGATTTTGCTACGTACTACTGTCAACAGGCTAATCCGGCGCCTCTGATGTTCGGCCAA
GGGACCAAGGTGGAAATCAAACGGGC
>DOM16-39-200 (SEQ ID NO:315)
GACATCCAGATGACCCAGTCTCCATCCTCCCTGTCTGCATCTGTAGGAGACCGTGTCACC
ATCACTTGCCGGGCAAGTCAGTGGATTGGTATTTTGTTAGATTGGTACCAGCAGAAACCA
GGGAAAGCCCCTAAGCTCCTGATCTATTATGCTTCCTTTTTGCAAAGTGGGGTCCCATCA
CGTTTCAGTGGCAGTGGATCTGGGACAGATTTCACTCTCACCATCAGCAGTCTGCAACCT
GAAGATTTTGCTACGTACTACTGTCAACAGGCTAATCCGGCGCCTCTGACGTTCGGCCAA
GGGACCAAGGTGGAAATCAAACGGGC
>DOM16-39-201 (SEQ ID NO:316)
GACATCCAGATGACCCAGTCTCCATCCTCCCTGTCTGCATCTGTAGGAGACCGTGTCACC
ATCACTTGCCGGGCAAGTCAGTGGATTGGTATTTTGGTAGATTGGTACCAGCAGAAACCA
GGGAAAGCCCCTAAGCTCCTGATCTATTATGCTTCCTTTTTGCAAAGTGGGGTCCCATCA
CGTTTCAGTGGCAGTGGATCTGGGACAGATTTCACTCTCACCATCAGCAGTCTGCAACCT
GAAGATTTTGCTACGTACTACTGTCAACAGGCTAATCCGGCGCCTCTGACGTTCGGCCAA
GGGACCAAGGTGGAAATCAAACGGGC
>DOM16-39-202 (SEQ ID NO:317)
GACATCCAGATGACCCAGTCTCCATCCTCCCTGTCTGCATCTGTAGGAGACCGTGTCACC
ATCACTTGCCGGGCAAGTCAGTGGATTGGTATTTTGTTAGATTGGTACCAGCAGAAACCA
GGGAAAGCCCCTAAGCTCCTGATCTATTATGCTTCCTTTTTGCAAAGTGGGGTCCCATCA
CGTTTCAGTGGCAGTGGATCTGGGACAGATTTCACTCTCACCATCAGCAGTCTGCAACCT
GAAGATTTTGCTACGTACTACTGTCAACAGGCTAATCCGGCGCCTCTGAGGTTCGGCCAA
GGGACCAAGGTGGAAATCAAACGGGC
>DOM16-39-203 (SEQ ID NO:318)
GACATCCAGATGACCCAGTCTCCATCCTCCCTGTCTGCATCTGTAGGAGACCGTGTCACC
ATCACTTGCCGGGCAAGTCAGTGGATTGGTATTTTGATAGATTGGTACCAGCAGAAACCA
GGGAAAGCCCCTAAGCTCCTGATCTATTATGCTTCCTTTTTGCAAAGTGGGGTCCCATCA
CGTTTCAGTGGCAGTGGATCTGGGACAGATTTCACTCTCACCATCAGCAGTCTGCAACCT
GAAGATTTTGCTACGTACTACTGTCAACAGGCTAATCCGGCGCCTCTGACGTTCGGCCAA
GGGACCAAGGTGGAAATCAAACGGGC
>DOM16-39-204 (SEQ ID NO:319)
GACATCCAGATGACCCAGTCTCCATCCTCCCTGTCTGCATCTGTAGGAGACCGTGTCACC
ATCACTTGCCGGGCAAGTCAGTGGATTGGTAATTTGGTAGATTGGTACCAGCAGAAACCA
GGGAAAGCCCCTAAGCTCCTGATCTATTATGCTTCCTTTTTGCAAAGTGGGGTCCCATCA
CGTTTCAGTGGCAGTGGATCTGGGACAGATTTCACTCTCACCATCAGCAGTCTGCAACCT
GAAGATTTTGCTACGTACTACTGTCAACAGGCTAATCCGGCGCCTCTGACGTTCGGCCAA
GGGACCAAGGTGGAAATCAAACGGGC
>DOM16-39-205 (SEQ ID NO:320)
GACATCCAGATGACCCAGTCTCCATCCTCCCTGTCTGCATCTGTAGGAGACCGTGTCACC
ATCACTTGCCGGGCAAGTCAGTGGATTGGTAATTTGGTAGATTGGTACCAGCAGAAACCA
GGGAAAGCCCCTAAGCTCCTGATCTATTATGCTTCCTTTTTGCAAAGTGGGGTCCCATCA
CGTTTCAGTGGCAGTGGATCTGGGACAGATTTCACTCTCACCATCAGCAGTCTGCAACCT
GAAGATTTTGCTACGTACTACTGTCAACAGGCTAATCCGGCGCCTCCGACGTTCGGCCAA

FIG. 9N

```
GGGACCAAGGTGGAAATCAAACGGGC
>DOM16-39-206 (SEQ ID NO:321)
GACATCCAGATGACCCAGTCTCCATCCTCCCTGTCTGCATCTGTAGGAGACCGTGTCACC
ATCACTTGCCGGGCAAGTCAGTGGATTGGTATCAACTTAGACTGGTACCAGCAGAAACCA
GGGAAAGCCCCTAAGCTCCTGATCTATTATGCTTCCTTTTTGCAAAGTGGGGTCCCATCA
CGTTTCAGTGGCAGTGGATCTGGGACAGATTTCACTCTCACCATCAGCAGTCTGCAACCG
GAAGATTTTGCTACGTACTACTGTCAACAGGCTAATCCGGCGCCTCTGACGTTCGGCCAA
GGGACCAAGGTGGAAATCAAACGGGC
>DOM16-39-207 (SEQ ID NO:322)
GACATCCAGATGACCCAGTCTCCATCCTCCCTGTCTGCATCTGTAGGAGACCGTGTCACC
ATCACTTGCCGGGCAAGTCAGAACATTGGCAACTTGTTAGATTGGTACCAGCAGAAACCA
GGGAAAGCCCCTAAGCTCCTGATCTATTATGCTTCCTTTTTGCAAAGTGGGGTCCCATCA
CGTTTCAGTGGCAGTGGATTTGGGACAGATTTCACTCTCACCATCAGCAGTCTGCAACCT
GAAGATTTTGCTACGTACTACTGTCAACAGGCTAATCCGGCGCCTCTGACGTTCGGCCAA
GGGACCAAGGTGGAAATCAAACGGGC
>DOM16-39-209 (SEQ ID NO:323)
GACATCCAGATGACCCAGTCTCCATCCTCCCTGTCTGCATCTGTAGGAGACCGTGTCACC
ATCACTTGCCGGGCAAGTCAGTGGATTGGTATCAACTTAGACTGGTACCAGCAGAAACCA
GGGAAAGCCCCTAGGCTCCTGATCTATTATGCTTCCTTTTTGCAAAGTGGGGTCCCATCA
CGTTTCAGTGGCAGTGGATCTGGGACAGATTTCACTCTCACCATCAGCAGTCTGCAACCT
GAAGATTTTGCTACGTACTACTGTCAACAGGCTAATCCGGCGCCTCTGACGTTCGGCCAA
GGGACCAAGGTGGAAATCAAACGGGC
>DOM16-52 (SEQ ID NO:324)
GAGGTGCAGCTGTTGGAGTCTGGGGGAGGCTTGGTACAGCCTGGGGGGTCCCTGCGTCTC
TCCTGTGCTGCCTCCGGATTCACCTTTGCTGAGCAGCCGATGACTTGGGCCCGCCAGGCT
CCAGGGAAGGGTCTAGAGTGGGTCTCAAGTATTTCTAGTTTTGGTGATCTTACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGAAAGGTGTG
TATCGGATTAGTCGGTTTGACTACTGGGGTCAGGGAACCCTGGTCACCGTCTCGAGC
```

FIG. 9O

DOM16-17 (SEQ ID NO:325)
DIQMTQSPSSLSASVGDRVTITCRASQYIGAELSWYQQKPGKAPKLLIYW
ISELQSGVPSRFSGSGSGTDFTLTISSLQPEDFATYYCQQSSNTPYTFGQ
GTKVEIKR
DOM16-18 (SEQ ID NO:326)
DIQMTQSPSSLSASVGDRVTITCRASQYIGINLIWYQQKPGKAPKLLIYW
ASVLQSGVPSRFSGSGSGTDFTLTISSLQPEDFATYYCQQSVYDPPTYGQ
GTKVEIKR
DOM16-19 (SEQ ID NO:327)
DIQMTQSPSSLSASVGDRVTITCRASQDIFWLLSWYQQKPGKAPTLLIYS
TSILQSGVPSRFSGSGSGTDFTLTISSLQPEDFATYYCQQYYLDPPTFSQ
GTKVEIKR
DOM16-20 (SEQ ID NO:328)
DIQMTQSPSSLSASVGDRVTITCRASQFIGVNLNWYQQKPGKAPRLLIYL
SSILQSGVPSRFSGSGSGTDFTLTISSLQPEDFATYYCQQTYDIPTTFGQ
GTKVEIKR
DOM16-21 (SEQ ID NO:329)
DIQMTQSPSSLSASVGDRVTITCRASQNIGINLQWYQQKPRKAPKLLIYY
ASILQSGVPSRFSGSGSGTDFTLTISSLQPEDFATYYCQQDYDTPFTFGQ
GTKVEIKR
DOM16-22 (SEQ ID NO:330)
DIQMTQFPSSLSASVGDRVTITCRASQHIERWLNWYQQKPGKAPKLLIYR
SSYLQSGVPSRFSGSGSGTDFTLTISSLQPEDFATYYCQQDAILPHTFGQ
GTKVEIKR
DOM16-23 (SEQ ID NO:331)
DIQMTQSPSSLSASVGDRVTITCRASQGIGVNLQWYQQKPGKAPKLLIYF
SSVLQSGVPSRFSGSGSGTDFTLTISSLQPEDFATYYCQQDFDFPQTFGQ
GTKVEIKR
DOM16-24 (SEQ ID NO:332)
DIQMTQSPSSLSASVGDRVTITCRASQNIGINLQWYQQKPRKAPKLLIYY
ASILQSGVPSRFSGSGSGTDFTLTISSLQPEDFATYYCQQEYDYPNTFGQ
GTKVEIKR
DOM16-25 (SEQ ID NO:333)
DIQMTQSPSSLSASVGDRVTITCRASSSIGSGLEWYQQKPGKAPKLLIVG
WSGLQSGVPSRFSGSGSGTDFTLTISSLQPEDFATYYCRQCVGLPCTFGQ
GTKVEIKR
DOM16-26 (SEQ ID NO:334)
DIQMTQSPSSLSASVGDRVTITCRASQWIGVELSWYQQKPGKAPKLLIYW
GSELQSGVPSRFSGSGSGTDFTLTISSLQPEDFATYYCQQLALPPFTFGQ
GTKVEIKR
DOM16-27 (SEQ ID NO:335)
DIQMTQSPSSLSASVGDRVTITCRASHDIGVSLDWYQQKPGKAPKLLIVW
ASVLQSGVPSRFSGSGSGTDFTLTISSLQPEDFATYYCLQVGAGPMTFGQ
GTKVEIKR
DOM16-28 (SEQ ID NO:336)
DIQMTQSPSSLSASVGDGVTITCRASQYIGIDLAWYQRKPGKAPRLLIYK
ASALQSGVPSRFSGSGSGTDFTLTISSLQPEDFATYYCQQYADYPATFGQ
GTKVEIKR
DOM16-29 (SEQ ID NO:337)
DIQMTQSPSSLSASVGDRVTITCRASQEIEHYLSWYQQKPGKAPKLLIYL
SSRLQSGVPSRFSGSGSGTDFTLTISSLQPEDFATYYCQQNVQLPITFGQ
GTKVEIKR
DOM16-30 (SEQ ID NO:338)
DIQMTQSPSSLSASVGDRVTITCRASQEIGVSLSWYQQKPGKAPKLLIYW
GSELQSGVPSRFSGSGSGTDFTLTISSLQPEDFATYYCQQDHNWPMTFGQ
GTKVEIKR
DOM16-31 (SEQ ID NO:339)
DIQMTQSPSSLSASVGDRVTITCRASALIMGDLDWYQQKPGKAPKLLIAG
VSFLQSGVPSRFSGSGSGTDFTLTISSLQPEDFATYYCAQSRSWPYTFGQ

FIG. 10A

GTKVEIKR
DOM16-32 (SEQ ID NO:340)
DIQMTQSPSSLSASVGDRVTITCRASKMIDENLAWYQQKPGKAPKLLILR
SSGLQSGVPSRFSGSGSGTDFTLTISSLQPEDFATYYCHQGHSAPGTFGQ
GTKVEIKR
DOM16-33 (SEQ ID NO:341)
DIQMTQSPSSLSASVGDRVTITCRASRYIGVSLDWYQQKPGKAPKLLIMW
GSALQSGVPSRFSGSGSGTDFTLTISSLQPEDFATYYCLQSAAPPATFGQ
GTKVEIKR
DOM16-35 (SEQ ID NO:342)
DIQMTQSPSSLSASVGDRVTITCRASQEIGVSLSWYQQKPGKAPKLLIYW
ASALQSGVPSRFSGSGSGTDFTLTISSLQPEDFATYYCQQSYLPPDTFGQ
GTKVEIKR
DOM16-37 (SEQ ID NO:343)
DIQMTQSPSSLSASVGDRVTITCRASQEIASDLLWYQQKPGKAPKLLIYN
GSSLQSGVPSRFSGSGSGTDFTLTISRLQPEDFATYYCQWLWSEPLTFGQ
GTKVEIKR
DOM16-38 (SEQ ID NO:344)
DIQMTQSPSSLSASVGDRVTITCRASQHIGDALWWYQQKPGKAPKLLIYW
TSNLQSGVPSRFSGSGSGTDFTLTISSLQPEDFATYYCQQTIRRPYTFGQ
GTKVKIKR
DOM16-39 (SEQ ID NO:345)
DIQMTQSPSSLSASVGDRVTITCRASQWIGILLDWYQQKPGEAPKLLIYY
ASFLQSGVPSRFSGSGSGTDFTLTISSLQPEDFATYYCQQANPAPLTFGQ
GTKVEIKR
DOM16-40 (SEQ ID NO:346)
DIQMTQSPSSLSASVGDRVTITCRASQNIGINLQWYQQKPRKAPKLLIYY
ASILQSGVPSRFSGSGSGTDFTLTISSLQPEDFATYYCQQSYDLPKTFGQ
GTKVEIKR
DOM16-41 (SEQ ID NO:347)
DIQMIQSPSSLSASVGDRVTITCRASQEIGVSLSWYQQKPGKAPKLLIYW
GSELQSGVPSRFSGSGSGTDFTLTISSLQPEDFATYYCQQWYGWPDTFGQ
GTKVGIKR
DOM16-42 (SEQ ID NO:348)
DIQMTQSPSSLSASVGDRVTITCRASQHIGIELNWYQQKPGKAPKLLIYW
ASVLQSGVPSRFSGSGSGTDFTLTISSLQPEDFATYYCQQSVYVPTTFGQ
GTKVEIKR
DOM16-43 (SEQ ID NO:349)
DIQMTQSPSSLSASVGDRVTITCRASQWIGAELVWYQQKPGKAPKLLIYW
SSVLQSGVPSRFSGSGSGTDFTLTISSLQPEDFATYYCQQAAHSPPTFGQ
GTKVEIKR
DOM16-44 (SEQ ID NO:350)
DIQMTQSPSSLSASVGDRVTITCRASQDISRSLAWYQRKPGKAPRLLIYM
SSTLQSGVPSRFSGSGSGTDFTLTISSLQPEDFATYYCQQYDSYPSTFGQ
GTKVEIKR
DOM16-45 (SEQ ID NO:351)
DIQMTQSPSSLSASVGDRVTITCRASRMIGGMLLWYQQKPGKAPKLLITY
GSVLQSGVPSRFSGSGSGTDFTLTISSLQPEDFATYYCAQEFWWPHTFGQ
GTKVEIKR
DOM16-46 (SEQ ID NO:352)
DIQMTQSPSSLSASVGDRVTITCRASRPIGDRLTWYQQKPGKAPKLLISW
VSVLQSGVPSRFSGSGSGTDFTLTISSLQPEDFATYYCRQLGGGPFTFGQ
GTKVEIKR
DOM16-47 (SEQ ID NO:353)
DIQMTQSPSSLSASVGDRVTITCRASQYIGVSLSWYQQKPGKAPKLLIYF
ASALQSGVPSRFSGSGSGTDFTLTISSLQPEDFATYYCQQDRDWPATFGQ
GTKVEIKR
DOM16-48 (SEQ ID NO:354)
DIQMTQSPSSLSASVGDRVTITCRASGAIGDRLKWYQQKPGKAPKLLISW
ASVLQSGVPSRFSGSGSGTDFTLTISSLQPEDFATYYCVQGPGVPLTFGQ

FIG. 10B

GTKVEIKR
DOM16-49 (SEQ ID NO:355)
DIQMTQSPSSLSASVGDRVTITCRASQPIARWLAWYQQKPGKAPKLLIYG
SSVLQSGVPSRFSGSGSGTDFTLTISSLQPEDFATYYCQQDLRLPPTFGQ
GTKVEIKR
DOM16-50 (SEQ ID NO:356)
DIQMTQSPSSLSASVGDRVTITCRASQNIGVSLSWYQQKPGKAPRLLIYY
GSNLLSGVPSRFSGSGSGTDFTLTISSLQPEDFATYYCQQEFSWPVTFGQ
GTKVEIKR
DOM16-59 (SEQ ID NO:357)
DIQMTQSPSSLSASVGDRVTITCRASLPIDDGLGWYQQKPGKAPKLLICG
VSGLQSGVPLRFSGSGSGTDFTLTISSLQPEDFATYYCGQGQVQPSTFGQ
GTKVEIKR
DOM16-60 (SEQ ID NO:358)
DIQMTQSPSSLSASVGDRVTITCRASQNIGINLQWYQQKPRKAPKLLIYY
ASILQSGVPSRFSGSGSGTDFTLTISSLQPEDFATYYCQQSYDAPTTFGQ
GTKVEIKR
DOM16-61 (SEQ ID NO:359)
DIQMTQSPSSLSASVGDRVTITCRASQSIGVNLMWYQQKPGKAPKLLIYF
ASILQSGVPSRFSGSGSGTDFTLTISSLQPEDFATYYCQQNYDIPKTFGQ
GTKVEIKR
DOM16-62 (SEQ ID NO:360)
DIQMTQSPSSLSASVGDRVTITCRASQWIGISLSWYQQKPGKAPKLLIYY
GSVLQSGVPSRFSGSGSGTDFTLTISSLQPEDFATYYCQQSHDLPVTFGQ
GTKVEIKR
DOM16-63 (SEQ ID NO:361)
DIQMTQSPSSLSASVGDRVTITCRASQWIGVSLSWYQQKPGKAPKLLIYY
ASILQSGVPSRFSGSGSGTDFTLTISSLQPEDFATYYCQQEMSYPPTFGQ
GTKVEIKR
DOM16-64 (SEQ ID NO:362)
DIQMTQSPSSLSASVGDRVTITCRASQDIGVSLEWYQQKPGKAPKLLIYW
SSALQSGVPSRFSGSGSGTDFTLTISSLQPEDLATYYCQQGHTYPSTFGQ
GTKVEIKR
DOM16-65 (SEQ ID NO:363)
DIQMTQSPSSLSASVGDRVTITCRASQYIGVYLSWYQQKPGKAPKLLIYW
ASLLQSGVPSRFSGSGSGTDFTLTISSLQPEDFATYYCQQTVRDPITFGQ
GTKVEIKR
DOM16-66 (SEQ ID NO:364)
DIQMTQSPSFLSASVGDRVTITCRASQSIYTMLNWYQQKPGKAPKLLIYR
ASYLQSGVPSRFSGSGSGTDFTLTISSLLPEDSATYYCQQDFSYPSTFGQ
GTKVEIKR
DOM16-67 (SEQ ID NO:365)
DIQMTQSPSSLSASVGDRVTITCRASQYIGANLSWYQQKPGKAPKLLIYY
ISVLQSGVPSRFSGSGSGTDFTLTISSLQPEDFATYYCQQELYTPHTFGQ
GTKVEIKR
DOM16-68 (SEQ ID NO:366)
DIQLTQSPSSLSASVGDRVTITCRASQYIGVTLMWYQQKPGKAPKLLIYY
ASQLQSGVPSRFSGSGSGTDFTLTISSLQPEDFATYYCQQEVSYPYTFGQ
GTKVEIKR
DOM16-69 (SEQ ID NO:367)
DIQMTQSPSSLSASVGDRVTITCRASQHIGVSLTWYQQKPGKAPKLLIYF
ASILQSGVPSRFSGSGSGTDFTLTISSLQPEDYATYYCQQDMSYPPTFGQ
GTKVGIKR
DOM16-70 (SEQ ID NO:368)
DIQMTQSPSSLSASVGDRVTITCRASQDIGISLEWYQQKPGKAPKLLIYF
ASQLQSGVPSRFSGSGSGTDFTLTISSLQPEDFATYYCQQVYDFPNTFGQ
GTKVEIKR
DOM16-71 (SEQ ID NO:369)
DIQMTQSPSSLSASVGDRVTITCRASQHIGVSLNWYQQKPGKVPKLLIYW
ASILQSGVPSRFSGSGSGTDFTLTISSLQPEDFATYYCQQEHTIPSTFGQ

FIG. 10C

```
GTKVEIKR
DOM16-72 (SEQ ID NO:370)
DIQMTQSPSSLSASVGDRVTITCRASQHIGVSLDWYQQKPGKAPKLLIYY
GSELQSGVPSRFSGSGSGTDFTLTISSLQPEDFATYYCQQYVTHPTTFGQ
GTKVEIKR
DOM16-73 (SEQ ID NO:371)
DIQMTQSPSSLSASVGDRVTITCRASQRIGMMLDWYQQKPGKAPKLLIYG
GSKLQSGVPSRFSGSGSGTDFTLTISSLQPEDFATYYCQHRGWYPLTFGQ
GTKVEIKR
DOM16-74 (SEQ ID NO:372)
DIQMTQSPSSLSASVGDRVTITCRASQPIGDRLSWYQQKPGKAPKLLIYF
SSVLQSGVPSRFSGSGSGTDFTLTISSLQPEDFATYYCQQHGLRPDTFGQ
GTKVEIKR
DOM16-75 (SEQ ID NO:373)
DIQMTQSPSSLSASVGDRVTITCRASQWIGSSLMWYQQKPGKAPKLLIYW
ASELQSGVPSRFSGSGSGTDFTLTISSLQPEDFATYYCQQEYSYPSTFGQ
GTKVEIKR
DOM16-76 (SEQ ID NO:374)
DIQMTQSPSSLSASVGDRVTITCRASQDIGVSLAWYQQKPGKAPKLLIYF
GSVSLSGVPSRFSGSGSGTDFTLTISSLQPEDFATYYCQQSHLPPTTFGQ
GTKVEIKR
DOM16-77 (SEQ ID NO:375)
DIQMTQSPSSLSASVGDRVTITCRASQWIGVELNWYQQKPGKAPKLLIYW
TSILQSGVPSRFSGSGSGTDFTLTISSLQPEDFATYYCQQVINSPYTFGQ
GTKVEIKR
dom16-78 (SEQ ID NO:376)
DIQMTQSPSSLSASVGDRVTITCRASQDIGKWLEWYQQKPGKAPKLLIGA
TSWLQSGVPSRFSGSGSGTDFTLTISSLQPEDFATYYCVQQGRRPGTFGQ
GTKVEIKR
DOM16-79 (SEQ ID NO:377)
DIQMTQSPSSLSASVGDRVTITCRASQWIGILLDWYQQKPGEAPKLLIYY
ASFLQSGVPSRFSGSGSGTDFTLTISSLQPEDFATYYCQRSDLSPLTFGQ
GTKVEIKR
DOM16-80 (SEQ ID NO:378)
DIQMTQSPSSLSASVGDRVTITCRASQNIYMNLEWYQQKPGKAPKLLIVF
GSWLQSGVPSRFSGSGSGTDFTLTISSLQPEDFATYYCRQTEAPPSTFGQ
GTKVEIKR
DOM16-81 (SEQ ID NO:379)
DIRMTQSPSSLSASVGDRVTITCRASQHIGSSLSWYQQKPGKAPKLLIYY
ASVLQSGVPSRFSGSGSGTDFTLTISSLQPEDFATYYCQQEYSWPPTLGQ
GTKVEIKR
DOM16-82 (SEQ ID NO:380)
DIQMTQSPSSLSASVGDRVTITCRASQDIRTLLRWYQQKPGKAPKLLIYW
SSELQSGVPSRFSGSGSGTDFTLTISSLQPEDFATYYCQQTFHAPNTFGQ
GTKVEIKR
DOM16-83 (SEQ ID NO:381)
DIRMTQSPSSLSASVGDRVTITCRASQYIGKYLSWYQQKPGKAPKLLIYL
SSTLQSGVPSRFSGSGSGTDFTLTISSLQPEDFATYYCQQNDRLPLTLGQ
GTKVEIKR
DOM16-84 (SEQ ID NO:382)
DIQMTQSPSSLSASVGDRVTITCQASQLIGNMLSWYQQKPGKAPTLLIYI
GSSLQSGVPSRFSGSGSGTDFTLTISSLQPEDFATYYCQQTYFDPPTFGQ
GTKVEIKR
DOM16-85 (SEQ ID NO:383)
DIQMTQSPSSLSASVGDRVTITCRASQYIGINLRWYQQKPGKAPKLLIYY
SSTLLSGVPSRFSGSGSGTDFTLTISSLQPEDFATYYCQQSYDSPVTFGQ
GTKVEIKR
DOM16-87 (SEQ ID NO:384)
DIQMTQSPSSLSASVGDRVTITCRASWAIGDRLEWYQQKPGKAPKLLIAW
GSVLQSGVPSRFSGSGSGTDFTLTISSLQPEDFATYYCSQLGSRPRTFGQ
```

FIG. 10D

```
GTKVEIKR
DOM16-88 (SEQ ID NO:385)
DIQMTQSPSSLSASVGDRVTITCRASQSIDNWLAWYQQKPGEAPKLLIYG
TSRLQSGVPSRFSGSGSGTDFTLTISSLQPEDFATYYCQQYNFFPSTFGQ
GTKVEIKR
DOM16-89 (SEQ ID NO:386)
DIQMTQSPSSLSASVGDRVTITCRASTFIGNVLNWYQQKPGKAPKLLISY
VSMLQSGVPSRFSGSGSGTDFTLTISSLQPEDFATYYCCQSYDVPFTFGQ
GTQVEIKR
DOM16-90 (SEQ ID NO:387)
DIQMTQSPSSLSASVGDRVTITCRASQWIGVSLVWYQQKPGKAPKLLIYW
ASVLQSGVPSRFSGSGSGTDFTLTISSLQPEDFATYYCQQTHAGPHTFGQ
GTKVEIKR
DOM16-91 (SEQ ID NO:388)
DIQMTQSPSSLSASVGDRVTITCRASQWIGILLDWYQQKPGEAPKLLIYY
ASFLQSGVPSRFSGSGSGTDFTLTISSLQPEDFATYYCQQSSVDPLTFGQ
GTKVEIKR
DOM16-92 (SEQ ID NO:389)
DIQMTQSPSSLSASVGDRVTITCRASQDIGVSLRWYQQKPGKAPKLLIYW
ASELQSGVPSRFSGSGSGTDFTLTISSLQPEDFATYYCQQLYDYPPTFGQ
GTKVEIKR
DOM16-94 (SEQ ID NO:390)
DIQMTQSPSSLSASVGDRVTITCRASRFIASGLDWYQQKPGKAPKLLISR
FSGLQSGVPSRFSGSGSGTDFTLTISSLQPEDFATYYCKQGFGAPATFGQ
GTKVEIKR
DOM16-95 (SEQ ID NO:391)
DIQMTQSPSSLSASVGDRVTITCRASQYISTELEWYQQKPGKAPKLLIYS
SSMLQSGVPSRFSGSGSGTDFTLTISSLQPEDFATYYCQQSASALPLTFG
QGTKVEIKR
DOM16-96 (SEQ ID NO:392)
DIQMTQSPSSLSASVGDRVTITCRASQWIGASLQWYQQKPGQAPKLLIYY
MSVLQSGVPSRFSGSGSGTDFTLTISSLQPEDFATYYCQQTALTPATFGQ
GTKVEIKR
DOM16-97 (SEQ ID NO:393)
DIQMTQSPSSLSASVGDRVTITCRASQVIGDYLSWYQQKPGKAPKLLIYF
RSVLQSGVPSRFSGSGSGTDFTLTISSLQPEDFATYYCQQNWNLPVTFGQ
GTKVEIKR
DOM16-98 (SEQ ID NO:394)
DIQMTQSPSSLSASVGDRVTITCRASQYIGVNLSWYQQKPGKAPKLLIYY
VSVLQSGVPSRFSGSGSGTDFTLTISSLQPEDFATYYCQQTYDIPSTFGQ
GTKVEIKR
DOM16-99 (SEQ ID NO:395)
DIQMTQSPSTLSASVGDRVTITCRASQWIGVSLSWYQQKPGKAPKLLIYY
TSYLQSGVPSRFSGSGSGTDFTLTISSLQPEDFATYYCQQETTWPYTFGQ
GTKVEIKR
DOM16-100 (SEQ ID NO:396)
DIQMTQSPSSLSASVGDRVTITCRASQYIGAELNWYQQKPGKAPKLLIYW
TSVLQSGVPSRFSGSGSGTDFTLTISSLQPEDFATYYCQQAILAPLTFGQ
GTKVEIKR
DOM16-101 (SEQ ID NO:397)
DIQMTQSPSSLSASVGDRVTITCRASQWIGVSLNWYQQKPGKAPKLLIYF
ASVLQSGVPSRFSGSGSGTDFTLTISSLQPEDFATYYCQQNAFYPDTFGQ
GTKVEIKR
DOM16-102 (SEQ ID NO:398)
DIQMTQSPSSLSASVGDRVTITCRASQWIGAELNWYQQKPGKAPKLLIYW
MSVLQSGVPSRFSGSGSGTDFTLTISSLQPEDFATYYCQQTSFFPITFGQ
GTKVEIKR
DOM16-103 (SEQ ID NO:399)
DIQMTQSPSSLSASVGDRVAITCRASQDIRTLLAWYQQKPGKAPMLLIYW
ASELQSGVPSRFSGSGSGTDFTLTISSLQPEDFATYYCQQSLSWPSTFGQ
```

FIG. 10E

GTKVEIKR
DOM16-104 (SEQ ID NO:400)
DIQMTQSPSSLSASVGDRVTITCRASQYIGVSLDWYQQKPGKAPKLLIYY
SSMLQSGVPSRFSGSGSGTDFTLTISSLQPEDFATYYCQQYYTVPDTFGQ
GTKVEIKR
DOM16-105 (SEQ ID NO:401)
DIQMTQSPSSLSASVGDRVTITCRASWPIGDRLNWYQQKPGKAPKLLIAW
VSVLQSGVPSRFSGSGSGTDFTLTISSLQPEDFATYYCGQLGGGPRTFGQ
GTKVEIKR
DOM16-106 (SEQ ID NO:402)
DIQMTQSPSSLSASVGDRVSITCRASQFIGWELAWYQQKPGKAPMLLIYP
YSTLQSGVPSRFSGSGSGTDFTLTISSLQPEDFATYYCQQLAGFPYTFGQ
GTKVEIKR
DOM16-107 (SEQ ID NO:403)
DIQMTQSPSSLSASVGDRVTITCRASQPIGDRLSWYQQKPGKAPKLLIYF
VSQLQSGVPSRFSGSGSGTDFTLTISSLQPEDFATYYCQQSHPNPKTFGQ
GTKVEIKR
DOM16-108 (SEQ ID NO:404)
DIQMTQSPSSLSASVGDGVTITCRASQWIGVELSWYQQKPGKAPKLLIYW
GSELQSGVPSRFSGSGSGTDFTLTISSLQPEDFATYYCQQLALPPFTFGQ
GTKVEIKR
DOM16-109 (SEQ ID NO:405)
DIQMTQSPSSLSASVGDRVTITCRASQEIGASLEWYQQKPGKAPKLLIYW
ASVLQSGVPSRFSGSGSGTDFTLTISSLQPEDFATYYCQQMHHTPFTFGQ
GTKVEIKR
DOM16-110 (SEQ ID NO:406)
DIQMTQSPSSLSASVGDRVTITCRASQHIGQFLSWYQQKPGKAPKLLIYL
ASRLQSGVPSRFSGSGSGTDFTLTISSLQPEDFATYYCQQVDRIPVTFGQ
GTKVEIKR
DOM16-111 (SEQ ID NO:407)
DIQMTQSPSSLSASVGDRVTITCRASQGIDHFLSWYQQKPGKAPKLLIYF
ASTLQSGVPSRFSGSGSGTDFTLTISSLQPEDFATYYCQQNASIPITFGQ
GTKVEIKR
DOM16-112 (SEQ ID NO:408)
DIQMTQSPSSLSASVGDRVTITCRASQNIGTNLKWYQQKPEKAPKLLIYY
GSLLQSGVPSRFSGSGSGTDFTLTISSLQPEDFATYYCQQDYDFPYTFGQ
GTKVEIKR
DOM16-113 (SEQ ID NO:409)
DIQMTQSPSSLSASVGDRVSITCRASQWIGGELNWYQQKPGKAPKLLIYW
VSTLQSGVPSRFSGSGSGTDFTLTISSLQPEDFATYYCQQIARYPATFGQ
GTKVEIKR
DOM16-114 (SEQ ID NO:410)
DIQMTQSPSSLSASVGDRVTITCRASQNIGVNLIWYQQKPGKAPRLLIYF
SSLLQSGVPSRFSGSGSGTDFTLTISSLQPEDFATYYCQQDYDVPQTFGQ
GTKVEIKR
DOM16-115 (SEQ ID NO:411)
DIQMTQSPSSLSASVGDRVTITCRASQNIGSGLHWYQQKPGKAPKLLIVS
WSGLQSGVPSRFSGSGSGTDFTLTISSLQPEDFATYYCGQDVLGPPTFGQ
GTKVEIKR
DOM16-116 (SEQ ID NO:412)
DIQMTQSPSSLSASVGDRVTITCRASQWIGASLAWYQQKPGKAPKLLIYF
MSELQSGVPSRFSGSGSGTDFTLTISSLQPEDFATYYCQQDYGYPTTFGQ
GTKVEIKR
DOM16-117 (SEQ ID NO:413)
DIQMTQSPSSLSASVGDRVTITCRASQWIGVNLLWYQQKPGKAPKLLIYY
GSILQSGVPSRFSGSGSGTDFTLTISSLQPEDFATYYCQQDYHGPYTFGQ
GTKVEIKR
DOM16-118 (SEQ ID NO:414)
DIQMTQSPSSLSASVGDRVTITCRTSQDIGSLLSWYQQKPGKAPKLLIYM
VSMLQSGVPSRFSGSGSGTDFTLTISSLQPEDFATYYCQHNSWYPITFGQ

FIG. 10F

GTKVEIKR
DOM16-119 (SEQ ID NO:415)
DIQMTQSPSSLSASVGDRVTITCRASQFIYTMLNWYQQKPGKAPKLLIYR
TSWLQSGVPSRFSGSGSGTDFTLTISSLQPEDFATYYCQQDYASPFTFGQ
GTKVEIKR
DOM16-39-6 (SEQ ID NO:416)
DIQMTQSPSSLSASVGDRVTITCRASQWIGILLDWYQQKPGEAPKLLIYY
ASFLQSGVPSRFSGSGFGTDFTLTISSLQPEDFATYYCQQANPAPLTFGQ
GTKVEIKR
DOM16-39-8 (SEQ ID NO:417)
DIQMTQSPSSLSASVGDRVTITCRASQWIGILIDWYQQKPGEAPKLLIYY
ASFLQSGVPSRFSGSGSGTDFTLTISSLQPEDSATYYCQQANPAPLTFGQ
GTKVEIKR
DOM16-39-34 (SEQ ID NO:418)
DIQLTQSPSSLSASVGDRVTITCRASQWIGILLDWYQQKPGEAPKLLIYY
ASFLQSGVPSRFSGSGSGTDFTLTINSLQPEDFATYYCQQANPAPLTFGQ
GTKVEIKR
DOM16-39-48 (SEQ ID NO:419)
DIQMTQSPSFLSASVGDRVTITCRASQWIGILLDWYQQKPGEAPKLLIYY
ASFLQSGVPSRFSGSGSGTDFTLTISSLQPEDFATYYCQQANPAPLTLGQ
GTKVEIKR
DOM16-39-87 (SEQ ID NO:420)
DIQMTQSPSSLSASVGDRVTITCRASQWIGILVDWYQQKPGEAPKLLIYY
ASFLQSGVPSRFSGSGSGTDFTLTISSLQPEDFATYYCQQANPAPLRFGQ
GTKVEIKR
DOM16-39-90 (SEQ ID NO:421)
DIQMTQSPSSLSASVGDRVTITCRASQWIGILLDWYQQKPGEAPKLLIYY
ASFLQNGVPSRFSGSGSGTDFTLTISSLQPEDFATYYCQQANPAPLTFGQ
GTKVEIKR
DOM16-39-96 (SEQ ID NO:422)
DIQMIQSPSSLSASVGDRVTITCRASQWIGILLDWYQQKPGEAPKLLIYY
ASFLQSGVPSRFSGSGSGTDFTLTISNLQPEDFATYYCQQANPAPLTFGQ
GTKVEIKR
DOM16-39-100 (SEQ ID NO:423)
DIQMTQSPSSLSASVGDRVTITCRASQWIGILVDWYQQKPGEAPKLLIYY
ASFLQSGVPSRFSGSGFGTDFTLTISSLHPEDFATYYCQQANPAPLTFGQ
GTKVEIKR
DOM16-39-101 (SEQ ID NO:424)
DIQMTQSPSSLSASVGDRVTITCRASQWIGILLDWYQQKPGEAPKLLIYY
ASFLQSGVPSRFSGSGSGTDFTLTISNLQPEDFATYYCQQADPAPLTFGQ
GTKVEIKR
DOM16-39-102 (SEQ ID NO:425)
DIQMTQSPSSLSASVGDSVTITCRASQWIGILLDWYQQKPGEAPKLLIYY
ASFLQSGVPSRFSGSGSGTDFTLTISSLQPEDFATYYCQQANPAPLTFGQ
GTKVEIKR
DOM16-39-103 (SEQ ID NO:426)
DIQMTQYPSSLSASVGDRVTITCRASQWIGILLDWYQQKPGEAPKLLIYY
ASFLQSGVPSRFSGSGSGTDFTLTISSLQPEDFGTYYCQQANPAPLTFGQ
GTKVEIKR
DOM16-39-104 (SEQ ID NO:427)
DIQMTQSPSSLYASVGDRVTITCRASQWIGILLDWYQQKPGEAPKLLIYY
ASFLQSGVPSRFSGSGSGTDFTLTISSLQPEDFATYYCQQANPAPLTFGQ
GTKVEIKR
DOM16-39-105 (SEQ ID NO:428)
DIQMTQSPSSLSASVGDRVTITCRASQWIGILLDWYQQKPGEAPKLLIYY
ASFLQSGVPSRFSGSGSGTDFTLTISSLQPEDFATYYCQPANPAPLTFGQ
GTKVEIKR
DOM16-39-106 (SEQ ID NO:429)
DIQMTQSPSSLSASVGDRVTITCRSSRWIGILLDWYQQKPGEAPKLLIYY
ASFLQSGVPSRFSGSGSGTDFTLTISSLQPEDVATYYCQQANPAPLTFGQ

FIG. 10G

```
GTKVEIKR
DOM16-39-107 (SEQ ID NO:430)
DIQMTQSPSSLSASVGDRVTITCRASQWIGILVDWYQQKPGEAPKLLIYY
ASFLQSGVPSRFSGSGSGTDFTLTISSLQPEDFATYYCQQANPAPLTFGQ
GTKVEIKR
DOM16-39-108 (SEQ ID NO:431)
DIQLTQSPSSLSASVGDRVTITCRASQWIGILLDWYQQKPGEAPKLLIYY
ASFLQSGVPSRFSGSGSGTDFTLTISSLQPEDFATYYCQQANPAPLTFGQ
GTKVEIKR
DOM16-39-109 (SEQ ID NO:432)
DIQMTQSPTSLSASVGDRVTITCRASQWIGNLLDWYQQKPGEAPKLLIYY
ASFLQSGVPSRFSGGGFGTDFTLTISSLQPEDFATYYCQQANPAPLTFGQ
GTKVEIKR
DOM16-39-110 (SEQ ID NO:433)
DIQMTQSPSSLSASVGDRVTITCRASQWIGILLDWYQQKPGEAPKLLIYY
ASFLQSGVPSRFSGSGSGTDFTLTISSLQPEDFATYYCQQANPAPPTFGQ
GTKVEIKR
DOM16-39-111 (SEQ ID NO:434)
DIQMTQSPSSLSASVGDRVTITCRASQWIGILLDWYQQKPGEDPKLLIYY
ASFLQSGVPSRFSGSGSGTDFTLTISSLQPEDFATYYCQQANPAPLTFGQ
GTKVEIKR
DOM16-39-112 (SEQ ID NO:435)
DIQMTQSPTSLSASVGDRVTITCRASQWIGILLDWYQQKPGEAPKLLIYY
ASFLQSGVPSRFSGSGSGTDFTLTISSLQPEDFATYYCQQANPAPLTFGQ
GTKVEIKR
DOM16-39-113 (SEQ ID NO:436)
DIQMTQSPSSLSASVGDRVTITCRASQWIGILVDWYQQKPGEAPKLLIYY
GSFLQSGVPSRFSGSGSGTDFTLTISSLQPEDFATYYCQQANPAPLTFGQ
GTKVEIKR
DOM16-39-114 (SEQ ID NO:437)
DIQMTQSPSSLSASVGDRVTITCRASQWIGILLDWYQQKPGEAPKLLIYY
ASFLQSGVPSRFSGSGSGTDFTLTISSLQPEDFATYYCQQANPAPLTFGQ
GTKVEIRR
DOM16-39-115 (SEQ ID NO:438)
DIQMTQSPSSLSASVGDRVTITCRASQWIGILLDWYQQKPGEAPKLLIYY
ASFLQSGVPSRFSGSGYGTDFTLTISSLQPEDFATYYCQQANPAPLTFGQ
GTKVEIKR
DOM16-39-116 (SEQ ID NO:439)
DIQMTQSPSSLSASVGDRVTITCRASQWIGILLDWYQQKPGEAPKLLIYY
ASFLQSGVPSRFSGSGSGTDFTLTISSLQPEDFATYYCQQANPAPLTFGQ
GTKVEMKR
DOM16-39-117 (SEQ ID NO:440)
DIQMTQSPSSLSASVGDRVTITCRASQWIGILLDWYQQKPGEDPKLLIYY
ASFLQSGVPSRFSGSGSGTDFTLTISSLQPEDFATYYCQQANPAPLMFGQ
GTKVEIKR
DOM16-39-200 (SEQ ID NO:441)
DIQMTQSPSSLSASVGDRVTITCRASQWIGILLDWYQQKPGKAPKLLIYY
ASFLQSGVPSRFSGSGSGTDFTLTISSLQPEDFATYYCQQANPAPLTFGQ
GTKVEIKR
DOM16-39-201 (SEQ ID NO:442)
DIQMTQSPSSLSASVGDRVTITCRASQWIGILVDWYQQKPGKAPKLLIYY
ASFLQSGVPSRFSGSGSGTDFTLTISSLQPEDFATYYCQQANPAPLTFGQ
GTKVEIKR
DOM16-39-202 (SEQ ID NO:443)
DIQMTQSPSSLSASVGDRVTITCRASQWIGILLDWYQQKPGKAPKLLIYY
ASFLQSGVPSRFSGSGSGTDFTLTISSLQPEDFATYYCQQANPAPLRFGQ
GTKVEIKR
DOM16-39-203 (SEQ ID NO:444)
DIQMTQSPSSLSASVGDRVTITCRASQWIGILIDWYQQKPGKAPKLLIYY
ASFLQSGVPSRFSGSGSGTDFTLTISSLQPEDFATYYCQQANPAPLTFGQ
```

FIG. 10H

GTKVEIKR
DOM16-39-204 (SEQ ID NO:445)
DIQMTQSPSSLSASVGDRVTITCRASQWIGNLVDWYQQKPGKAPKLLIYY
ASFLQSGVPSRFSGSGSGTDFTLTISSLQPEDFATYYCQQANPAPLTFGQ
GTKVEIKR
DOM16-39-205 (SEQ ID NO:446)
DIQMTQSPSSLSASVGDRVTITCRASQWIGNLVDWYQQKPGKAPKLLIYY
ASFLQSGVPSRFSGSGSGTDFTLTISSLQPEDFATYYCQQANPAPPTFGQ
GTKVEIKR
DOM16-39-206 (SEQ ID NO:447)
DIQMTQSPSSLSASVGDRVTITCRASQWIGINLDWYQQKPGKAPKLLIYY
ASFLQSGVPSRFSGSGSGTDFTLTISSLQPEDFATYYCQQANPAPLTFGQ
GTKVEIKR
DOM16-39-207 (SEQ ID NO:448)
DIQMTQSPSSLSASVGDRVTITCRASQNIGNLLDWYQQKPGKAPKLLIYY
ASFLQSGVPSRFSGSGFGTDFTLTISSLQPEDFATYYCQQANPAPLTFGQ
GTKVEIKR
DOM16-39-209 (SEQ ID NO:449)
DIQMTQSPSSLSASVGDRVTITCRASQWIGINLDWYQQKPGKAPRLLIYY
ASFLQSGVPSRFSGSGSGTDFTLTISSLQPEDFATYYCQQANPAPLTFGQ
GTKVEIKR1
DOM16-52 (SEQ ID NO:450)
EVQLLESGGGLVQPGGSLRLSCAASGFTFAEQPMTWARQAPGKGLEWVSS
ISSFGDLTYYADSVKGRFTISRDNSKNTLYLQMNSLRAEDTAVYYCAKGV
YRISRFDYWGQGTLVTVSS

| Seq ID | Name | Sequence |
|---|---|---|
| 451 | NB1 | EVQLVESGGGLVQAGGSLRLSCAASGRTFSNYVMGWFRQAPGKERDFVVGIGRSGGDNTYYADSVKGRFTISWDNAKNTMYLQMNSLKPEDTAVYYCAASTYSRDTIFTKWANYNYWGQGTQVTVSS |
| 452 | NB2 | QVQLQESGGGLVKAGGSLRLSCAASGRTFSSYVMGWFRQAPGKEREFVGAIHWSGGRTYYADSVKGRFTISSDNAKNTLYLQMNSLKPEDTAVYYCAASRIIYSYVNYVNPGEYDYWGQGTQVTVSS |
| 453 | NB3 | EVQLVESGGGLVQPGGSLRLSCAASGFTFSSHYMSWFRQAPGKEREFVAAITSSSRTYYTESVKGRFTISRDNAKNTVYLQMNSLKSEDTAVYYCAADRTFYGSTWSKYDYRGQGTQVTVSS |
| 454 | NB4 | QVQLQESGGGLVQAGGSLRLSCAASGRTFSKYAMGWFRQAPGKEREFVSAISWSDGSTYYADSVKGRFTISRDNAKNTVYLQVNSLKPEDTAVYYCAATYLVDVWAVHVPIRPYEYDYWGQGTQVTVSS |
| 455 | NB5 | QVQLQDSGGGLVQAGDSLRLSCAASGRSFGGYAMGWFRQAPGKEREFVAAISWSGGSTYYADSLKGRFTISRDNAKNTVYLQMNSLKPEDTALYYCAAGLRPSPNYNHERSYDYWGQGTQVTVSS |
| 456 | NB6 | QVQLQESGGGLVQAGGSLLLSCAASGRTFSSYAMGWFRQAPGKEREFVAAINWSGGSTSYADSVKGRFTISRDNTKNTVYLQMNSLKPEDTAAFYCAATYNPYSRDHYFPRMTTEYDYWGQGTQVTVSS |
| 457 | NB7 | QVQLQESGGRLVQTGGSLRLSCAASGGTFGTYALGWFRQAPGKEREFVAAISRFGSTYYADSVKGRFTISRDNANNTVYLEMNSLKPEDTAVYYCAAREGVALGLRNDANYWGQGTQVTVSS |
| 458 | NB8 | QVQLQDSGGGLVQAGGSLRLSCAASGGTFSSYAMGWFRQAPGKEREFVAAIGLNTYYADSVKGRFTISRDNAKNTVYLQMNSLKPEDTAVYYCAARTSGVVGGTPKRYDYWGQGTQVTVSS |
| 459 | NB9 | QVQLQESGGGSVQAGGSLKLSCAASGRGFSRYAMGWFRQAPGQDREFVATISWTNSTDYADSVKGRFAISRDNAKNTAYLQMNSLKPEDTAVYYCAADKWASSTRSIDYDYWGQGIQVTVSS |
| 460 | NB10 | QVQLQESGGGLVQAGGSLRLSCAASGRTFSNYAMGWFRQAPGKEREFVAAINWGGGNTYYADSVKGRFTISRDNAKNTVYLQMNSLKPEDTAVYYCAASEWGGSDYDHDYDYWGQGTQVTVSS |
| 461 | NB11 | EVQLVESGGGLVQAGGSLRLSCAASGRSFSSYAMAWFRQAPGKEREFVAAISWGGGSTYYAVSVKGRFTISRDNAKNTVYLQMNSLKPEDTARYYCAADETFHSSAYGEYEYWGQGTQVTVSS |
| 462 | NB12 | EVQLVESGGGLVQAGGSLRLSCTASGRTFSSYAMGWFRQTPGKEREFVAAITSSGGSTYYADSVKGRFTISRDNAKSTMYLQMDSLMLDDTSVYYCAADSSRPQYSDSALRRILSLSNSYPYWGQGTQVTVSS |

FIG. 11A

| 463 | NB13 | EVQLVESGGGLVQPGGSLRLSCVASGFTFADYAMSWVRQAPGKGLQWVSSISYNGDTTYYAESMKDRFTISRDNAKNTLYLQMNSLKSEDTAVYYCASSGSYYPGHFESWGQGTQVTVSS |
|---|---|---|
| 464 | NB14 | QVQLQESGGGLVQAGGSLRLSCAASGRTFSGYAMGWFRQAPGEEREFVAAISWRGTSTYYGDSAKGRFTISRDNAKNTVYLQMNSLKPEDTAVYYCAAGSHSDYAPDYDYWGQGTQVTVSS |
| 465 | NB15 | QVQLQESGGGLVQAGGSLRLSCAASGRTFSSYAIGWFRQAPGKEREFVAAISWGGSNTYYADSVKGRFTISRDNAKNTVYLQMNSLKPEDTAVYYCAAGEVSNSDYAYEYDYWGQGTQVTVSS |
| 466 | NB16 | QVQLQESGGGLVQTGGSLRLSCAASGRYIMGWFRQAPGKEREFVAGISRSGASTAYADSVKDRFTISRDSALNTVYLQMNSLKAEDTAVYFCAAALAIRLGIPRGETEYEYWGQGTQVTVSS |
| 467 | NB17 | QVKLEESGGGLVQAGGSLRLSCSASGLTFSNYAMAWFRQAPGKEREFVATISQRGGMRHYLDSVKDRFTISRDNAKNTVYLQMNSLKPDDTAVYYCAADLMYGVDRRYDYWGRGTQVTVSS |
| 468 | NB18 | QVKLEESGGGLVQAGDSLRLSCAASGRSFSSITMGWFRQAPGKERQFVSAINSNGNRYYADSVKGRFTISRDNAKNTVYLQMNSLKPEDTAVYYCAAVQAYSSSSDYYSQEGAYDYWGQGTQVTVSS |
| 469 | NB19 | EVQLVESGGGLVQAGGSLRLSCAVSGRTFSSMGWFRQAPGKEREFVATINLSGDRTDYADSVKGRFTISRDNPKNTVYLQMDSLEPEDSAVYYCAGTSLYPSNLRYYTLPGTYADWGQGTQVTVSS |
| 470 | NB20 | QVKLEESGGGLVQAGGSLRLSCAASGSIFSINAMGWYRQAPGKQRELVARITGTGTGITGAVSTNYADSVKGRFTISRDNARNTVYLQMNSLKPEDTAVYYCAADRSRTIVVPDYWGQGTQVTVSS |
| 471 | NB21 | QVQLQDSGGGLVQAGGSLRLSCAASRFSSAQYAIGWFRQAPGKEREGVSYITFSGGPTGYADSVKGRFTVSRDNAKNTVYLQMNSLKPEDTAVYYCAARPYTRPGSMWVSSLYDNWGQGTQVTVSS |
| 472 | NB22 | QVQLQESGGRLVQAGGSLRLSCAASEHTFRGYAIGWFRQAPGKEREFVSSITYDGTLTNYADSVTGRFTISRDNAKNTVYLQMNSLKPEDTAVYVCAAGYSYRYTTLNQYDSWGQGTQVTVSS |

FIG. 11B

VKs selected vs MSA

| Kabat_Numbering | 5 | 10 | 15 | 20 | 25 | 30 | 35 |
|---|---|---|---|---|---|---|---|
| MSA16 | DIQM | TQSPS | SLSAS | VGDRV | TITCR | ASQSI | I KHLK W |
| MSA 12 | DIQM | TQSPS | SLSAS | VGDRV | TITCR | ASQSI | F RHLK W |
| MSA 26 | DIQM | TQSPS | SLSAS | VGDRV | TITCR | ASQSI | Y YHLK W |

| Kabat_Numbering | 40 | 45 | 50 | 55 | 60 | 65 | 70 |
|---|---|---|---|---|---|---|---|
| MSA16 | YQQK | PGKAP | KLLIY | G ASRL | QSGVP | SRFSG | SGSTD |
| MSA 12 | YQQK | PGKAP | KLLIY | A ASRL | QSGVP | SRFSG | SGSTD |
| MSA 26 | YQQK | PGKAP | KLLIY | K ASTL | QSGVP | SRFSG | SGSTD |

| Kabat_Numbering | 75 | 80 | 85 | 90 | 95 | 100 | 105 |
|---|---|---|---|---|---|---|---|
| MSA16 | FTLT | ISSLQ | PEDFA | TYYCQ | Q GARW | PQTFG | QGTKV E |
| MSA 12 | FTLT | ISSLQ | PEDFA | TYYCQ | Q VALY | PKTFG | QGTKV E |
| MSA 26 | FTLT | ISSLQ | PEDFA | TYYCQ | Q VRKV | PRTFG | QGTKV E |

| Kabat_Numbering | |
|---|---|
| MSA16 | IKR |
| MSA 12 | IKR |
| MSA 26 | IKR |

FIG. 12A

VKs selected vs RSA

| Kabat_Numbering | 5 | 10 | 15 | 20 | 25 | 30 | 35 |
|---|---|---|---|---|---|---|---|
| DOM7r-1 | DIQT | TQSPS | SLSAS | VGDRV | TITCR | ASQYI | GRYLR W |
| DOM7r-3 | DIQM | TQSPS | SLSAS | VGDRV | TITCR | ASQYI | GRYLR W |
| DOM7r-4 | DIQM | TQSPS | SLSAS | VGDRV | TITCR | ASQWI | GRYLR W |
| DOM7r-5 | DIQM | TQSPS | SLSAS | VGDRV | TITCR | ASQYI | SRQLR W |
| DOM7r-7 | DIQM | TQSPS | SLSAS | VGDRV | TITCR | ASQYI | GRYLR W |
| DOM7r-8 | DIQM | TQSPS | SLSAS | VGDRV | TITCR | ASQWI | HRQLK W |

| Kabat_Numbering | 40 | 45 | 50 | 55 | 60 | 65 | 70 |
|---|---|---|---|---|---|---|---|
| DOM7r-1 | YQQK | PGKAP | KLLIY | DSSVL | QSGVP | SRFSG | SGSGT D |
| DOM7r-3 | YQQK | PGKAP | KLLIY | DSSVL | QSGVP | SRFSG | SGSGT D |
| DOM7r-4 | YQQK | PGKAP | KLLIY | NGSQL | QSGVP | SRFSG | SGSGT D |
| DOM7r-5 | YQQK | PGKAP | RLLIY | GASVL | QSGIP | SRFSG | SGSGT D |
| DOM7r-7 | YQQK | PGKAP | KLLIY | DSSVL | QSGVP | SRFSG | SGSGT D |
| DOM7r-8 | YQQK | PGKAP | KLLIY | YASIL | QSGVP | SRFSG | SGSGT D |

| Kabat_Numbering | 75 | 80 | 85 | 90 | 95 | 100 | 105 |
|---|---|---|---|---|---|---|---|
| DOM7r-1 | FTLT | ISSLQ | PEDFA | TYYCQ | QRYRM | PYTFG | QGTRV E |
| DOM7r-3 | FTLT | ISSLQ | PEDFA | TYYCQ | QRYMQ | PFTFG | QGTKV E |
| DOM7r-4 | FTLT | ISSLQ | PEDFA | TYYCQ | QRYLQ | PYTFG | QGTKV E |
| DOM7r-5 | FTLT | ISSLQ | PEDFA | TYYCQ | QRYIT | PYTFG | QGTKV E |
| DOM7r-7 | FTLT | ISSLQ | PEDFA | TYYCQ | QRYSS | PYTFG | QGTKV E |
| DOM7r-8 | FTLT | ISSLQ | PEDFA | TYYCQ | QTFSK | PSTFG | QGTKV E |

| Kabat_Numbering | |
|---|---|
| DOM7r-1 | IKR |
| DOM7r-3 | IKR |
| DOM7r-4 | IKR |
| DOM7r-5 | VKR |
| DOM7r-7 | IKR |
| DOM7r-8 | IKR |

FIG. 12B

VKs selected vs HSA

| Kabat_Numbering | 5 | 10 | 15 | 20 | 25 | 30 | 35 |
|---|---|---|---|---|---|---|---|
| DOM7h-2 | DIQM | TQSPS | SLSAS | VGDRV | TITCR | ASQKI | ATYLN W |
| DOM7h-3 | DIQM | TQSPS | SLSAS | VGDRV | TITCR | ASQWI | DTGLA W |
| DOM7h-4 | DIQM | TQSPS | SLSAS | VGDRV | TITCR | ASQEI | YSWLA W |
| DOM7h-6 | DIQM | TQSPS | SLSAS | VGDRV | TITCR | ASQSI | SSYLN W |
| DOM7h-1 | DIQM | TQSPS | SLSAS | VGDRV | TITCR | ASQSI | SSYLN W |
| DOM7h-7 | DIQM | TQSPS | SLSAS | VGDRV | TITCR | ASQSI | SSYLN W |

| Kabat_Numbering | 40 | 45 | 50 | 55 | 60 | 65 | 70 |
|---|---|---|---|---|---|---|---|
| DOM7h-2 | YQQK | PGKAP | KLLIY | RSSSL | QSAVP | SRFSG | SGSGT V |
| DOM7h-3 | YQQK | PGKAP | RLLIY | NVSRL | QSGVP | SRFSG | SGSGT D |
| DOM7h-4 | YQQR | PGKAP | KLLIY | NASHL | QSGVP | SRFSG | SGSGT D |
| DOM7h-6 | YQQK | PGKAP | TLLIY | RLSVL | QSGVP | SRFSG | SGSGT D |
| DOM7h-1 | YQQK | PGKAP | KLLIY | RNSFL | QSGVP | SRFSG | SGSGT D |
| DOM7h-7 | YQQK | PGKAP | KLLIY | RNSQL | QSGVP | SRFSG | SGSGT D |

| Kabat_Numbering | 75 | 80 | 85 | 90 | 95 | 100 | 105 |
|---|---|---|---|---|---|---|---|
| DOM7h-2 | FTLT | ISSLQ | PEDFA | TYYCQ | QTYAV | PPTFG | QGTKV E |
| DOM7h-3 | FTLT | ISSLQ | PEDFA | TYYCQ | QYWGS | PTTFG | QGTKV E |
| DOM7h-4 | FTLT | ISSLQ | PEDFA | TYYCQ | QVIGD | PVTFG | QGTKV E |
| DOM7h-6 | FTLT | ISSLQ | PEDFA | TYYCQ | QTYNV | PPTFG | QGTKV E |
| DOM7h-1 | FTLT | ISSLQ | PEDFA | TYYCQ | QTYTV | PPTFG | QGTKV E |
| DOM7h-7 | FTLT | ISSLQ | PEDFA | TYYCQ | QTFAV | PPTFG | QGTKV E |

| Kabat_Numbering | |
|---|---|
| DOM7h-2 | IKR |
| DOM7h-3 | IKR |
| DOM7h-4 | IKR |
| DOM7h-6 | IKR |
| DOM7h-1 | IKQ |
| DOM7h-7 | IKR |

FIG. 12C

VHs selected vs HSA

| Kabat_Numbering | | | 5 | | | 10 | | | 15 | | | 20 | | | 25 | | | 30 | | | 35 |
|---|---|---|---|---|---|---|---|---|---|---|---|---|---|---|---|---|---|---|---|---|---|
| DOM7h-22 | E V Q L | L | E S G G | G | L V Q P | G | G S L R | L | S C A A | S | G F T F | S | K Y W M | S |
| DOM7h-23 | E V Q L | L | E S G G | G | L V Q P | G | G S L R | L | S C A A | S | G F T F | Y | D Y N M | S |
| DOM7h-24 | E V Q L | L | E S G G | G | L V Q P | G | G S L R | L | S C A A | S | G F T F | H | R Y S M | S |
| DOM7h-25 | E V Q L | L | E S G G | G | L V Q P | G | G S L R | L | S C A A | S | G F T F | W | K Y N M | A |
| DOM7h-26 | E V Q L | L | E S G G | G | L V Q P | G | G S L R | L | S C T A | S | G F T F | D | E Y N M | S |
| DOM7h-21 | E V Q L | L | E S G G | G | L V Q P | G | G S L R | L | S C A A | S | G F T F | D | L Y D M | S |
| DOM7h-27 | E V Q L | L | E S G G | G | L V Q P | G | G S L R | L | S C A A | S | G F T F | S | D Y R M | S |
| Consensus | E V Q L | L | E S G G | G | L V Q P | G | G S L R | L | S C A A | S | G F T F | X | X Y N M | S |

| Kabat_Numbering | 40 | | 45 | | 50 | | 54 | | 59 | | 64 | | 69 |
|---|---|---|---|---|---|---|---|---|---|---|---|---|---|
| DOM7h-22 | W V R Q | A | P G K G | L | E W V S | S | I D F M | G | P H T Y | Y | A D S V | K | G R F T | I |
| DOM7h-23 | W V R Q | A | P G K G | L | E W V S | T | I T H T | G | G V T Y | Y | A D S V | K | G R F T | I |
| DOM7h-24 | W V R Q | A | P G K G | L | E W V S | T | I L P G | G | D V T Y | Y | A D S V | K | G R F T | I |
| DOM7h-25 | W V R Q | A | P G K G | L | E W V S | T | I L G E | G | N N T Y | Y | A D S V | K | G R F T | I |
| DOM7h-26 | W V R Q | A | P G K G | L | E W V S | T | I L P H | G | D R T Y | Y | A D S V | K | G R F T | I |
| DOM7h-21 | W V R Q | A | P G K G | L | E W V S | S | I V N S | G | V R T Y | Y | A D S V | K | G R F T | I |
| DOM7h-27 | W V R Q | A | P G K G | L | E W V S | T | I I S N | G | K F T Y | Y | A D S V | K | G R F T | I |

| Kabat_Numbering | 74 | | 79 | | 82b | | 86 | | 91 | | 96 | | 100a |
|---|---|---|---|---|---|---|---|---|---|---|---|---|---|
| DOM7h-22 | S R D N | S | K N T L | Y | L Q M N | S | L R A E | D | T A V Y | Y | C A K G | R | T S M L | P |
| DOM7h-23 | S R D N | S | K N T L | Y | L Q M N | S | L R A E | D | T A V Y | Y | C A K Q | N | P S Y Q | - |
| DOM7h-24 | S R D N | S | K N T L | Y | L Q M N | S | L R A E | D | T A V Y | Y | C A K Q | T | P D Y M | - |
| DOM7h-25 | S R D N | S | K N T L | Y | L Q M N | S | L R A E | D | T A V Y | Y | C A K T | M | D Y K - | - |
| DOM7h-26 | S R D N | S | K N T L | Y | L Q M N | S | L R A E | D | T A V Y | Y | C A K Q | D | P L Y R | - |
| DOM7h-21 | S R D N | S | K N T L | Y | L Q M N | S | L R A E | D | T A V Y | Y | C A K L | N | Q S Y H | W |
| DOM7h-27 | S R D N | S | K N T L | Y | L Q M N | S | L R A E | D | T A V Y | Y | C A K Q | D | W M Y M | - |

| Kabat_Numbering | 100o | | 105 | | 110 |
|---|---|---|---|---|---|
| DOM7h-22 | M K G K | F | D Y W G | Q | G T L V | T | V S S |
| DOM7h-23 | - - - - | F | D Y W G | Q | G T L V | T | V S S |
| DOM7h-24 | - - - - | F | D Y W G | Q | G T L V | T | V S S |
| DOM7h-25 | - - - - | F | D Y W G | Q | G T L V | T | V S S |
| DOM7h-26 | - - - - | F | D Y W G | Q | G T L V | T | V S S |
| DOM7h-21 | D - - - | F | D Y W G | Q | G T L V | T | V S S |
| DOM7h-27 | - - - - | F | D Y W G | Q | G T L V | T | V S S |

FIG. 12D

VKs selected vs HSA and RSA

| Kabat_Numbering | | | 5 | | | 10 | | | 15 | | | 20 | | | 25 | | | 30 | | | 35 |
|---|---|---|---|---|---|---|---|---|---|---|---|---|---|---|---|---|---|---|---|---|---|
| DOM7h-8 | D I Q M | T | Q S P S | S | L S A S | V | G D R V | T | I T C R | A | S Q S I | S | S Y L N | W |
| DOM7r-13 | D I Q M | T | Q S P S | S | L S A S | V | G D R V | T | I T C R | A | S Q H I | H | R E L R | W |
| DOM7r-14 | D I Q M | T | Q S P S | S | L S A S | V | G D R V | T | I T C R | A | S Q H I | H | R E L R | W |

| Kabat_Numbering | | 40 | | 45 | | 50 | | 55 | | 60 | | 65 | | 70 |
|---|---|---|---|---|---|---|---|---|---|---|---|---|---|---|
| DOM7h-8 | Y Q Q K | P G K A P | K | L L I Y | R | N S P L | Q | S G V P | S | R F S G | S | G S G T | D |
| DOM7r-13 | Y Q Q K | P G K A P | K | L L I Y | Q | A S R L | Q | S G V P | S | R F S G | S | G S G T | D |
| DOM7r-14 | Y Q Q K | P G K A P | K | L L I Y | Q | A S R L | Q | S G V P | S | R F S G | S | G S G T | D |

| Kabat_Numbering | | 75 | | 80 | | 85 | | 90 | | 95 | | 100 | | 105 |
|---|---|---|---|---|---|---|---|---|---|---|---|---|---|---|
| DOM7h-8 | F T L T | I | S S L Q | P | E D F A | T | Y Y C Q | Q | T Y R V | P | P T F G | Q | G T K V | E |
| DOM7r-13 | F T L T | I | S S L Q | P | E D F A | T | Y Y C Q | Q | K Y L P | P | Y T F G | Q | G T K V | E |
| DOM7r-14 | F T L T | I | S S L Q | P | E D F A | T | Y Y C Q | Q | R Y R V | P | Y T F G | Q | G T K V | E |

| Kabat_Numbering | |
|---|---|
| DOM7h-8 | I K R |
| DOM7r-13 | I K R |
| DOM7r-14 | I K R |

FIG. 12E

| Kabat_Numbering | | 5 | | 10 | | 15 | | 20 | | 25 | | 30 | | 35 |
|---|---|---|---|---|---|---|---|---|---|---|---|---|---|---|
| DOM7r-15 | D I Q M | T | Q S P S | S | L S A S | V | G D R V | T | I T C R | A | S Q S I | G | R R L K | W |
| DOM7r-16 | D I Q M | T | Q S P S | S | L S A S | V | G D R V | T | I T C R | A | S Q K I | Y | K N L R | W |
| DOM7r-17 | D I Q M | T | Q S P S | S | L S A S | V | G D R V | T | I T C R | A | S Q K I | Y | N N L R | W |
| DOM7r-18 | D I Q M | T | Q S P S | S | L S A S | V | G D R V | T | I T C R | A | S Q W I | Y | K S L G | W |
| DOM7r-19 | D I Q M | T | Q S P S | S | L S A S | V | G D R V | T | I T C R | A | S Q W I | Y | R H L R | W |

| Kabat_Numbering | | 40 | | 45 | | 50 | | 55 | | 60 | | 65 | | 70 |
|---|---|---|---|---|---|---|---|---|---|---|---|---|---|---|
| DOM7r-15 | Y Q Q K | P | G A A P | R | L L I Y | R | T S W L | Q | S G V P | S | R F S G | S | G S G T | D |
| DOM7r-16 | Y Q Q K | P | G K A P | K | L L I Y | N | S S I L | Q | S G V P | S | R F S G | S | G S G T | D |
| DOM7r-17 | Y Q Q K | P | G K A P | K | L L I Y | N | T S I L | Q | S G V P | S | R F S G | S | G S G T | D |
| DOM7r-18 | Y Q Q K | P | G K A P | K | L L I Y | Q | S S L L | Q | S G V P | S | R F S G | S | G S G T | D |
| DOM7r-19 | Y Q Q K | P | G K A P | K | L L I Y | D | A S R L | Q | S G V P | T | R F S G | S | G S G T | D |

| Kabat_Numbering | | 75 | | 80 | | 85 | | 90 | | 95 | | 100 | | 105 |
|---|---|---|---|---|---|---|---|---|---|---|---|---|---|---|
| DOM7r-15 | F T L T | I | S S L Q | P | E D F A | T | Y Y C Q | Q | T S Q W | P | H T F G | Q | G T K V | E |
| DOM7r-16 | F T L T | I | S S L Q | P | E D F A | T | Y Y C Q | Q | R Y L S | P | Y T F G | Q | G T K V | E |
| DOM7r-17 | F T L T | I | S S L Q | P | E D F A | T | Y Y C Q | Q | R W R A | P | Y T F G | Q | G T K V | E |
| DOM7r-18 | F T L T | I | S S L Q | P | E D F A | T | Y Y C Q | Q | Y H Q M | P | R T F G | Q | G T K V | E |
| DOM7r-19 | F T L T | I | S S L Q | P | E D F A | T | Y Y C Q | Q | T H N P | P | K T F G | Q | G T K V | E |

| Kabat_Numbering | |
|---|---|
| DOM7r-15 | I K R |
| DOM7r-16 | I K R |
| DOM7r-17 | I K R |
| DOM7r-18 | I K R |
| DOM7r-19 | I K R |

FIG. 13

| Kabat_Numbering | | | | 5 | | | | | 10 | | | | | 15 | | | | | 20 | | | | | 25 | | | | | 30 | | | | | 35 |
|---|---|---|---|---|---|---|---|---|---|---|---|---|---|---|---|---|---|---|---|---|---|---|---|---|---|---|---|---|---|---|---|---|---|---|
| DOM7r-20 | E | V | Q | L | L | E | S | G | G | G | L | V | Q | P | G | G | S | L | R | L | S | C | A | A | S | G | F | T | F | W | P | Y | T | M | S |
| DOM7r-21 | E | V | Q | L | L | E | S | G | G | G | L | V | Q | P | G | G | S | L | R | L | S | C | A | A | S | G | F | T | F | W | P | Y | T | M | S |
| DOM7r-22 | E | V | Q | L | L | E | S | G | G | G | L | V | Q | P | G | G | S | L | R | L | S | C | A | A | S | G | F | T | F | W | P | Y | T | M | S |
| DOM7r-23 | E | V | Q | L | L | E | S | G | G | G | L | V | Q | P | G | G | S | L | R | L | S | C | A | A | S | G | F | T | F | W | P | Y | T | M | S |
| DOM7r-24 | E | V | Q | L | L | E | S | G | G | G | L | V | Q | P | G | G | S | L | R | L | S | C | A | A | S | G | F | T | F | W | P | Y | T | M | S |
| DOM7r-25 | E | V | Q | L | L | E | S | G | G | G | L | V | Q | P | G | G | S | L | R | L | S | C | A | A | S | G | F | T | F | W | P | Y | T | M | S |
| DOM7r-26 | E | V | Q | L | L | E | S | G | G | G | L | V | Q | P | G | G | S | L | R | L | S | C | A | A | S | G | F | T | F | W | P | Y | T | M | S |
| DOM7r-27 | E | V | Q | L | L | E | S | G | G | G | L | V | Q | P | G | G | S | L | R | L | S | C | A | A | S | G | F | T | F | W | P | Y | T | M | S |
| DOM7r-28 | E | V | Q | L | L | E | S | G | G | G | L | V | Q | P | G | G | S | L | R | L | S | C | A | A | S | G | F | T | F | M | A | Y | Q | M | A |
| DOM7r-29 | E | V | Q | L | L | E | S | G | G | G | L | V | Q | P | G | G | S | L | R | L | S | C | A | A | S | G | F | T | F | K | D | Y | D | M | T |
| DOM7r-30 | E | V | Q | L | L | E | S | G | G | G | L | V | Q | P | G | G | S | L | R | L | S | C | A | A | S | G | F | T | F | H | D | Y | V | M | G |
| DOM7r-31 | E | V | Q | L | L | E | S | G | G | G | L | V | Q | P | G | G | S | L | R | L | S | C | T | A | S | G | F | T | F | R | H | Y | R | M | G |
| DOM7r-32 | E | V | Q | L | L | E | S | G | G | G | L | V | Q | P | G | G | S | L | R | L | S | C | A | A | S | G | F | T | F | M | W | D | K | M | G |
| DOM7r-33 | E | V | Q | L | L | E | S | G | G | G | L | V | Q | P | G | G | S | L | R | L | S | C | A | A | S | G | F | T | F | W | A | Y | P | M | S |

| Kabat_Numbering | | | | 40 | | | | | 45 | | | | | 50 | | | | 54 | | | | | 59 | | | | | 64 | | | | 69 |
|---|---|---|---|---|---|---|---|---|---|---|---|---|---|---|---|---|---|---|---|---|---|---|---|---|---|---|---|---|---|---|---|---|
| DOM7r-20 | W | V | R | Q | A | P | G | K | G | L | E | W | V | S | T | I | S | P | F | G | S | T | T | Y | Y | A | D | S | V | K | G | R | F | T | I |
| DOM7r-21 | W | V | R | Q | A | P | G | K | G | L | E | W | V | S | T | I | S | P | F | G | S | T | T | Y | Y | A | D | S | V | K | G | R | F | T | I |
| DOM7r-22 | W | V | R | Q | A | P | G | K | G | L | E | W | V | S | T | I | S | P | F | G | S | T | T | Y | Y | A | D | S | V | K | G | R | F | T | I |
| DOM7r-23 | W | V | R | Q | A | P | G | K | G | L | E | W | V | S | T | I | S | P | F | G | S | T | T | Y | Y | A | D | S | V | K | G | R | F | T | I |
| DOM7r-24 | W | V | R | Q | A | P | G | K | G | L | E | W | V | S | T | I | S | P | F | G | S | T | T | Y | Y | A | D | S | V | K | G | R | F | T | I |
| DOM7r-25 | W | V | R | Q | A | P | G | K | G | L | E | W | V | S | T | I | S | P | F | G | S | T | T | Y | Y | A | D | S | V | K | G | R | F | T | I |
| DOM7r-26 | W | V | R | Q | A | P | G | K | G | L | E | W | V | S | T | I | S | P | F | G | S | T | T | Y | Y | A | D | S | V | K | G | R | F | T | I |
| DOM7r-27 | W | V | R | Q | A | P | G | K | G | L | E | W | V | S | T | I | S | P | F | G | S | T | T | Y | Y | A | D | S | V | K | G | R | F | T | I |
| DOM7r-28 | W | V | R | Q | A | P | G | K | G | L | E | W | V | S | T | I | H | Q | T | G | F | S | T | Y | Y | A | D | S | V | K | G | R | F | T | I |
| DOM7r-29 | W | V | R | Q | A | P | G | K | G | L | E | W | V | S | M | I | S | S | S | G | L | W | T | Y | Y | A | D | S | V | K | G | R | F | T | I |
| DOM7r-30 | W | A | R | Q | A | P | G | K | G | L | E | W | V | S | L | I | K | P | N | G | S | P | T | Y | Y | A | D | S | V | K | G | R | F | T | I |
| DOM7r-31 | W | V | R | Q | A | P | G | K | G | L | E | W | V | S | W | I | R | P | D | G | T | F | T | Y | Y | A | D | S | V | K | G | R | F | T | I |
| DOM7r-32 | W | V | R | Q | A | P | G | K | G | L | E | W | V | S | F | I | G | R | E | G | Y | G | T | Y | Y | A | D | S | V | K | G | R | F | T | I |
| DOM7r-33 | W | V | R | Q | A | P | G | K | G | L | E | W | V | S | S | I | S | S | W | G | T | G | T | Y | Y | A | D | S | V | K | G | R | F | T | I |

| Kabat_Numbering | | | | 74 | | | | | 79 | | | | 82 | | | | 86 | | | | | 91 | | | | | 96 | | | | | 10 |
|---|---|---|---|---|---|---|---|---|---|---|---|---|---|---|---|---|---|---|---|---|---|---|---|---|---|---|---|---|---|---|---|---|
| DOM7r-20 | S | R | D | N | S | K | N | T | L | Y | L | Q | M | N | S | L | R | A | E | D | T | A | V | Y | Y | C | A | K | G | G | K | D | F | - | - |
| DOM7r-21 | S | R | D | N | S | K | N | T | L | Y | L | Q | M | N | S | L | R | A | E | D | T | A | V | Y | Y | C | A | K | G | N | L | E | P | F | - |
| DOM7r-22 | S | R | D | N | S | K | N | T | L | Y | L | Q | M | N | S | L | R | A | E | D | T | A | V | Y | Y | C | A | K | K | L | S | N | G | F | - |
| DOM7r-23 | S | R | D | N | S | K | N | T | L | Y | L | Q | M | N | S | L | R | A | E | D | T | A | V | Y | Y | C | A | K | V | V | K | D | N | T | F |
| DOM7r-24 | S | R | D | N | S | K | N | T | L | Y | L | Q | M | N | S | L | R | A | E | D | T | A | V | Y | Y | C | A | K | N | T | G | G | K | Q | F |
| DOM7r-25 | S | R | D | N | S | K | N | T | L | Y | L | Q | M | N | S | L | R | A | E | D | T | A | V | Y | Y | C | A | K | K | T | G | P | S | S | F |
| DOM7r-26 | S | R | D | N | S | K | N | T | L | Y | L | Q | M | N | S | L | R | A | E | D | T | A | V | Y | Y | C | A | K | R | T | E | N | R | G | V |
| DOM7r-27 | S | R | D | N | S | K | N | T | L | Y | L | Q | M | N | S | L | R | A | E | D | T | A | V | Y | Y | C | A | K | S | D | V | L | K | T | G |
| DOM7r-28 | S | R | D | N | S | K | N | T | L | Y | L | Q | M | N | S | L | R | A | E | D | T | A | V | Y | Y | C | A | K | V | R | S | M | R | P | Y |
| DOM7r-29 | S | R | D | N | S | K | N | T | L | Y | L | Q | M | N | S | L | R | A | E | D | T | A | V | Y | Y | C | A | K | G | F | R | L | F | P | R |
| DOM7r-30 | S | R | D | N | S | K | N | T | L | Y | L | Q | M | N | S | L | R | A | E | D | T | A | V | Y | Y | C | A | K | G | R | G | R | F | N | V |
| DOM7r-31 | S | R | D | N | S | K | N | T | L | Y | L | Q | M | N | S | L | R | A | E | D | T | A | V | Y | Y | C | A | K | S | Y | M | G | D | R | F |
| DOM7r-32 | S | R | D | N | S | K | N | T | L | Y | L | Q | M | N | S | L | R | A | E | D | T | A | V | Y | Y | C | A | K | S | V | A | S | F | - | - |
| DOM7r-33 | S | R | D | N | S | K | N | T | L | Y | L | Q | M | N | S | L | R | A | E | D | T | A | V | Y | Y | C | A | K | G | G | Q | G | S | F | - |

FIG. 14A

| Kabat_Numbering | | | | | | | | 10 | | | | 10 | | | | 11 | | |
|---|---|---|---|---|---|---|---|---|---|---|---|---|---|---|---|---|---|---|
| DOM7r-20 | - | - | - | - | D | Y | W | G | Q | G | T | L | V | T | V | S | S |
| DOM7r-21 | - | - | - | - | D | Y | W | G | Q | G | T | L | V | T | V | S | S |
| DOM7r-22 | - | - | - | - | D | Y | W | G | Q | G | T | L | V | T | V | S | S |
| DOM7r-23 | - | - | - | - | D | Y | W | G | Q | G | T | L | V | T | V | S | S |
| DOM7r-24 | - | - | - | - | D | Y | W | G | Q | G | T | L | V | T | V | S | S |
| DOM7r-25 | - | - | - | - | D | Y | W | G | Q | G | T | L | V | T | V | S | S |
| DOM7r-26 | S | F | - | - | D | Y | W | G | Q | G | T | L | V | T | V | S | S |
| DOM7r-27 | L | D | G | F | D | Y | W | G | Q | G | T | L | V | T | V | S | S |
| DOM7r-28 | K | F | - | - | D | Y | W | G | Q | G | T | L | V | T | V | S | S |
| DOM7r-29 | T | F | - | - | D | Y | W | G | Q | G | T | L | V | T | V | S | S |
| DOM7r-30 | L | Q | F | - | D | Y | W | G | Q | G | T | L | V | T | V | S | S |
| DOM7r-31 | - | - | - | - | D | Y | W | G | Q | G | T | L | V | T | V | S | S |
| DOM7r-32 | - | - | - | - | D | Y | W | G | Q | G | T | L | V | T | V | S | S |
| DOM7r-33 | - | - | - | - | D | Y | W | G | Q | G | T | L | V | T | V | S | S |

| | Sequence |
|---|---|
| | Anti-mouse serum albumin |
| A | QVQLQESGGGLVQPGGSLRLSCEASGFTFSRFGMTWVRQAPGKGVEWV SGISSLGDSTLYADSVKGRFTISRDNAKNTLYLQMNSLKPEDTAVYYC TIGGSLNPGGQGTQVTVSS |
| B | QVQLQESGGGLVQPGNSLRLSCAASGFTFRNFGMSWVRQAPGKEPEWV SSISGSGSNTIYADSVKDRFTISRDNAKSTLYLQMNSLKPEDTAVYYC TIGGSLSRSSQGTQVTVSS |
| C | QVQLQESGGGLVQPGGSLRLTCTASGFTFSSFGMSWVRQAPGKGLEWV SAISSDSGTKNYADSVKGRFTISRDNAKKMLFLQMNSLRPEDTAVYYC VIGRGSPSSQGTQVTVSS |
| D | QVQLQESGGGLVQPGGSLRLTCTASGFTFRSFGMSWVRQAPGKGLEWV SAISADGSDKRYADSVKGRFTISRDNGKKMLTLDMNSLKPEDTAVYYC VIGRGSPASQGTQVTVSS |
| E | AVQLVESGGGLVQAGDSLRLSCVVSGTTFSSAAMGWFRQAPGKEREFV GAIKWSGTSTYYTDSVKGRFTISRDNVKNTVYLQMNNLKPEDTGVYTC AADRDRYRDRMGPMTTTDFRFWGQGTQVTVSS |
| F | QVKLEESGGGLVQTGGSLRLSCAASGRTFSSFAMGWFRQAPGREREFV ASIGSSGITTNYADSVKGRFTISRDNAKNTVYLQMNSLKPEDTGLCYC AVNRYGIPYRSGTQYQNWGQGTQVTVSS |
| G | EVQLEESGGGLVQPGGSLRLSCAASGLTFNDYAMGWYRQAPGKERDMV ATISIGGRTYYADSVKGRFTISRDNAKNTVYLQMNSLKPEDTAIYYCV AHRQTVVRGPYLLWGQGTQVTVSS |
| H | QVQLVESGGKLVQAGGSLRLSCAASGRTFSNYAMGWFRQAPGKEREFV AGSGRSNSYNYYSDSVKGRFTISRDNAKNTVYLQMNSLKPEDTAVYYC AASTNLWPRDRNLYAYWGQGTQVTVSS |
| I | EVQLVESGGGLVQAGDSLRLSCAASGRSLGIYRMGWFRQVPGKEREFV AAISWSGGTTRYLDSVKGRFTISRDSTKNAVYLQMNSLKPEDTAVYYC AVDSSGRLYWTLSTSYDYWGQGTQVTVSS |
| J | QVQLVEFGGGLVQAGDSLRLSCAASGRSLGIYKMAWFRQVPGKEREFV AAISWSGGTTRYIDSVKGRFTLSRDNTKNMVYLQMNSLKPDDTAVYYC AVDSSGRLYWTLSTSYDYWGQGTQVTVSS |
| K | EVQLVESGGGLVQAGGSLSLSCAASGRTFSPYTMGWFRQAPGKEREFL AGVTWSGSSTFYGDSVKGRFTASRDSAKNTVTLEMNSLNPEDTAVYYC AAAYGGGLYRDPRSYDYWGRGTQVTVSS |
| L | AVQLVESGGGLVQAGGSLRLSCAASGFTLDAWPIAWFRQAPGKEREGV SCIRDGTTYYADSVKGRFTISSDNANNTVYLQTNSLKPEDTAVYYCAA PSGPATGSSHTFGIYWNLRDDYDNWGQGTQVTVSS |
| M | EVQLVESGGGLVQAGGSLRLSCAASGFTFDHYTIGWFRQVPGKEREGV SCISSSDGSTYYADSVKGRFTISSDNAKNTVYLQMNTLPDDTAVYYC AAGGLLLRVEELQASDYDYWGQGIQVTVSS |
| N | AVQLVDSGGGLVQPGGSLRLSCTASGFTLDYYAIGWFRQAPGKEREGV ACISNSDGSTYYGDSVKGRFTISRDNAKTTVYLQMNSLKPEDTAVYYC ATADRHYSASHHPPADFAFNSWGQGTQVTVSS |
| O | EVQLVESGGGLVQAGGSLRLSCAAYGLTFWRAAMAWFRRAPGKERELV VARNWGDGSTRYADSVKGRFTISRDNAKNTVYLQMNSLKPEDTAVYYC AAVRTYGSATYDIWGQGTQVTVSS |
| P | EVQLVESGGGLVQDGGSLRLSCIFSGRTFANYAMGWFRQAPGKEREFV AAINRNGGTTNYADALKGRFTISRDNTKNTAFLQMNSLKPDDTAVYYC AAREWPFSTIPSGWRYWGQGTQVTVSS |
| Q | DVQLVESGGGWVQPGGSLRLSCAASGPTASSHAIGWFRQAPGKEREFV VGINRGGVTRDYADSVKGRFAVSRDNVKNTVYLQMNRLKPEDSAIYIC AARPEYSFTAMSKGDMDYWGKGTLVTVSS |

US 7,696,320 B2

LIGANDS THAT HAVE BINDING SPECIFICITY FOR VEGF AND/OR EGFR AND METHODS OF USE THEREFOR

RELATED APPLICATIONS

This application is a continuation-in-part of U.S. application Ser. No. 11/098,758, filed Apr. 4, 2005, which is a continuation-in-part of U.S. application Ser. No. 10/925,366, filed Aug. 24, 2004. The entire teachings of the above applications are incorporated herein by reference.

BACKGROUND OF THE INVENTION

Cancer is a leading cause of mortality and morbidity. Approaches to treating cancer include surgical intervention to remove tumors and chemotherapy. These approaches can successful cure some patients. However, even patients that appear to have been cured often suffer a recurrence of the cancer necessitating further therapy. Chemotherapeutic agents generally are nonselective agents that are toxic to cells, such as proliferating cells. Accordingly, such agents may effectively kill cancer cells but also kill health cells producing sever deleterious side effects.

Certain cancer cells express or overexpress certain cellular components such as cell surface proteins, or express different cellular components when compared to normal cells. One approach to address the short comings of surgical and chemotherapeutic approaches to cancer therapy and diagnosis involves targeting cancer cells, for example using antibodies or antibody fragments that bind to proteins that are expressed or overexpressed on cancerous cells. A number of such target proteins have been identified. Amoung such proteins is the epidermal growth factor receptor (EGFR).

EGFR is a member of the ErbB1 family and transduces signals that lead to cellular proliferation and survival, and the elaboration of motailtiy, growth and angiogenic factors upon binding epidermal growth factor (EGF) and or transforming growth factor alpha (TGF alpha). Accordingly, EGFR has been demonstrated to be involved in tumor growth, metastasis and angiogenesis. Further many cancer express EGFR, such as bladder cancer, ovarian cancer, colorectal cancer, breast cancer, lung cancer (e.g., non-small cell lung carcinoma), gastric cancer, pancreatic cancer, prostate cancer, head and neck cancer, renal cancer and gall bladder cancer. ERBITUX (cetuximab; Imclone Systems Inc) is a chimeric mouse/human antibody that binds human EGFR that has been approved for treating certain EGFR-expressing cancers in combination with irinotecan.

An important pathophysiological process that facilitates tumor formation, metastasis and recurrence is tumor angiogenesis. This process is mediated by the elaboration of angiogenesis factors by the tumor, such as vascular endothelial growth factor (VEGF), which induce the formation of blood vessels that deliver nutrients to the tumor. Accordingly, another approach to treating certain cancers is to inhibit tumor angiogenesis mediated by VEGF, thereby starving the tumor. AVISTIN (bevacizumab; Genetech, Inc.) is a humanized antibody that binds human VEGF that has been approved for treating colorectal cancer. An antibody referenced to as antibody 2C3 (ATCC Accession No. PTA 1595) is reported to bind VEGF and inhibit binding of VEGF to epidermal growth factor receptor 2.

Targering EGFR or VEGF with currently available therapeutics is not effective in all patients, or for all cancers (e.g., EGFR-expressing cancers). Thus, a need exists for improved agents for treating cancer and other pathological conditions.

SUMMARY OF THE INVENTION

The invention relates to ligands that have binding specificity for VEGF (e.g., human VEGF), ligands that have binding specificity for EGFR (e.g., human EGFR), and to ligands that have binding specificity for VEGF and EGFR (e.g., human VEGF and human EGFR). For example, the ligand can comprise a polypeptide domain having a binding site with binding specificity for VEGF, a polypeptide domain having a binding site with binding specificity EGFR, or comprise a polypeptide domain having a binding site with binding specificity for VEGF and a polypeptide domain having a binding site with binding specificity EGFR.

In one aspect, the invention relates to a ligand that has binding specificity for VEGF and for EGFR. Such ligands comprise at least one protein moiety that has a binding site with binding specificity for VEGF and at least one protein moiety that has a binding site with binding specificity for EGFR. The protein moiety that has a binding site with binding specificity for VEGF and the protein moiety that has a binding site with binding specificity for EGFR can each be any suitable binding moiety. The protein moieties can be a peptide moiety, polypeptide moiety or protein moiety. For example, the protein moieties can be provided by an antibody fragment that has a binding site with binding specificity for VEGF or EGFR, such as an immunoglobulin single variable domain that has binding specificity for VEGF or EGFR.

The ligand can comprise a protein moiety that has a binding site with binding specificity for VEGF that competes for binding to VEGF with AVASTIN (bevacizumab; Genentech, Inc.) and/or antibody 2C3 (ATCC Accession No. PTA 1595). The ligand can comprise a protein moiety that has a binding site with binding specificity for EGFR that competes for binding to EGFR with ERBITUX (cetuximab; Imclone Systems, Inc.). In some embodiments, the ligand comprises a protein moiety that has a binding site with binding specificity for VEGF that competes for binding to VEGF with bevacizumab and/or antibody 2C3 (ATCC Accession No. PTA 1595), and further comprises a protein moiety that has a binding site with binding specificity for EGFR that competes for binding to EGFR with cetuximab.

In some embodiments, the ligand comprises a protein moiety that has a binding site with binding specificity for VEGF (e.g., an immunoglobulin single variable domain) that competes for binding to VEGF with an anti-VEGF domain antibody (dAb) selected from the group consisting of TAR15-1 (SEQ ID NO:100), TAR15-3 (SEQ ID NO:101), TAR15-4 (SEQ ID NO:102), TAR15-9 (SEQ ID NO:103), TAR15-10 (SEQ ID NO:104), TAR15-11 (SEQ ID NO:105), TAR15-12 (SEQ ID NO:106), TAR15-13 (SEQ ID NO:107), TAR15-14 (SEQ ID NO:108), TAR15-15 (SEQ ID NO:109), TAR15-16 (SEQ ID NO:110), TAR15-17 (SEQ ID NO:111), TAR15-18 (SEQ ID NO:112), TAR15-19 (SEQ ID NO:113), TAR15-20 (SEQ ID NO:114), TAR15-22 (SEQ ID NO:115), TAR15-5 (SEQ ID NO:116), TAR15-6 (SEQ ID NO:117), TAR15-7 (SEQ ID NO:118), TAR15-8 (SEQ ID NO:119), TAR15-23 (SEQ ID NO:120), TAR15-24 (SEQ ID NO:121), TAR15-25 (SEQ ID NO:122), TAR15-26 (SEQ ID NO:123), TAR15-27 (SEQ ID NO:124), TAR15-29 (SEQ ID NO:125), TAR15-30 (SEQ ID NO:126), TAR15-6-500 (SEQ ID NO:127), TAR15-6-501 (SEQ ID NO:128), TAR15-6-502 (SEQ ID NO:129), TAR15-6-503 (SEQ ID NO:130), TAR15-6-504 (SEQ BD NO:131), TAR15-6-505 (SEQ ID NO:132), TAR15-6-506 (SEQ ID NO:133), TAR15-6-507 (SEQ ID NO:134), TAR15-6-508 (SEQ ID NO:135), TAR15-6-509 (SEQ ID NO:136), TAR15-6-510 (SEQ ID NO:137), TAR15-8-500 (SEQ ID NO:138), TAR15-8-501 (SEQ ID NO:139), TAR15-8-502

(SEQ ID NO:140), TAR15-8-503 (SEQ ID NO:141), TAR15-8-505 (SEQ ID NO:142), TAR15-8-506 (SEQ ID NO:143), TAR15-8-507 (SEQ ID NO:144), TAR15-8-508 (SEQ ID NO:145), TAR15-8-509 (SEQ ID NO:146), TAR15-8-510 (SEQ ID NO:147), TAR15-8-511 (SEQ ID NO:148), TAR15-26-500 (SEQ ID NO:149), TAR15-26-501 (SEQ BD NO:150), TAR15-26-502 (SEQ ID NO:151), TAR15-26-503 (SEQ ID NO:152), TAR15-26-504 (SEQ ID NO:153), TAR15-26-505 (SEQ ID NO:154), TAR15-26-506 (SEQ ID NO:155), TAR15-26-507 (SEQ ID NO:156), TAR15-26-508 (SEQ ID NO:157), TAR15-26-509 (SEQ ID NO:158), TAR15-26-510 (SEQ ID NO:159), TAR15-26-511 (SEQ ID NO:160), TAR15-26-512 (SEQ ID NO:161), TAR15-26-513 (SEQ ID NO:162), TAR15-26-514 (SEQ ID NO:163), TAR15-26-515 (SEQ ID NO:164), TAR15-26-516 (SEQ ID NO:165), TAR15-26-517 (SEQ ID NO:166), TAR15-26-518 (SEQ ID NO:167), TAR15-26-519 (SEQ ID NO:168), TAR15-26-520 (SEQ ID NO:169), TAR15-26-521 (SEQ ID NO:170), TAR15-26-522 (SEQ ID NO:171), TAR15-26-523 (SEQ ID NO:172), TAR15-26-524 (SEQ ID NO:173), TAR15-26-525 (SEQ ID NO:174), TAR15-26-526 (SEQ ID NO:175), TAR15-26-527 (SEQ ID NO:176), TAR15-26-528 (SEQ ID NO:177), TAR15-26-529 (SEQ ID NO:178), TAR15-26-530 (SEQ ID NO:179), TAR15-26-531 (SEQ ID NO:180), TAR15-26-532 (SEQ ID NO:181), TAR15-26-533 (SEQ ID NO:182), TAR15-26-534 (SEQ ID NO:183), TAR15-26-535 (SEQ ID NO:184), TAR15-26-536 (SEQ ID NO:185), TAR15-26-537 (SEQ ID NO:186), TAR15-26-538 (SEQ ID NO:187), TAR15-26-539 (SEQ ID NO:188), TAR15-26-540 (SEQ ID NO:189), TAR15-26-541 (SEQ ID NO:190), TAR15-26-542 (SEQ ID NO:191), TAR15-26-543 (SEQ ID NO:192), TAR15-26-544 (SEQ ID NO:193), TAR15-26-545 (SEQ ID NO:194), TAR15-26-546 (SEQ ID NO:195), TAR15-26-547 (SEQ ID NO:196), TAR15-26-548 (SEQ ID NO:197), TAR15-26-549 (SEQ ID NO:198), TAR15-26-550 (SEQ ID NO:539), and TAR15-26-551 (SEQ ID NO:540).

Additionally, or in other embodiments, the ligand can comprise a protein moiety that has a binding site with binding specificity for EGFR (e.g., an immunoglobulin single variable domain) that competes for binding to EGFR with an anti-EGFR domain antibody (dAb) selected from the group consisting of DOM16-17 (SEQ ID NO:325), DOM16-18 (SEQ ID NO:326), DOM16-19 (SEQ ID NO:327), DOM16-20 (SEQ ID NO:328), DOM16-21 (SEQ ID NO:329), DOM16-22 (SEQ ID NO:330), DOM16-23 (SEQ ID NO:331), DOM16-24 (SEQ ID NO:332), DOM16-25 (SEQ ID NO:333), DOM16-26 (SEQ ID NO:334), DOM16-27 (SEQ ID NO:335), DOM16-28 (SEQ ID NO:336), DOM16-29 (SEQ ID NO:337), DOM16-30 (SEQ ID NO:338), DOM16-31 (SEQ ID NO:339), DOM16-32 (SEQ ID NO:340), DOM16-33 (SEQ ID NO:341), DOM16-35 (SEQ ID NO:342), DOM16-37 (SEQ ID NO:343), DOM16-38 (SEQ ID NO:344), DOM16-39 (SEQ ID NO:345), DOM16-40 (SEQ ID NO:346), DOM16-41 (SEQ ID NO:347), DOM16-42 (SEQ ID NO:348), DOM16-43 (SEQ ID NO:349), DOM16-44 (SEQ ID NO:350), DOM16-45 (SEQ ID NO:351), DOM16-46 (SEQ ID NO:352), DOM16-47 (SEQ ID NO:353), DOM16-48 (SEQ ID NO:354), DOM16-49 (SEQ ID NO:355), DOM16-50 (SEQ ID NO:356), DOM16-59 (SEQ ID NO:357), DOM16-60 (SEQ ID NO:358), DOM16-61 (SEQ ID NO:359), DOM16-62 (SEQ ID NO:360), DOM16-63 (SEQ ID NO:361), DOM16-64 (SEQ ID NO:362), DOM16-65 (SEQ ID NO:363), DOM16-66 (SEQ ID NO:364), DOM16-67 (SEQ ID NO:365), DOM16-68 (SEQ ID NO:366), DOM16-69 (SEQ ID NO:367), DOM16-70 (SEQ ID NO:368), DOM16-71 (SEQ ID NO:369), DOM16-72 (SEQ ID NO:370), DOM16-73 (SEQ ID NO:371), DOM16-74 (SEQ ID NO:372), DOM16-75 (SEQ ID NO:373), DOM16-76 (SEQ ID NO:374), DOM16-77 (SEQ ID NO:375), DOM16-78 (SEQ ID NO:376), DOM16-79 (SEQ ID NO:377), DOM16-80 (SEQ ID NO:378), DOM16-81 (SEQ ID NO:379), DOM16-82 (SEQ ID NO:380), DOM16-83 (SEQ ID NO:381), DOM16-84 (SEQ ID NO:382), DOM16-85 (SEQ ID NO:383), DOM16-87 (SEQ ID NO:384), DOM16-88 (SEQ ID NO:385), DOM16-89 (SEQ ID NO:386), DOM16-90 (SEQ ID NO:387), DOM16-91 (SEQ ID NO:388), DOM16-92 (SEQ ID NO:389), DOM16-94 (SEQ ID NO:390), DOM16-95 (SEQ ID NO:391), DOM16-96 (SEQ ID NO:392), DOM16-97 (SEQ ID NO:393), DOM16-98 (SEQ ID NO:394), DOM16-99 (SEQ ID NO:395), DOM16-100 (SEQ ID NO:396), DOM16-101 (SEQ ID NO:397), DOM16-102 (SEQ ID NO:398), DOM16-103 (SEQ ID NO:399), DOM16-104 (SEQ ID NO:400), DOM16-105 (SEQ ID NO:401), DOM16-106 (SEQ ID NO:402), DOM16-107 (SEQ ID NO:403), DOM16-108 (SEQ ID NO:404), DOM16-109 (SEQ ID NO:405), DOM16-110 (SEQ ID NO:406), DOM16-111 (SEQ ID NO:407), DOM16-112 (SEQ ID NO:408), DOM16-113 (SEQ ID NO:409), DOM16-114 (SEQ ID NO:410), DOM16-115 (SEQ ID NO:411), DOM16-116 (SEQ ID NO:412), DOM16-117 (SEQ ID NO:413), DOM16-118 (SEQ ID NO:414), DOM16-119 (SEQ ID NO:415), DOM16-39-6 (SEQ ID NO:416), DOM16-39-8 (SEQ ID NO:417), DOM16-39-34 (SEQ ID NO:418), DOM16-39-48 (SEQ ID NO:419), DOM16-39-87 (SEQ ID NO:420), DOM16-39-90 (SEQ ID NO:421), DOM16-39-96 (SEQ ID NO:422), DOM16-39-100 (SEQ ID NO:423), DOM16-39-101 (SEQ ID NO:424), DOM16-39-102 (SEQ ID NO:425), DOM16-39-103 (SEQ ID NO:426), DOM16-39-104 (SEQ ID NO:427), DOM16-39-105 (SEQ ID NO:428), DOM16-39-106 (SEQ ID NO:429), DOM16-39-107 (SEQ ID NO:430), DOM16-39-108 (SEQ ID NO:431), DOM16-39-109 (SEQ ID NO:432), DOM16-39-110 (SEQ ID NO:433), DOM16-39-111 (SEQ ID NO:434), DOM16-39-112 (SEQ ID NO:435), DOM16-39-113 (SEQ ID NO:436), DOM16-39-114 (SEQ ID NO:437), DOM16-39-115 (SEQ ID NO:438), DOM16-39-116 (SEQ ID NO:439), DOM16-39-117 (SEQ ID NO:440), DOM16-39-200 (SEQ ID NO:441), DOM16-39-201 (SEQ ID NO:442), DOM16-39-202 (SEQ ID NO:443), DOM16-39-203 (SEQ ID NO:444), DOM16-39-204 (SEQ ID NO:445), DOM16-39-205 (SEQ ID NO:446), DOM16-39-206 (SEQ ID NO:447), DOM16-39-207 (SEQ ID NO:448), DOM16-39-209 (SEQ ID NO:449), DOM16-52 (SEQ ID NO:450), NB1 (SEQ ID NO:451), NB2 (SEQ ID NO:452), NB3 (SEQ ID NO:453), NB4 (SEQ ID NO:454), NB5 (SEQ ID NO:455), NB6 (SEQ ID NO:456), NB7 (SEQ ID NO:457), NB8 (SEQ ID NO:458), NB9 (SEQ ID NO:459), NB10 (SEQ ID NO:460), NB11 (SEQ ID NO:461), NB12 (SEQ ID NO:462), NB13 (SEQ ID NO:463), NB14 (SEQ ID NO:464), NB15 (SEQ ID NO:465), NB16 (SEQ ID NO:466), NB17 (SEQ ID NO:467), NB18 (SEQ ID NO: 468), NB19 (SEQ ID NO:469), NB20 (SEQ ID NO:470), NB21 (SEQ ID NO:471), and NB22 (SEQ ID NO:472).

In particular embodiments, the ligand has binding specificity for VEGF and for EGFR and comprises a protein moiety that has a binding site with binding specificity for VEGF that competes for binding to VEGF with an anti-VEGF domain antibody (dAb) selected from the group consisting of TAR15-6 (SEQ ID NO:117), TAR15-8 (SEQ ID NO:119), and TAR15-26 (SEQ ID NO:123), and further comprises a protein moiety that has a binding site with binding specificity for EGFR that competes for binding to EGFR with an anti- EGFR domain antibody (dAb) selected from the group consisting of DOM16-39 (SEQ ID NO:345), DOM16-39-87 (SEQ ID NO:420), DOM16-39-100 (SEQ ID NO:423), DOM16-39-107 (SEQ ID NO:430), DOM16-39-109 (SEQ ID NO:432), DOM16-39-115 (SEQ ID NO:438), and DOM16-39-200 (SEQ ID NO:441).

In more particular embodiments, the ligand has binding specificity for VEGF and for EGFR and comprises at least one immunoglobulin single variable domain with binding specificity for VEGF and at least one immunoglobulin single variable domain with binding specificity for EGFR, wherein an immunoglobulin single variable domain with binding specificity for VEGF competes for binding to VEGF with an anti-VEGF domain antibody (dAb) selected from the group consisting of TAR15-1 (SEQ ID NO:100), TAR15-3 (SEQ ID NO:101), TAR15-4 (SEQ ID NO:102), TAR15-9 (SEQ ID NO:103), TAR15-10 (SEQ ID NO:104), TAR15-11 (SEQ ID NO:105), TAR15-12 (SEQ ID NO:106), TAR15-13 (SEQ ID NO:107), TAR15-14 (SEQ ID NO:108), TAR15-15 (SEQ ID NO:109), TAR15-16 (SEQ ID NO:110), TAR15-17 (SEQ ID NO:111), TAR15-18 (SEQ ID NO:112), TAR15-19 (SEQ ID NO:113), TAR15-20 (SEQ ID NO:114), TAR15-22 (SEQ ID NO:115), TAR15-5 (SEQ ID NO:116), TAR15-6 (SEQ ID NO:117), TAR15-7 (SEQ ID NO:118), TAR15-8 (SEQ ID NO:119), TAR15-23 (SEQ ID NO:120), TAR15-24 (SEQ ID NO:121), TAR15-25 (SEQ ID NO:122), TAR15-26 (SEQ ID NO:123), TAR15-27 (SEQ ID NO:124), TAR15-29 (SEQ ID NO:125), TAR15-30 (SEQ ID NO:126), TAR15-6-500 (SEQ ID NO:127), TAR15-6-501 (SEQ ID NO:128), TAR15-6-502 (SEQ ID NO:129), TAR15-6-503 (SEQ ID NO:130), TAR15-6-504 (SEQ ID NO:131), TAR15-6-505 (SEQ ID NO:132), TAR15-6-506 (SEQ ID NO:133), TAR15-6-507 (SEQ ID NO:134), TAR15-6-508 (SEQ ID NO:135), TAR15-6-509 (SEQ ID NO:136), TAR15-6-510 (SEQ ID NO:137), TAR15-8-500 (SEQ ID NO:138), TAR15-8-501 (SEQ ID NO:139), TAR15-8-502 (SEQ ID NO:140), TAR15-8-503 (SEQ ID NO:141), TAR15-8-505 (SEQ ID NO:142), TAR15-8-506 (SEQ ID NO:143), TAR15-8-507 (SEQ ID NO:144), TAR15-8-508 (SEQ ID NO:145), TAR15-8-509 (SEQ ID NO:146), TAR15-8-510 (SEQ ID NO:147), TAR15-8-511 (SEQ ID NO:148), TAR15-26-500 (SEQ ID NO:149), TAR15-26-501 (SEQ ID NO:150), TAR15-26-502 (SEQ ID NO:151), TAR15-26-503 (SEQ ID NO:152), TAR15-26-504 (SEQ ID NO:153), TAR15-26-505 (SEQ ID NO:154), TAR15-26-506 (SEQ ID NO:155), TAR15-26-507 (SEQ ID NO:156), TAR15-26-508 (SEQ ID NO:157), TAR15-26-509 (SEQ ID NO:158), TAR15-26-510 (SEQ ID NO:159), TAR15-26-511 (SEQ ID NO:160), TAR15-26-512 (SEQ ID NO:161), TAR15-26-513 (SEQ ID NO:162), TAR15-26-514 (SEQ ID NO:163), TAR15-26-515 (SEQ ID NO:164), TAR15-26-516 (SEQ ID NO:165), TAR15-26-517 (SEQ ID NO:166), TAR15-26-518 (SEQ ID NO:167), TAR15-26-519 (SEQ ID NO:168), TAR15-26-520 (SEQ ID NO:169), TAR15-26-521 (SEQ ID NO:170), TAR15-26-522 (SEQ ID NO:171), TAR15-26-523 (SEQ ID NO:172), TAR15-26-524 (SEQ ID NO:173), TAR15-26-525 (SEQ ID NO:174), TAR15-26-526 (SEQ ID NO:175), TAR15-26-527 (SEQ ID NO:176), TAR15-26-528 (SEQ ID NO:177), TAR15-26-529 (SEQ ID NO:178), TAR15-26-530 (SEQ ID NO:179), TAR15-26-531 (SEQ ID NO:180), TAR15-26-532 (SEQ ID NO:181), TAR15-26-533 (SEQ ID NO:182), TAR15-26-534 (SEQ ID NO:183), TAR15-26-535 (SEQ ID NO:184), TAR15-26-536 (SEQ ID NO:185), TAR15-26-537 (SEQ ID NO:186), TAR15-26-538 (SEQ ID NO:187), TAR15-26-539 (SEQ ID NO:188), TAR15-26-540 (SEQ BD NO:189), TAR15-26-541 (SEQ ID NO:190), TAR15-26-542 (SEQ ID NO:191), TAR15-26-543 (SEQ ID NO:192), TAR15-26-544 (SEQ ID NO:193), TAR15-26-545 (SEQ ID NO:194), TAR15-26-546 (SEQ ID NO:195), TAR15-26-547 (SEQ ID NO:196), TAR15-26-548 (SEQ ID NO:197), and TAR15-26-549 (SEQ ID NO:198), TAR15-26-550 (SEQ ID NO:539), and TAR15-26-551 (SEQ ID NO:540).

For example, the immunoglobulin single variable domain with binding specificity for VEGF can comprise an amino acid sequence that has at least about 85% amino acid sequence identity with the amino acid sequence of a dAb selected from the group consisting of TAR15-1 (SEQ ID NO:100), TAR15-3 (SEQ ID NO:101), TAR15-4 (SEQ ID NO:102), TAR15-9 (SEQ ID NO:103), TAR15-10 (SEQ ID NO:104), TAR15-11 (SEQ ID NO: 105), TAR15-12 (SEQ ID NO:106), TAR15-13 (SEQ ID NO:107), TAR15-14 (SEQ ID NO:108), TAR15-15 (SEQ ID NO:109), TAR15-16 (SEQ ID NO:110), TAR15-17 (SEQ ID NO:111), TAR15-18 (SEQ ID NO:112), TAR15-19 (SEQ ID NO:113), TAR15-20 (SEQ ID NO:114), TAR15-22 (SEQ ID NO:115), TAR15-5 (SEQ ID NO:116), TAR15-6 (SEQ ID NO:117), TAR15-7 (SEQ ID NO:118), TAR15-8 (SEQ ID NO:119), TAR15-23 (SEQ ID NO:120), TAR15-24 (SEQ ID NO:121), TAR15-25 (SEQ ID NO:122), TAR15-26 (SEQ ID NO:123), TAR15-27 (SEQ ID NO:124), TAR15-29 (SEQ ID NO:125), TAR15-30 (SEQ ID NO:126), TAR15-6-500 (SEQ ID NO:127), TAR15-6-501 (SEQ ID NO:128), TAR15-6-502 (SEQ ID NO:129), TAR15-6-503 (SEQ ID NO:130), TAR15-6-504 (SEQ ID NO:131), TAR15-6-505 (SEQ ID NO:132), TAR15-6-506 (SEQ ID NO:133), TAR15-6-507 (SEQ ID NO:134), TAR15-6-508 (SEQ ID NO:135), TAR15-6-509 (SEQ ID NO:136), TAR15-6-510 (SEQ ID NO:137), TAR15-8-500 (SEQ ID NO:138), TAR15-8-501 (SEQ ID NO:139), TAR15-8-502 (SEQ ID NO:140), TAR15-8-503 (SEQ ID NO:141), TAR15-8-505 (SEQ ID NO:142), TAR15-8-506 (SEQ ID NO:143), TAR15-8-507 (SEQ ID NO:144), TAR15-8-508 (SEQ ID NO:145), TAR15-8-509 (SEQ ID NO:146), TAR15-8-510 (SEQ ID NO:147), TAR15-8-511 (SEQ ID NO:148), TAR15-26-500 (SEQ ID NO:149), TAR15-26-501 (SEQ ID NO:150), TAR15-26-502 (SEQ ID NO:151), TAR15-26-503 (SEQ ID NO:152), TAR15-26-504 (SEQ ID NO:153), TAR15-26-505 (SEQ ID NO:154), TAR15-26-506 (SEQ ID NO:155), TAR15-26-507 (SEQ ID NO:156), TAR15-26-508 (SEQ ID NO:157), TAR15-26-509 (SEQ ID NO:158), TAR15-26-510 (SEQ ID NO:159), TAR15-26-511 (SEQ ID NO:160), TAR15-26-512 (SEQ ID NO:161), TAR15-26-513 (SEQ ID NO:162), TAR15-26-514 (SEQ ID NO:163), TAR15-26-515 (SEQ ID NO:164), TAR15-26-516 (SEQ ID NO:165), TAR15-26-517 (SEQ ID NO:166), TAR15-26-518 (SEQ ID NO:167), TAR15-26-519 (SEQ ID NO:168), TAR15-26-520 (SEQ ID NO:169), TAR15-26-521 (SEQ ID NO:170), TAR15-26-522 (SEQ ID NO:171), TAR15-26-523 (SEQ ID NO:172), TAR15-26-524 (SEQ ID NO:173), TAR15-26-525 (SEQ ID NO:174), TAR15-26-526 (SEQ ID NO:175), TAR15-26-527 (SEQ ID NO:176), TAR15-26-528 (SEQ ID NO:177), TAR15-26-529 (SEQ ID NO:178), TAR15-26-530 (SEQ ID NO:179), TAR15-26-531 (SEQ ID NO:180), TAR15-26-532 (SEQ ID NO:181), TAR15-26-533 (SEQ ID NO:182), TAR15-26-534 (SEQ ID NO:183), TAR15-26-535 (SEQ ID NO:184), TAR15-26-536 (SEQ ID NO:185), TAR15-26-537 (SEQ ID NO:186), TAR15-26-538 (SEQ ID NO:187), TAR15-26-539 (SEQ ID NO:188), TAR15-26-540 (SEQ BD NO:189), TAR15-26-541 (SEQ ID NO:190), TAR15-26-542 (SEQ ID NO:191), TAR15-26-543 (SEQ BD NO:192), TAR15-26-544 (SEQ ID NO:193), TAR15-26-545 (SEQ ID NO:194), TAR15-26-546 (SEQ ID NO:195), TAR15-26-547 (SEQ ID NO:196), TAR15-26-548 (SEQ ID NO:197), and TAR15-26-549 (SEQ ID NO:198), TAR15-26-550 (SEQ ID NO:539), and TAR15-26-551 (SEQ ID NO:540).

In other particular embodiments, the ligand has binding specificity for VEGF and for EGFR and comprises at least one immunoglobulin single variable domain with binding specificity for VEGF and at least one immunoglobulin single variable domain with binding specificity for EGFR, wherein an immunoglobulin single variable domain with binding specificity for EGFR competes for binding to EGFR with an anti-EGFR domain antibody (dAb) selected from the group consisting of DOM16-17 (SEQ ID NO:325), DOM16-18 (SEQ ID NO:326), DOM16-19 (SEQ ID NO:327), DOM16-20 (SEQ ID NO:328), DOM16-21 (SEQ ID NO:329), DOM16-22 (SEQ ID NO:330), DOM16-23 (SEQ ID NO:331), DOM16-24 (SEQ ID NO:332), DOM16-25 (SEQ ID NO:333), DOM16-26 (SEQ ID NO:334), DOM16-27 (SEQ ID NO:335), DOM16-28 (SEQ ID NO:336), DOM16-29 (SEQ ID NO:337), DOM16-30 (SEQ ID NO:338), DOM16-31 (SEQ ID NO:339), DOM16-32 (SEQ ID NO:340), DOM16-33 (SEQ ID NO:341), DOM16-35 (SEQ ID NO:342), DOM16-37 (SEQ ID NO:343), DOM16-38 (SEQ ID NO:344), DOM16-39 (SEQ ID NO:345), DOM16-40 (SEQ ID NO:346), DOM16-41 (SEQ ID NO:347), DOM16-42 (SEQ ID NO:348), DOM16-43 (SEQ ID NO:349), DOM16-44 (SEQ ID NO:350), DOM16-45 (SEQ ID NO:351), DOM16-46 (SEQ ID NO:352), DOM16-47 (SEQ ID NO:353), DOM16-48 (SEQ ID NO:354), DOM16-49 (SEQ ID NO:355), DOM16-50 (SEQ ID NO:356), DOM16-59 (SEQ ID NO:357), DOM16-60 (SEQ ID NO:358), DOM16-61 (SEQ ID NO:359), DOM16-62 (SEQ ID NO:360), DOM16-63 (SEQ ID NO:361), DOM16-64 (SEQ ID NO:362), DOM16-65 (SEQ ID NO:363), DOM16-66 (SEQ ID NO:364), DOM16-67 (SEQ ID NO:365), DOM16-68 (SEQ ID NO:366), DOM16-69 (SEQ ID NO:367), DOM16-70 (SEQ ID NO:368), DOM16-71 (SEQ ID NO:369), DOM16-72 (SEQ ID NO:370), DOM16-73 (SEQ ID NO:371), DOM16-74 (SEQ ID NO:372), DOM16-75 (SEQ ID NO:373), DOM16-76 (SEQ ID NO:374), DOM16-77 (SEQ ID NO:375), DOM16-78 (SEQ ID NO:376), DOM16-79 (SEQ ID NO:377), DOM16-80 (SEQ ID NO:378), DOM16-81 (SEQ ID NO:379), DOM16-82 (SEQ ID NO:380), DOM16-83 (SEQ ID NO:381), DOM16-84 (SEQ ID NO:382), DOM16-85 (SEQ ID NO:383), DOM16-87 (SEQ ID NO:384), DOM16-88 (SEQ ID NO:385), DOM16-89 (SEQ ID NO:386), DOM16-90 (SEQ ID NO:387), DOM16-91 (SEQ ID NO:388), DOM16-92 (SEQ ID NO:389), DOM16-94 (SEQ ID NO:390), DOM16-95 (SEQ ID NO:391), DOM16-96 (SEQ ID NO:392), DOM16-97 (SEQ ID NO:393), DOM16-98 (SEQ ID NO:394), DOM16-99 (SEQ ID NO:395), DOM16-100 (SEQ ID NO:396), DOM16-101 (SEQ ID NO:397), DOM16-102 (SEQ ID NO:398), DOM16-103 (SEQ ID NO:399), DOM16-104 (SEQ ID NO:400), DOM16-105 (SEQ ID NO:401), DOM16-106 (SEQ ID NO:402), DOM16-107 (SEQ ID NO:403), DOM16-108 (SEQ ID NO:404), DOM16-109 (SEQ ID NO:405), DOM16-110 (SEQ ID NO:406), DOM16-111 (SEQ ID NO:407), DOM16-112 (SEQ ID NO:408), DOM16-113 (SEQ ID NO:409), DOM16-114 (SEQ ID NO:410), DOM16-115 (SEQ ID NO:411), DOM16-116 (SEQ ID NO:412), DOM16-117 (SEQ ID NO:413), DOM16-118 (SEQ ID NO:414), DOM16-119 (SEQ ID NO:415), DOM16-39-6 (SEQ ID NO:416), DOM16-39-8 (SEQ ID NO:417), DOM16-39-34 (SEQ ID NO:418), DOM16-39-48 (SEQ ID NO:419), DOM16-39-87 (SEQ ID NO:420), DOM16-39-90 (SEQ ID NO:421), DOM16-39-96 (SEQ ID NO:422), DOM16-39-100 (SEQ ID NO:423), DOM16-39-101 (SEQ ID NO:424), DOM16-39-102 (SEQ ID NO:425), DOM16-39-103 (SEQ ID NO:426), DOM16-39-104 (SEQ ID NO:427), DOM16-39-105 (SEQ ID NO:428), DOM16-39-106 (SEQ ID NO:429), DOM16-39-107 (SEQ ID NO:430), DOM16-39-108 (SEQ ID NO:431), DOM16-39-109 (SEQ ID NO:432), DOM16-39-110 (SEQ ID NO:433), DOM16-39-111 (SEQ ID NO:434), DOM16-39-112 (SEQ ID NO:435), DOM16-39-113 (SEQ ID NO:436), DOM16-39-114 (SEQ ID NO:437), DOM16-39-115 (SEQ ID NO:438), DOM16-39-116 (SEQ ID NO:439), DOM16-39-117 (SEQ ID NO:440), DOM16-39-200 (SEQ ID NO:441), DOM16-39-201 (SEQ ID NO:442), DOM16-39-202 (SEQ ID NO:443), DOM16-39-203 (SEQ ID NO:444), DOM16-39-204 (SEQ ID NO:445), DOM16-39-205 (SEQ ID NO:446), DOM16-39-206 (SEQ ID NO:447), DOM16-39-207 (SEQ ID NO:448), DOM16-39-209 (SEQ ID NO:449), DOM16-52 (SEQ ID NO:450), NB1 (SEQ ID NO:451), NB2 (SEQ ID NO:452), NB3 (SEQ ID NO:453), NB4 (SEQ ID NO:454), NB5 (SEQ ID NO:455), NB6 (SEQ ID NO:456), NB7 (SEQ ID NO:457), NB8 (SEQ ID NO:458), NB9 (SEQ ID NO:459), NB10 (SEQ ID NO:460), NB11 (SEQ ID NO:461), NB12 (SEQ ID NO:462), NB13 (SEQ ID NO:463), NB14 (SEQ ID NO:464), NB15 (SEQ ID NO:465), NB16 (SEQ ID NO:466), NB17 (SEQ ID NO:467), NB18 (SEQ ID NO:468), NB19 (SEQ ID NO:469), NB20 (SEQ ID NO:470), NB21 (SEQ ID NO:471), and NB22 (SEQ ID NO:472).

For example, the immunoglobulin single variable domain with binding specificity for EGFR can comprise an amino acid sequence that has at least about 85% amino acid sequence identity with the amino acid sequence of a dAb selected from the group consisting of DOM16-17 (SEQ ID NO:325), DOM16-18 (SEQ ID NO:326), DOM16-19 (SEQ ID NO:327), DOM16-20 (SEQ ID NO:328), DOM16-21 (SEQ ID NO:329), DOM16-22 (SEQ ID NO:330), DOM16-23 (SEQ ID NO:331), DOM16-24 (SEQ ID NO:332), DOM16-25 (SEQ ID NO:333), DOM16-26 (SEQ ID NO:334), DOM16-27 (SEQ ID NO:335), DOM16-28 (SEQ ID NO:336), DOM16-29 (SEQ ID NO:337), DOM16-30 (SEQ ID NO:338), DOM16-31 (SEQ ID NO:339), DOM16-32 (SEQ ID NO:340), DOM16-33 (SEQ ID NO:341), DOM16-35 (SEQ ID NO:342), DOM16-37 (SEQ ID NO:343), DOM16-38 (SEQ ID NO:344), DOM16-39 (SEQ ID NO:345), DOM16-40 (SEQ ID NO:346), DOM16-41 (SEQ ID NO:347), DOM16-42 (SEQ ID NO:348), DOM16-43 (SEQ ID NO:349), DOM16-44 (SEQ ID NO:350), DOM16-45 (SEQ ID NO:351), DOM16-46 (SEQ ID NO:352), DOM16-47 (SEQ ID NO:353), DOM16-48 (SEQ ID NO:354), DOM16-49 (SEQ ID NO:355), DOM16-50 (SEQ ID NO:356), DOM16-59 (SEQ ID NO:357), DOM16-60 (SEQ ID NO:358), DOM16-61 (SEQ ID NO:359), DOM16-62 (SEQ ID NO:360), DOM16-63 (SEQ ID NO:361), DOM16-64 (SEQ ID NO:362), DOM16-65 (SEQ ID NO:363), DOM16-66 (SEQ ID NO:364), DOM16-67 (SEQ ID NO:365), DOM16-68 (SEQ ID NO:366), DOM16-69 (SEQ ID NO:367), DOM16-70 (SEQ ID NO:368), DOM16-71 (SEQ ID NO:369), DOM16-72 (SEQ ID NO:370), DOM16-73 (SEQ ID NO:371), DOM16-74 (SEQ ID NO:372), DOM16-75 (SEQ ID NO:373), DOM16-76 (SEQ ID NO:374), DOM16-77 (SEQ ID NO:375), DOM16-78 (SEQ ID NO:376), DOM16-79 (SEQ ID NO:377), DOM16-80 (SEQ ID NO:378), DOM16-81 (SEQ ID NO:379), DOM16-82 (SEQ ID NO:380), DOM16-83 (SEQ ID NO:381), DOM16-84 (SEQ ID NO:382), DOM16-85 (SEQ ID NO:383), DOM16-87 (SEQ ID NO:384), DOM16-88 (SEQ ID NO:385), DOM16-89 (SEQ ID NO:386), DOM16-90 (SEQ ID NO:387), DOM16-91 (SEQ ID NO:388), DOM16-92 (SEQ ID NO:389), DOM16-94 (SEQ ID NO:390), DOM16-95 (SEQ ID NO:391), DOM16-96 (SEQ ID NO:392), DOM16-97 (SEQ ID NO:393), DOM16-98 (SEQ ID NO:394), DOM16-99 (SEQ ID NO:395), DOM16-100 (SEQ ID NO:396), DOM16-101 (SEQ ID NO:397), DOM16-102 (SEQ ID NO:398), DOM16-103 (SEQ ID NO:399), DOM16-104 (SEQ ID NO:400), DOM16-105 (SEQ ID NO:401), DOM16-106 (SEQ ID NO:402), DOM16-107 (SEQ ID NO:403), DOM16-108 (SEQ ID NO:404), DOM16-109 (SEQ ID NO:405), DOM16-110 (SEQ ID NO:406), DOM16-111 (SEQ ID NO:407), DOM16-112 (SEQ ID NO:408), DOM16-113 (SEQ ID NO:409), DOM16-114 (SEQ ID NO:410), DOM16-115 (SEQ ID NO:411), DOM16-116 (SEQ ID NO:412), DOM16-117 (SEQ ID NO:413), DOM16-118 (SEQ ID NO:414), DOM16-119 (SEQ ID NO:415), DOM16-39-6 (SEQ ID NO:416), DOM16-39-8 (SEQ ID NO:417), DOM16-39-34 (SEQ ID NO:418), DOM16-39-48 (SEQ ID NO:419), DOM16-39-87 (SEQ ID NO:420), DOM16-39-90 (SEQ ID NO:421), DOM16-39-96 (SEQ ID NO:422), DOM16-39-100 (SEQ ID NO:423), DOM16-39-101 (SEQ ID NO:424), DOM16-39-102 (SEQ ID NO:425), DOM16-39-103 (SEQ ID NO:426), DOM16-39-104 (SEQ ID NO:427), DOM16-39-105 (SEQ ID NO:428), DOM16-39-106 (SEQ ID NO:429), DOM16-39-107 (SEQ ID NO:430), DOM16-39-108 (SEQ ID NO:431), DOM16-39-109 (SEQ ID NO:432), DOM16-39-110 (SEQ ID NO:433), DOM16-39-111 (SEQ ID NO:434), DOM16-39-112 (SEQ ID NO:435), DOM16-39-113 (SEQ ID NO:436), DOM16-39-114 (SEQ ID NO:437), DOM16-39-115 (SEQ ID NO:438), DOM16-39-116 (SEQ ID NO:439), DOM16-39-117 (SEQ ID NO:440), DOM16-39-200 (SEQ ID NO:441), DOM16-39-201 (SEQ ID NO:442), DOM16-39-202 (SEQ ID NO:443), DOM16-39-203 (SEQ ID NO:444), DOM16-39-204 (SEQ ID NO:445), DOM16-39-205 (SEQ ID NO:446), DOM16-39-206 (SEQ ID NO:447), DOM16-39-207 (SEQ ID NO:448), DOM16-39-209 (SEQ ID NO:449), DOM16-52 (SEQ ID NO:450), NB1 (SEQ ID NO:451), NB2 (SEQ ID NO:452), NB3 (SEQ ID NO:453), NB4 (SEQ ID NO:454), NB5 (SEQ ID NO:455), NB6 (SEQ ID NO:456), NB7 (SEQ ID NO:457), NB8 (SEQ ID NO:458), NB9 (SEQ ID NO:459), NB10 (SEQ ID NO:460), NB11 (SEQ ID NO:461), NB12 (SEQ ID NO:462), NB13 (SEQ ID NO:463), NB14 (SEQ ID NO:464), NB15 (SEQ ID NO:465), NB16 (SEQ ID NO:466), NB17 (SEQ ID NO:467), NB18 (SEQ ID NO:468), NB19 (SEQ ID NO:469), NB20 (SEQ ID NO:470), NB21 (SEQ ID NO:471), and NB22 (SEQ ID NO:472).

In some embodiments, the ligand has binding specificity for VEGF and for EGFR and comprises at least one immunoglobulin single variable domain with binding specificity for VEGF and at least one immunoglobulin single variable domain with binding specificity for EGFR, wherein an immunoglobulin single variable domain with binding specificity for VEGF competes for binding to VEGF with an anti-VEGF domain antibody (dAb) selected from the group consisting of TAR15-1 (SEQ ID NO:100), TAR15-3 (SEQ ID NO:101), TAR15-4 (SEQ ID NO:102), TAR15-9 (SEQ ID NO:103), TAR15-10 (SEQ BD NO:104), TAR15-11 (SEQ ID NO:105), TAR15-12 (SEQ ID NO:106), TAR15-13 (SEQ ID NO:107), TAR15-14 (SEQ ID NO:108), TAR15-15 (SEQ ID NO:109), TAR15-16 (SEQ ID NO:10), TAR15-17 (SEQ ID NO:111), TAR15-18 (SEQ ID NO:112), TAR15-19 (SEQ ID NO:113), TAR15-20 (SEQ ID NO:114), TAR15-22 (SEQ ID NO:115), TAR15-5 (SEQ ID NO:116), TAR15-6 (SEQ ID NO:117), TAR15-7 (SEQ ID NO:118), TAR15-8 (SEQ ID NO:119), TAR15-23 (SEQ ID NO:120), TAR15-24 (SEQ ID NO:121), TAR15-25 (SEQ ID NO:122), TAR15-26 (SEQ ID NO:123), TAR15-27 (SEQ ID NO:124), TAR15-29 (SEQ ID NO:125), TAR15-30 (SEQ ID NO:126), TAR15-6-500 (SEQ BD NO:127), TAR15-6-501 (SEQ ID NO:128), TAR15-6-502 (SEQ ID NO:129), TAR15-6-503 (SEQ ID NO:130), TAR15-6-504 (SEQ ID NO:131), TAR15-6-505 (SEQ ID NO:132), TAR15-6-506 (SEQ ID NO:133), TAR15-6-507 (SEQ ID NO:134), TAR15-6-508 (SEQ ID NO:135), TAR15-6-509 (SEQ ID NO:136), TAR15-6-510 (SEQ BD NO:137), TAR15-8-500 (SEQ ID NO:138), TAR15-8-501 (SEQ ID NO:139), TAR15-8-502 (SEQ ID NO:140), TAR15-8-503 (SEQ ID NO:141), TAR15-8-505 (SEQ ID NO:142), TAR15-8-506 (SEQ ID NO:143), TAR15-8-507 (SEQ ID NO:144), TAR15-8-508 (SEQ ID NO:145), TAR15-8-509 (SEQ ID NO:146), TAR15-8-510 (SEQ ID NO:147), TAR15-8-511 (SEQ ID NO:148), TAR15-26-500 (SEQ ID NO:149), TAR15-26-501 (SEQ ID NO:150), TAR15-26-502 (SEQ ID NO:151), TAR15-26-503 (SEQ ID NO:152), TAR15-26-504 (SEQ ID NO:153), TAR15-26-505 (SEQ ID NO:154), TAR15-26-506 (SEQ ID NO:155), TAR15-26-507 (SEQ ID NO:156), TAR15-26-508 (SEQ ID NO:157), TAR15-26-509 (SEQ ID NO:158), TAR15-26-510 (SEQ ID NO:159), TAR15-26-511 (SEQ ID NO:160), TAR15-26-512 (SEQ ID NO:161), TAR15-26-513 (SEQ ID NO:162), TAR15-26-514 (SEQ ID NO:163), TAR15-26-515 (SEQ ID NO:164), TAR15-26-516 (SEQ ID NO:165), TAR15-26-517 (SEQ ID NO:166), TAR15-26-518 (SEQ ID NO:167), TAR15-26-519 (SEQ ID NO:168), TAR15-26-520 (SEQ ID NO:169), TAR15-26-521 (SEQ ID NO:170), TAR15-26-522 (SEQ ID NO:171), TAR15-26-523 (SEQ ID NO:172), TAR15-26-524 (SEQ ID NO:173), TAR15-26-525 (SEQ ID NO:174), TAR15-26-526 (SEQ ID NO:175), TAR15-26-527 (SEQ ID NO:176), TAR15-26-528 (SEQ ID NO:177), TAR15-26-529 (SEQ ID NO:178), TAR15-26-530 (SEQ ID NO:179), TAR15-26-531 (SEQ ID NO:180), TAR15-26-532 (SEQ ID NO:181), TAR15-26-533 (SEQ ID NO:182), TAR15-26-534 (SEQ ID NO:183), TAR15-26-535 (SEQ ID NO:184), TAR15-26-536 (SEQ ID NO:185), TAR15-26-537 (SEQ ID NO:186), TAR15-26-538 (SEQ ID NO:187), TAR15-26-539 (SEQ ID NO:188), TAR15-26-540 (SEQ ID NO:189), TAR15-26-541 (SEQ ID NO:190), TAR15-26-542 (SEQ ID NO:191), TAR15-26-543 (SEQ ID NO:192), TAR15-26-544 (SEQ ID NO:193), TAR15-26-545 (SEQ ID NO:194), TAR15-26-546 (SEQ ID NO:195), TAR15-26-547 (SEQ ID NO:196), TAR15-26-548 (SEQ ID NO:197), and TAR15-26-549 (SEQ ID NO:198), TAR15-26-550 (SEQ ID NO:539), and TAR15-26-551 (SEQ ID NO:540); and wherein an immunoglobulin single variable domain with binding specificity for EGFR competes for binding to EGFR with an anti-EGFR domain antibody (dAb) selected from the group consisting of DOM16-17 (SEQ ID NO:325), DOM16-18 (SEQ ID NO:326), DOM16-19 (SEQ ID NO:327), DOM16-20 (SEQ ID NO:328), DOM16-21 (SEQ ID NO:329), DOM16-22 (SEQ ID NO:330), DOM16-23 (SEQ ID NO:331), DOM16-24 (SEQ ID NO:332), DOM16-25 (SEQ ID NO:333), DOM16-26 (SEQ ID NO:334), DOM16-27 (SEQ ID NO:335), DOM16-28 (SEQ ID NO:336), DOM16-29 (SEQ ID NO:337), DOM16-30 (SEQ ID NO:338), DOM16-31 (SEQ ID NO:339), DOM16-32 (SEQ ID NO:340), DOM16-33 (SEQ ID NO:341), DOM16-35 (SEQ ID NO:342), DOM16-37 (SEQ ID NO:343), DOM16-38 (SEQ ID NO:344), DOM16-39 (SEQ ID NO:345), DOM16-40 (SEQ ID NO:346), DOM16-41 (SEQ ID NO:347), DOM16-42 (SEQ ID NO:348), DOM16-43 (SEQ ID NO:349), DOM16-44 (SEQ ID NO:350), DOM16-45 (SEQ ID NO:351), DOM16-46 (SEQ ID NO:352), DOM16-47 (SEQ ID NO:353), DOM16-48 (SEQ ID NO:354), DOM16-49 (SEQ ID NO:355), DOM16-50 (SEQ ID NO:356), DOM16-

59 (SEQ ID NO:357), DOM16-60 (SEQ ID NO:358), DOM16-61 (SEQ ID NO:359), DOM16-62 (SEQ ID NO:360), DOM16-63 (SEQ ID NO:361), DOM16-64 (SEQ ID NO:362), DOM16-65 (SEQ ID NO:363), DOM16-66 (SEQ ID NO:364), DOM16-67 (SEQ ID NO:365), DOM16-68 (SEQ ID NO:366), DOM16-69 (SEQ ID NO:367), DOM16-70 (SEQ ID NO:368), DOM16-71 (SEQ ID NO:369), DOM16-72 (SEQ ID NO:370), DOM16-73 (SEQ ID NO:371), DOM16-74 (SEQ ID NO:372), DOM16-75 (SEQ ID NO:373), DOM16-76 (SEQ ID NO:374), DOM16-77 (SEQ ID NO:375), DOM16-78 (SEQ ID NO:376), DOM16-79 (SEQ ID NO:377), DOM16-80 (SEQ ID NO:378), DOM16-81 (SEQ ID NO:379), DOM16-82 (SEQ ID NO:380), DOM16-83 (SEQ ID NO:381), DOM16-84 (SEQ ID NO:382), DOM16-85 (SEQ ID NO:383), DOM16-87 (SEQ ID NO:384), DOM16-88 (SEQ ID NO:385), DOM16-89 (SEQ ID NO:386), DOM16-90 (SEQ ID NO:387), DOM16-91 (SEQ ID NO:388), DOM16-92 (SEQ ID NO:389), DOM16-94 (SEQ ID NO:390), DOM16-95 (SEQ ID NO:391), DOM16-96 (SEQ ID NO:392), DOM16-97 (SEQ ID NO:393), DOM16-98 (SEQ ID NO:394), DOM16-99 (SEQ ID NO:395), DOM16-100 (SEQ ID NO:396), DOM16-101 (SEQ ID NO:397), DOM16-102 (SEQ ID NO:398), DOM16-103 (SEQ ID NO:399), DOM16-104 (SEQ ID NO:400), DOM16-105 (SEQ ID NO:401), DOM16-106 (SEQ ID NO:402), DOM16-107 (SEQ ID NO:403), DOM16-108 (SEQ ID NO:404), DOM16-109 (SEQ ID NO:405), DOM16-110 (SEQ ID NO:406), DOM16-111 (SEQ ID NO:407), DOM16-112 (SEQ ID NO:408), DOM16-113 (SEQ ID NO:409), DOM16-114 (SEQ ID NO:410), DOM16-115 (SEQ ID NO:411), DOM16-116 (SEQ ID NO:412), DOM16-117 (SEQ ID NO:413), DOM16-118 (SEQ ID NO:414), DOM16-119 (SEQ ID NO:415), DOM16-39-6 (SEQ ID NO:416), DOM16-39-8 (SEQ ID NO:417), DOM16-39-34 (SEQ ID NO:418), DOM16-39-48 (SEQ ID NO:419), DOM16-39-87 (SEQ ID NO:420), DOM16-39-90 (SEQ ID NO:421), DOM16-39-96 (SEQ ID NO:422), DOM16-39-100 (SEQ ID NO:423), DOM16-39-101 (SEQ ID NO:424), DOM16-39-102 (SEQ ID NO:425), DOM16-39-103 (SEQ ID NO:426), DOM16-39-104 (SEQ ID NO:427), DOM16-39-105 (SEQ ID NO:428), DOM16-39-106 (SEQ ID NO:429), DOM16-39-107 (SEQ ID NO:430), DOM16-39-108 (SEQ ID NO:431), DOM16-39-109 (SEQ ID NO:432), DOM16-39-110 (SEQ ID NO:433), DOM16-39-111 (SEQ ID NO:434), DOM16-39-112 (SEQ ID NO:435), DOM16-39-113 (SEQ ID NO:436), DOM16-39-114 (SEQ ID NO:437), DOM16-39-115 (SEQ ID NO:438), DOM16-39-116 (SEQ ID NO:439), DOM16-39-117 (SEQ ID NO:440), DOM16-39-200 (SEQ ID NO:441), DOM16-39-201 (SEQ ID NO:442), DOM16-39-202 (SEQ ID NO:443), DOM16-39-203 (SEQ ID NO:444), DOM16-39-204 (SEQ ID NO:445), DOM16-39-205 (SEQ ID NO:446), DOM16-39-206 (SEQ ID NO:447), DOM16-39-207 (SEQ ID NO:448), DOM16-39-209 (SEQ ID NO:449), DOM16-52 (SEQ ID NO:450), NB1 (SEQ ID NO:451), NB2 (SEQ ID NO:452), NB3 (SEQ ID NO:453), NB4 (SEQ ID NO:454), NB5 (SEQ ID NO:455), NB6 (SEQ ID NO:456), NB7 (SEQ ID NO:457), NB8 (SEQ ID NO:458), NB9 (SEQ ID NO:459), NB10 (SEQ ID NO:460), NB11 (SEQ ID NO:461), NB12 (SEQ ID NO:462), NB13 (SEQ ID NO:463), NB14 (SEQ ID NO:464), NB15 (SEQ ID NO:465), NB16 (SEQ ID NO:466), NB17 (SEQ ID NO:467), NB18 (SEQ ID NO:468), NB19 (SEQ ID NO:469), NB20 (SEQ ID NO:470), NB21 (SEQ ID NO:471), and NB22 (SEQ ID NO:472).

For example, the ligand can comprise an immunoglobulin single variable domain with binding specificity for VEGF that comprises an amino acid sequence that has at least about 85% amino acid sequence identity with the amino acid sequence of a dAb selected from the group consisting of TAR15-1 (SEQ ID NO:100), TAR15-3 (SEQ ID NO:101), TAR15-4 (SEQ ID NO:102), TAR15-9 (SEQ ID NO:103), TAR15-10 (SEQ ID NO:104), TAR15-11 (SEQ ID NO:105), TAR15-12 (SEQ ID NO:106), TAR15-13 (SEQ ID NO:107), TAR15-14 (SEQ ID NO:108), TAR15-15 (SEQ ID NO:109), TAR15-16 (SEQ ID NO:110), TAR15-17 (SEQ ID NO:111), TAR15-18 (SEQ ID NO:112), TAR15-19 (SEQ ID NO:113), TAR15-20 (SEQ ID NO:114), TAR15-22 (SEQ ID NO:115), TAR15-5 (SEQ ID NO:116), TAR15-6 (SEQ ID NO:117), TAR15-7 (SEQ ID NO:118), TAR15-8 (SEQ ID NO:119), TAR15-23 (SEQ ID NO:120), TAR15-24 (SEQ ID NO:121), TAR15-25 (SEQ ID NO:122), TAR15-26 (SEQ ID NO:123), TAR15-27 (SEQ ID NO:124), TAR15-29 (SEQ ID NO:125), TAR15-30 (SEQ ID NO:126), TAR15-6-500 (SEQ ID NO:127), TAR15-6-501 (SEQ ID NO:128), TAR15-6-502 (SEQ ID NO:129), TAR15-6-503 (SEQ ID NO:130), TAR15-6-504 (SEQ ID NO:131), TAR15-6-505 (SEQ ID NO:132), TAR15-6-506 (SEQ ID NO:133), TAR15-6-507 (SEQ ID NO:134), TAR15-6-508 (SEQ ID NO:135), TAR15-6-509 (SEQ ID NO:136), TAR15-6-510 (SEQ ID NO:137), TAR15-8-500 (SEQ ID NO:138), TAR15-8-501 (SEQ ID NO:139), TAR15-8-502 (SEQ ID NO:140), TAR15-8-503 (SEQ ID NO:141), TAR15-8-505 (SEQ ID NO:142), TAR15-8-506 (SEQ ID NO:143), TAR15-8-507 (SEQ ID NO:144), TAR15-8-508 (SEQ ID NO:145), TAR15-8-509 (SEQ ID NO:146), TAR15-8-510 (SEQ ID NO:147), TAR15-8-511 (SEQ ID NO:148), TAR15-26-500 (SEQ ID NO:149), TAR15-26-501 (SEQ ID NO:150), TAR15-26-502 (SEQ ID NO:151), TAR15-26-503 (SEQ ID NO:152), TAR15-26-504 (SEQ ID NO:153), TAR15-26-505 (SEQ ID NO:154), TAR15-26-506 (SEQ ID NO:155), TAR15-26-507 (SEQ ID NO:156), TAR15-26-508 (SEQ ID NO:157), TAR15-26-509 (SEQ ID NO:158), TAR15-26-510 (SEQ ID NO:159), TAR15-26-511 (SEQ ID NO:160), TAR15-26-512 (SEQ ID NO:161), TAR15-26-513 (SEQ ID NO:162), TAR15-26-514 (SEQ ID NO:163), TAR15-26-515 (SEQ ID NO:164), TAR15-26-516 (SEQ ID NO:165), TAR15-26-517 (SEQ ID NO:166), TAR15-26-518 (SEQ ID NO:167), TAR15-26-519 (SEQ ID NO:168), TAR15-26-520 (SEQ BD NO:169), TAR15-26-521 (SEQ ID NO:170), TAR15-26-522 (SEQ ID NO:171), TAR15-26-523 (SEQ ID NO:172), TAR15-26-524 (SEQ ID NO:173), TAR15-26-525 (SEQ ID NO:174), TAR15-26-526 (SEQ ID NO:175), TAR15-26-527 (SEQ ID NO:176), TAR15-26-528 (SEQ ID NO:177), TAR15-26-529 (SEQ ID NO:178), TAR15-26-530 (SEQ ID NO:179), TAR15-26-531 (SEQ ID NO:180), TAR15-26-532 (SEQ ID NO:181), TAR15-26-533 (SEQ ID NO:182), TAR15-26-534 (SEQ ID NO:183), TAR15-26-535 (SEQ ID NO:184), TAR15-26-536 (SEQ ID NO:185), TAR15-26-537 (SEQ ID NO:186), TAR15-26-538 (SEQ ID NO:187), TAR15-26-539 (SEQ ID NO:188), TAR15-26-540 (SEQ ID NO:189), TAR15-26-541 (SEQ ID NO:190), TAR15-26-542 (SEQ ID NO:191), TAR15-26-543 (SEQ ID NO:192), TAR15-26-544 (SEQ ID NO:193), TAR15-26-545 (SEQ ID NO:194), TAR15-26-546 (SEQ ID NO:195), TAR15-26-547 (SEQ ID NO:196), TAR15-26-548 (SEQ ID NO:197), and TAR15-26-549 (SEQ ID NO:198), TAR15-26-550 (SEQ ID NO:539), and TAR15-26-551 (SEQ ID NO:540); and further comprise an immunoglobulin single variable domain with binding specificity for EGFR that comprise an amino acid sequence that has at least about 85% amino acid sequence identity with the amino acid sequence of a dAb selected from the group consisting of DOM16-17 (SEQ ID NO:325), DOM16-18 (SEQ ID NO:326), DOM16-19 (SEQ ID NO:327), DOM16-20 (SEQ ID NO:328), DOM16-21 (SEQ ID NO:329), DOM16-22 (SEQ ID NO:330), DOM16-23 (SEQ ID NO:331), DOM16-24 (SEQ ID NO:332), DOM16-25 (SEQ ID NO:333), DOM16-26 (SEQ ID NO:334), DOM16-27 (SEQ ID NO:335), DOM16-28 (SEQ ID NO:336), DOM16-29 (SEQ ID NO:337), DOM16-30 (SEQ ID NO:338), DOM16-31 (SEQ ID NO:339), DOM16-32 (SEQ ID NO:340), DOM16-33 (SEQ ID NO:341), DOM16-35 (SEQ ID NO:342), DOM16-37 (SEQ ID NO:343), DOM16-38 (SEQ ID NO:344), DOM16-39 (SEQ ID NO:345), DOM16-40 (SEQ ID NO:346), DOM16-41 (SEQ ID NO:347), DOM16-42 (SEQ ID NO:348), DOM16-43 (SEQ ID NO:349), DOM16-44 (SEQ ID NO:350), DOM16-45 (SEQ ID NO:351), DOM16-46 (SEQ ID NO:352), DOM16-47 (SEQ ID NO:353), DOM16-48 (SEQ ID NO:354), DOM16-49 (SEQ ID NO:355), DOM16-50 (SEQ ID NO:356), DOM16-59 (SEQ ID NO:357), DOM16-60 (SEQ ID NO:358), DOM16-61 (SEQ ID NO:359), DOM16-62 (SEQ ID NO:360), DOM16-63 (SEQ ID NO:361), DOM16-64 (SEQ ID NO:362), DOM16-65 (SEQ ID NO:363), DOM16-66 (SEQ ID NO:364), DOM16-67 (SEQ ID NO:365), DOM16-68 (SEQ ID NO:366), DOM16-69 (SEQ ID NO:367), DOM16-70 (SEQ ID NO:368), DOM16-71 (SEQ ID NO:369), DOM16-72 (SEQ ID NO:370), DOM16-73 (SEQ ID NO:371), DOM16-74 (SEQ ID NO:372), DOM16-75 (SEQ ID NO:373), DOM16-76 (SEQ ID NO:374), DOM16-77 (SEQ ID NO:375), DOM16-78 (SEQ ID NO:376), DOM16-79 (SEQ ID NO:377), DOM16-80 (SEQ ID NO:378), DOM16-81 (SEQ ID NO:379), DOM16-82 (SEQ ID NO:380), DOM16-83 (SEQ ID NO:381), DOM16-84 (SEQ ID NO:382), DOM16-85 (SEQ ID NO:383), DOM16-87 (SEQ ID NO:384), DOM16-88 (SEQ ID NO:385), DOM16-89 (SEQ ID NO:386), DOM16-90 (SEQ ID NO:387), DOM16-91 (SEQ ID NO:388), DOM16-92 (SEQ ID NO:389), DOM16-94 (SEQ ID NO:390), DOM16-95 (SEQ ID NO:391), DOM16-96 (SEQ ID NO:392), DOM16-97 (SEQ ID NO:393), DOM16-98 (SEQ ID NO:394), DOM16-99 (SEQ ID NO:395), DOM16-100 (SEQ ID NO:396), DOM16-101 (SEQ ID NO:397), DOM16-102 (SEQ ID NO:398), DOM16-103 (SEQ ID NO:399), DOM16-104 (SEQ ID NO:400), DOM16-105 (SEQ ID NO:401), DOM16-106 (SEQ ID NO:402), DOM16-107 (SEQ ID NO:403), DOM16-108 (SEQ ID NO:404), DOM16-109 (SEQ ID NO:405), DOM16-110 (SEQ ID NO:406), DOM16-111 (SEQ ID NO:407), DOM16-112 (SEQ ID NO:408), DOM16-113 (SEQ ID NO:409), DOM16-114 (SEQ ID NO:410), DOM16-115 (SEQ ID NO:411), DOM16-116 (SEQ ID NO:412), DOM16-117 (SEQ ID NO:413), DOM16-118 (SEQ ID NO:414), DOM16-119 (SEQ ID NO:415), DOM16-39-6 (SEQ ID NO:416), DOM16-39-8 (SEQ ID NO:417), DOM16-39-34 (SEQ ID NO:418), DOM16-39-48 (SEQ ID NO:419), DOM16-39-87 (SEQ ID NO:420), DOM16-39-90 (SEQ ID NO:421), DOM16-39-96 (SEQ ID NO:422), DOM16-39-100 (SEQ ID NO:423), DOM16-39-101 (SEQ ID NO:424), DOM16-39-102 (SEQ ID NO:425), DOM16-39-103 (SEQ ID NO:426), DOM16-39-104 (SEQ ID NO:427), DOM16-39-105 (SEQ ID NO:428), DOM16-39-106 (SEQ ID NO:429), DOM16-39-107 (SEQ ID NO:430), DOM16-39-108 (SEQ ID NO:431), DOM16-39-109 (SEQ ID NO:432), DOM16-39-110 (SEQ ID NO:433), DOM16-39-111 (SEQ ID NO:434), DOM16-39-112 (SEQ ID NO:435), DOM16-39-113 (SEQ ID NO:436), DOM16-39-114 (SEQ ID NO:437), DOM16-39-115 (SEQ ID NO:438), DOM16-39-116 (SEQ ID NO:439), DOM16-39-117 (SEQ ID NO:440), DOM16-39-200 (SEQ ID NO:441), DOM16-39-201 (SEQ ID NO:442), DOM16-39-202 (SEQ ID NO:443), DOM16-39-203 (SEQ ID NO:444), DOM16-39-204 (SEQ ID NO:445), DOM16-39-205 (SEQ ID NO:446), DOM16-39-206 (SEQ ID NO:447), DOM16-39-207 (SEQ ID NO:448), DOM16-39-209 (SEQ ID NO:449), DOM16-52 (SEQ ID NO:450), NB1 (SEQ ID NO:451), NB2 (SEQ ID NO:452), NB3 (SEQ ID NO:453), NB4 (SEQ ID NO:454), NB5 (SEQ ID NO:455), NB6 (SEQ ID NO:456), NB7 (SEQ ID NO:457), NB8 (SEQ ID NO:458), NB9 (SEQ ID NO:459), NB10 (SEQ ID NO:460), NB11 (SEQ ID NO:461), NB12 (SEQ ID NO:462), NB13 (SEQ ID NO:463), NB14 (SEQ ID NO:464), NB15 (SEQ ID NO:465), NB16 (SEQ ID NO:466), NB17 (SEQ ID NO:467), NB18 (SEQ ID NO:468), NB19 (SEQ ID NO:469), NB20 (SEQ ID NO:470), NB21 (SEQ ID NO:471), and NB22 (SEQ ID NO:472).

In some embodiments, the ligand has binding specificity for VEGF and for EGFR and comprises at least one immunoglobulin single variable domain with binding specificity for VEGF and at least one immunoglobulin single variable domain with binding specificity for EGFR, wherein an immunoglobulin single variable domain with binding specificity for VEGF competes for binding to VEGF with an anti-VEGF domain antibody (dAb) selected from the group consisting of TAR15-1 (SEQ ID NO:100), TAR15-3 (SEQ ID NO:101), TAR15-4 (SEQ ID NO:102), TAR15-9 (SEQ ID NO:103), TAR15-10 (SEQ ID NO:104), TAR15-11 (SEQ ID NO:105), TAR15-12 (SEQ ID NO:106), TAR15-13 (SEQ ID NO:107), TAR15-14 (SEQ ID NO:108), TAR15-15 (SEQ ID NO:109), TAR15-16 (SEQ ID NO:110), TAR15-17 (SEQ ID NO:111), TAR15-18 (SEQ ID NO:112), TAR15-19 (SEQ ID NO:113), TAR15-20 (SEQ ID NO:114), TAR15-22 (SEQ ID NO:115), TAR15-5 (SEQ ID NO:116), TAR15-6 (SEQ ID NO:117), TAR15-7 (SEQ ID NO:118), TAR15-8 (SEQ ID NO:119), TAR15-23 (SEQ ID NO:120), TAR15-24 (SEQ ID NO:121), TAR15-25 (SEQ ID NO:122), TAR15-26 (SEQ ID NO:123), TAR15-27 (SEQ ID NO:124), TAR15-29 (SEQ ID NO:125), TAR15-30 (SEQ ID NO:126), TAR15-6-500 (SEQ ID NO:127), TAR15-6-501 (SEQ ID NO:128), TAR15-6-502 (SEQ ID NO:129), TAR15-6-503 (SEQ ID NO:130), TAR15-6-504 (SEQ ID NO:131), TAR15-6-505 (SEQ ID NO:132), TAR15-6-506 (SEQ ID NO:133), TAR15-6-507 (SEQ ID NO:134), TAR15-6-508 (SEQ ID NO:135), TAR15-6-509 (SEQ ID NO:136), TAR15-6-510 (SEQ ID NO:137), TAR15-8-500 (SEQ ID NO:138), TAR15-8-501 (SEQ ID NO:139), TAR15-8-502 (SEQ ID NO:140), TAR15-8-503 (SEQ ID NO:141), TAR15-8-505 (SEQ ID NO:142), TAR15-8-506 (SEQ ID NO:143), TAR15-8-507 (SEQ ID NO:144), TAR15-8-508 (SEQ ID NO:145), TAR15-8-509 (SEQ ID NO:146), TAR15-8-510 (SEQ ID NO:147), TAR15-8-511 (SEQ ID NO:148), TAR15-26-500 (SEQ ID NO:149), TAR15-26-501 (SEQ ID NO:150), TAR15-26-502 (SEQ ID NO:151), TAR15-26-503 (SEQ ID NO:152), TAR15-26-504 (SEQ ID NO:153), TAR15-26-505 (SEQ ID NO:154), TAR15-26-506 (SEQ ID NO:155), TAR15-26-507 (SEQ ID NO:156), TAR15-26-508 (SEQ ID NO:157), TAR15-26-509 (SEQ ID NO:158), TAR15-26-510 (SEQ ID NO:159), TAR15-26-511 (SEQ ID NO:160), TAR15-26-512 (SEQ ID NO:161), TAR15-26-513 (SEQ ID NO:162), TAR15-26-514 (SEQ ID NO:163), TAR15-26-515 (SEQ ID NO:164), TAR15-26-516 (SEQ ID NO:165), TAR15-26-517 (SEQ ID NO:166), TAR15-26-518 (SEQ ID NO:167), TAR15-26-519 (SEQ ID NO:168), TAR15-26-520 (SEQ ID NO:169), TAR15-26-521 (SEQ ID NO:170), TAR15-26-522 (SEQ ID NO:171), TAR15-26-523 (SEQ ID NO:172), TAR15-26-524 (SEQ ID NO:173), TAR15-26-525 (SEQ ID NO:174), TAR15-26-526 (SEQ ID NO:175), TAR15-26-527 (SEQ ID NO:176), TAR15-26-528 (SEQ ID NO:177), TAR15-26-529 (SEQ ID NO:178), TAR15-26-530 (SEQ ID NO:179), TAR15-26-531

(SEQ ID NO:180), TAR15-26-532 (SEQ ID NO:181), TAR15-26-533 (SEQ ID NO:182), TAR15-26-534 (SEQ ID NO:183), TAR15-26-535 (SEQ ID NO:184), TAR15-26-536 (SEQ ID NO:185), TAR15-26-537 (SEQ ID NO:186), TAR15-26-538 (SEQ ID NO:187), TAR15-26-539 (SEQ ID NO:188), TAR15-26-540 (SEQ ID NO:189), TAR15-26-541 (SEQ ID NO:190), TAR15-26-542 (SEQ ID NO:191), TAR15-26-543 (SEQ ID NO:192), TAR15-26-544 (SEQ ID NO:193), TAR15-26-545 (SEQ ID NO:194), TAR15-26-546 (SEQ ID NO:195), TAR15-26-547 (SEQ ID NO:196), TAR15-26-548 (SEQ ID NO:197), and TAR15-26-549 (SEQ ID NO:198), TAR15-26-550 (SEQ ID NO:539), and TAR15-26-551 (SEQ ID NO:540); and an immunoglobulin single variable domain with binding specificity for EGFR competes for binding to EGFR with cetuximab.

For example, the immunoglobulin single variable domain with binding specificity for VEGF can comprise an amino acid sequence that has at least about 85% amino acid sequence identity with the amino acid sequence of a dAb selected from the group consisting of TAR15-1 (SEQ ID NO:100), TAR15-3 (SEQ ID NO:101), TAR15-4 (SEQ ID NO:102), TAR15-9 (SEQ ID NO:103), TAR15-10 (SEQ ID NO:104), TAR15-11 (SEQ ID NO:105), TAR15-12 (SEQ ID NO:106), TAR15-13 (SEQ ID NO:107), TAR15-14 (SEQ ID NO:108), TAR15-15 (SEQ ID NO:109), TAR15-16 (SEQ ID NO:110), TAR15-17 (SEQ ID NO:111), TAR15-18 (SEQ ID NO:112), TAR15-19 (SEQ ID NO:113), TAR15-20 (SEQ ID NO:114), TAR15-22 (SEQ ID NO:115), TAR15-5 (SEQ ID NO:116), TAR15-6 (SEQ ID NO:117), TAR15-7 (SEQ ID NO:118), TAR15-8 (SEQ ID NO:119), TAR15-23 (SEQ ID NO:120), TAR15-24 (SEQ ID NO:121), TAR15-25 (SEQ ID NO:122), TAR15-26 (SEQ ID NO:123), TAR15-27 (SEQ ID NO:124), TAR15-29 (SEQ ID NO:125), TAR15-30 (SEQ ID NO:126), TAR15-6-500 (SEQ ID NO:127), TAR15-6-501 (SEQ ID NO:128), TAR15-6-502 (SEQ ID NO:129), TAR15-6-503 (SEQ ID NO:130), TAR15-6-504 (SEQ ID NO:131), TAR15-6-505 (SEQ ID NO:132), TAR15-6-506 (SEQ ID NO:133), TAR15-6-507 (SEQ ID NO:134), TAR15-6-508 (SEQ ID NO:135), TAR15-6-509 (SEQ ID NO:136), TAR15-6-510 (SEQ ID NO:137), TAR15-8-500 (SEQ ID NO:138), TAR15-8-501 (SEQ ID NO:139), TAR15-8-502 (SEQ ID NO:140), TAR15-8-503 (SEQ ID NO:141), TAR15-8-505 (SEQ ID NO:142), TAR15-8-506 (SEQ ID NO:143), TAR15-8-507 (SEQ ID NO:144), TAR15-8-508 (SEQ ID NO:145), TAR15-8-509 (SEQ ID NO:146), TAR15-8-510 (SEQ ID NO:147), TAR15-8-511 (SEQ ID NO:148), TAR15-26-500 (SEQ ID NO:149), TAR15-26-501 (SEQ ID NO:150), TAR15-26-502 (SEQ ID NO:151), TAR15-26-503 (SEQ ID NO:152), TAR15-26-504 (SEQ ID NO:153), TAR15-26-505 (SEQ ID NO:154), TAR15-26-506 (SEQ ID NO:155), TAR15-26-507 (SEQ ID NO:156), TAR15-26-508 (SEQ ID NO:157), TAR15-26-509 (SEQ ID NO:158), TAR15-26-510 (SEQ ID NO:159), TAR15-26-511 (SEQ ID NO:160), TAR15-26-512 (SEQ ID NO:161), TAR15-26-513 (SEQ ID NO:162), TAR15-26-514 (SEQ ID NO:163), TAR15-26-515 (SEQ ID NO:164), TAR15-26-516 (SEQ ID NO:165), TAR15-26-517 (SEQ ID NO:166), TAR15-26-518 (SEQ ID NO:167), TAR15-26-519 (SEQ ID NO:168), TAR15-26-520 (SEQ ID NO:169), TAR15-26-521 (SEQ ID NO:170), TAR15-26-522 (SEQ ID NO:171), TAR15-26-523 (SEQ ID NO:172), TAR15-26-524 (SEQ ID NO:173), TAR15-26-525 (SEQ ID NO:174), TAR15-26-526 (SEQ ID NO:175), TAR15-26-527 (SEQ ID NO:176), TAR15-26-528 (SEQ ID NO:177), TAR15-26-529 (SEQ ID NO:178), TAR15-26-530 (SEQ ID NO:179), TAR15-26-531 (SEQ ID NO:180), TAR15-26-532 (SEQ ID NO:181), TAR15-26-533 (SEQ ID NO:182), TAR15-26-534 (SEQ ID NO:183), TAR15-26-535 (SEQ ID NO:184), TAR15-26-536 (SEQ ID NO:185), TAR15-26-537 (SEQ ID NO:186), TAR15-26-538 (SEQ ID NO:187), TAR15-26-539 (SEQ ID NO:188), TAR15-26-540 (SEQ ID NO:189), TAR15-26-541 (SEQ ID NO:190), TAR15-26-542 (SEQ ID NO:191), TAR15-26-543 (SEQ ID NO:192), TAR15-26-544 (SEQ ID NO:193), TAR15-26-545 (SEQ ID NO:194), TAR15-26-546 (SEQ ID NO:195), TAR15-26-547 (SEQ ID NO:196), TAR15-26-548 (SEQ ID NO:197), and TAR15-26-549 (SEQ ID NO:198), TAR15-26-550 (SEQ ID NO:539), and TAR15-26-551 (SEQ ID NO:540).

In other embodiments, the ligand has binding specificity for VEGF and for EGFR and comprises at least one immunoglobulin single variable domain with binding specificity for VEGF and at least one immunoglobulin single variable domain with binding specificity for EGFR, wherein an immunoglobulin single variable domain with binding specificity for VEGF competes for binding to VEGF with bevacizumab and/or antibody 2C3 (ATCC Accession No. PTA 1595); and an immunoglobulin single variable domain with binding specificity for EGFR competes for binding to EGFR with an anti-EGFR domain antibody (dAb) selected from the group consisting of DOM16-17 (SEQ ID NO:325), DOM16-18 (SEQ ID NO:326), DOM16-19 (SEQ ID NO:327), DOM16-20 (SEQ ID NO:328), DOM16-21 (SEQ ID NO:329), DOM16-22 (SEQ ID NO:330), DOM16-23 (SEQ ID NO:331), DOM16-24 (SEQ ID NO:332), DOM16-25 (SEQ ID NO:333), DOM16-26 (SEQ ID NO:334), DOM16-27 (SEQ ID NO:335), DOM16-28 (SEQ ID NO:336), DOM16-29 (SEQ ID NO:337), DOM16-30 (SEQ ID NO:338), DOM16-31 (SEQ ID NO:339), DOM16-32 (SEQ ID NO:340), DOM16-33 (SEQ ID NO:341), DOM16-35 (SEQ ID NO:342), DOM16-37 (SEQ ID NO:343), DOM16-38 (SEQ ID NO:344), DOM16-39 (SEQ ID NO:345), DOM16-40 (SEQ ID NO:346), DOM16-41 (SEQ ID NO:347), DOM16-42 (SEQ ID NO:348), DOM16-43 (SEQ ID NO:349), DOM16-44 (SEQ ID NO:350), DOM16-45 (SEQ ID NO:351), DOM16-46 (SEQ ID NO:352), DOM16-47 (SEQ ID NO:353), DOM16-48 (SEQ ID NO:354), DOM16-49 (SEQ ID NO:355), DOM16-50 (SEQ ID NO:356), DOM16-59 (SEQ ID NO:357), DOM16-60 (SEQ ID NO:358), DOM16-61 (SEQ ID NO:359), DOM16-62 (SEQ ID NO:360), DOM16-63 (SEQ ID NO:361), DOM16-64 (SEQ ID NO:362), DOM16-65 (SEQ ID NO:363), DOM16-66 (SEQ ID NO:364), DOM16-67 (SEQ ID NO:365), DOM16-68 (SEQ ID NO:366), DOM16-69 (SEQ ID NO:367), DOM16-70 (SEQ ID NO:368), DOM16-71 (SEQ ID NO:369), DOM16-72 (SEQ ID NO:370), DOM16-73 (SEQ ID NO:371), DOM16-74 (SEQ ID NO:372), DOM16-75 (SEQ ID NO:373), DOM16-76 (SEQ ID NO:374), DOM16-77 (SEQ ID NO:375), DOM16-78 (SEQ ID NO:376), DOM16-79 (SEQ ID NO:377), DOM16-80 (SEQ ID NO:378), DOM16-81 (SEQ ID NO:379), DOM16-82 (SEQ ID NO:380), DOM16-83 (SEQ ID NO:381), DOM16-84 (SEQ ID NO:382), DOM16-85 (SEQ ID NO:383), DOM16-87 (SEQ ID NO:384), DOM16-88 (SEQ ID NO:385), DOM16-89 (SEQ ID NO:386), DOM16-90 (SEQ ID NO:387), DOM16-91 (SEQ ID NO:388), DOM16-92 (SEQ ID NO:389), DOM16-94 (SEQ ID NO:390), DOM16-95 (SEQ ID NO:391), DOM16-96 (SEQ ID NO:392), DOM16-97 (SEQ ID NO:393), DOM16-98 (SEQ ID NO:394), DOM16-99 (SEQ ID NO:395), DOM16-100 (SEQ ID NO:396), DOM16-101 (SEQ ID NO:397), DOM16-102 (SEQ ID NO:398), DOM16-103 (SEQ ID NO:399), DOM16-104 (SEQ ID NO:400), DOM16-105 (SEQ ID NO:401), DOM16-106 (SEQ ID NO:402), DOM16-107 (SEQ ID NO:403), DOM16-108 (SEQ ID NO:404), DOM16-109 (SEQ ID NO:405), DOM16-110 (SEQ ID NO:406), DOM16-111 (SEQ ID NO:407), DOM16-112 (SEQ ID NO:408), DOM16-113 (SEQ ID NO:409), DOM16-114 (SEQ ID NO:410), DOM16-115 (SEQ ID NO:411), DOM16-116 (SEQ ID NO:412), DOM16-117 (SEQ ID NO:413), DOM16-118 (SEQ ID NO:414), DOM16-119 (SEQ ID NO:415), DOM16-39-6 (SEQ ID NO:416), DOM16-39-8 (SEQ ID NO:417), DOM16-39-34 (SEQ ID NO:418), DOM16-39-48 (SEQ ID NO:419), DOM16-39-87 (SEQ ID NO:420), DOM16-39-90 (SEQ ID NO:421), DOM16-39-96 (SEQ ID NO:422), DOM16-39-100 (SEQ ID NO:423), DOM16-39-101 (SEQ ID NO:424), DOM16-39-102 (SEQ ID NO:425), DOM16-39-103 (SEQ ID NO:426), DOM16-39-104 (SEQ ID NO:427), DOM16-39-105 (SEQ ID NO:428), DOM16-39-106 (SEQ ID NO:429), DOM16-39-107 (SEQ ID NO:430), DOM16-39-108 (SEQ ID NO:431), DOM16-39-109 (SEQ ID NO:432), DOM16-39-110 (SEQ ID NO:433), DOM16-39-111 (SEQ ID NO:434), DOM16-39-112 (SEQ ID NO:435), DOM16-39-113 (SEQ ID NO:436), DOM16-39-114 (SEQ ID NO:437), DOM16-39-115 (SEQ ID NO:438), DOM16-39-116 (SEQ ID NO:439), DOM16-39-117 (SEQ ID NO:440), DOM16-39-200 (SEQ ID NO:441), DOM16-39-201 (SEQ ID NO:442), DOM16-39-202 (SEQ ID NO:443), DOM16-39-203 (SEQ ID NO:444), DOM16-39-204 (SEQ ID NO:445), DOM16-39-205 (SEQ ID NO:446), DOM16-39-206 (SEQ ID NO:447), DOM16-39-207 (SEQ ID NO:448), DOM16-39-209 (SEQ ID NO:449), DOM16-52 (SEQ ID NO:450), NB1 (SEQ ID NO:451), NB2 (SEQ ID NO:452), NB3 (SEQ ID NO:453), NB4 (SEQ ID NO:454), NB5 (SEQ ID NO:455), NB6 (SEQ ID NO:456), NB7 (SEQ ID NO:457), NB8 (SEQ ID NO:458), NB9 (SEQ ID NO:459), NB10 (SEQ ID NO:460), NB11 (SEQ ID NO:461), NB12 (SEQ ID NO:462), NB13 (SEQ ID NO:463), NB14 (SEQ ID NO:464), NB15 (SEQ ID NO:465), NB16 (SEQ ID NO:466), NB17 (SEQ ID NO:467), NB18 (SEQ ID NO:468), NB19 (SEQ ID NO:469), NB20 (SEQ ID NO:470), NB21 (SEQ ID NO:471), and NB22 (SEQ ID NO:472).

For example, the immunoglobulin single variable domain with binding specificity for EGFR can comprise an amino acid sequence that has at least about 85% amino acid sequence identity with the amino acid sequence of a dAb selected from the group consisting of DOM16-17 (SEQ ID NO:325), DOM16-18 (SEQ ID NO:326), DOM16-19 (SEQ ID NO:327), DOM16-20 (SEQ ID NO:328), DOM16-21 (SEQ ID NO:329), DOM16-22 (SEQ ID NO:330), DOM16-23 (SEQ ID NO:331), DOM16-24 (SEQ ID NO:332), DOM16-25 (SEQ ID NO:333), DOM16-26 (SEQ ID NO:334), DOM16-27 (SEQ ID NO:335), DOM16-28 (SEQ ID NO:336), DOM16-29 (SEQ ID NO:337), DOM16-30 (SEQ ID NO:338), DOM16-31 (SEQ ID NO:339), DOM16-32 (SEQ ID NO:340), DOM16-33 (SEQ ID NO:341), DOM16-35 (SEQ ID NO:342), DOM16-37 (SEQ ID NO:343), DOM16-38 (SEQ ID NO:344), DOM16-39 (SEQ ID NO:345), DOM16-40 (SEQ ID NO:346), DOM16-41 (SEQ ID NO:347), DOM16-42 (SEQ ID NO:348), DOM16-43 (SEQ ID NO:349), DOM16-44 (SEQ ID NO:350), DOM16-45 (SEQ ID NO:351), DOM16-46 (SEQ ID NO:352), DOM16-47 (SEQ ID NO:353), DOM16-48 (SEQ ID NO:354), DOM16-49 (SEQ ID NO:355), DOM16-50 (SEQ ID NO:356), DOM16-59 (SEQ ID NO:357), DOM16-60 (SEQ ID NO:358), DOM16-61 (SEQ ID NO:359), DOM16-62 (SEQ ID NO:360), DOM16-63 (SEQ ID NO:361), DOM16-64 (SEQ ID NO:362), DOM16-65 (SEQ ID NO:363), DOM16-66 (SEQ ID NO:364), DOM16-67 (SEQ ID NO:365), DOM16-68 (SEQ ID NO:366), DOM16-69 (SEQ ID NO:367), DOM16-70 (SEQ ID NO:368), DOM16-71 (SEQ ID NO:369), DOM16-72 (SEQ ID NO:370), DOM16-73 (SEQ ID NO:371), DOM16-74 (SEQ ID NO:372), DOM16-75 (SEQ ID NO:373), DOM16-76 (SEQ ID NO:374), DOM16-77 (SEQ ID NO:375), DOM16-78 (SEQ ID NO:376), DOM16-79 (SEQ ID NO:377), DOM16-80 (SEQ ID NO:378), DOM16-81 (SEQ ID NO:379), DOM16-82 (SEQ ID NO:380), DOM16-83 (SEQ ID NO:381), DOM16-84 (SEQ ID NO:382), DOM16-85 (SEQ ID NO:383), DOM16-87 (SEQ ID NO:384), DOM16-88 (SEQ ID NO:385), DOM16-89 (SEQ ID NO:386), DOM16-90 (SEQ ID NO:387), DOM16-91 (SEQ ID NO:388), DOM16-92 (SEQ ID NO:389), DOM16-94 (SEQ ID NO:390), DOM16-95 (SEQ ID NO:391), DOM16-96 (SEQ ID NO:392), DOM16-97 (SEQ ID NO:393), DOM16-98 (SEQ ID NO:394), DOM16-99 (SEQ ID NO:395), DOM16-100 (SEQ ID NO:396), DOM16-101 (SEQ ID NO:397), DOM16-102 (SEQ ID NO:398), DOM16-103 (SEQ ID NO:399), DOM16-104 (SEQ ID NO:400), DOM16-105 (SEQ ID NO:401), DOM16-106 (SEQ ID NO:402), DOM16-107 (SEQ ID NO:403), DOM16-108 (SEQ ID NO:404), DOM16-109 (SEQ ID NO:405), DOM16-110 (SEQ ID NO:406), DOM16-111 (SEQ ID NO:407), DOM16-112 (SEQ ID NO:408), DOM16-113 (SEQ ID NO:409), DOM16-114 (SEQ ID NO:410), DOM16-115 (SEQ ID NO:411), DOM16-116 (SEQ ID NO:412), DOM16-117 (SEQ ID NO:413), DOM16-118 (SEQ ID NO:414), DOM16-119 (SEQ ID NO:415), DOM16-39-6 (SEQ ID NO:416), DOM16-39-8 (SEQ ID NO:417), DOM16-39-34 (SEQ ID NO:418), DOM16-39-48 (SEQ ID NO:419), DOM16-39-87 (SEQ ID NO:420), DOM16-39-90 (SEQ ID NO:421), DOM16-39-96 (SEQ ID NO:422), DOM16-39-100 (SEQ ID NO:423), DOM16-39-101 (SEQ ID NO:424), DOM16-39-102 (SEQ ID NO:425), DOM16-39-103 (SEQ ID NO:426), DOM16-39-104 (SEQ ID NO:427), DOM16-39-105 (SEQ ID NO:428), DOM16-39-106 (SEQ ID NO:429), DOM16-39-107 (SEQ ID NO:430), DOM16-39-108 (SEQ ID NO:431), DOM16-39-109 (SEQ ID NO:432), DOM16-39-110 (SEQ ID NO:433), DOM16-39-111 (SEQ ID NO:434), DOM16-39-112 (SEQ ID NO:435), DOM16-39-113 (SEQ ID NO:436), DOM16-39-114 (SEQ ID NO:437), DOM16-39-115 (SEQ ID NO:438), DOM16-39-116 (SEQ ID NO:439), DOM16-39-117 (SEQ ID NO:440), DOM16-39-200 (SEQ ID NO:441), DOM16-39-201 (SEQ ID NO:442), DOM16-39-202 (SEQ ID NO:443), DOM16-39-203 (SEQ ID NO:444), DOM16-39-204 (SEQ ID NO:445), DOM16-39-205 (SEQ ID NO:446), DOM16-39-206 (SEQ ID NO:447), DOM16-39-207 (SEQ. ID NO:448), DOM16-39-209 (SEQ ID NO:449), DOM16-52 (SEQ ID NO:450), NB1 (SEQ ID NO:451), NB2 (SEQ ID NO:452), NB3 (SEQ ID NO:453), NB4 (SEQ ID NO:454), NB5 (SEQ ID NO:455), NB6 (SEQ ID NO:456), NB7 (SEQ ID NO:457), NB8 (SEQ ID NO:458), NB9 (SEQ ID NO:459), NB10 (SEQ ID NO:460), NB11 (SEQ ID NO:461), NB12 (SEQ ID NO:462), NB13 (SEQ ID NO:463), NB14 (SEQ ID NO:464), NB15 (SEQ ID NO:465), NB16 (SEQ ID NO:466), NB17 (SEQ ID NO:467), NB18 (SEQ ID NO:468), NB19 (SEQ ID NO:469), NB20 (SEQ ID NO:470), NB21 (SEQ ID NO:471), and NB22 (SEQ ID NO:472).

In other embodiments, the ligand that has binding specificity for VEGF and for EGFR comprises a first immunoglobulin single variable domain with binding specificity for VEGF and a second immunoglobulin single variable domain with binding specificity for EGFR, wherein said first immunoglobulin single variable domain competes for binding to VEGF with bevacizumab and/or antibody 2C3 (ATCC Accession No. PTA 1595); and said second immunoglobulin single variable domain competes for binding to EGFR with cetuximab.

In particular embodiments, the ligand has binding specificity for VEGF and for EGFR and comprises at least one immunoglobulin single variable domain with binding specificity for VEGF and at least one immunoglobulin single variable domain with binding specificity for EGFR, wherein the ligand comprises an immunoglobulin single variable domain with binding specificity for VEGF that comprises an amino acid sequence that has at least 90% amino acid sequence identity with the amino acid sequence of an anti-VEGF dAb selected from the group consisting of TAR15-6 (SEQ ID NO:117), TAR15-8 (SEQ ID NO:119), and TAR15-26 (SEQ ID NO:123), and further comprises an immunoglobulin single variable domain with binding specificity for EGFR that comprises an amino acid sequence that has at least 90% amino acid sequence identity with an amino acid sequence selected from the group consisting of DOM16-39 (SEQ ID NO:345), DOM16-39-87 (SEQ ID NO:420), DOM16-39-100 (SEQ ID NO:423), DOM16-39-107 (SEQ ID NO:430), DOM16-39-109 (SEQ ID NO:432), DOM16-39-115 (SEQ ID NO:438), or DOM16-39-200 (SEQ ID NO:441).

The ligand that has binding specificity for VEGF and for EGFR can inhibit binding of epidermal growth factor (EGF) and/or transforming growth factor alpha (TGFalpha) to EGFR, inhibit the activity of EGFR, and/or inhibit the activity of EGFR without substantially inhibiting binding of epidermal growth factor (EGF) and/or transforming growth factor alpha (TGFalpha) to EGFR. In addition, or alternatively, the ligand that has binding specificity for VEGF and for EGFR can inhibit binding of VEGF to vascular endothelial growth factor receptor 1 (VEGFR1) and/or vascular endothelial growth factor receptor 2 (VEGFR2), inhibit the activity of VEGF and/or inhibit the activity of VEGF without substantially inhibiting binding of VEGF to VEGFR1 and/or VEGFR2.

The ligand that has binding specificity for VEGF and for EGFR can contain a protein binding moiety (e.g., immunoglobulin single variable domain) with binding specificity for VEGF that binds VEGF with an affinity (KD) that is between about 100 nM and about 1 pM, as determined by surface plasmon resonance.

The ligand that has binding specificity for VEGF and for EGFR can contain a protein binding moiety (e.g., immunoglobulin single variable domain) with binding specificity for EGFR that binds EGFR with an affinity (KD) that is between about 100 nM and about 1 pM or about 10 nM to about 100 pM, as determined by surface plasmon resonance.

The ligand that has binding specificity for VEGF and for EGFR can bind VEGF with an affinity (KD) that is between about 100 nM and about 1 pM, as determined by surface plasmon resonance.

The ligand that has binding specificity for VEGF and for EGFR can bind EGFR with an affinity (KD) that is between about 100 nM and about 1 pM or about 10 nM to about 100 pM, as determined by surface plasmon resonance.

The ligand that has binding specificity for VEGF and for EGFR can comprise an immunoglobulin single variable domain with binding specificity for VEGF that is a $V_{HH}$ and/or an immunoglobulin single variable domain with binding specificity for EGFR that is a $V_{HH}$.

The ligand that has binding specificity for VEGF and for EGFR can comprise an immunoglobulin single variable domain with binding specificity for VEGF and an immunoglobulin single variable domain with binding specificity for EGFR, wherein the immunoglobuoin single domains are selected from the group consisting of a human $V_H$ and a human $V_L$.

In some embodiments, the ligand that has binding specificity for VEGF and for EGFR can be an IgG-like format comprising two immunoglobulin single variable domains with binding specificity for VEGF, and two immunoglobulin single variable domains with binding specificity for EGFR.

In some embodiments, the ligand that has binding specificity for VEGF and for EGFR can comprise an antibody Fc region.

The invention also relates to a ligand that has binding specificity for VEGF, comprising at least one immunoglobulin single variable domain with binding specificity for VEGF, wherein an immunoglobulin single variable domain with binding specificity for VEGF competes for binding to VEGF with an anti-VEGF domain antibody (dAb) selected from the group consisting of TAR15-1 (SEQ ID NO:100), TAR15-3 (SEQ ID NO:101), TAR15-4 (SEQ ID NO:102), TAR15-9 (SEQ ID NO:103), TAR15-10 (SEQ ID NO:104), TAR15-11 (SEQ ID NO:105), TAR15-12 (SEQ ID NO:106), TAR15-13 (SEQ ID NO:107), TAR15-14 (SEQ ID NO:108), TAR15-15 (SEQ ID NO:109), TAR15-16 (SEQ ID NO:10), TAR15-17 (SEQ ID NO:11), TAR15-18 (SEQ ID NO:112), TAR15-19 (SEQ ID NO:113), TAR15-20 (SEQ ID NO:114), TAR15-22 (SEQ ID NO:115), TAR15-5 (SEQ ID NO:116), TAR15-6 (SEQ ID NO:117), TAR15-7 (SEQ ID NO:118), TAR15-8 (SEQ ID NO:119), TAR15-23 (SEQ ID NO:120), TAR15-24 (SEQ ID NO:121), TAR15-25 (SEQ ID NO:122), TAR15-26 (SEQ ID NO:123), TAR15-27 (SEQ ID NO:124), TAR15-29 (SEQ ID NO:125), TAR15-30 (SEQ ID NO:126), TAR15-6-500 (SEQ ID NO:127), TAR15-6-501 (SEQ ID NO:128), TAR15-6-502 (SEQ ID NO:129), TAR15-6-503 (SEQ ID NO:130), TAR15-6-504 (SEQ ID NO:131), TAR15-6-505 (SEQ ID NO:132), TAR15-6-506 (SEQ ID NO:133), TAR15-6-507 (SEQ ID NO:134), TAR15-6-508 (SEQ ID NO:135), TAR15-6-509 (SEQ ID NO:136), TAR15-6-510 (SEQ ID NO:137), TAR15-8-500 (SEQ ID NO:138), TAR15-8-501 (SEQ ID NO:139), TAR15-8-502 (SEQ ID NO:140), TAR15-8-503 (SEQ ID NO:141), TAR15-8-505 (SEQ ID NO:142), TAR15-8-506 (SEQ ID NO:143), TAR15-8-507 (SEQ ID NO:144), TAR15-8-508 (SEQ ID NO:145), TAR15-8-509 (SEQ ID NO:146), TAR15-8-510 (SEQ ID NO:147), TAR15-8-511 (SEQ ID NO:148), TAR15-26-500 (SEQ ID NO:149), TAR15-26-501 (SEQ ID NO:150), TAR15-26-502 (SEQ ID NO:151), TAR15-26-503 (SEQ ID NO:152), TAR15-26-504 (SEQ ID NO:153), TAR15-26-505 (SEQ ID NO:154), TAR15-26-506 (SEQ ID NO:155), TAR15-26-507 (SEQ ID NO:156), TAR15-26-508 (SEQ ID NO:157), TAR15-26-509 (SEQ ID NO:158), TAR15-26-510 (SEQ ID NO:159), TAR15-26-511 (SEQ ID NO:160), TAR15-26-512 (SEQ ID NO:161), TAR15-26-513 (SEQ ID NO:162), TAR15-26-514 (SEQ ID NO:163), TAR15-26-515 (SEQ ID NO:164), TAR15-26-516 (SEQ ID NO:165), TAR15-26-517 (SEQ ID NO:166), TAR15-26-518 (SEQ ID NO:167), TAR15-26-519 (SEQ ID NO:168), TAR15-26-520 (SEQ ID NO:169), TAR15-26-521 (SEQ ID NO:170), TAR15-26-522 (SEQ ID NO:171), TAR15-26-523 (SEQ ID NO:172), TAR15-26-524 (SEQ ID NO:173), TAR15-26-525 (SEQ ID NO:174), TAR15-26-526 (SEQ ID NO:175), TAR15-26-527 (SEQ ID NO:176), TAR15-26-528 (SEQ ID NO:177), TAR15-26-529 (SEQ ID NO:178), TAR15-26-530 (SEQ ID NO:179), TAR15-26-531 (SEQ ID NO:180), TAR15-26-532 (SEQ ID NO:181), TAR15-26-533 (SEQ ID NO:182), TAR15-26-534 (SEQ ID NO:183), TAR15-26-535 (SEQ ID NO:184), TAR15-26-536 (SEQ ID NO:185), TAR15-26-537 (SEQ ID NO:186), TAR15-26-538 (SEQ ID NO:187), TAR15-26-539

(SEQ ID NO:188), TAR15-26-540 (SEQ ID NO:189), TAR15-26-541 (SEQ ID NO:190), TAR15-26-542 (SEQ ID NO:191), TAR15-26-543 (SEQ ID NO:192), TAR15-26-544 (SEQ ID NO:193), TAR15-26-545 (SEQ ID NO:194), TAR15-26-546 (SEQ ID NO:195), TAR15-26-547 (SEQ ID NO:196), TAR15-26-548 (SEQ ID NO:197), and TAR15-26-549 (SEQ ID NO:198), TAR15-26-550 (SEQ ID NO:539), and TAR15-26-551 (SEQ ID NO:540).

For example, the an immunoglobulin single variable domain with binding specificity for VEGF can comprise an amino acid sequence that has at least about 85% amino acid sequence identity with the amino acid sequence of a dAb selected from the group consisting of TAR15-1 (SEQ ID NO:100), TAR15-3 (SEQ ID NO:101), TAR15-4 (SEQ ID NO:102), TAR15-9 (SEQ ID NO:103), TAR15-10 (SEQ ID NO:104), TAR15-11 (SEQ ID NO:105), TAR15-12 (SEQ ID NO:106), TAR15-13 (SEQ ID NO:107), TAR15-14 (SEQ ID NO:108), TAR15-15 (SEQ ID NO:109), TAR15-16 (SEQ ID NO:110), TAR15-17 (SEQ ID NO:111), TAR15-18 (SEQ ID NO:112), TAR15-19 (SEQ ID NO:113), TAR15-20 (SEQ ID NO:114), TAR15-22 (SEQ ID NO:115), TAR15-5 (SEQ ID NO:116), TAR15-6 (SEQ ID NO:117), TAR15-7 (SEQ ID NO:118), TAR15-8 (SEQ ID NO:119), TAR15-23 (SEQ ID NO:120), TAR15-24 (SEQ ID NO:121), TAR15-25 (SEQ ID NO:122), TAR15-26 (SEQ ID NO:123), TAR15-27 (SEQ ID NO:124), TAR15-29 (SEQ ID NO:125), TAR15-30 (SEQ ID NO:126), TAR15-6-500 (SEQ ID NO:127), TAR15-6-501 (SEQ ID NO:128), TAR15-6-502 (SEQ ID NO:129), TAR15-6-503 (SEQ ID NO:130), TAR15-6-504 (SEQ ID NO:131), TAR15-6-505 (SEQ ID NO:132), TAR15-6-506 (SEQ ID NO:133), TAR15-6-507 (SEQ ID NO:134), TAR15-6-508 (SEQ ID NO:135), TAR15-6-509 (SEQ ID NO:136), TAR15-6-510 (SEQ ID NO:137), TAR15-8-500 (SEQ ID NO:138), TAR15-8-501 (SEQ ID NO:139), TAR15-8-502 (SEQ ID NO:140), TAR15-8-503 (SEQ ID NO:141), TAR15-8-505 (SEQ ID NO:142), TAR15-8-506 (SEQ ID NO:143), TAR15-8-507 (SEQ ID NO:144), TAR15-8-508 (SEQ ID NO:145), TAR15-8-509 (SEQ ID NO:146), TAR15-8-510 (SEQ ID NO:147), TAR15-8-511 (SEQ ID NO:148), TAR15-26-500 (SEQ ID NO:149), TAR15-26-501 (SEQ ID NO:150), TAR15-26-502 (SEQ ID NO:151), TAR15-26-503 (SEQ ID NO:152), TAR15-26-504 (SEQ ID NO:153), TAR15-26-505 (SEQ ID NO:154), TAR15-26-506 (SEQ ID NO:155), TAR15-26-507 (SEQ ID NO:156), TAR15-26-508 (SEQ ID NO:157), TAR15-26-509 (SEQ ID NO:158), TAR15-26-510 (SEQ ID NO:159), TAR15-26-511 (SEQ ID NO:160), TAR15-26-512 (SEQ ID NO:161), TAR15-26-513 (SEQ ID NO:162), TAR15-26-514 (SEQ ID NO:163), TAR15-26-515 (SEQ ID NO:164), TAR15-26-516 (SEQ ID NO:165), TAR15-26-517 (SEQ ID NO:166), TAR15-26-518 (SEQ ID NO:167), TAR15-26-519 (SEQ ID NO:168), TAR15-26-520 (SEQ ID NO:169), TAR15-26-521 (SEQ ID NO:170), TAR15-26-522 (SEQ ID NO:171), TAR15-26-523 (SEQ ID NO:172), TAR15-26-524 (SEQ ID NO:173), TAR15-26-525 (SEQ ID NO:174), TAR15-26-526 (SEQ ID NO:175), TAR15-26-527 (SEQ ID NO:176), TAR15-26-528 (SEQ ID NO:177), TAR15-26-529 (SEQ ID NO:178), TAR15-26-530 (SEQ ID NO:179), TAR15-26-531 (SEQ ID NO:180), TAR15-26-532 (SEQ ID NO:181), TAR15-26-533 (SEQ ID NO:182), TAR15-26-534 (SEQ ID NO:183), TAR15-26-535 (SEQ ID NO:184), TAR15-26-536 (SEQ ID NO:185), TAR15-26-537 (SEQ ID NO:186), TAR15-26-538 (SEQ ID NO:187), TAR15-26-539 (SEQ ID NO:188), TAR15-26-540 (SEQ ID NO:189), TAR15-26-541 (SEQ ID NO:190), TAR15-26-542 (SEQ ID NO:191), TAR15-26-543 (SEQ ID NO:192), TAR15-26-544 (SEQ ID NO:193), TAR15-26-545 (SEQ ID NO:194), TAR15-26-546 (SEQ ID NO:195), TAR15-26-547 (SEQ ID NO:196), TAR15-26-548 (SEQ ID NO:197), and TAR15-26-549 (SEQ ID NO:198), TAR15-26-550 (SEQ ID NO:539), and TAR15-26-551 (SEQ ID NO:540).

The ligand that has binding specificity for VEGF can inhibit binding of VEGF to vascular endothelial growth factor receptor 1 (VEGFR1) and/or vascular endothelial growth factor receptor 2 (VEGFR2), inhibit the activity of VEGF and/or inhibit the activity of VEGF without substantially inhibiting binding of VEGF to VEGFR1 and/or VEGFR2.

The ligand that has binding specificity for VEGF can contain an immunoglobulin single variable domain with binding specificity for VEGF that binds VEGF with an affinity (KD) that is between about 100 nM and about 1 pM, as determined by surface plasmon resonance.

The ligand that has binding specificity for VEGF can bind VEGF with an affinity (KD) that is between about 100 nM and about 1 pM, as determined by surface plasmon resonance.

The ligand that has binding specificity for VEGF can comprise an immunoglobulin single variable domain with binding specificity for VEGF that is a $V_{HH}$.

The ligand that has binding specificity for VEGF can comprise an immunoglobulin single variable domain with binding specificity for VEGF that is selected from the group consisting of a human $V_H$ and a human $V_L$.

In some embodiments, the ligand that has binding specificity for VEGF is an IgG-like format comprising at least two immunoglobulin single variable domains with binding specificity for VEGF.

In some embodiments, the ligand that has binding specificity for VEGF comprises an antibody Fc region.

The invention also relates to a ligand that has binding specificity for EGFR comprising at least one immunoglobulin single variable domain with binding specificity for EGFR, wherein an immunoglobulin single variable domain with binding specificity for EGFR competes for binding to EGFR with an anti-EGFR domain antibody (dAb) selected from the group consisting of DOM16-17 (SEQ ID NO:325), DOM16-18 (SEQ ID NO:326), DOM16-19 (SEQ ID NO:327), DOM16-20 (SEQ ID NO:328), DOM16-21 (SEQ ID NO:329), DOM16-22 (SEQ ID NO:330), DOM16-23 (SEQ ID NO:331), DOM16-24 (SEQ ID NO:332), DOM16-25 (SEQ ID NO:333), DOM16-26 (SEQ ID NO:334), DOM16-27 (SEQ ID NO:335), DOM16-28 (SEQ ID NO:336), DOM16-29 (SEQ ID NO:337), DOM16-30 (SEQ ID NO:338), DOM16-31 (SEQ ID NO:339), DOM16-32 (SEQ ID NO:340), DOM16-33 (SEQ ID NO:341), DOM16-35 (SEQ ID NO:342), DOM16-37 (SEQ ID NO:343), DOM16-38 (SEQ ID NO:344), DOM16-39 (SEQ ID NO:345), DOM16-40 (SEQ ID NO:346), DOM16-41 (SEQ ID NO:347), DOM16-42 (SEQ ID NO:348), DOM16-43 (SEQ ID NO:349), DOM16-44 (SEQ ID NO:350), DOM16-45 (SEQ ID NO:351), DOM16-46 (SEQ ID NO:352), DOM16-47 (SEQ ID NO:353), DOM16-48 (SEQ ID NO:354), DOM16-49 (SEQ ID NO:355), DOM16-50 (SEQ ID NO:356), DOM16-59 (SEQ ID NO:357), DOM16-60 (SEQ ID NO:358), DOM16-61 (SEQ ID NO:359), DOM16-62 (SEQ ID NO:360), DOM16-63 (SEQ ID NO:361), DOM16-64 (SEQ ID NO:362), DOM16-65 (SEQ ID NO:363), DOM16-66 (SEQ ID NO:364), DOM16-67 (SEQ ID NO:365), DOM16-68 (SEQ ID NO:366), DOM16-69 (SEQ ID NO:367), DOM16-70 (SEQ ID NO:368), DOM16-71 (SEQ ID NO:369), DOM16-72 (SEQ ID NO:370), DOM16-73 (SEQ ID NO:371), DOM16-74 (SEQ ID NO:372), DOM16-75 (SEQ ID NO:373), DOM16-76 (SEQ ID NO:374), DOM16-77 (SEQ ID NO:375), DOM16-78 (SEQ ID NO:376), DOM16-79 (SEQ ID NO:377), DOM16-80

(SEQ ID NO:378), DOM16-81 (SEQ ID NO:379), DOM16-82 (SEQ ID NO:380), DOM16-83 (SEQ ID NO:381), DOM16-84 (SEQ ID NO:382), DOM16-85 (SEQ ID NO:383), DOM16-87 (SEQ ID NO:384), DOM16-88 (SEQ ID NO:385), DOM16-89 (SEQ ID NO:386), DOM16-90 (SEQ ID NO:387), DOM16-91 (SEQ ID NO:388), DOM16-92 (SEQ ID NO:389), DOM16-94 (SEQ ID NO:390), DOM16-95 (SEQ ID NO:391), DOM16-96 (SEQ ID NO:392), DOM16-97 (SEQ ID NO:393), DOM16-98 (SEQ ID NO:394), DOM16-99 (SEQ ID NO:395), DOM16-100 (SEQ ID NO:396), DOM16-101 (SEQ ID NO:397), DOM16-102 (SEQ ID NO:398), DOM16-103 (SEQ ID NO:399), DOM16-104 (SEQ ID NO:400), DOM16-105 (SEQ ID NO:401), DOM16-106 (SEQ ID NO:402), DOM16-107 (SEQ ID NO:403), DOM16-108 (SEQ ID NO:404), DOM16-109 (SEQ ID NO:405), DOM16-110 (SEQ ID NO:406), DOM16-111 (SEQ ID NO:407), DOM16-112 (SEQ ID NO:408), DOM16-113 (SEQ ID NO:409), DOM16-114 (SEQ ID NO:410), DOM16-115 (SEQ ID NO:411), DOM16-116 (SEQ ID NO:412), DOM16-117 (SEQ ID NO:413), DOM16-118 (SEQ ID NO:414), DOM16-119 (SEQ ID NO:415), DOM16-39-6 (SEQ ID NO:416), DOM16-39-8 (SEQ ID NO:417), DOM16-39-34 (SEQ ID NO:418), DOM16-39-48 (SEQ ID NO:419), DOM16-39-87 (SEQ ID NO:420), DOM16-39-90 (SEQ ID NO:421), DOM16-39-96 (SEQ ID NO:422), DOM16-39-100 (SEQ ID NO:423), DOM16-39-101 (SEQ ID NO:424), DOM16-39-102 (SEQ ID NO:425), DOM16-39-103 (SEQ ID NO:426), DOM16-39-104 (SEQ ID NO:427), DOM16-39-105 (SEQ ID NO:428), DOM16-39-106 (SEQ ID NO:429), DOM16-39-107 (SEQ ID NO:430), DOM16-39-108 (SEQ ID NO:431), DOM16-39-109 (SEQ ID NO:432), DOM16-39-110 (SEQ ID NO:433), DOM16-39-111 (SEQ ID NO:434), DOM16-39-112 (SEQ ID NO:435), DOM16-39-113 (SEQ ID NO:436), DOM16-39-114 (SEQ ID NO:437), DOM16-39-115 (SEQ ID NO:438), DOM16-39-116 (SEQ ID NO:439), DOM16-39-117 (SEQ ID NO:440), DOM16-39-200 (SEQ ID NO:441), DOM16-39-201 (SEQ ID NO:442), DOM16-39-202 (SEQ ID NO:443), DOM16-39-203 (SEQ ID NO:444), DOM16-39-204 (SEQ ID NO:445), DOM16-39-205 (SEQ ID NO:446), DOM16-39-206 (SEQ ID NO:447), DOM16-39-207 (SEQ ID NO:448), DOM16-39-209 (SEQ ID NO:449), DOM16-52 (SEQ ID NO:450), NB1 (SEQ ID NO:451), NB2 (SEQ ID NO:452), NB3 (SEQ ID NO:453), NB4 (SEQ ID NO:454), NB5 (SEQ ID NO:455), NB6 (SEQ ID NO:456), NB7 (SEQ ID NO:457), NB8 (SEQ ID NO:458), NB9 (SEQ ID NO:459), NB10 (SEQ ID NO:460), NB11 (SEQ ID NO:461), NB12 (SEQ ID NO:462), NB13 (SEQ ID NO:463), NB14 (SEQ ID NO:464), NB15 (SEQ ID NO:465), NB16 (SEQ ID NO:466), NB17 (SEQ ID NO:467), NB18 (SEQ ID NO:468), NB19 (SEQ ID NO:469), NB20 (SEQ ID NO:470), NB21 (SEQ ID NO:471), and NB22 (SEQ ID NO:472).

For example, the immunoglobulin single variable domain with binding specificity for EGFR can comprise an amino acid sequence that has at least about 85% amino acid sequence identity with the amino acid sequence of a dAb selected from the group consisting of DOM16-17 (SEQ ID NO:325), DOM16-18 (SEQ ID NO:326), DOM16-19 (SEQ ID NO:327), DOM16-20 (SEQ ID NO:328), DOM16-21 (SEQ ID NO:329), DOM16-22 (SEQ ID NO:330), DOM16-23 (SEQ ID NO:331), DOM16-24 (SEQ ID NO:332), DOM16-25 (SEQ ID NO:333), DOM16-26 (SEQ ID NO:334), DOM16-27 (SEQ ID NO:335), DOM16-28 (SEQ ID NO:336), DOM16-29 (SEQ ID NO:337), DOM16-30 (SEQ ID NO:338), DOM16-31 (SEQ ID NO:339), DOM16-32 (SEQ ID NO:340), DOM16-33 (SEQ ID NO:341), DOM16-35 (SEQ ID NO:342), DOM16-37 (SEQ ID NO:343), DOM16-38 (SEQ ID NO:344), DOM16-39 (SEQ ID NO:345), DOM16-40 (SEQ ID NO:346), DOM16-41 (SEQ ID NO:347), DOM16-42 (SEQ ID NO:348), DOM16-43 (SEQ ID NO:349), DOM16-44 (SEQ ID NO:350), DOM16-45 (SEQ ID NO:351), DOM16-46 (SEQ ID NO:352), DOM16-47 (SEQ ID NO:353), DOM16-48 (SEQ ID NO:354), DOM16-49 (SEQ ID NO:355), DOM16-50 (SEQ ID NO:356), DOM16-59 (SEQ ID NO:357), DOM16-60 (SEQ ID NO:358), DOM16-61 (SEQ ID NO:359), DOM16-62 (SEQ ID NO:360), DOM16-63 (SEQ ID NO:361), DOM16-64 (SEQ ID NO:362), DOM16-65 (SEQ ID NO:363), DOM16-66 (SEQ ID NO:364), DOM16-67 (SEQ ID NO:365), DOM16-68 (SEQ ID NO:366), DOM16-69 (SEQ ID NO:367), DOM16-70 (SEQ ID NO:368), DOM16-71 (SEQ ID NO:369), DOM16-72 (SEQ ID NO:370), DOM16-73 (SEQ ID NO:371), DOM16-74 (SEQ ID NO:372), DOM16-75 (SEQ ID NO:373), DOM16-76 (SEQ ID NO:374), DOM16-77 (SEQ ID NO:375), DOM16-78 (SEQ ID NO:376), DOM16-79 (SEQ ID NO:377), DOM16-80 (SEQ ID NO:378), DOM16-81 (SEQ ID NO:379), DOM16-82 (SEQ ID NO:380), DOM16-83 (SEQ ID NO:381), DOM16-84 (SEQ ID NO:382), DOM16-85 (SEQ ID NO:383), DOM16-87 (SEQ ID NO:384), DOM16-88 (SEQ ID NO:385), DOM16-89 (SEQ ID NO:386), DOM16-90 (SEQ ID NO:387), DOM16-91 (SEQ ID NO:388), DOM16-92 (SEQ ID NO:389), DOM16-94 (SEQ ID NO:390), DOM16-95 (SEQ ID NO:391), DOM16-96 (SEQ ID NO:392), DOM16-97 (SEQ ID NO:393), DOM16-98 (SEQ ID NO:394), DOM16-99 (SEQ ID NO:395), DOM16-100 (SEQ ID NO:396), DOM16-101 (SEQ ID NO:397), DOM16-102 (SEQ ID NO:398), DOM16-103 (SEQ ID NO:399), DOM16-104 (SEQ ID NO:400), DOM16-105 (SEQ ID NO:401), DOM16-106 (SEQ ID NO:402), DOM16-107 (SEQ ID NO:403), DOM16-108 (SEQ ID NO:404), DOM16-109 (SEQ ID NO:405), DOM16-110 (SEQ ID NO:406), DOM16-111 (SEQ ID NO:407), DOM16-112 (SEQ ID NO:408), DOM16-113 (SEQ ID NO:409), DOM16-114 (SEQ ID NO:410), DOM16-115 (SEQ ID NO:411), DOM16-116 (SEQ ID NO:412), DOM16-117 (SEQ ID NO:413), DOM16-118 (SEQ ID NO:414), DOM16-119 (SEQ ID NO:415), DOM16-39-6 (SEQ ID NO:416), DOM16-39-8 (SEQ ID NO:417), DOM16-39-34 (SEQ ID NO:418), DOM16-39-48 (SEQ ID NO:419), DOM16-39-87 (SEQ ID NO:420), DOM16-39-90 (SEQ ID NO:421), DOM16-39-96 (SEQ ID NO:422), DOM16-39-100 (SEQ ID NO:423), DOM16-39-101 (SEQ ID NO:424), DOM16-39-102 (SEQ ID NO:425), DOM16-39-103 (SEQ ID NO:426), DOM16-39-104 (SEQ ID NO:427), DOM16-39-105 (SEQ ID NO:428), DOM16-39-106 (SEQ ID NO:429), DOM16-39-107 (SEQ ID NO:430), DOM16-39-108 (SEQ ID NO:431), DOM16-39-109 (SEQ ID NO:432), DOM16-39-110 (SEQ ID NO:433), DOM16-39-111 (SEQ ID NO:434), DOM16-39-112 (SEQ ID NO:435), DOM16-39-113 (SEQ ID NO:436), DOM16-39-114 (SEQ ID NO:437), DOM16-39-115 (SEQ ID NO:438), DOM16-39-116 (SEQ ID NO:439), DOM16-39-117 (SEQ ID NO:440), DOM16-39-200 (SEQ ID NO:441), DOM16-39-201 (SEQ ID NO:442), DOM16-39-202 (SEQ ID NO:443), DOM16-39-203 (SEQ ID NO:444), DOM16-39-204 (SEQ ID NO:445), DOM16-39-205 (SEQ ID NO:446), DOM16-39-206 (SEQ ID NO:447), DOM16-39-207 (SEQ ID NO:448), DOM16-39-209 (SEQ ID NO:449), DOM16-52 (SEQ ID NO:450), NB1 (SEQ ID NO:451), NB2 (SEQ ID NO:452), NB3 (SEQ ID NO:453), NB4 (SEQ ID NO:454), NB5 (SEQ ID NO:455), NB6 (SEQ ID NO:456), NB7 (SEQ ID NO:457), NB8 (SEQ ID NO:458), NB9 (SEQ ID NO:459), NB10 (SEQ ID NO:460), NB11 (SEQ ID NO:461), NB12 (SEQ ID NO:462), NB13 (SEQ ID NO:463), NB14 (SEQ ID NO:464), NB15 (SEQ ID NO:465), NB16 (SEQ ID NO:466), NB17 (SEQ ID NO:467), NB18 (SEQ ID NO:468), NB19 (SEQ ID NO:469), NB20 (SEQ ID NO:470), NB21 (SEQ ID NO:471), and NB22 (SEQ ID NO:472).

The ligand that has binding specificity for EGFR can inhibit binding of epidermal growth factor (EGF) and/or transforming growth factor alpha (TGFalpha) to EGFR, inhibit the activity of EGFR, and/or inhibit the activity of EGFR without substantially inhibiting binding of epidermal growth factor (EGF) and/or transforming growth factor alpha (TGFalpha) to EGFR.

The ligand that has binding specificity for EGFR can contain an immunoglobulin single variable domain with binding specificity for EGFR that binds EGFR with an affinity (KD) that is between about 100 nM and about 1 pM or about 10 nM to about 100 pM, as determined by surface plasmon resonance.

The ligand that has binding specificity for VEGF and for EGFR can bind EGFR with an affinity (KD) that is between about 100 nM and about 1 pM or about 10 nM to about 100 pM, as determined by surface plasmon resonance.

The ligand that has binding specificity for EGFR can comprise an immunoglobulin single variable domain with binding specificity for EGFR that is a $V_{HH}$.

The ligand that has binding specificity for EGFR can comprise an immunoglobulin single variable domain with binding specificity for EGFR that is selected from the group consisting of a human $V_H$ and a human $V_L$.

In some embodiments, the ligand that has binding specificity for EGFR is an IgG-like format comprising at least two immunoglobulin single variable domains with binding specificity for EGFR.

In some embodiments, the ligand that has binding specificity for EGFR comprises an antibody Fc region.

In some embodiments, the ligand comprises a single immunoglobulin variable domain polypeptide that antagonizes (inhibits) human EGFR binding to a receptor, wherein said single immunoglobulin variable domain polypeptide comprises a CDR3 sequence that is the same that the sequence of CDR3 of an anti-EGFR dAb disclosed herein.

In other embodiments, the ligand comprises a single immunoglobulin variable domain polypeptide that binds EGFR, wherein the polypeptide has an amino acid sequence that is identical to the amino acid sequence of an anti-EGFR dAb disclosed herein, or differs from the amino acid sequence of an anti-EGFR dAb disclosed herein at no more than 25 amino acid positions and has a CDR1 sequence that has at least 50% identity to the CDR1 sequence of the anti-EGFR dAb.

In other embodiments, the ligand comprises single immunoglobulin variable domain polypeptide that binds to EGFR, wherein the polypeptide has an amino acid sequence that is identical to the amino acid sequence of anti-EGFR dAb disclosed herein, or differs from the amino acid sequence of anti-EGFR dAb disclosed herein at no more than 25 amino acid positions and has a CDR2 sequence that has at least 50% identity to the CDR2 sequence of the anti-EGFR dAb.

In other embodiments, the ligand comprises an immunoglobulin single variable domain polypeptide that binds EGFR, wherein the polypeptide has an amino acid sequence that is identical to the amino acid sequence of anti-EGFR dAb disclosed herein, or differs from the amino acid sequence of anti-EGFR dAb disclosed herein at no more than 25 amino acid positions and has a CDR3 sequence that has at least 50% identity to the CDR3 sequence of the anti-EGFR dAb.

In other embodiments, the ligand comprises an immunoglobulin single variable domain polypeptide that binds EGFR, wherein the polypeptide has an amino acid sequence that is identical to the amino acid sequence of an anti-EGFR dAb disclosed herein, or differs from the amino acid sequence of an anti-EGFR dAb disclosed herein at no more than 25 amino acid positions and has a CDR1 sequence that has at least 50% identity to the CDR1 sequence of the anti-EGFR dAb and has a CDR2 sequence has at least 50% identity to the CDR2 sequence of the anti-EGFR dAb.

In other embodiments, the ligand comprises an immunoglobulin single variable domain polypeptide that binds EGFR, wherein the polypeptide has an amino acid sequence that is identical to the amino acid sequence of an anti-EGFR dAb disclosed herein, or differs from the amino acid sequence of an anti-EGFR dAb disclosed herein at no more than 25 amino acid positions and has a CDR2 sequence that has at least 50% identity to the CDR2 sequence of the anti-EGFR dAb and has a CDR3 sequence that has at least 50% identity to the CDR3 sequence of the anti-EGFR dAb.

In other embodiments, the ligand comprises an immunoglobulin single variable domain polypeptide that binds EGFR, wherein the polypeptide has an amino acid sequence that is identical to the amino acid sequence of an anti-EGFR dAb disclosed herein, or differs from the amino acid sequence of an anti-EGFR dAb disclosed herein at no more than 25 amino acid positions and has a CDR1 sequence that has at least 50% identity to the CDR1 sequence of the anti-EGFR dAb and has a CDR3 sequence that has at least 50% identity to the CDR3 sequence of the anti-EGFR dAb.

In other embodiments, the ligand comprises an immunoglobulin single variable domain polypeptide that binds EGFR, wherein the polypeptide has an amino acid sequence that is identical to the amino acid sequence of an anti-EGFR dAb disclosed herein, or differs from the amino acid sequence of an anti-EGFR dAb disclosed herein at no more than 25 amino acid positions and has a CDR1 sequence that has at least 50% identity to the CDR1 sequence of the anti-EGFR dAb and has a CDR2 sequence that has at least 50% identity to the CDR2 sequence of the anti-EGFR dAb and has a CDR3 sequence that has at least 50% identity to the CDR3 sequence of the anti-EGFR dAb.

In another embodiment, the invention is an EGFR antagonist having a CDR1 sequence that has at least 50% identity to the CDR1 sequence of an anti-EGFR dAb disclosed herein.

In another embodiment, the invention is an EGFR antagonist having a CDR2 sequence that has at least 50% identity to the CDR2 sequence of an anti-EGFR dAb disclosed herein.

In another embodiment, the invention is an EGFR antagonist having a CDR3 sequence that has at least 50% identity to the CDR3 sequence of an anti-EGFR dAb disclosed herein.

In another embodiment, the invention is an EGFR antagonist having a CDR1 sequence that has at least 50% identity to the CDR1 sequence of an anti-EGFR dAb disclosed herein and a CDR2 sequence that has at least 50% identity to the CDR2 sequence of the anti-EGFR dAb.

In another embodiment, the invention is an EGFR antagonist having a CDR2 sequence that has at least 50% identity to the CDR2 sequence of an anti-EGFR dAb disclosed herein and a CDR3 sequence that has at least 50% identity to the CDR3 sequence of the anti-EGFR dAb.

In another embodiment, the invention is an EGFR antagonist having a CDR1 sequence that has at least 50% identity to the CDR1 sequence of an anti-EGFR dAb disclosed herein and a CDR3 sequence that has at least 50% identity to the CDR3 sequence of the anti-EGFR dAb.

In another embodiment, the invention is an EGFR antagonist having a CDR1 sequence that has at least 50% identity to the CDR1 sequence of an anti-EGFR dAb disclosed herein and a CDR2 sequence that has at least 50% identity to the CDR2 sequence of the anti-EGFR dAb and a CDR3 sequence that has at least 50% identity to the CDR3 sequence of the anti-EGFR dAb.

In some embodiments, the ligand comprises a single immunoglobulin variable domain polypeptide that antagonizes (inhibits) human VEGF binding to a receptor, wherein said single immunoglobulin variable domain polypeptide comprises a CDR3 sequence that is the same that the sequence of CDR3 of an anti-VEGF dAb disclosed herein.

In other embodiments, the ligand comprises a single immunoglobulin variable domain polypeptide that binds VEGF, wherein the polypeptide has an amino acid sequence that is identical to the amino acid sequence of an anti-VEGF dAb disclosed herein, or differs from the amino acid sequence of an anti-VEGF dAb disclosed herein at no more than 25 amino acid positions and has a CDR1 sequence that has at least 50% identity to the CDR1 sequence of the anti-VEGF dAb.

In other embodiments, the ligand comprises single immunoglobulin variable domain polypeptide that binds to VEGF, wherein the polypeptide has an amino acid sequence that is identical to the amino acid sequence of anti-VEGF dAb disclosed herein, or differs from the amino acid sequence of anti-VEGF dAb disclosed herein at no more than 25 amino acid positions and has a CDR2 sequence that has at least 50% identity to the CDR2 sequence of the anti-VEGF dAb.

In other embodiments, the ligand comprises an immunoglobulin single variable domain polypeptide that binds VEGF, wherein the polypeptide has an amino acid sequence that is identical to the amino acid sequence of anti-VEGF dAb disclosed herein, or differs from the amino acid sequence of anti-VEGF dAb disclosed herein at no more than 25 amino acid positions and has a CDR3 sequence that has at least 50% identity to the CDR3 sequence of the anti-VEGF dAb.

In other embodiments, the ligand comprises an immunoglobulin single variable domain polypeptide that binds VEGF, wherein the polypeptide has an amino acid sequence that is identical to the amino acid sequence of an anti-VEGF dAb disclosed herein, or differs from the amino acid sequence of an anti-VEGF dAb disclosed herein at no more than 25 amino acid positions and has a CDR1 sequence that is has at least 50% identity to the CDR1 sequence of the anti-VEGF dAb and has a CDR2 sequence has at least 50% identity to the CDR2 sequence of the anti-VEGF dAb.

In other embodiments, the ligand comprises an immunoglobulin single variable domain polypeptide that binds VEGF, wherein the polypeptide has an amino acid sequence that is identical to the amino acid sequence of an anti-VEGF dAb disclosed herein, or differs from the amino acid sequence of an anti-VEGF dAb disclosed herein at no more than 25 amino acid positions and has a CDR2 sequence that has at least 50% identity to the CDR2 sequence of the anti-VEGF dAb and has a CDR3 sequence that has at least 50% identity to the CDR3 sequence of the anti-VEGF dAb.

In other embodiments, the ligand comprises an immunoglobulin single variable domain polypeptide that binds VEGF, wherein the polypeptide has an amino acid sequence that is identical to the amino acid sequence of an anti-VEGF dAb disclosed herein, or differs from the amino acid sequence of an anti-VEGF dAb disclosed herein at no more than 25 amino acid positions and has a CDR1 sequence that has at least 50% identity to the CDR1 sequence of the anti-VEGF dAb and has a CDR3 sequence that has at least 50% identity to the CDR3 sequence of the anti-VEGF dAb.

In other embodiments, the ligand comprises an immunoglobulin single variable domain polypeptide that binds VEGF, wherein the polypeptide has an amino acid sequence that is identical to the amino acid sequence of an anti-VEGF dAb disclosed herein, or differs from the amino acid sequence of an anti-VEGF dAb disclosed herein at no more than 25 amino acid positions and has a CDR1 sequence that has at least 50% identity to the CDR1 sequence of the anti-VEGF dAb and has a CDR2 sequence that has at least 50% identity to the CDR2 sequence of the anti-VEGF dAb and has a CDR3 sequence that has at least 50% identity to the CDR3 sequence of the anti-VEGF dAb.

In another embodiment, the invention is an VEGF antagonist having a CDR1 sequence that has at least 50% identity to the CDR1 sequence of an anti-VEGF dAb disclosed herein.

In another embodiment, the invention is an VEGF antagonist having a CDR2 sequence that has at least 50% identity to the CDR2 sequence of an anti-VEGF dAb disclosed herein.

In another embodiment, the invention is an VEGF antagonist having a CDR3 sequence that has at least 50% identity to the CDR3 sequence of an anti-VEGF dAb disclosed herein.

In another embodiment, the invention is an VEGF antagonist having a CDR1 sequence that has at least 50% identity to the CDR1 sequence of an anti-VEGF dAb disclosed herein and a CDR2 sequence that has at least 50% identity to the CDR2 sequence of the anti-VEGF dAb.

In another embodiment, the invention is an VEGF antagonist having a CDR2 sequence that has at least 50% identity to the CDR2 sequence of an anti-VEGF dAb disclosed herein and a CDR3 sequence that has at least 50% identity to the CDR3 sequence of the anti-VEGF dAb.

In another embodiment, the invention is an VEGF antagonist having a CDR1 sequence that has at least 50% identity to the CDR1 sequence of an anti-VEGF dAb disclosed herein and a CDR3 sequence that has at least 50% identity to the CDR3 sequence of the anti-VEGF dAb.

In another embodiment, the invention is an VEGF antagonist having a CDR1 sequence that has at least 50% identity to the CDR1 sequence of an anti-VEGF dAb disclosed herein and a CDR2 sequence that has at least 50% identity to the CDR2 sequence of the anti-VEGF dAb and a CDR3 sequence that has at least 50% identity to the CDR3 sequence of the anti-VEGF dAb.

In additional embodiments, any of the ligands described herein further comprise a toxin, such as a cytotoxin, free radical generator, antimetabolite, protein, polypeptide, peptide, photoactive agent, antisense compound, chemotherapeutic, radionuclide or intrabody. In particular embodiments, the toxin is a surface active toxin (e.g., a free radical generator, a radionuclide).

In other embodiments, the ligand further comprises a half-life extending moiety, such as a polyalkylene glycol moiety, serum albumin or a fragment thereof, transferrin receptor or a transferrin-binding portion thereof, or a moiety comprising a binding site for a polypeptide that enhances half-life in vivo. In some embodiments, the half-life extending moiety is a moiety comprising a binding site for a polypeptide that enhances half-life in vivo selected from the group consisting of an affibody, an SpA domain, an LDL receptor class A domain, an EGF domain, and an avimer.

In other embodiments, the half-life extending moiety is an antibody or antibody fragment (e.g., an immunoglobulin single variable domain) comprising a binding site for serum albumin or neonatal Fc receptor.

In particular embodiments, the half-life extending moiety is an immunoglobulin single variable domain comprising a binding site for serum albumin that competes for binding to human serum albumin with a dAb selected from the group consisting of DOM7m-16 (SEQ ID NO: 473), DOM7m-12 (SEQ ID NO: 474), DOM7m-26 (SEQ ID NO: 475), DOM7r-1 (SEQ ID NO: 476), DOM7r-3 (SEQ ID NO: 477), DOM7r-4 (SEQ ID NO: 478), DOM7r-5 (SEQ ID NO: 479), DOM7r-7 (SEQ ID NO: 480), DOM7r-8 (SEQ ID NO: 481), DOM7h-2 (SEQ ID NO: 482), DOM7h-3 (SEQ ID NO: 483), DOM7h-4 (SEQ ID NO: 484), DOM7h-6 (SEQ ID NO: 485), DOM7h-1 (SEQ ID NO: 486), DOM7h-7 (SEQ ID NO: 487), DOM7h-22 (SEQ ID NO: 489), DOM7h-23 (SEQ ID NO: 490), DOM7h-24 (SEQ ID NO: 491), DOM7h-25 (SEQ ID NO: 492), DOM7h-26 (SEQ ID NO: 493), DOM7h-21 (SEQ ID NO: 494), DOM7h-27 (SEQ ID NO: 495), DOM7h-8 (SEQ ID NO: 496), DOM7r-13 (SEQ ID NO: 497), DOM7r-14 (SEQ ID NO: 498), DOM7r-15 (SEQ ID NO: 499), DOM7r-16 (SEQ ID NO: 500), DOM7r-17 (SEQ ID NO: 501), DOM7r-18 (SEQ ID NO: 502), DOM7r-19 (SEQ ID NO: 503), DOM7r-20 (SEQ ID NO: 504), DOM7r-21 (SEQ ID NO: 505), DOM7r-22 (SEQ ID NO: 506), DOM7r-23 (SEQ ID NO: 507), DOM7r-24 (SEQ ID NO: 508), DOM7r-25 (SEQ ID NO: 509), DOM7r-26 (SEQ ID NO: 510), DOM7r-27 (SEQ ID NO: 511), DOM7r-28 (SEQ ID NO: 512), DOM7r-29 (SEQ ID NO: 513), DOM7r-30 (SEQ ID NO: 514), DOM7r-31 (SEQ ID NO: 515), DOM7r-32 (SEQ ID NO: 516), and DOM7r-33 (SEQ ID NO: 517).

For example, the immunoglobulin single variable domain comprising a binding sire for serum albumin can comprise an amino acid sequence that has at least 85% amino acid sequence identity with the amino acid sequence of a dAb selected from the group consisting of DOM7m-16 (SEQ ID NO: 473), DOM7m-12 (SEQ ID NO: 474), DOM7m-26 (SEQ ID NO: 475), DOM7r-1 (SEQ ID NO: 476), DOM7r-3 (SEQ ID NO: 477), DOM7r-4 (SEQ ID NO: 478), DOM7r-5 (SEQ ID NO: 479), DOM7r-7 (SEQ ID NO: 480), DOM7r-8 (SEQ ID NO: 481), DOM7h-2 (SEQ ID NO: 482), DOM7h-3 (SEQ ID NO: 483), DOM7h-4 (SEQ ID NO: 484), DOM7h-6 (SEQ ID NO: 485), DOM7h-1 (SEQ ID NO: 486), DOM7h-7 (SEQ ID NO: 487), DOM7h-22 (SEQ ID NO: 489), DOM7h-23 (SEQ ID NO: 490), DOM7h-24 (SEQ ID NO: 491), DOM7h-25 (SEQ ID NO: 492), DOM7h-26 (SEQ ID NO: 493), DOM7h-21 (SEQ ID NO: 494), DOM7h-27 (SEQ ID NO: 495), DOM7h-8 (SEQ ID NO: 496), DOM7r-13 (SEQ ID NO: 497), DOM7r-14 (SEQ ID NO: 498), DOM7r-15 (SEQ ID NO: 499), DOM7r-16 (SEQ ID NO: 500), DOM7r-17 (SEQ ID NO: 501), DOM7r-18 (SEQ ID NO: 502), DOM7r-19 (SEQ ID NO: 503), DOM7r-20 (SEQ ID NO: 504), DOM7r-21 (SEQ ID NO: 505), DOM7r-22 (SEQ ID NO: 506), DOM7r-23 (SEQ ID NO: 507), DOM7r-24 (SEQ ID NO: 508), DOM7r-25 (SEQ ID NO: 509), DOM7r-26 (SEQ ID NO: 510), DOM7r-27 (SEQ ID NO: 511), DOM7r-28 (SEQ ID NO: 512), DOM7r-29 (SEQ ID NO: 513), DOM7r-30 (SEQ ID NO: 514), DOM7r-31 (SEQ ID NO: 515), DOM7r-32 (SEQ ID NO: 516), and DOM7r-33 (SEQ ID NO: 517).

The invention also relates to an isolated or recombinant nucleic acid encoding a ligand described herein, and to a vector (e.g., recombinant vector) comprising such a the recombinant nucleic acid. The invention also relates to a host cell (e.g., recombinant host cell, isolated host cell) comprising a recombinant nucleic acid or vector of the invention. The invention also relates to a method for producing a ligand, comprising maintaining a host cell of the invention under conditions suitable for expression of said nucleic acid or vector, whereby a ligand is produced. In some embodiments, the method further comprising isolating the ligand.

The invention also relates to a ligand of the invention for use in therapy or diagnosis, and to the use of a ligand of the invention for the manufacture of a medicament for treatment, prevention or suppression of a disease described herein (e.g., cancer).

The invention also relates to a pharmaceutical compositon for the treatment, prevention or suppression of a disease described herein (e.g., cancer) comprising as an active ingredient a ligand of the invention.

In some embodiments, the invention relates to a ligand for use in treating cancer, or cancer cells that overexpress EGFR and/or VEGF.

In other embodiments, the invention relates to use of a ligand for the manufacture of a medicament for killing cells (e.g., selectively killing cancer cells over normal cells).

In other embodiments, the invention relates to use of a ligand for the manufacture of a medicament for treating cancer cells that overexpress EGFR and/or VEGF.

The invention also relates to therapeutic methods that comprise administering a therapeutically effective amount of a ligand of the invention to a subject in need thereof. In one embodiment, the invention relates to a method for treating cancer comprising administering to a subject in need thereof a therapeutically effective amount of ligand of the invention. In some embodiments, the method further comprises administering to the subject a chemotherapeutic agent (e.g., at a low dose).

In other embodiments, the method for treating cancer comprises administering to a subject in need thereof a therapeutically effective amount of ligand of the invention and an anti-neoplastic composition, wherein said anti-neoplastic composition comprises at least one chemotherapeutic agent. The chemotherapeutic agent can be selected from the group consisting of alkylating agents, antimetabolites, folic acid analogs, pyrimidine analogs, purine analogs and related inhibitors, vinca alkaloids, epipodopyyllotoxins, antibiotics, L-Asparaginase, topoisomerase inhibitor, interferons, platinum coordination complexes, anthracenedione substituted urea, methyl hydrazine derivatives, adrenocortical suppressant, adrenocorticosteroides, progestins, estrogens, antiestrogen, androgens, antiandrogen, and gonadotropin-releasing hormone analog. In some embodiments, the chemotherapeutic agent is selected from the group consisting of cisplatin, dicarbazine, dactinomycin, mechlorethamine, streptozocin, cyclophosphamide, capecitabine, carmustine, lomustine, doxorubicin, daunorubicin, procarbazine, mitomycin, cytarabine, etoposide, methotrexate, 5-fluorouracil, vinbiastine, vincristine, bleomycin, paclitaxel, docetaxel, doxetaxe, aldesleukin, asparaginase, busulfan, carboplatin, cladribine, dacarbazine, floxuridine, fludarabine, hydroxyurea, ifosfamide, interferon alpha, irinotecan, leuprolide, leucovorin, megestrol, melphalan, mercaptopurine, oxaliplatin, plicamycin, mitotane, pegaspargase, pentostatin, pipobroman, plicamycin, streptozocin, tamoxifen, teniposide, testolactone, thioguanine, thiotepa, uracil mustard, vinorelbine, chlorambucil, taxol, an additional growth factor receptor antagonist, and a combination of any of the foregoing.

In some embodiments, the method is a method of treating a cancer selected from the group consisting of bladder cancer, ovarian cancer, colorectal cancer (colorectal carcinoma), breast cancer, lung cancer (non-small cell lung carcinoma), gastric cancer, pancreatic cancer, prostate cancer, head and neck cancer, renal cancer and gall bladder cancer.

The invention also relates to a method of administering to a subject anti-VEGF treatment and anti-EGFR treatment, the method comprising simultaneous administration of an anti-VEGF treatment and an anti-EGFR treatment by administering to said subject a therapeutically effective amount of a ligand that has binding specificity for VEGF and EGFR.

The invention also relates to a composition (e.g., pharmaceutical composition) comprising a ligand of the invention and a physiologically or pharmaceutically acceptable carrier. In some embodiments, the composition comprises a vehicle for intravenous, intramuscular, intraperitoneal, intraarterial, intrathecal, intraarticular subcutaneous administration, pulmonary, intranasal, vaginal, or rectal administration.

The invention also relates to a drug delivery device comprising the composition (e.g., pharmaceutical composition) of the invention or a ligand of the invention. In one embodiment, the drug delivery device is for simultaneously administering to a subject anti-VEGF treatment and anti-EGFR treatment, and the device comprising a ligand that has binding specificity for VEGF and EGFR. In some embodiments, the drug device comprises a plurality of therapeutically effective doses of ligand.

In other embodiments, the drug delivery device is selected from the group consisting of a parenteral delivery device, intravenous delivery device, intramuscular delivery device, intraperitoneal delivery device, transdermal delivery device, pulmonary delivery device, intraarterial delivery device, intrathecal delivery device, intraarticular delivery device, subcutaneous delivery device, intranasal delivery device, vaginal delivery device, rectal delivery device, a syringe, a transdermal delivery device, a capsule, a tablet, a nebulizer, an inhaler, an atomizer, an aerosolizer, a mister, a dry powder inhaler, a metered dose inhaler, a metered dose sprayer, a metered dose mister, a metered dose atomizer, a catheter.

BRIEF DESCRIPTION OF THE DRAWINGS

FIG. 1A-1E illustrates twenty-seven nucleotide sequences that encode human (*Homo sapiens*) domain antibodies (dAbs) that specifically bind human VEGF. The nucleotide sequences presented are SEQ ID NOS:1-27, 535 and 536.

FIG. 2A-2C is a alignment of twelve nucleotide sequences that encode human dAbs that bind human VEGF. The nucleotide sequences presented are SEQ ID NO:18 and SEQ ID NOS:28-38.

FIG. 3A-3D is a alignment of twelve nucleotide sequences that encode human dAbs that bind human VEGF. The nucleotide sequences presented are SEQ ID NO:20 and SEQ ID NOS:39-49.

Figure 4D:
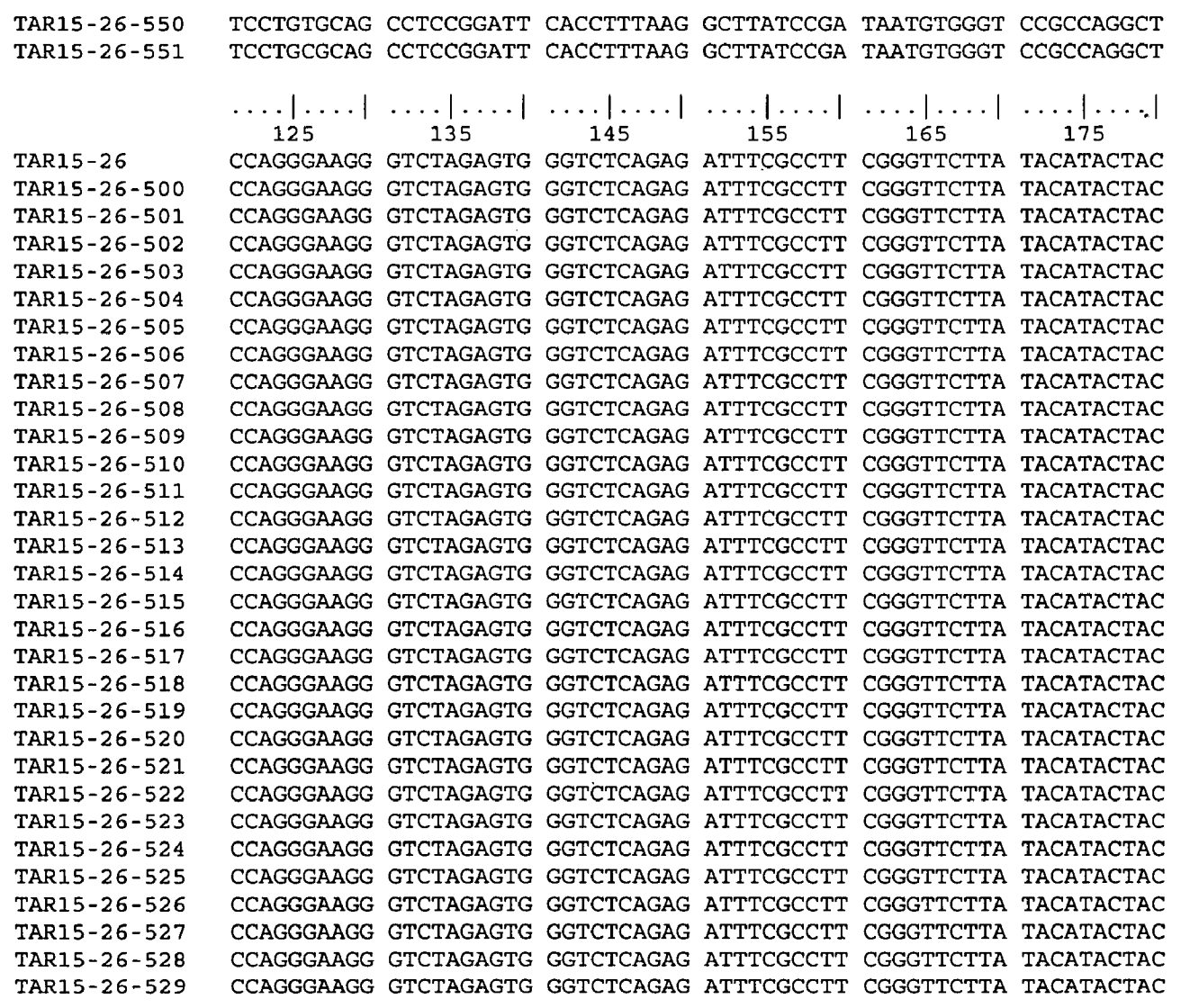

FIG. 4A-4J is a alignment of fifty-three nucleotide sequences that encode human dAbs that bind human VEGF. The nucleotide sequences presented are SEQ ID NO:24, 50-99, 537 and 538.

FIG. 5A-5C illustrates the amino acid sequences of dabs encoded by several of the nucleic acid sequences shown in FIG. 1A-1E. The amino acid sequences presented are SEQ ID NOS:100-126.

FIG. 6 is an alignment of the amino acid seqiemces of the dAbs encoded by the nucleic acid sequences shown in FIG. 2A-2C. The amino acid sequences presented are SEQ ID NO:117 AND SEQ ID NOS:127-137.

FIG. 7A-7B is an alignment of the amino acid seqiemces of the dabs encoded by the nucleic acid sequences shown in FIG. 3A-2D. The symbol ~ has been inserted into the sequence of TAR15-8-500 to facilitate alignment. The amino acid sequences presented are SEQ ID NO:119 and SEQ ID NOS: 138-148.

FIG. 8A-8D is an alignment of the amino acid seqiemces of the dAbs encoded by the nucleic acid sequences shown in FIG. 4A-4J. The amino acid sequences presented are SEQ ID NO:123, 149-198, 539 and 540.

FIG. 9A-9O illustrates several nucleotide sequences that encode human (*Homo sapiens*) domain antibodies (dAbs) that specifically bind human EGFR. The nucleotide sequences presented are SEQ ID NOS:199-324.

FIG. 10A-10I illustrates the amino acid sequences of the dAbs encoded by the nucleic acid sequences shown in FIG. 9A-9O. The amino acid sequences presented are SEQ ID NOS:325-450.

FIG. 11A-11B illustrates the amino acid sequences of several Camelid $V_{HH}$s that bind EGFR that are disclosed in WO 2005/044858. NB1 (SEQ ID NO:451), NB2 (SEQ ID NO:452), NB3 (SEQ ID NO:453), NB4 (SEQ ID NO:454), NB5 (SEQ ID NO:455), NB6 (SEQ ID NO:456), NB7 (SEQ ID NO:457), NB8 (SEQ ID NO:458), NB9 (SEQ ID NO:459), NB10 (SEQ ID NO:460), NB11 (SEQ ID NO:461), NB12 (SEQ ID NO:462), NB13 (SEQ ID NO:463), NB14 (SEQ ID NO:464), NB15 (SEQ ID NO:465), NB16 (SEQ ID NO:466), NB17 (SEQ ID NO:467), NB18 (SEQ ID NO:468), NB19 (SEQ ID NO:469), NB20 (SEQ ID NO:470), NB21 (SEQ ID NO:471), NB22 (SEQ ID NO:472).

FIG. 12A is an alignment of the amino acid sequences of three V$\kappa$s that bind mouse serum albumin (MSA). The aligned amino acid sequences are from V$\kappa$s designated MSA16, which is also referred to as DOM7m-16 (SEQ ID NO: 473), MSA 12, which is also referred to as DOM7m-12 (SEQ ID NO: 474), and MSA 26, which is also referred to as DOM7m-26 (SEQ ID NO: 475).

FIG. 12B is an alignment of the amino acid sequences of six V$\kappa$s that bind rat serum albumin (RSA). The aligned amino acid sequences are from V$\kappa$s designated DOM7r-1 (SEQ ID NO: 476), DOM7r-3 (SEQ ID NO: 477), DOM7r-4 (SEQ ID NO: 478), DOM7r-5 (SEQ ID NO: 479), DOM7r-7 (SEQ ID NO: 480), and DOM7r-8 (SEQ ID NO: 481).

FIG. 12C is an alignment of the amino acid sequences of six V$\kappa$s that bind human serum albumin (HSA). The aligned amino acid sequences are from V$_{\kappa S}$ designated DOM7h-2 (SEQ ID NO: 482), DOM7h-3 (SEQ ID NO: 483), DOM7h-4 (SEQ ID NO: 484), DOM7h-6 (SEQ ID NO: 485), DOM7h-1 (SEQ ID NO: 486), and DOM7h-7 (SEQ ID NO: 487).

FIG. 12D is an alignment of the amino acid sequences of seven $V_H$s that bind human serum albumin and a consensus sequence (SEQ ID NO: 488). The aligned sequences are from $V_H$s designated DOM7h-22 (SEQ ID NO: 489), DOM7h-23 (SEQ ID NO: 490), DOM7h-24 (SEQ ID NO: 491), DOM7h-25 (SEQ ID NO: 492), DOM7h-26 (SEQ ID NO: 493), DOM7h-21 (SEQ ID NO: 494), and DOM7h-27 (SEQ ID NO: 495).

FIG. 12E is an alignment of the amino acid sequences of three V$\kappa$s that bind human serum albumin and rat serum albumin. The aligned amino acid sequences are from V$\kappa$s designated DOM7h-8 (SEQ ID NO: 496), DOM7r-13 (SEQ ID NO: 497), and DOM7r-14 (SEQ ID NO: 498).

FIG. 13 is an illustration of the amino acid sequences of V$\kappa$s that bind rat serum albumin (RSA). The illustrated sequences are from V$\kappa$s designated DOM7r-15 (SEQ ID NO: 499), DOM7r-16 (SEQ ID NO: 500), DOM7r-17 (SEQ ID NO: 501), DOM7r-18 (SEQ ID NO: 502), DOM7r-19 (SEQ ID NO: 503).

FIG. 14A-14B is an illustration of the amino acid sequences of the amino acid sequences of $V_H$s that bind rat serum albumin (RSA). The illustrated sequences are from $V_H$s designated DOM7r-20 (SEQ ID NO: 504), DOM7r-21 (SEQ ID NO: 505), DOM7r-22 (SEQ ID NO: 506), DOM7r-23 (SEQ ID NO: 507), DOM7r-24 (SEQ ID NO: 508), DOM7r-25 (SEQ ID NO: 509), DOM7r-26 (SEQ ID NO: 510), DOM7r-27 (SEQ ID NO: 511), DOM7r-28 (SEQ ID NO: 512), DOM7r-29 (SEQ ID NO: 513), DOM7r-30 (SEQ ID NO: 514), DOM7r-31 (SEQ ID NO: 515), DOM7r-32 (SEQ ID NO: 516), and DOM7r-33 (SEQ ID NO: 517).

FIG. 15 illustrates the amino acid sequences of several Camelid $V_{HH}$s that bind mouse serum albumin that are disclosed in WO 2004/041862. Sequence A (SEQ ID NO: 518), Sequence B (SEQ ID NO: 519), Sequence C (SEQ ID NO: 520), Sequence D (SEQ ID NO: 521), Sequence E (SEQ ID NO: 522), Sequence F (SEQ ID NO: 523), Sequence G (SEQ ID NO: 524), Sequence H (SEQ ID NO: 525), Sequence I (SEQ ID NO:526), Sequence J (SEQ ID NO:527), Sequence K (SEQ ID NO: 528), Sequence L (SEQ ID NO:529), Sequence M (SEQ ID NO:530), Sequence N (SEQ ID NO:531), Sequence O (SEQ ID NO: 532), Sequence P (SEQ ID NO:533), Sequence Q (SEQ ID NO:534).

DETAILED DESCRIPTION OF THE INVENTION

Figure 16:
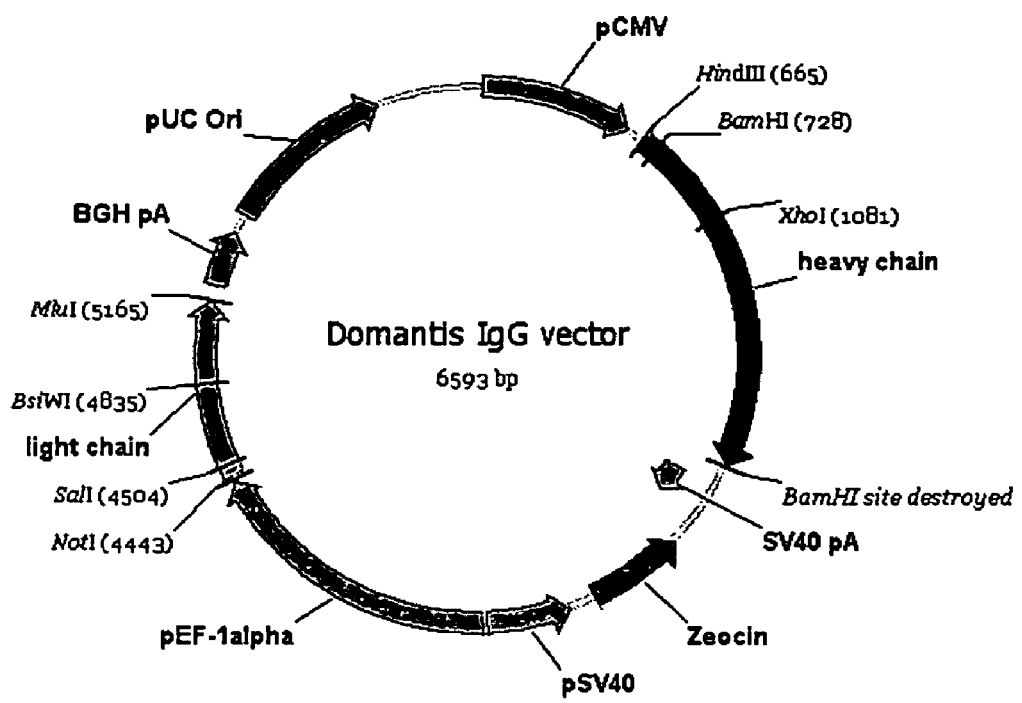
FIG. 16 is a map of a vector used to prepare IgG-like formats.

Within this specification embodiments have been described in a way which enables a clear and concise specification to be written, but it is intended and will be appreciated that embodiments may be variously combined or separated without parting from the invention.

As used herein, the term "ligand" refers to a compound that comprises at least one peptide, polypeptide or protein moiety that has a binding site with binding specificity for a desired endogenous target compound. The ligands according to the invention preferably comprise immunoglobulin variable domains which have different binding specificities, and do not contain variable domain pairs which have the same specificity. Preferably each domain which has a binding site that has binding specificity for a cell surface target is an immunoglobulin single variable domain (e.g., immunoglobulin single heavy chain variable domain (e.g., $V_H$, $V_{HH}$) immunoglobulin single light chain variable domain (e.g., $V_L$)) that has binding specificity for a desired cell surface target (e.g., a membrane protein, such as a receptor protein). Each polypeptide domain which has a binding site that has binding specificity for a cell surface target can also comprise one or more complementarity determining regions (CDRs) of an antibody or antibody fragment (e.g., an immunoglobulin single variable domain) that has binding specificity for a desired cell surface target in a suitable format, such that the binding domain has binding specificity for the cell surface target. For example, the CDRs can be grafted onto a suitable protein scaffold or skeleton, such as an affibody, an SpA scaffold, an LDL receptor class A domain, or an EGF domain. Further, the ligand can be bivalent (heterobivalent) or multivalent (heteromultivalent) as described herein. The first and second domains lack domains that share the same specificity. Thus, "ligands" include polypeptides that comprise two dAbs wherein each dAb binds to a different cell surface target. Ligands also include polypeptides that comprise at least two dAbs that bind different cell surface targets (or the CDRs of a dAbs) in a suitable format, such as an antibody format (e.g., IgG-like format, scFv, Fab, Fab', F(ab')$_2$) or a suitable protein scaffold or skeleton, such as an affibody, an SpA scaffold, an LDL receptor class A domain, an EGF domain, avimer and multispecific ligands as described herein. The polypeptide domain which has a binding site that has binding specificity for a cell surface target (i.e., first or second cell surface target) can also be a protein domain comprising a binding site for a desired target, e.g., a protein domain is selected from an affibody, an SpA domain, an LDL receptor class A domain, an avimer (see, e.g., U.S. Patent Application Publication Nos. 2005/0053973, 2005/0089932, 2005/0164301). If desired, a "ligand" can further comprise one or more additional moieties, that can each independently be a peptide, polypeptide or protein moiety or a non-peptidic moiety (e.g., a polyalkylene glycol, a lipid, a carbohydrate). For example, the ligand can further comprise a half-life extending moiety as described herein (e.g., a polyalkylene glycol moiety, a moiety comprising albumin, an albumin fragment or albumin variant, a moiety comprising transferrin, a transferrin fragment or transferrin variant, a moiety that binds albumin, a moiety that binds neonatal Fc receptor).

As used herein, the phrase "target" refers to a biological molecule (e.g., peptide, polypeptide, protein, lipid, carbohydrate) to which a polypeptide domain which has a binding site can bind. The target can be, for example, an intracellular target (e.g., an intracellular protein target) or a cell surface target (e.g., a membrane protein, a receptor protein). Preferably, the target is VEGF or EGFR.

The phrase "immunoglobulin single variable domain" refers to an antibody variable region ($V_H$, $V_{HH}$, $V_L$) that specifically binds a target, antigen or epitope independently of other V domains; however, as the term is used herein, an immunoglobulin single variable domain can be present in a format (e.g., hetero-multimer) with other variable regions or variable domains where the other regions or domains are not required for antigen binding by the single immunoglobulin variable domain (i.e., where the immunoglobulin single variable domain binds antigen independently of the additional variable domains). Each "Immunoglobulin single variable domain" encompasses not only an isolated antibody single variable domain polypeptide, but also larger polypeptides that comprise one or more monomers of an antibody single variable domain polypeptide sequence. A "domain antibody" or "dAb" is the same as an "immunoglobulin single variable domain" polypeptide as the term is used herein. An immunoglobulin single variable domain polypeptide, as used herein refers to a mammalian immunoglobulin single variable domain polypeptide, preferably human, but also includes rodent (for example, as disclosed in WO 00/29004, the contents of which are incorporated herein by reference in their entirety) or camelid $V_{HH}$ dAbs. As used herein, camelid dAbs are immunoglobulin single variable domain polypeptides which are derived from species including camel, llama, alpaca, dromedary, and guanaco, and comprise heavy chain antibodies naturally devoid of light chain ($V_{HH}$). Similar dAbs, can be obtained for single chain antibodies from other species, such as nurse shark. Preferred ligands comprises at least two different immunoglobulin single variable domain polypeptides or at least two different dAbs.

As used herein "vascular endothelial growth factor" (VEGF) refers to naturally occurring or endogenous mammalian VEGF-A proteins and to proteins having an amino acid sequence which is the same as that of a naturally occurring or endogenous corresponding mammalian VEGF-A protein (e.g., recombinant proteins, synthetic proteins (i.e., produced using the methods of synthetic organic chemistry)). Accordingly, as defined herein, the term includes mature VEGF-A protein, polymorphic or allelic variants, and other isoforms of a VEGF-A (e.g., produced by alternative splicing or other cellular processes), and modified or unmodified forms of the foregoing (e.g., lipidated, glycosylated). Alternative splicing of RNA encoding human (*Homo sapiens*) VEGF-A yield several isoforms of human VEGF-A that differ in the number of amino acids in the protein sequence. For example, isoforms referred to as VEGF-121, VEGF-165, VEGF-189 and VEGF-206 are produced in humans. (See, e.g., Ferrara, N., *Endocrine Reviews,* 25(4):581-611 (2004).) This isoforms and other naturally occurring isoforms are expressly encompassed by the term "VEGF". Naturally occurring or endogenous VEGF-A include wild type proteins such as mature VEGF-A, polymorphic or allelic variants and other isoforms which occur naturally in mammals (e.g., humans, non-human primates). Such proteins can be recovered or isolated from a source which naturally produces VEGF-A, for example. These proteins and proteins having the same amino acid sequence as a naturally occurring or endogenous corresponding VEGF, are referred to by the name of the corresponding mammal. For example, where the corresponding mammal is a human, the protein is designated as a human VEGF.

A ligand (e.g., immunoglobulin single variable domain) that inhibits binding of VEGF to VEGFR1 or VEGFR2 inhibits binding in the VEGFR1 binding assay or VEGFR2 assay described herein by at least about 40%, at least about 50%, at least about 60%, at least about 70%, at least about 80%, at least about 85%, at least about 90%, or at least about 95% when the ligand is assayed at a concentration of about 1 nM, about 10 nM, about 50 nM, about 100 nM, about 1 µM, about 10 µM or about 100 µM. A ligand that inhibits binding of VEGF to VEGFR1 or VEGFR2, can also or alternatively, inhibit binding in the VEGFR1 binding assay or VEGFR2 assay with an IC50 of about 1 µM or less, about 500 nM or less, about 100 nM or less, about 75 nM or less, about 50 nM or less, about 10 nM or less or about 1 nM or less.

A ligand (e.g., immunoglobulin single variable domain) that inhibits activity of VEGF inhibits viability in the VEGF bioassay described herein by at least about 20%, at least about 30%, at least about 40%, at least about 50%, at least about 60%, at least about 70%, at least about 80%, at least about 85%, at least about 90%, or at least about 90%.

A ligand (e.g., immunoglobulin single variable domain) that does not substantially inhibit binding of VEGF to VEGFR1 or VEGFR2 does not significantly inhibit binding in the VEGFR1 binding assay or VEGFR2 assay described herein. For example, such a ligand might inhibit binding of VEGF in the VEGFR1 binding assay or VEGFR2 assay described herein with an IC50 of about 1 mM or higher, or inhibit binding by no more than about 20%, no more than about 15%, no more than about 10% or no more than about 5%.

As used herein "epidermal growth factor receptor" (EGFR, ErbB1, HER1) refers to naturally occurring or endogenous mammalian EGFR proteins and to proteins having an amino acid sequence which is the same as that of a naturally occurring or endogenous corresponding mammalian EGFR protein (e.g., recombinant proteins, synthetic proteins (i.e., produced using the methods of synthetic organic chemistry)). Accordingly, as defined herein, the term includes mature EGFR protein, polymorphic or allelic variants, and other isoforms of a EGFR (e.g., produced by alternative splicing or other cellular processes), and modified or unmodified forms of the foregoing (e.g., lipidated, glycosylated). Naturally occurring or endogenous EGFR include wild type proteins such as mature EGFR, polymorphic or allelic variants and other isoforms which occur naturally in mammals (e.g., humans, non-human primates). Such proteins can be recovered or isolated from a source which naturally produces EGFR, for example. These proteins and proteins having the same amino acid sequence as a naturally occurring or endogenous corresponding EGFR, are referred to by the name of the corresponding mammal. For example, where the corresponding mammal is a human, the protein is designated as a human EGFR.

A ligand (e.g., immunoglobulin single variable domain) that inhibits binding of EGF and/or TGF alpha to EGFR inhibits binding in the EGFR binding assay or EGFR kinase assay described herein with an IC50 of about 1 µM or less, about 500 nM or less, about 100 nM or less, about 75 nM or less, about 50 nM or less, about 10 nM or less or about 1 nM or less.

A ligand (e.g., immunoglobulin single variable domain) inhibits activity of EGFR inhibits kinase activity of EGFR in the EGFR kinase assay described herein with an IC50 of about 1 µM or less, about 500 nM or less, about 100 nM or less, about 75 nM or less, about 50 nM or less, about 10 nM or less or about 1 nM or less.

A ligand (e.g., immunoglobulin single variable domain) that does not substantially inhibit binding of EGF or TGF alpha to EGFR does not significantly inhibit binding of EGF and/or TGF alpha to EGFR in the receptor binding assay or kinase assay described herein. For example, such a ligand might inhibit binding of EGF or TGF alpha to EGFR in the receptor binding assay or kinase assay described herein with an IC50 of about 1 mM or higher.

"Affinity" and "avidity" are terms of art that describe the strength of a binding interaction. With respect to the ligands of the invention, avidity refers to the overall strength of binding between the targets (e.g., first cell surface target and second cell surface target) on the cell and the ligand. Avidity is more than the sum of the individual affinities for the individual targets.

As used herein, "toxin moiety" refers to a moiety that comprises a toxin. A toxin is an agent that has deleterious effects on or alters cellular physiology (e.g., causes cellular necrosis, apoptosis or inhibibs cellular division).

As used herein, the term "dose" refers to the quantity of ligand administered to a subject all at one time (unit dose), or in two or more administrations over a defined time interval. For example, dose can refer to the quantity of ligand (e.g., ligand comprising an immunoglobulin single variable domain that binds VEGF and an immunoglobulin single variable domain that binds EGFR) administered to a subject over the course of one day (24 hours) (daily dose), two days, one week, two weeks, three weeks or one or more months (e.g., by a single administration, or by two or more administrations). The interval between doses can be any desired amount of time.

As used herein "complementary" refers to when two immunoglobulin domains belong to families of structures which form cognate pairs or groups or are derived from such families and retain this feature. For example, a $V_H$ domain and a $V_L$ domain of an antibody are complementary; two $V_H$ domains are not complementary, and two $V_L$ domains are not complementary. Complementary domains may be found in other members of the immunoglobulin superfamily, such as the $V_\alpha$ and $V_\beta$ (or γ and δ) domains of the T-cell receptor. Domains which are artificial, such as domains based on protein scaffolds which do not bind epitopes unless engineered to do so, are non-complementary. Likewise, two domains based on (for example) an immunoglobulin domain and a fibronectin domain are not complementary.

As used herein, "immunoglobulin" refers to a family of polypeptides which retain the immunoglobulin fold characteristic of antibody molecules, which contains two β sheets and, usually, a conserved disulphide bond. Members of the immunoglobulin superfamily are involved in many aspects of cellular and non-cellular interactions in vivo, including widespread roles in the immune system (for example, antibodies, T-cell receptor molecules and the like), involvement in cell adhesion (for example the ICAM molecules) and intracellular signaling (for example, receptor molecules, such as the PDGF receptor). The present invention is applicable to all immunoglobulin superfamily molecules which possess binding domains. Preferably, the present invention relates to antibodies.

As used herein "domain" refers to a folded protein structure which retains its tertiary structure independently of the rest of the protein. Generally, domains are responsible for discrete functional properties of proteins, and in many cases may be added, removed or transferred to other proteins without loss of function of the remainder of the protein and/or of the domain. By single antibody variable domain is meant a folded polypeptide domain comprising sequences characteristic of antibody variable domains. It therefore includes complete antibody variable domains and modified variable domains, for example in which one or more loops have been replaced by sequences which are not characteristic of antibody variable domains, or antibody variable domains which have been truncated or comprise N- or C-terminal extensions, as well as folded fragments of variable domains which retain at least in part the binding activity and specificity of the full-length domain. Thus, each ligand comprises at least two different domains.

"Repertoire" A collection of diverse variants, for example polypeptide variants which differ in their primary sequence. A library used in the present invention will encompass a repertoire of polypeptides comprising at least 1000 members.

"Library" The term library refers to a mixture of heterogeneous polypeptides or nucleic acids. The library is composed of members, each of which have a single polypeptide or nucleic acid sequence. To this extent, library is synonymous with repertoire. Sequence differences between library members are responsible for the diversity present in the library. The library may take the form of a simple mixture of polypeptides or nucleic acids, or may be in the form of organisms or cells, for example bacteria, viruses, animal or plant cells and the like, transformed with a library of nucleic acids. Preferably, each individual organism or cell contains only one or a limited number of library members. Advantageously, the nucleic acids are incorporated into expression vectors, in order to allow expression of the polypeptides encoded by the nucleic acids. In a preferred aspect, therefore, a library may take the form of a population of host organisms, each organism containing one or more copies of an expression vector containing a single member of the library in nucleic acid form which can be expressed to produce its corresponding polypeptide member. Thus, the population of host organisms has the potential to encode a large repertoire of genetically diverse polypeptide variants.

As used herein an antibody refers to IgG, IgM, IgA, IgD or IgE or a fragment (such as a Fab, F(ab')$_2$, Fv, disulphide linked Fv, scFv, closed conformation multispecific antibody, disulphide-linked scFv, diabody) whether derived from any species naturally producing an antibody, or created by recombinant DNA technology; whether isolated from serum, B-cells, hybridomas, transfectomas, yeast or bacteria.

As described herein an "antigen' is a molecule that is bound by a binding domain according to the present invention. Typically, antigens are bound by antibody ligands and are capable of raising an antibody response in vivo. It may be a polypeptide, protein, nucleic acid or other molecule. Generally, the dual-specific ligands according to the invention are selected for target specificity against two particular targets (e.g., antigens). In the case of conventional antibodies and fragments thereof, the antibody binding site defined by the variable loops (L1, L2, L3 and H1, H2, H3) is capable of binding to the antigen.

An "epitope" is a unit of structure conventionally bound by an immunoglobulin $V_H/V_L$ pair. Epitopes define the minimum binding site for an antibody, and thus represent the target of specificity of an antibody. In the case of a single domain antibody, an epitope represents the unit of structure bound by a variable domain in isolation.

"Universal framework" refers to a single antibody framework sequence corresponding to the regions of an antibody conserved in sequence as defined by Kabat ("Sequences of Proteins of Immunological Interest", US Department of Health and Human Services) or corresponding to the human germline immunoglobulin repertoire or structure as defined by Chothia and Lesk, (1987) J. Mol. Biol. 196:910-917. The invention provides for the use of a single framework, or a set of such frameworks, which has been found to permit the derivation of virtually any binding specificity though variation in the hypervariable regions alone.

The phrase, "half-life," refers to the time taken for the serum concentration of the ligand to reduce by 50%, in vivo, for example due to degradation of the ligand and/or clearance or sequestration of the dual-specific ligand by natural mechanisms. The ligands of the invention are stabilized in vivo and their half-life increased by binding to molecules which resist degradation and/or clearance or sequestration. Typically, such molecules are naturally occurring proteins which themselves have a long half-life in vivo. The half-life of a ligand is increased if its functional activity persists, in vivo, for a longer period than a similar ligand which is not specific for the half-life increasing molecule. Thus a ligand specific for HSA and two target molecules is compared with the same ligand wherein the specificity to HAS is not present, that is does not binde HAS but binds another molecule. For example, it may bind a third target on the cell. Typically, the half life is increased by 10%, 20%, 30%, 40%, 50% or more. Increases in the range of 2×, 3×, 4×, 5×, 10×, 20×, 30×, 40×, 50× or more of the half life are possible. Alternatively, or in addition, increases in the range of up to 30×, 40×, 50×, 60×, 70×, 80×, 90×, 100×, 150× of the half life are possible.

As referred to herein, the term "competes" means that the binding of a first target to its cognate target binding domain is inhibited when a second target is bound to its cognate target binding domain. For example, binding may be inhibited sterically, for example by physical blocking of a binding domain or by alteration of the structure or environment of a binding domain such that its affinity or avidity for a target is reduced.

As used herein, the terms "low stringency," "medium stringency," "high stringency," or "very high stringency conditions" describe conditions for nucleic acid hybridization and washing. Guidance for performing hybridization reactions can be found in Current Protocols in Molecular Biology, John Wiley & Sons, N.Y. (1989), 6.3.1-6.3.6, which is incorporated herein by reference in its entirety. Aqueous and non-aqueous methods are described in that reference and either can be used. Specific hybridization conditions referred to herein are as follows: (1) low stringency hybridization conditions in 6× sodium chloride/sodium citrate (SSC) at about 45C, followed by two washes in 0.2×SSC, 0.1% SDS at least at 50C (the temperature of the washes can be increased to 55C for low stringency conditions); (2) medium stringency hybridization conditions in 6×SSC at about 45C, followed by one or more washes in 0.2×SSC, 0.1% SDS at 60C; (3) high stringency hybridization conditions in 6×SSC at about 45C, followed by one or more washes in 0.2×SSC, 0.1% SDS at 65C; and preferably (4) very high stringency hybridization conditions are 0.5M sodium phosphate, 7% SDS at 65C, followed by one or more washes at 0.2×SSC, 1% SDS at 65C. Very high stringency conditions (4) are the preferred conditions and the ones that should be used unless otherwise specified.

Sequences similar or homologous (e.g., at least about 70% sequence identity) to the sequences disclosed herein are also part of the invention. In some embodiments, the sequence identity at the amino acid level can be about 80%, 85%, 90%, 91%, 92%, 93%, 94%, 95%, 96%, 97%, 98%, 99% or higher. At the nucleic acid level, the sequence identity can be about 70%, 75%, 80%, 85%, 90%, 91%, 92%, 93%, 94%, 95%, 96%, 97%, 98%, 99% or higher. Alternatively, substantial identity exists when the nucleic acid segments will hybridize under selective hybridization conditions (e.g., very high stringency hybridization conditions), to the complement of the strand. The nucleic acids may be present in whole cells, in a cell lysate, or in a partially purified or substantially pure form.

Calculations of "homology" or "sequence identity" or "similarity" between two sequences (the terms are used interchangeably herein) are performed as follows. The sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, the length of a reference sequence aligned for comparison purposes is at least 30%, preferably at least 40%, more preferably at least 50%, even more preferably at least 60%, and even more preferably at least 70%, 80%, 90%, 100% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "homology" is equivalent to amino acid or nucleic acid "identity"). The percent identity between the two sequences is a function of the number of identical positions shared by the sequences, taking into account the number of gaps, and the length of each gap, which need to be introduced for optimal alignment of the two sequences.

Amino acid and nucleotide sequence alignments and homology, similarity or identity, as defined herein are preferably prepared and determined using the algorithm BLAST 2 Sequences, using default parameters (Tatusova, T. A. et al., FEMS Microbiol Lett, 174:187-188 (1999)). Alternatively, the BLAST algorithm (version 2.0) is employed for sequence alignment, with parameters set to default values. BLAST (Basic Local Alignment Search Tool) is the heuristic search algorithm employed by the programs blastp, blastn, blastx, tblastn, and tblastx; these programs ascribe significance to their findings using the statistical methods of Karlin and Altschul, 1990, Proc. Natl. Acad. Sci. USA 87(6):2264-8

Unless defined otherwise, all technical and scientific terms used herein have the same meaning as commonly understood by one of ordinary skill in the art (e.g., in cell culture, molecular genetics, nucleic acid chemistry, hybridization techniques and biochemistry). Standard techniques are used for molecular, genetic and biochemical methods (see generally, Sambrook et al., Molecular Cloning: A Laboratory Manual, 2d ed. (1989) Cold Spring Harbor Laboratory Press, Cold Spring Harbor, N.Y. and Ausubel et al., Short Protocols in Molecular Biology (1999) 4th Ed, John Wiley & Sons, Inc. which are incorporated herein by reference) and chemical methods.

The invention relates to ligands that have binding specificity for VEGF (e.g., human VEGF), ligands that have binding specificity for EGFR (e.g., human EGFR), and to ligands that have binding specificity for VEGF and EGFR (e.g., human VEGF and human EGFR). For example, the ligand can comprise a polypeptide domain having a binding site with binding specificity for VEGF, a polypeptide domain having a binding site with binding specificity EGFR, or comprise a polypeptide domain having a binding site with binding specificity for VEGF and a polypeptide domain having a binding site with binding specificity EGFR.

The ligands of the invention provide several advantages. For example, as described herein, the ligand can be tailored to have a desired in vivo serum half-life. Thus, the ligands can be used to control, reduce, or eliminate general toxicity of therapeutic agents, such as cytotoxin used to treat cancer. Further, dAbs are much smaller than conventional antibodies, and can be administered to achieve better tissue penetration than conventional antibodies. Thus, dAbs and ligands that comprise a dAb provide advantages over convential antibodies when administered to treat cancer, for example by targeting solid tumors. Moreover, many cancers overexpress EGFR, and ligands that have binding specificity for EGFR and VEGF can be administered to target VEGF-inhibitory activity to tumors or the environment of cancer cells. This approach provides two beneficial activities directly at the site of a tumor or cancer, i.e., direct anti-cancer activity by binding to EGFR and inhibiting binidng of ligands (e.g., EGF, TGF alpha) to the receptor, and inhibition of angiogenesis that supports tumor formation and development. Accordingly, ligands that have binding specificity for VEGF and EGFR can be administered to a patient with cancer (e.g., EGFR-expressing cancer) to provide superior therapy using a single therapeutic agent.

Further, signals transduced through EGFR can lead to the production of angiogenic factors, such as VEGF. Cancer cells (e.g., in a tumor) that express or overexpress EGFR can produce a high level of VEGF that acts locally to induce formation of tumor vasculature. Accordingly, the ligands of the invention that have binding specificity for VEGF and EGFR can be administed to a subject to target delivery of the VEGF inhibitory activity of the ligand to cells that overexpress EGFR. Accordingly, anti-angiogenic therapy can be delivered specifically to sites where VEGF is being produced (e.g., to cells that overexpress EGFR).

In some embodiments, the ligand has binding specificity for VEGF and comprises an (at least one) immunoglobulin single variable domain with binding specificity for VEGF. In other embodiments, the ligand has binding specificity for EGFR and comprises an (at least one) immunoglobulin single variable domain with binding specificity for EGFR. In certain embodiments, the ligand has binding specificity for VEGF and EGFR, and comprises an (at least one) immunoglobulin single variable domain with binding specificity for VEGF and an (at least one) immunoglobulin single variable domain with binding specificity for EGFR.

The ligand of the invention can be formatted as described herein For example, the ligand of the invention can be formatted to tailor in vivo serum half-life. If desired, the ligand can further comprises a toxin or a toxin moiety as described herein. In some embodiments, the ligand comprises a surface active toxin, such as a free radical generator (e.g., selenium containing toxin) or a radionuclide. In other embodiments, the toxin or toxin moiety is a polypeptide domain (e.g., a dAb) having a binding site with binding specificity for an intracellular target. In particular embodiments, the ligand is an IgG-like format that has binding specificity for VEGF and EGFR (e.g., human VEGF and human EGFR).

Ligand Formats

The ligand of the invention can be formatted as a monospecific, dual specific or multispecific ligand as described herein. See, also WO 03/002609, the entire teachings of which are incorporated herein by reference, regarding ligand formatting. Such dual specific ligands comprise immunoglobulin single variable domains that have different binding specificities. Such dual specific ligands can comprise combinations of heavy and light chain domains. For example, the dual specific ligand may comprise a $V_H$ domain and a $V_L$ domain, which may be linked together in the form of an scFv (e.g., using a suitable linker such as Gly₄Ser)(SEQ ID NO: 541)) formatted into a bispecific antibody or antigen-binding fragment thereof (e.g. F(ab')₂ fragment). The dual specific ligands do not comprise complementary $V_H/V_L$ pairs which form a conventional two chain antibody antigen-binding site that binds antigen or epitope co-operatively. Instead, the dual format ligands comprise a $V_H/V_L$ complementary pair, wherein the V domains have different binding specificities.

In addition, the dual specific ligands may comprise one or more $C_H$ or $C_L$ domains if desired. A hinge region domain may also be included if desired. Such combinations of domains may, for example, mimic natural antibodies, such as IgG or IgM, or fragments thereof, such as Fv, scFv, Fab or F(ab')₂ molecules. Other structures, such as a single arm of an IgG molecule comprising $V_H$, $V_L$, $C_H1$ and $C_L$ domains, are envisaged. Preferably, the dual specific ligand of the invention comprises only two variable domains although several such ligands may be incorporated together into the same protein, for example two such ligands can be incorporated into an IgG or a multimeric immunoglobulin, such as IgM. Alternatively, in another embodiment a plurality of dual specific ligands are combined to form a multimer. For example, two different dual specific ligands are combined to create a tetra-specific molecule. It will be appreciated by one skilled in the art that the light and heavy variable regions of a dual-specific ligand produced according to the method of the present invention may be on the same polypeptide chain, or alternatively, on different polypeptide chains. In the case that the variable regions are on different polypeptide chains, then they may be linked via a linker, generally a flexible linker (such as a polypeptide chain), a chemical linking group, or any other method known in the art.

Ligands can be formatted as bi- or multispecific antibodies or antibody fragments or into bi- or multispecific non-antibody structures. Suitable formats include, any suitable polypeptide structure in which an antibody variable domain or one or more of the CDRs thereof can be incorporated so as to confer binding specificity for antigen on the structure. A variety of suitable antibody formats are known in the art, such as, bispecific IgG-like formats (e.g., chimeric antibodies, humanized antibodies, human antibodies, single chain antibodies, heterodimers of antibody heavy chains and/or light chains, antigen-binding fragments of any of the foregoing (e.g., a Fv fragment (e.g., single chain Fv (scFv), a disulfide bonded Fv), a Fab fragment, a Fab' fragment, a F(ab')₂ fragment), a single variable domain (e.g., $V_H$, $V_L$, $V_{HH}$), a dAb, and modified versions of any of the foregoing (e.g., modified by the covalent attachment of polyalkylene glycol (e.g., polyethylene glycol, polypropylene glycol, polybutylene glycol) or other suitable polymer). See, PCT/GB03/002804, filed Jun. 30, 2003, which designated the United States, (WO 2004/081026) regarding PEGylated of single variable domains and dAbs, suitable methods for preparing same, increased in vivo half life of the PEGylated single variable domains and dAb monomers and multimers, suitable PEGs, preferred hydrodynamic sizes of PEGs, and preferred hydrodynamic sizes of PEGylated single variable domains and dAb monomers and multimers. The entire teaching of PCT/GB03/002804 (WO 2004/081026), including the portions referred to above, are incorporated herein by reference.

The ligand can be formatted using a suitable linker such as $(Gly_4Ser)_n$, where n=from 1 to 8, e.g., 2, 3, 4, 5, 6 or 7. If desired, ligands, including dAb monomers, dimers and trimers, can be linked to an antibody Fc region, comprising one or both of $C_H2$ and $C_H3$ domains, and optionally a hinge region. For example, vectors encoding ligands linked as a single nucleotide sequence to an Fc region may be used to prepare such polypeptides.

Ligands and dAb monomers can also be combined and/or formatted into non-antibody multi-ligand structures to form multivalent complexes, which bind target molecules with the same antigen, thereby providing superior avidity. For example natural bacterial receptors such as SpA can been used as scaffolds for the grafting of CDRs to generate ligands which bind specifically to one or more epitopes. Details of this procedure are described in U.S. Pat. No. 5,831,012. Other suitable scaffolds include those based on fibronectin and affibodies. Details of suitable procedures are described in WO 98/58965. Other suitable scaffolds include lipocallin and CTLA4, as described in van den Beuken et al., J. Mol. Biol. 310:591-601 (2001), and scaffolds such as those described in WO 00/69907 (Medical Research Council), which are based for example on the ring structure of bacterial GroEL or other chaperone polypeptides. Protein scaffolds may be combined; for example, CDRs may be grafted on to a CTLA4 scaffold and used together with immunoglobulin $V_H$ or $V_L$ domains to form a ligand. Likewise, fibronectin, lipocallin and other scaffolds may be combined A variety of suitable methods for preparing any desired format are known in the art. For example, antibody chains and formats (e.g., bispecific IgG-like formats, chimeric antibodies, humanized antibodies, human antibodies, single chain antibodies, homodimers and heterodimers of antibody heavy chains and/or light chains) can be prepared by expression of suitable expression constructs and/or culture of suitable cells (e.g., hybridomas, heterohybridomas, recombinant host cells containing recombinant constructs encoding the format). Further, formats such as antigen-binding fragments of antibodies or antibody chains (e.g., bispecific binding fragments, such as a Fv fragment (e.g., single chain Fv (scFv), a disulfide bonded Fv), a Fab fragment, a Fab' fragment, a F(ab')₂ fragment), can be prepared by expression of suitable expression constructs or by enzymatic digestion of antibodies, for example using papain or pepsin.

The ligand can be formatted as a multispecific ligand, for example as described in WO 03/002609, the entire teachings of which are incorporated herein by reference. Such multi-specific ligand possesses more than one epitope binding specificity. Generally, the multi-specific ligand comprises two or more epitope binding domains, such dabs or non-antibody protein domain comprising a binding site for an epitope, e.g., an affibody, an SpA domain, an LDL receptor class A domain, an EGF domain, an avimer. Multispecific ligands can be formatted further as described herein.

In some embodiments, the ligand is an IgG-like format. Such formats have the conventional four chain structure of an IgG molecule (2 heavy chains and two light chains), in which one or more of the variable regions ($V_H$ and or $V_L$) have been replaced with a dAb or single variable domain of a desired specificity. Preferably, each of the variable regions (2 $V_H$ regions and 2 $V_L$ regions) is replaced with a dAb or single variable domain. The dAb(s) or single variable domain(s) that are included in an IgG-like format can have the same specificity or different specificities. In some embodiments, the IgG-like format is tetravalent and can have one, two, three or four specificities. For example, the IgG-like format can be monospecific and comprises 4 dAbs that have the same specificity; bispecific and comprises 3 dAbs that have the same specificity and another dAb that has a different specificity; bispecific and comprise two dAbs that have the same specificity and two dAbs that have a common but different specificity; trispecific and comprises first and second dAbs that have the same specificity, a third dAbs with a different specificity and a fourth dAb with a different specificity from the first, second and third dAbs; or tetraspecific and comprise four dAbs that each have a different specificity. Antigen-binding fragments of IgG-like formats (e.g., Fab, F(ab')$_2$, Fab', Fv, scFv) can be prepared. In addition, a particular constant region of Fc portion (e.g., of an IgG, such as IgG1), variant or portion thereof can be selected in order to tailor effector function. For example, if complement activation and/or antibody dependent cellular cytotoxicity (ADCC) function is desired, the ligand can be an IgG1-like format. If desired, the IgG-like format can comprise a mutated constant region (variant IgG heavy chain constant region) to minimize binding to Fc receptors and/or ability to fix complement (see e.g. Winter et al, GB 2,209,757 B; Morrison et al., WO 89/07142; Morgan et al., WO 94/29351, Dec. 22, 1994).

The ligands of the invention can be formatted as a fusion protein that contains a first immunoglobulin single variable domain that is fused directly to a second immunoglobulin single variable domain. If desired such a format can further comprise a half life extending moiety. For example, the ligand can comprise a first immunoglobulin single variable domain that is fused directly to a second immunoglobulin single variable domain that is fused directly to an immunoglobulin single variable domain that binds serum albumin.

Generally the orientation of the polypeptide domains that have a binding site with binding specificity for a cell surface targer and whether the ligand comprises a linker is a matter of design choice. However, some orientations, with or without linkers, may provide better binding characteristics than other orientations. All orientations (e.g., dAb1-linker-dAb2; dAb2-linker-dAb1) are encompassed by the invention are ligands that contain an orientation that provides desired binding characteristics can be easily identified by screening.

Half-Life Extended Formats

The ligand, and dAb monomers disclosed herein, can be formatted to extend its in vivo serum half life. Increased in vivo half-life is useful in vivo applications of immunoglobulins, especially antibodies and most especially antibody fragments of small size such as dAbs. Such fragments (Fvs, disulphide bonded Fvs, Fabs, scFvs, dAbs) are rapidly cleared from the body, which can severely limit clinical applications.

A ligand can be formatted be formatted as a larger antigen-binding fragment of an antibody or as and antibody (e.g., formatted as a Fab, Fab', F(ab)$_2$, F(ab')$_2$, IgG, scFv) that has larger hydrodynamic size. Ligands can also be formatted to have a larger hydrodynamic size, for example, by attachment of a polyalkyleneglycol group (e.g. polyethyleneglycol (PEG) group, polypropylene glycol, polybutylene glycol), serum albumin, transferrin, transferrin receptor or at least the transferrin-binding portion thereof, an antibody Fc region, or by conjugation to an antibody domain. In some embodiments, the ligand (e.g., dAb monomer) is PEGylated. Preferably the PEGylated ligand (e.g., dAb monomer) binds VEGR and/or EGFR with substantially the same affinity or avidity as the same ligand that is not PEGylated. For example, the ligand can be a PEGylated ligand comprising a dAb that binds VEGF or EGFR with an avidity that differs from the avidity of ligand in unPEGylated form by no more than a factor of about 1000, preferably no more than a factor of about 100, more preferably no more than a factor of about 10, or with avidity substantially unchanged affinity relative to the unPEGylated form. See, PCT/GB03/002804, filed Jun. 30, 2003, which designated the United States, (WO 2004/081026) regarding PEGylated of single variable domains and dAbs, suitable methods for preparing same, increased in vivo half life of the PEGylated single variable domains and dAb monomers and multimers, suitable PEGs, preferred hydrodynamic sizes of PEGs, and preferred hydrodynamic sizes of PEGylated single variable domains and dAb monomers and multimers. The entire teaching of PCT/GB03/002804 (WO 2004/081026), including the portions referred to above, are incorporated herein by reference.

Hydrodynamic size of the ligands (e.g., dAb monomers and multimers) of the invention may be determined using methods which are well known in the art. For example, gel filtration chromatography may be used to determine the hydrodynamic size of a ligand. Suitable gel filtration matrices for determining the hydrodynamic sizes of ligands, such as cross-linked agarose matrices, are well known and readily available.

The size of a ligand format (e.g., the size of a PEG moiety attached to a dAb monomer), can be varied depending on the desired application. For example, where ligand is intended to leave the circulation and enter into peripheral tissues, it is desirable to keep the hydrodynamic size of the ligand low to facilitate extravazation from the blood stream. Alternatively, where it is desired to have the ligand remain in the systemic circulation for a longer period of time the size of the ligand can be increased, for example by formatting as and Ig like protein or by addition of a 30 to 60 kDa PEG moiety (e.g., linear or branched PEG 30 to 40 kDa PEG, such as addition of two 20 kDa PEG moieties.) The size of the ligand format can be tailored to achieve a desired in vivo serum half life, for example to control exposure to a toxin and/or to reduce side effects of toxic agents.

The hydrodynaminc size of ligand (e.g., dAb monomer) and its serum half-life can also be increased by conjugating or linking the ligand to a binding domain (e.g., antibody or antibody fragment) that binds an antigen or epitope that increases half-live in vivo, as described herein. For example, the ligand (e.g., dAb monomer) can be conjugated or linked to an anti-serum albumin or anti-neonatal Fc receptor antibody or antibody fragment, eg an anti-SA or anti-neonatal Fc receptor dAb, Fab, Fab' or scFV, or to an anti-SA affibody or anti-neonatal Fc receptor affibody.

Examples of suitable albumin, albumin fragments or albumin variants for use in a ligand according to the invention are described in WO 2005/077042A2, which is incorporated herein by reference in its entirety. In particular, the following albumin, albumin fragments or albumin variants can be used in the present invention:

SEQ ID NO:1 (as disclosed in WO 2005/077042A2, this sequence being explicitly incorporated into the present disclosure by reference);

Albumin fragment or variant comprising or consisting of amino acids 1-387 of SEQ ID NO:1 in WO 2005/077042A2;

Albumin, or fragment or variant thereof, comprising an amino acid sequence selected from the group consisting of: (a) amino acids 54 to 61 of SEQ ID NO:1 in WO 2005/077042A2; (b) amino acids 76 to 89 of SEQ ID NO:1 in WO 2005/077042A2; (c) amino acids 92 to 100 of SEQ ID NO:1 in WO 2005/077042A2; (d) amino acids 170 to 176 of SEQ ID NO:1 in WO 2005/077042A2; (e) amino acids 247 to 252 of SEQ ID NO:1 in WO 2005/077042A2; (f) amino acids 266 to 277 of SEQ ID NO:1 in WO 2005/077042A2; (g) amino acids 280 to 288 of SEQ ID NO:1 in WO 2005/077042A2; (h) amino acids 362 to 368 of SEQ ID NO:1 in WO 2005/077042A2; (i) amino acids 439 to 447 of SEQ ID NO:1 in WO 2005/077042A2 (j) amino acids 462 to 475 of SEQ ID NO:1 in WO 2005/077042A2; (k) amino acids 478 to 486 of SEQ ID NO:1 in WO 2005/077042A2; and (1) amino acids 560 to 566 of SEQ ID NO:1 in WO 2005/077042A2.

Further examples of suitable albumin, fragments and analogs for use in a ligand according to the invention are described in WO 03/076567A2, which is incorporated herein by reference in its entirety. In particular, the following albumin, fragments or variants can be used in the present invention:

Human serum albumin as described in WO 03/076567A2, eg, in FIG. 3 (this sequence information being explicitly incorporated into the present disclosure by reference);

Human serum albumin (HA) consisting of a single non-glycosylated polypeptide chain of 585 amino acids with a formula molecular weight of 66,500 (See, Meloun, et al., *FEBS Letters* 58:136 (1975); Behrens, et al., *Fed. Proc.* 34:591 (1975); Lawn, et al., *Nucleic Acids Research* 9:6102-6114 (1981); Minghetti, et al., *J. Biol. Chem.* 261:6747 (1986));

A polymorphic variant or analog or fragment of albumin as described in Weitkamp, et al., *Ann. Hum. Genet.* 37:219 (1973);

An albumin fragment or variant as described in EP 322094, eg, HA(1-373., HA(1-388), HA(1-389), HA(1-369), and HA(1-419) and fragments between 1-369 and 1-419;

An albumin fragment or variant as described in EP 399666, eg, HA(1-177) and HA(1-200) and fragments between HA(1-X), where X is any number from 178 to 199.

Where a (one or more) half-life extending moiety (eg, albumin, transferrin and fragments and analogues thereof) is used in the ligands of the invention, it can be conjugated to the ligand using any suitable method, such as, by direct fusion to the target-binding moiety (eg, dAb or antibody fragment), for example by using a single nucleotide construct that encodes a fusion protein, wherein the fusion protein is encoded as a single polypeptide chain with the half-life extending moiety located N- or C-terminally to the cell surface target binding moieties. Alternatively, conjugation can be achieved by using a peptide linker between moieties, eg, a peptide linker as described in WO 03/076567A2 or WO 2004/003019 (these linker disclosures being incorporated by reference in the present disclosure to provide examples for use in the present invention). Typically, a polypeptide that enhances serum half-life in vivo is a polypeptide which occurs naturally in vivo and which resists degradation or removal by endogenous mechanisms which remove unwanted material from the organism (e.g., human). For example, a polypeptide that enhances serum half-life in vivo can be selected from proteins from the extracellular matrix, proteins found in blood, proteins found at the blood brain barrier or in neural tissue, proteins localized to the kidney, liver, lung, heart, skin or bone, stress proteins, disease-specific proteins, or proteins involved in Fc transport.

Suitable polypeptides that enhance serum half-life in vivo include, for example, transferrin receptor specific ligand-neuropharmaceutical agent fusion proteins (see U.S. Pat. No. 5,977,307, the teachings of which are incorporated herein by reference), brain capillary endothelial cell receptor, transferrin, transferrin receptor (e.g., soluble transferrin receptor), insulin, insulin-like growth factor 1 (IGF 1) receptor, insulin-like growth factor 2 (IGF 2) receptor, insulin receptor, blood coagulation factor X, α1-antitrypsin and HNF 1α. Suitable polypeptides that enhance serum half-life also include alpha-1 glycoprotein (orosomucoid; AAG), alpha-1 antichymotrypsin (ACT), alpha-1 microglobulin (protein HC; AIM), antithrombin III (AT III), apolipoprotein A-1 (Apo A-1), apolipoprotein B (Apo B), ceruloplasmin (Cp), complement component C3 (C3), complement component C4 (C4), C1 esterase inhibitor (C1 INH), C-reactive protein (CRP), ferritin (FER), hemopexin (HPX), lipoprotein(a) (Lp(a)), mannose-binding protein (MBP), myoglobin (Myo), prealbumin (transthyretin; PAL), retinol-binding protein (RBP), and rheumatoid factor (RF).

Suitable proteins from the extracellular matrix include, for example, collagens, laminins, integrins and fibronectin. Collagens are the major proteins of the extracellular matrix. About 15 types of collagen molecules are currently known, found in different parts of the body, e.g. type I collagen (accounting for 90% of body collagen) found in bone, skin, tendon, ligaments, cornea, internal organs or type II collagen found in cartilage, vertebral disc, notochord, and vitreous humor of the eye.

Suitable proteins from the blood include, for example, plasma proteins (e.g., fibrin, α-2 macroglobulin, serum albumin, fibrinogen (e.g., fibrinogen A, fibrinogen B), serum amyloid protein A, haptoglobin, profilin, ubiquitin, uteroglobulin and β-2-microglobulin), enzymes and enzyme inhibitors (e.g., plasminogen, lysozyme, cystatin C, alpha-1-antitrypsin and pancreatic trypsin inhibitor), proteins of the immune system, such as immunoglobulin proteins (e.g., IgA, IgD, IgE, IgG, IgM, immunoglobulin light chains (kappa/lambda)), transport proteins (e.g., retinol binding protein, α-1 microglobulin), defensins (e.g., beta-defensin 1, neutrophil defensin 1, neutrophil defensin 2 and neutrophil defensin 3) and the like.

Suitable proteins found at the blood brain barrier or in neural tissue include, for example, melanocortin receptor, myelin, ascorbate transporter and the like.

Suitable polypeptides that enhances serum half-life in vivo also include proteins localized to the kidney (e.g., polycystin, type IV collagen, organic anion transporter K1, Heymann's antigen), proteins localized to the liver (e.g., alcohol dehydrogenase, G250), proteins localized to the lung (e.g., secretory component, which binds IgA), proteins localized to the heart (e.g., HSP 27, which is associated with dilated cardiomyopathy), proteins localized to the skin (e.g., keratin), bone specific proteins such as morphogenic proteins (BMPs), which are a subset of the transforming growth factor β superfamily of proteins that demonstrate osteogenic activity (e.g., BMP-2, BMP-4, BMP-5, BMP-6, BMP-7, BMP-8), tumor specific proteins (e.g., trophoblast antigen, herceptin receptor, oestrogen receptor, cathepsins (e.g., cathepsin B, which can be found in liver and spleen)).

Suitable disease-specific proteins include, for example, antigens expressed only on activated T-cells, including LAG-3 (lymphocyte activation gene), osteoprotegerin ligand (OPGL; see *Nature* 402, 304-309 (1999)), OX40 (a member of the TNF receptor family, expressed on activated T cells and specifically up-regulated in human T cell leukemia virus type-I (HTLV-I)-producing cells; see *Immunol.* 165 (1):263-70 (2000)). Suitable disease-specific proteins also include, for example, metalloproteases (associated with arthritis/cancers) including CG6512 *Drosophila*, human paraplegin, human FtsH, human AFG3L2, murine ftsH; and angiogenic growth factors, including acidic fibroblast growth factor (FGF-1), basic fibroblast growth factor (FGF-2), vascular endothelial growth factor/vascular permeability factor (VEGF/VPF), transforming growth factor-α (TGF α), tumor necrosis factor-alpha (TNF-α), angiogenin, interleukin-3 (IL-3), interleukin-8 (IL-8), platelet-derived endothelial growth factor (PD-ECGF), placental growth factor (P1GF), midkine platelet-derived growth factor-BB (PDGF), and fractalkine.

Suitable polypeptides that enhance serum half-life in vivo also include stress proteins such as heat shock proteins (HSPs). HSPs are normally found intracellularly. When they are found extracellularly, it is an indicator that a cell has died and spilled out its contents. This unprogrammed cell death (necrosis) occurs when as a result of trauma, disease or injury, extracellular HSPs trigger a response from the immune system. Binding to extracellular HSP can result in localizing the compositions of the invention to a disease site.

Suitable proteins involved in Fc transport include, for example, Brambell receptor (also known as FcRB). This Fc receptor has two functions, both of which are potentially useful for delivery. The functions are (1) transport of IgG from mother to child across the placenta (2) protection of IgG from degradation thereby prolonging its serum half-life. It is thought that the receptor recycles IgG from endosomes. (See, Holliger et al, *Nat Biotechnol* 15(7):632-6 (1997).)

Methods for pharmacokinetic analysis and determination of ligand half-life will be familiar to those skilled in the art. Details may be found in Kenneth, A et al: Chemical Stability of Pharmaceuticals: A Handbook for Pharmacists and in Peters et al, Pharmacokinetc analysis: A Practical Approach (1996). Reference is also made to "Pharmacokinetics", M Gibaldi & D Perron, published by Marcel Dekker, $2^{nd}$ Rev. ex edition (1982), which describes pharmacokinetic parameters such as t alpha and t beta half lives and area under the curve (AUC).

Ligands the Contain a Toxin Moiety or Toxin

The invention also relates to ligands that comprise a toxin moiety or toxin. Suitable toxin moieties comprise a toxin (e.g., surface active toxin, cytotoxin). The toxin moiety or toxin can be linked or conjugated to the ligand using any suitable method. For example, the toxin moiety or toxin can be covalently bonded to the ligand directly or through a suitable linker. Suitable linkers can include noncleavable or cleavable linkers, for example, pH cleavable linkers that comprise a cleavage site for a cellular enzyme (e.g., cellular esterases, cellular proteases such as cathepsin B). Such cleavable linkers can be used to prepare a ligand that can release a toxin moiety or toxin after the ligand is internalized.

A variety of methods for linking or conjugating a toxin moiety or toxin to a ligand can be used. The particular method selected will depend on the toxin moiety or toxin and ligand to be linked or conjugated. If desired, linkers that contain terminal functional groups can be used to link the ligand and toxin moiety or toxin. Generally, conjugation is accomplished by reacting toxin moiety or toxin that contains a reactive functional group (or is modified to contain a reactive functional group) with a linker or directly with a ligand. Covalent bonds formed by reacting an toxin moiety or toxin that contains (or is modified to contain) a chemical moiety or functional group that can, under appropriate conditions, react with a second chemical group thereby forming a covalent bond. If desired, a suitable reactive chemical group can be added to ligand or to a linker using any suitable method. (See, e.g., Hermanson, G. T., *Bioconjugate Techniques*, Academic Press: San Diego, Calif. (1996).) Many suitable reactive chemical group combinations are known in the art, for example an amine group can react with an electrophilic group such as tosylate, mesylate, halo (chloro, bromo, fluoro, iodo), N-hydroxysuccinimidyl ester (NHS), and the like. Thiols can react with maleimide, iodoacetyl, acrylolyl, pyridyl disulfides, 5-thiol-2-nitrobenzoic acid thiol (TNB-thiol), and the like. An aldehyde functional group can be coupled to amine- or hydrazide-containing molecules, and an azide group can react with a trivalent phosphorous group to form phosphoramidate or phosphorimide linkages. Suitable methods to introduce activating groups into molecules are known in the art (see for example, Hermanson, G. T., *Bioconjugate Techniques*, Academic Press: San Diego, Calif. (1996)).

Suitable toxin moieties and toxins include, for example, a maytansinoid (e.g., maytansinol, e.g., DM1, DM4), a taxane, a calicheamicin, a duocarmycin, or derivatives thereof. The maytansinoid can be, for example, maytansinol or a maytansinol analogue. Examples of maytansinol analogues include those having a modified aromatic ring (e.g., C-19-decloro, C-20-demethoxy, C-20-acyloxy) and those having modifications at other positions (e.g., C-9-CH, C-14-alkoxymethyl, C-14-hydroxymethyl or aceloxymethyl, C-15-hydroxy/acyloxy, C-15-methoxy, C-18-N-demethyl, 4,5-deoxy). Maytansinol and maytansinol analogues are described, for example, in U.S. Pat. Nos. 5,208,020 and 6,333,410, the contents of which is incorporated herein by reference. Maytansinol can be coupled to antibodies and antibody fragmetns using, e.g., an N-succinimidyl 3-(2-pyridyldithio)proprionate (also known as N-succinimidyl 4-(2-pyridyldithio)pentanoate or SPP), 4-succinimidyl-oxycarbonyl-a-(2-pyridyldithio)-toluene (SMPT), N-succinimidyl-3-(2-pyridyldithio)butyrate (SDPB), 2 iminothiolane, or S-acetylsuccinic anhydride. The taxane can be, for example, a taxol, taxotere, or novel taxane (see, e.g., WO 01/38318). The calicheamicin can be, for example, a bromo-complex calicheamicin (e.g., an alpha, beta or gamma bromo-complex), an iodo-complex calicheamicin (e.g., an alpha, beta or gamma iodo-complex), or analogs and mimics thereof. Bromo-complex calicheamicins include I1-BR, I2-BR, I3-BR, I4-BR, J1-BR, J2-BR and K1-BR. Iodo-complex calicheamicins include I1-I, I2-I, I3-I, J1-I, J2-I, L1-I and K1-BR. Calicheamicin and mutants, analogs and mimics thereof are described, for example, in U.S. Pat. Nos. 4,970, 198; 5,264,586; 5,550,246; 5,712,374, and 5,714,586, the contents of each of which are incorporated herein by reference. Duocarmycin analogs (e.g., KW-2189, DC88, DC89 CBI-TMI, and derivatives thereof are described, for example, in U.S. Pat. No. 5,070,092, U.S. Pat. No. 5,187,186, U.S. Pat. No. 5,641,780, U.S. Pat. No. 5,641,780, U.S. Pat. No. 4,923, 990, and U.S. Pat. No. 5,101,038, the contents of each of which are incorporated herein by reference.

Examples of other toxins include, but are not limited to antimetabolites (e.g., methotrexate, 6-mercaptopurine, 6-thioguanine, cytarabine, 5-fluorouracil decarbazine), alkylating agents (e.g., mechlorethamine, thioepa chlorambucil, CC-1065 (see U.S. Pat. Nos. 5,475,092, 5,585,499, 5,846, 545), melphalan, carmustine (BSNU) and lomustine (CCNU), cyclophosphamide, busulfan, dibromomannitol, streptozotocin, mitomycin C, and cis-dichlorodiamine platinum(II)(DDP)cisplatin), anthracyclines (e.g., daunorubicin (formerly daunomycin) and doxorubicin), antibiotics (e.g., dactinomycin (formerly actinomycin), bleomycin, mithramycin, mitomycin, puromycin anthramycin (AMC)), duocarmycin and analogs or derivatives thereof, and anti-mitotic agents (e.g., vincristine, vinblastine, taxol, auristatins (e.g., auristatin E) and maytansinoids, and analogs or homologs thereof.

The toxin can also be a surface active toxin, such as a toxin that is a free radical generator (e.g. selenium containing toxin moieties), or radionuclide containing moiety. Suitable radio-nuclide containing moieties, include for example, moieties that contain radioactive iodine ($^{131}$I or $^{125}$I), yttrium ($^{90}$Y), lutetium ($^{177}$Lu), actinium ($^{25}$Ac), praseodymium, astatine ($^{211}$At), rhenium ($^{186}$Re), bismuth ($^{212}$Bi or $^{213}$Bi), indium ($^{111}$In), technetium ($^{99}$mTc), phosphorus ($^{32}$P), rhodium ($^{188}$Rh), sulfur ($^{35}$S), carbon ($^{14}$C), tritium ($^3$H), chromium ($^{51}$Cr), chlorine ($^{36}$Cl), cobalt ($^{57}$Co or $^{58}$Co), iron ($^{59}$Fe), selenium ($^{75}$Se), or gallium ($^{67}$Ga).

The toxin can be a protein, polypeptide or peptide, from bacterial sources, e.g., diphtheria toxin, pseudomonas exotoxin (PE) and plant proteins, e.g., the A chain of ricin (RTA), the ribosome inactivating proteins (RIPs) gelonin, pokeweed antiviral protein, saporin, and dodecandron are contemplated for use as toxins.

Antisense compounds of nucleic acids designed to bind, disable, promote degradation or prevent the production of the mRNA responsible for generating a particular target protein can also be used as a toxin. Antisense compounds include antisense RNA or DNA, single or double stranded, oligonucleotides, or their analogs, which can hybridize specifically to individual mRNA species and prevent transcription and/or RNA processing of the mRNA species and/or translation of the encoded polypeptide and thereby effect a reduction in the amount of the respective encoded polypeptide. Ching, et al., *Proc. Natl. Acad. Sci. U.S.A.* 86: 10006-10010 (1989); Broder, et al., *Ann. Int. Med.* 113: 604-618 (1990); Loreau, et al., *FEBS Letters* 274: 53-56 (1990); Useful antisense therapeutics include for example: Veglin™ (VasGene) and OGX-011 (Oncogenix).

Toxins can also be photoactive agents. Suitable photoactive agents include porphyrin-based materials such as porfimer sodium, the green porphyrins, chlorin E6, hematoporphyrin derivative itself, phthalocyanines, etiopurpurins, texaphrin, and the like.

The toxin can be an antibody or antibody fragment that binds an intracellulare target, such as a dAb that binds an intracellular target (an intrabody). Such antibodies or antibody fragments (dAbs) can be directed to defined subcellular compartments or targets. For example, the antibodies or antibody fragments (dAbs) can bin an intracellular target selected from erbB2, EGFR, BCR-ABL, p21Ras, Caspase3, Caspase7, Bcl-2, p53, Cyclin E, ATF-1/CREB, HPV16 E7, HP1, Type IV collagenases, cathepsin L as well as others described in Kontermann, R. E., Methods, 34:163-170 (2004), incorporated herein by reference in its entirety.

Polypeptide Domains that Bind VEGF

The invention provides polypeptide domains (e.g., immunoglobuline single variable domains, dAb monomers) that have a binding site with binding specificity for VEGF. In preferred embodiments, the polypeptide domain (e.g., dAb) binds to VEGF with an affinity (KD; KD=$K_{off}$(kd)/$K_{on}$(ka)) of 300 nM to 1 pM (ie, $3\times10^{-7}$ to $5\times10^{-12}$M), preferably 50 nM to 1 pM, more preferably 5 nM to 1 pM and most preferably 1 nM to 1 pM, for example and $K_D$ of $1\times10^{-7}$ M or less, preferably $1\times10^{-8}$ M or less, more preferably $1\times10^{-9}$ M or less, advantageously $1\times10^{-10}$ M or less and most preferably $1\times10^{-11}$ M or less; and/or a $K_{off}$ rate constant of $5\times10^{-1}$ s$^{-1}$ to $1\times10^{-7}$ s$^{-1}$, preferably $1\times10^{-2}$ s$^{-1}$ to $1\times10^{-6}$ s$^{-1}$, more preferably $5\times10^{-3}$ s$^{-1}$ to $1\times10^{-5}$ s$^{-1}$, for example $5\times10^{-1}$ s$^{-1}$ or less, preferably $1\times10^{-2}$ s$^{-1}$ or less, advantageously $1\times10^{-3}$ s$^{-1}$ or less, more preferably $1\times10^{-4}$ s$^{-1}$ or less, still more preferably $1\times10^{-5}$ s$^{-1}$ or less, and most preferably $1\times10^{-6}$ s$^{-1}$ or less as determined by surface plasmon resonance.

In some embodiments, the polypeptide domain that has a binding site with binding specificity for VEGF competes for binding to VEGF with a dAb selected from the group consisting of TAR15-1 (SEQ ID NO:100), TAR15-3 (SEQ ID NO:101), TAR15-4 (SEQ ID NO:102), TAR15-9 (SEQ ID NO:103), TAR15-10 (SEQ ID NO:104), TAR15-11 (SEQ ID NO:105), TAR15-12 (SEQ ID NO:106), TAR15-13 (SEQ ID NO:107), TAR15-14 (SEQ ID NO:108), TAR15-15 (SEQ ID NO:109), TAR15-16 (SEQ ID NO:110), TAR15-17 (SEQ ID NO:111), TAR15-18 (SEQ ID NO:112), TAR15-19 (SEQ ID NO:113), TAR15-20 (SEQ ID NO:114), TAR15-22 (SEQ ID NO:115), TAR15-5 (SEQ ID NO:116), TAR15-6 (SEQ ID NO:117), TAR15-7 (SEQ ID NO:118), TAR15-8 (SEQ ID NO:119), TAR15-23 (SEQ ID NO:120), TAR15-24 (SEQ ID NO:121), TAR15-25 (SEQ ID NO:122), TAR15-26 (SEQ ID NO:123), TAR15-27 (SEQ ID NO:124), TAR15-29 (SEQ ID NO:125), TAR15-30 (SEQ ID NO:126), TAR15-6-500 (SEQ ID NO:127), TAR15-6-501 (SEQ ID NO:128), TAR15-6-502 (SEQ ID NO:129), TAR15-6-503 (SEQ ID NO:130), TAR15-6-504 (SEQ ID NO:131), TAR15-6-505 (SEQ ID NO:132), TAR15-6-506 (SEQ ID NO:133), TAR15-6-507 (SEQ ID NO:134), TAR15-6-508 (SEQ ID NO:135), TAR15-6-509 (SEQ ID NO:136), TAR15-6-510 (SEQ ID NO:137), TAR15-8-500 (SEQ ID NO:138), TAR15-8-501 (SEQ ID NO:139), TAR15-8-502 (SEQ ID NO:140), TAR15-8-503 (SEQ ID NO:141), TAR15-8-505 (SEQ ID NO:142), TAR15-8-506 (SEQ ID NO:143), TAR15-8-507 (SEQ ID NO:144), TAR15-8-508 (SEQ ID NO:145), TAR15-8-509 (SEQ ID NO:146), TAR15-8-510 (SEQ ID NO:147), TAR15-8-511 (SEQ ID NO:148), TAR15-26-500 (SEQ ID NO:149), TAR15-26-501 (SEQ ID NO:150), TAR15-26-502 (SEQ ID NO:151), TAR15-26-503 (SEQ ID NO:152), TAR15-26-504 (SEQ ID NO:153), TAR15-26-505 (SEQ ID NO:154), TAR15-26-506 (SEQ ID NO:155), TAR15-26-507 (SEQ ID NO:156), TAR15-26-508 (SEQ ID NO:157), TAR15-26-509 (SEQ ID NO:158), TAR15-26-510 (SEQ ID NO:159), TAR15-26-511 (SEQ ID NO:160), TAR15-26-512 (SEQ ID NO:161), TAR15-26-513 (SEQ ID NO:162), TAR15-26-514 (SEQ ID NO:163), TAR15-26-515 (SEQ ID NO:164), TAR15-26-516 (SEQ ID NO:165), TAR15-26-517 (SEQ ID NO:166), TAR15-26-518 (SEQ ID NO:167), TAR15-26-519 (SEQ ID NO:168), TAR15-26-520 (SEQ ID NO:169), TAR15-26-521 (SEQ ID NO:170), TAR15-26-522 (SEQ ID NO:171), TAR15-26-523 (SEQ ID NO:172), TAR15-26-524 (SEQ ID NO:173), TAR15-26-525 (SEQ ID NO:174), TAR15-26-526 (SEQ ID NO:175), TAR15-26-527 (SEQ ID NO:176), TAR15-26-528 (SEQ ID NO:177), TAR15-26-529 (SEQ ID NO:178), TAR15-26-530 (SEQ ID NO:179), TAR15-26-531 (SEQ ID NO:180), TAR15-26-532 (SEQ ID NO:181), TAR15-26-533 (SEQ ID NO:182), TAR15-26-534 (SEQ ID NO:183), TAR15-26-535 (SEQ ID NO:184), TAR15-26-536 (SEQ ID NO:185), TAR15-26-537 (SEQ ID NO:186), TAR15-26-538 (SEQ ID NO:187), TAR15-26-539 (SEQ ID NO:188), TAR15-26-540 (SEQ ID NO:189), TAR15-26-541 (SEQ ID NO:190), TAR15-26-542 (SEQ ID NO:191), TAR15-26-543 (SEQ ID NO:192), TAR15-26-544 (SEQ ID NO:193), TAR15-26-545 (SEQ ID NO:194), TAR15-26-546 (SEQ ID NO:195), TAR15-26-547 (SEQ ID NO:196), TAR15-26-548 (SEQ ID NO:197), TAR15-26-549 (SEQ ID NO:198), TAR15-26-550 (SEQ ID NO:539), and TAR15-26-551 (SEQ ID NO:540).

In some embodiments, the polypeptide domain that has a binding site with binding specificity for VEGF comprises an amino acid sequence that has at least about 80%, at least about 85%, at least about 90%, at least about 91%, at least about 92%, at least about 93%, at least about 94%, at least about 95%, at least about 96%, at least about 97%, at least about 98%, or at least about 99% amino acid sequence identity with the amino acid sequence or a dAb selected from the group consisting of TAR15-1 (SEQ ID NO:100), TAR15-3 (SEQ ID NO:101), TAR15-4 (SEQ ID NO:102), TAR15-9 (SEQ ID NO:103), TAR15-10 (SEQ ID NO:104), TAR15-11 (SEQ ID NO:105), TAR15-12 (SEQ ID NO:106), TAR15-13 (SEQ ID NO:107), TAR15-14 (SEQ ID NO:108), TAR15-15 (SEQ ID NO:109), TAR15-16 (SEQ ID NO:110), TAR15-17 (SEQ ID NO:111), TAR15-18 (SEQ ID NO:112), TAR15-19 (SEQ ID NO:113), TAR15-20 (SEQ ID NO:114), TAR15-22 (SEQ ID NO:115), TAR15-5 (SEQ ID NO:116), TAR15-6 (SEQ ID NO:117), TAR15-7 (SEQ ID NO:118), TAR15-8 (SEQ ID NO:119), TAR15-23 (SEQ ID NO:120), TAR15-24 (SEQ ID NO:121), TAR15-25 (SEQ ID NO:122), TAR15-26 (SEQ ID NO:123), TAR15-27 (SEQ ID NO:124), TAR15-29 (SEQ ID NO:125), TAR15-30 (SEQ ID NO:126), TAR15-6-500 (SEQ ID NO:127), TAR15-6-501 (SEQ ID NO:128), TAR15-6-502 (SEQ ID NO:129), TAR15-6-503 (SEQ ID NO:130), TAR15-6-504 (SEQ ID NO:131), TAR15-6-505 (SEQ ID NO:132), TAR15-6-506 (SEQ ID NO:133), TAR15-6-507 (SEQ ID NO:134), TAR15-6-508 (SEQ ID NO:135), TAR15-6-509 (SEQ ID NO:136), TAR15-6-510 (SEQ ID NO:137), TAR15-8-500 (SEQ ID NO:138), TAR15-8-501 (SEQ ID NO:139), TAR15-8-502 (SEQ ID NO:140), TAR15-8-503 (SEQ ID NO:141), TAR15-8-505 (SEQ ID NO:142), TAR15-8-506 (SEQ ID NO:143), TAR15-8-507 (SEQ ID NO:144), TAR15-8-508 (SEQ ID NO:145), TAR15-8-509 (SEQ ID NO:146), TAR15-8-510 (SEQ ID NO:147), TAR15-8-511 (SEQ ID NO:148), TAR15-26-500 (SEQ ID NO:149), TAR5-26-501 (SEQ ID NO:150), TAR15-26-502 (SEQ ID NO:151), TAR15-26-503 (SEQ ID NO:152), TAR15-26-504 (SEQ ID NO:153), TAR15-26-505 (SEQ ID NO:154), TAR15-26-506 (SEQ ID NO:155), TAR15-26-507 (SEQ ID NO:156), TAR15-26-508 (SEQ ID NO:157), TAR15-26-509 (SEQ ID NO:158), TAR15-26-510 (SEQ ID NO:159), TAR15-26-511 (SEQ ID NO:160), TAR15-26-512 (SEQ ID NO:161), TAR15-26-513 (SEQ ID NO:162), TAR15-26-514 (SEQ ID NO:163), TAR15-26-515 (SEQ ID NO:164), TAR15-26-516 (SEQ ID NO:165), TAR15-26-517 (SEQ ID NO:166), TAR15-26-518 (SEQ ID NO:167), TAR15-26-519 (SEQ ID NO:168), TAR15-26-520 (SEQ ID NO:169), TAR15-26-521 (SEQ ID NO:170), TAR15-26-522 (SEQ ID NO:171), TAR15-26-523 (SEQ ID NO:172), TAR15-26-524 (SEQ ID NO:173), TAR15-26-525 (SEQ ID NO:174), TAR15-26-526 (SEQ ID NO:175), TAR15-26-527 (SEQ ID NO:176), TAR15-26-528 (SEQ ID NO:177), TAR15-26-529 (SEQ ID NO:178), TAR15-26-530 (SEQ ID NO:179), TAR15-26-531 (SEQ ID NO:180), TAR15-26-532 (SEQ ID NO:181), TAR15-26-533 (SEQ ID NO:182), TAR15-26-534 (SEQ ID NO:183), TAR15-26-535 (SEQ ID NO:184), TAR15-26-536 (SEQ ID NO:185), TAR15-26-537 (SEQ ID NO:186), TAR15-26-538 (SEQ ID NO:187), TAR15-26-539 (SEQ ID NO:188), TAR15-26-540 (SEQ ID NO:189), TAR15-26-541 (SEQ ID NO:190), TAR15-26-542 (SEQ ID NO:191), TAR15-26-543 (SEQ ID NO:192), TAR15-26-544 (SEQ ID NO:193), TAR15-26-545 (SEQ ID NO:194), TAR15-26-546 (SEQ ID NO:195), TAR15-26-547 (SEQ ID NO:196), TAR15-26-548 (SEQ ID NO:197), TAR15-26-549 (SEQ ID NO:198), TAR15-26-550 (SEQ ID NO:539), and TAR15-26-551 (SEQ ID NO:540).

In preferred embodiments, the polypeptide domain that has a binding site with binding specificity for VEGF comprises an amino acid sequence that has at least about 90%, at least about 91%, at least about 92%, at least about 93%, at least about 94%, at least about 95%, at least about 96%, at least about 97%, at least about 98%, or at least about 99% amino acid sequence identity with the amino acid sequence or a dAb selected from the group consisting of TAR15-6 (SEQ ID NO:117), TAR15-8 (SEQ ID NO:119), and TAR15-26 (SEQ ID NO:123). For example, the polypeptide domain that has a binding site with binding specificity for VEGF can comprise TAR15-6 (SEQ ID NO:117), TAR15-8 (SEQ ID NO:119), or TAR15-26 (SEQ ID NO:123).

In some embodiments, the polypeptide domain that has a binding site with binding specificity for VEGF competes with any of the dAbs disclosed herein for binding to VEGF.

Preferably the polypeptide domain that has a binding site with binding specificity for VEGF is an immunoglobuline single variable domain. The polypeptide domain that has a binding site with binding specificity for VEGF can comprise any suitable immunoglobulin variable domain, and preferably comprises a human variable domain or a variable domain that comprises human framework regions. In certain embodiments, the polypeptide domain that has a binding site with binding specificity for VEGF comprises a universal framework, as described herein.

The universal framework can be a $V_L$ framework (Vλ or Vκ), such as a framework that comprises the framework amino acid sequences encoded by the human germline DPK1, DPK2, DPK3, DPK4, DPK5, DPK6, DPK7, DPK8, DPK9, DPK10, DPK12, DPK13, DPK15, DPK16, DPK18, DPK19, DPK20, DPK21, DPK22, DPK23, DPK24, DPK25, DPK26 or DPK 28 immunoglobulin gene segment. If desired, the $V_L$ framework can further comprises the framework amino acid sequence encoded by the human germline $J_κ1$, $J_κ2$, $J_κ3$, $J_κ4$, or $J_κ5$ immunoglobulin gene segment.

In other embodiments the universal framework can be a $V_H$ framework, such as a framework that comprises the framework amino acid sequences encoded by the human germline DP4, DP7, DP8, DP9, DP10, DP31, DP33, DP38, DP45, DP46, DP47, DP49, DP50, DP51, DP53, DP54, DP65, DP66, DP67, DP68 or DP69 immunoglobulin gene segment. If desired, the $V_H$ framework can further comprises the framework amino acid sequence encoded by the human germline $J_H1$, $J_H2$, $J_H3$, $J_H4$, $J_H4b$, $J_H5$ and $J_H6$ immunoglobulin gene segment.

In certain embodiments, the polypeptide domain that has a binding site with binding specificity for VEGF comprises one or more framework regions comprising an amino acid sequence that is the same as the amino acid sequence of a corresponding framework region encoded by a human germline antibody gene segment, or the amino acid sequences of one or more of said framework regions collectively comprise up to 5 amino acid differences relative to the amino acid sequence of said corresponding framework region encoded by a human germline antibody gene segment.

In other embodiments, the amino acid sequences of FW1, FW2, FW3 and FW4 of the polypeptide domain that has a binding site with binding specificity for VEGF are the same as the amino acid sequences of corresponding framework regions encoded by a human germline antibody gene segment, or the amino acid sequences of FW1, FW2, FW3 and FW4 collectively contain up to 10 amino acid differences relative to the amino acid sequences of corresponding framework regions encoded by said human germline antibody gene segment.

In other embodiments, the polypeptide domain that has a binding site with binding specificity for VEGF comprises FW1, FW2 and FW3 regions, and the amino acid sequence of said FW1, FW2 and FW3 regions are the same as the amino acid sequences of corresponding framework regions encoded by human germline antibody gene segments.

In particular embodiments, the polypeptide domain that has a binding site with binding specificity for VEGF comprises the DPK9 $V_L$ framework, or a $V_H$ framework selected from the group consisting of DP47, DP45 and DP38. The polypeptide domain that has a binding site with binding specificity for VEGF can comprises a binding site for a generic ligand, such as protein A, protein L and protein G.

In certain embodiments, the polypeptide domain that has a binding site with binding specificity for VEGF is substantially resistant to aggregation. For example, in some embodiments, less than about 10%, less than about 9%, less than about 8%, less than about 7%, less than about 6%, less than about 5%, less than about 4%, less than about 3%, less than about 2% or less than about 1% of the polypeptide domain that has a binding site with binding specificity for VEGF aggregates when a 1-5 mg/ml, 5-10 mg/ml, 10-20 mg/ml, 20-50 mg/ml, 50-100 mg/ml, 100-200 mg/ml or 200-500 mg/ml solution of ligand or dAb in a solvent that is routinely used for drug formulation such as saline, buffered saline, citrate buffer saline, water, an emulsion, and, any of these solvents with an acceptable excipient such as those approved by the FDA, is maintained at about 22° C., 22-25° C., 25-30° C., 30-37° C., 37-40° C., 40-50° C., 50-60° C., 60-70° C., 70-80° C., 15-20° C., 10-15° C., 5-10° C., 2-5° C., 0-2° C., –10° C. to 0° C., –20° C. to –10° C., –40° C. to –20° C., –60° C. to –40° C., or –80° C. to –60° C., for a period of about time, for example, 10 minutes, 1 hour, 8 hours, 24 hours, 2 days, 3 days, 4 days, 1 week, 2 weeks, 3 weeks, 1 month, 2 months, 3 months, 4 months, 6 months, 1 year, or 2 years.

Aggregation can be assessed using any suitable method, such as, by microscopy, assessing turbidity of a solution by visual inspection or spectroscopy or any other suitable method. Preferably, aggregation is assessed by dynamic light scattering. Polypeptide domains that have a binding site with binding specificity for VEGF that are resistant to aggregation provide several advantages. For example, such polypeptide domains that have a binding site with binding specificity for VEGF can readily be produced in high yield as soluble proteins by expression using a suitable biological production system, such as $E.\ coli$, and can be formulated and/or stored at higher concentrations than conventional polypeptides, and with less aggregation and loss of activity.

In addition, the polypeptide domain that has a binding site with binding specificity for VEGF that are resistant to aggregation can be produced more economically than other antigen- or epitope-binding polypeptides (e.g., conventional antibodies). For example, generally, preparation of antigen- or epitope-binding polypeptides intended for in vivo applications includes processes (e.g., gel filtration) that remove aggregated polypeptides. Failure to remove such aggregates can result in a preparation that is not suitable for in vivo applications because, for example, aggregates of an antigen-binding polypeptide that is intended to act as an antagonist can function as an agonist by inducing cross-linking or clustering of the target antigen. Protein aggregates can also reduce the efficacy of therapeutic polypeptide by inducing an immune response in the subject to which they are administered.

In contrast, the aggregation resistant polypeptide domain that has a binding site with binding specificity for VEGF of the invention can be prepared for in vivo applications without the need to include process steps that remove aggregates, and can be used in vivo applications without the aforementioned disadvantages caused by polypeptide aggregates.

In some embodiments, polypeptide domain that has a binding site with binding specificity for VEGF unfolds reversibly when heated to a temperature (Ts) and cooled to a temperature (Tc), wherein Ts is greater than the melting temperature (Tm) of the polypeptide domain that has a binding site with binding specificity for VEGF, and Tc is lower than the melting temperature of the polypeptide domain that has a binding site with binding specificity for VEGF. For example, polypeptide domain that has a binding site with binding specificity for VEGF can unfold reversibly when heated to 80° C. and cooled to about room temperature. A polypeptide that unfolds reversibly loses function when unfolded but regains function upon refolding. Such polypeptides are distinguished from polypeptides that aggregate when unfolded or that improperly refold (misfolded polypeptides), i.e., do not regain function.

Polypeptide unfolding and refolding can be assessed, for example, by directly or indirectly detecting polypeptide structure using any suitable method. For example, polypeptide structure can be detected by circular dichroism (CD) (e.g., far-UV CD, near-UV CD), fluorescence (e.g., fluorescence of tryptophan side chains), susceptibility to proteolysis, nuclear magnetic resonance (NMR), or by detecting or measuring a polypeptide function that is dependent upon proper folding (e.g., binding to target ligand, binding to generic ligand). In one example, polypeptide unfolding is assessed using a functional assay in which loss of binding function (e.g., binding a generic and/or target ligand, binding a substrate) indicates that the polypeptide is unfolded.

The extent of unfolding and refolding of a polypeptide domain that has a binding site with binding specificity for VEGF can be determined using an unfolding or denaturation curve. An unfolding curve can be produced by plotting temperature as the ordinate and the relative concentration of folded polypeptide as the abscissa. The relative concentration of folded polypeptide domain that has a binding site with binding specificity for VEGF can be determined directly or indirectly using any suitable method (e.g., CD, fluorescence, binding assay). For example, a polypeptide domain that has a binding site with binding specificity for VEGF solution can be prepared and ellipticity of the solution determined by CD. The ellipticity value obtained represents a relative concentration of folded ligand or dAb monomer of 100%. The polypeptide domain that has a binding site with binding specificity for VEGF in the solution is then unfolded by incrementally raising the temperature of the solution and ellipticity is determined at suitable increments (e.g., after each increase of one degree in temperature). The polypeptide domain that has a binding site with binding specificity for VEGF in solution is then refolded by incrementally reducing the temperature of the solution and ellipticity is determined at suitable increments. The data can be plotted to produce an unfolding curve and a refolding curve. The unfolding and refolding curves have a characteristic sigmoidal shape that includes a portion in which the polypeptide domain that has a binding site with binding specificity for VEGF molecules are folded, an unfolding/refolding transition in which polypeptide domain that has a binding site with binding specificity for VEGF molecules are unfolded to various degrees, and a portion in which polypeptide domain that has a binding site with binding specificity for VEGF are unfolded. The y-axis intercept of the refolding curve is the relative amount of refolded polypeptide domain that has a binding site with binding specificity for VEGF recovered. A recovery of at least about 50%, or at least about 60%, or at least about 70%, or at least about 75%, or at least about 80%, or at least about 85%, or at least about 90%, or at least about 95% is indicative that the ligand or dAb monomer unfolds reversibly.

In a preferred embodiment, reversibility of unfolding of polypeptide domain that has a binding site with binding specificity for VEGF is determined by preparing a polypeptide domain that has a binding site with binding specificity for VEGF solution and plotting heat unfolding and refolding curves. The polypeptide domain that has a binding site with binding specificity for VEGF solution can be prepared in any suitable solvent, such as an aqueous buffer that has a pH suitable to allow polypeptide domain that has a binding site with binding specificity for VEGF to dissolve (e.g., pH that is about 3 units above or below the isoelectric point (pI)). The polypeptide domain that has a binding site with binding specificity for VEGF solution is concentrated enough to allow unfolding/folding to be detected. For example, the ligand or dAb monomer solution can be about 0.1 µM to about 100 µM, or preferably about 1 µM to about 10 µM.

If the melting temperature (Tm) of polypeptide domain that has a binding site with binding specificity for VEGF is known, the solution can be heated to about ten degrees below the Tm (Tm−10) and folding assessed by ellipticity or fluorescence (e.g., far-UV CD scan from 200 nm to 250 nm, fixed wavelength CD at 235 nm or 225 nm; tryptophan fluorescent emission spectra at 300 to 450 nm with excitation at 298 nm) to provide 100% relative folded ligand or dAb monomer. The solution is then heated to at least ten degrees above Tm (Tm+10) in predetermined increments (e.g., increases of about 0.1 to about 1 degree), and ellipticity or fluorescence is determined at each increment. Then, the polypeptide domain that has a binding site with binding specificity for VEGF is refolded by cooling to at least Tm−10 in predetermined increments and ellipticity or fluorescence determined at each increment. If the melting temperature of polypeptide domain that has a binding site with binding specificity for VEGF is not known, the solution can be unfolded by incrementally heating from about 25° C. to about 100° C. and then refolded by incrementally cooling to at least about 25° C., and ellipticity or fluorescence at each heating and cooling increment is determined. The data obtained can be plotted to produce an unfolding curve and a refolding curve, in which the y-axis intercept of the refolding curve is the relative amount of refolded protein recovered. In some embodiments, the polypeptide domain that has a binding site with binding specificity for VEGF does not comprise a Camelid immunoglobulin variable domain, or one or more framework amino acids that are unique to immunoglobulin variable domains encoded by Camelid germline antibody gene segments.

Preferably, the polypeptide domain that has a binding site with binding specificity for VEGF is secreted in a quantity of at least about 0.5 mg/L when expressed in *E. coli* or in *Pichia* species (e.g., *P. pastoris*). In other preferred embodiments, polypeptide domain that has a binding site with binding specificity for VEGF is secreted in a quantity of at least about 0.75 mg/L, at least about 1 mg/L, at least about 4 mg/L, at least about 5 mg/L, at least about 10 mg/L, at least about 15 mg/L, at least about 20 mg/L, at least about 25 mg/L, at least about 30 mg/L, at least about 35 mg/L, at least about 40 mg/L, at least about 45 mg/L, or at least about 50 mg/L, or at least about 100 mg/L, or at least about 200 mg/L, or at least about 300 mg/L, or at least about 400 mg/L, or at least about 500 mg/L, or at least about 600 mg/L, or at least about 700 mg/L, or at least about 800 mg/L, at least about 900 mg/L, or at least about g/L when expressed in *E. coli* or in *Pichia* species (e.g., *P. pastoris*). In other preferred embodiments, polypeptide domain that has a binding site with binding specificity for VEGF is secreted in a quantity of at least about 1 mg/L to at least about 1 g/L, at least about 1 mg/L to at least about 750 mg/L, at least about 100 mg to at least about 1 g/L, at least about 200 mg/L to at least about 1 g/L, at least about 300 mg/L to at least about 1 g/L, at least about 400 mg/L to at least about 1 g/L, at least about 500 mg/L to at least about 1 g/L, at least about 600 mg/L to at least about 1 g/L, at least about 700 mg/L to at least about 1 g/L, at least about 800 mg/L to at least about 1 g/L, or at least about 900 mg/L to at least about 1 g/L when expressed in *E. coli* or in *Pichia* species (e.g., *P. pastoris*).

Although, polypeptide domain that has a binding site with binding specificity for VEGF described herein can be secretable when expressed in *E. coli* or in *Pichia* species (e.g., *P. pastoris*), they can be produced using any suitable method, such as synthetic chemical methods or biological production methods that do not employ *E. coli* or *Pichia* species.

Polypeptide Domains that Bind EGFR

The invention provides polypeptide domains (e.g., dAb) that has a binding site with binding specificity for EGFR. In preferred embodiments, the polypeptide domain (e.g., dAb) binds to EGFR with an affinity (KD; $KD=K_{off}(kd)/K_{on}(ka)$) of 300 nM to 1 pM (ie, $3\times10^{-7}$ to $5\times10^{-12}$M), preferably 100 nM to 1 pM, or 50 nM to 10 pM, more preferably 10 nM to 100 pM and most preferably about 1 nM, for example and $K_D$ of $1\times10^{-7}$ M or less, preferably $1\times10^{-8}$ M or less, more preferably about $1\times10^{-9}$ M or less, $1\times10^{-10}$ M or less or $1\times10^{-11}$ M or less; and/or a $K_{off}$ rate constant of $5\times10^{-1}$ $s^{-1}$ to $1\times10^{-7}$ $s^{-1}$, preferably $1\times10^{-2}$ $s^{-1}$ to $1\times10^{6}$ $s^{-1}$, more preferably $5\times10^{-3}$ $s^{-1}$ to $1\times10^{-5}$ $s^{-1}$, for example $5\times10^{-1}$ $s^{-1}$ or less, preferably $1\times10^{-2}$ $s^{-1}$ or less, advantageously $1\times10^{-3}$ $s^{-1}$ or less, more preferably $1\times10^{-4}$ $s^{-1}$ or less, still more preferably $1\times10^{-5}$ $s^{-1}$ or less, and most preferably $1\times10^{-6}$ $s^{-1}$ or less as determined by surface plasmon resonance.

In some embodiments, the a polypeptide domain that has a binding site with binding specificity for EGFR competes for binding to EGFR with a dAb selected from the group consisting of DOM16-17 (SEQ ID NO:325), DOM16-18 (SEQ ID NO:326); DOM16-19 (SEQ ID NO:327), DOM16-20 (SEQ ID NO:328), DOM16-21 (SEQ ID NO:329), DOM16-22 (SEQ ID NO:330), DOM16-23 (SEQ ID NO:331), DOM16-24 (SEQ ID NO:332), DOM16-25 (SEQ ID NO:333), DOM16-26 (SEQ ID NO:334), DOM16-27 (SEQ ID NO:335), DOM16-28 (SEQ ID NO:336), DOM16-29 (SEQ ID NO:337), DOM16-30 (SEQ ID NO:338), DOM16-31 (SEQ ID NO:339), DOM16-32 (SEQ ID NO:340), DOM16-33 (SEQ ID NO:341), DOM16-35 (SEQ ID NO:342), DOM16-37 (SEQ ID NO:343), DOM16-38 (SEQ ID NO:344), DOM16-39 (SEQ ID NO:345), DOM16-40 (SEQ ID NO:346), DOM16-41 (SEQ ID NO:347), DOM16-42 (SEQ ID NO:348), DOM16-43 (SEQ ID NO:349), DOM16-44 (SEQ ID NO:350), DOM16-45 (SEQ ID NO:351), DOM16-46 (SEQ ID NO:352), DOM16-47 (SEQ ID NO:353), DOM16-48 (SEQ ID NO:354), DOM16-49 (SEQ ID NO:355), DOM16-50 (SEQ ID NO:356), DOM16-59 (SEQ ID NO:357), DOM16-60 (SEQ ID NO:358), DOM16-61 (SEQ ID NO:359), DOM16-62 (SEQ ID NO:360), DOM16-63 (SEQ ID NO:361), DOM16-64 (SEQ ID NO:362), DOM16-65 (SEQ ID NO:363), DOM16-66 (SEQ ID NO:364), DOM16-67 (SEQ ID NO:365), DOM16-68 (SEQ ID NO:366), DOM16-69 (SEQ ID NO:367), DOM16-70 (SEQ ID NO:368), DOM16-71 (SEQ ID NO:369), DOM16-72 (SEQ ID NO:370), DOM16-73 (SEQ ID NO:371), DOM16-74 (SEQ ID NO:372), DOM16-75 (SEQ ID NO:373), DOM16-76 (SEQ ID NO:374), DOM16-77 (SEQ ID NO:375), DOM16-78 (SEQ ID NO:376), DOM16-79 (SEQ ID NO:377), DOM16-80 (SEQ ID NO:378), DOM16-81 (SEQ ID NO:379), DOM16-82 (SEQ ID NO:380), DOM16-83 (SEQ ID NO:381), DOM16-84 (SEQ ID NO:382), DOM16-85 (SEQ ID NO:383), DOM16-87 (SEQ ID NO:384), DOM16-88 (SEQ ID NO:385), DOM16-89 (SEQ ID NO:386), DOM16-90 (SEQ ID NO:387), DOM16-91 (SEQ ID NO:388), DOM16-92 (SEQ ID NO:389), DOM16-94 (SEQ ID NO:390), DOM16-95 (SEQ ID NO:391), DOM16-96 (SEQ ID NO:392), DOM16-97 (SEQ ID NO:393), DOM16-98 (SEQ ID NO:394), DOM16-99 (SEQ ID NO:395), DOM16-100 (SEQ ID NO:396), DOM16-101 (SEQ ID NO:397), DOM16-102 (SEQ ID NO:398), DOM16-103 (SEQ ID NO:399), DOM16-104 (SEQ ID NO:400), DOM16-105 (SEQ ID NO:401), DOM16-106 (SEQ ID NO:402), DOM16-107 (SEQ ID NO:403), DOM16-108 (SEQ ID NO:404), DOM16-109 (SEQ ID NO:405), DOM16-110 (SEQ ID NO:406), DOM16-111 (SEQ ID NO:407), DOM16-112 (SEQ ID NO:408), DOM16-113 (SEQ ID NO:409), DOM16-114 (SEQ ID NO:410), DOM16-115 (SEQ ID NO:411), DOM16-116 (SEQ ID NO:412), DOM16-117 (SEQ ID NO:413), DOM16-118 (SEQ ID NO:414), DOM16-119 (SEQ ID NO:415), DOM16-39-6 (SEQ ID NO:416), DOM16-39-8 (SEQ ID NO:417), DOM16-39-34 (SEQ ID NO:418), DOM16-39-48 (SEQ ID NO:419), DOM16-39-87 (SEQ ID NO:420), DOM16-39-90 (SEQ ID NO:421), DOM16-39-96 (SEQ ID NO:422), DOM16-39-100 (SEQ ID NO:423), DOM16-39-101 (SEQ ID NO:424), DOM16-39-102 (SEQ ID NO:425), DOM16-39-103 (SEQ ID NO:426), DOM16-39-104 (SEQ ID NO:427), DOM16-39-105 (SEQ ID NO:428), DOM16-39-106 (SEQ ID NO:429), DOM16-39-107 (SEQ ID NO:430), DOM16-39-108 (SEQ ID NO:431), DOM16-39-109 (SEQ ID NO:432), DOM16-39-110 (SEQ ID NO:433), DOM16-39-111 (SEQ ID NO:434), DOM16-39-112 (SEQ ID NO:435), DOM16-39-113 (SEQ ID NO:436), DOM16-39-114 (SEQ ID NO:437), DOM16-39-115 (SEQ ID NO:438), DOM16-39-116 (SEQ ID NO:439), DOM16-39-117 (SEQ ID NO:440), DOM16-39-200 (SEQ ID NO:441), DOM16-39-201 (SEQ ID NO:442), DOM16-39-202 (SEQ ID NO:443), DOM16-39-203 (SEQ ID NO:444), DOM16-39-204 (SEQ ID NO:445), DOM16-39-205 (SEQ ID NO:446), DOM16-39-206 (SEQ ID NO:447), DOM16-39-207 (SEQ ID NO:448), DOM16-39-209 (SEQ ID NO:449), DOM16-52 (SEQ ID NO:450), NB1 (SEQ ID NO:451), NB2 (SEQ ID NO:452), NB3 (SEQ ID NO:453), NB4 (SEQ ID NO:454), NB5 (SEQ ID NO:455), NB6 (SEQ ID NO:456), NB7 (SEQ ID NO:457), NB8 (SEQ ID NO:458), NB9 (SEQ ID NO:459), NB10 (SEQ ID NO:460), NB11 (SEQ ID NO:461), NB12 (SEQ ID NO:462), NB13 (SEQ ID NO:463), NB14 (SEQ ID NO:464), NB15 (SEQ ID NO:465), NB16 (SEQ ID NO:466), NB17 (SEQ ID NO:467), NB18 (SEQ ID NO:468), NB19 (SEQ ID NO:469), NB20 (SEQ ID NO:470), NB21 (SEQ ID NO:471), and NB22 (SEQ ID NO:472).

In some embodiments, the polypeptide domain that has a binding site with binding specificity for EGFR comprises an amino acid sequence that has at least about 80%, at least about 85%, at least about 90%, at least about 91%, at least about 92%, at least about 93%, at least about 94%, at least about 95%, at least about 96%, at least about 97%, at least about 98%, or at least about 99% amino acid sequence identity with the amino acid sequence or a dAb selected from the group consisting of DOM16-17 (SEQ ID NO:325), DOM16-18 (SEQ ID NO:326), DOM16-19 (SEQ ID NO:327), DOM16-20 (SEQ ID NO:328), DOM16-21 (SEQ ID NO:329), DOM16-22 (SEQ ID NO:330), DOM16-23 (SEQ ID NO:331), DOM16-24 (SEQ ID NO:332), DOM16-25 (SEQ ID NO:333), DOM16-26 (SEQ ID NO:334), DOM16-27 (SEQ ID NO:335), DOM16-28 (SEQ ID NO:336), DOM16-29 (SEQ ID NO:337), DOM16-30 (SEQ ID NO:338), DOM16-31 (SEQ ID NO:339), DOM16-32 (SEQ ID NO:340), DOM16-33 (SEQ ID NO:341), DOM16-35 (SEQ ID NO:342), DOM16-37 (SEQ ID NO:343), DOM16-38 (SEQ ID NO:344), DOM16-39 (SEQ ID NO:345), DOM16-40 (SEQ ID NO:346), DOM16-41 (SEQ ID NO:347), DOM16-42 (SEQ ID NO:348), DOM16-43 (SEQ ID NO:349), DOM16-44 (SEQ ID NO:350), DOM16-45 (SEQ ID NO:351), DOM16-46 (SEQ ID NO:352), DOM16-47 (SEQ ID NO:353), DOM16-48 (SEQ ID NO:354), DOM16-49 (SEQ ID NO:355), DOM16-50 (SEQ ID NO:356), DOM16-59 (SEQ ID NO:357), DOM16-60 (SEQ ID NO:358), DOM16-61 (SEQ ID NO:359), DOM16-62 (SEQ ID NO:360), DOM16-63 (SEQ ID NO:361), DOM16-64 (SEQ ID NO:362), DOM16-65 (SEQ ID NO:363), DOM16-66 (SEQ ID NO:364), DOM16-67 (SEQ ID NO:365), DOM16-68 (SEQ ID NO:366), DOM16-69 (SEQ ID NO:367), DOM16-70 (SEQ ID NO:368), DOM16-71 (SEQ ID NO:369), DOM16-72 (SEQ ID NO:370), DOM16-73 (SEQ ID NO:371), DOM16-74 (SEQ ID NO:372), DOM16-75 (SEQ ID NO:373), DOM16-76 (SEQ ID NO:374), DOM16-77 (SEQ ID NO:375), DOM16-78 (SEQ ID NO:376), DOM16-79 (SEQ ID NO:377), DOM16-80 (SEQ ID NO:378), DOM16-81 (SEQ ID NO:379), DOM16-82 (SEQ ID NO:380), DOM16-83 (SEQ ID NO:381), DOM16-84 (SEQ ID NO:382), DOM16-85 (SEQ ID NO:383), DOM16-87 (SEQ ID NO:384), DOM16-88 (SEQ ID NO:385), DOM16-89 (SEQ ID NO:386), DOM16-90 (SEQ ID NO:387), DOM16-91 (SEQ ID NO:388), DOM16-92 (SEQ ID NO:389), DOM16-94 (SEQ ID NO:390), DOM16-95 (SEQ ID NO:391), DOM16-96 (SEQ ID NO:392), DOM16-97 (SEQ ID NO:393), DOM16-98 (SEQ ID NO:394), DOM16-99 (SEQ ID NO:395), DOM16-100 (SEQ ID NO:396), DOM16-101 (SEQ ID NO:397), DOM16-102 (SEQ ID NO:398), DOM16-103 (SEQ ID NO:399), DOM16-104 (SEQ ID NO:400), DOM16-105 (SEQ ID NO:401), DOM16-106 (SEQ ID NO:402), DOM16-107 (SEQ ID NO:403), DOM16-108 (SEQ ID NO:404), DOM16-109 (SEQ ID NO:405), DOM16-110 (SEQ ID NO:406), DOM16-111 (SEQ ID NO:407), DOM16-112 (SEQ ID NO:408), DOM16-113 (SEQ ID NO:409), DOM16-114 (SEQ ID NO:410), DOM16-115 (SEQ ID NO:411), DOM16-116 (SEQ ID NO:412), DOM16-117 (SEQ ID NO:413), DOM16-118 (SEQ ID NO:414), DOM16-119 (SEQ ID NO:415), DOM16-39-6 (SEQ ID NO:416), DOM16-39-8 (SEQ ID NO:417), DOM16-39-34 (SEQ ID NO:418), DOM16-39-48 (SEQ ID NO:419), DOM16-39-87 (SEQ ID NO:420), DOM16-39-90 (SEQ ID NO:421), DOM16-39-96 (SEQ ID NO:422), DOM16-39-100 (SEQ ID NO:423), DOM16-39-101 (SEQ ID NO:424), DOM16-39-102 (SEQ ID NO:425), DOM16-39-103 (SEQ ID NO:426), DOM16-39-104 (SEQ ID NO:427), DOM16-39-105 (SEQ ID NO:428), DOM16-39-106 (SEQ ID NO:429), DOM16-39-107 (SEQ ID NO:430), DOM16-39-108 (SEQ ID NO:431), DOM16-39-109 (SEQ ID NO:432), DOM16-39-110 (SEQ ID NO:433), DOM16-39-111 (SEQ ID NO:434), DOM16-39-112 (SEQ ID NO:435), DOM16-39-113 (SEQ ID NO:436), DOM16-39-114 (SEQ ID NO:437), DOM16-39-115 (SEQ ID NO:438), DOM16-39-116 (SEQ ID NO:439), DOM16-39-117 (SEQ ID NO:440), DOM16-39-200 (SEQ ID NO:441), DOM16-39-201 (SEQ ID NO:442), DOM16-39-202 (SEQ ID NO:443), DOM16-39-203 (SEQ ID NO:444), DOM16-39-204 (SEQ ID NO:445), DOM16-39-205 (SEQ ID NO:446), DOM16-39-206 (SEQ ID NO:447), DOM16-39-207 (SEQ ID NO:448), DOM16-39-209 (SEQ ID NO:449), DOM16-52 (SEQ ID NO:450), NB1 (SEQ ID NO:451), NB2 (SEQ ID NO:452), NB3 (SEQ ID NO:453), NB4 (SEQ ID NO:454), NB5 (SEQ ID NO:455), NB6 (SEQ ID NO:456), NB7 (SEQ ID NO:457), NB8 (SEQ ID NO:458), NB9 (SEQ ID NO:459), NB10 (SEQ ID NO:460), NB11 (SEQ ID NO:461), NB12 (SEQ ID NO:462), NB13 (SEQ ID NO:463), NB14 (SEQ ID NO:464), NB15 (SEQ ID NO:465), NB16 (SEQ ID NO:466), NB17 (SEQ ID NO:467), NB18 (SEQ ID NO:468), NB19 (SEQ ID NO:469), NB20 (SEQ ID NO:470), NB21 (SEQ ID NO:471), and NB22 (SEQ ID NO:472).

In preferred embodiments, the polypeptide domain that has a binding site with binding specificity for EGFR comprises an amino acid sequence that has at least about 90%, at least about 91%, at least about 92%, at least about 93%, at least about 94%, at least about 95%, at least about 96%, at least about 97%, at least about 98%, or at least about 99% amino acid sequence identity with the amino acid sequence of DOM16-39 (SEQ ID NO:345). For example, the polypeptide domain that has a binding site with binding specificity for EGFR can comprise the amino acid sequence of DOM16-39-87 (SEQ ID NO:420), DOM16-39-100 (SEQ ID NO:423), DOM16-39-107 (SEQ ID NO:430), DOM16-39-109 (SEQ ID NO:432), DOM16-39-115 (SEQ ID NO:438), or DOM16-39-200 (SEQ ID NO:441).

In some embodiments, the polypeptide domain that has a binding site with binding specificity for EGFR competes with any of the dAbs disclosed herein for binding to EGFR.

Preferably the polypeptide domain that has a binding site with binding specificity for EGFR is an immunoglobuline single variable domain. The polypeptide domain that has a binding site with binding specificity for EGFR can comprise any suitable immunoglobulin variable domain, and preferably comprises a human variable domain or a variable domain that comprises human framework regions. In certain embodiments, the polypeptide domain that has a binding site with binding specificity for EGFR comprises a universal framework, as described herein.

In certain embodiments, polypeptide domain that has a binding site with binding specificity for EGFR resists aggregation, unfolds reversibly, comprises a framework region and/or is secreted as described above for the polypeptide domain that has a binding site with binding specificity for VEGF.

dAb Monomers that Bind Serum Albumin

The ligands of the invention can further comprise a dAb monomer that binds serum albumin (SA) with a $K_d$ of 1 nM to 500 µM (ie, ×10$^{-9}$ to 5×10$^{-4}$), preferably 100 nM to 10 µM. Preferably, for a ligand comprising an anti-SA dAb, the binding (eg $K_d$ and/or $K_{off}$ as measured by surface plasmon resonance, e.g., using BiaCore) of the ligand its target(s) is from 1 to 100000 times (preferably 100 to 100000, more preferably 1000 to 100000, or 10000 to 100000 times) stronger than for SA. Preferably, the serum albumin is human serum albumin (HSA). In one embodiment, the first dAb (or a dAb monomer) binds SA (eg, HSA) with a $K_d$ of approximately 50, preferably 70, and more preferably 100, 150 or 200 nM.

In certain embodiments, the dAb monomer that binds SA resists aggregation, unfolds reversibly and/or comprises a framework region as described above for dAb monomers that bind CD38.

In particular embodiments, the antigen-binding fragment of an antibody that binds serum albumin is a dAb that binds human serum albumin. In certain embodiments, the dAb binds human serum albumin and competes for binding to albumin with a dAb selected from the group consisting of DOM7m-16 (SEQ ID NO: 473), DOM7m-12 (SEQ ID NO: 474), DOM7m-26 (SEQ ID NO: 475), DOM7r-1 (SEQ ID NO: 476), DOM7r-3 (SEQ ID NO: 477), DOM7r-4 (SEQ ID NO: 478), DOM7r-5 (SEQ ID NO: 479), DOM7r-7 (SEQ ID NO: 480), DOM7r-8 (SEQ ID NO: 481), DOM7h-2 (SEQ ID NO: 482), DOM7h-3 (SEQ ID NO: 483), DOM7h-4 (SEQ ID NO: 484), DOM7h-6 (SEQ ID NO: 485), DOM7h-1 (SEQ ID NO: 486), DOM7h-7 (SEQ ID NO: 487), DOM7h-22 (SEQ ID NO: 489), DOM7h-23 (SEQ ID NO: 490), DOM7h-24 (SEQ ID NO: 491), DOM7h-25 (SEQ ID NO: 492), DOM7h-26 (SEQ ID NO: 493), DOM7h-21 (SEQ ID NO: 494), DOM7h-27 (SEQ ID NO: 495), DOM7h-8 (SEQ ID NO: 496), DOM7r-13 (SEQ ID NO: 497), DOM7r-14 (SEQ ID NO: 498), DOM7r-15 (SEQ ID NO: 499), DOM7r-16 (SEQ ID NO: 500), DOM7r-17 (SEQ ID NO: 501), DOM7r-18 (SEQ ID NO: 502), DOM7r-19 (SEQ ID NO: 503), DOM7r-20 (SEQ ID NO: 504), DOM7r-21 (SEQ ID NO: 505), DOM7r-22 (SEQ ID NO: 506), DOM7r-23 (SEQ ID NO: 507), DOM7r-24 (SEQ ID NO: 508), DOM7r-25 (SEQ ID NO: 509), DOM7r-26 (SEQ ID NO: 510), DOM7r-27 (SEQ ID NO: 511), DOM7r-28 (SEQ ID NO: 512), DOM7r-29 (SEQ ID NO: 513), DOM7r-30 (SEQ ID NO: 514), DOM7r-31 (SEQ ID NO: 515), DOM7r-32 (SEQ ID NO: 516), and DOM7r-33 (SEQ ID NO: 517).

In certain embodiments, the dAb binds human serum albumin and comprises an amino acid sequence that has at least about 80%, or at least about 85%, or at least about 90%, or at least about 95%, or at least about 96%, or at least about 97%, or at least about 98%, or at least about 99% amino acid sequence identity with the amino acid sequence of a dAb selected from the group consisting of DOM7m-16 (SEQ ID NO: 473), DOM7m-12 (SEQ ID NO: 474), DOM7m-26 (SEQ ID NO: 475), DOM7r-1 (SEQ ID NO: 476), DOM7r-3 (SEQ ID NO: 477), DOM7r-4 (SEQ ID NO: 478), DOM7r-5 (SEQ ID NO: 479), DOM7r-7 (SEQ ID NO: 480), DOM7r-8 (SEQ ID NO: 481), DOM7h-2 (SEQ ID NO: 482), DOM7h-3 (SEQ ID NO: 483), DOM7h-4 (SEQ ID NO: 484), DOM7h-6 (SEQ ID NO: 485), DOM7h-1 (SEQ ID NO: 486), DOM7h-7 (SEQ ID NO: 487), DOM7h-22 (SEQ ID NO: 489), DOM7h-23 (SEQ ID NO: 490), DOM7h-24 (SEQ ID NO: 491), DOM7h-25 (SEQ ID NO: 492), DOM7h-26 (SEQ ID NO: 493), DOM7h-21 (SEQ ID NO: 494), DOM7h-27 (SEQ ID NO: 495), DOM7h-8 (SEQ ID NO: 496), DOM7r-13 (SEQ ID NO: 497), DOM7r-14 (SEQ ID NO: 498), DOM7r-15 (SEQ ID NO: 499), DOM7r-16 (SEQ ID NO: 500), DOM7r-17 (SEQ ID NO: 501), DOM7r-18 (SEQ ID NO: 502), DOM7r-19 (SEQ ID NO: 503), DOM7r-20 (SEQ ID NO: 504), DOM7r-21 (SEQ ID NO: 505), DOM7r-22 (SEQ ID NO: 506), DOM7r-23 (SEQ ID NO: 507), DOM7r-24 (SEQ ID NO: 508), DOM7r-25 (SEQ ID NO: 509), DOM7r-26 (SEQ ID NO: 510), DOM7r-27 (SEQ ID NO: 511), DOM7r-28 (SEQ ID NO: 512), DOM7r-29 (SEQ ID NO: 513), DOM7r-30 (SEQ ID NO: 514), DOM7r-31 (SEQ ID NO: 515), DOM7r-32 (SEQ ID NO: 516), and DOM7r-33 (SEQ ID NO: 517).

For example, the dAb that binds human serum albumin can comprise an amino acid sequence that has at least about 90%, or at least about 95%, or at least about 96%, or at least about 97%, or at least about 98%, or at least about 99% amino acid sequence identity with DOM7h-2 (SEQ ID NO:482), DOM7h-3 (SEQ ID NO:483), DOM7h-4 (SEQ ID NO:484), DOM7h-6 (SEQ ID NO:485), DOM7h-1 (SEQ ID NO:486), DOM7h-7 (SEQ ID NO:487), DOM7h-8 (SEQ ID NO:496), DOM7r-13 (SEQ ID NO:497), DOM7r-14 (SEQ ID NO:498), DOM7h-22 (SEQ ID NO:489), DOM7h-23 (SEQ ID NO:490), DOM7h-24 (SEQ ID NO:491), DOM7h-25 (SEQ ID NO:492), DOM7h-26 (SEQ ID NO:493), DOM7h-21 (SEQ ID NO:494), and DOM7h-27 (SEQ ID NO:495).

Amino acid sequence identity is preferably determined using a suitable sequence alignment algorithm and default parameters, such as BLAST P (Karlin and Altschul, *Proc. Natl. Acad. Sci. USA* 87(6):2264-2268 (1990)).

In more particular embodiments, the dAb is a $V_\kappa$ dAb that binds human serum albumin and has a amino acid sequence selected from the group consisting of DOM7h-2 (SEQ ID NO:482), DOM7h-3 (SEQ ID NO:483), DOM7h-4 (SEQ ID NO:484), DOM7h-6 (SEQ ID NO:485), DOM7h-1 (SEQ ID NO:486), DOM7h-7 (SEQ ID NO:487), DOM7h-8 (SEQ ID NO:496), DOM7r-13 (SEQ ID NO:497), and DOM7r-14 (SEQ ID NO:498), or a $V_H$ dAb that has an amino acid sequence selected from the group consisting of: DOM7h-22 (SEQ ID NO:489), DOM7h-23 (SEQ ID NO:490), DOM7h-24 (SEQ ID NO:491), DOM7h-25 (SEQ ID NO:492), DOM7h-26 (SEQ ID NO:493), DOM7h-21 (SEQ ID NO:494), DOM7h-27 (SEQ ID NO:495). In other embodiments, the antigen-binding fragment of an antibody that binds serum albumin is a dAb that binds human serum albumin and comprises the CDRs of any of the foregoing amino acid sequences.

Suitable Camelid $V_{HH}$ that bind serum albumin include those disclosed in WO 2004/041862 (Ablynx N.V.) and herein, such as Sequence A (SEQ ID NO:518), Sequence B (SEQ ID NO:519), Sequence C (SEQ ID NO:520), Sequence D (SEQ ID NO:521), Sequence E (SEQ ID NO:522), Sequence F (SEQ ID NO:523), Sequence G (SEQ ID NO:524), Sequence H (SEQ ID NO:525), Sequence I (SEQ ID NO:526), Sequence J (SEQ ID NO:527), Sequence K (SEQ ID NO:528), Sequence L (SEQ ID NO:529), Sequence M (SEQ ID NO:530), Sequence N (SEQ ID NO:531), Sequence O (SEQ ID NO:532), Sequence P (SEQ ID NO:533), Sequence Q (SEQ ID NO:534). In certain embodiments, the Camelid $V_{HH}$ binds human serum albumin and comprises an amino acid sequence that has at least about 80%, or at least about 85%, or at least about 90%, or at least about 95%, or at least about 96%, or at least about 97%, or at least about 98%, or at least about 99% amino acid sequence identity with any one of SEQ ID NOS:518-534.

Amino acid sequence identity is preferably determined using a suitable sequence alignment algorithm and default parameters, such as BLAST P (Karlin and Altschul, *Proc. Natl. Acad. Sci. USA* 87(6):2264-2268 (1990)).

In some embodiments, the ligand comprises an anti-serum albumin dAb that competes with any anti-serum albumin dAb disclosed herein for binding to serum albumin (e.g., human serum albumin).

Nucleic Acid Molecules, Vectors and Host Cells

The invention also provides isolated and/or recombinant nucleic acid molecules encoding ligands, (dual-specific ligands and multi specific ligands) as described herein. Nucleic acids referred to herein as "isolated" are nucleic acids which have been separated away from the nucleic acids of the genomic DNA or cellular RNA of their source of origin (e.g., as it exists in cells or in a mixture of nucleic acids such as a library), and include nucleic acids obtained by methods described herein or other suitable methods, including essentially pure nucleic acids, nucleic acids produced by chemical synthesis, by combinations of biological and chemical methods, and recombinant nucleic acids which are isolated (see e.g., Daugherty, B. L. et al., *Nucleic Acids Res.*, 19(9): 2471-2476 (1991); Lewis, A. P. and J. S. Crowe, *Gene*, 101: 297-302 (1991)).

Nucleic acids referred to herein as "recombinant" are nucleic acids which have been produced by recombinant DNA methodology, including those nucleic acids that are generated by procedures which rely upon a method of artificial recombination, such as the polymerase chain reaction (PCR) and/or cloning into a vector using restriction enzymes.

In certain embodiments, the isolated and/or recombinant nucleic acid comprises a nucleotide sequence encoding a ligand, as described herein, wherein said ligand comprises an amino acid sequence that has at least about 80%, at least about 85%, at least about 90%, at least about 91%, at least about 92%, at least about 93%, at least about 94%, at least about 95%, at least about 96%, at least about 97%, at least about 98%, or at least about 99% amino acid sequence identity with the amino acid sequence of a dAb that binds VEGF disclosed herein, or a dAb that binds EGFR disclosed herein.

For example, in some embodiments, the isolated and/or recombinant nucleic acid comprises a nucleotide sequence encoding a ligand that has binding specificity for VEGFA, as described herein, wherein said ligand comprises an amino acid sequence that has at least about 80%, at least about 85%, at least about 90%, at least about 91%, at least about 92%, at least about 93%, at least about 94%, at least about 95%, at least about 96%, at least about 97%, at least about 98%, or at least about 99% amino acid sequence identity with the amino acid sequence of a dAb selected from the group consisting of TAR15-1 (SEQ ID NO:100), TAR15-3 (SEQ ID NO:101), TAR15-4 (SEQ ID NO:102), TAR15-9 (SEQ ID NO:103), TAR15-10 (SEQ ID NO:104), TAR15-11 (SEQ ID NO:105), TAR15-12 (SEQ ID NO:106), TAR15-13 (SEQ ID NO:107), TAR15-14 (SEQ ID NO:108), TAR15-15 (SEQ ID NO:109), TAR15-16 (SEQ ID NO:110), TAR15-17 (SEQ ID NO:111), TAR15-18 (SEQ ID NO:112), TAR15-19 (SEQ ID NO:113), TAR15-20 (SEQ ID NO:114), TAR15-22 (SEQ ID NO:115), TAR15-5 (SEQ ID NO:116), TAR15-6 (SEQ ID NO:117), TAR15-7 (SEQ ID NO:118), TAR15-8 (SEQ ID NO:119), TAR15-23 (SEQ ID NO:120), TAR15-24 (SEQ ID NO:121), TAR15-25 (SEQ ID NO:122), TAR15-26 (SEQ ID NO:123), TAR15-27 (SEQ ID NO:124), TAR15-29 (SEQ ID NO:125), TAR15-30 (SEQ ID NO:126), TAR15-6-500 (SEQ ID NO:127), TAR15-6-501 (SEQ ID NO:128), TAR15-6-502 (SEQ ID NO:129), TAR15-6-503 (SEQ ID NO:130), TAR15-6-504 (SEQ ID NO:131), TAR15-6-505 (SEQ ID NO:132), TAR15-6-506 (SEQ ID NO:133), TAR15-6-507 (SEQ ID NO:134), TAR15-6-508 (SEQ ID NO:135), TAR15-6-509 (SEQ ID NO:136), TAR15-6-510 (SEQ ID NO:137), TAR15-8-500 (SEQ ID NO:138), TAR15-8-501 (SEQ ID NO:139), TAR15-8-502 (SEQ ID NO:140), TAR15-8-503 (SEQ ID NO:141), TAR15-8-505 (SEQ ID NO:142), TAR15-8-506 (SEQ ID NO:143), TAR15-8-507 (SEQ ID NO:144), TAR15-8-508 (SEQ ID NO:145), TAR15-8-509 (SEQ ID NO:146), TAR15-8-510 (SEQ ID NO:147), TAR15-8-511 (SEQ ID NO:148), TAR15-26-500 (SEQ ID NO:149), TAR15-26-501 (SEQ ID NO:150), TAR15-26-502 (SEQ ID NO:151), TAR15-26-503 (SEQ ID NO:152), TAR15-26-504 (SEQ ID NO:153), TAR15-26-505 (SEQ ID NO:154), TAR15-26-506 (SEQ ID NO:155), TAR15-26-507 (SEQ ID NO:156), TAR15-26-508 (SEQ ID NO:157), TAR15-26-509 (SEQ ID NO:158), TAR15-26-510 (SEQ ID NO:159), TAR15-26-511 (SEQ ID NO:160), TAR15-26-512 (SEQ ID NO:161), TAR15-26-513 (SEQ ID NO:162), TAR15-26-514 (SEQ ID NO:163), TAR15-26-515 (SEQ ID NO:164), TAR15-26-516 (SEQ ID NO:165), TAR15-26-517 (SEQ ID NO:166), TAR15-26-518 (SEQ ID NO:167), TAR15-26-519 (SEQ ID NO:168), TAR15-26-520 (SEQ ID NO:169), TAR15-26-521 (SEQ ID NO:170), TAR15-26-522 (SEQ ID NO:171), TAR15-26-523 (SEQ ID NO:172), TAR15-26-524 (SEQ ID NO:173), TAR15-26-525 (SEQ ID NO:174), TAR15-26-526 (SEQ ID NO:175), TAR15-26-527 (SEQ ID NO:176), TAR15-26-528 (SEQ ID NO:177), TAR15-26-529 (SEQ ID NO:178), TAR15-26-530 (SEQ ID NO:179), TAR15-26-531 (SEQ ID NO:180), TAR15-26-532 (SEQ ID NO:181), TAR15-26-533 (SEQ ID NO:182), TAR15-26-534 (SEQ ID NO:183), TAR15-26-535 (SEQ ID NO:184), TAR15-26-536 (SEQ ID NO:185), TAR15-26-537 (SEQ ID NO:186), TAR15-26-538 (SEQ ID NO:187), TAR15-26-539 (SEQ ID NO:188), TAR15-26-540 (SEQ ID NO:189), TAR15-26-541 (SEQ ID NO:190), TAR15-26-542 (SEQ ID NO:191), TAR15-26-543 (SEQ ID NO:192), TAR15-26-544 (SEQ ID NO:193), TAR15-26-545 (SEQ ID NO:194), TAR15-26-546

(SEQ ID NO:195), TAR15-26-547 (SEQ ID NO:196), TAR15-26-548 (SEQ ID NO:197), TAR15-26-549 (SEQ ID NO:198), TAR15-26-550 (SEQ ID NO:539), and TAR15-26-551 (SEQ ID NO:540).

In other embodiments, the isolated and/or recombinant nucleic acid comprises a nucleotide sequence encoding a ligand that has binding specificity for EGFR, as described herein, wherein said ligand comprises an amino acid sequence that has at least about 80%, at least about 85%, at least about 90%, at least about 91%, at least about 92%, at least about 93%, at least about 94%, at least about 95%, at least about 96%, at least about 97%, at least about 98%, or at least about 99% amino acid sequence identity with the amino acid sequence of a dAb selected from the group consisting of DOM16-17 (SEQ ID NO:325), DOM16-18 (SEQ ID NO:326), DOM16-19 (SEQ ID NO:327), DOM16-20 (SEQ ID NO:328), DOM16-21 (SEQ ID NO:329), DOM16-22 (SEQ ID NO:330), DOM16-23 (SEQ ID NO:331), DOM16-24 (SEQ ID NO:332), DOM16-25 (SEQ ID NO:333), DOM16-26 (SEQ ID NO:334), DOM16-27 (SEQ ID NO:335), DOM16-28 (SEQ ID NO:336), DOM16-29 (SEQ ID NO:337), DOM16-30 (SEQ ID NO:338), DOM16-31 (SEQ ID NO:339), DOM16-32 (SEQ ID NO:340), DOM16-33 (SEQ ID NO:341), DOM16-35 (SEQ ID NO:342), DOM16-37 (SEQ ID NO:343), DOM16-38 (SEQ ID NO:344), DOM16-39 (SEQ ID NO:345), DOM16-40 (SEQ ID NO:346), DOM16-41 (SEQ ID NO:347), DOM16-42 (SEQ ID NO:348), DOM16-43 (SEQ ID NO:349), DOM16-44 (SEQ ID NO:350), DOM16-45 (SEQ ID NO:351), DOM16-46 (SEQ ID NO:352), DOM16-47 (SEQ ID NO:353), DOM16-48 (SEQ ID NO:354), DOM16-49 (SEQ ID NO:355), DOM16-50 (SEQ ID NO:356), DOM16-59 (SEQ ID NO:357), DOM16-60 (SEQ ID NO:358), DOM16-61 (SEQ ID NO:359), DOM16-62 (SEQ ID NO:360), DOM16-63 (SEQ ID NO:361), DOM16-64 (SEQ ID NO:362), DOM16-65 (SEQ ID NO:363), DOM16-66 (SEQ ID NO:364), DOM16-67 (SEQ ID NO:365), DOM16-68 (SEQ ID NO:366), DOM16-69 (SEQ ID NO:367), DOM16-70 (SEQ ID NO:368), DOM16-71 (SEQ ID NO:369), DOM16-72 (SEQ ID NO:370), DOM16-73 (SEQ ID NO:371), DOM16-74 (SEQ ID NO:372), DOM16-75 (SEQ ID NO:373), DOM16-76 (SEQ ID NO:374), DOM16-77 (SEQ ID NO:375), DOM16-78 (SEQ ID NO:376), DOM16-79 (SEQ ID NO:377), DOM16-80 (SEQ ID NO:378), DOM16-81 (SEQ ID NO:379), DOM16-82 (SEQ ID NO:380), DOM16-83 (SEQ ID NO:381), DOM16-84 (SEQ ID NO:382), DOM16-85 (SEQ ID NO:383), DOM16-87 (SEQ ID NO:384), DOM16-88 (SEQ ID NO:385), DOM16-89 (SEQ ID NO:386), DOM16-90 (SEQ ID NO:381), DOM16-91 (SEQ ID NO:388), DOM16-92 (SEQ ID NO:389), DOM16-94 (SEQ ID NO:390), DOM16-95 (SEQ ID NO:391), DOM16-96 (SEQ ID NO:392), DOM16-97 (SEQ ID NO:393), DOM16-98 (SEQ ID NO:394), DOM16-99 (SEQ ID NO:395), DOM16-100 (SEQ ID NO:396), DOM16-101 (SEQ ID NO:397), DOM16-102 (SEQ ID NO:398), DOM16-103 (SEQ ID NO:399), DOM16-104 (SEQ ID NO:400), DOM16-105 (SEQ ID NO:401), DOM16-106 (SEQ ID NO:402), DOM16-107 (SEQ ID NO:403), DOM16-108 (SEQ ID NO:404), DOM16-109 (SEQ ID NO:405), DOM16-110 (SEQ ID NO:406), DOM16-111 (SEQ ID NO:407), DOM16-112 (SEQ ID NO:408), DOM16-113 (SEQ ID NO:409), DOM16-114 (SEQ ID NO:410), DOM16-115 (SEQ ID NO:411), DOM16-116 (SEQ ID NO:412), DOM16-117 (SEQ ID NO:413), DOM16-118 (SEQ ID NO:414), DOM16-119 (SEQ ID NO:415), DOM16-39-6 (SEQ ID NO:416), DOM16-39-8 (SEQ ID NO:417), DOM16-39-34 (SEQ ID NO:418), DOM16-39-48 (SEQ ID NO:419), DOM16-39-87 (SEQ ID NO:420), DOM16-39-90 (SEQ ID NO:421), DOM16-39-96 (SEQ ID NO:422), DOM16-39-100 (SEQ ID NO:423), DOM16-39-101 (SEQ ID NO:424), DOM16-39-102 (SEQ ID NO:425), DOM16-39-103 (SEQ ID NO:426), DOM16-39-104 (SEQ ID NO:427), DOM16-39-105 (SEQ ID NO:428), DOM16-39-106 (SEQ ID NO:429), DOM16-39-107 (SEQ ID NO:430), DOM16-39-108 (SEQ ID NO:431), DOM16-39-109 (SEQ ID NO:432), DOM16-39-110 (SEQ ID NO:433), DOM16-39-111 (SEQ ID NO:434), DOM16-39-112 (SEQ ID NO:435), DOM16-39-113 (SEQ ID NO:436), DOM16-39-114 (SEQ ID NO:437), DOM16-39-115 (SEQ ID NO:438), DOM16-39-116 (SEQ ID NO:439), DOM16-39-117 (SEQ ID NO:440), DOM16-39-200 (SEQ ID NO:441), DOM16-39-201 (SEQ ID NO:442), DOM16-39-202 (SEQ ID NO:443), DOM16-39-203 (SEQ ID NO:444), DOM16-39-204 (SEQ ID NO:445), DOM16-39-205 (SEQ ID NO:446), DOM16-39-206 (SEQ ID NO:447), DOM16-39-207 (SEQ ID NO:448), DOM16-39-209 (SEQ ID NO:449), DOM16-52 (SEQ ID NO:450), NB1 (SEQ ID NO:451), NB2 (SEQ ID NO:452), NB3 (SEQ ID NO:453), NB4 (SEQ ID NO:454), NB5 (SEQ ID NO:455), NB6 (SEQ ID NO:456), NB7 (SEQ ID NO:457), NB8 (SEQ ID NO:458), NB9 (SEQ ID NO:459), NB10 (SEQ ID NO:460), NB11 (SEQ ID NO:461), NB12 (SEQ ID NO:462), NB13 (SEQ ID NO:463), NB14 (SEQ ID NO:464), NB15 (SEQ ID NO:465), NB16 (SEQ ID NO:466), NB17 (SEQ ID NO:467), NB18 (SEQ ID NO:468), NB19 (SEQ ID NO:469), NB20 (SEQ ID NO:470), NB21 (SEQ ID NO:471), and NB22 (SEQ ID NO:472).

In other embodiments, the isolated and/or recombinant nucleic acid encoding a ligand that has binding specificity for VEGF, as described herein, wherein said nucleic acid comprises a nucleotide sequence has at least about 80%, at least about 85%, at least about 90%, at least about 91%, at least about 92%, at least about 93%, at least about 94%, at least about 95%, at least about 96%, at least about 97%, at least about 98%, or at least about 99% nucleotide sequence identity with a nucleotide sequence encoding an anti-VEGF dAb selected from the group consisting of TAR15-1 (SEQ ID NO:1), TAR15-3 (SEQ ID NO:2), TAR15-4 (SEQ ID NO:3), TAR15-9 (SEQ ID NO:4), TAR15-10 (SEQ ID NO:5), TAR15-11 (SEQ ID NO:6), TAR15-12 (SEQ ID NO:7), TAR15-13 (SEQ ID NO:8), TAR15-14 (SEQ ID NO:9), TAR15-15 (SEQ ID NO:10), TAR15-16 (SEQ ID NO:11), TAR15-17 (SEQ ID NO:12), TAR15-18 (SEQ ID NO:13), TAR15-19 (SEQ ID NO:14), TAR15-20 (SEQ ID NO:15), TAR15-22 (SEQ ID NO:16), TAR15-5 (SEQ ID NO:17), TAR15-6 (SEQ ID NO:18), TAR15-7 (SEQ ID NO:19), TAR15-8 (SEQ ID NO:20), TAR15-23 (SEQ ID NO:21), TAR15-24 (SEQ ID NO:22), TAR15-25 (SEQ ID NO:23), TAR15-26 (SEQ ID NO:24), TAR15-27 (SEQ ID NO:25), TAR15-29 (SEQ ID NO:26), TAR15-30 (SEQ ID NO:27), TAR15-6-500 (SEQ ID NO:28), TAR15-6-501 (SEQ ID NO:29), TAR15-6-502 (SEQ ID NO:30), TAR15-6-503 (SEQ ID NO:31), TAR15-6-504 (SEQ ID NO:32), TAR15-6-505 (SEQ ID NO:33), TAR15-6-506 (SEQ ID NO:34), TAR15-6-507 (SEQ ID NO:35), TAR15-6-508 (SEQ ID NO:36), TAR15-6-509 (SEQ ID NO:37), TAR15-6-510 (SEQ ID NO:38), TAR15-8-500 (SEQ ID NO:39), TAR15-8-501 (SEQ ID NO:40), TAR15-8-502 (SEQ ID NO:41), TAR15-8-503 (SEQ ID NO:42), TAR15-8-505 (SEQ ID NO:43), TAR15-8-506 (SEQ ID NO:44), TAR15-8-507 (SEQ ID NO:45), TAR15-8-508 (SEQ ID NO:46), TAR15-8-509 (SEQ ID NO:47), R15-8-510 (SEQ ID NO:48), TAR15-8-511 (SEQ ID NO:49), TAR15-26-500 (SEQ ID NO:50), TAR15-26-501 (SEQ ID NO:51), TAR15-26-502

(SEQ ID NO:52), TAR15-26-503 (SEQ ID NO:53), TAR15-26-504 (SEQ ID NO:54), TAR15-26-505 (SEQ ID NO:55), TAR15-26-506 (SEQ ID NO:56), TAR15-26-507 (SEQ ID NO:57), TAR15-26-508 (SEQ ID NO:58), TAR15-26-509 (SEQ ID NO:59), TAR15-26-510 (SEQ ID NO:60), TAR15-26-511 (SEQ ID NO:61), TAR15-26-512 (SEQ ID NO:62), TAR15-26-513 (SEQ ID NO:63), TAR15-26-514 (SEQ ID NO:64), TAR15-26-515 (SEQ ID NO:65), TAR15-26-516 (SEQ ID NO:66), TAR15-26-517 (SEQ ID NO:67), TAR15-26-518 (SEQ ID NO:68), TAR15-26-519 (SEQ ID NO:69), TAR15-26-520 (SEQ ID NO:70), TAR15-26-521 (SEQ ID NO:71), TAR15-26-522 (SEQ ID NO:72), TAR15-26-523 (SEQ ID NO:73), TAR15-26-524 (SEQ ID NO:74), TAR15-26-525 (SEQ ID NO:75), TAR15-26-526 (SEQ ID NO:76), TAR15-26-527 (SEQ ID NO:77), TAR15-26-528 (SEQ ID NO:78), TAR15-26-529 (SEQ ID NO:79), TAR15-26-530 (SEQ ID NO:80), TAR15-26-531 (SEQ ID NO:81), TAR15-26-532 (SEQ ID NO:82), TAR15-26-533 (SEQ ID NO:83), TAR15-26-534 (SEQ ID NO:84), TAR15-26-535 (SEQ ID NO:85), TAR15-26-536 (SEQ ID NO:86), TAR15-26-537 (SEQ ID NO:87), TAR15-26-538 (SEQ ID NO:88), TAR15-26-539 (SEQ ID NO:89), TAR15-26-540 (SEQ ID NO:90), TAR15-26-541 (SEQ ID NO:91), TAR15-26-542 (SEQ ID NO:92), TAR15-26-543 (SEQ ID NO:93), TAR15-26-544 (SEQ ID NO:94), TAR15-26-545 (SEQ ID NO:95), TAR15-26-546 (SEQ ID NO:96), TAR15-26-547 (SEQ ID NO:97), TAR15-26-548 (SEQ ID NO:98), TAR15-26-549 (SEQ ID NO:99), TAR15-21 (SEQ ID NO:535), TAR15-2 (SEQ ID NO:536), TAR15-26-550 (SEQ ID NO:537), and TAR15-26-551 (SEQ ID NO:538). Prefereably, nucleotide sequence identity is determined over the whole length of the nucleotice sequence that encodes the selected anti-VEGF dAb.

In other embodiments, the isolated and/or recombinant nucleic acid encoding a ligand that has binding specificity for EGFR, as described herein, wherein said nucleic acid comprises a nucleotide sequence has at least about 80%, at least about 85%, at least about 90%, at least about 91%, at least about 92%, at least about 93%, at least about 94%, at least about 95%, at least about 96%, at least about 97%, at least about 98%, or at least about 99% nucleotide sequence identity with a nucleotide sequence encoding an anti-VEGF dAb selected from the group consisting of DOM16-17 (SEQ ID NO:199), DOM16-18 (SEQ ID NO:200), DOM16-19 (SEQ ID NO:201), DOM16-20 (SEQ ID NO:202), DOM16-21 (SEQ ID NO:203), DOM16-22 (SEQ ID NO:204), DOM16-23 (SEQ ID NO:205), DOM16-24 (SEQ ID NO:206), DOM16-25 (SEQ ID NO:207), DOM16-26 (SEQ ID NO:208), DOM16-27 (SEQ ID NO:209), DOM16-28 (SEQ ID NO:210), DOM16-29 (SEQ ID NO:211), DOM16-30 (SEQ ID NO:212), DOM16-31 (SEQ ID NO:213), DOM16-32 (SEQ ID NO:214), DOM16-33 (SEQ ID NO:215), DOM16-35 (SEQ ID NO:216), DOM16-37 (SEQ ID NO:217), DOM16-38 (SEQ ID NO:218), DOM16-39 (SEQ ID NO:219), DOM16-40 (SEQ ID NO:220), DOM16-41 (SEQ ID NO:221), DOM16-42 (SEQ ID NO:222), DOM16-43 (SEQ ID NO:223), DOM16-44 (SEQ ID NO:224), DOM16-45 (SEQ ID NO:225), DOM16-46 (SEQ ID NO:226), DOM16-47 (SEQ ID NO:227), DOM16-48 (SEQ ID NO:228), DOM16-49 (SEQ ID NO:229), DOM16-50 (SEQ ID NO:230), DOM16-59 (SEQ ID NO:231), DOM16-60 (SEQ ID NO:232), DOM16-61 (SEQ ID NO:233), DOM16-62 (SEQ ID NO:234), DOM16-63 (SEQ ID NO:235), DOM16-64 (SEQ ID NO:236), DOM16-65 (SEQ ID NO:237), DOM16-66 (SEQ ID NO:238), DOM16-67 (SEQ ID NO:239), DOM16-68 (SEQ ID NO:240), DOM16-69 (SEQ ID NO:241), DOM16-70 (SEQ ID NO:242), DOM16-71 (SEQ ID NO:243), DOM16-72 (SEQ ID NO:244), DOM16-73 (SEQ ID NO:245), DOM16-74 (SEQ ID NO:246), DOM16-75 (SEQ ID NO:247), DOM16-76 (SEQ ID NO:248), DOM16-77 (SEQ ID NO:249), DOM16-78 (SEQ ID NO:250), DOM16-79 (SEQ ID NO:251), DOM16-80 (SEQ ID NO:252), DOM16-81 (SEQ ID NO:253), DOM16-82 (SEQ ID NO:254), DOM16-83 (SEQ ID NO:255), DOM16-84 (SEQ ID NO:256), DOM16-85 (SEQ ID NO:257), DOM16-87 (SEQ ID NO:258), DOM16-88 (SEQ ID NO:259), DOM16-89 (SEQ ID NO:260), DOM16-90 (SEQ ID NO:261), DOM16-91 (SEQ ID NO:262), DOM16-92 (SEQ ID NO:263), DOM16-94 (SEQ ID NO:264), DOM16-95 (SEQ ID NO:265), DOM16-96 (SEQ ID NO:266), DOM16-97 (SEQ ID NO:267), DOM16-98 (SEQ ID NO:268), DOM16-99 (SEQ ID NO:269), DOM16-100 (SEQ ID NO:270), DOM16-101 (SEQ ID NO:271), DOM16-102 (SEQ ID NO:272), DOM16-103 (SEQ ID NO:273), DOM16-104 (SEQ ID NO:274), DOM16-105 (SEQ ID NO:275), DOM16-106 (SEQ ID NO:276), DOM16-107 (SEQ ID NO:277), DOM16-108 (SEQ ID NO:278), DOM16-109 (SEQ ID NO:279), DOM16-110 (SEQ ID NO:280), DOM16-111 (SEQ ID NO:281), DOM16-112 (SEQ ID NO:282), DOM16-113 (SEQ ID NO:283), DOM16-114 (SEQ ID NO:284), DOM16-115 (SEQ ID NO:285), DOM16-116 (SEQ ID NO:286), DOM16-117 (SEQ ID NO:287), DOM16-118 (SEQ ID NO:288), DOM16-119 (SEQ ID NO:289), DOM16-39-6 (SEQ ID NO:290), DOM16-39-8 (SEQ ID NO:291), DOM16-39-34 (SEQ ID NO:292), DOM16-39-48 (SEQ ID NO:293), DOM16-39-87 (SEQ ID NO:294), DOM16-39-90 (SEQ ID NO:295), DOM16-39-96 (SEQ ID NO:296), DOM16-39-100 (SEQ ID NO:297), DOM16-39-101 (SEQ ID NO:298), DOM16-39-102 (SEQ ID NO:299), DOM16-39-103 (SEQ ID NO:300), DOM16-39-104 (SEQ ID NO:301), DOM16-39-105 (SEQ ID NO:302), DOM16-39-106 (SEQ ID NO:303), DOM16-39-107 (SEQ ID NO:304), DOM16-39-108 (SEQ ID NO:305), DOM16-39-109 (SEQ ID NO:306), DOM16-39-110 (SEQ ID NO:307), DOM16-39-111 (SEQ ID NO:308), DOM16-39-112 (SEQ ID NO:309), DOM16-39-113 (SEQ ID NO:310), DOM16-39-114 (SEQ ID NO:311), DOM16-39-115 (SEQ ID NO:312), DOM16-39-116 (SEQ ID NO:313), DOM16-39-117 (SEQ ID NO:314), DOM16-39-200 (SEQ ID NO:315), DOM16-39-201 (SEQ ID NO:316), DOM16-39-202 (SEQ ID NO:317), DOM16-39-203 (SEQ ID NO:318), DOM16-39-204 (SEQ ID NO:319), DOM16-39-205 (SEQ ID NO:320), DOM16-39-206 (SEQ ID NO:321), DOM16-39-207 (SEQ ID NO:322), DOM16-39-209 (SEQ ID NO:323), and DOM16-52 (SEQ ID NO:324). Prefereably, nucleotide sequence identity is determined over the whole length of the nucleotice sequence that encodes the selected anti-EGFR dAb.

The invention also provides a vector comprising a recombinant nucleic acid molecule of the invention. In certain embodiments, the vector is an expression vector comprising one or more expression control elements or sequences that are operably linked to the recombinant nucleic acid of the invention The invention also provides a recombinant host cell comprising a recombinant nucleic acid molecule or vector of the invention. Suitable vectors (e.g., plasmids, phagmids), expression control elements, host cells and methods for producing recombinant host cells of the invention are well-known in the art, and examples are further described herein.

Suitable expression vectors can contain a number of components, for example, an origin of replication, a selectable marker gene, one or more expression control elements, such as a transcription control element (e.g., promoter, enhancer, terminator) and/or one or more translation signals, a signal sequence or leader sequence, and the like. Expression control elements and a signal sequence, if present, can be provided by the vector or other source. For example, the transcriptional and/or translational control sequences of a cloned nucleic acid encoding an antibody chain can be used to direct expression.

A promoter can be provided for expression in a desired host cell. Promoters can be constitutive or inducible. For example, a promoter can be operably linked to a nucleic acid encoding an antibody, antibody chain or portion thereof, such that it directs transcription of the nucleic acid. A variety of suitable promoters for procaryotic (e.g., lac, tac, T3, T7 promoters for *E. coli*) and eucaryotic (e.g., simian virus 40 early or late promoter, Rous sarcoma virus long terminal repeat promoter, cytomegalovirus promoter, adenovirus late promoter) hosts are available.

In addition, expression vectors typically comprise a selectable marker for selection of host cells carrying the vector, and, in the case of a replicable expression vector, an origin or replication. Genes encoding products which confer antibiotic or drug resistance are common selectable markers and may be used in procaryotic (e.g., lactamase gene (ampicillin resistance), Tet gene for tetracycline resistance) and eucaryotic cells (e.g., neomycin (G418 or geneticin), gpt (mycophenolic acid), ampicillin, or hygromycin resistance genes). Dihydrofolate reductase marker genes permit selection with methotrexate in a variety of hosts. Genes encoding the gene product of auxotrophic markers of the host (e.g., LEU2, URA3, HIS3) are often used as selectable markers in yeast. Use of viral (e.g., baculovirus) or phage vectors, and vectors which are capable of integrating into the genome of the host cell, such as retroviral vectors, are also contemplated. Suitable expression vectors for expression in mammalian cells and prokaryotic cells (*E. coli*), insect cells (*Drosophila* Schnieder S2 cells, Sf9) and yeast (*P. methanolica, P. pastoris, S. cerevisiae*) are well-known in the art.

Suitable host cells can be prokaryotic, including bacterial cells such as *E. coli, B. subtilis* and/or other suitable bacteria; eukaryotic cells, such as fungal or yeast cells (e.g., *Pichia pastoris, Aspergillus* sp., *Saccharomyces cerevisiae, Schizosaccharomyces pombe, Neurospora crassa*), or other lower eukaryotic cells, and cells of higher eukaryotes such as those from insects (e.g., *Drosophila* Schnieder S2 cells, Sf9 insect cells (WO 94/26087 (O'Connor)), mammals (e.g., COS cells, such as COS-1 (ATCC Accession No. CRL-1650) and COS-7 (ATCC Accession No. CRL-1651), CHO (e.g., ATCC Accession No. CRL-9096, CHO DG44 (Urlaub, G. and Chasin, L A., *Proc. Natl. Acac. Sci. USA,* 77(7):4216-4220 (1980))), 293 (ATCC Accession No. CRL-1573), HeLa (ATCC Accession No. CCL-2), CV1 (ATCC Accession No. CCL-70), WOP (Dailey, L., et al., *J. Virol.,* 54:739-749 (1985), 3T3, 293T (Pear, W. S., et al., *Proc. Natl. Acad. Sci. U.S.A.,* 90:8392-8396 (1993)) NS0 cells, SP2/0, HuT 78 cells and the like, or plants (e.g., tobacco). (See, for example, Ausubel, F. M. et al., eds. *Current Protocols in Molecular Biology,* Greene Publishing Associates and John Wiley & Sons Inc. (1993).) In some embodiments, the host cell is an isolated host cell and is not part of a multicellular organism (e.g., plant or animal). In preferred embodiments, the host cell is a non-human host cell.

The invention also provides a method for producing a ligand (e.g., dual-specific ligand, multispecific ligand) of the invention, comprising maintaining a recombinant host cell comprising a recombinant nucleic acid of the invention under conditions suitable for expression of the recombinant nucleic acid, whereby the recombinant nucleic acid is expressed and a ligand is produced. In some embodiments, the method further comprises isolating the ligand.

Preparation of Immunoglobulin Based Ligands

Ligands (e.g., dual specific ligands, multispecific) according to the invention can be prepared according to previously established techniques, used in the field of antibody engineering, for the preparation of scFv, "phage" antibodies and other engineered antibody molecules. Techniques for the preparation of antibodies are for example described in the following reviews and the references cited therein: Winter & Milstein, (1991) Nature 349:293-299; Pluckthun (1992) Immunological Reviews 13 0:151-188; Wright et al., (1992) Crti. Rev. Immunol. 12:125-168; Holliger, P. & Winter, G. (1993) Curr. Op. Biotechn. 4, 446-449; Carter, et al. (1995) J. Hematother. 4, 463-470; Chester, K. A. & Hawkins, R. E. (1995) Trends Biotechn. 13, 294-300; Hoogenboom, H. R. (1997) Nature Biotechnol. 15, 125-126; Fearon, D. (1997) Nature Biotechnol. 15, 618-619; Plückthun, A. & Pack, P. (1997) Immunotechnology 3, 83-105; Carter, P. & Merchant, A. M. (1997) Curr. Opin. Biotechnol. 8, 449-454; Holliger, P. & Winter, G. (1997) Cancer Immunol. Immunother. 45, 128-130.

Suitable techniques employed for selection of antibody variable domains with a desired specificity employ libraries and selection procedures which are known in the art. Natural libraries (Marks et al. (1991) *J. Mol. Biol.,* 222: 581; Vaughan et al. (1996) *Nature Biotech.,* 14: 309) which use rearranged V genes harvested from human B cells are well known to those skilled in the art. Synthetic libraries (Hoogenboom & Winter (1992) *J. Mol. Biol.,* 227: 381; Barbas et al. (1992) *Proc. Natl. Acad. Sci. USA,* 89: 4457; Nissim et al. (1994) *EMBO J.,* 13: 692; Griffiths et al. (1994) *EMBO J.,* 13: 3245; De Kruif et al. (1995) *J. Mol. Biol.,* 248: 97) are prepared by cloning immunoglobulin V genes, usually using PCR. Errors in the PCR process can lead to a high degree of randomisation. $V_H$ and/or $V_L$ libraries may be selected against target antigens or epitopes separately, in which case single domain binding is directly selected for, or together.

Library Vector Systems

A variety of selection systems are known in the art which are suitable for use in the present invention. Examples of such systems are described below.

Bacteriophage lambda expression systems may be screened directly as bacteriophage plaques or as colonies of lysogens, both as previously described (Huse et al. (1989) *Science,* 246: 1275; Caton and Koprowski (1990) *Proc. Natl. Acad. Sci. U.S.A.,* 87; Mullinax et al. (1990) *Proc. Natl. Acad. Sci. U.S.A.,* 87: 8095; Persson et al. (1991) *Proc. Natl. Acad. Sci. U.S.A.,* 88: 2432) and are of use in the invention. Whilst such expression systems can be used to screen up to $10^6$ different members of a library, they are not really suited to screening of larger numbers (greater than $10^6$ members). Of particular use in the construction of libraries are selection display systems, which enable a nucleic acid to be linked to the polypeptide it expresses. As used herein, a selection display system is a system that permits the selection, by suitable display means, of the individual members of the library by binding the generic and/or target.

Selection protocols for isolating desired members of large libraries are known in the art, as typified by phage display techniques. Such systems, in which diverse peptide sequences are displayed on the surface of filamentous bacteriophage (Scott and Smith (1990) *Science,* 249: 386), have proven useful for creating libraries of antibody fragments (and the nucleotide sequences that encoding them) for the in vitro selection and amplification of specific antibody fragments that bind a target antigen (McCafferty et al., WO 92/01047). The nucleotide sequences encoding the variable regions are linked to gene fragments which encode leader signals that direct them to the periplasmic space of E. coli and as a result the resultant antibody fragments are displayed on the surface of the bacteriophage, typically as fusions to bacteriophage coat proteins (e.g., pIII or pVIII). Alternatively, antibody fragments are displayed externally on lambda phage capsids (phagebodies). An advantage of phage-based display systems is that, because they are biological systems, selected library members can be amplified simply by growing the phage containing the selected library member in bacterial cells. Furthermore, since the nucleotide sequence that encode the polypeptide library member is contained on a phage or phagemid vector, sequencing, expression and subsequent genetic manipulation is relatively straightforward.

Methods for the construction of bacteriophage antibody display libraries and lambda phage expression libraries are well known in the art (McCafferty et al. (1990) *Nature*, 348: 552; Kang et al. (1991) *Proc. Natl. Acad. Sci. U.S.A.*, 88: 4363; Clackson et al. (1991) *Nature*, 352: 624; Lowman et al. (1991) *Biochemistry*, 30: 10832; Burton et al. (1991) *Proc. Natl. Acad. Sci U.S.A.*, 88: 10134; Hoogenboom et al. (1991) *Nucleic Acids Res.*, 19: 4133; Chang et al. (1991) *J. Immunol.*, 147: 3610; Breitling et al. (1991) *Gene*, 104: 147; Marks et al. (1991) supra; Barbas et al. (1992) supra; Hawkins and Winter (1992) *J. Immunol.*, 22: 867; Marks et al., 1992, *J. Biol. Chem.*, 267: 16007; Lerner et al. (1992) *Science*, 258: 1313, incorporated herein by reference).

One particularly advantageous approach has been the use of scFv phage-libraries (Huston et al., 1988, Proc. Natl. Acad. Sci U.S.A., 85: 5879-5883; Chaudhary et al. (1990) Proc. Natl. Acad. Sci U.S.A., 87: 1066-1070; McCafferty et al. (1990) supra; Clackson et al. (1991) *Nature*, 352: 624; Marks et al. (1991) *J. Mol. Biol.*, 222: 581; Chiswell et al. (1992) Trends Biotech., 10: 80; Marks et al. (1992) *J. Biol. Chem.*, 267). Various embodiments of scFv libraries displayed on bacteriophage coat proteins have been described. Refinements of phage display approaches are also known, for example as described in WO96/06213 and WO92/01047 (Medical Research Council et al.) and WO97/08320 (Morphosys), which are incorporated herein by reference.

Other systems for generating libraries of polypeptides involve the use of cell-free enzymatic machinery for the in vitro synthesis of the library members. In one method, RNA molecules are selected by alternate rounds of selection against a target and PCR amplification (Tuerk and Gold (1990) *Science*, 249: 505; Ellington and Szostak (1990) *Nature*, 346: 818). A similar technique may be used to identify DNA sequences which bind a predetermined human transcription factor (Thiesen and Bach (1990) *Nucleic Acids Res.*, 18:3203; Beaudry and Joyce (1992) *Science*, 257:635; WO92/05258 and WO92/14843). In a similar way, in vitro translation can be used to synthesise polypeptides as a method for generating large libraries. These methods which generally comprise stabilised polysome complexes, are described further in WO88/08453, WO90/05785, WO90/07003, WO91/02076, WO91/05058, and WO92/02536. Alternative display systems which are not phage-based, such as those disclosed in WO95/22625 and WO95/11922 (Affymax) use the polysomes to display polypeptides for selection.

A still further category of techniques involves the selection of repertoires in artificial compartments, which allow the linkage of a gene with its gene product. For example, a selection system in which nucleic acids encoding desirable gene products may be selected in microcapsules formed by water-in-oil emulsions is described in WO99/02671, WO00/40712 and Tawfik & Griffiths (1998) *Nature Biotechnol* 16(7), 652-6. Genetic elements encoding a gene product having a desired activity are compartmentalised into microcapsules and then transcribed and/or translated to produce their respective gene products (RNA or protein) within the microcapsules. Genetic elements which produce gene product having desired activity are subsequently sorted. This approach selects gene products of interest by detecting the desired activity by a variety of means.

Library Construction

Libraries intended for selection, may be constructed using techniques known in the art, for example as set forth above, or may be purchased from commercial sources. Libraries which are useful in the present invention are described, for example, in WO99/20749. Once a vector system is chosen and one or more nucleic acid sequences encoding polypeptides of interest are cloned into the library vector, one may generate diversity within the cloned molecules by undertaking mutagenesis prior to expression; alternatively, the encoded proteins may be expressed and selected, as described above, before mutagenesis and additional rounds of selection are performed. Mutagenesis of nucleic acid sequences encoding structurally optimized polypeptides is carried out by standard molecular methods. Of particular use is the polymerase chain reaction, or PCR, (Mullis and Faloona (1987) *Methods Enzymol.*, 155: 335, herein incorporated by reference). PCR, which uses multiple cycles of DNA replication catalyzed by a thermostable, DNA-dependent DNA polymerase to amplify the target sequence of interest, is well known in the art. The construction of various antibody libraries has been discussed in Winter et al. (1994) Ann. Rev. Immunology 12, 433-55, and references cited therein.

PCR is performed using template DNA (at least 1 fg; more usefully, 1-1000 ng) and at least 25 pmol of oligonucleotide primers; it may be advantageous to use a larger amount of primer when the primer pool is heavily heterogeneous, as each sequence is represented by only a small fraction of the molecules of the pool, and amounts become limiting in the later amplification cycles. A typical reaction mixture includes: 2 µl of DNA, 25 pmol of oligonucleotide primer, 2.5 µl of 10×PCR buffer 1 (Perkin-Elmer, Foster City, Calif.), 0.4 µl of 1.25 µM dNTP, 0.15 µl (or 2.5 units) of Taq DNA polymerase (Perkin Elmer, Foster City, Calif.) and deionized water to a total volume of 25 µl. Mineral oil is overlaid and the PCR is performed using a programmable thermal cycler. The length and temperature of each step of a PCR cycle, as well as the number of cycles, is adjusted in accordance to the stringency requirements in effect. Annealing temperature and timing are determined both by the efficiency with which a primer is expected to anneal to a template and the degree of mismatch that is to be tolerated; obviously, when nucleic acid molecules are simultaneously amplified and mutagenised, mismatch is required, at least in the first round of synthesis. The ability to optimise the stringency of primer annealing conditions is well within the knowledge of one of moderate skill in the art. An annealing temperature of between 30° C. and 72° C. is used. Initial denaturation of the template molecules normally occurs at between 92° C. and 99° C. for 4 minutes, followed by 20-40 cycles consisting of denaturation (94-99° C. for 15 seconds to 1 minute), annealing (temperature determined as discussed above; 1-2 minutes), and extension (72° C. for 1-5 minutes, depending on the length of the amplified product). Final extension is generally for 4 minutes at 72° C., and may be followed by an indefinite (0-24 hour) step at 4° C.

Combining Single Variable Domains

Domains useful in the invention, once selected, may be combined by a variety of methods known in the art, including covalent and non-covalent methods. Preferred methods include the use of polypeptide linkers, as described, for example, in connection with scFv molecules (Bird et al., (1988) Science 242:423-426). Discussion of suitable linkers is provided in Bird et al. Science 242, 423-426; Hudson et al, Journal Immunol Methods 231 (1999) 177-189; Hudson et al, Proc Nat Acad Sci USA 85, 5879-5883. Linkers are preferably flexible, allowing the two single domains to interact. One linker example is a $(Gly_4 Ser)_n$ linker, where n=1 to 8, eg, 2, 3, 4, 5 or 7. The linkers used in diabodies, which are less flexible, may also be employed (Holliger et al., (1993) PNAS (USA) 90:6444-6448). In one embodiment, the linker employed is not an immunoglobulin hinge region.

Variable domains may be combined using methods other than linkers. For example, the use of disulphide bridges, provided through naturally-occurring or engineered cysteine residues, may be exploited to stabilize $V_H$-$V_H$, $V_L$-$V_L$ or $V_H$-$V_L$ dimers (Reiter et al., (1994) Protein Eng. 7:697-704) or by remodelling the interface between the variable domains to improve the "fit" and thus the stability of interaction (Ridgeway et al., (1996) Protein Eng. 7:617-621; Zhu et al., (1997) Protein Science 6:781-788). Other techniques for joining or stabilizing variable domains of immunoglobulins, and in particular antibody $V_H$ domains, may be employed as appropriate.

Characterisation of Ligands

The binding of a dual-specific ligand to the cell or the binding of each binding domain to each specific target can be tested by methods which will be familiar to those skilled in the art and include ELISA. In a preferred embodiment of the invention binding is tested using monoclonal phage ELISA. Phage ELISA may be performed according to any suitable procedure: an exemplary protocol is set forth below.

Populations of phage produced at each round of selection can be screened for binding by ELISA to the selected antigen or epitope, to identify "polyclonal" phage antibodies. Phage from single infected bacterial colonies from these populations can then be screened by ELISA to identify "monoclonal" phage antibodies. It is also desirable to screen soluble antibody fragments for binding to antigen or epitope, and this can also be undertaken by ELISA using reagents, for example, against a C- or N-terminal tag (see for example Winter et al. (1994) Ann. Rev. Immunology 12, 433-55 and references cited therein.

The diversity of the selected phage monoclonal antibodies may also be assessed by gel electrophoresis of PCR products (Marks et al. 1991, supra; Nissim et al. 1994 supra), probing (Tomlinson et al., 1992) J. Mol. Biol. 227, 776) or by sequencing of the vector DNA.

Structure of Ligands

In the case that each variable domains are selected from V-gene repertoires selected for instance using phage display technology as herein described, then these variable domains comprise a universal framework region, such that is they may be recognized by a specific generic dual-specific ligand as herein defined. The use of universal frameworks, generic ligands and the like is described in WO99/20749.

Where V-gene repertoires are used variation in polypeptide sequence is preferably located within the structural loops of the variable domains. The polypeptide sequences of either variable domain may be altered by DNA shuffling or by mutation in order to enhance the interaction of each variable domain with its complementary pair. DNA shuffling is known in the art and taught, for example, by Stemmer, 1994, Nature 370: 389-391 and U.S. Pat. No. 6,297,053, both of which are incorporated herein by reference. Other methods of mutagenesis are well known to those of skill in the art.

In general, nucleic acid molecules and vector constructs required for selection, preparation and formatting dual-specific ligands may be constructed and manipulated as set forth in standard laboratory manuals, such as Sambrook et al. (1989) *Molecular Cloning: A Laboratory Manual*, Cold Spring Harbor, USA.

The manipulation of nucleic acids useful in the present invention is typically carried out in recombinant vectors. As used herein, vector refers to a discrete element that is used to introduce heterologous DNA into cells for the expression and/or replication thereof. Methods by which to select or construct and, subsequently, use such vectors are well known to one of ordinary skill in the art. Numerous vectors are publicly available, including bacterial plasmids, bacteriophage, artificial chromosomes and episomal vectors. Such vectors may be used for simple cloning and mutagenesis; alternatively gene expression vector is employed. A vector of use according to the invention may be selected to accommodate a polypeptide coding sequence of a desired size, typically from 0.25 kilobase (kb) to 40 kb or more in length A suitable host cell is transformed with the vector after in vitro cloning manipulations. Each vector contains various functional components, which generally include a cloning (or "polylinker") site, an origin of replication and at least one selectable marker gene. If given vector is an expression vector, it additionally possesses one or more of the following: enhancer element, promoter, transcription termination and signal sequences, each positioned in the vicinity of the cloning site, such that they are operatively linked to the gene encoding a dual-specific ligand according to the invention.

Both cloning and expression vectors generally contain nucleic acid sequences that enable the vector to replicate in one or more selected host cells. Typically in cloning vectors, this sequence is one that enables the vector to replicate independently of the host chromosomal DNA and includes origins of replication or autonomously replicating sequences. Such sequences are well known for a variety of bacteria, yeast and viruses. The origin of replication from the plasmid pBR322 is suitable for most Gram-negative bacteria, the 2 micron plasmid origin is suitable for yeast, and various viral origins (e.g. SV 40, adenovirus) are useful for cloning vectors in mammalian cells. Generally, the origin of replication is not needed for mammalian expression vectors unless these are used in mammalian cells able to replicate high levels of DNA, such as COS cells.

Advantageously, a cloning or expression vector may contain a selection gene also referred to as selectable marker. This gene encodes a protein necessary for the survival or growth of transformed host cells grown in a selective culture medium. Host cells not transformed with the vector containing the selection gene will therefore not survive in the culture medium. Typical selection genes encode proteins that confer resistance to antibiotics and other toxins, e.g. ampicillin, neomycin, methotrexate or tetracycline, complement auxotrophic deficiencies, or supply critical nutrients not available in the growth media.

Since the replication of vectors encoding a dual-specific ligand according to the present invention is most conveniently performed in *E. coli*, an *E. coli*-selectable marker, for example, the β-lactamase gene that confers resistance to the antibiotic ampicillin, is of use. These can be obtained from *E. coli* plasmids, such as pBR322 or a pUC plasmid such as pUC18 or pUC19.

Expression vectors usually contain a promoter that is recognised by the host organism and is operably linked to the coding sequence of interest. Such a promoter may be inducible or constitutive. The term "operably linked" refers to a juxtaposition wherein the components described are in a relationship permitting them to function in their intended manner. A control sequence "operably linked" to a coding sequence is ligated in such a way that expression of the coding sequence is achieved under conditions compatible with the control sequences.

Promoters suitable for use with prokaryotic hosts include, for example, the β-lactamase and lactose promoter systems, alkaline phosphatase, the tryptophan (trp) promoter system and hybrid promoters such as the tac promoter. Promoters for use in bacterial systems will also generally contain a Shine-Delgarno sequence operably linked to the coding sequence.

The preferred vectors The preferred vectors are expression vectors that enables the expression of a nucleotide sequence corresponding to a polypeptide library member. Thus, selection with the first and/or second antigen or epitope can be performed by separate propagation and expression of a single clone expressing the polypeptide library member or by use of any selection display system. As described above, the preferred selection display system is bacteriophage display. Thus, phage or phagemid vectors may be used, eg pIT1 or pIT2. Leader sequences useful in the invention include pelB, stII, ompA, phoA, bla and pelA. One example are phagemid vectors which have an E. coli. origin of replication (for double stranded replication) and also a phage origin of replication (for production of single-stranded DNA). The manipulation and expression of such vectors is well known in the art (Hoogenboom and Winter (1992) supra; Nissim et al. (1994) supra). Briefly, the vector contains a β-lactamase gene to confer selectivity on the phagemid and a lac promoter upstream of a expression cassette that consists (N to C terminal) of a pelB leader sequence (which directs the expressed polypeptide to the periplasmic space), a multiple cloning site (for cloning the nucleotide version of the library member), optionally, one or more peptide tag (for detection), optionally, one or more TAG stop codon and the phage protein pIII. Thus, using various suppressor and non-suppressor strains of E. coli and with the addition of glucose, iso-propyl thio-β-D-galactoside (IPTG) or a helper phage, such as VCS M13, the vector is able to replicate as a plasmid with no expression, produce large quantities of the polypeptide library member only or produce phage, some of which contain at least one copy of the polypeptide-pIII fusion on their surface.

Construction of vectors encoding dual-specific ligands according to the invention employs conventional ligation techniques. Isolated vectors or DNA fragments are cleaved, tailored, and religated in the form desired to generate the required vector. If desired, analysis to confirm that the correct sequences are present in the constructed vector can be performed in a known fashion. Suitable methods for constructing expression vectors, preparing in vitro transcripts, introducing DNA into host cells, and performing analyses for assessing expression and function are known to those skilled in the art. The presence of a gene sequence in a sample is detected, or its amplification and/or expression quantified by conventional methods, such as Southern or Northern analysis, Western blotting, dot blotting of DNA, RNA or protein, in situ hybridisation, immunocytochemistry or sequence analysis of nucleic acid or protein molecules. Those skilled in the art will readily envisage how these methods may be modified, if desired.

Skeletons

Skeletons may be based on immunoglobulin molecules or may be non-immunoglobulin in origin as set forth above. Each domain of the dual-specific ligand may be a different skeleton. Preferred immunoglobulin skeletons as herein defined includes any one or more of those selected from the following: an immunoglobulin molecule comprising at least (i) the CL (kappa or lambda subclass) domain of an antibody; or (ii) the CH1 domain of an antibody heavy chain; an immunoglobulin molecule comprising the CH1 and CH2 domains of an antibody heavy chain; an immunoglobulin molecule comprising the CH1, CH2 and CH3 domains of an antibody heavy chain; or any of the subset (ii) in conjunction with the CL (kappa or lambda subclass) domain of an antibody. A hinge region domain may also be included. Such combinations of domains may, for example, mimic natural antibodies, such as IgG or IgM, or fragments thereof, such as Fv, scFv, Fab or F(ab')$_2$ molecules. Those skilled in the art will be aware that this list is not intended to be exhaustive.

Protein Scaffolds

Each binding domain comprises a protein scaffold and one or more CDRs which are involved in the specific interaction of the domain with one or more epitopes. Advantageously, an epitope binding domain according to the present invention comprises three CDRs. Suitable protein scaffolds include any of those selected from the group consisting of the following: those based on immunoglobulin domains, those based on fibronectin, those based on affibodies, those based on CTLA4, those based on chaperones such as GroEL, those based on lipocallin and those based on the bacterial Fc receptors SpA and SpD. Those skilled in the art will appreciate that this list is not intended to be exhaustive.

Scaffolds for Use in Constructing Ligands

Selection of the Main-Chain Conformation

The members of the immunoglobulin superfamily all share a similar fold for their polypeptide chain. For example, although antibodies are highly diverse in terms of their primary sequence, comparison of sequences and crystallographic structures has revealed that, contrary to expectation, five of the six antigen binding loops of antibodies (H1, H2, L1, L2, L3) adopt a limited number of main-chain conformations, or canonical structures (Chothia and Lesk (1987) *J. Mol. Biol.*, 196: 901; Chothia et al. (1989) *Nature*, 342: 877). Analysis of loop lengths and key residues has therefore enabled prediction of the main-chain conformations of H1, H2, L1, L2 and L3 found in the majority of human antibodies (Chothia et al. (1992) *J. Mol. Biol.*, 227: 799; Tomlinson et al. (1995) *EMBO J.*, 14: 4628; Williams et al. (1996) *J. Mol. Biol.*, 264: 220). Although the H3 region is much more diverse in terms of sequence, length and structure (due to the use of D segments), it also forms a limited number of main-chain conformations for short loop lengths which depend on the length and the presence of particular residues, or types of residue, at key positions in the loop and the antibody framework (Martin et al. (1996) *J. Mol. Biol.*, 263: 800; Shirai et al. (1996) *FEBS Letters*, 399: 1).

Libraries of ligands and/or binding domains can be designed in which certain loop lengths and key residues have been chosen to ensure that the main-chain conformation of the members is known. Advantageously, these are real conformations of immunoglobulin superfamily molecules found in nature, to minimize the chances that they are non-functional, as discussed above. Germline V gene segments serve as one suitable basic framework for constructing antibody or T-cell receptor libraries; other sequences are also of use. Variations may occur at a low frequency, such that a small number of functional members may possess an altered main-chain conformation, which does not affect its function.

Canonical structure theory is also of use to assess the number of different main-chain conformations encoded by ligands, to predict the main-chain conformation based on dual-specific ligand sequences and to choose residues for diversification which do not affect the canonical structure. It is known that, in the human $V_\kappa$ domain, the L1 loop can adopt one of four canonical structures, the L2 loop has a single canonical structure and that 90% of human $V_\kappa$ domains adopt one of four or five canonical structures for the L3 loop (Tomlinson et al. (1995) supra); thus, in the $V_\kappa$ domain alone, different canonical structures can combine to create a range of different main-chain conformations. Given that the $V_\lambda$ domain encodes a different range of canonical structures for the L1, L2 and L3 loops and that $V_\kappa$ and $V_\lambda$ domains can pair with any $V_H$ domain which can encode several canonical structures for the H1 and H2 loops, the number of canonical structure combinations observed for these five loops is very large. This implies that the generation of diversity in the main-chain conformation may be essential for the production of a wide range of binding specificities. However, by constructing an antibody library based on a single known main-chain conformation it has been found, contrary to expectation, that diversity in the main-chain conformation is not required to generate sufficient diversity to target substantially all antigens. Even more surprisingly, the single main-chain conformation need not be a consensus structure—a single naturally occurring conformation can be used as the basis for an entire library. Thus, in a preferred aspect, the ligands of the invention possess a single known main-chain conformation.

The single main-chain conformation that is chosen is preferably commonplace among molecules of the immunoglobulin superfamily type in question. A conformation is commonplace when a significant number of naturally occurring molecules are observed to adopt it. Accordingly, in a preferred aspect of the invention, the natural occurrence of the different main-chain conformations for each binding loop of an immunoglobulin domain are considered separately and then a naturally occurring variable domain is chosen which possesses the desired combination of main-chain conformations for the different loops. If none is available, the nearest equivalent may be chosen. It is preferable that the desired combination of main-chain conformations for the different loops is created by selecting germline gene segments which encode the desired main-chain conformations. It is more preferable, that the selected germline gene segments are frequently expressed in nature, and most preferable that they are the most frequently expressed of all natural germline gene segments.

In designing ligands (e.g., ds-dAbs) or libraries thereof the incidence of the different main-chain conformations for each of the six antigen binding loops may be considered separately. For H1, H2, L1, L2 and L3, a given conformation that is adopted by between 20% and 100% of the antigen binding loops of naturally occurring molecules is chosen. Typically, its observed incidence is above 35% (i.e. between 35% and 100%) and, ideally, above 50% or even above 65%. Since the vast majority of H3 loops do not have canonical structures, it is preferable to select a main-chain conformation which is commonplace among those loops which do display canonical structures. For each of the loops, the conformation which is observed most often in the natural repertoire is therefore selected. In human antibodies, the most popular canonical structures (CS) for each loop are as follows: H1-CS 1 (79% of the expressed repertoire), H2-CS 3 (46%), L1-CS 2 of $V_\kappa$ (39%), L2-CS 1 (100%), L3-CS 1 of $V_\kappa$ (36%) (calculation assumes a κ:λ ratio of 70:30, Hood et al. (1967) *Cold Spring Harbor Symp. Quant. Biol.*, 48: 133). For H3 loops that have canonical structures, a CDR3 length (Kabat et al. (1991) Sequences of proteins of immunological interest, U.S. Department of Health and Human Services) of seven residues with a salt-bridge from residue 94 to residue 101 appears to be the most common. There are at least 16 human antibody sequences in the EMBL data library with the required H3 length and key residues to form this conformation and at least two crystallographic structures in the protein data bank which can be used as a basis for antibody modelling (2cgr and 1tet). The most frequently expressed germline gene segments that this combination of canonical structures are the $V_H$ segment 3-23 (DP-47), the $J_H$ segment JH4b, the $V_\kappa$ segment O2/O12 (DPK9) and the $J_\kappa$ segment $J_\kappa 1$. $V_H$ segments DP45 and DP38 are also suitable. These segments can therefore be used in combination as a basis to construct a library with the desired single main-chain conformation.

Alternatively, instead of choosing the single main-chain conformation based on the natural occurrence of the different main-chain conformations for each of the binding loops in isolation, the natural occurrence of combinations of main-chain conformations is used as the basis for choosing the single main-chain conformation. In the case of antibodies, for example, the natural occurrence of canonical structure combinations for any two, three, four, five or for all six of the antigen binding loops can be determined. Here, it is preferable that the chosen conformation is commonplace in naturally occurring antibodies and most preferable that it observed most frequently in the natural repertoire. Thus, in human antibodies, for example, when natural combinations of the five antigen binding loops, H1, H2, L1, L2 and L3, are considered, the most frequent combination of canonical structures is determined and then combined with the most popular conformation for the H3 loop, as a basis for choosing the single main-chain conformation.

Diversification of the Canonical Sequence

Having selected several known main-chain conformations or, preferably a single known main-chain conformation, dual-specific ligands (e.g., ds-dAbs) or libraries for use in the invention can be constructed by varying each binding site of the molecule in order to generate a repertoire with structural and/or functional diversity. This means that variants are generated such that they possess sufficient diversity in their structure and/or in their function so that they are capable of providing a range of activities.

The desired diversity is typically generated by varying the selected molecule at one or more positions. The positions to be changed can be chosen at random or are preferably selected. The variation can then be achieved either by randomisation, during which the resident amino acid is replaced by any amino acid or analogue thereof, natural or synthetic, producing a very large number of variants or by replacing the resident amino acid with one or more of a defined subset of amino acids, producing a more limited number of variants.

Various methods have been reported for introducing such diversity. Error-prone PCR (Hawkins et al. (1992) *J. Mol. Biol.*, 226: 889), chemical mutagenesis (Deng et al. (1994) *J. Biol. Chem.*, 269: 9533) or bacterial mutator strains (Low et al. (1996) *J. Mol. Biol.*, 260: 359) can be used to introduce random mutations into the genes that encode the molecule. Methods for mutating selected positions are also well known in the art and include the use of mismatched oligonucleotides or degenerate oligonucleotides, with or without the use of PCR. For example, several synthetic antibody libraries have been created by targeting mutations to the antigen binding loops. The H3 region of a human tetanus toxoid-binding Fab has been randomised to create a range of new binding specificities (Barbas et al. (1992) *Proc. Natl. Acad. Sci. USA*, 89: 4457). Random or semi-random H3 and L3 regions have been appended to germline V gene segments to produce large libraries with unmutated framework regions (Hoogenboom & Winter (1992) *J. Mol. Biol.,* 227: 381; Barbas et al. (1992) *Proc. Natl. Acad. Sci. USA,* 89: 4457; Nissim et al. (1994) *EMBO J.,* 13: 692; Griffiths et al. (1994) *EMBO J.,* 13: 3245; De Kruif et al. (1995) *J. Mol. Biol.,* 248: 97). Such diversification has been extended to include some or all of the other antigen binding loops (Crameri et al. (1996) *Nature Med.,* 2: 100; Riechmann et al. (1995) *Bio/Technology,* 13: 475; Morphosys, WO97/08320, supra).

Since loop randomization has the potential to create approximately more than $10^{15}$ structures for H3 alone and a similarly large number of variants for the other five loops, it is not feasible using current transformation technology or even by using cell free systems to produce a library representing all possible combinations. For example, in one of the largest libraries constructed to date, $6 \times 10^{10}$ different antibodies, which is only a fraction of the potential diversity for a library of this design, were generated (Griffiths et al. (1994) supra).

Preferably, only the residues that are directly involved in creating or modifying the desired function of each domain of the dual-specific ligand molecule are diversified. For many molecules, the function of each domain will be to bind a target and therefore diversity should be concentrated in the target binding site, while avoiding changing residues which are crucial to the overall packing of the molecule or to maintaining the chosen main-chain conformation.

Diversification of the Canonical Sequence as it Applies to Antibody Domains

In the case of antibody based ligands (e.g., ds-dAbs), the binding site for each target is most often the antigen binding site. Thus, preferably only those residues in the antigen binding site are varied. These residues are extremely diverse in the human antibody repertoire and are known to make contacts in high-resolution antibody/antigen complexes. For example, in L2 it is known that positions 50 and 53 are diverse in naturally occurring antibodies and are observed to make contact with the antigen. In contrast, the conventional approach would have been to diversify all the residues in the corresponding Complementarity Determining Region (CDR1) as defined by Kabat et al. (1991, supra), some seven residues compared to the two diversified in the library for use according to the invention. This represents a significant improvement in terms of the functional diversity required to create a range of antigen binding specificities.

In nature, antibody diversity is the result of two processes: somatic recombination of germline V, D and J gene segments to create a naive primary repertoire (so called germline and junctional diversity) and somatic hypermutation of the resulting rearranged V genes. Analysis of human antibody sequences has shown that diversity in the primary repertoire is focused at the centre of the antigen binding site whereas somatic hypermutation spreads diversity to regions at the periphery of the antigen binding site that are highly conserved in the primary repertoire (see Tomlinson et al. (1996) *J. Mol. Biol.,* 256: 813). This complementarity has probably evolved as an efficient strategy for searching sequence space and, although apparently unique to antibodies, it can easily be applied to other polypeptide repertoires. The residues which are varied are a subset of those that form the binding site for the target. Different (including overlapping) subsets of residues in the target binding site are diversified at different stages during selection, if desired.

In the case of an antibody repertoire, an initial 'naive' repertoire can be created where some, but not all, of the residues in the antigen binding site are diversified. As used herein in this context, the term "naive" refers to antibody molecules that have no pre-determined target. These molecules resemble those which are encoded by the immunoglobulin genes of an individual who has not undergone immune diversification, as is the case with fetal and newborn individuals, whose immune systems have not yet been challenged by a wide variety of antigenic stimuli. This repertoire is then selected against a range of antigens or epitopes. If required, further diversity can then be introduced outside the region diversified in the initial repertoire. This matured repertoire can be selected for modified function, specificity or affinity.

Naive repertoires of binding domains for the construction of dual-specific ligands in which some or all of the residues in the antigen binding site are varied are known in the art. (See, WO 2004/058821, WO 2004/003019, and WO 03/002609). The "primary" library mimics the natural primary repertoire, with diversity restricted to residues at the centre of the antigen binding site that are diverse in the germline V gene segments (germline diversity) or diversified during the recombination process (junctional diversity). Those residues which are diversified include, but are not limited to, H50, H52, H52a, H53, H55, H56, H58, H95, H96, H97, H98, L50, L53, L91, L92, L93, L94 and L96. In the "somatic" library, diversity is restricted to residues that are diversified during the recombination process (junctional diversity) or are highly somatically mutated). Those residues which are diversified include, but are not limited to: H31, H33, H35, H95, H96, H97, H98, L30, L31, L32, L34 and L96. All the residues listed above as suitable for diversification in these libraries are known to make contacts in one or more antibody-antigen complexes. Since in both libraries, not all of the residues in the antigen binding site are varied, additional diversity is incorporated during selection by varying the remaining residues, if it is desired to do so. It shall be apparent to one skilled in the art that any subset of any of these residues (or additional residues which comprise the antigen binding site) can be used for the initial and/or subsequent diversification of the antigen binding site.

In the construction of libraries for use in the invention, diversification of chosen positions is typically achieved at the nucleic acid level, by altering the coding sequence which specifies the sequence of the polypeptide such that a number of possible amino acids (all 20 or a subset thereof) can be incorporated at that position. Using the IUPAC nomenclature, the most versatile codon is NNK, which encodes all amino acids as well as the TAG stop codon. The NNK codon is preferably used in order to introduce the required diversity. Other codons which achieve the same ends are also of use, including the NNN codon, which leads to the production of the additional stop codons TGA and TAA.

A feature of side-chain diversity in the antigen binding site of human antibodies is a pronounced bias which favors certain amino acid residues. If the amino acid composition of the ten most diverse positions in each of the $V_H$, $V_\kappa$ and $V_\lambda$ regions are summed, more than 76% of the side-chain diversity comes from only seven different residues, these being, serine (24%), tyrosine (14%), asparagine (11%), glycine (9%), alanine (7%), aspartate (6%) and threonine (6%). This bias towards hydrophilic residues and small residues which can provide main-chain flexibility probably reflects the evolution of surfaces which are predisposed to binding a wide range of antigens or epitopes and may help to explain the required promiscuity of antibodies in the primary repertoire.

Since it is preferable to mimic this distribution of amino acids, the distribution of amino acids at the positions to be varied preferably mimics that seen in the antigen binding site of antibodies. Such bias in the substitution of amino acids that permits selection of certain polypeptides (not just antibody polypeptides) against a range of target antigens is easily applied to any polypeptide repertoire. There are various methods for biasing the amino acid distribution at the position to be varied (including the use of tri-nucleotide mutagenesis, see WO97/08320), of which the preferred method, due to ease of synthesis, is the use of conventional degenerate codons. By comparing the amino acid profile encoded by all combinations of degenerate codons (with single, double, triple and quadruple degeneracy in equal ratios at each position) with the natural amino acid use it is possible to calculate the most representative codon. The codons (AGT)(AGC)T, (AGT)(AGC)C and (AGT)(AGC)(CT)—that is, DVT, DVC and DVY, respectively using IUPAC nomenclature—are those closest to the desired amino acid profile: they encode 22% serine and 11% tyrosine, asparagine, glycine, alanine, aspartate, threonine and cysteine. Preferably, therefore, libraries are constructed using either the DVT, DVC or DVY codon at each of the diversified positions.

Therapeutic and Diagnostic Compositions and Uses

The invention provides compositions comprising the ligands of the invention and a pharmaceutically acceptable carrier, diluent or excipient, and therapeutic and diagnostic methods that employ the ligands or compositions of the invention. The ligands according to the method of the present invention may be employed in vivo therapeutic and prophylactic applications, in vivo diagnostic applications and the like.

Therapeutic and prophylactic uses of ligands of the invention involve the administration of ligands according to the invention to a recipient mammal, such as a human. The ligands bind to targets with high affinity and/or avidity. In some embodiments, such as IgG-like ligands, the ligands can allow recruitment of cytotoxic cells to mediate killing of camcer cells, for example by antibody dependent cellular cytoxicity.

Substantially pure ligands of at least 90 to 95% homogeneity are preferred for administration to a mammal, and 98 to 99% or more homogeneity is most preferred for pharmaceutical uses, especially when the mammal is a human. Once purified, partially or to homogeneity as desired, the ligands may be used diagnostically or therapeutically (including extracorporeally) or in developing and performing assay procedures, immunofluorescent stainings and the like (Lefkovite and Pernis, (1979 and 1981) Immunological Methods, Volumes I and II, Academic Press, NY).

For example, the ligands, of the present invention will typically find use in preventing, suppressing or treating disease states. For example, ligands can be administered to treat, suppress or prevent a chronic inflammatory disease, allergic hypersensitivity, cancer, bacterial or viral infection, autoimmune disorders (which include, but are not limited to, Type I diabetes, asthma, multiple sclerosis, rheumatoid arthritis, juvenile rheumatoid arthritis, psoriatic arthritis, spondylarthropathy (e.g., ankylosing spondylitis), systemic lupus erythematosus, inflammatory bowel disease (e.g., Crohn's disease, ulcerative colitis), myasthenia gravis and Behcet's syndrome), psoriasis, endometriosis, and abdominal adhesions (e.g., post abdominal surgery).

The ligands are useful for treating infectious diseases in which cells infected with an infectious agent contain higer levels of cell surface EGFR than uninfected cells or that contain one or more cell surface targets that are not present on ininfected cells, such as a protein that is encoded by the infectious agent (e.g., bacteria, virus).

Ligands according to the invention that are able to bind to EGFR can be internalized by cells that express EGFR (e.g., endocytosed), and can deliver therapeutic agents (e.g., a toxin) intracellularly (e.g., deliver a dAb that binds an intracellular target). In addition, ligands, provide a means by which a binding domain (e.g., a dAb monomer) that is specificity able to bind to an intracellular target can be delivered to an intracellular environment. This strategy requires, for example, a binding domain with physical properties that enable it to remain functional inside the cell. Alternatively, if the final destination intracellular compartment is oxidising, a well folding ligand may not need to be disulphide free.

In the instant application, the term "prevention" involves administration of the protective composition prior to the induction of the disease. "Suppression" refers to administration of the composition after an inductive event, but prior to the clinical appearance of the disease. "Treatment" involves administration of the protective composition after disease symptoms become manifest. Treatment includes ameliorating symptoms associated with the disease, and also preventing or delaying the onset of the disease and also lessening the severity or frequency of symptoms of the disease.

The terms "cancer" refers to the pathological condition in mammals that is typically characterized by dysregulated cellular proliferation or survival. Examples of cancer include, but are not limited to, carcinoma, lymphoma, blastoma, sarcoma, and leukemia and lymphoid malignancies. More particular examples of cancers include squamous cell cancer (e.g. epithelial squamous cell cancer), lung cancer (e.g., small-cell lung carcinoma, non-small cell lung carcinoma, adenocarcinoma of the lung, squamous carcinoma of the lung), cancer of the peritoneum, hepatocellular cancer, gastric or stomach cancer including gastrointestinal cancer, pancreatic cancer, glioblastoma, cervical cancer, ovarian cancer, liver cancer, bladder cancer, gall bladder cancer, hepatoma, breast cancer, colon cancer, rectal cancer, colorectal cancer, multiple myeloma, chronic myelogenous leukemia, acute myelogenous leukemia, endometrial or uterine carcinoma, salivary gland carcinoma, kidney or renal cancer, prostate cancer, vulval cancer, thyroid cancer, hepatic carcinoma, anal carcinoma, penile carcinoma, head and neck cancer, and the like. Cancers characterized by expression of EGFR on the surface of cancerous cells (EGFR-expressing cancers) include, for example, bladder cancer, ovarian cancer, colorectal cancer, breast cancer, lung cancer (e.g., non-small cell lung carcinoma), gastric cancer, pancreatic cancer, prostate cancer, head and neck cancer, renal cancer and gall bladder cancer.

Animal model systems which can be used to assess efficacy of the ligands of the inventon in preventing treating or suppressing disease (e.g., cancer) are available. Suitable models of cancer include, for example, xenograft and orthotopic models of human cancers in animal models, such as the SCID-hu myeloma model (Epstein J, and Yaccoby, S., *Methods Mol Med.* 113:183-90 (2005), Tassone P, et al., *Clin Cancer Res.* 11(11):4251-8 (2005)), mouse models of human lung cancer (e.g., Meuwissen R and Berns A, *Genes Dev.* 19(6):643-64 (2005)), and mouse models of metastatic cancers (e.g., Kubota T., *J Cell Biochem.* 56(1):4-8 (1994)).

Generally, the present ligands will be utilized in purified form together with pharmacologically appropriate carriers. Typically, these carriers include aqueous or alcoholic/aqueous solutions, emulsions or suspensions, any including saline and/or buffered media. Parenteral vehicles include sodium chloride solution, Ringer's dextrose, dextrose and sodium chloride and lactated Ringer's. Suitable physiologically-acceptable adjuvants, if necessary to keep a polypeptide complex in suspension, may be chosen from thickeners such as carboxymethylcellulose, polyvinylpyrrolidone, gelatin and alginates.

Intravenous vehicles include fluid and nutrient replenishers and electrolyte replenishers, such as those based on Ringer's dextrose. Preservatives and other additives, such as antimicrobials, antioxidants, chelating agents and inert gases, may also be present (Mack (1982) *Remington's Pharmaceutical Sciences,* 16th Edition). A variety of suitable formulations can be used, including extended release formulations.

The ligand of the present invention may be used as separately administered compositions or in conjunction with other agents. The ligands can be administered and or formulated together with one or more additional therapeutic or active agents. When a lligand is administered with an additional therapeutic agent, the ligand can be administered before, simultaneously with or subsequent to administration of the additional agent. Generally, the ligand) and additional agent are administered in a manner that provides an overlap of therapeutic effect. Additional agents that can be administered or formulated with the ligand of the invention include, for example, various immunotherapeutic drugs, such as cylcosporine, methotrexate, adriamycin or cisplatinum, antibiotics, antimycotics, anti-viral agents and immunotoxins. For example, when the antagonist is administered to prevent, suppress or treat lung inflammation or a respiratory disease, it can be administered in conjuction with phosphodiesterase inhibitors (e.g., inhibitors of phosphodiesterase 4), bronchodilators (e.g., beta2-agonists, anticholinergerics, theophylline), short-acting beta-agonists (e.g., albuterol, salbutamol, bambuterol, fenoterol, isoetherine, isoproterenol, levalbuterol, metaproterenol, pirbuterol, terbutaline and tomlate), long-acting beta-agonists (e.g., formoterol and salmeterol), short acting anticholinergics (e.g., ipratropium bromide and oxitropium bromide), long-acting anticholinergics (e.g., tiotropium), theophylline (e.g. short acting formulation, long acting formulation), inhaled steroids (e.g., beclomethasone, beclometasone, budesonide, flunisolide, fluticasone propionate and triamcinolone), oral steroids (e.g., methylprednisolone, prednisolone, prednisolon and prednisone), combined short-acting beta-agonists with anticholinergics (e.g., albuterol/salbutamol/ipratopium, and fenoterol/ipratopium), combined long-acting beta-agonists with inhaled steroids (e.g., salmeterol/fluticasone, and formoterol/budesonide) and mucolytic agents (e.g., erdosteine, acetylcysteine, bromheksin, carbocysteine, guiafenesin and iodinated glycerol.

The ligands of the invention can be coadministered (e.g., to treat cancer, an inflammatory disease or other disease) with a variety of suitable co-therapeutic agents, including cytokines, analgesics/antipyretics, antiemetics, and chemotherapeutics. Further suitable co-therapeutic agents include immunosuppressive agents selected from the group consisting of cyclosporine, azathioprine, mycophenolic acid, mycophenolate mofetil, corticosteroids, methotrexate, gold salts, sulfasalazine, antimalarials, brequinar, leflunomide, mizoribine, 15-deoxyspergualine, 6-mercaptopurine, cyclophosphamide, rapamycin, tacrolimus (FK-506), OKT3, and anti-thymocyte globulin, anti-inflammatory agents selected from the group consisting of aspirin, other salicylates, steroidal drugs, NSAIDs (nonsteroidal anti-inflammatory drugs), Cox-2 inhibitors, and DMARDs (disease modifying antirheumatic drugs); anti-psoriasis agents selected from the group consisting of coal tar, A vitamin, anthralin, calcipotrien, tarazotene, corticosteroids, methotrexate, retinoids, cyclosporine, etanercept, alefacept, efaluzimab, 6-thioguanine, mycophenolate mofetil, tacrolimus (FK-506), and hydroxyurea.

Cytokines include, without limitation, a lymphokine, tumor necrosis factors, tumor necrosis factor-like cytokine, lymphotoxin, interferon, macrophage inflammatory protein, granulocyte monocyte colony stimulating factor, interleukin (including, without limitation, interleukin-1, interleukin-2, interleukin-6, interleukin-12, interleukin-15, interleukin-18), growth factors, which include, without limitation, (e.g., growth hormone, insulin-like growth factor 1 and 2 (IGF-1 and IGF-2), granulocyte colony stimulating factor (GCSF), platelet derived growth factor (PGDF), epidermal growth factor (EGF), and agents for erythropoiesis stimulation, e.g., recombinant human erythropoietin (Epoetin alfa), EPO, a hormonal agonist, hormonal antagonists (e.g., flutamide, tamoxifen, leuprolide acetate (LUPRON)), and steroids (e.g., dexamethasone, retinoid, betamethasone, cortisol, cortisone, prednisone, dehydrotestosterone, glucocorticoid, mineralocorticoid, estrogen, testosterone, progestin).

Analgesics/antipyretics can include, without limitation, (e.g., aspirin, acetaminophen, ibuprofen, naproxen sodium, buprenorphine hydrochloride, propoxyphene hydrochloride, propoxyphene napsylate, meperidine hydrochloride, hydromorphone hydrochloride, morphine sulfate, oxycodone hydrochloride, codeine phosphate, dihydrocodeine bitartrate, pentazocine hydrochloride, hydrocodone bitartrate, levorphanol tartrate, diflunisal, trolamine salicylate, nalbuphine hydrochloride, mefenamic acid, butorphanol tartrate, choline salicylate, butalbital, phenyltoloxamine citrate, diphenhydramine citrate, methotrimeprazine, cinnamedrine hydrochloride, meprobamate, and the like).

Antiemetics can also be coadministered to prevent or treat nausea and vomiting, e,g., suitable antiemetics include meclizine hydrochloride, nabilone, prochlorperazine, dimenhydrinate, promethazine hydrochloride, thiethylperazine, scopolamine, and the like).

Chemotherapeutic agents, as that term is used herein, include, but are not limited to, for example antimicrotubule agents, e.g., taxol (paclitaxel), taxotere (docetaxel); alkylating agents, e.g., cyclophosphamide, carmustine, lomustine, and chlorambucil; cytotoxic antibiotics, e.g., dactinomycin, doxorubicin, mitomycin-C, and bleomycin; antimetabolites, e.g., cytarabine, gemcitatin, methotrexate, and 5-fluorouracil; antimiotics, e.g., vincristine vinca alkaloids, e.g., etoposide, vinblastine, and vincristine; and others such as cisplatin, dacarbazine, procarbazine, and hydroxyurea; and combinations thereof.

The ligands of the invention can be used to treat cancer in combination with another therapeutic agent. Fore example, a ligand of the invention can be administered in combination with a chemotherapeutic agent or an antineoplastic compositon comprising a (at least one) chemotherapeutic agent. Advantageously, in such a therapeutic approach, the amount of chemotherapeutic agent that must be administered to be effective can be reduced. Thus the invention provides a method of treating cancer comprising administering to a patient in need thereof a therapeutically effective amount ot a ligand of the invention and a chemotherapeutic agent, wherein the chemotherapeutic agent is administered at a low dose. Generally the amount of chemotherapeutic agent that is coadministered with a ligand of the invention is about 80%, or about 70%, or about 60%, or about 50%, or about 40%, or about 30%, or about 20%, or about 10% or less, of the dose of chemotherapeutic agent alone that is normally administered to a patient. Thus, cotherapy is particularly advantageous when the chemotherapeutic agent causes deleterious or undesirable side effects that may be reduced or eliminated at a lower doses.

Pharmaceutical compositions can include "cocktails" of various cytotoxic or other agents in conjunction with ligands of the present invention, or even combinations of ligands according to the present invention having different specificities, such as ligands selected using different target antigens or epitopes, whether or not they are pooled prior to administration.

The route of administration of pharmaceutical compositions according to the invention may be any suitable route, such as any of those commonly known to those of ordinary skill in the art. For therapy, including without limitation immunotherapy, the ligands of the invention can be administered to any patient in accordance with standard techniques. The administration can be by any appropriate mode, including parenterally, intravenously, intramuscularly, intraperitoneally, transdermally, intrathecally, intraarticularly, via the pulmonary route, or also, appropriately, by direct infusion (e.g., with a catheter). The dosage and frequency of administration will depend on the age, sex and condition of the patient, concurrent administration of other drugs, counter-indications and other parameters to be taken into account by the clinician. Administration can be local (e.g., local delivery to the lung by pulmonary administration, (e.g., intranasal administration) or local injection directly into a tumor) or systemic as indicated.

The ligands of this invention can be lyophilised for storage and reconstituted in a suitable carrier prior to use. This technique has been shown to be effective with conventional immunoglobulins and art-known lyophilisation and reconstitution techniques can be employed. It will be appreciated by those skilled in the art that lyophilisation and reconstitution can lead to varying degrees of antibody activity loss (e.g. with conventional immunoglobulins, IgM antibodies tend to have greater activity loss than IgG antibodies) and that use levels may have to be adjusted upward to compensate.

The compositions containing the ligands can be administered for prophylactic and/or therapeutic treatments. In certain therapeutic applications, an adequate amount to accomplish at least partial inhibition, suppression, modulation, killing, or some other measurable parameter, of a population of selected cells is defined as a "therapeutically-effective dose". Amounts needed to achieve this dosage will depend upon the severity of the disease and the general state of the patient's health, but generally range from 0.005 to 5.0 mg of ligand per kilogram of body weight, with doses of 0.05 to 2.0 mg/kg/dose being more commonly used. For prophylactic applications, compositions containing the present ligands or cocktails thereof may also be administered in similar or slightly lower dosages, to prevent, inhibit or delay onset of disease (e.g., to sustain remission or quiescence, or to prevent acute phase). The skilled clinician will be able to determine the appropriate dosing interval to treat, suppress or prevent disease. When a ligand is administered to treat, suppress or prevent a disease, it can be administered up to four times per day, twice weekly, once weekly, once every two weeks, once a month, or once every two months, at a dose off, for example, about 10 µg/kg to about 80 mg/kg, about 100 µg/kg to about 80 mg/kg, about 1 mg/kg to about 80 mg/kg, about 1 mg/kg to about 70 mg/kg, about 1 mg/kg to about 60 mg/kg, about 1 mg/kg to about 50 mg/kg, about 1 mg/kg to about 40 mg/kg, about 1 mg/kg to about 30 mg/kg, about 1 mg/kg to about 20 mg/kg, about 1 mg/kg to about 10 mg/kg, about 10 µg/kg to about 10 mg/kg, about 10 µg/kg to about 5 mg/kg, about 10 µg/kg to about 2.5 mg/kg, about 1 mg/kg, about 2 mg/kg, about 3 mg/kg, about 4 mg/kg, about 5 mg/kg, about 6 mg/kg, about 7 mg/kg, about 8 mg/kg, about 9 mg/kg or about 10 mg/kg. In particular embodiments, the dual-specific ligand is administered to treat, suppress or prevent a chronic inflammatory disease once every two weeks or once a month at a dose of about 10 µg/kg to about 10 mg/kg (e.g., about 10 µg/kg, about 100 µg/kg, about 1 mg/kg, about 2 mg/kg, about 3 mg/kg, about 4 mg/kg, about 5 mg/kg, about 6 mg/kg, about 7 mg/kg, about 8 mg/kg, about 9 mg/kg or about 10 mg/kg.)

In particular embodiments, the ligand of the invention is administered at a dose that provides saturation of EGFR or a desired serum concentration in vivo. The skilled physician can determine appropriate dosing to achieve saturation, for example by titrating ligand and monitoring the amount of free binding sites on EGFR expressing cells or the serum concentration of ligand. Therapeutic regiments that involve administering a therapeutic agent to achieve target saturation or a desired serum concentration of agent are common in the art, particularly in the field of oncology.

Treatment or therapy performed using the compositions described herein is considered "effective" if one or more symptoms are reduced (e.g., by at least 10% or at least one point on a clinical assessment scale), relative to such symptoms present before treatment, or relative to such symptoms in an individual (human or model animal) not treated with such composition or other suitable control. Symptoms will obviously vary depending upon the disease or disorder targeted, but can be measured by an ordinarily skilled clinician or technician. Such symptoms can be measured, for example, by monitoring the level of one or more biochemical indicators of the disease or disorder (e.g., levels of an enzyme or metabolite correlated with the disease, affected cell numbers, etc.), by monitoring physical manifestations (e.g., inflammation, tumor size, etc.), or by an accepted clinical assessment scale, for example, the Expanded Disability Status Scale (for multiple sclerosis), the Irvine Inflammatory Bowel Disease Questionnaire (32 point assessment evaluates quality of life with respect to bowel function, systemic symptoms, social function and emotional status—score ranges from 32 to 224, with higher scores indicating a better quality of life), the Quality of Life Rheumatoid Arthritis Scale, or other accepted clinical assessment scale as known in the field. A sustained (e.g., one day or more, preferably longer) reduction in disease or disorder symptoms by at least 10% or by one or more points on a given clinical scale is indicative of "effective" treatment. Similarly, prophylaxis performed using a composition as described herein is "effective" if the onset or severity of one or more symptoms is delayed, reduced or abolished relative to such symptoms in a similar individual (human or animal model) not treated with the composition.

A composition containing ligands according to the present invention may be utilized in prophylactic and therapeutic settings to aid in the alteration, inactivation, killing or removal of a select target cell population in a mammal. In addition, the ligands and selected repertoires of polypeptides described herein may be used extracorporeally or in vitro selectively to kill, deplete or otherwise effectively remove a target cell population from a heterogeneous collection of cells. Blood from a mammal may be combined extracorporeally with the ligands, e.g. antibodies, cell-surface receptors or binding proteins thereof whereby the undesired cells are killed or otherwise removed from the blood for return to the mammal in accordance with standard techniques.

In one embodiment, the invention relates to a method for delivering anti-angiogenic therapy (anti-VEGF therapy) to a site containing cells that express or overexpress EGFR, comprising administereing an effective amount of a ligand that has binding specificity for VEGF and for EGFR to a subject in need thereof.

The invention also relates to use of a ligand that has binding specificity for VEGF and for EGFR for delivering anti-angiogenic therapy (anti-VEGF therapy) to a site containing cells that express or overexpress EGFR. The invention also relates to use of a ligand of a ligand that has binding specificity for VEGF and for EGFR for the manufacture of a medicament for i delivering anti-angiogenic therapy (anti-VEGF therapy) to a site containing cells that express or overexpress EGFR, or for inhibiting angiogenesis at a site containing cells that express of overexpress EGFR.

In particular embodiments, the invention relates to a method of treating cancer comprising administering to a subject in need thereof a therapeutically effective amount of a ligand, as described herein, that has binding specificity for VEGF and for EGFR. In particular embodiments, the patient has an EGFR-expressing cancer, such as, bladder cancer, ovarian cancer, colorectal cancer, breast cancer, lung cancer (e.g., non-small cell lung carcinoma), gastric cancer, pancreatic cancer, prostate cancer, head and neck cancer, renal cancer and gall bladder cancer.

In other embodiments, the invention relates to a method for treating cancer, comprising administering to a subject in need thereof a therapeutically effective amount of ligand, as described herein, (e.g., a ligand that has binding specificity for VEGF, a ligand that has binding specificity for EGFR, a ligand that has binding specificity for VEGF and EGFR) and an anti-neoplastic composition, wherein said anti-neoplastic composition comprises at least one chemotherapeutic agent selected from the group consisting of alkylating agents, antimetabolites, folic acid analogs, pyrimidine analogs, purine analogs and related inhibitors, vinca alkaloids, epipodopyyllotoxins, antibiotics, L-Asparaginase, topoisomerase inhibitor, interferons, platinum cooridnation complexes, anthracenedione substituted urea, methyl hydrazine derivatives, adrenocortical suppressant, adrenocorticosteroides, progestins, estrogens, antiestrogen, androgens, antiandrogen, and gonadotropin-releasing hormone analog. In some embodiments, the chemotherapeutic agent is selected from the group consisting of cisplatin, dicarbazine, dactinomycin, mechlorethamine, streptozocin, cyclophosphamide, capecitabine, carmustine, lomustine, doxorubicin, daunorubicin, procarbazine, mitomycin, cytarabine, etoposide, methotrexate, 5-fluorouracil, vinbiastine, vincristine, bleomycin, paclitaxel, docetaxel, doxetaxe, aldesleukin, asparaginase, busulfan, carboplatin, cladribine, dacarbazine, floxuridine, fludarabine, hydroxyurea, ifosfamide, interferon alpha, irinotecan, leuprolide, leucovorin, megestrol, melphalan, mercaptopurine, oxaliplatin, plicamycin, mitotane, pegaspargase, pentostatin, pipobroman, plicamycin, streptozocin, tamoxifen, teniposide, testolactone, thioguanine, thiotepa, uracil mustard, vinorelbine, chlorambucil, taxol, an additional growth factor receptor antagonist, and a combination of any of the foregoing.

Assays for Evaluating Ligands

The ligands of the invention can be assayed using any suitable in vitro or in vivo assay. For example, using the receptor binding assays or bioassays described herein.

Bioassay for VEGF Activity:

This bioassay measures the ability of ligands (e.g., dAbs) and to neutralise the VEGF induced proliferation of HUVE (human vascular endothelial) cells. HUVE cells plated in 96 well plates are incubated for 72 hours with pre-equilibrated VEGF and dAb protein. Cell number is then measured using a cell viability dye.

The assay is performed as follows. HUVE cells are trypsinized from a sub-confluent 175 cm$^2$ flask. Medium is aspirated off, the cells are washed with 5 ml trypsin and then incubated with 2 ml trypsin at room temperature for 5 min. The cells are gently dislodged from the base of the flask by knocking against your hand. 8 ml of induction medium are then added to the flask, pipetting the cells to disperse any clumps. Viable cells are counted using trypan blue stain.

Cells are spun down and washed 2× in induction medium, spinning cells down and aspirating the medium after each wash. After the final aspiration the cells are diluted to $10^5$ cells/ml (in induction medium) and plated at 100 µl per well into a 96 well plate (10,000 cells/well). The plate is incubated for >2 h @ 37C to allow attachment of cells.

60 µl dAb protein and 60 1l induction media containing 40 ng/ml VEGF$_{165}$ (for a final concentration of 10 ng/ml) is added to a v bottom 96 well plate and sealed with film. The dAb/VEGF mixture is then incubated at 37C for 0.5-1 hour.

The dAb/VEGF plate is removed from the incubator and 100 1l of solution added to each well of the HUVEC containing plate (final volume of 200 µl). This plate is then returned to the 37° C. incubator for a period of at least 72 hours.

Control wells include the following: wells containing cells, but no VEGF; wells containing cells, a positive control neutralising anti-VEGF antibody and VEGF; and control wells containing cells and VEGF only.

Cell viability is assessed by adding 20 µl per well Cellti-ter96 reagent, and the plate incubated at 37° C. for 2-4h until a brown colour develops. The reaction is stopped by the addition of 20 µl per well of 10% (w/v) SDS. The absorbance is then read at 490 nm using a Wallac microplate reader.

The absorbance of the no VEGF control wells is subtracted from all other values. Absorbance is proportional to cell number. The control wells containing control anti-VEGF antibodies should also exhibit minimum cell proliferation. The wells containing VEGF only should exhibit maximum cell proliferation.

EXAMPLES

Example 1

VEGF Receptor Binding Assays

VEGF is a specific mitogen for endothelial cells in vitro and a potent angiogenic factor in vivo, with high levels of the protein being expressed in various types of tumours. It is a 45 kDa glycoprotein that is active as a homodimer. Several isoforms have been described which occur through alternative mRNA splicing. Of these isoforms VEGF-121 and VEGF-165 appear to be the most abundant.

The specific action of VEGF on endothelial cells is mainly regulated by two types of receptor tyrosine kinases (RTK), VEGF R1 (Flt-1), and VEGF R2 (KDR/Flk-1). However, it appears that the VEGF activities such as mitogenicity, chemotaxis, and induction of morphological changes are mediated by VEGF R2, even though both receptors undergo phosphorylation upon binding of VEGF.

VEGF Receptor 2 Binding Assay

This method describes a VEGF receptor binding assay for measuring the ability of ligands (e.g., dAbs) to prevent binding of VEGF-165 to VEGF Receptor 2. A recombinant human VEGF R2/Fc chimera was used in this assay, comprising the extracellular domain of human VEGF R2 fused to the Fc region of human IgG$_1$. Briefly, the receptor was captured on an ELISA plate, then the plate was blocked to prevent non-specific binding. A mixture of VEGF-165 and ligand was then added, the plate was washed and receptor bound VEGF-165 detected using a biotinylated anti-VEGF antibody and an HRP conjugated anti-biotin antibody. The plate was developed using a colorimetric substrate and the OD read at 450 nm. If the dAb blocks VEGF binding to the receptor then no colour is detected.

The assay was performed as follows. A 96 well Nunc Maxisorp assay plate was coated overnight at 4° C. with 100 µl per well of recombinant human VEGF R2/Fc (R&D Systems, Cat. No: 357-KD-050) @ 0.5 µg/ml in carbonate buffer. Wells were washed 3 times with 0.05% tween/PBS and 3 times with PBS. 200 µl per well of 2% BSA in PBS is added to block the plate and the plate was incubated for a minimum of 1 h at room temperature.

Wells were washed (as above), then 50 µl per well of ligand was added to each well. 50 µl of VEGF, @ 6 ng/ml in diluent (for a final concentration of 3 ng/ml), was then added to each well and the plate was incubated for 2 hours at room temperature (for assay of supernatants; 80 µl of supernatant was added to each well then 20 µl of VEGF @ 15 ng/ml).

The following controls were included: 0 ng/ml VEGF (diluent only); 3 ng/ml VEGF (R&D Systems, Cat No: 293-VE-050); 3 ng/ml VEGF with 0.1 µg/ml anti-VEGF neutralizing antibody (R&D Systems cat#MAB293).

The plate was washed (as above) and then 100 µl biotinylated anti-VEGF antibody (R&D Systems, Cat No: BAF293), 0.5 µg/ml in diluent, was added and incubated for 2 hours at room temperature.

Wells were washed (as above) then add 100 µl HRP conjugated anti-biotin antibody (1:5000 dilution in diluent; Stratech, Cat No: 200-032-096). The plate was then incubated for 1 hour at room temperature.

The plate was washed (as above) ensuring any traces of Tween-20 had been removed to limit background in the subsequent peroxidase assay and to help the prevention of bubbles in the assay plate wells that will give inaccurate OD readings.

100 µl of SureBlue 1-Component TMB MicroWell Peroxidase solution was added to each well, and the plate was left at room temperature for up to 20 min. A deep blue soluble product developed as bound HRP labelled conjugate reacted with the substrate. The reaction was stopped by the addition of 100 µl 1M hydrochloric acid (the blue colour turned yellow). The OD, at 450 nm, of the plate was read in a 96-well plate reader within 30 min of acid addition. The OD450 nm is proportional to the amount of bound streptavidin-HRP conjugate.

For some assays protein L was added. Protein L cross links two dAb monomers.

Expected result from the controls are as follows: 0 ng/ml VEGF should give a low signal of <0.15 OD; 3 ng/ml VEGF should give a signal of >0.5 OD; and 3 ng/ml VEGF pre-incubated with 0.1 µg/ml neutralising antibody should give a signal <0.2 OD.

VEGF Receptor 1 Binding Assay

This assay measures the binding of VEGF-165 to VEGF R1 and the ability of ligands to block this interaction. A recombinant human VEGF R1/Fc chimera was used here, comprising the extracellular domain of human VEGF R1 fused to the Fc region of human $IgG_1$. The receptor was captured on an ELISA plate then the plate was blocked to prevent non specific binding. A mixture of VEGF-165 and ligand was then added, the plate was washed and receptor bound VEGF-165 detected using a biotinylated anti-VEGF antibody and an HRP conjugated anti-biotin antibody. The plate was developed using a colorimetric substrate and the OD read at 450 nm.

The assay was performed as follows. A 96 well Nunc Maxisorp assay plate was coated overnight at 4° C. with 100 µl per well of recombinant human VEGF R1/Fc (R&D Systems, Cat No: 321-FL-050) @ 0.1 µg/ml in carbonate buffer. Wells were washed 3 times with 0.05% tween/PBS and 3 times with PBS.

200 µl per well of 2% BSA in PBS was added to block the plate and the plate was incubated for a minimum of 1 h at room temperature.

Wells were washed (as above), then 50 µl per well of purified dAb protein was added to each well. 50 µl of VEGF, @ 1 ng/ml in diluent (for a final concentration of 500 pg/ml), was then added to each well and the plate incubated for 1 hr at room temperature (assay of supernatants; 80 µl of supernatant was added to each well then 20 µl of VEGF @ 2.5 ng/ml).

The following controls were be included: 0 ng/ml VEGF (diluent only); 500 pg/ml VEGF; and 500 pg/ml VEGF with 1 µg/ml anti-VEGF antibody (R&D Systems cat#MAB293).

The plate was washed (as above) and then 100 µl biotinylated anti-VEGF antibody, 50 ng/ml in diluent, was added and incubated for 1 hr at room temperature.

Wells were washed (as above) then 100 µl HRP conjugated anti-biotin antibody was added (1:5000 dilution in diluent). The plate was then incubated for 1 hr at room temperature.

The plate was washed (as above), ensuring any traces of Tween-20 have been removed to limit background in the subsequent peroxidase assay and to help the prevention of bubbles in the assay plate wells that will give inaccurate OD readings.

100 µl of SureBlue 1-Component TMB MicroWell Peroxidase solution was added to each well, and the plate was left at room temperature for up to 20 min. A deep blue soluble product developed as bound HRP labelled conjugate reacts with the substrate. The reaction was stopped by the addition of 100 µl 1M hydrochloric acid. The OD, at 450 nm, of the plate was be read in a 96-well plate reader within 30 min of acid addition. The OD450 nm is proportional to the amount of bound streptavidin-HRP conjugate.

Expected result from the controls: 0 ng/ml VEGF should give a low signal of <0.15 OD; 500 pg/ml VEGF should give a signal of >0.8 OD; and 500 pg/ml VEGF pre-incubated with 1 µg/ml neutralising antibody should give a signal <0.3 OD

TABLE 1

| dAb | | RBA (VEGFR2) IC50 − protein L (nM) | RBA (VEGFR2) IC50 + protein L (nM) |
|---|---|---|---|
| TAR15-1 | VK | 171 | 7.4 |
| TAR15-10 | VK | 12.2 | 0.3 |
| TAR15-16 | VK | 31 | 1.7 |
| TAR15-17 | VK | 38 | 0.5 |
| TAR15-18 | VK | 174 | 0.4 |
| TAR15-20 | VK | 28 | 0.3 |

The TAR15-1 had a Kd of 50-80 nM when tested at various concentrations on a low density BIAcore chip. Other VK dAbs were passed over the low density chip at one concentration (50 nM). Different dAbs showed different binding kinetics.

TABLE 2

| dAb | | More than 50% reduction in supernatant RBA (VEGFR2)* |
|---|---|---|
| TAR15-5 | VH | + |
| TAR15-6 | VH | + |
| TAR15-7 | VH | + |
| TAR15-8 | VH | + |
| TAR15-23 | VH | + |
| TAR15-24 | VH | + |
| TAR15-25 | VH | + |
| TAR15-26 | VH | + |
| TAR15-27 | VH | + |
| TAR15-29 | VH | + |
| TAR15-30 | VH | + |

*dAb was assayed at 50 nM

VH dAbs were passed over the low density VEGF chip on a BIAcore at one concentration (50 nM). Different dAbs showed different binding kinetics.

Example 2

EGFR Binding

EGFR Binding Assay

25 μl of ligand (e.g., dAb) were plated into a 96 well plate and then 25 ul streptavidin-Alexa Fluor (1 ug/ml) (Molecular Probes) and 25 ul A431 cells (ATCC No, CRL-1555) ($8\times10^5$/ml) were added. All reagents were prepared in PBS/1% BSA. The plate was incubated for 30 minutes at room temperature.

Without disturbing the cells, 25 ul biotinylated EGF (Invitrogen) at 40 ng/ml was added to each well, and the plate was incubated for three hours at room temperature. Fluoresecence was measured using the AB8200 Cellular Detection System (Applied Biosystems).

Ligands (e.g., dAbs) that inhibited the binding of biotinylated EGF to EGFR expressed on A431 cells resulted in lower fluorescence counts. Wells without ligand provided a reference of the maximum fluorescence (i.e., biotinyulated EGF binding) and wells without ligand or biotinylated EGF provide a reference or the background level of fluorescence. These controls were included in all assays.

Results obtained in this assay using certain anti-EGFR dAbs are presented in the Table 3.

EGFR Kinase Assay

In a 96 well plate, $5\times10^4$ A431 cells (ATCC No, CRL-1555) were plated per well in RPMI-1640 supplemented with 10% foetal calf serum. The plate was incubated overnight at 37° C./5% $CO_2$ to allow the cells to adhere, then the medium was replaced with RPMI-1640. The plate was incubated for 4 hours at 37° C./5% $CO_2$. The ligand (prepared in RPMI-1640) was added to the wells and the plate was incubated for 45 minutes at 37° C./5% $CO_2$. EGF (Invitrogen) was added to the wells to give a final concentration of 100 ng/ml and the plate was incubated for 10 minutes at room temperature. The wells were washed twice with ice cold PBS. Cold lysis buffer (1% NP-40, 20 mM Tris, 137 mM NaCl, 10% glycerol, 2 mM EDTA, 1 mM sodium orthovanadate, 10 ug/ml aprotinin, 10 ug/ml leupeptin) was added and the plate was incubated on ice for 10 minutes.

The supernatants were transfered to an ELISA plate which had been coated overnight with anti-EGFR antibody (R&D Systems) at 1 ug/ml in carbonate buffer. The ELISA plate was incubated for 2 hours at room temperature. The plate was washed three times with PBS/0.05% tween 20. Anti-phosphotyrosine antibody conjugated to horse-radish peroxidase (Upstate Biotechnology) at 1 ug/ml was added and the plate was incubated for 1 hour at room temperature. The plate was washed three times with PBS/Tween and three times with PBS. The reaction was developed with SureBlue TMB 1-component microwell peroxidase substrate (KPL) and the reaction was stoped with 1M HCl after 25 minutes. The absorbance was read using a Wallac plate reader.

Results obtained in this assay using certain anti-EGFR dAbs are presented in the Table 3.

TABLE 3

| dAb | KD (nM) | Receptor Binding Assay IC50 (nM)* | Kinase Assay IC50 (nM)* |
|---|---|---|---|
| DOM16-39 | 27.3 | 28.68 to 112.6 (56.84) | 31.16 to 100.9 (56.07) |
| DOM16-200 | 15.3 | 12.47 to 37.88 (21.74) | 30.29 to 111.9 (58.21) |
| DOM16-39-87 | 6.81 | 4.471 to 10.39 (6.8) | 11.95 to 252.4 (54.92) |
| DOM16-39-100 | 1.24 | 1.007 to 2.757 (1.67) | 9.142 t0 17.56 (12.67) |
| DOM16-39-107 | 7.09 | 1.472 to 4.208 (2.49) | 12.00 to 34.99 (20.49) |
| DOM16-39-109 | 1.01 | 0.746 to 1.472 (1.05) | 6.817 to 11.08 (8.69) |
| DOM16-39-115 | 6.90 | 1.085 to 6.886 (2.73) | 21.52 to 83.34 (42.35) |
| ERBITUX (cetuximab, Imclone Systems, Inc.) | — | 1.422 to 5.388 (2.77) | 3.875 to 7.689 (5.46) |

*the data presented are the lowest to highest values obtained and the (average)

Example 3

IgG-Like Formats that Have Binding Specificity for VEGF and EGFR

Vectors

The pBudCE4.1 backbone (Invitrogen) was used for cloning immuno globulin constant regions, such as the IgG1 heavy chain constant region and light chain kappa constant region (see Figure * for overview). An Ig Kappa chain leader was used to facilitate secretion of the expressed protein. Ig constant regions (human IgG1 and CK) were produced by GeneArt (Germany).

The heavy chain constant region and signal peptide were cloned into pBudCE4.1 as a Hind III/BglII fragment into the HindIII/BamH I restriction sites.

The light chain constant region and signal peptide were cloned into pBudCE4.1 as a NotI/Mlu I fragment.

Cloning of dAb in IgG Vectors and Production of IgG-Like Format

VK dAb (specific to VEGF or EGFR) was cloned into IgG vector as a SalI/BsiWI fragment. VH dAb (specific to VEGF or EGFR was cloned into IgG vector as a BamHI/XhoI fragment.

The plasmid was then transfected into HEK293T cells (ATCC CRL-11268) and IgG was expressed transiently for five days. The produced IgG was purified using streamline Protein A.

Purified IgG was checked on a reducing and non-reducing SDS gel and bands of expected size were observed.

Several dAbs that bind VEGF or EGFR were formatted into IgG-like formats that have binding specificity for VEGF and EGFR. The IgG-like formats were prepared by producing constructs that encoded an IgG heavy chain wherein VH is a dAb, and an Kappa light chain wherein VK is a dAb. The IgG-like formats that were prepared are shown in Table 4, and the results obtained for some of the IgG-like formats in assays are presented in Table 5. (Dummy VH and Dummy VK are germ line sequences that do not bind VEGF or EGFR).

TABLE 4

| IgG-like format No. | Heavy Chain V region | Light Chain V Region |
|---|---|---|
| 1 | DOM16-39 VK | DOM16-39 VK |
| 2 | DOM16-32 VK | TAR15-10 VK |
| 3 | DOM16-39 VK | TAR15-10 VK |
| 4 | DOM16-72 VK | TAR15-10 VK |
| 5 | TAR15-26 VH | DOM16-32 VK |
| 6 | TAR15-26 VH | DOM16-39 VK |
| 7 | TAR15-26 VH | DOM16-72 VK |
| 8 | TAR15-26 VH | TAR15-10 VK |
| 9 | DOM16-52 VH | TAR15-10 VK |
| 10 | TAR15-26 VH | DOM16-52 VH |
| 11 | TAR15-10 VK | TAR15-26 VH |
| 12 | TAR15-10 VK | TAR15-10 VK |
| 13 | DOM16-200 VK | DOM16-200 VK |
| 14 | TAR15-10 VK | DOM16-200 VK |
| 15 | TAR15-10 VK | DOM16-32 VK |
| 16 | TAR15-10 VK | DOM16-72 VK |
| 17 | TAR15-10 VK | DOM16-39 VK |

TABLE 4-continued

| IgG-like format No. | Heavy Chain V region | Light Chain V Region |
|---|---|---|
| 21 | TAR15-26 VH | dCDR2/DOM16-200 VK |
| 22 | TAR15-26 VH | dCDR3/DOM16-200 VK |
| 23 | TAR15-26-501 VH | DOM16-200 VK |
| 24 | TAR15-6-506VH | DOM16-200 VK |
| 25 | TAR15-8-505 VH | DOM16-200 VK |
| 26 | TAR15-26 VH | TAR15-26 VH |
| 27 | TAR15-26-534 VH | DOM16-200 VK |
| 28 | TAR15-26-501 VH | DOM16-39-500 VK |
| 29 | TAR15-26-501 VH | DOM16-39-201 VK |
| 29a | TAR15-26-501 VH | DOM16-39-501 VK |
| 30 | TAR15-26-501 VH | DOM16-39-502 VK |
| 31 | TAR15-26-534 VH | DOM16-39-501 VK |
| 32 | Dummy VH | DOM16-200 VK |
| 33 | Dummy VH | DOM16-39-201 VK |
| 34 | TAR15-26-501 VH | DOM16-39-204 VK |
| 35 | TAR15-26-501 VH | DOM16-39-206 VK |
| 36 | TAR15-26-501 VH | DOM16-39-207 VK |
| 37 | TAR15-26-501 VH | DOM16-39-209 VK |
| 38 | TAR15-26-501 VH | DOM16-39-203 VK |
| 39 | TAR15-26-501 VH | DOM16-39-214 VK |
| 40 | TAR15-26-501 VH | DOM16-39-217 VK |
| 41 | TAR15-26-501 VH | Dummy VK VK |

TABLE 5

| IgG | CH | CK | VEGF (bioassay) ND50 (nM) | VEGF (RBA) IC50 (nM) | EGFR (cell RBA) EC50 (nM) | EGFR (Kinase assay) ND50 (nM) |
|---|---|---|---|---|---|---|
| 1 | DOM16-39 VK | DOM16-39 VK | | | 17 | 22 |
| 3 | DOM16-39 VK | TAR15-10 VK | | 1.5 | | |
| 4 | DOM16-72 VK | TAR15-10 VK | | | | |
| 6 | TAR15-26 VH | DOM16-39 VK | 1 | | 126 | 22 |
| 10 | TAR15-26 VH | DOM16-52 VH | 0.2 | 0.05 | | |
| 11 | TAR15-10 VK | TAR15-26 VH | | 0.03 | | |
| 18 | TAR15-26 VH | DOM16-200 VK | | 0.4 | 5 | |
| 19 | TAR15-26 VH | Dummy VK | | 4.8 | | |
| 20 | TAR15-26 VH | dCDR1/DOM16-200 VK | | 4.1 | | |
| 21 | TAR15-26 VH | dCDR2/DOM16-200 VK | | 0.1 | | |
| 23 | TAR15-26-501 VH | DOM16-200 VK | 0.16 | 0.16 | 23 | |
| 24 | TAR15-6-506VH | DOM16-200 VK | | 12 | 26 | |
| 25 | TAR15-8-505 VH | DOM16-200 VK | | | 34 | |
| 27 | TAR15-26-534 VH | DOM16-200 VK | | 0.5 | 137 | |
| 28 | TAR15-26-501 VH | DOM16-39-500 VK | | 0.8 | 43 | |
| 30 | TAR15-26-501 VH | DOM16-39-502 VK | | 0.2 | 17 | |

TABLE 4-continued

| IgG-like format No. | Heavy Chain V region | Light Chain V Region |
|---|---|---|
| 18 | TAR15-26 VH | DOM16-200 VK |
| 19 | TAR15-26 VH | Dummy VK |
| 20 | TAR15-26 VH | dCDR1/DOM16-200 VK |

While this invention has been particularly shown and described with references to preferred embodiments thereof, it will be understood by those skilled in the art that various changes in form and details may be made therein without departing from the scope of the invention encompassed by the appended claims.

What is claimed is:

1. A ligand that has binding specificity for vascular endothelial growth factor (VEGF) and epidermal growth factor receptor (EGFR), comprising at least one immunoglobulin single variable domain that has a binding site with binding specificity for VEGF, wherein each said immunoglobulin single variable domain with binding specificity for VEGF comprises an amino acid sequence that has at least 95% amino acid sequence identity with the amino acid sequence of a dAb selected from the group consisting of TAR15-6 (SEQ ID NO:117), TAR15-8 (SEQ ID NO:119), and TAR15-26 (SEQ ID NO:123), and at least one immunoglobulin single variable domain that has a binding site with binding specificity for EGFR, wherein each said immunoglobulin single variable domain with binding specificity for EGFR comprises an amino acid sequence that has at least 95% amino acid sequence identity with the amino acid sequence of a dAb DOM16-39 (SEQ ID NO:345).

2. The ligand of claim 1, wherein each said immunoglobulin single variable domain that has a binding site with binding specificity for VEGF competes for binding to VEGF with bevacizumab.

3. The ligand of claim 1, wherein said immunoglobulin single variable domain that has a binding site with binding specificity for EGFR competes for binding to EGFR with cetuximab.

4. A ligand that has binding specificity for vascular endothelial growth factor (VEGF) and epidermal growth factor receptor (EGFR), comprising at least one immunoglobulin single variable domain with binding specificity for VEGF, wherein each said immunoglobulin single variable domain with binding specificity for VEGF competes for binding to VEGF with an anti-VEGF domain antibody (dAb) selected from the group consisting of TAR15-6 (SEQ ID NO:117), TAR15-8 (SEQ ID NO:119), and TAR15-26 (SEQ ID NO:123), and at least one immunoglobulin single variable domain with binding specificity for EGFR, wherein each said immunoglobulin single variable domain with binding specificity for EGFR competes for binding to EGFR with an anti-EGFR domain antibody (dAb) DOM16-39 (SEQ ID NO:345).

5. The ligand of claim 4, wherein each said immunoglobulin single variable domain with binding specificity for VEGF comprises an amino acid sequence that has at least 95% amino acid sequence identity with the amino acid sequence of a dAb selected from the group consisting of TAR15-6 (SEQ ID NO:117), TAR15-8 (SEQ ID NO:119), and TAR15-26 (SEQ ID NO:123).

6. The ligand of claim 1, wherein said ligand inhibits binding of epidermal growth factor (EGF) and transforming growth factor alpha (TGFalpha) to EGFR.

7. The ligand of claim 1 wherein said ligand inhibits the activity of EGFR.

8. The ligand of claim 1, wherein said ligand inhibits the activity of EGFR without substantially inhibiting binding of epidermal growth factor (EGF) and transforming growth factor alpha (TGFalpha) to EGFR.

9. The ligand of claim 1, wherein said ligand inhibits binding of VEGF to vascular endothelial growth factor receptor 1 (VEGFR1) and vascular endothelial growth factor receptor 2 (VEGFR2).

10. The ligand of claim 1, wherein said ligand inhibits the activity of VEGF.

11. The ligand of claim 1, wherein said ligand inhibits the activity of VEGF without substantially inhibiting binding of VEGF to vascular endothelial growth factor receptor 1 (VEGFR1) and vascular endothelial growth factor receptor 2 (VEGFR2).

12. The ligand of claim 1, wherein each said immunoglobulin single variable domain with binding specificity for VEGF is a $V_{HH}$ and wherein each said immunoglobulin single variable domain with binding specificity for EGFR is a $V_{HH}$.

13. The ligand of claim 1, wherein each said immunoglobulin single variable domain with binding specificity for VEGF is selected from the group consisting of a human $V_H$ and a human $V_L$ and wherein each said immunoglobulin single variable domain with binding specificity for EGFR is selected from the group consisting of a human $V_H$ and a human $V_L$.

14. The ligand of claim 1, wherein said ligand is an IgG-like format comprising two immunoglobulin single variable domains with binding specificity for VEGF, and two immunoglobulin single variable domains with binding specificity for EGFR.

15. The ligand of claim 1, wherein said ligand comprises an antibody Fc region.

16. A ligand that has binding specificity for vascular endothelial growth factor (VEGF) and epidermal growth factor receptor (EGFR), comprising at least one immunoglobulin single variable domain with binding specificity for VEGF, wherein each said immunoglobulin single variable domain with binding specificity for VEGF competes for binding to VEGF with an anti-VEGF domain antibody (dAb) selected from the group consisting of TAR15-6 (SEQ ID NO:117), TAR15-8 (SEQ ID NO:119), and TAR15-26 (SEQ ID NO:123), and
at least one immunoglobulin single variable domain with binding specificity for EGFR, wherein each said immunoglobulin single variable domain with binding specificity for EGFR competes for binding to EGFR with an anti-EGFR domain antibody (dAb) DOM16-39 (SEQ ID NO:345); and
each said immunoglobulin single variable domain with binding specificity for EGFR competes for binding to EGFR with cetuximab.

17. The ligand of claim 16, wherein each said immunoglobulin single variable domain with binding specificity for VEGF comprises an amino acid sequence that has at least 95% amino acid sequence identity with the amino acid sequence of a dAb selected from the group consisting of TAR15-6 (SEQ ID NO:117), TAR15-8 (SEQ ID NO:119), and TAR15-26 (SEQ ID NO:123).

18. A ligand that has binding specificity for vascular endothelial growth factor (VEGF) and epidermal growth factor receptor (EGFR), comprising a first immunoglobulin single variable domain with binding specificity for VEGF, wherein each said first immunoglobulin single variable domain with binding specificity for VEGF comprises an amino acid sequence that has at least 95% amino acid sequence identity with the amino acid sequence of a dAb selected from the group consisting of TAR15-6 (SEQ ID NO:117), TAR15-8 (SEQ ID NO:119), and TAR15-26 (SEQ ID NO:123), and a second immunoglobulin single variable domain with binding specificity for EGFR, wherein each said second immunoglobulin single variable domain with binding specificity for EGFR comprises an amino acid sequence that has at least 95% amino acid sequence identity with the amino acid sequence of a dAb DOM16-39 (SEQ ID NO:345),
wherein said first immunoglobulin single variable domain competes for binding to VEGF with bevacizumab; and
said second immunoglobulin single variable domain competes for binding to EGFR with cetuximab.

19. The ligand of claim 16, wherein said ligand inhibits binding of epidermal growth factor (EGF) and transforming growth factor alpha (TGFalpha) to EGFR.

20. The ligand of claim 16, wherein said ligand inhibits the activity of EGFR.

21. The ligand of claim 16, wherein said ligand inhibits the activity of EGFR without substantially inhibiting binding of epidermal growth factor (EGF) and transforming growth factor alpha (TGFalpha) to EGFR.

22. The ligand of claim 16, wherein said ligand inhibits binding of VEGF to vascular endothelial growth factor receptor 1 (VEGFR 1) and vascular endothelial growth factor receptor 2 (VEGFR2).

23. The ligand of claim 16, wherein said ligand inhibits the activity of VEGF.

24. The ligand of claim 16, wherein said ligand inhibits the activity of VEGF without substantially inhibiting binding of VEGF to vascular endothelial growth factor receptor 1 (VEGFR1) and vascular endothelial growth factor receptor 2 (VEGFR2).

25. The ligand of claim 16, wherein each said immunoglobulin single variable domain with binding specificity for VEGF is a $V_{HH}$ and wherein each said an immunoglobulin single variable domain with binding specificity for EGFR is a $V_{HH}$.

26. The ligand of claim 16, wherein each said immunoglobulin single variable domain with binding specificity for VEGF is selected from the group consisting of a human $V_H$ and a human $V_L$, and each said immunoglobulin single variable domain with binding specificity for EGFR is selected from the group consisting of a human $V_H$ and a human $V_L$.

27. The ligand of claim 16, wherein said ligand is an IgG-like format comprising two immunoglobulin single variable domains with binding specificity for VEGF, and two immunoglobulin single variable domains with binding specificity for EGFR.

28. The ligand of claim 16, wherein said ligand comprises an antibody Fc region.

29. A ligand that has binding specificity for vascular endothelial growth factor (VEGF), comprising at least one immunoglobulin single variable domain with binding specificity for VEGF, wherein each said immunoglobulin single variable domain with binding specificity for VEGF competes for binding to VEGF with an anti-VEGF domain antibody (dAb) selected from the group consisting of TAR15-6 (SEQ ID NO:117), TAR15-8 (SEQ ID NO:119), and TAR15-26 (SEQ ID NO:123).

30. The ligand of claim 29, wherein said ligand inhibits binding of VEGF to vascular endothelial growth factor receptor 1 (VEGFR 1) and vascular endothelial growth factor receptor 2 (VEGFR2).

31. The ligand of claim 29, wherein each said immunoglobulin single variable domain with binding specificity for VEGF is a $V_{HH}$.

32. The ligand of claim 29, wherein each said immunoglobulin single variable domain with binding specificity for VEGF is selected from the group consisting of a human $V_H$ and a human $V_L$.

33. The ligand of claim 29, wherein each said immunoglobulin single variable domain with binding specificity for VEGF comprises an amino acid sequence that has at least 95% amino acid sequence identity with the amino acid sequence of a dAb selected from the group consisting of TAR15-6 (SEQ ID NO:117), TAR15-8 (SEQ ID NO:119), and TAR15-26 (SEQ ID NO:123).

34. The ligand of claim 1, wherein said ligand further comprises a toxin.

35. The ligand of claim 34, wherein said toxin is a surface active toxin.

36. The ligand of claim 35, wherein said surface active toxin comprises a free radical generator or a radionuclide.

37. The ligand of claim 34, wherein said toxin is a cytotoxin, free radical generator, antimetabolite, protein, polypeptide, peptide, photoactive agent, chemotherapeutic, radionuclide or intrabody.

38. The ligand of claim 1, wherein said ligand further comprises a half-life extending moiety.

39. The ligand of claim 38, wherein said half-life extending moiety is a polyalkylene glycol moiety, serum albumin or a fragment thereof, transfeffin receptor or a transferrin-binding portion thereof, or a moiety comprising a binding site for a polypeptide that enhances half-life in vivo.

40. The ligand of claim 39, wherein said half-life extending moiety is a moiety comprising a binding site for a polypeptide that enhances half-life in vivo, said moiety being selected from the group consisting of an affibody, an SpA domain, an LDL receptor class A domain, an EGF domain, and an avimer.

41. The ligand of claim 39, wherein said half-life extending moiety is a polyethylene glycol moiety.

42. The ligand of claim 39, wherein said half-life extending moiety is an antibody or antibody fragment comprising a binding site for serum albumin or neonatal Fc receptor.

43. The ligand of claim 42, wherein said antibody or antibody fragment comprising a binding site for serum albumin or neonatal Fc receptor is an antibody fragment, and said antibody fragment is an immunoglobulin single variable domain comprising a binding site for serum albumin.

44. The ligand of claim 43, wherein said immunoglobulin single variable domain comprising a binding site for serum albumin competes for binding to human serum albumin with a dAb selected from the group consisting of DOM7m-16 (SEQ ID NO:473), DOM7m-12 (SEQ ID NO: 474), DOM7m-26 (SEQ ID NO: 475), DOM7r-1 (SEQ ID NO: 476), DOM7r-3 (SEQ ID NO: 477), DOM7r-4 (SEQ ID NO: 478), DOM7r-5 (SEQ ID NO: 479), DOM7r-7 (SEQ ID NO: 480), DOM7r-8 (SEQ ID NO: 481), DOM7h-2 (SEQ ID NO: 482), DOM7h-3 (SEQ ID NO: 483), DOM7h-4 (SEQ ID NO: 484), DOM7h-6 (SEQ ID NO: 485), DOM7h-1 (SEQ ID NO: 486), DOM7h-7 (SEQ ID NO: 487), DOM7h-22 (SEQ ID NO: 489), DOM7h-23 (SEQ ID NO: 490), DOM7h-24 (SEQ ID NO: 491), DOM7h-25 (SEQ ID NO: 492), DOM7h-26 (SEQ ID NO: 493), DOM7h-21 (SEQ ID NO: 494), DOM7h-27 (SEQ ID NO: 495), DOM7h-8 (SEQ ID NO: 496), DOM7r-13 (SEQ ID NO: 497), DOM7r-14 (SEQ ID NO: 498), DOM7r-15 (SEQ ID NO: 499), DOM7r-16 (SEQ ID NO: 500), DOM7r-17 (SEQ ID NO: 501), DOM7r-18 (SEQ ID NO: 502), DOM7r-19 (SEQ ID NO: 503), DOM7r-20 (SEQ ID NO: 504), DOM7r-21 (SEQ ID NO: 505), DOM7r-22 (SEQ ID NO: 506), DOM7r-23 (SEQ ID NO: 507), DOM7r-24 (SEQ ID NO: 508), DOM7r-25 (SEQ ID NO: 509), DOM7r-26 (SEQ ID NO: 510), DOM7r-27 (SEQ ID NO: 511), DOM7r-28 (SEQ ID NO: 512), DOM7r-29 (SEQ ID NO: 513), DOM7r-30 (SEQ ID NO: 514), DOM7r-31 (SEQ ID NO: 515), DOM7r-32 (SEQ ID NO: 516), and DOM7r-33 (SEQ ID NO: 517).

45. The ligand of claim 43, wherein said immunoglobulin single variable domain comprising a binding site for serum albumin comprises an amino acid sequence that has at least 95% amino acid sequence identity with the amino acid sequence of a dAb selected from the group consisting of DOM7m-16 (SEQ ID NO: 473), DOM7m-12 (SEQ ID NO: 474), DOM7m-26 (SEQ ID NO: 475), DOM7r-1 (SEQ ID NO: 476), DOM7r-3 (SEQ ID NO: 477), DOM7r-4 (SEQ ID NO: 478), DOM7r-5 (SEQ ID NO: 479), DOM7r-7 (SEQ ID NO: 480), DOM7r-8 (SEQ ID NO: 481), DOM7h-2 (SEQ ID NO: 482), DOM7h-3 (SEQ ID NO: 483), DOM7h-4 (SEQ ID NO: 484), DOM7h-6 (SEQ ID NO: 485), DOM7h-1 (SEQ ID NO: 486), DOM7h-7 (SEQ ID NO: 487), DOM7h-22 (SEQ ID NO: 489), DOM7h-23 (SEQ ID NO: 490), DOM7h-24 (SEQ ID NO: 491), DOM7h-25 (SEQ ID NO: 492), DOM7h-26 (SEQ ID NO: 493), DOM7h-21 (SEQ ID NO: 494), DOM7h-27 (SEQ ID NO: 495), DOM7h-8 (SEQ ID NO: 496), DOM7r-13 (SEQ ID NO: 497), DOM7r-14 (SEQ ID NO: 498), DOM7r-15 (SEQ ID NO: 499), DOM7r-16 (SEQ ID NO: 500), DOM7r-17 (SEQ ID NO: 501), DOM7r-18 (SEQ ID NO: 502), DOM7r-19 (SEQ ID NO: 503), DOM7r-20 (SEQ ID NO: 504), DOM7r-21 (SEQ ID NO: 505), DOM7r-22 (SEQ ID NO: 506), DOM7r-23 (SEQ ID NO: 507), DOM7r-24 (SEQ ID NO: 508), DOM7r-25 (SEQ ID NO: 509), DOM7r-26 (SEQ ID NO: 510), DOM7r-27 (SEQ ID NO: 511), DOM7r-28 (SEQ ID NO: 512), DOM7r-29 (SEQ ID NO: 513), DOM7r-30 (SEQ ID NO: 514), DOM7r-31 (SEQ ID NO: 515), DOM7r-32 (SEQ ID NO: 516), and DOM7r-33 (SEQ ID NO: 517).

46. A composition comprising a ligand of claim 1 or 29 and a physiologically acceptable carrier.

47. A composition comprising a single domain antibody polypeptide construct that antagonizes human VEGF binding to a receptor, wherein said single domain antibody polypeptide construct comprises a CDR1, CDR2, and CDR3 sequence that is the same as the sequence of CDR1, CDR2, and CDR3 of a dAb selected from the group consisting of TAR15-1 (SEQ ID NO:100), TAR15-3 (SEQ ID NO:101), TAR15-4 (SEQ ID NO:102), TAR15-9 (SEQ ID NO:103), TAR15-10 (SEQ ID NO:104), TAR15-11 (SEQ ID NO:105), TAR15-12 (SEQ ID NO:106), TAR15-13 (SEQ ID NO:107), TAR15-14 (SEQ ID NO:108), TAR15-15 (SEQ ID NO:109), TAR15-16 (SEQ ID NO:110), TAR15-17 (SEQ ID NO:111), TAR15-18 (SEQ ID NO:112), TAR15-19 (SEQ ID NO:113), TAR15-20 (SEQ ID NO:114), TAR15-22 (SEQ ID NO:115), TAR15-5 (SEQ ID NO:116), TAR15-6 (SEQ ID NO:117), TAR15-7 (SEQ ID NO:118), TAR15-8 (SEQ ID NO:119), TAR15-23 (SEQ ID NO:120), TAR15-24 (SEQ ID NO:121), TAR15-25 (SEQ ID NO:122), TAR15-26 (SEQ ID NO:123), TAR15-27 (SEQ ID NO:124), TAR15-29 (SEQ ID NO:125), and TAR15-30 (SEQ ID NO:126).

48. A composition comprising a single domain antibody polypeptide construct that antagonizes human VEGF binding to a receptor, wherein said single domain antibody polypeptide construct comprises an amino acid sequence selected from the group consisting of TAR15-1 (SEQ ID NO:100), TAR15-3 (SEQ ID NO:101), TAR15-4 (SEQ ID NO:102), TAR15-9 (SEQ ID NO:103), TAR15-10 (SEQ ID NO:104), TAR15-11 (SEQ ID NO:105), TAR15-12 (SEQ ID NO:106), TAR15-13 (SEQ ID NO:107), TAR15-14 (SEQ ID NO:108), TAR15-15 (SEQ ID NO:109), TAR15-16 (SEQ ID NO:110), TAR15-17 (SEQ ID NO:111), TAR15-18 (SEQ ID NO:112), TAR15-19 (SEQ ID NO:113), TAR15-20 (SEQ ID NO:114), TAR 15-22 (SEQ ID NO:115), TAR15-5 (SEQ ID NO:116), TAR15-6 (SEQ ID NO:117), TAR15-7 (SEQ ID NO:118), TAR15-8 (SEQ ID NO:119), TAR15-23 (SEQ ID NO:120), TAR15-24 (SEQ ID NO:121), TAR15-25 (SEQ ID NO:122), TAR15-26 (SEQ ID NO:123), TAR15-27 (SEQ ID NO:124), TAR15-29 (SEQ ID NO:125), and TAR15-30 (SEQ ID NO:126) or a sequence at least 95% identical thereto.

49. A composition of claim 47 wherein said single domain antibody polypeptide construct comprises a tetravalent, dual-specific antibody polypeptide construct comprising:
 a) a first copy of a first fusion protein comprising a single domain antibody polypeptide that binds a first epitope, fused to an IgG heavy chain constant domain;
 b) a second copy of said first fusion protein;
 c) a first copy of a second fusion protein comprising a single domain antibody polypeptide that binds a second epitope, fused to a light chain constant domain;
 d) a second copy of said second fusion protein; wherein said first and said second copies of said first fusion protein are disulfide bonded to each other via their respective IgG heavy chain constant domains, and wherein said light chain constant domain of said first copy of said second fusion protein is disulfide bonded to the IgG heavy chain constant domain of said first copy of said first fusion protein, and wherein said light chain constant domain of said second copy of second fusion protein is disulfide bonded to the IgG heavy chain constant domain of said second copy of said first fusion protein, and wherein said polypeptide construct binds said first and said second epitopes.

50. The composition of claim 49 wherein said first and said second epitope is a VEGF epitope.

51. The ligand and of claim 4, wherein each said immunoglobulin single variable domain with binding specificity for EGFR comprises an amino acid sequence that has at least 95% amino acid sequence identity with the amino acid sequence of a dAb DOM16- 39 (SEQ ID NO:345).

52. The ligand of claim 1, wherein said ligand inhibits binding of epidermal growth factor (EGF) or transforming growth factor alpha (TGFalpha) to EGFR.

53. The ligand of claim 1, wherein said ligand inhibits the activity of EGFR without substantially inhibiting binding of epidermal growth factor (EGF) or transforming growth factor alpha (TGFalpha) to EGFR.

54. The ligand of claim 1, wherein said ligand inhibits binding of VEGF to vascular endothelial growth factor receptor 1 (VEGFR1) or vascular endothelial growth factor receptor 2 (VEGFR2).

55. The ligand of claim 1, wherein said ligand inhibits the activity of VEGF without substantially inhibiting binding of VEGF to vascular endothelial growth factor receptor 1 (VEGFR1) or vascular endothelial growth factor receptor 2 (VEGFR2).

56. The ligand of claim 1, wherein each said immunoglobulin single variable domain with binding specificity for VEGF is a $V_{HH}$ or wherein each said immunoglobulin single variable domain with binding specificity for EGFR is a $V_{HH}$.

57. The ligand of claim 16, wherein said ligand inhibits binding of epidermal growth factor (EGF) or transforming growth factor alpha (TGFalpha) to EGFR.

58. The ligand of claim 16, wherein said ligand inhibits the activity of EGFR without substantially inhibiting binding of epidermal growth factor (EGF) or transforming growth factor alpha (TGFalpha) to EGFR.

59. The ligand of claim 16, wherein said ligand inhibits binding of VEGF to vascular endothelial growth factor receptor 1 (VEGFR1) or vascular endothelial growth factor receptor 2 (VEGFR2).

60. The ligand of claim 16, wherein said ligand inhibits the activity of VEGF without substantially inhibiting binding of VEGF to vascular endothelial growth factor receptor 1 (VEGFR1) or vascular endothelial growth factor receptor 2 (VEGFR2).

61. The ligand of claim 16, wherein each said immunoglobulin single variable domain with binding specificity for VEGF is a $V_{HH}$ or wherein each said an immunoglobulin single variable domain with binding specificity for EGFR is a $V_{HH}$.

62. The ligand of claim 29, wherein said ligand inhibits binding of VEGF to vascular endothelial growth factor receptor 1 (VEGFR1) or vascular endothelial growth factor receptor 2 (VEGFR2).

63. The composition of claim 49 wherein said first or said second epitope is a VEGF epitope.

64. A composition comprising a single domain antibody polypeptide construct that antagonizes human VEGF binding to a receptor, wherein said single domain antibody polypeptide construct competes for binding to VEGF with a single domain antibody polypeptide construct selected from the group consisting of: TAR15-1 (SEQ ID NO:100), TAR15-3 (SEQ ID NO:101), TAR15-4 (SEQ ID NO:102), TAR15-9 (SEQ ID NO:103), TAR15-10 (SEQ ID NO:104), TAR15-11 (SEQ ID NO:105), TAR15-12 (SEQ ID NO:106), TAR15-13 (SEQ ID NO:107), TAR15-14 (SEQ ID NO:108), TAR15-15 (SEQ ID NO:109), TAR15-16 (SEQ ID NO:110), TAR15-17 (SEQ ID NO:111), TAR15-18 (SEQ ID NO:112), TAR15-19 (SEQ ID NO:113), TAR15-20 (SEQ ID NO:114), TAR15-22 (SEQ ID NO:115), TAR15-5 (SEQ ID NO:116), TAR15-6 (SEQ ID NO:117), TAR15-7 (SEQ ID NO:118), TAR15-8 (SEQ ID NO:119), TAR15-23 (SEQ ID NO:120), TAR15-24 (SEQ ID NO:121), TAR15-25 (SEQ ID NO:122), TAR15-26 (SEQ ID NO:123), TAR15-27 (SEQ ID NO:124), TAR15-29 (SEQ ID NO:125), and TAR15-30 (SEQ ID NO:126).

65. A composition comprising a single domain antibody polypeptide construct that antagonizes human VEGF binding to a receptor, wherein said single domain antibody polypeptide construct competes for binding to VEGF with a single domain antibody polypeptide construct selected from the group consisting of: TAR15-6-500 (SEQ ID NO:127), TAR15-6-501 (SEQ ID NO:128), TAR15-6-502 (SEQ ID NO:129), TAR15-6-503 (SEQ ID NO:130), TAR15- 6-504 (SEQ ID NO:13 1), TAR15-6-505 (SEQ ID NO:132), TAR15-6-506 (SEQ ID NO:133), TAR15-6-507 (SEQ ID NO:134), TAR15-6-508 (SEQ ID NO:135), TAR15-6-509 (SEQ ID NO:136), TAR15-6-510 (SEQ ID NO:137), TAR15-8-500 (SEQ ID NO:138), TAR15-8-501 (SEQ ID NO:139), TAR15-8-502 (SEQ ID NO:140), TAR15-8-503 (SEQ ID NO:141), TAR15- 8-505 (SEQ ID NO:142), TAR15-8-506 (SEQ ID NO:143), TAR15-8-507 (SEQ ID NO:144), TAR15-8-508 (SEQ ID NO:145), TAR15-8-509 (SEQ ID NO:146), TAR15-8-510 (SEQ ID NO:147), TAR15-8-511 (SEQ ID NO:148), TAR15-26-500 (SEQ ID NO:149), TAR15-26-501 (SEQ ID NO:150), TAR15-26-502 (SEQ ID NO:15 1), TAR15-26-503 (SEQ ID NO:152), TAR15-26-504 (SEQ ID NO:153), TAR15-26-505 (SEQ ID NO:154), TAR15-26-506 (SEQ ID NO:155), TAR15-26-507 (SEQ ID NO:156), TAR15-26-508 (SEQ ID NO:157), TAR15-26-509 (SEQ ID NO:158), TAR15-26-510 (SEQ ID NO:159), TAR15-26-511 (SEQ ID NO:160), TAR15-26-512 (SEQ ID NO:161), TAR15-26-513 (SEQ ID NO:162), TAR15-26-514 (SEQ ID NO:163), TAR15-26-515 (SEQ ID NO:164), TAR15-26-516 (SEQ ID NO:165), TAR15-26-517 (SEQ ID NO:166), TAR15-26-518 (SEQ ID NO:167), TAR15-26-519 (SEQ ID NO:168), TAR15-26-520 (SEQ ID NO:169), TAR15-26-521 (SEQ ID NO: 170), TAR15-26-522 (SEQ ID NO:171), TAR15-26-523 (SEQ ID NO:172), TAR15-26-524 (SEQ ID NO:173), TAR15-26-525 (SEQ ID NO:174), TAR15-26-526 (SEQ ID NO:175), TAR15-26-527 (SEQ ID NO:176), TAR15-26-528 (SEQ ID NO:177), TAR15-26-529 (SEQ ID NO: 178), TAR15-26-530 (SEQ ID NO:179), TAR15-26-531 (SEQ ID NO:180), TAR15-26-532 (SEQ ID NO:181), TAR15-26-533 (SEQ ID NO:182), TAR15-26-534 (SEQ ID NO:183), TAR15-26-535 (SEQ ID NO:184), TAR15-26-536 (SEQ ID NO:185), TAR15-26-537 (SEQ ID NO:186), TAR15-26-538 (SEQ ID NO:187), TAR15-26-539 (SEQ ID NO:188), TAR15-26-540 (SEQ ID NO:189), TAR15-26-541 (SEQ ID NO:190), TAR15-26-542 (SEQ ID NO:191), TAR15-26-543 (SEQ ID NO:192), TAR15-26-544 (SEQ ID NO:193), TAR15-26-545 (SEQ ID NO:194), TAR15-26-546 (SEQ ID NO:195), TAR15-26-547 (SEQ ID NO:196), TAR15-26-548 (SEQ ID NO:197), TAR15-26-549 (SEQ ID NO:198), TAR15-26-550 (SEQ ID NO:539), and TAR15-26-551 (SEQ ID NO:540).

* * * * *

SEQUENCE LISTING

<160> NUMBER OF SEQ ID NOS: 541

<210> SEQ ID NO 1
<211> LENGTH: 324
<212> TYPE: DNA
<213> ORGANISM: Homo sapiens

<400> SEQUENCE: 1

| gacatccaga tgacccagtc tccatcctcc ctgtctgcat ctgtaggaga ccgtgtcacc | 60 |
| atcacttgcc gggcaagtca gtggattggt cctgagttaa gttggtacca gcagaaacca | 120 |
| gggaaagccc ctaagctcct gatctatcat ggttccattt tgcaaagtgg ggtcccatca | 180 |
| cgtttcagtg gcagtggatc tgggacagat ttcactctca ccatcagcag tctgcaacct | 240 |
| gaagattttg ctacgtacta ctgtcaacag cgtatgtatc ggcctgctac gttcggccaa | 300 |
| gggaccaagg tggaaatcaa acgg | 324 |

<210> SEQ ID NO 2
<211> LENGTH: 324
<212> TYPE: DNA
<213> ORGANISM: Homo sapiens

<400> SEQUENCE: 2

| gacatccaga tgacccagtc tccatcctcc ctgtctgcat ctgtaggaga ccgtgtcacc | 60 |
| atcacttgcc gggcaagtca gtggattggt agggagttaa agtggtatca gcagaaacca | 120 |
| gggaaagccc ctaggctcct gatctatcat ggttccgtgt tgcaaagtgg ggtcccatca | 180 |
| cgtttcagtg gcagtggatc tgggacagat ttcactctca ccatcagcag tctgcaacct | 240 |
| gaagattttg ctacgtacta ctgtcaacag gattttttg ttcctgatac gttcggccaa | 300 |
| gggaccaagg tggaaatcaa acgg | 324 |

<210> SEQ ID NO 3
<211> LENGTH: 324
<212> TYPE: DNA
<213> ORGANISM: Homo sapiens

<400> SEQUENCE: 3

| gacatccaga tgacccagtc tccatcctcc ctgtctgcat ctgtaggaga ccgtgtcacc | 60 |
| atcacttgcc gggcaagtca ggatattgcg aatgatttaa tgtggtacca gcagaaacca | 120 |
| gggaaagccc ctaagctcct gatctatcgt aattcccgtt tgcaaggtgg ggtcccatca | 180 |
| cgtttcagtg gcagtggatc tgggacagat ttcactctca ccatcagcag tctgcaacct | 240 |
| gaagattttg ctacgtacta ctgtcaacag cttgttcatc gcccttatac gatcggccaa | 300 |
| gggaccaagg tggaaatcaa acgg | 324 |

<210> SEQ ID NO 4
<211> LENGTH: 324
<212> TYPE: DNA
<213> ORGANISM: Homo sapiens

<400> SEQUENCE: 4

| gacatccaga tgacccagtc tccatcctcc ctgtctgcat ctgtaggaga ccgtgtcacc | 60 |
| atcacttgcc gggcaagtca gtttattggg ccgcatttaa cgtggtatca gcagaaacca | 120 |
| gggaaagccc ctaagctcct gatctatcat tcttccttgt tgcaaagtgg ggtcccatca | 180 |
| cgtttcagtg gcagtggatc tgggacagat ttcactctca ccatcagcag tctgcagcct | 240 |

```
gaagatttcg ctacgtacta ctgtcaacag tatatgtatt atccttctac gttcggccaa    300
gggaccaagg tgaaaatcaa gcgg                                           324

<210> SEQ ID NO 5
<211> LENGTH: 324
<212> TYPE: DNA
<213> ORGANISM: Homo sapiens

<400> SEQUENCE: 5
gacatccaga tgacccagtc tccatcctcc ctgtctgcat ctgtaggaga ccgtgtcacc     60
atcacttgcc gggcaagtca gtggattggt ccggagttaa gttggtacca gcagaaacca    120
gggaaagccc ctaagctcct gatctatcat acgtccattt tgcaaagtgg ggtcccatca    180
cgtttcagtg gcagtggatc tgggacagat ttcactctca ccatcagcag tctgcaacct    240
gaagattttg ctacgtacta ctgtcaacag tatatgtttc agcctaggac gttcggccaa    300
gggaccaagg tggaaatcag acgg                                           324

<210> SEQ ID NO 6
<211> LENGTH: 324
<212> TYPE: DNA
<213> ORGANISM: Homo sapiens

<400> SEQUENCE: 6
gacatccaga tgatccagtc tccatcctcc ctgtccgcat ctgtaggaga ccgtgtcacc     60
atcacttgcc gggcaagtca gtttattggt aatgagttaa gttggtatca gcagaaacca    120
gggaaagccc ctaagctcct gatctatcat gcttccagtt tgcaaagtgg ggtcccatca    180
cgtttcagtg gcagtggatc tgggacagat ttcactctca ccatcagcag tctgcaacct    240
gaagattttg ctacgtacta ctgtcaacag gttctgggtt atccttatac gttcggccaa    300
gggaccaagg tggaaatcaa acgg                                           324

<210> SEQ ID NO 7
<211> LENGTH: 324
<212> TYPE: DNA
<213> ORGANISM: Homo sapiens

<400> SEQUENCE: 7
gacatccaga tgacccagtc tccatcctcc ctgtctgcat ctgtaggaga ccgtgtcacc     60
atcacttgcc gggcaagtca gtggattggt cctgagttaa gttggtacca gcagaaacca    120
gggaaagccc ctaagctcct gatctatcat ggttccattt tgcaaagtgg ggtcccatca    180
cgtttcagtg gcagtggatc tgggacagat ttcactctca ccatcagcag tctgcaacct    240
gaagattttg ctacgtacta ctgtcaacag gttctgtata gtcctttgac gttcggccaa    300
gggaccaagg tggaaatcaa acgg                                           324

<210> SEQ ID NO 8
<211> LENGTH: 324
<212> TYPE: DNA
<213> ORGANISM: Homo sapiens

<400> SEQUENCE: 8
gacatccaga tgacccagtc tccatcctcc ctgtctgcat ctgtaggaga ccgtgtcacc     60
atcacttgcc gggcaagtca gtggattggg aatgagttaa agtggtatca gcagaaacca    120
gggaaagccc ctaagctcct gatctatatg tcttcccttt tgcaaagtgg ggtcccatca    180
```

```
cgtttcagtg gcagtggatc tgggacagat ttcactctca ccatcagcag tctgcaacct    240
gaagatttag ctacgtacta ctgtcaacag acgcttttgc ttccttttac gttcggccaa    300
gggaccaagg tggaaatcaa acgg                                           324

<210> SEQ ID NO 9
<211> LENGTH: 324
<212> TYPE: DNA
<213> ORGANISM: Homo sapiens

<400> SEQUENCE: 9
gacatccaga tgacccagtc tccatcctcc ctgtctgcat ctgtaggaga ccgtgtcacc     60
atcacttgcc gggcaagtca gtggattggt cctgagttaa gttggtacca gcagaaacca    120
gggaaagccc ctaagctcct gatctatcat ggttccattt tgcaaagtgg ggtcccatca    180
cgtttcagtg gcagtggatc tgggacagat ttcactctca ccatcagcag tctgcaacct    240
gaagattttg ctacgtacta ctgtcaacag cgtctgtatt atcctggtac gttcggccaa    300
gggaccaagg tggaaatcaa acgg                                           324

<210> SEQ ID NO 10
<211> LENGTH: 324
<212> TYPE: DNA
<213> ORGANISM: Homo sapiens

<400> SEQUENCE: 10
gacatccaga tgacccagtc tccatcctcc ctgtctgcat ctgtaggaga ccgtgtcacc     60
atcacttgcc gggcaagtca gtctattggg cgtgagttaa gttggtacca gcagaaacca    120
gggaaagccc ctatgctcct gatctatcat agttccaatt tgcaaagtgg ggtcccatca    180
cgtttcagtg gcagtggatc tgggacagat ttcactctca ccatcagcag tctgcaacct    240
gaagattttg ctacgtacta ctgtcaacag gggatgtatt ggccttatac gttcggccaa    300
gggaccaagg tggaaatcaa acgg                                           324

<210> SEQ ID NO 11
<211> LENGTH: 324
<212> TYPE: DNA
<213> ORGANISM: Homo sapiens

<400> SEQUENCE: 11
gacatccaga tgacccagtc tccatcctcc ctgtctgcat ctgtaggaga ccgtgtcacc     60
atcacttgcc gggcaagtca gtggattaag ccggccttac attggtacca gcagaaacca    120
gggaaagccc ctaagctcct gatctatcat ggttccattt tgcaaagtgg ggtcccatca    180
cgtttcagtg gcagtggatc tgggacagat ttcactctca ccattagcag tctgcaacct    240
gaagattttg ctacgtacta ctgtcaacag actcttttta tgccttatac gttcggccaa    300
gggaccaagg tggaaatcaa acgg                                           324

<210> SEQ ID NO 12
<211> LENGTH: 324
<212> TYPE: DNA
<213> ORGANISM: Homo sapiens

<400> SEQUENCE: 12
gacatccaga tgacccagtc tccatcctcc ctgtctgcat ctgtaggaga ccgtgtcacc     60
atcacttgcc gggcaagtca gtctattagt actgcgttac tgtggtatca gcagaaacca    120
gggaaagccc ctaagctcct gatctataat ggttccatgt tgccaaatgg ggtcccatca    180
```

| | |
|---|---:|
| cgtttcagtg gcagtggatc tgggacagat ttcactctca ccatcagcag tctgcaacct | 240 |
| gaagattttg ctacgtacta ctgtcaacag acttgggata ctcctatgac gttcggccaa | 300 |
| gggaccaagg tggaaatcaa acgg | 324 |

<210> SEQ ID NO 13
<211> LENGTH: 324
<212> TYPE: DNA
<213> ORGANISM: Homo sapiens

<400> SEQUENCE: 13

| | |
|---|---:|
| gacatccaga tgacccagtc tccatcctcc ctgtctgcat ctgtaggaga ccgtgtcacc | 60 |
| atcacttgcc gggcaagtca gtggattggg catgatttat cgtggtacca gcagaaacca | 120 |
| gggaaagccc ctaagctcct gatctatcat tcgtcctctt tgcaaagtgg ggtcccatca | 180 |
| cgtttcagtg gcagtggatc tgggacagat ttcactctca ccatcagcag tctgcaacct | 240 |
| gaagatgttg ctacgtacta ctgtcaacag cttatgggtt atccttttac gttcggccaa | 300 |
| gggaccaagg tggaaatcaa acgg | 324 |

<210> SEQ ID NO 14
<211> LENGTH: 324
<212> TYPE: DNA
<213> ORGANISM: Homo sapiens

<400> SEQUENCE: 14

| | |
|---|---:|
| gacatccaga tgacccagtc tccatcctcc ctgtctgcat ctgtaggaga ccgtgtcacc | 60 |
| atcacttgcc gggcaagtca ggatattggg ggtttgttag tgtggtatca gcagaaacca | 120 |
| gggaaagccc ctaagctcct gatctaccgg agttcctatt tgcaaagtgg ggtcccatca | 180 |
| cgtttcagtg gcagtggatc tgggacagat ttcactctca ccatcagcag tctgcaacct | 240 |
| gaagatttcg ctacgtacta ctgtcaacag acgtgggta ttcctcatac gttcggccaa | 300 |
| gggaccaagg tggaaatcaa acgg | 324 |

<210> SEQ ID NO 15
<211> LENGTH: 324
<212> TYPE: DNA
<213> ORGANISM: Homo sapiens

<400> SEQUENCE: 15

| | |
|---|---:|
| gacatccaga tgacccagtc tccatcctcc ctgtctgcat ctgtaggaga ccgtgtcacc | 60 |
| atcacttgcc gggcaagtca gaagattttt aatggtttaa gttggtatca gcagaaacca | 120 |
| gggaaagccc ctaagctcct gatctatcat agttccacgt tgcaaagtgg ggtcccatca | 180 |
| cgtttcagtg gcagtggatc tgggacagat ttcactctca ccatcagcag tctgcaacct | 240 |
| gaagattttg ctacgtacta ctgtcaacag gttcttctgt atccttatac gttcggccaa | 300 |
| gggaccaagg tggaaatcaa acgg | 324 |

<210> SEQ ID NO 16
<211> LENGTH: 324
<212> TYPE: DNA
<213> ORGANISM: Homo sapiens

<400> SEQUENCE: 16

| | |
|---|---:|
| gacatccaga tgacccagtc tccatcctcc ctgtctgcat ctgtaggaga ccgtgtcacc | 60 |
| atcacttgcc gggcaagtca gagtattggg actaatttat cttggtacca gcagaaacct | 120 |

```
gggaaagccc ctaggctcct gatctatcgg acgtccatgt tgcaaagtgg ggtcccatca      180
cgtttcagtg gcagtggatc tgggacagat ttcactctca ccatcagcag tctgcaacct      240
gaagattttg ctacgtacta ctgtcaacag cagttttttt ggcctcatac gttcggccaa      300
gggaccaagg tggaaatcaa acgg                                             324

<210> SEQ ID NO 17
<211> LENGTH: 354
<212> TYPE: DNA
<213> ORGANISM: Homo sapiens

<400> SEQUENCE: 17
gaggtgcagc tgttggagtc tgggggaggc ttggtacagc ctgggggtc cctgcgtctc       60 tcctgtgcag cctccggatt cacctttagg ttgtatgata tggtttgggt ccgccaggct     120
ccagggaagg gtctggagtg ggtctcatat attagttctg ggggttctgg tacatactac     180
gcagactccg tgaagggccg gttcaccatc tcccgcgaca attccaagaa cacgctgtat     240
ctgcaaatga acagcctgcg tgccgaggac accgcggtat attactgtgc gaaagcgggg     300
gggcgggcta gttttgacta ctggggtcag gaaccctggg tcaccgtctc gagc           354

<210> SEQ ID NO 18
<211> LENGTH: 348
<212> TYPE: DNA
<213> ORGANISM: Homo sapiens

<400> SEQUENCE: 18
gaggtgcagc tgttggagtc tgggggaggc ttggtacagc ctgggggtc cctgcgtctc       60 tcctgtgcag cctccggatt cacctttcat ctttatgata tgatgtgggt ccgccaggct     120
ccagggaagg gtctagagtg ggtctcattt attgggggg atggtcttaa tacatactac      180
gcagactccg tgaagggccg gttcaccatc tcccgcgaca attccaagaa cacgctgtat     240
ctgcaaatga acagcctgcg tgccgaggac accgcggtat attactgtgc gaaagcgggg     300
actcagtttg actactgggg tcagggaacc ctggtcaccg tctcgagc                   348

<210> SEQ ID NO 19
<211> LENGTH: 357
<212> TYPE: DNA
<213> ORGANISM: Homo sapiens

<400> SEQUENCE: 19
gaggtgcagc tgttggagtc tgggggaggc ttggtacagc ctgggggtc cctgcgtctc       60 tcctgtgcag cctccggatt cacctttaat aagtatccta tgatgtgggt ccgccaggct     120
ccagggaagg gtctagagtg ggtctcagag atttctccgt ctggtcagga tacatactac     180
gcagactccg tgaagggccg gttcaccatc tcccgcgaca attccaagaa cacgctgtat     240
ctgcaaatga acagcctgcg tgccgaggac accgcggtat attactgtgc gaaaaatcct    300
cagattctgt ctaattttga ctactggggt cagggaaccc tggtcaccgt ctcgagc        357

<210> SEQ ID NO 20
<211> LENGTH: 372
<212> TYPE: DNA
<213> ORGANISM: Homo sapiens

<400> SEQUENCE: 20
gaggtgcagc tgttggagtc tgggggaggc ttggtacagc ctgggggtc cctgcgtctc       60 tcctgtgcgg cctccggatt cacctttcag tggtatccta tgtggtgggt ccgccaggct     120
```

```
ccagggaagg gtcttgagtg ggtctcactg attgaggggc agggtgatag gacatactac      180
gcagactccg tgaagggccg gttcaccatc tcccgcgaca attccaagaa cacgctgtat      240
ctgcaaatga acagcctgcg tgccgaggac accgcggtat attactgtgc gaaagcgggg      300
gatcgtacgg ctgggtctag ggtaattct tttgactact ggggtcaggg aaccctggtc      360
accgtctcga gc                                                          372

<210> SEQ ID NO 21
<211> LENGTH: 363
<212> TYPE: DNA
<213> ORGANISM: Homo sapiens

<400> SEQUENCE: 21
gaggtgcagc tgttggagtc tgggggaggc ttggtacagc ctggggggtc cctgcgtctc       60
tcctgtgcag cctccggatt cacctttaag gcttatgaga tgggttgggt ccgccaggct      120
ccagggaagg gtctggagtg ggtctcaggt atttctccta atggtggttg gacatactac      180
gcagactccg tgaagggccg gttcaccatc tcccgcgaca attccaagaa cacgctgtat      240
ctgcaaatga acagcctgcg tgccgaggat accgcggtat attactgtgc gaaagagtcg      300
attagtccta ctccgttggg gttt gactac tgggg tcagg gaaccctggt caccgtctcg      360
agc                                                                    363

<210> SEQ ID NO 22
<211> LENGTH: 348
<212> TYPE: DNA
<213> ORGANISM: Homo sapiens

<400> SEQUENCE: 22
gaggtgcagc tgttggagtc tgggggaggc ttggtacagc ctggggggtc cctgcgtctc       60
tcctgtgcag cctccggatt cacctttact gggtatgaga tggggtgggt ccgccaggct      120
ccagggaagg gtctagagtg ggtctcatat atttctaggg gtggtcggtg gacatactac      180
gcagactccg tgaagggccg gttcaccatc tcccgcgaca attccaagaa cacgctgtat      240
ctgcaaatga acagcctgcg tgccgaggac accgcggtat attactgtgc gaaatcggat      300
actatgtttg actactgggg tcagggaacc ctggtcaccg tctcgagc                   348

<210> SEQ ID NO 23
<211> LENGTH: 348
<212> TYPE: DNA
<213> ORGANISM: Homo sapiens

<400> SEQUENCE: 23
gaggtgcagc tgttggagtc tgggggaggc ttggtacagc ctggggggtc cctgcgtctc       60
tcctgtgcag cctccggatt cacctttagt gcttatgaga tgggttgggt ccgccaggct      120
ccagggaagg gtctagagtg ggtctcattt atttctgggg gggtcggtg gacatactac       180 gcagactccg tgaagggccg gttcaccatc tcccgcgaca attccaagaa cacgctgtat      240
ctgcaaatga acagcctgcg tgccgaggac accgcggtat attactgtgc gaaatattcg      300
gaggattttg actactgggg tcagggaacc ctggtcaccg tctcgagc                   348

<210> SEQ ID NO 24
<211> LENGTH: 348
<212> TYPE: DNA
<213> ORGANISM: Homo sapiens
```

<400> SEQUENCE: 24

```
gaggtgcagc tgttggagtc tgggggaggc ttggtacagc ctgggggtc cctgcgtctc      60
tcctgtgcag cctccggatt cacctttggg gcttatccga tgatgtgggt ccgccaggct    120
ccagggaagg gtctagagtg ggtctcagag atttcgcctt cgggttctta tacatactac   180
gcagactccg tgaagggccg gttcaccatc tcccgcgaca attccaagaa cacgctgtat    240
ctgcaaatga acagcctgcg tgccgaggac accgcggtat attactgtgc gaaagatcct   300
cggaagtttg actactgggg tcagggaacc ctggtcaccg tctcgagc                348
```

<210> SEQ ID NO 25
<211> LENGTH: 369
<212> TYPE: DNA
<213> ORGANISM: Homo sapiens

<400> SEQUENCE: 25

```
gaggtgcagc tgttggagtc tgggggaggc ttggtacagc ctgggggtc cctgcgtctc      60
tcctgtgcag cctccggatt cacctttcag ttttataaga tgggttgggt ccgccaggct   120
ccggggaagg gtctagagtg ggtctcatct attagtagtg tgggtgatgc gacatactac    180
gcagactccg tgaagggccg gttcaccatc tcccgcgaca attccaagaa cacgctgtat    240
ctgcaaatga acagcctgcg tgccgaggac accgcggtat attactgtgc gaaaatgggg   300
ggggggcctc ctacgtatgt tgtgtatttt gactactggg gtcagggaac cctggtcacc   360
gtctcgagc                                                             369
```

<210> SEQ ID NO 26
<211> LENGTH: 369
<212> TYPE: DNA
<213> ORGANISM: Homo sapiens

<400> SEQUENCE: 26

```
gaggtgcagc tgttggagtc tgggggaggc ttggtacagc ctgggggtc cctgcgtctc      60
tcctgtgcag cctccggatt cacctttggg gagtatggga tgtattgggt ccgccaggct   120
ccagggaagg gtctagagtg ggtctcatct attagtgagc gtggtcggtt gacatactac    180
gcagactccg tgaagggccg gttcaccatc tcccgcgaca attccaagaa cacgctgtat    240
ctgcaaatga acaacctgcg tgccgaggat accgcggtat attactgtgc gaaatcggcg   300
ctttcgtctg agggttttc gcgttctttt gactactggg gtcagggaac cctggtcacc   360
gtctcgagc                                                             369
```

<210> SEQ ID NO 27
<211> LENGTH: 369
<212> TYPE: DNA
<213> ORGANISM: Homo sapiens

<400> SEQUENCE: 27

```
gaggtgcagc tgttggagtc tgggggaggc ttggtacagc ctgggggtc cctgcgtctc      60
tcctgtgcag cctccggatt cacctttagt gattatgcga tgtattgggt ccgccaggct   120
ccagggaagg gtctagagtg ggtctcatcg attacggcta ggggttttat tacatactac    180
gcagactccg tgaagggccg gttcaccatc tcccgcgaca attccaagaa cacgctgtat    240
ctgcaaatga acagcctgcg tgccgaggac accgcggtat attactgtgc gaaatcgggt   300
tttccgcata agtcgggttc gaattatttt gactactggg gtcagggaac cctggtcacc   360
gtctcgagc                                                             369
```

<210> SEQ ID NO 28
<211> LENGTH: 348
<212> TYPE: DNA
<213> ORGANISM: Homo sapiens

<400> SEQUENCE: 28

```
gaggtgcagc tgttggagtc tgggggaggc ttggtacagc ctgggggtc cctgcgtctc      60
tcctgcgcag cctccggatt cacctttagg ttgtacgata tgatgtgggt ccgccaggct    120
ccagggaagg gtctagagtg gtctcatttt attgggggg atggtcttaa tacatactac    180
gcagactccg tgaagggccg gttcaccatc tcccgcgaca attccaagaa cacgctgtat    240
ctgcaaatga acagcctgcg tgccgaggac accgcggtat attactgtgc gaaagatcct    300
cggaagtttg actactgggg tcagggaacc ctggtcaccg tctcgagc                 348
```

<210> SEQ ID NO 29
<211> LENGTH: 348
<212> TYPE: DNA
<213> ORGANISM: Homo sapiens

<400> SEQUENCE: 29

```
gaggtgcagc tgttggagtc tgggggaggc ttggtacagc ctgggggtc cctgcgtctc      60
tcctgtgcag cctccggatt caccttttcc ttcttcgata tgatgtgggt ccgccaggct    120
ccagggaagg gtctagagtg gtctcatttt attgggggg atggtcttaa tacatactac    180
gcagactccg tgaagggccg gttcaccatc tcccgcgaca attccaagaa cacgctgtat    240
ctgcaaatga acagcctgcg tgccgaggac accgcggtat attactgtgc gaaagcgggg    300
actcagtttg actactgggg tcagggaacc ctggtcaccg tctcgagc                 348
```

<210> SEQ ID NO 30
<211> LENGTH: 348
<212> TYPE: DNA
<213> ORGANISM: Homo sapiens

<400> SEQUENCE: 30

```
gaggtgcagc tgttggagtc tgggggaggc ttggtacagc ctgggggtc cctgcgtctc      60
tcctgtgcag cctccggatt cacctttatg ctcttcgata tgatgtgggt ccgccaggct    120
ccagggaagg gtctagagtg gtctcatttt attgggggg atggtcttaa tacatactac    180
gcagactccg tgaagggccg gttcaccatc tcccgcgaca attccaagaa cacgctgtat    240
ctgcaaatga acagcctgcg tgccgaggac accgcggtat attactgtgc gaaagcgggg    300
actcagtttg actactgggg tcagggaacc ctggtcaccg tctcgagc                 348
```

<210> SEQ ID NO 31
<211> LENGTH: 348
<212> TYPE: DNA
<213> ORGANISM: Homo sapiens

<400> SEQUENCE: 31

```
gaggtgcagc tgttggagtc tgggggaggc ttggtacagc ctgggggtc cctgcgtctc      60
tcctgtgcag cctccggatt cacctttccg ttgtacgata tgatgtgggt ccgccaggct    120
ccagggaagg gtctagagtg gtctcatttt attgggggg atggtcttaa tacatactac    180
gcagactccg tgaagggccg gttcaccatc tcccgcgaca attccaagaa cacgctgtat    240
ctgcaaatga acagcctgcg tgccgaggac accgcggtat attactgtgc gaaagcgggg    300
```

```
actcagtttg actactgggg tcagggaacc ctggtcaccg tctcgagc              348
```

<210> SEQ ID NO 32
<211> LENGTH: 348
<212> TYPE: DNA
<213> ORGANISM: Homo sapiens

<400> SEQUENCE: 32

```
gaggtgcagc tgttggagtc tgggggaggc ttggtacagc ctggggggtc cctgcgtctc    60
tcctgtgcag cctccggatt cacctttccc ctctacgata tgatgtgggt ccgccaggct   120
ccagggaagg gtctagagtg gtctcatttc attgggggg atggtcttaa tacatactac   180
gcagactccg tgaagggccg gttcaccatc tcccgcgaca attccaagaa cacgctgtat   240
ctgcaaatga acagcctgcg tgccgaggac accgcggtat attactgtgc gaaagcgggg   300
actcagtttg actactgggg tcagggaacc ctggtcaccg tctcgagc              348
```

<210> SEQ ID NO 33
<211> LENGTH: 348
<212> TYPE: DNA
<213> ORGANISM: Homo sapiens

<400> SEQUENCE: 33

```
gaggtgcagc tgttggagtc tgggggaggc ttggtacagc ctggggggtc cctgcgtctc    60
tcctgtgcag cctccggatt cacctttcag tacttcgata tgatgtgggt ccgccaggct   120
ccagggaagg gtctagagtg gtctcatttc attgggggg atggtcttaa tacatactac   180
gcagactccg tgaagggccg gttcaccatc tcccgcgaca attccaagaa cacgctgtat   240
ctgcaaatga acagcctgcg tgccgaggac accgcggtat attactgtgc gaaagcgggg   300
actcagtttg actactgggg tcagggaacc ctggtcaccg tctcgagc              348
```

<210> SEQ ID NO 34
<211> LENGTH: 348
<212> TYPE: DNA
<213> ORGANISM: Homo sapiens

<400> SEQUENCE: 34

```
gaggtgcagc tgttggagtc tgggggaggc ttggtacagc ctggggggtc cctgcgtctc    60
tcctgtgcag cctccggatt cacctttcat ctttatgata tgatgtgggt ccgccaggct   120
ccagggaagg gtctagagtg gtctcatttc attgggggg atggtcttaa tacatactac   180
gcagactccg tgaagggccg gttcaccatc tcccgcgaca attccaagaa cacgctgtat   240
ctgcaaatga acagcctgcg tgccgaggac accgcggtat attactgtgc gaaatccccc   300
cgccagtttg actactgggg tcagggaacc ctggtcaccg tctcgagc              348
```

<210> SEQ ID NO 35
<211> LENGTH: 348
<212> TYPE: DNA
<213> ORGANISM: Homo sapiens

<400> SEQUENCE: 35

```
gaggtgcagc tgttggagtc tgggggaggc ttggtacagc ctggggggtc cctgcgtctc    60
tcctgtgcag cctccggatt cacctttcat ctttatgata tgatgtgggt ccgccaggct   120
ccagggaagg gtctagagtg gtctcatttc attgggggg atggtcttaa tacatactac   180
gcagactccg tgaagggccg gttcaccatc tcccgcgaca attccaagaa cacgctgtat   240
ctgcaaatga acagcctgcg tgccgaggac accgcggtat attactgtgc gaaaaacccc   300
```

-continued

```
aggcagtttg actactgggg tcagggaacc ctggtcaccg tctcgagc            348

<210> SEQ ID NO 36
<211> LENGTH: 348
<212> TYPE: DNA
<213> ORGANISM: Homo sapiens

<400> SEQUENCE: 36
gaggtgcagc tgttggagtc tgggggaggc ttggtacagc ctgggggtc  cctgcgtctc   60 tcctgtgcag cctccggatt cacctttcat ctttatgata tgatgtgggt ccgccaggct  120
ccagggaagg gtctagagtg ggtctcattt attggggggg atggtcttaa tacatactac  180
gcagactccg tgaagggccg gttcaccatc tcccgcgaca attccaagaa cacgctgtat  240
ctgcaaatga acagcctgcg tgccgaggac accgcggtat attactgtgc gaaaaagtcg  300
atgcagtttg actactgggg tcagggaacc ctggtcaccg tctcgagc             348

<210> SEQ ID NO 37
<211> LENGTH: 348
<212> TYPE: DNA
<213> ORGANISM: Homo sapiens

<400> SEQUENCE: 37
gaggtgcagc tgttggagtc tgggggaggc ttggtacagc ctgggggtc  cctgcgtctc   60 tcctgtgcag cctccggatt cacctttcat ctttatgata tgatgtgggt ccgccaggct  120
ccagggaagg gtctagagtg ggtctcattt attggggggg atggtcttaa tacatactac  180
gcagactccg tgaagggccg gttcaccatc tcccgcgaca attccaagaa cacgctgtat  240
ctgcaaatga acagcctgcg tgccgaggac accgcggtat attactgtgc gaaatccccc  300
cgcaagtttg actactgggg tcagggaacc ctggtcaccg tctcgagc             348

<210> SEQ ID NO 38
<211> LENGTH: 348
<212> TYPE: DNA
<213> ORGANISM: Homo sapiens

<400> SEQUENCE: 38
gaggtgcagc tgttggagtc tgggggaggc ttggtacagc ctgggggtc  cctgcgtctc   60 tcctgtgcag cctccggatt cacctttcat ctttatgata tgatgtgggt ccgccaggct  120
ccagggaagg gtctagagtg ggtctcattt attggggggg atggtcttaa tacatactac  180
gcagactccg tgaagggccg gttcaccatc tcccgcgaca attccaagaa cacgctgtat  240
ctgcaaatga acagcctgcg tgccgaggac accgcggtat attactgtgc gaaagatcct  300
cggaagtttg actactgggg tcagggaacc ctggtcaccg tctcgagc             348

<210> SEQ ID NO 39
<211> LENGTH: 357
<212> TYPE: DNA
<213> ORGANISM: Homo sapiens

<400> SEQUENCE: 39
gaggtgcagc tgttggagtc tgggggaggc ttggtacagc ctgggggtc  cctgcgtctc   60 tcctgtgcgg cctccggata ccctatgtgg tgggtccgcc aggctccagg gaagggtcct  120
gagtgggtct cactgattga ggggcagggt gataggacat actacgcaga ctccgtgaag  180
ggccggttca ccatctcccg cgacaattcc aagaacacgc tgtatctgca aatgaacagc  240
```

```
ctgcgcgccg aggacaccgc ggtatattac tgtgcgaaag cggggatcg tacggctggg      300 tctagggta attcttttga ctactgggt cagggaaccc tggtcaccgt ctcgagc          357

<210> SEQ ID NO 40
<211> LENGTH: 372
<212> TYPE: DNA
<213> ORGANISM: Homo sapiens

<400> SEQUENCE: 40
gaggtgcagc tgttggagtc tgggggaggc ttggtacagc ctgggggtc cctgcgtctc       60 tcctgtgcgg cctccggatt cacctttcag tgggccccca tgccctgggt ccgccaggct     120
ccagggaagg gtcttgagtg gtctcactg attgaggggc aggtgatag acatactac        180 gcagactccg tgaagggccg gttcaccatc tcccgcgaca attccaagaa cacgctgtat     240
ctgcaaatga acagcctgcg tgccgaggac accgcggtat attactgtgc gaaagcgggg     300
gatcgtacgg ctgggtctag ggtaattct tttgactact ggggtcaggg aaccctggtc     360
accgtctcga gc                                                         372

<210> SEQ ID NO 41
<211> LENGTH: 372
<212> TYPE: DNA
<213> ORGANISM: Homo sapiens

<400> SEQUENCE: 41
gaggtgcagc tgttggagtc tgggggaggc ttggtacagc ctgggggtc cctgcgtctc       60 tcctgtgcgg cctccggatt cacctttcag tgccccaca tgccctgggt ccgccaggct     120
ccagggaagg gtcttgagtg gtctcactg attgaggggc aggtgatag acatactac        180 gcagactccg tgaagggccg gttcaccatc tcccgcgaca attccaagaa cacgctgtat     240
ctgcaaatga acagcctgcg tgccgaggac accgcggtat attactgtgc gaaagcgggg     300
gatcgtacgg ctgggtctag ggtaattct tttgactact ggggtcaggg aaccctggtc     360
accgtctcga gc                                                         372

<210> SEQ ID NO 42
<211> LENGTH: 372
<212> TYPE: DNA
<213> ORGANISM: Homo sapiens
<220> FEATURE:
<221> NAME/KEY: unsure
<222> LOCATION: 88, 90
<223> OTHER INFORMATION: n = A,T,C or G

<400> SEQUENCE: 42
gaggtgcagc tgttggagtc tgggggaggc ttggtacagc ctgggggtc cctgcgtctc       60 tcctgtgcgg cctccggatt caccttnan tggccccaca tgcactgggt ccgccaggct     120
ccagggaagg gtcttgagtg gtctcactg attgaggggc aggtgatag acatactac        180 gcagactccg tgaagggccg gttcaccatc tcccgcgaca attccaagaa cacgctgtat     240
ctgcaaatga acagcctgcg tgccgaggac accgcggtat attactgtgc gaaagcgggg     300
gatcgtacgg ctgggtctag ggtaattct tttgactact ggggtcaggg aaccctggtc     360
accgtctcga gc                                                         372

<210> SEQ ID NO 43
<211> LENGTH: 372
<212> TYPE: DNA
<213> ORGANISM: Homo sapiens
```

<400> SEQUENCE: 43

```
gaggtgcagc tgttggagtc tgggggaggc ttggtacagc ctggggggtc cctgcgtctc      60
tcctgtgcgg cctccggatt caccttcag tggtatccta tgtggtgggt ccgccaggct      120
ccagggaagg gtcttgagtg gtctcactg attgaggggc aggtgatag gacatactac      180
gcagactccg tgaagggccg gttcaccatc tcccgcgaca attccaagaa cacgctgtat      240
ctgcaaatga acagcctgcg tgccgaggac accgcggtat attactgtgc gaaagcgggg      300
gatcgttggg tgttgtctag gggtaattct tttgactact ggggtcaggg aaccctggtc      360
accgtctcga gc                                                         372
```

<210> SEQ ID NO 44
<211> LENGTH: 372
<212> TYPE: DNA
<213> ORGANISM: Homo sapiens

<400> SEQUENCE: 44

```
gaggtgcagc tgttggagtc tgggggaggc ttggtacagc ctggggggtc cctgcgtctc      60
tcctgtgcgg cctccggatt caccttcag tggtatccta tgtggtgggt ccgccaggct      120
ccagggaagg gtcttgagtg gtctcactg attgaggggc aggtgatag gacatactac      180
gcagactccg tgaagggccg gttcaccatc tcccgcgaca attccaagaa cacgctgtat      240
ctgcaaatga acagcctgcg tgccgaggac accgcggtat attactgtgc gaaagcgggg      300
gatcgtcgct tcctctctag gggtaattct tttgactact ggggtcaggg aaccctggtc      360
accgtctcga gc                                                         372
```

<210> SEQ ID NO 45
<211> LENGTH: 372
<212> TYPE: DNA
<213> ORGANISM: Homo sapiens

<400> SEQUENCE: 45

```
gaggtgcagc tgttggagtc tgggggaggc ttggtacagc ctggggggtc cctgcgtctc      60
tcctgtgcgg cctccggatt caccttcag tggtatccta tgtggtgggt ccgccaggct      120
ccagggaagg gtcttgagtg gtctcactg attgaggggc aggtgatag gacatactac      180
gcagactccg tgaagggccg gttcaccatc tcccgcgaca attccaagaa cacgctgtat      240
ctgcaaatga acagcctgcg tgccgaggac accgcggtat attactgtgc gaaagcgggg      300
gatcgtcaca ggacctctag gggtaattct tttgactact ggggtcaggg aaccctggtc      360
accgtctcga gc                                                         372
```

<210> SEQ ID NO 46
<211> LENGTH: 372
<212> TYPE: DNA
<213> ORGANISM: Homo sapiens

<400> SEQUENCE: 46

```
gaggtgcagc tgttggagtc tgggggaggc ttggtacagc ctggggggtc cctgcgtctc      60
tcctgtgcgg cctccggatt caccttcag tggtatccta tgtggtgggt ccgccaggct      120
ccagggaagg gtcttgagtg gtctcactg attgaggtgc aggtgatag gacatactac      180
gcagactccg tgaagggccg gttcaccatc tcccgcgaca attccaagaa cacgctgtat      240
ctgcaaatga acagcctgcg tgccgaggac accgcggtat attactgtgc gaaagcgggg      300
```

```
cccccttcg ctgggtctag gggtaattct tttgactact ggggtcaggg aaccctggtc      360
accgtctcga gc                                                         372

<210> SEQ ID NO 47
<211> LENGTH: 372
<212> TYPE: DNA
<213> ORGANISM: Homo sapiens

<400> SEQUENCE: 47
gaggtgcagc tgttggagtc tgggggaggc ttggtacagc ctgggggtc cctgcgtctc       60 tcctgtgcgg cctccggatt cacctttcag tggtatccta tgtggtgggt ccgccaggct     120
ccagggaagg gtcttgagtg gtctcactg attgaggggc aggtgatag gacatactac       180 gcagactccg tgaagggccg gttcaccatc tcccgcgaca attccaagaa cacgctgtat     240
ctgcaaatga acagcctgcg tgccgaggac accgcggtat attactgtgc gaaagcgggg    300
accaacaacg ctgggtctag gggtaattct tttgactact ggggtcaggg aaccctggtc     360
accgtctcga gc                                                         372

<210> SEQ ID NO 48
<211> LENGTH: 372
<212> TYPE: DNA
<213> ORGANISM: Homo sapiens

<400> SEQUENCE: 48
gaggtgcagc tgttggagtc tgggggaggc ttggtacagc ctgggggtc cctgcgtctc       60 tcctgtgcgg cctccggatt cacctttcag tggtatccta tgtggtgggt ccgccaggct     120
ccagggaagg gtcttgagtg gtctcactg attgaggggc aggtgatag gacatactac       180 gcagactccg tgaagggccg gttcaccatc tcccgcgaca attccaagaa cacgctgtat     240
ctgcaaatga acagcctgcg tgccgaggac accgcggtat attactgtgc gaaagcgggg    300
gatcgtacgg ctcagaacag cggtaattct tttgactact ggggtcgggg aaccctggtc     360
accgtctcga gc                                                         372

<210> SEQ ID NO 49
<211> LENGTH: 372
<212> TYPE: DNA
<213> ORGANISM: Homo sapiens

<400> SEQUENCE: 49
gaggtgcagc tgttggagtc tgggggaggc ttggtacagc ctgggggtc cctgcgtctc       60 tcctgtgcgg cctccggatt cacctttcag tggtatccta tgtggtgggt ccgccaggct     120
ccagggaagg gtcttgagtg gtctcactg attgaggggc agggtgatag gacatactac      180
gcagactccg tgaagggccg gttcaccatc tcccgcgaca attccaagaa cacgctgtat     240
ctgcaaatga acagcctgcg tgccgaggac accgcggtat attactgtgc gaaagcgggg    300
aacagcaacg ctgggtctag gggtaattct tttgactact ggggtcaggg aaccctggtc    360
accgtctcga gc                                                         372

<210> SEQ ID NO 50
<211> LENGTH: 348
<212> TYPE: DNA
<213> ORGANISM: Homo sapiens

<400> SEQUENCE: 50
gaggtgcagc tgttggagtc tgggggaggc ttggtacagc ctgggggtc cctgcgtctc       60
```

```
tcctgtgcag cctccggatt cacctttccc gcttatccga tgatgtgggt ccgccaggct    120
ccagggaagg gtctagagtg ggtctcagag atttcgcctt cgggttctta tacatactac    180
gcagactccg tgaagggccg gttcaccatc tcccgcgaca attccaagaa cacgctgtat    240
ctgcaaatga acagcctgcg tgccgaggac accgcggtat attactgtgc gaaagatcct    300
cggaagtttg actactgggg tcagggaacc ctggtcaccg tctcgagc                 348

<210> SEQ ID NO 51
<211> LENGTH: 348
<212> TYPE: DNA
<213> ORGANISM: Homo sapiens

<400> SEQUENCE: 51
gaggtgcagc tgttggagtc tgggggaggc ttggtacagc ctggggggtc cctgcgtctc     60
tcctgtgcag cctccggatt cacctttaag gcttatccga taatgtgggt ccgccaggct    120
ccagggaagg gtctagagtg ggtctcagag atttcgcctt cgggttctta tacatactac    180
gcagactccg tgaagggccg gttcaccatc tcccgcgaca attccaagaa cacgctgtat    240
ctgcaaatga acagcctgcg tgccgaggac accgcggtat attactgtgc gaaagatcct    300
cggaagtttg actactgggg tcagggaacc ctggtcaccg tctcgagc                 348

<210> SEQ ID NO 52
<211> LENGTH: 348
<212> TYPE: DNA
<213> ORGANISM: Homo sapiens

<400> SEQUENCE: 52
gaggtgcagc tgttggagtc tgggggaggc ttggtacagc ctggggggtc cctgcgtctc     60
tcctgtgcag cctccggatt cacctttacg gcttatccga tgatgtgggt ccgccaggct    120
ccagggaagg gtctagagtg ggtctcagag atttcgcctt cgggttctta tacatactac    180
gcagactccg tgaagggccg gttcaccatc tcccgcgaca attccaagaa cacgctgtat    240
ctgcaaatga acagcctgcg tgccgaggac accgcggtat attactgtgc gaaagatcct    300
cggaagtttg actactgggg tcagggaacc ctggtcaccg tctaaagc                 348

<210> SEQ ID NO 53
<211> LENGTH: 348
<212> TYPE: DNA
<213> ORGANISM: Homo sapiens

<400> SEQUENCE: 53
gaggtgcagc tgttggagtc tgggggaggc ttggtacagc ctggggggtc cctgcgtctc     60
tcctgtgcag cctccggatt cacctttggg tggtatccga tgatgtgggt ccgccaggct    120
ccagggaagg gtctagagtg ggtctcagag atttcgcctt cgggttctta tacatactac    180
gcagactccg tgaagggccg gttcaccatc tcccgcgaca attccaagaa cacgctgtat    240
ctgcaaatga acagcctgcg tgccgaggac accgcggtat attactgtgc gaaagatcct    300
cggaagtttg actactgggg tcagggaacc ctggtcaccg tctcgagc                 348

<210> SEQ ID NO 54
<211> LENGTH: 348
<212> TYPE: DNA
<213> ORGANISM: Homo sapiens

<400> SEQUENCE: 54
```

```
gaggtgcagc tgttggagtc tgggggaggc ttggtacagc ctgggggtc cctgcgtctc      60 tcctgtgcag cctccggatt cacctttggg ctctatccga tgatgtgggt ccgccaggct    120
ccagggaagg gtctagagtg ggtctcagag atttcgcctt cgggttctta tacatactac    180
gcagactccg tgaagggccg gttcaccatc tcccgcgaca attccaagaa cacgctgtat    240
ctgcaaatga acagcctgcg tgccgaggac accgcggtat attactgtgc gaaagatcct    300
cggaagtttg actactgggg tcagggaacc ctggtcaccg tctagagc                 348
```

<210> SEQ ID NO 55
<211> LENGTH: 348
<212> TYPE: DNA
<213> ORGANISM: Homo sapiens

<400> SEQUENCE: 55

```
gaggtgcagc tgttggagtc tgggggaggc ttggtacagc ctgggggtc cctgcgtctc      60 tcctgtgcag cctccggatt cacctttctg gcttatccga tgatgtgggt ccgccaggct    120
ccagggaagg gtctagagtg ggtctcagag atttcgcctt cgggttctta tacatactac    180
gcagactccg tgaagggccg gttcaccatc tcccgcgaca attccaagaa cacgctatat    240
ctgcaaatga acagcctgcg tgccgaggac accgcggtat attactgtgc gaaagatcct    300
cggaagtttg actactgggg tcagggaacc ctggtcaccg tctcgagc                 348
```

<210> SEQ ID NO 56
<211> LENGTH: 348
<212> TYPE: DNA
<213> ORGANISM: Homo sapiens

<400> SEQUENCE: 56

```
gaggtgcagc tgttggagtc tgggggaggc ttggtacagc ctgggggtc cctgcgtctc      60 tcctgtgcag cctccggatt cacctttggg aggtatccga tgatgtgggt ccgccaggct    120
ccagggaagg gtctagagtg ggtctcagag atttcgcctt cgggttctta tacatactac    180
gcagactccg tgaagggccg gttcaccatc tcccgcgaca attccaagaa cacgctgtat    240
ctgcaaatga acagcctgcg tgccgaggac accgcggtat attactgtgc gaaagatcct    300
cggaagtttg actactgggg tcagggaacc ctggtcaccg tctcgagc                 348
```

<210> SEQ ID NO 57
<211> LENGTH: 348
<212> TYPE: DNA
<213> ORGANISM: Homo sapiens

<400> SEQUENCE: 57

```
gaggtgcagc tgttggagtc tgggggaggc ttggtacagc ctgggggtc cctgcgtctc      60 tcctgtgcag cctccggatt cacctttggg gctttcccga tgatgtgggt ccgccaggct    120
ccagggaagg gtctagagtg ggtctcagag atttcgcctt cgggttctta tacatactac    180
gcagactccg tgaagggccg gttcaccatc tcccgcgaca attccaagaa cacgctgtat    240
ctgcaaatga acagcctgcg tgccgaggac accgcggtat attactgtgc gaaagatcct    300
cggaagtttg actactgggg tcagggaacc ctggtcaccg tctcgagc                 348
```

<210> SEQ ID NO 58
<211> LENGTH: 348
<212> TYPE: DNA
<213> ORGANISM: Homo sapiens

<400> SEQUENCE: 58

```
gaggtgcagc tgttggagtc tgggggaggc ttggtacagc ctgggggtc cctgcgtctc      60 tcctgtgcag cctccggatt cacctttggg gcttatccga tgttgtgggt ccgccaggct    120
ccagggaagg gtctagagtg ggtctcagag atttcgcctt cgggttctta tacatactac    180
gcagactccg tgaagggccg gttcaccatc tcccgcgaca attccaagaa cacgctgtat    240
ctgcaaatga acagcctgcg tgccgaggac accgcggtat attactgtgc gaaagatcct    300
cggaagtttg actactgggg tcagggaacc ctggtcaccg tctcgagc                 348
```

<210> SEQ ID NO 59
<211> LENGTH: 348
<212> TYPE: DNA
<213> ORGANISM: Homo sapiens

<400> SEQUENCE: 59

```
gaggtgcagc tgttggagtc tgggggaggc ttggtacagc ctgggggtc cctgcgtctc      60 tcctgtgcag cctccggatt cacctttttcc ctcttcccga tgatgtgggt ccgccaggct   120
ccagggaagg gtctagagtg ggtctcagag atttcgcctt cgggttctta tacatactac    180
gcagactccg tgaagggccg gttcaccatc tcccgcgaca attccaagaa cacgctgtat    240
ctgcaaatga acagcctgcg tgccgaggac accgcggtat attactgtgc gaaagatcct    300
cggaagtttg actactgggg tcagggaacc ctggtcaccg tctcgagc                 348
```

<210> SEQ ID NO 60
<211> LENGTH: 348
<212> TYPE: DNA
<213> ORGANISM: Homo sapiens

<400> SEQUENCE: 60

```
gaggtgcagc tgttggagtc tgggggaggc ttggtacagc ctgggggtc cctgcgtctc      60 tcctgtgcag cctccggatt cacctttttc ttgttcccga tgatgtgggt ccgccaggct    120
ccagggaagg gtctagagtg ggtctcagag atttcgcctt cgggttctta tacatactac    180
gcagactccg tgaagggccg gttcaccatc tcccgcgaca attccaagaa cacgctgtat    240
ctgcaaatga acagcctgcg tgccgaggac accgcggtat attactgtgc gaaagatcct    300
cggaagtttg actactgggg tcagggaacc ctggtcaccg tctcgagc                 348
```

<210> SEQ ID NO 61
<211> LENGTH: 348
<212> TYPE: DNA
<213> ORGANISM: Homo sapiens

<400> SEQUENCE: 61

```
gaggtgcagc tgttggagtc cgggggaggc ttggtacagc ctgggggtc cctgcgtctc      60 tcctgtgcag cctccggatt cacctttttcg tacttcccga tgatgtgggt ccgccaggct   120
ccagggaagg gtctagagtg ggtctcagag atttcgcctt cgggttctta tacatactac    180
gcagactccg tgaagggccg gttcaccatc tcccgcgaca attccaagaa cacgctgtat    240
ctgcaaatga acagcctgcg tgccgaggac accgcggtat attactgtgc gaaagatcct    300
cggaagtttg actactgggg tcagggaacc ctggtcaccg tctcgagc                 348
```

<210> SEQ ID NO 62
<211> LENGTH: 348
<212> TYPE: DNA
<213> ORGANISM: Homo sapiens

<400> SEQUENCE: 62

```
gaggtgcagc tgttggagtc tgggggaggc ttggtacagc ctgggggtc cctgcgtctc      60
tcctgtgcag cctccggatt cacctttgcc ttcgccccga tgatgtgggt ccgccaggct    120
ccagggaagg gtctagagtg ggtctcagag atttcgcctt cgggttctta tacatactac   180
gcagactccg tgaagggccg gttcaccatc tcccgcgaca attccaagaa cacgctgtat    240
ctgcaaatga acagcctgcg tgccgaggac accgcggtat attactgtgc gaaagatcct    300
cggaagtttg actactgggg tcagggaacc ctggtcaccg tctcaagc                 348
```

<210> SEQ ID NO 63
<211> LENGTH: 348
<212> TYPE: DNA
<213> ORGANISM: Homo sapiens

<400> SEQUENCE: 63

```
gaggtgcagc tgttggagtc tgggggaggc ttggtacagc ctgggggtc cctgcgtctc      60
tcctgtgcag cctccggatt cacctttgcc ccctacccga tgatgtgggt ccgccaggct    120
ccagggaagg gtctagagtg ggtctcagag atttcgcctt cgggttctta tacatactac   180
gcagactccg tgaagggccg gttcaccatc tcccgcgaca attccaagaa cacgctgtat    240
ctgcaaatga acagcctgcg tgccgaggac accgcggtat attactgtgc gaaagatcct    300
cggaagtttg actactgggg tcagggaacc ctggtcaccg tctcaagc                 348
```

<210> SEQ ID NO 64
<211> LENGTH: 348
<212> TYPE: DNA
<213> ORGANISM: Homo sapiens

<400> SEQUENCE: 64

```
gaggtgcagc tgttggagtc tgggggaggc ttggtacagc ctgggggtc cctgcgtctc      60
tcctgtgcag cctccggatt cacctttacc tcccacccga tgatgtgggt ccgccaggct    120
ccagggaagg gtctagagtg ggtctcagag atttcgcctt cgggttctta tacatactac   180
gcagactccg tgaagggccg gttcaccatc tcccgcgaca attccaagaa cacgctgtat    240
ctgcaaatga acagcctgcg tgccgaggac accgcggtat attactgtgc gaaagatcct    300
cggaagtttg actactgggg tcagggaacc ctggtcaccg tctcgagc                 348
```

<210> SEQ ID NO 65
<211> LENGTH: 348
<212> TYPE: DNA
<213> ORGANISM: Homo sapiens

<400> SEQUENCE: 65

```
gaggtgcagc tgttggagtc tgggggaggc ttggtacagc ctgggggtc cctgcgtctc      60
tcctgtgcag cctccggatt cacctttacg agccacccga tgatgtgggt ccgccaggct    120
ccagggaagg gtctagagtg ggtctcagag atttcgcctt cgggttctta tacatactac   180
gcagactccg tgaagggccg gttcaccatc tcccgcgaca attccaagaa cgcgctgtat    240
ctgcaaatga acagcctgcg tgccgaggac accgcggtat attactgtgc gaaagatcct    300
cggaagtttg actactgggg tcagggaacc ctggtcaccg tctcgagc                 348
```

<210> SEQ ID NO 66
<211> LENGTH: 348
<212> TYPE: DNA
<213> ORGANISM: Homo sapiens

<400> SEQUENCE: 66

| gaggtgcagc tgttggagtc tgggggaggc ttggtacagc ctggggggtc cctgcgtctc | 60 |
| tcctgtgcag cctccggatt cacctttcac gcttatccga tgatgtgggt ccgccaggct | 120 |
| ccagggaagg gtctagagtg ggtctcagag atttcgcctt cgggttctta tacatactac | 180 |
| gcagactccg tgaagggccg gttcaccatc tcccgcgaca attccaagaa cacgctgtat | 240 |
| ctgcaaatga acagcctgcg tgccgaggac accgcggtat attactgtgc gaaagatcct | 300 |
| cggaagtttg actactgggg tcagggaacc ctggtcaccg tctcgagc | 348 |

<210> SEQ ID NO 67
<211> LENGTH: 348
<212> TYPE: DNA
<213> ORGANISM: Homo sapiens

<400> SEQUENCE: 67

| gaggtgcagc tgttggagtc tgggggaggc ttggtacagc ctggggggtc cctgcgtctc | 60 |
| tcctgtgcag cctccggatt cacctttagg gcttatccga tgatgtgggt ccgccaggct | 120 |
| ccagggaagg gtctagagtg ggtctcagag atttcgcctt cgggttctta tacatactac | 180 |
| gcagactccg tgaagggccg gttcaccatc tcccgcgaca attccaagaa cacgctgtat | 240 |
| ctgcaaatga acagcctgcg tgccgaggac accgcggtat attactgtgc gaaagatcct | 300 |
| cggaagtttg actactgggg tcagggaacc ctggtcaccg tctcgagc | 348 |

<210> SEQ ID NO 68
<211> LENGTH: 348
<212> TYPE: DNA
<213> ORGANISM: Homo sapiens

<400> SEQUENCE: 68

| gaggtgcagc tgttggagtc tgggggaggc ttggtacagc ctggggggtc cctgcgtctc | 60 |
| tcctgtgcag cctccggatt cacctttttg gcttatccga tgatgtgggt ccgccaggct | 120 |
| ccagggaagg gtctagagtg ggtctcagag atttcgcctt cgggttctta tacatactac | 180 |
| gcagactccg tgaagggccg gttcaccatc tcccgcgaca attccaagaa cacgctgtat | 240 |
| ctgcaaatga acagcctgcg tgccgaggac accgcggtat attactgtgc gaaagatcct | 300 |
| cggaagtttg actactgggg tcagggaacc ctggtcaccg tctcgagc | 348 |

<210> SEQ ID NO 69
<211> LENGTH: 348
<212> TYPE: DNA
<213> ORGANISM: Homo sapiens

<400> SEQUENCE: 69

| gaggtgcagc tgttggagtc tgggggaggc ttggtacagc ctggggggtc cctgcgtctc | 60 |
| tcctgtgcag cctccggatt cacctttttg gcttatccga tgatgtgggt ccgccaggct | 120 |
| ccagggaagg gtctagagtg ggtctcagag atttcgcctt cgggttctta tacatactac | 180 |
| gcagactccg tgaagggccg gttcaccatc tcccgcgaca attccaagaa cacgctgtat | 240 |
| ctgcaaatga acagcctgcg tgccgaggac accgcggtat attactgtgc gaaagatcct | 300 |
| cggaagtttg actactgggg tcagggaacc ctggtcaccg tctcgagc | 348 |

<210> SEQ ID NO 70
<211> LENGTH: 348
<212> TYPE: DNA

<213> ORGANISM: Homo sapiens

<400> SEQUENCE: 70

```
gaggtgcagc agttggagtc tgggggaggc ttggtacagc ctgggggttc cctgcgtctc      60
tcctgtgcag cctccggatt caccttttgg gcttatccga tgatgtgggt ccgccaggct     120
ccagggaagg gtctagagtg ggtctcagag atttcgcctt cgggttctta tacatactac     180
gcagactccg tgaagggccg gttcaccatc tcccgcgaca attccaagaa cacgctgtat     240
ctgcaaatga acagcctgcg tgccgaggac accgcggtat attactgtgc gaaagatcct     300
cggaagtttg actactgggg tcagggaacc ctggtcaccg tctcgagc                  348
```

<210> SEQ ID NO 71
<211> LENGTH: 348
<212> TYPE: DNA
<213> ORGANISM: Homo sapiens

<400> SEQUENCE: 71

```
gaggtgcagc tgttggagtc tgggggaggc ttggtacagc ctgggggttc cctgcgtctc      60
tcctgtgcag cctccggatt cacctttcag gcttatccga tgatgtgggt ccgccaggct     120
ccagggaagg gtctagagtg ggtctcagag atttcgcctt cgggttctta tacatactac     180
gcagactccg tgaagggccg gttcaccatc tcccgcgaca attccaagaa cacgctgtat     240
ctgcaaatga acagcctgcg tgccgaggac accgcggtat attactgtgc gaaagatcct     300
cggaagtttg actactgggg tcagggaacc ctggtcaccg tctagagc                  348
```

<210> SEQ ID NO 72
<211> LENGTH: 348
<212> TYPE: DNA
<213> ORGANISM: Homo sapiens

<400> SEQUENCE: 72

```
gaggtgcagc tgttggagtc tgggggaggc ttggtacagc ctgggggttc cctgcgcctc      60
tcctgtgcag cctccggatt cacctttggg cactatccga tgatgtgggt ccgccaggct     120
ccagggaagg gtctagagtg ggtctcagag atttcgcctt cgggttctta tacatactac     180
gcagactccg tgaagggccg gttcaccatc tcccgcgaca attccaagaa cacgctgtat     240
ctgcaaatga acagcctgcg tgccgaggac accgcggtat attactgtgc gaaagatcct     300
cggaagtttg actactgggg tcagggaacc ctggtcaccg tctcgagc                  348
```

<210> SEQ ID NO 73
<211> LENGTH: 348
<212> TYPE: DNA
<213> ORGANISM: Homo sapiens

<400> SEQUENCE: 73

```
gaggtgcagc tgttggagtc tgggggaggc ttggtacagc ctgggggtc cctgcgtctc       60
tcctgtgcag cctccggatt cacctttggg ttgtatccga tgatgtgggt ccgccaggct     120
ccagggaagg gtctagagtg ggtctcagag atttcgcctt cgggttctta tacatactac     180
gcagactccg tgaagggccg gttcaccatc tcccgcgaca attccaagaa cacgctgtat     240
ctgcaaatga acagcctgcg tgccgaggac accgcggtat attactgtgc gaaagatcct     300
cggaagtttg actactgggg tcagggaacc ctggtcaccg tctcgagc                  348
```

<210> SEQ ID NO 74
<211> LENGTH: 348

```
<212> TYPE: DNA
<213> ORGANISM: Homo sapiens

<400> SEQUENCE: 74
gaggtgcagc tgttggagtc tgggggaggc ttggtacagc ctgggggtc  cctgcgtctc    60 tcctgtgcag cctccggatt cacctttggg tggtatccga tgatgtgggt ccgccaggct   120
ccagggaagg gtctagagtg ggtctcagag atttcgcctt cgggttctta tacatactac   180
gcagactccg tgaagggccg gttcaccatc tcccgcgaca attccaagaa cacgctgtat   240
ctgcaaatga acagcctgcg tgccgaggac accgcggtat attactgtgc gaaagatcct   300
cggaagtttg actactgggg tcagggaacc ctggtcaccg tctcgagc                348

<210> SEQ ID NO 75
<211> LENGTH: 348
<212> TYPE: DNA
<213> ORGANISM: Homo sapiens

<400> SEQUENCE: 75
gaggtgcagc tgttggagtc tgggggaggc ttggtacagc ctgggggtc  cctgcgtctc    60 tcctgtgcag cctccggatt cacctttggg gctttcccga tgatgtgggt ccgccaggct   120
ccagggaagg gtctagagtg ggtctcagag atttcgcctt cgggttctta tacatactac   180
gcagactccg tgaagggccg gttcaccatc tcccgcgaca attccaagaa cacgctgtat   240
ctgcaaatga acagcctgcg tgccgaggac accgcggtat attactgtgc gaaagatcct   300
cggaagtttg actactgggg tcagggaacc ctggtcaccg tctcgagc                348

<210> SEQ ID NO 76
<211> LENGTH: 348
<212> TYPE: DNA
<213> ORGANISM: Homo sapiens

<400> SEQUENCE: 76
gaggtgcagc tgttggagtc tgggggaggc ttggtacagc ctgggggtc  cctgcgtctc    60 tcctgtgcag cctccggatt cacctttaag gcttatccga taatgtgggt ccgccaggct   120
ccagggaagg gtctagagtg ggtctcagag atttcgcctt cgggttctta tacatactac   180
gcagactccg tgaagggccg gttcaccatc tcccgcgaca attccaagaa cacgctgtat   240
ctgcaaatga acagcctgcg tgccgaggac accgcggtat attactgtgc gaaagatccc   300
cgcgcctttg actactgggg tcagggaacc ctggtcaccg tctcgagc                348

<210> SEQ ID NO 77
<211> LENGTH: 348
<212> TYPE: DNA
<213> ORGANISM: Homo sapiens

<400> SEQUENCE: 77
gaggtgcagc tgttggagtc tgggggaggc ttggtacagc ctgggggtc  cctgcgtctc    60 tcctgtgcag cctccggatt cacctttaag gcttatccga taatgtgggt ccgccaggct   120
ccagggaagg gtctagagtg ggtctcagag atttcgcctt cgggttctta tacatactac   180
gcagactccg tgaagggccg gttcaccatc tcccgcgaca attccaagaa cacgctgtat   240
ctgcaaatga acagcctgcg tgccgaggac accgcggtat attactgtgc gaaatccccc   300
cgcaagtttg actactgggg tcagggaacc ctggtcaccg tctcgagc                348

<210> SEQ ID NO 78
```

```
<211> LENGTH: 348
<212> TYPE: DNA
<213> ORGANISM: Homo sapiens

<400> SEQUENCE: 78
gaggtgcagc tgttggagtc tgggggaggc ttggtacagc ctggggggtc cctgcgtctc      60
tcctgtgcag cctccggatt cacctttaag gcttatccga taatgtgggt ccgccaggct     120
ccagggaagg gtctagagtg ggtctcagag atttcgcctt cgggttctta tacatactac     180
gcagactccg tgaagggccg gttcaccatc tcccgcgaca actccaagaa cacgctgtat     240
ctgcaaatga acagcctgcg tgccgaggac accgcggtat attactgtgc gaaaaccccc     300
cgcaagtttg actactgggg tcggggaacc ctggtcaccg tctcgagc                  348

<210> SEQ ID NO 79
<211> LENGTH: 348
<212> TYPE: DNA
<213> ORGANISM: Homo sapiens

<400> SEQUENCE: 79
gaggtgcagc tgttggagtc tgggggaggt ttggtacagc ctggggggtc cctgcgtctc      60
tcctgtgcag cctccggatt cacctttaag gcttatccga taatgtgggt ccgccaggct     120
ccagggaagg gtctagagtg ggtctcagag atttcgcctt cgggttctta tacatactac     180
gcagactccg tgaagggccg gttcaccatc tcccgcgaca attccaagaa cacgctgtat     240
ctgcaaatga acagcctgcg tgccgaggac accgcggtat attactgtgc gaaagatcct     300
cgggagtttg actactgggg tcagggaacc ctggtcaccg tctcgagc                  348

<210> SEQ ID NO 80
<211> LENGTH: 348
<212> TYPE: DNA
<213> ORGANISM: Homo sapiens

<400> SEQUENCE: 80
gaggtgcagc tgttggagtc tgggggaggc ttggtacagc ctggggggtc cctgcgtctc      60
tcctgtgcag cctccggatt cacctttaag gcttatccga taatgtgggt ccgccaggct     120
ccagggaagg gtctagagtg ggtctcagag atttcgcctt cgggttctta tacatactac     180
gcagactccg tgaagggccg gttcaccatc tcccgcgaca attccaagaa cacgctgtat     240
ctgcaaatga acagcctgcg tgccgaggac accgcggtat attactgtgc gaaagatccc     300
cggcgctttg actactgggg tcagggaacc ctggtcaccg tctcgagc                  348

<210> SEQ ID NO 81
<211> LENGTH: 348
<212> TYPE: DNA
<213> ORGANISM: Homo sapiens

<400> SEQUENCE: 81
gaggtgcagc tgttggagtc tgggggaggc ttggtacagc ctggggggtc cctgcgtctc      60
tcctgtgcag cctccggatt cacctttaag gcttatccga taatgtgggt ccgccaggct     120
ccagggaagg gtctagagtg ggtctcagag atttcgcctt cgggttctta tacatactac     180
gcagactccg tgaagggccg gttcaccatc tcccgcgaca attccaagaa cacgctgtat     240
ctgcaaatga acagcctgcg tgccgaggac accgcggtat attactgtgc gaaagatccc     300
cgcttctttg actactgggg tcagggaacc ctggtcaccg tctcgagc                  348
```

<210> SEQ ID NO 82
<211> LENGTH: 348
<212> TYPE: DNA
<213> ORGANISM: Homo sapiens

<400> SEQUENCE: 82
gaggtgcagc tgttggagtc tgggggaggc ttggtacagc ctggggggtc cctgcgtctc     60
tcctgtgcag cctccggatt cacctttaag gcttatccga taatgtgggt ccgccaggct    120
ccagggaagg gtctagagtg ggtctcagag atttcgcctt cgggttctta tacatactac    180
gcagactccg tgaagggccg gttcaccatc tcccgcgaca attccaagaa cacgctgtat    240
ctgcaaatga acagcctgcg tgccgaggac accgcggtat attactgtgc gaaaaccccc    300
atcaagtttg actactgggg tcagggaacc ctggtcaccg tctcgagc                 348

<210> SEQ ID NO 83
<211> LENGTH: 348
<212> TYPE: DNA
<213> ORGANISM: Homo sapiens

<400> SEQUENCE: 83
gaggtgcagc tgttggagtc tgggggaggc ttggtacagc ctggggggtc cctgcgtctc     60
tcctgtgcag cctccggatt cacctttaag gcttatccga taatgtgggt ccgccaggct    120
ccagggaagg gtctagagtg ggtctcagag atttcgcctt cgggttctca tacatactac    180
gcagactccg tgaagggccg gttcaccatc tcccgcgaca attccaagaa cacgctgtat    240
ctgcaaatga acagcctgcg tgccgaggac accgcggtat attactgtgc gaaagatttc    300
tcgcagtttg actactgggg tcagggaacc ctggtcaccg tctcgagc                 348

<210> SEQ ID NO 84
<211> LENGTH: 348
<212> TYPE: DNA
<213> ORGANISM: Homo sapiens

<400> SEQUENCE: 84
gaggtgcagc tgttggagtc tgggggaggc ttggtacagc ctggggggtc cctgcgtctc     60
tcctgtgcag cctccggatt cacctttaag gcttatccga tattgtgggt ccgccaggct    120
ccagggaagg gtctagagtg ggtctcagag atttcgcctt cgggttctta tacatactac    180
gcagactccg tgaagggccg gttcaccatc tcccgcgaca attccaagaa cacgctgtat    240
ctgcaaatga acagcctgcg tgccgaggac accgcggtat attactgtgc gaaagatcct    300
cggaagtttg actactgggg tcagggaacc ctggtcaccg tctcgagc                 348

<210> SEQ ID NO 85
<211> LENGTH: 348
<212> TYPE: DNA
<213> ORGANISM: Homo sapiens

<400> SEQUENCE: 85
gaggtgcagc tgttggagtc tgggggaggc ttggtacagc ctggggggtc cctgcgtctc     60
tcctgtgcag cctccggatt cacctttaag gcttatccga taatgtgggt ccgccaggcc    120
ccagggaagg gtctagagtg ggtctcagag atttcgcctt cgggcaagat gaagtactac    180
gcagactccg tgaagggccg gttcaccatc tcccgcgaca attccaagaa cacgctgtat    240
ctgcaaatga acagcctgcg tgccgaggac accgcggtat attactgtgc gaaaaccccc    300
cgcaagtttg actactgggg tcggggaacc ctggtcaccg tctccagc                 348

<210> SEQ ID NO 86
<211> LENGTH: 348
<212> TYPE: DNA
<213> ORGANISM: Homo sapiens

<400> SEQUENCE: 86

```
gaggtgcagc tgttggagtc tgggggaggc ttggtacagc ctgggggtc cctgcgtctc        60
tcctgtgcag cctccggatt cacctttaag gcttatccga taatgtgggt ccgccaggct      120
ccagggaagg gtctagagtg ggtctcagag atttcgccca ccggttctta tacatactac      180
gcagactccg tgaagggccg gttcaccatc tcccgcgaca attccaagaa cacgctgtat      240
ctgcaaatga acagcctgcg tgccgaggac accgcggtat attactgtgc gaaatccccc      300
cgcaagtttg actactgggg tcagggaacc ctggtcaccg tctcgagc                   348
```

<210> SEQ ID NO 87
<211> LENGTH: 348
<212> TYPE: DNA
<213> ORGANISM: Homo sapiens

<400> SEQUENCE: 87

```
gaggtgcagc tgttggagtc tgggggaggc ttggtacagc ctgggggtc cctgcgtctc        60
tcctgtgcag cctccggatt cacctttaag gcttatccga taatgtgggt ccgccaggct      120
ccagggaagg gtctagagtg ggtctcagag atttcgcctt cgggttctta tacatactac      180
gcaaactccg tgaagggccg gttcaccatc tcccgcgaca attccaagaa cacgctgtat      240
ctgcaaatga acagcctgcg tgccgaggac accgcggtat attactgtgc gaaagatccc      300
cgcgcctttg actactgggg tcagggaacc ctggtcaccg tctcgagc                   348
```

<210> SEQ ID NO 88
<211> LENGTH: 348
<212> TYPE: DNA
<213> ORGANISM: Homo sapiens

<400> SEQUENCE: 88

```
gaggtgcagc tgttggagtc tgggggaggc ttggtacagc ctgggggtc cctgcgtctc        60
tcctgtgcag cctccggatt cacctttaag gcttatccga taatgtgggt ccgccaggct      120
ccagggaagg gtctagagtg ggtctcagag atttcgccct ccggttctta tacatactac      180
gcagactccg tgaagggccg gttcaccatc tcccgcgaca attccaagaa cacgctgtat      240
ctgcaaatga acagcctgcg tgccgaggac accgcggtat attactgtgc gaaaaccccc      300
cgcaagtttg actactgggg tcagggaacc ctggtcaccg tctcgagc                   348
```

<210> SEQ ID NO 89
<211> LENGTH: 348
<212> TYPE: DNA
<213> ORGANISM: Homo sapiens

<400> SEQUENCE: 89

```
gaggtgcagc tgttggagtc tgggggaggc ttggtacagc ctgggggtc cctgcgtctc        60
tcctgtgcag cctccggatt cacctttaag gcttatccga taatgtgggt ccgccaggct      120
ccagggaagg gtctagagtg ggtctcagag atttcgcctt cggtcagat gaggtactac       180
gcagactccg tgaagggccg gttcaccatc tcccgcgaca attccaagaa cacgctgtat      240
ctgcaaatga acagcctgcg tgccgaggac accgcggtat attactgtgc gaaagatcct      300
cgggagtttg actactgggg tcagggaacc ctggtcaccg tctcgagc                   348
```

<210> SEQ ID NO 90
<211> LENGTH: 348
<212> TYPE: DNA
<213> ORGANISM: Homo sapiens

<400> SEQUENCE: 90

```
gaggtgcagc tgttggagtc tgggggaggc ttggtacagc ctgggggtc cctgcgtctc      60 tcctgtgcag cctccggatt cacctttaag gcttatccga taatgtgggt ccgccaggct    120
ccagggaagg gtctagagtg ggtctcagag atttcgcctt cgggtaggtc gcggtactac    180
gcagactccg tgaagggccg gttcaccatc tcccgcgaca attccaagaa cacgctgtat    240
ctgcaaatga acagcctgcg tgccgaggac accgcggtat attactgtgc gaaagatcct    300
cgggagtttg actactgggg tcagggaacc ctggtcaccg tctcgagc                 348
```

<210> SEQ ID NO 91
<211> LENGTH: 348
<212> TYPE: DNA
<213> ORGANISM: Homo sapiens

<400> SEQUENCE: 91

```
gaggtgcagc tgttggagtc tgggggaggc ttggtacagc ctgggggtc cctgcgtctc      60 tcctgtgcag cctccggatt cacctttaag gcttatccga taatgtgggt ccgccaggct    120
ccagggaagg gtctagagtg ggtctcagag atttcgcctt cgggtaggta cagctactac    180
gcagactccg tgaagggccg gttcaccatc tcccgcgaca attccaagaa cacgctgtat    240
ctgcaaatga acagcctgcg tgccgaggac accgcggtat attactgtgc gaaagatccc    300
cggcgctttg actactgggg tcagggaacc ctggtcaccg tctcgagc                 348
```

<210> SEQ ID NO 92
<211> LENGTH: 348
<212> TYPE: DNA
<213> ORGANISM: Homo sapiens

<400> SEQUENCE: 92

```
gaggtgcagc tgttggagtc tgggggaggc ttggtacagc ctgggggtc cctgcgtctc      60 tcctgtgcag cctccggatt cacctttaag gcttatccga taatgtgggt ccgccaggct    120
ccagggaagg gtctagagtg ggtctcagag atttcgcctt cgggtgaggc gaggtactac    180
gcagactccg tgaagggccg gttcaccatc tcccgcgaca attccaagaa cacgctgtat    240
ctgcaaatga acagcctgcg tgccgaggac accgcggtat attactgtgc gaaagatccc    300
cgcgcctttg actactgggg tcagggaacc ctggtcaccg tctcgagc                 348
```

<210> SEQ ID NO 93
<211> LENGTH: 348
<212> TYPE: DNA
<213> ORGANISM: Homo sapiens

<400> SEQUENCE: 93

```
gaggtgcagc tgttggagtc tgggggaggc ttggtacagc ctgggggtc cctgcgtctc      60 tcctgtgcag cctccggatt cacctttagg gcttatccga taatgtgggt ccgccaggct    120
ccagggaagg gtctagagtg ggtctcagag atttcgcctt cgggtgagaa gcggtactac    180
gcagactccg tgaagggccg gttcaccatc tcccgcgaca attccaagaa cacgctgtat    240
ctgcaaatga acagcctgcg tgccgaggac accgcggtat attactgtgc gaaagatccc    300
```

```
cgcgcctttg actactgggg tcagggaacc ctggtcaccg tctcgagc            348
```

<210> SEQ ID NO 94
<211> LENGTH: 348
<212> TYPE: DNA
<213> ORGANISM: Homo sapiens

<400> SEQUENCE: 94

```
gaggtgcagc tgttggagtc tgggggaggc ttggtacagc ctgggggtc cctgcgtctc    60
tcctgtgcag cctccggatt cacctttaag gcttatccga taatgtgggt ccgccaggct  120
ccagggaagg gtctagagtg ggtctcagag atttcgcctt cgggtgagga ggagtactac  180
gcagactccg tgaagggccg gttcaccatc tcccgcgaca attccaagaa cacgctgtat  240
ctgcaaatga acagcctgcg tgccgaggac accgcggtat attactgtgc gaaagatccc  300
cgcgcctttg actactgggg tcagggaacc ctggtcaccg tctcgagc            348
```

<210> SEQ ID NO 95
<211> LENGTH: 348
<212> TYPE: DNA
<213> ORGANISM: Homo sapiens

<400> SEQUENCE: 95

```
gaggtgcagc tgttggagtc tgggggaggc ttggtacagc ctgggggtc cctgcgtctc    60
tcctgtgcag cctccggatt cacctttaag gcttatccga taatgtgggt ccgccaggct  120
ccagggaagg gtctagagtg ggtctcagag atttcgcctt cgggtaagaa gacgtactac  180
gcagactccg tgcagggccg gttcaccatc tcccgcgaca attccaagaa cacgctgtat  240
ctgcaaatga acagcctgcg tgccgaggac accgcggtat attactgtgc gaaagatccc  300
cgcgcctttg actactgggg tcagggaacc ctggtcaccg tctcgagc            348
```

<210> SEQ ID NO 96
<211> LENGTH: 348
<212> TYPE: DNA
<213> ORGANISM: Homo sapiens

<400> SEQUENCE: 96

```
gaggtgcagc tgttggagtc tgggggaggc ttggtacagc ctgggggtc cctgcgtctc    60
tcctgtgcag cctccggatt cacctttaag gcttatccga taatgtgggt ccgccaggct  120
ccagggaagg gtctagagtg ggtctcagag atttcgcctt cgggtaagaa gaagtactac  180
gcagactccg tgaagggccg gttcaccatc tcccgcgaca attccaagaa cacgctgtat  240
ctgcaaatga acagcctgcg tgccgaggac accgcggtat attactgtgc gaaagatccc  300
cgcgcctttg actactgggg tcagggaacc ctggtcaccg tctcgagc            348
```

<210> SEQ ID NO 97
<211> LENGTH: 348
<212> TYPE: DNA
<213> ORGANISM: Homo sapiens

<400> SEQUENCE: 97

```
gaggtgcagc tgttggagtc tgggggaggc ttggtacagc ctgggggtc cctgcgtctc    60
tcctgtgcag cctccggatt cacctttaag gcttatccga taatgtgggt ccgccaggct  120
ccagggaagg gtctagagtg ggtctcagag atttcgcctt cgggtgggta tacatactac  180
gcagactccg tgaagggccg gttcaccatc tcccgcgaca attccaagaa cacgctgtat  240
ctgcaaatga acagcctgcg tgccgaggac accgcggtat attactgtgc gaaagatcct  300
```

```
cggaagtttg actactgggg tcagggaacc ctggtcaccg tctcgagc            348
```

<210> SEQ ID NO 98
<211> LENGTH: 348
<212> TYPE: DNA
<213> ORGANISM: Homo sapiens

<400> SEQUENCE: 98

```
gaggtgcagc tgttggagtc tgggggaggc ttggtacagc ctggggggtc cctgcgtctc     60
tcctgtgcag cctccggatt cacctttaag gcttatccga taatgtgggt ccgccaggct    120
ccagggaagg gtctagagtg ggtctcagag atttcgcctt cgggttctta tacatactac    180
gcagacgagt gaagggccg gttcaccatc tcccgcgaca attccaagaa cacgctgtat     240
ctgcaaatga acagcctgcg tgccgaggac accgcggtat attactgtgc gaaagatcct    300
cggaagtttg actactgggg tcagggaacc ctggtcaccg tctcgagc                 348
```

<210> SEQ ID NO 99
<211> LENGTH: 348
<212> TYPE: DNA
<213> ORGANISM: Homo sapiens

<400> SEQUENCE: 99

```
gaggtgcagc tgttggagtc tgggggaggc ttggtacagc ctggggggtc cctgcgtctc     60
tcctgtgcag cctccggatt cacctttaag gcttatccga taatgtgggt ccgccaggct    120
ccagggaagg gtctagagtg ggtctcagag atttcgcctt cgggtcacaa caagtactac    180
gcagactccg tgaagggccg gttcaccatc tcccgcgaca attccaagaa cacgctgtat    240
ctgcaaatga acagcctgcg tgccgaggac accgcggtat attactgtgc gaaagatcct    300
cggaggtttg actactgggg tcagggaacc ctggtcaccg tctcgagc                 348
```

<210> SEQ ID NO 100
<211> LENGTH: 108
<212> TYPE: PRT
<213> ORGANISM: Homo sapiens

<400> SEQUENCE: 100

```
Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Trp Ile Gly Pro Glu
             20                  25                  30

Leu Ser Trp Tyr Gln Gln Lys Pro Gly Lys Ala Pro Lys Leu Leu Ile
         35                  40                  45

Tyr His Gly Ser Ile Leu Gln Ser Gly Val Pro Ser Arg Phe Ser Gly
     50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Arg Met Tyr Arg Pro Ala
             85                  90                  95

Thr Phe Gly Gln Gly Thr Lys Val Glu Ile Lys Arg
            100                 105
```

<210> SEQ ID NO 101
<211> LENGTH: 108
<212> TYPE: PRT
<213> ORGANISM: Homo sapiens

<400> SEQUENCE: 101

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Trp Ile Gly Arg Glu
            20                  25                  30

Leu Lys Trp Tyr Gln Gln Lys Pro Gly Lys Ala Pro Arg Leu Leu Ile
        35                  40                  45

Tyr His Gly Ser Val Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Asp Phe Val Pro Asp
                85                  90                  95

Thr Phe Gly Gln Gly Thr Lys Val Glu Ile Lys Arg
            100                 105

<210> SEQ ID NO 102
<211> LENGTH: 108
<212> TYPE: PRT
<213> ORGANISM: Homo sapiens

<400> SEQUENCE: 102

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ala Asn Asp
            20                  25                  30

Leu Met Trp Tyr Gln Gln Lys Pro Gly Lys Ala Pro Lys Leu Leu Ile
        35                  40                  45

Tyr Arg Asn Ser Arg Leu Gln Gly Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Leu Val His Arg Pro Tyr
                85                  90                  95

Thr Ile Gly Gln Gly Thr Lys Val Glu Ile Lys Arg
            100                 105

<210> SEQ ID NO 103
<211> LENGTH: 108
<212> TYPE: PRT
<213> ORGANISM: Homo sapiens

<400> SEQUENCE: 103

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Phe Ile Gly Pro His
            20                  25                  30

Leu Thr Trp Tyr Gln Gln Lys Pro Gly Lys Ala Pro Lys Leu Leu Ile
        35                  40                  45

Tyr His Ser Ser Leu Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Met Tyr Tyr Pro Ser
                85                  90                  95

Thr Phe Gly Gln Gly Thr Lys Val Lys Ile Lys Arg
            100                 105

<210> SEQ ID NO 104
<211> LENGTH: 108
<212> TYPE: PRT
<213> ORGANISM: Homo sapiens

<400> SEQUENCE: 104

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Trp Ile Gly Pro Glu
            20                  25                  30

Leu Ser Trp Tyr Gln Gln Lys Pro Gly Lys Ala Pro Lys Leu Leu Ile
        35                  40                  45

Tyr His Thr Ser Ile Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Met Phe Gln Pro Arg
                85                  90                  95

Thr Phe Gly Gln Gly Thr Lys Val Glu Ile Arg Arg
            100                 105

<210> SEQ ID NO 105
<211> LENGTH: 108
<212> TYPE: PRT
<213> ORGANISM: Homo sapiens

<400> SEQUENCE: 105

Asp Ile Gln Met Ile Gln Ser Pro Ser Ser Leu Ser Ala Ser Val Gly
1               5                   10                  15

Asp Arg Val Thr Ile Thr Cys Arg Ala Ser Gln Phe Ile Gly Asn Glu
            20                  25                  30

Leu Ser Trp Tyr Gln Gln Lys Pro Gly Lys Ala Pro Lys Leu Leu Ile
        35                  40                  45

Tyr His Ala Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Val Leu Gly Tyr Pro Tyr
                85                  90                  95

Thr Phe Gly Gln Gly Thr Lys Val Glu Ile Lys Arg
            100                 105

<210> SEQ ID NO 106
<211> LENGTH: 108
<212> TYPE: PRT
<213> ORGANISM: Homo sapiens

<400> SEQUENCE: 106

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Trp Ile Gly Pro Glu
            20                  25                  30

Leu Ser Trp Tyr Gln Gln Lys Pro Gly Lys Ala Pro Lys Leu Leu Ile
        35                  40                  45

Tyr His Gly Ser Ile Leu Gln Ser Gly Val Pro Ser Arg Phe Ser Gly
    50                  55                  60

```
Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Val Leu Tyr Ser Pro Leu
                 85                  90                  95

Thr Phe Gly Gln Gly Thr Lys Val Glu Ile Lys Arg
            100                 105

<210> SEQ ID NO 107
<211> LENGTH: 108
<212> TYPE: PRT
<213> ORGANISM: Homo sapiens

<400> SEQUENCE: 107

Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Trp Ile Gly Asn Glu
             20                  25                  30

Leu Lys Trp Tyr Gln Gln Lys Pro Gly Lys Ala Pro Lys Leu Leu Ile
         35                  40                  45

Tyr Met Ser Ser Leu Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Leu Ala Thr Tyr Tyr Cys Gln Gln Thr Leu Leu Pro Phe
                 85                  90                  95

Thr Phe Gly Gln Gly Thr Lys Val Glu Ile Lys Arg
            100                 105

<210> SEQ ID NO 108
<211> LENGTH: 108
<212> TYPE: PRT
<213> ORGANISM: Homo sapiens

<400> SEQUENCE: 108

Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Trp Ile Gly Pro Glu
             20                  25                  30

Leu Ser Trp Tyr Gln Gln Lys Pro Gly Lys Ala Pro Lys Leu Leu Ile
         35                  40                  45

Tyr His Gly Ser Ile Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Arg Leu Tyr Tyr Pro Gly
                 85                  90                  95

Thr Phe Gly Gln Gly Thr Lys Val Glu Ile Lys Arg
            100                 105

<210> SEQ ID NO 109
<211> LENGTH: 108
<212> TYPE: PRT
<213> ORGANISM: Homo sapiens

<400> SEQUENCE: 109

Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Ser Ile Gly Arg Glu
```

-continued

```
                20                  25                  30

Leu Ser Trp Tyr Gln Gln Lys Pro Gly Lys Ala Pro Met Leu Leu Ile
            35                  40                  45

Tyr His Ser Ser Asn Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Met Tyr Trp Pro Tyr
                85                  90                  95

Thr Phe Gly Gln Gly Thr Lys Val Glu Ile Lys Arg
            100                 105

<210> SEQ ID NO 110
<211> LENGTH: 108
<212> TYPE: PRT
<213> ORGANISM: Homo sapiens

<400> SEQUENCE: 110

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Trp Ile Lys Pro Ala
            20                  25                  30

Leu His Trp Tyr Gln Gln Lys Pro Gly Lys Ala Pro Lys Leu Leu Ile
            35                  40                  45

Tyr His Gly Ser Ile Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Thr Leu Phe Met Pro Tyr
                85                  90                  95

Thr Phe Gly Gln Gly Thr Lys Val Glu Ile Lys Arg
            100                 105

<210> SEQ ID NO 111
<211> LENGTH: 108
<212> TYPE: PRT
<213> ORGANISM: Homo sapiens

<400> SEQUENCE: 111

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Thr Ala
            20                  25                  30

Leu Leu Trp Tyr Gln Gln Lys Pro Gly Lys Ala Pro Lys Leu Leu Ile
            35                  40                  45

Tyr Asn Gly Ser Met Leu Pro Asn Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Thr Trp Asp Thr Pro Met
                85                  90                  95

Thr Phe Gly Gln Gly Thr Lys Val Glu Ile Lys Arg
            100                 105

<210> SEQ ID NO 112
<211> LENGTH: 108
<212> TYPE: PRT
```

<213> ORGANISM: Homo sapiens

<400> SEQUENCE: 112

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Trp Ile Gly His Asp
            20                  25                  30

Leu Ser Trp Tyr Gln Gln Lys Pro Gly Lys Ala Pro Lys Leu Leu Ile
        35                  40                  45

Tyr His Ser Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Gln Leu Met Gly Tyr Pro Phe
                85                  90                  95

Thr Phe Gly Gln Gly Thr Lys Val Glu Ile Lys Arg
            100                 105
```

<210> SEQ ID NO 113
<211> LENGTH: 108
<212> TYPE: PRT
<213> ORGANISM: Homo sapiens

<400> SEQUENCE: 113

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Gly Gly Leu
            20                  25                  30

Leu Val Trp Tyr Gln Gln Lys Pro Gly Lys Ala Pro Lys Leu Leu Ile
        35                  40                  45

Tyr Arg Ser Ser Tyr Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Thr Trp Gly Ile Pro His
                85                  90                  95

Thr Phe Gly Gln Gly Thr Lys Val Glu Ile Lys Arg
            100                 105
```

<210> SEQ ID NO 114
<211> LENGTH: 108
<212> TYPE: PRT
<213> ORGANISM: Homo sapiens

<400> SEQUENCE: 114

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Lys Ile Phe Asn Gly
            20                  25                  30

Leu Ser Trp Tyr Gln Gln Lys Pro Gly Lys Ala Pro Lys Leu Leu Ile
        35                  40                  45

Tyr His Ser Ser Thr Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Val Leu Leu Tyr Pro Tyr
                85                  90                  95
```

```
Thr Phe Gly Gln Gly Thr Lys Val Glu Ile Lys Arg
            100                 105
```

<210> SEQ ID NO 115
<211> LENGTH: 108
<212> TYPE: PRT
<213> ORGANISM: Homo sapiens

<400> SEQUENCE: 115

```
Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Ser Ile Gly Thr Asn
             20                  25                  30

Leu Ser Trp Tyr Gln Gln Lys Pro Gly Lys Ala Pro Arg Leu Leu Ile
         35                  40                  45

Tyr Arg Thr Ser Met Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Phe Phe Trp Pro His
                 85                  90                  95

Thr Phe Gly Gln Gly Thr Lys Val Glu Ile Lys Arg
            100                 105
```

<210> SEQ ID NO 116
<211> LENGTH: 118
<212> TYPE: PRT
<213> ORGANISM: Homo sapiens

<400> SEQUENCE: 116

```
Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Arg Leu Tyr
             20                  25                  30

Asp Met Val Trp Val Arg Gln Ala Pro Gly Lys Gly Leu Glu Trp Val
         35                  40                  45

Ser Tyr Ile Ser Ser Gly Gly Ser Gly Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Ala Gly Gly Arg Ala Ser Phe Asp Tyr Trp Gly Gln Gly Thr
            100                 105                 110

Leu Val Thr Val Ser Ser
        115
```

<210> SEQ ID NO 117
<211> LENGTH: 116
<212> TYPE: PRT
<213> ORGANISM: Homo sapiens

<400> SEQUENCE: 117

```
Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe His Leu Tyr
             20                  25                  30
```

```
Asp Met Met Trp Val Arg Gln Ala Pro Gly Lys Gly Leu Glu Trp Val
        35                  40                  45

Ser Phe Ile Gly Gly Asp Gly Leu Asn Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Ala Gly Thr Gln Phe Asp Tyr Trp Gly Gln Gly Thr Leu Val
                100                 105                 110

Thr Val Ser Ser
        115

<210> SEQ ID NO 118
<211> LENGTH: 119
<212> TYPE: PRT
<213> ORGANISM: Homo sapiens

<400> SEQUENCE: 118

Glu Val Gln Leu Leu Glu Ser Gly Gly Gly Leu Val Gln Pro Gly Gly
 1               5                   10                  15

Ser Leu Arg Leu Ser Cys Ala Ala Ser Gly Phe Thr Phe Asn Lys Tyr
                20                  25                  30

Pro Met Met Trp Val Arg Gln Ala Pro Gly Lys Gly Leu Glu Trp Val
        35                  40                  45

Ser Glu Ile Ser Pro Ser Gly Gln Asp Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Asn Pro Gln Ile Leu Ser Asn Phe Asp Tyr Trp Gly Gln Gly
                100                 105                 110

Thr Leu Val Thr Val Ser Ser
        115

<210> SEQ ID NO 119
<211> LENGTH: 124
<212> TYPE: PRT
<213> ORGANISM: Homo sapiens

<400> SEQUENCE: 119

Glu Val Gln Leu Leu Glu Ser Gly Gly Gly Leu Val Gln Pro Gly Gly
 1               5                   10                  15

Ser Leu Arg Leu Ser Cys Ala Ala Ser Gly Phe Thr Phe Gln Trp Tyr
                20                  25                  30

Pro Met Trp Trp Val Arg Gln Ala Pro Gly Lys Gly Leu Glu Trp Val
        35                  40                  45

Ser Leu Ile Glu Gly Gln Gly Asp Arg Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Ala Gly Asp Arg Thr Ala Gly Ser Arg Gly Asn Ser Phe Asp
                100                 105                 110
```

Tyr Trp Gly Gln Gly Thr Leu Val Thr Val Ser Ser
            115                 120

<210> SEQ ID NO 120
<211> LENGTH: 121
<212> TYPE: PRT
<213> ORGANISM: Homo sapiens

<400> SEQUENCE: 120

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Lys Ala Tyr
            20                  25                  30

Glu Met Gly Trp Val Arg Gln Ala Pro Gly Lys Gly Leu Glu Trp Val
        35                  40                  45

Ser Gly Ile Ser Pro Asn Gly Gly Trp Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Glu Ser Ile Ser Pro Thr Pro Leu Gly Phe Asp Tyr Trp Gly
            100                 105                 110

Gln Gly Thr Leu Val Thr Val Ser Ser
            115                 120

<210> SEQ ID NO 121
<211> LENGTH: 116
<212> TYPE: PRT
<213> ORGANISM: Homo sapiens

<400> SEQUENCE: 121

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Thr Gly Tyr
            20                  25                  30

Glu Met Gly Trp Val Arg Gln Ala Pro Gly Lys Gly Leu Glu Trp Val
        35                  40                  45

Ser Tyr Ile Ser Arg Gly Gly Arg Trp Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Asp Thr Met Phe Asp Tyr Trp Gly Gln Gly Thr Leu Val
            100                 105                 110

Thr Val Ser Ser
        115

<210> SEQ ID NO 122
<211> LENGTH: 116
<212> TYPE: PRT
<213> ORGANISM: Homo sapiens

<400> SEQUENCE: 122

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ala Tyr

|   |   | 20 |   |   |   | 25 |   |   |   | 30 |   |
|---|---|---|---|---|---|---|---|---|---|---|---|

Glu Met Gly Trp Val Arg Gln Ala Pro Gly Lys Gly Leu Glu Trp Val
     35               40               45

Ser Phe Ile Ser Gly Gly Gly Arg Trp Thr Tyr Tyr Ala Asp Ser Val
  50               55               60

Lys Gly Arg Phe Thr Ile Ser Arg Asp Asn Ser Lys Asn Thr Leu Tyr
65                 70               75               80

Leu Gln Met Asn Ser Leu Arg Ala Glu Asp Thr Ala Val Tyr Tyr Cys
            85               90               95

Ala Lys Tyr Ser Glu Asp Phe Asp Tyr Trp Gly Gln Gly Thr Leu Val
         100             105             110

Thr Val Ser Ser
     115

<210> SEQ ID NO 123
<211> LENGTH: 116
<212> TYPE: PRT
<213> ORGANISM: Homo sapiens

<400> SEQUENCE: 123

Glu Val Gln Leu Leu Glu Ser Gly Gly Gly Leu Val Gln Pro Gly Gly
1               5                 10               15

Ser Leu Arg Leu Ser Cys Ala Ala Ser Gly Phe Thr Phe Gly Ala Tyr
         20              25              30

Pro Met Met Trp Val Arg Gln Ala Pro Gly Lys Gly Leu Glu Trp Val
     35               40               45

Ser Glu Ile Ser Pro Ser Gly Ser Tyr Thr Tyr Tyr Ala Asp Ser Val
  50               55               60

Lys Gly Arg Phe Thr Ile Ser Arg Asp Asn Ser Lys Asn Thr Leu Tyr
65                 70               75               80

Leu Gln Met Asn Ser Leu Arg Ala Glu Asp Thr Ala Val Tyr Tyr Cys
            85               90               95

Ala Lys Asp Pro Arg Lys Phe Asp Tyr Trp Gly Gln Gly Thr Leu Val
         100             105             110

Thr Val Ser Ser
     115

<210> SEQ ID NO 124
<211> LENGTH: 123
<212> TYPE: PRT
<213> ORGANISM: Homo sapiens

<400> SEQUENCE: 124

Glu Val Gln Leu Leu Glu Ser Gly Gly Gly Leu Val Gln Pro Gly Gly
1               5                 10               15

Ser Leu Arg Leu Ser Cys Ala Ala Ser Gly Phe Thr Phe Gln Phe Tyr
         20              25              30

Lys Met Gly Trp Val Arg Gln Ala Pro Gly Lys Gly Leu Glu Trp Val
     35               40               45

Ser Ser Ile Ser Ser Val Gly Asp Ala Thr Tyr Tyr Ala Asp Ser Val
  50               55               60

Lys Gly Arg Phe Thr Ile Ser Arg Asp Asn Ser Lys Asn Thr Leu Tyr
65                 70               75               80

Leu Gln Met Asn Ser Leu Arg Ala Glu Asp Thr Ala Val Tyr Tyr Cys
            85               90               95

Ala Lys Met Gly Gly Gly Pro Pro Thr Tyr Val Val Tyr Phe Asp Tyr

Trp Gly Gln Gly Thr Leu Val Thr Val Ser Ser
            115                 120

<210> SEQ ID NO 125
<211> LENGTH: 123
<212> TYPE: PRT
<213> ORGANISM: Homo sapiens

<400> SEQUENCE: 125

Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Gly Glu Tyr
             20                  25                  30

Gly Met Tyr Trp Val Arg Gln Ala Pro Gly Lys Gly Leu Glu Trp Val
         35                  40                  45

Ser Ser Ile Ser Glu Arg Gly Arg Leu Thr Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Asn Leu Arg Ala Glu Asp Thr Ala Val Tyr Tyr Cys
                 85                  90                  95

Ala Lys Ser Ala Leu Ser Ser Glu Gly Phe Ser Arg Ser Phe Asp Tyr
            100                 105                 110

Trp Gly Gln Gly Thr Leu Val Thr Val Ser Ser
            115                 120

<210> SEQ ID NO 126
<211> LENGTH: 123
<212> TYPE: PRT
<213> ORGANISM: Homo sapiens

<400> SEQUENCE: 126

Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Ser Asp Tyr
             20                  25                  30

Ala Met Tyr Trp Val Arg Gln Ala Pro Gly Lys Gly Leu Glu Trp Val
         35                  40                  45

Ser Ser Ile Thr Ala Arg Gly Phe Ile Thr Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Ser Gly Phe Pro His Lys Ser Gly Ser Asn Tyr Phe Asp Tyr
            100                 105                 110

Trp Gly Gln Gly Thr Leu Val Thr Val Ser Ser
            115                 120

<210> SEQ ID NO 127
<211> LENGTH: 116
<212> TYPE: PRT
<213> ORGANISM: Homo sapiens

<400> SEQUENCE: 127

Glu Val Gln Leu Leu Glu Ser Gly Gly Gly Leu Val Gln Pro Gly Gly
  1               5                  10                  15

```
Ser Leu Arg Leu Ser Cys Ala Ala Ser Gly Phe Thr Phe Arg Leu Tyr
            20                  25                  30

Asp Met Met Trp Val Arg Gln Ala Pro Gly Lys Gly Leu Glu Trp Val
            35                  40                  45

Ser Phe Ile Gly Gly Asp Gly Leu Asn Thr Tyr Tyr Ala Asp Ser Val
            50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
            85                  90                  95

Ala Lys Asp Pro Arg Lys Phe Asp Tyr Trp Gly Gln Gly Thr Leu Val
            100                 105                 110

Thr Val Ser Ser
        115

<210> SEQ ID NO 128
<211> LENGTH: 116
<212> TYPE: PRT
<213> ORGANISM: Homo sapiens

<400> SEQUENCE: 128

Glu Val Gln Leu Leu Glu Ser Gly Gly Gly Leu Val Gln Pro Gly Gly
 1                   5                  10                  15

Ser Leu Arg Leu Ser Cys Ala Ala Ser Gly Phe Thr Phe Ser Phe Phe
            20                  25                  30

Asp Met Met Trp Val Arg Gln Ala Pro Gly Lys Gly Leu Glu Trp Val
            35                  40                  45

Ser Phe Ile Gly Gly Asp Gly Leu Asn Thr Tyr Tyr Ala Asp Ser Val
            50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
            85                  90                  95

Ala Lys Ala Gly Thr Gln Phe Asp Tyr Trp Gly Gln Gly Thr Leu Val
            100                 105                 110

Thr Val Ser Ser
        115

<210> SEQ ID NO 129
<211> LENGTH: 116
<212> TYPE: PRT
<213> ORGANISM: Homo sapiens

<400> SEQUENCE: 129

Glu Val Gln Leu Leu Glu Ser Gly Gly Gly Leu Val Gln Pro Gly Gly
 1                   5                  10                  15

Ser Leu Arg Leu Ser Cys Ala Ala Ser Gly Phe Thr Phe Met Leu Phe
            20                  25                  30

Asp Met Met Trp Val Arg Gln Ala Pro Gly Lys Gly Leu Glu Trp Val
            35                  40                  45

Ser Phe Ile Gly Gly Asp Gly Leu Asn Thr Tyr Tyr Ala Asp Ser Val
            50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
            85                  90                  95
```

Ala Lys Ala Gly Thr Gln Phe Asp Tyr Trp Gly Gln Gly Thr Leu Val
            100                 105                 110

Thr Val Ser Ser
        115

<210> SEQ ID NO 130
<211> LENGTH: 116
<212> TYPE: PRT
<213> ORGANISM: Homo sapiens

<400> SEQUENCE: 130

Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Pro Leu Tyr
             20                  25                  30

Asp Met Met Trp Val Arg Gln Ala Pro Gly Lys Gly Leu Glu Trp Val
         35                  40                  45

Ser Phe Ile Gly Gly Asp Gly Leu Asn Thr Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Ala Gly Thr Gln Phe Asp Tyr Trp Gly Gln Gly Thr Leu Val
            100                 105                 110

Thr Val Ser Ser
        115

<210> SEQ ID NO 131
<211> LENGTH: 116
<212> TYPE: PRT
<213> ORGANISM: Homo sapiens

<400> SEQUENCE: 131

Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Pro Leu Tyr
             20                  25                  30

Asp Met Met Trp Val Arg Gln Ala Pro Gly Lys Gly Leu Glu Trp Val
         35                  40                  45

Ser Phe Ile Gly Gly Asp Gly Leu Asn Thr Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Ala Gly Thr Gln Phe Asp Tyr Trp Gly Gln Gly Thr Leu Val
            100                 105                 110

Thr Val Ser Ser
        115

<210> SEQ ID NO 132
<211> LENGTH: 116
<212> TYPE: PRT
<213> ORGANISM: Homo sapiens

<400> SEQUENCE: 132

-continued

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Gln Tyr Phe
            20                  25                  30

Asp Met Met Trp Val Arg Gln Ala Pro Gly Lys Gly Leu Glu Trp Val
        35                  40                  45

Ser Phe Ile Gly Gly Asp Gly Leu Asn Thr Tyr Tyr Ala Asp Ser Val
50                      55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ala Gly Thr Gln Phe Asp Tyr Trp Gly Gln Gly Thr Leu Val
            100                 105                 110

Thr Val Ser Ser
        115

<210> SEQ ID NO 133
<211> LENGTH: 116
<212> TYPE: PRT
<213> ORGANISM: Homo sapiens

<400> SEQUENCE: 133

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe His Leu Tyr
            20                  25                  30

Asp Met Met Trp Val Arg Gln Ala Pro Gly Lys Gly Leu Glu Trp Val
        35                  40                  45

Ser Phe Ile Gly Gly Asp Gly Leu Asn Thr Tyr Tyr Ala Asp Ser Val
50                      55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Pro Arg Gln Phe Asp Tyr Trp Gly Gln Gly Thr Leu Val
            100                 105                 110

Thr Val Ser Ser
        115

<210> SEQ ID NO 134
<211> LENGTH: 116
<212> TYPE: PRT
<213> ORGANISM: Homo sapiens

<400> SEQUENCE: 134

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe His Leu Tyr
            20                  25                  30

Asp Met Met Trp Val Arg Gln Ala Pro Gly Lys Gly Leu Glu Trp Val
        35                  40                  45

Ser Phe Ile Gly Gly Asp Gly Leu Asn Thr Tyr Tyr Ala Asp Ser Val
50                      55                  60

Lys Gly Arg Phe Thr Ile Ser Arg Asp Asn Ser Lys Asn Thr Leu Tyr
65                  70                  75                  80

```
Leu Gln Met Asn Ser Leu Arg Ala Glu Asp Thr Ala Val Tyr Tyr Cys
                85                  90                  95

Ala Lys Asn Pro Arg Gln Phe Asp Tyr Trp Gly Gln Gly Thr Leu Val
            100                 105                 110

Thr Val Ser Ser
        115

<210> SEQ ID NO 135
<211> LENGTH: 116
<212> TYPE: PRT
<213> ORGANISM: Homo sapiens

<400> SEQUENCE: 135

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe His Leu Tyr
            20                  25                  30

Asp Met Met Trp Val Arg Gln Ala Pro Gly Lys Gly Leu Glu Trp Val
            35                  40                  45

Ser Phe Ile Gly Gly Asp Gly Leu Asn Thr Tyr Tyr Ala Asp Ser Val
            50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Lys Ser Met Gln Phe Asp Tyr Trp Gly Gln Gly Thr Leu Val
            100                 105                 110

Thr Val Ser Ser
        115

<210> SEQ ID NO 136
<211> LENGTH: 116
<212> TYPE: PRT
<213> ORGANISM: Homo sapiens

<400> SEQUENCE: 136

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe His Leu Tyr
            20                  25                  30

Asp Met Met Trp Val Arg Gln Ala Pro Gly Lys Gly Leu Glu Trp Val
            35                  40                  45

Ser Phe Ile Gly Gly Asp Gly Leu Asn Thr Tyr Tyr Ala Asp Ser Val
            50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Pro Arg Lys Phe Asp Tyr Trp Gly Gln Gly Thr Leu Val
            100                 105                 110

Thr Val Ser Ser
        115

<210> SEQ ID NO 137
<211> LENGTH: 116
<212> TYPE: PRT
<213> ORGANISM: Homo sapiens
```

-continued

<400> SEQUENCE: 137

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe His Leu Tyr
            20                  25                  30

Asp Met Met Trp Val Arg Gln Ala Pro Gly Lys Gly Leu Glu Trp Val
        35                  40                  45

Ser Phe Ile Gly Gly Asp Gly Leu Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Pro Arg Lys Phe Asp Tyr Trp Gly Gln Gly Thr Leu Val
            100                 105                 110

Thr Val Ser Ser
        115

<210> SEQ ID NO 138
<211> LENGTH: 119
<212> TYPE: PRT
<213> ORGANISM: Homo sapiens

<400> SEQUENCE: 138

Glu Val Gln Leu Leu Glu Ser Gly Gly Gly Leu Val Gln Pro Gly Gly
1               5                   10                  15

Ser Leu Arg Leu Ser Cys Ala Ala Ser Gly Tyr Pro Met Trp Trp Val
            20                  25                  30

Arg Gln Ala Pro Gly Lys Gly Pro Glu Trp Val Ser Leu Ile Glu Gly
        35                  40                  45

Gln Gly Asp Arg Thr Tyr Tyr Ala Asp Ser Val Lys Gly Arg Phe Thr
    50                  55                  60

Ile Ser Arg Asp Asn Ser Lys Asn Thr Leu Tyr Leu Gln Met Asn Ser
65                  70                  75                  80

Leu Arg Ala Glu Asp Thr Ala Val Tyr Tyr Cys Ala Lys Ala Gly Asp
                85                  90                  95

Arg Thr Ala Gly Ser Arg Gly Asn Ser Phe Asp Tyr Trp Gly Gln Gly
            100                 105                 110

Thr Leu Val Thr Val Ser Ser
        115

<210> SEQ ID NO 139
<211> LENGTH: 124
<212> TYPE: PRT
<213> ORGANISM: Homo sapiens

<400> SEQUENCE: 139

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Gln Trp Ala
            20                  25                  30

Pro Met Pro Trp Val Arg Gln Ala Pro Gly Lys Gly Leu Glu Trp Val
        35                  40                  45

Ser Leu Ile Glu Gly Gln Gly Asp Arg Thr Tyr Tyr Ala Asp Ser Val
    50                  55                  60

Lys Gly Arg Phe Thr Ile Ser Arg Asp Asn Ser Lys Asn Thr Leu Tyr

```
                 65                  70                  75                  80
Leu Gln Met Asn Ser Leu Arg Ala Glu Asp Thr Ala Val Tyr Tyr Cys
                    85                  90                  95

Ala Lys Ala Gly Asp Arg Thr Ala Gly Ser Arg Gly Asn Ser Phe Asp
                100                 105                 110

Tyr Trp Gly Gln Gly Thr Leu Val Thr Val Ser Ser
            115                 120

<210> SEQ ID NO 140
<211> LENGTH: 124
<212> TYPE: PRT
<213> ORGANISM: Homo sapiens

<400> SEQUENCE: 140

Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Gln Trp Pro
                 20                  25                  30

His Met Pro Trp Val Arg Gln Ala Pro Gly Lys Gly Leu Glu Trp Val
             35                  40                  45

Ser Leu Ile Glu Gly Gln Gly Asp Arg Thr Tyr Tyr Ala Asp Ser Val
         50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                    85                  90                  95

Ala Lys Ala Gly Asp Arg Thr Ala Gly Ser Arg Gly Asn Ser Phe Asp
                100                 105                 110

Tyr Trp Gly Gln Gly Thr Leu Val Thr Val Ser Ser
            115                 120

<210> SEQ ID NO 141
<211> LENGTH: 124
<212> TYPE: PRT
<213> ORGANISM: Homo sapiens
<220> FEATURE:
<221> NAME/KEY: UNSURE
<222> LOCATION: 30
<223> OTHER INFORMATION: Xaa = Any Amino Acid

<400> SEQUENCE: 141

Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Xaa Trp Pro
                 20                  25                  30

His Met His Trp Val Arg Gln Ala Pro Gly Lys Gly Leu Glu Trp Val
             35                  40                  45

Ser Leu Ile Glu Gly Gln Gly Asp Arg Thr Tyr Tyr Ala Asp Ser Val
         50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                    85                  90                  95

Ala Lys Ala Gly Asp Arg Thr Ala Gly Ser Arg Gly Asn Ser Phe Asp
                100                 105                 110

Tyr Trp Gly Gln Gly Thr Leu Val Thr Val Ser Ser
            115                 120
```

<210> SEQ ID NO 142
<211> LENGTH: 124
<212> TYPE: PRT
<213> ORGANISM: Homo sapiens

<400> SEQUENCE: 142

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Gln Trp Tyr
            20                  25                  30

Pro Met Trp Trp Val Arg Gln Ala Pro Gly Lys Gly Leu Glu Trp Val
        35                  40                  45

Ser Leu Ile Glu Gly Gln Gly Asp Arg Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ala Gly Asp Arg Trp Val Leu Ser Arg Gly Asn Ser Phe Asp
            100                 105                 110

Tyr Trp Gly Gln Gly Thr Leu Val Thr Val Ser Ser
        115                 120

<210> SEQ ID NO 143
<211> LENGTH: 124
<212> TYPE: PRT
<213> ORGANISM: Homo sapiens

<400> SEQUENCE: 143

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Gln Trp Tyr
            20                  25                  30

Pro Met Trp Trp Val Arg Gln Ala Pro Gly Lys Gly Leu Glu Trp Val
        35                  40                  45

Ser Leu Ile Glu Gly Gln Gly Asp Arg Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ala Gly Asp Arg Arg Phe Leu Ser Arg Gly Asn Ser Phe Asp
            100                 105                 110

Tyr Trp Gly Gln Gly Thr Leu Val Thr Val Ser Ser
        115                 120

<210> SEQ ID NO 144
<211> LENGTH: 124
<212> TYPE: PRT
<213> ORGANISM: Homo sapiens

<400> SEQUENCE: 144

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Gln Trp Tyr
            20                  25                  30

Pro Met Trp Trp Val Arg Gln Ala Pro Gly Lys Gly Leu Glu Trp Val

-continued

```
                35                  40                  45
Ser Leu Ile Glu Gly Gln Gly Asp Arg Thr Tyr Tyr Ala Asp Ser Val
 50                  55                  60
Lys Gly Arg Phe Thr Ile Ser Arg Asp Asn Ser Lys Asn Thr Leu Tyr
 65                  70                  75                  80
Leu Gln Met Asn Ser Leu Arg Ala Glu Asp Thr Ala Val Tyr Tyr Cys
                 85                  90                  95
Ala Lys Ala Gly Asp Arg His Arg Thr Ser Arg Gly Asn Ser Phe Asp
                100                 105                 110
Tyr Trp Gly Gln Gly Thr Leu Val Thr Val Ser Ser
            115                 120
```

<210> SEQ ID NO 145
<211> LENGTH: 124
<212> TYPE: PRT
<213> ORGANISM: Homo sapiens

<400> SEQUENCE: 145

```
Glu Val Gln Leu Leu Glu Ser Gly Gly Gly Leu Val Gln Pro Gly Gly
 1               5                  10                  15
Ser Leu Arg Leu Ser Cys Ala Ala Ser Gly Phe Thr Phe Gln Trp Tyr
                20                  25                  30
Pro Met Trp Trp Val Arg Gln Ala Pro Gly Lys Gly Leu Glu Trp Val
                35                  40                  45
Ser Leu Ile Glu Val Gln Gly Asp Arg Thr Tyr Tyr Ala Asp Ser Val
 50                  55                  60
Lys Gly Arg Phe Thr Ile Ser Arg Asp Asn Ser Lys Asn Thr Leu Tyr
 65                  70                  75                  80
Leu Gln Met Asn Ser Leu Arg Ala Glu Asp Thr Ala Val Tyr Tyr Cys
                 85                  90                  95
Ala Lys Ala Gly Pro Pro Phe Ala Gly Ser Arg Gly Asn Ser Phe Asp
                100                 105                 110
Tyr Trp Gly Gln Gly Thr Leu Val Thr Val Ser Ser
            115                 120
```

<210> SEQ ID NO 146
<211> LENGTH: 124
<212> TYPE: PRT
<213> ORGANISM: Homo sapiens

<400> SEQUENCE: 146

```
Glu Val Gln Leu Leu Glu Ser Gly Gly Gly Leu Val Gln Pro Gly Gly
 1               5                  10                  15
Ser Leu Arg Leu Ser Cys Ala Ala Ser Gly Phe Thr Phe Gln Trp Tyr
                20                  25                  30
Pro Met Trp Trp Val Arg Gln Ala Pro Gly Lys Gly Leu Glu Trp Val
                35                  40                  45
Ser Leu Ile Glu Gly Gln Gly Asp Arg Thr Tyr Tyr Ala Asp Ser Val
 50                  55                  60
Lys Gly Arg Phe Thr Ile Ser Arg Asp Asn Ser Lys Asn Thr Leu Tyr
 65                  70                  75                  80
Leu Gln Met Asn Ser Leu Arg Ala Glu Asp Thr Ala Val Tyr Tyr Cys
                 85                  90                  95
Ala Lys Ala Gly Thr Asn Asn Ala Gly Ser Arg Gly Asn Ser Phe Asp
                100                 105                 110
Tyr Trp Gly Gln Gly Thr Leu Val Thr Val Ser Ser
```

<210> SEQ ID NO 147
<211> LENGTH: 124
<212> TYPE: PRT
<213> ORGANISM: Homo sapiens

<400> SEQUENCE: 147

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Gln Trp Tyr
            20                  25                  30

Pro Met Trp Trp Val Arg Gln Ala Pro Gly Lys Gly Leu Glu Trp Val
        35                  40                  45

Ser Leu Ile Glu Gly Gln Gly Asp Arg Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ala Gly Asp Arg Thr Ala Gln Asn Ser Gly Asn Ser Phe Asp
            100                 105                 110

Tyr Trp Gly Arg Gly Thr Leu Val Thr Val Ser Ser
        115                 120

<210> SEQ ID NO 148
<211> LENGTH: 124
<212> TYPE: PRT
<213> ORGANISM: Homo sapiens

<400> SEQUENCE: 148

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Gln Trp Tyr
            20                  25                  30

Pro Met Trp Trp Val Arg Gln Ala Pro Gly Lys Gly Leu Glu Trp Val
        35                  40                  45

Ser Leu Ile Glu Gly Gln Gly Asp Arg Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ala Gly Asn Ser Asn Ala Gly Ser Arg Gly Asn Ser Phe Asp
            100                 105                 110

Tyr Trp Gly Gln Gly Thr Leu Val Thr Val Ser Ser
        115                 120

<210> SEQ ID NO 149
<211> LENGTH: 116
<212> TYPE: PRT
<213> ORGANISM: Homo sapiens

<400> SEQUENCE: 149

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Pro Ala Tyr
            20                  25                  30

```
Pro Met Met Trp Val Arg Gln Ala Pro Gly Lys Gly Leu Glu Trp Val
            35                  40                  45

Ser Glu Ile Ser Pro Ser Gly Ser Tyr Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Lys Asp Pro Arg Lys Phe Asp Tyr Trp Gly Gln Gly Thr Leu Val
                100                 105                 110

Thr Val Ser Ser
        115

<210> SEQ ID NO 150
<211> LENGTH: 116
<212> TYPE: PRT
<213> ORGANISM: Homo sapiens

<400> SEQUENCE: 150

Glu Val Gln Leu Leu Glu Ser Gly Gly Gly Leu Val Gln Pro Gly Gly
 1               5                   10                  15

Ser Leu Arg Leu Ser Cys Ala Ala Ser Gly Phe Thr Phe Lys Ala Tyr
                20                  25                  30

Pro Ile Met Trp Val Arg Gln Ala Pro Gly Lys Gly Leu Glu Trp Val
            35                  40                  45

Ser Glu Ile Ser Pro Ser Gly Ser Tyr Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Lys Asp Pro Arg Lys Phe Asp Tyr Trp Gly Gln Gly Thr Leu Val
                100                 105                 110

Thr Val Ser Ser
        115

<210> SEQ ID NO 151
<211> LENGTH: 114
<212> TYPE: PRT
<213> ORGANISM: Homo sapiens

<400> SEQUENCE: 151

Glu Val Gln Leu Leu Glu Ser Gly Gly Gly Leu Val Gln Pro Gly Gly
 1               5                   10                  15

Ser Leu Arg Leu Ser Cys Ala Ala Ser Gly Phe Thr Phe Thr Ala Tyr
                20                  25                  30

Pro Met Met Trp Val Arg Gln Ala Pro Gly Lys Gly Leu Glu Trp Val
            35                  40                  45

Ser Glu Ile Ser Pro Ser Gly Ser Tyr Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Lys Asp Pro Arg Lys Phe Asp Tyr Trp Gly Gln Gly Thr Leu Val
                100                 105                 110
```

<210> SEQ ID NO 152
<211> LENGTH: 116
<212> TYPE: PRT
<213> ORGANISM: Homo sapiens

<400> SEQUENCE: 152

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Gly Trp Tyr
            20                  25                  30

Pro Met Met Trp Val Arg Gln Ala Pro Gly Lys Gly Leu Glu Trp Val
        35                  40                  45

Ser Glu Ile Ser Pro Ser Gly Ser Tyr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Pro Arg Lys Phe Asp Tyr Trp Gly Gln Gly Thr Leu Val
            100                 105                 110

Thr Val Ser Ser
        115

<210> SEQ ID NO 153
<211> LENGTH: 114
<212> TYPE: PRT
<213> ORGANISM: Homo sapiens

<400> SEQUENCE: 153

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Gly Leu Tyr
            20                  25                  30

Pro Met Met Trp Val Arg Gln Ala Pro Gly Lys Gly Leu Glu Trp Val
        35                  40                  45

Ser Glu Ile Ser Pro Ser Gly Ser Tyr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Pro Arg Lys Phe Asp Tyr Trp Gly Gln Gly Thr Leu Val
            100                 105                 110

Thr Val

<210> SEQ ID NO 154
<211> LENGTH: 116
<212> TYPE: PRT
<213> ORGANISM: Homo sapiens

<400> SEQUENCE: 154

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Leu Ala Tyr
            20                  25                  30

-continued

Pro Met Met Trp Val Arg Gln Ala Pro Gly Lys Gly Leu Glu Trp Val
            35                  40                  45

Ser Glu Ile Ser Pro Ser Gly Ser Tyr Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Lys Asp Pro Arg Lys Phe Asp Tyr Trp Gly Gln Gly Thr Leu Val
                100                 105                 110

Thr Val Ser Ser
        115

<210> SEQ ID NO 155
<211> LENGTH: 116
<212> TYPE: PRT
<213> ORGANISM: Homo sapiens

<400> SEQUENCE: 155

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Gly Arg Tyr
                20                  25                  30

Pro Met Met Trp Val Arg Gln Ala Pro Gly Lys Gly Leu Glu Trp Val
            35                  40                  45

Ser Glu Ile Ser Pro Ser Gly Ser Tyr Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Lys Asp Pro Arg Lys Phe Asp Tyr Trp Gly Gln Gly Thr Leu Val
                100                 105                 110

Thr Val Ser Ser
        115

<210> SEQ ID NO 156
<211> LENGTH: 116
<212> TYPE: PRT
<213> ORGANISM: Homo sapiens

<400> SEQUENCE: 156

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Gly Ala Phe
                20                  25                  30

Pro Met Met Trp Val Arg Gln Ala Pro Gly Lys Gly Leu Glu Trp Val
            35                  40                  45

Ser Glu Ile Ser Pro Ser Gly Ser Tyr Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Lys Asp Pro Arg Lys Phe Asp Tyr Trp Gly Gln Gly Thr Leu Val
                100                 105                 110

Thr Val Ser Ser
        115

<210> SEQ ID NO 157
<211> LENGTH: 116
<212> TYPE: PRT
<213> ORGANISM: Homo sapiens

<400> SEQUENCE: 157

Glu Val Gln Leu Leu Glu Ser Gly Gly Gly Leu Val Gln Pro Gly Gly
 1               5                   10                  15

Ser Leu Arg Leu Ser Cys Ala Ala Ser Gly Phe Thr Phe Gly Ala Tyr
            20                  25                  30

Pro Met Leu Trp Val Arg Gln Ala Pro Gly Lys Gly Leu Glu Trp Val
        35                  40                  45

Ser Glu Ile Ser Pro Ser Gly Ser Tyr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Pro Arg Lys Phe Asp Tyr Trp Gly Gln Gly Thr Leu Val
            100                 105                 110

Thr Val Ser Ser
        115

<210> SEQ ID NO 158
<211> LENGTH: 116
<212> TYPE: PRT
<213> ORGANISM: Homo sapiens

<400> SEQUENCE: 158

Glu Val Gln Leu Leu Glu Ser Gly Gly Gly Leu Val Gln Pro Gly Gly
 1               5                   10                  15

Ser Leu Arg Leu Ser Cys Ala Ala Ser Gly Phe Thr Phe Ser Leu Phe
            20                  25                  30

Pro Met Met Trp Val Arg Gln Ala Pro Gly Lys Gly Leu Glu Trp Val
        35                  40                  45

Ser Glu Ile Ser Pro Ser Gly Ser Tyr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Pro Arg Lys Phe Asp Tyr Trp Gly Gln Gly Thr Leu Val
            100                 105                 110

Thr Val Ser Ser
        115

<210> SEQ ID NO 159
<211> LENGTH: 116
<212> TYPE: PRT
<213> ORGANISM: Homo sapiens

<400> SEQUENCE: 159

Glu Val Gln Leu Leu Glu Ser Gly Gly Gly Leu Val Gln Pro Gly Gly
 1               5                   10                  15

```
Ser Leu Arg Leu Ser Cys Ala Ala Ser Gly Phe Thr Phe Phe Leu Phe
            20                  25                  30

Pro Met Met Trp Val Arg Gln Ala Pro Gly Lys Gly Leu Glu Trp Val
        35                  40                  45

Ser Glu Ile Ser Pro Ser Gly Ser Tyr Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Asp Pro Arg Lys Phe Asp Tyr Trp Gly Gln Gly Thr Leu Val
            100                 105                 110

Thr Val Ser Ser
        115

<210> SEQ ID NO 160
<211> LENGTH: 116
<212> TYPE: PRT
<213> ORGANISM: Homo sapiens

<400> SEQUENCE: 160

Glu Val Gln Leu Leu Glu Ser Gly Gly Gly Leu Val Gln Pro Gly Gly
 1               5                   10                  15

Ser Leu Arg Leu Ser Cys Ala Ala Ser Gly Phe Thr Phe Ser Tyr Phe
            20                  25                  30

Pro Met Met Trp Val Arg Gln Ala Pro Gly Lys Gly Leu Glu Trp Val
        35                  40                  45

Ser Glu Ile Ser Pro Ser Gly Ser Tyr Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Asp Pro Arg Lys Phe Asp Tyr Trp Gly Gln Gly Thr Leu Val
            100                 105                 110

Thr Val Ser Ser
        115

<210> SEQ ID NO 161
<211> LENGTH: 116
<212> TYPE: PRT
<213> ORGANISM: Homo sapiens

<400> SEQUENCE: 161

Glu Val Gln Leu Leu Glu Ser Gly Gly Gly Leu Val Gln Pro Gly Gly
 1               5                   10                  15

Ser Leu Arg Leu Ser Cys Ala Ala Ser Gly Phe Thr Phe Ala Phe Ala
            20                  25                  30

Pro Met Met Trp Val Arg Gln Ala Pro Gly Lys Gly Leu Glu Trp Val
        35                  40                  45

Ser Glu Ile Ser Pro Ser Gly Ser Tyr Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95
```

Ala Lys Asp Pro Arg Lys Phe Asp Tyr Trp Gly Gln Gly Thr Leu Val
                100                 105                 110

Thr Val Ser Ser
        115

<210> SEQ ID NO 162
<211> LENGTH: 116
<212> TYPE: PRT
<213> ORGANISM: Homo sapiens

<400> SEQUENCE: 162

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ala Pro Tyr
            20                  25                  30

Pro Met Met Trp Val Arg Gln Ala Pro Gly Lys Gly Leu Glu Trp Val
        35                  40                  45

Ser Glu Ile Ser Pro Ser Gly Ser Tyr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Pro Arg Lys Phe Asp Tyr Trp Gly Gln Gly Thr Leu Val
                100                 105                 110

Thr Val Ser Ser
        115

<210> SEQ ID NO 163
<211> LENGTH: 116
<212> TYPE: PRT
<213> ORGANISM: Homo sapiens

<400> SEQUENCE: 163

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Thr Ser His
            20                  25                  30

Pro Met Met Trp Val Arg Gln Ala Pro Gly Lys Gly Leu Glu Trp Val
        35                  40                  45

Ser Glu Ile Ser Pro Ser Gly Ser Tyr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Pro Arg Lys Phe Asp Tyr Trp Gly Gln Gly Thr Leu Val
                100                 105                 110

Thr Val Ser Ser
        115

<210> SEQ ID NO 164
<211> LENGTH: 116
<212> TYPE: PRT
<213> ORGANISM: Homo sapiens

<400> SEQUENCE: 164

Glu Val Gln Leu Leu Glu Ser Gly Gly Gly Leu Val Gln Pro Gly Gly

```
                 1               5                  10                 15
Ser Leu Arg Leu Ser Cys Ala Ala Ser Gly Phe Thr Phe Thr Ser His
                    20                  25                  30

Pro Met Met Trp Val Arg Gln Ala Pro Gly Lys Gly Leu Glu Trp Val
                35                  40                  45

Ser Glu Ile Ser Pro Ser Gly Ser Tyr Thr Tyr Tyr Ala Asp Ser Val
            50                  55                  60

Lys Gly Arg Phe Thr Ile Ser Arg Asp Asn Ser Lys Asn Ala Leu Tyr
65                  70                  75                  80

Leu Gln Met Asn Ser Leu Arg Ala Glu Asp Thr Ala Val Tyr Tyr Cys
                85                  90                  95

Ala Lys Asp Pro Arg Lys Phe Asp Tyr Trp Gly Gln Gly Thr Leu Val
                100                 105                 110

Thr Val Ser Ser
        115

<210> SEQ ID NO 165
<211> LENGTH: 116
<212> TYPE: PRT
<213> ORGANISM: Homo sapiens

<400> SEQUENCE: 165

Glu Val Gln Leu Leu Glu Ser Gly Gly Gly Leu Val Gln Pro Gly Gly
1               5                  10                  15

Ser Leu Arg Leu Ser Cys Ala Ala Ser Gly Phe Thr Phe His Ala Tyr
                20                  25                  30

Pro Met Met Trp Val Arg Gln Ala Pro Gly Lys Gly Leu Glu Trp Val
                35                  40                  45

Ser Glu Ile Ser Pro Ser Gly Ser Tyr Thr Tyr Tyr Ala Asp Ser Val
            50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Pro Arg Lys Phe Asp Tyr Trp Gly Gln Gly Thr Leu Val
                100                 105                 110

Thr Val Ser Ser
        115

<210> SEQ ID NO 166
<211> LENGTH: 116
<212> TYPE: PRT
<213> ORGANISM: Homo sapiens

<400> SEQUENCE: 166

Glu Val Gln Leu Leu Glu Ser Gly Gly Gly Leu Val Gln Pro Gly Gly
1               5                  10                  15

Ser Leu Arg Leu Ser Cys Ala Ala Ser Gly Phe Thr Phe Arg Ala Tyr
                20                  25                  30

Pro Met Met Trp Val Arg Gln Ala Pro Gly Lys Gly Leu Glu Trp Val
                35                  40                  45

Ser Glu Ile Ser Pro Ser Gly Ser Tyr Thr Tyr Tyr Ala Asp Ser Val
            50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
```

```
                     85                  90                  95

Ala Lys Asp Pro Arg Lys Phe Asp Tyr Trp Gly Gln Gly Thr Leu Val
            100                 105                 110

Thr Val Ser Ser
        115

<210> SEQ ID NO 167
<211> LENGTH: 116
<212> TYPE: PRT
<213> ORGANISM: Homo sapiens

<400> SEQUENCE: 167

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Leu Ala Tyr
            20                  25                  30

Pro Met Met Trp Val Arg Gln Ala Pro Gly Lys Gly Leu Glu Trp Val
            35                  40                  45

Ser Glu Ile Ser Pro Ser Gly Ser Tyr Thr Tyr Tyr Ala Asp Ser Val
 50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Pro Arg Lys Phe Asp Tyr Trp Gly Gln Gly Thr Leu Val
            100                 105                 110

Thr Val Ser Ser
        115

<210> SEQ ID NO 168
<211> LENGTH: 116
<212> TYPE: PRT
<213> ORGANISM: Homo sapiens

<400> SEQUENCE: 168

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Leu Ala Tyr
            20                  25                  30

Pro Met Met Trp Val Arg Gln Ala Pro Gly Lys Gly Leu Glu Trp Val
            35                  40                  45

Ser Glu Ile Ser Pro Ser Gly Ser Tyr Thr Tyr Tyr Ala Asp Ser Val
 50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Pro Arg Lys Phe Asp Tyr Trp Gly Gln Gly Thr Leu Val
            100                 105                 110

Thr Val Ser Ser
        115

<210> SEQ ID NO 169
<211> LENGTH: 116
<212> TYPE: PRT
<213> ORGANISM: Homo sapiens

<400> SEQUENCE: 169
```

```
Glu Val Gln Gln Leu Glu Ser Gly Gly Gly Leu Val Gln Pro Gly Gly
  1               5                  10                  15

Ser Leu Arg Leu Ser Cys Ala Ala Ser Gly Phe Thr Phe Trp Ala Tyr
             20                  25                  30

Pro Met Met Trp Val Arg Gln Ala Pro Gly Lys Gly Leu Glu Trp Val
         35                  40                  45

Ser Glu Ile Ser Pro Ser Gly Ser Tyr Thr Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Asp Pro Arg Lys Phe Asp Tyr Trp Gly Gln Gly Thr Leu Val
             100                 105                 110

Thr Val Ser Ser
        115

<210> SEQ ID NO 170
<211> LENGTH: 114
<212> TYPE: PRT
<213> ORGANISM: Homo sapiens

<400> SEQUENCE: 170

Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Gln Ala Tyr
             20                  25                  30

Pro Met Met Trp Val Arg Gln Ala Pro Gly Lys Gly Leu Glu Trp Val
         35                  40                  45

Ser Glu Ile Ser Pro Ser Gly Ser Tyr Thr Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Asp Pro Arg Lys Phe Asp Tyr Trp Gly Gln Gly Thr Leu Val
             100                 105                 110

Thr Val

<210> SEQ ID NO 171
<211> LENGTH: 116
<212> TYPE: PRT
<213> ORGANISM: Homo sapiens

<400> SEQUENCE: 171

Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Gly His Tyr
             20                  25                  30

Pro Met Met Trp Val Arg Gln Ala Pro Gly Lys Gly Leu Glu Trp Val
         35                  40                  45

Ser Glu Ile Ser Pro Ser Gly Ser Tyr Thr Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80
```

-continued

Leu Gln Met Asn Ser Leu Arg Ala Glu Asp Thr Ala Val Tyr Tyr Cys
                85                  90                  95

Ala Lys Asp Pro Arg Lys Phe Asp Tyr Trp Gly Gln Gly Thr Leu Val
            100                 105                 110

Thr Val Ser Ser
        115

<210> SEQ ID NO 172
<211> LENGTH: 116
<212> TYPE: PRT
<213> ORGANISM: Homo sapiens

<400> SEQUENCE: 172

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Gly Leu Tyr
            20                  25                  30

Pro Met Met Trp Val Arg Gln Ala Pro Gly Lys Gly Leu Glu Trp Val
        35                  40                  45

Ser Glu Ile Ser Pro Ser Gly Ser Tyr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Pro Arg Lys Phe Asp Tyr Trp Gly Gln Gly Thr Leu Val
            100                 105                 110

Thr Val Ser Ser
        115

<210> SEQ ID NO 173
<211> LENGTH: 116
<212> TYPE: PRT
<213> ORGANISM: Homo sapiens

<400> SEQUENCE: 173

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Gly Trp Tyr
            20                  25                  30

Pro Met Met Trp Val Arg Gln Ala Pro Gly Lys Gly Leu Glu Trp Val
        35                  40                  45

Ser Glu Ile Ser Pro Ser Gly Ser Tyr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Pro Arg Lys Phe Asp Tyr Trp Gly Gln Gly Thr Leu Val
            100                 105                 110

Thr Val Ser Ser
        115

<210> SEQ ID NO 174
<211> LENGTH: 116
<212> TYPE: PRT
<213> ORGANISM: Homo sapiens

<400> SEQUENCE: 174

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Gly Ala Phe
            20                  25                  30

Pro Met Met Trp Val Arg Gln Ala Pro Gly Lys Gly Leu Glu Trp Val
        35                  40                  45

Ser Glu Ile Ser Pro Ser Gly Ser Tyr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Pro Arg Lys Phe Asp Tyr Trp Gly Gln Gly Thr Leu Val
            100                 105                 110

Thr Val Ser Ser
        115

<210> SEQ ID NO 175
<211> LENGTH: 116
<212> TYPE: PRT
<213> ORGANISM: Homo sapiens

<400> SEQUENCE: 175

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Lys Ala Tyr
            20                  25                  30

Pro Ile Met Trp Val Arg Gln Ala Pro Gly Lys Gly Leu Glu Trp Val
        35                  40                  45

Ser Glu Ile Ser Pro Ser Gly Ser Tyr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Pro Arg Ala Phe Asp Tyr Trp Gly Gln Gly Thr Leu Val
            100                 105                 110

Thr Val Ser Ser
        115

<210> SEQ ID NO 176
<211> LENGTH: 116
<212> TYPE: PRT
<213> ORGANISM: Homo sapiens

<400> SEQUENCE: 176

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Lys Ala Tyr
            20                  25                  30

Pro Ile Met Trp Val Arg Gln Ala Pro Gly Lys Gly Leu Glu Trp Val
        35                  40                  45

Ser Glu Ile Ser Pro Ser Gly Ser Tyr Thr Tyr Tyr Ala Asp Ser Val
    50                  55                  60

Lys Gly Arg Phe Thr Ile Ser Arg Asp Asn Ser Lys Asn Thr Leu Tyr

```
            65                  70                  75                  80
Leu Gln Met Asn Ser Leu Arg Ala Glu Asp Thr Ala Val Tyr Tyr Cys
                    85                  90                  95
Ala Lys Ser Pro Arg Lys Phe Asp Tyr Trp Gly Gln Gly Thr Leu Val
                100                 105                 110
Thr Val Ser Ser
        115

<210> SEQ ID NO 177
<211> LENGTH: 116
<212> TYPE: PRT
<213> ORGANISM: Homo sapiens

<400> SEQUENCE: 177

Glu Val Gln Leu Leu Glu Ser Gly Gly Gly Leu Val Gln Pro Gly Gly
  1               5                  10                  15
Ser Leu Arg Leu Ser Cys Ala Ala Ser Gly Phe Thr Phe Lys Ala Tyr
                 20                  25                  30
Pro Ile Met Trp Val Arg Gln Ala Pro Gly Lys Gly Leu Glu Trp Val
                 35                  40                  45
Ser Glu Ile Ser Pro Ser Gly Ser Tyr Thr Tyr Tyr Ala Asp Ser Val
         50                  55                  60
Lys Gly Arg Phe Thr Ile Ser Arg Asp Asn Ser Lys Asn Thr Leu Tyr
 65                  70                  75                  80
Leu Gln Met Asn Ser Leu Arg Ala Glu Asp Thr Ala Val Tyr Tyr Cys
                    85                  90                  95
Ala Lys Thr Pro Arg Lys Phe Asp Tyr Trp Gly Arg Gly Thr Leu Val
                100                 105                 110
Thr Val Ser Ser
        115

<210> SEQ ID NO 178
<211> LENGTH: 116
<212> TYPE: PRT
<213> ORGANISM: Homo sapiens

<400> SEQUENCE: 178

Glu Val Gln Leu Leu Glu Ser Gly Gly Gly Leu Val Gln Pro Gly Gly
  1               5                  10                  15
Ser Leu Arg Leu Ser Cys Ala Ala Ser Gly Phe Thr Phe Lys Ala Tyr
                 20                  25                  30
Pro Ile Met Trp Val Arg Gln Ala Pro Gly Lys Gly Leu Glu Trp Val
                 35                  40                  45
Ser Glu Ile Ser Pro Ser Gly Ser Tyr Thr Tyr Tyr Ala Asp Ser Val
         50                  55                  60
Lys Gly Arg Phe Thr Ile Ser Arg Asp Asn Ser Lys Asn Thr Leu Tyr
 65                  70                  75                  80
Leu Gln Met Asn Ser Leu Arg Ala Glu Asp Thr Ala Val Tyr Tyr Cys
                    85                  90                  95
Ala Lys Asp Pro Arg Glu Phe Asp Tyr Trp Gly Gln Gly Thr Leu Val
                100                 105                 110
Thr Val Ser Ser
        115

<210> SEQ ID NO 179
<211> LENGTH: 116
<212> TYPE: PRT
```

<213> ORGANISM: Homo sapiens

<400> SEQUENCE: 179

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Lys Ala Tyr
            20                  25                  30

Pro Ile Met Trp Val Arg Gln Ala Pro Gly Lys Gly Leu Glu Trp Val
        35                  40                  45

Ser Glu Ile Ser Pro Ser Gly Ser Tyr Thr Tyr Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Pro Arg Arg Phe Asp Tyr Trp Gly Gln Gly Thr Leu Val
            100                 105                 110

Thr Val Ser Ser
        115

<210> SEQ ID NO 180
<211> LENGTH: 116
<212> TYPE: PRT
<213> ORGANISM: Homo sapiens

<400> SEQUENCE: 180

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Lys Ala Tyr
            20                  25                  30

Pro Ile Met Trp Val Arg Gln Ala Pro Gly Lys Gly Leu Glu Trp Val
        35                  40                  45

Ser Glu Ile Ser Pro Ser Gly Ser Tyr Thr Tyr Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Pro Arg Phe Phe Asp Tyr Trp Gly Gln Gly Thr Leu Val
            100                 105                 110

Thr Val Ser Ser
        115

<210> SEQ ID NO 181
<211> LENGTH: 116
<212> TYPE: PRT
<213> ORGANISM: Homo sapiens

<400> SEQUENCE: 181

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Lys Ala Tyr
            20                  25                  30

Pro Ile Met Trp Val Arg Gln Ala Pro Gly Lys Gly Leu Glu Trp Val
        35                  40                  45

Ser Glu Ile Ser Pro Ser Gly Ser Tyr Thr Tyr Tyr Ala Asp Ser Val
50                  55                  60

```
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Thr Pro Ile Lys Phe Asp Tyr Trp Gly Gln Gly Thr Leu Val
            100                 105                 110

Thr Val Ser Ser
        115

<210> SEQ ID NO 182
<211> LENGTH: 116
<212> TYPE: PRT
<213> ORGANISM: Homo sapiens

<400> SEQUENCE: 182

Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Lys Ala Tyr
                 20                  25                  30

Pro Ile Met Trp Val Arg Gln Ala Pro Gly Lys Gly Leu Glu Trp Val
             35                  40                  45

Ser Glu Ile Ser Pro Ser Gly Ser His Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Asp Phe Ser Gln Phe Asp Tyr Trp Gly Gln Gly Thr Leu Val
            100                 105                 110

Thr Val Ser Ser
        115

<210> SEQ ID NO 183
<211> LENGTH: 116
<212> TYPE: PRT
<213> ORGANISM: Homo sapiens

<400> SEQUENCE: 183

Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Lys Ala Tyr
                 20                  25                  30

Pro Ile Leu Trp Val Arg Gln Ala Pro Gly Lys Gly Leu Glu Trp Val
             35                  40                  45

Ser Glu Ile Ser Pro Ser Gly Ser Tyr Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Asp Pro Arg Lys Phe Asp Tyr Trp Gly Gln Gly Thr Leu Val
            100                 105                 110

Thr Val Ser Ser
        115

<210> SEQ ID NO 184
```

```
<211> LENGTH: 116
<212> TYPE: PRT
<213> ORGANISM: Homo sapiens

<400> SEQUENCE: 184

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Lys Ala Tyr
            20                  25                  30

Pro Ile Met Trp Val Arg Gln Ala Pro Gly Lys Gly Leu Glu Trp Val
        35                  40                  45

Ser Glu Ile Ser Pro Ser Gly Lys Met Lys Tyr Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Thr Pro Arg Lys Phe Asp Tyr Trp Gly Arg Gly Thr Leu Val
            100                 105                 110

Thr Val Ser Ser
        115

<210> SEQ ID NO 185
<211> LENGTH: 116
<212> TYPE: PRT
<213> ORGANISM: Homo sapiens

<400> SEQUENCE: 185

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Lys Ala Tyr
            20                  25                  30

Pro Ile Met Trp Val Arg Gln Ala Pro Gly Lys Gly Leu Glu Trp Val
        35                  40                  45

Ser Glu Ile Ser Pro Thr Gly Ser Tyr Thr Tyr Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Pro Arg Lys Phe Asp Tyr Trp Gly Gln Gly Thr Leu Val
            100                 105                 110

Thr Val Ser Ser
        115

<210> SEQ ID NO 186
<211> LENGTH: 116
<212> TYPE: PRT
<213> ORGANISM: Homo sapiens

<400> SEQUENCE: 186

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Lys Ala Tyr
            20                  25                  30

Pro Ile Met Trp Val Arg Gln Ala Pro Gly Lys Gly Leu Glu Trp Val
        35                  40                  45
```

```
Ser Glu Ile Ser Pro Ser Gly Ser Tyr Thr Tyr Tyr Ala Asn Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Asp Pro Arg Ala Phe Asp Tyr Trp Gly Gln Gly Thr Leu Val
                100                 105                 110

Thr Val Ser Ser
        115

<210> SEQ ID NO 187
<211> LENGTH: 116
<212> TYPE: PRT
<213> ORGANISM: Homo sapiens

<400> SEQUENCE: 187

Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Lys Ala Tyr
             20                  25                  30

Pro Ile Met Trp Val Arg Gln Ala Pro Gly Lys Gly Leu Glu Trp Val
         35                  40                  45

Ser Glu Ile Ser Pro Ser Gly Ser Tyr Thr Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Thr Pro Arg Lys Phe Asp Tyr Trp Gly Gln Gly Thr Leu Val
                100                 105                 110

Thr Val Ser Ser
        115

<210> SEQ ID NO 188
<211> LENGTH: 116
<212> TYPE: PRT
<213> ORGANISM: Homo sapiens

<400> SEQUENCE: 188

Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Lys Ala Tyr
             20                  25                  30

Pro Ile Met Trp Val Arg Gln Ala Pro Gly Lys Gly Leu Glu Trp Val
         35                  40                  45

Ser Glu Ile Ser Pro Ser Gly Gln Met Arg Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Asp Pro Arg Glu Phe Asp Tyr Trp Gly Gln Gly Thr Leu Val
                100                 105                 110

Thr Val Ser Ser
        115
```

<210> SEQ ID NO 189
<211> LENGTH: 116
<212> TYPE: PRT
<213> ORGANISM: Homo sapiens

<400> SEQUENCE: 189

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Lys Ala Tyr
            20                  25                  30

Pro Ile Met Trp Val Arg Gln Ala Pro Gly Lys Gly Leu Glu Trp Val
        35                  40                  45

Ser Glu Ile Ser Pro Ser Gly Arg Ser Arg Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Pro Arg Glu Phe Asp Tyr Trp Gly Gln Gly Thr Leu Val
            100                 105                 110

Thr Val Ser Ser
        115

<210> SEQ ID NO 190
<211> LENGTH: 116
<212> TYPE: PRT
<213> ORGANISM: Homo sapiens

<400> SEQUENCE: 190

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Lys Ala Tyr
            20                  25                  30

Pro Ile Met Trp Val Arg Gln Ala Pro Gly Lys Gly Leu Glu Trp Val
        35                  40                  45

Ser Glu Ile Ser Pro Ser Gly Arg Tyr Ser Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Pro Arg Arg Phe Asp Tyr Trp Gly Gln Gly Thr Leu Val
            100                 105                 110

Thr Val Ser Ser
        115

<210> SEQ ID NO 191
<211> LENGTH: 116
<212> TYPE: PRT
<213> ORGANISM: Homo sapiens

<400> SEQUENCE: 191

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Lys Ala Tyr
            20                  25                  30

Pro Ile Met Trp Val Arg Gln Ala Pro Gly Lys Gly Leu Glu Trp Val

```
                35                  40                  45
Ser Glu Ile Ser Pro Ser Gly Glu Ala Arg Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Asp Pro Arg Ala Phe Asp Tyr Trp Gly Gln Gly Thr Leu Val
                100                 105                 110

Thr Val Ser Ser
        115

<210> SEQ ID NO 192
<211> LENGTH: 116
<212> TYPE: PRT
<213> ORGANISM: Homo sapiens

<400> SEQUENCE: 192

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Arg Ala Tyr
                 20                  25                  30

Pro Ile Met Trp Val Arg Gln Ala Pro Gly Lys Gly Leu Glu Trp Val
                 35                  40                  45

Ser Glu Ile Ser Pro Ser Gly Glu Lys Arg Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Asp Pro Arg Ala Phe Asp Tyr Trp Gly Gln Gly Thr Leu Val
                100                 105                 110

Thr Val Ser Ser
        115

<210> SEQ ID NO 193
<211> LENGTH: 116
<212> TYPE: PRT
<213> ORGANISM: Homo sapiens

<400> SEQUENCE: 193

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Lys Ala Tyr
                 20                  25                  30

Pro Ile Met Trp Val Arg Gln Ala Pro Gly Lys Gly Leu Glu Trp Val
                 35                  40                  45

Ser Glu Ile Ser Pro Ser Gly Glu Glu Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Asp Pro Arg Ala Phe Asp Tyr Trp Gly Gln Gly Thr Leu Val
                100                 105                 110

Thr Val Ser Ser
```

```
                115

<210> SEQ ID NO 194
<211> LENGTH: 116
<212> TYPE: PRT
<213> ORGANISM: Homo sapiens

<400> SEQUENCE: 194

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Lys Ala Tyr
            20                  25                  30

Pro Ile Met Trp Val Arg Gln Ala Pro Gly Lys Gly Leu Glu Trp Val
        35                  40                  45

Ser Glu Ile Ser Pro Ser Gly Lys Lys Thr Tyr Tyr Ala Asp Ser Val
    50                  55                  60

Gln Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Pro Arg Ala Phe Asp Tyr Trp Gly Gln Gly Thr Leu Val
            100                 105                 110

Thr Val Ser Ser
        115

<210> SEQ ID NO 195
<211> LENGTH: 116
<212> TYPE: PRT
<213> ORGANISM: Homo sapiens

<400> SEQUENCE: 195

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Lys Ala Tyr
            20                  25                  30

Pro Ile Met Trp Val Arg Gln Ala Pro Gly Lys Gly Leu Glu Trp Val
        35                  40                  45

Ser Glu Ile Ser Pro Ser Gly Lys Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Pro Arg Ala Phe Asp Tyr Trp Gly Gln Gly Thr Leu Val
            100                 105                 110

Thr Val Ser Ser
        115

<210> SEQ ID NO 196
<211> LENGTH: 116
<212> TYPE: PRT
<213> ORGANISM: Homo sapiens

<400> SEQUENCE: 196

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Lys Ala Tyr
            20                  25                  30
```

Pro Ile Met Trp Val Arg Gln Ala Pro Gly Lys Gly Leu Glu Trp Val
            35                  40                  45

Ser Glu Ile Ser Pro Ser Gly Tyr Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Asp Pro Arg Lys Phe Asp Tyr Trp Gly Gln Gly Thr Leu Val
             100                 105                 110

Thr Val Ser Ser
        115

<210> SEQ ID NO 197
<211> LENGTH: 116
<212> TYPE: PRT
<213> ORGANISM: Homo sapiens

<400> SEQUENCE: 197

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Lys Ala Tyr
             20                  25                  30

Pro Ile Met Trp Val Arg Gln Ala Pro Gly Lys Gly Leu Glu Trp Val
            35                  40                  45

Ser Glu Ile Ser Pro Ser Gly Ser Tyr Thr Tyr Tyr Ala Asp Glu Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Asp Pro Arg Lys Phe Asp Tyr Trp Gly Gln Gly Thr Leu Val
             100                 105                 110

Thr Val Ser Ser
        115

<210> SEQ ID NO 198
<211> LENGTH: 116
<212> TYPE: PRT
<213> ORGANISM: Homo sapiens

<400> SEQUENCE: 198

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Lys Ala Tyr
             20                  25                  30

Pro Ile Met Trp Val Arg Gln Ala Pro Gly Lys Gly Leu Glu Trp Val
            35                  40                  45

Ser Glu Ile Ser Pro Ser Gly His Asn Lys Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Asp Pro Arg Arg Phe Asp Tyr Trp Gly Gln Gly Thr Leu Val
             100                 105                 110

Thr Val Ser Ser
        115

<210> SEQ ID NO 199
<211> LENGTH: 326
<212> TYPE: DNA
<213> ORGANISM: Homo sapiens

<400> SEQUENCE: 199
gacatccaga tgacccagtc tccatcctcc ctgtctgcat ctgtaggaga ccgtgtcacc      60
atcacttgcc gggcaagtca gtatattggt gcggagttat cctggtacca gcagaaacca     120
gggaaagccc ctaagctcct gatctattgg atttccgagt tgcaaagtgg ggtcccatca     180
cgtttcagtg gcagtggatc tgggacagat ttcactctca ccatcagcag tctgcaacct     240
gaagattttg ctacgtacta ctgtcaacag tctagtaata ctccttatac gttcggccaa     300
gggaccaagg tggagatcaa acgggc                                          326

<210> SEQ ID NO 200
<211> LENGTH: 326
<212> TYPE: DNA
<213> ORGANISM: Homo sapiens

<400> SEQUENCE: 200
gacatccaga tgacccagtc tccatcctcc ctgtctgcat ctgtaggaga ccgtgtcacc      60
atcacttgcc gggcaagtca gtatattggt attaatttaa tttggtacca gcagaaacca     120
gggaaagccc ctaagctcct gatctattgg gcttccgttt tgcaaagtgg ggtcccatca     180
cgtttcagtg gcagtggatc tgggacagat ttcactctca ccatcagcag tctgcaacct     240
gaagattttg ctacgtacta ctgtcaacag tcggtgtatg atcctcctac gtacggccaa     300
gggaccaagg tggaaatcaa acgggc                                          326

<210> SEQ ID NO 201
<211> LENGTH: 326
<212> TYPE: DNA
<213> ORGANISM: Homo sapiens

<400> SEQUENCE: 201
gacatccaga tgacccagtc tccatcctcc ctgtctgcat ctgtaggaga ccgtgtcacc      60
atcacttgcc gggcaagtca ggatattttt tggttgttat cttggtacca gcagaaacca    120
gggaaagccc ctacgctcct gatctattct acttccattt tgcaaagtgg ggtcccatca     180
cgtttcagtg gcagtggatc tgggacagat ttcactctca ccatcagcag tctgcaacct     240
gaagattttg ctacgtacta ctgtcaacag tattatcttg atcctcctac gttcagccaa     300
gggaccaagg tggaaatcaa acgggc                                          326

<210> SEQ ID NO 202
<211> LENGTH: 326
<212> TYPE: DNA
<213> ORGANISM: Homo sapiens

<400> SEQUENCE: 202
gacatccaga tgacccagtc tccatcctcc ctgtctgcat ctgtaggaga ccgtgtcacc      60
atcacttgcc gggcaagtca gtttattggt gttaatttaa attggtacca gcagaaacca    120
gggaaagccc ctaggctcct gatctatttg tcgtccattc tgcaaagtgg ggtcccatca     180
cgtttcagtg gcagtggatc tgggacagat ttcactctca ccatcagcag tctgcaacct     240

```
gaagattttg ctacgtacta ctgtcaacag acttatgata ttcctactac gttcggccaa    300
gggaccaagg tggaaatcaa acgggc                                         326

<210> SEQ ID NO 203
<211> LENGTH: 326
<212> TYPE: DNA
<213> ORGANISM: Homo sapiens

<400> SEQUENCE: 203
gacatccaga tgacccagtc tccatcctcc ctgtctgcat ctgtaggaga ccgtgtcacc     60
atcacttgcc gggcaagtca gaacattggt attaatttgc agtggtatca gcagaaacca    120
aggaaagccc ctaagctcct gatctattat gcttccattt tgcaaagtgg ggtcccatca    180
cgtttcagtg gcagtggatc tgggacagat ttcactctca ccatcagcag tctgcaacct    240
gaagattttg ctacgtacta ctgtcaacag gattatgata ctccttttac gttcggccaa    300
gggaccaagg tggaaatcaa acgggc                                         326

<210> SEQ ID NO 204
<211> LENGTH: 326
<212> TYPE: DNA
<213> ORGANISM: Homo sapiens

<400> SEQUENCE: 204
gacatccaga tgacccagtt tccatcctcc ctgtctgcat ctgtaggaga ccgtgtcacc     60
atcacttgcc gggcgagtca gcatattgag aggtggttaa attggtatca gcagaaacca    120
gggaaagccc ctaagctcct gatctatcgt tcgtcctatt tgcaaagtgg ggtcccatca    180
cgtttcagtg gcagtggatc tgggacagat ttcactctca ccatcagcag tctgcaacct    240
gaagattttg ctacgtacta ctgtcaacag gatgctattc ttcctcatac gttcggccaa    300
gggaccaagg tggaaatcaa acgggc                                         326

<210> SEQ ID NO 205
<211> LENGTH: 326
<212> TYPE: DNA
<213> ORGANISM: Homo sapiens

<400> SEQUENCE: 205
gacatccaga tgacccagtc tccatcctcc ctgtctgcat ctgtaggaga ccgtgtcacc     60
atcacttgcc gggcaagtca ggggattggg gtgaatttac agtggtacca gcagaaacca    120
gggaaagccc ctaagctcct gatctatttt agttccgtgt tgcaaagtgg ggtcccatca    180
cgtttcagtg gcagtggatc tgggacagat ttcactctca ccatcagcag tctgcaacct    240
gaagattttg ctacgtacta ctgtcaacag gattttgatt ttcctcagac gttcggccaa    300
gggaccaagg tggaaatcaa acgggc                                         326

<210> SEQ ID NO 206
<211> LENGTH: 326
<212> TYPE: DNA
<213> ORGANISM: Homo sapiens

<400> SEQUENCE: 206
gacatccaga tgacccagtc tccatcctcc ctgtctgcat ctgtaggaga ccgtgtcacc     60
atcacttgcc gggcaagtca gaatattggt attaatttgc agtggtatca gcagaaacca    120
aggaaagccc ctaagctcct gatctattat gcttccattt tgcaaagtgg ggtcccatca    180
```

```
cgtttcagtg gcagtggatc tgggacagat ttcactctca ccatcagcag tctgcaacct    240
gaagattttg ctacgtacta ctgtcaacag gagtatgatt atcctaatac gttcggccaa    300
gggaccaagg tggaaatcaa acgggc                                         326
```

<210> SEQ ID NO 207
<211> LENGTH: 326
<212> TYPE: DNA
<213> ORGANISM: Homo sapiens

<400> SEQUENCE: 207

```
gacatccaga tgacccagtc tccatcctcc ctgtctgcat ctgtaggaga ccgtgtcacc    60
atcacttgcc gggcaagtag tagtattggg tcggggttag agtggtacca gcagaaacca   120
gggaaagccc ctaagctcct gatcgttggg tggtccgggt tgcaaagtgg ggtcccatca   180
cgtttcagtg gcagtggatc tgggacagat ttcactctca ccatcagcag tctgcaacct   240
gaagattttg ctacgtacta ctgtcggcag tgtgtgggtt tgccttgtac gttcggccaa   300
gggaccaagg tggaaatcaa acgggc                                        326
```

<210> SEQ ID NO 208
<211> LENGTH: 326
<212> TYPE: DNA
<213> ORGANISM: Homo sapiens

<400> SEQUENCE: 208

```
gacatccaga tgacccagtc tccatcctcc ctgtctgcat ctgtaggaga ccgtgtcacc    60
atcacttgcc gggcaagtca gtggattggg gtggagttaa gttggtatca gcagaaacca   120
gggaaagccc ctaagctcct gatctattgg ggttccgagt tgcaaagtgg ggtcccatca   180
cgtttcagtg gcagtggatc tgggacagat ttcactctca ccatcagcag tctgcaacct   240
gaagattttg ctacgtacta ctgtcaacag ttggcgttac ctccttttac gttcggccaa   300
gggaccaagg tggaaatcaa acgggc                                        326
```

<210> SEQ ID NO 209
<211> LENGTH: 326
<212> TYPE: DNA
<213> ORGANISM: Homo sapiens

<400> SEQUENCE: 209

```
gacatccaga tgacccagtc tccatcctcc ctgtctgcat ctgtaggaga ccgtgtcacc    60
atcacttgcc gggcaagtca tgatattggg gtgagtttag attggtacca gcagaaacca   120
gggaaagccc ctaagctcct gatcgtgtgg gcgtccgtgt tgcaaagtgg ggtcccatca   180
cgtttcagtg gcagtggatc tgggacagat ttcactctca ccatcagcag tctgcaacct   240
gaagattttg ctacgtacta ctgtctgcag gtgggtgctg ggcctatgac gttcggccaa   300
gggaccaagg tggaaatcaa acgggc                                        326
```

<210> SEQ ID NO 210
<211> LENGTH: 326
<212> TYPE: DNA
<213> ORGANISM: Homo sapiens

<400> SEQUENCE: 210

```
gacatccaga tgacccagtc tccatcctcc ctgtctgcat ctgtaggaga ccgtgtcacc    60
atcacttgcc gggcaagtca gtatattggt attgatttag cgtggtacca gcggaaacca   120
gggaaagccc ctaggctcct gatctataag gcttccgctt tgcaaagtgg ggtcccatca   180
```

```
cgtttcagtg gcagtggatc tgggacagat ttcactctca ccatcagcag tctgcaacct    240
gaagattttg ctacgtacta ctgtcaacag tatgcggatt atcctgctac gttcggccaa    300
gggaccaagg tggaaatcaa acgggc                                          326

<210> SEQ ID NO 211
<211> LENGTH: 326
<212> TYPE: DNA
<213> ORGANISM: Homo sapiens

<400> SEQUENCE: 211
gacatccaga tgacccagtc tccatcctcc ctgtctgcat ctgtaggaga ccgtgtcacc     60
atcacttgcc gggcaagtca ggagattgag cattatttat cttggtacca gcagaaacca    120
gggaaagccc ctaagctcct gatctatctt tcgtcccgtt tgcaaagtgg ggtcccatca    180
cgtttcagtg gcagtggatc tgggacagat ttcactctca ccatcagcag tctgcaaccc    240
gaagattttg ctacgtacta ctgtcaacag aatgtgcagc tgcctattac gttcggccaa    300
gggaccaagg tggaaatcaa acgggc                                          326

<210> SEQ ID NO 212
<211> LENGTH: 326
<212> TYPE: DNA
<213> ORGANISM: Homo sapiens

<400> SEQUENCE: 212
gacatccaga tgacccagtc tccatcctcc ctgtctgcat ctgtaggaga ccgtgtcacc     60
atcacttgcc gggcaagtca ggagattggt gttagtttat cgtggtacca gcagaaacca    120
gggaaagccc ctaagctcct gatctattgg ggttccgagt tgcaaagtgg ggtcccatca    180
cgtttcagtg gcagtggatc tgggacagat ttcactctca ccatcagcag tctgcaacct    240
gaagattttg ctacgtacta ctgtcaacag gatcataatt ggcctatgac gttcggccaa    300
gggaccaagg tggaaatcaa acgggc                                          326

<210> SEQ ID NO 213
<211> LENGTH: 326
<212> TYPE: DNA
<213> ORGANISM: Homo sapiens

<400> SEQUENCE: 213
gacatccaga tgacccagtc tccatcctcc ctgtctgcat ctgtaggaga ccgtgtcacc     60
atcacttgcc gggcaagtgc tcttattatg ggggatttag attggtacca gcagaaacca    120
gggaaagccc ctaagctcct gatcgcgggt gtgtccttt tgcaaagtgg ggtcccatca     180
cgtttcagtg gcagtggatc tgggacagat ttcactctca ccatcagcag tctgcaacct    240
gaagattttg ctacgtacta ctgtgctcag tctaggtcgt ggccttatac gttcggccaa    300
gggaccaagg tggaaatcaa acgggc                                          326

<210> SEQ ID NO 214
<211> LENGTH: 326
<212> TYPE: DNA
<213> ORGANISM: Homo sapiens

<400> SEQUENCE: 214
gacatccaga tgacccagtc tccatcctcc ctgtctgcat ctgtaggaga ccgtgtcacc     60
atcacttgcc gggcaagtaa gatgattgat gagaatttag cttggtacca gcagaaacca    120
```

| gggaaagccc ctaagctcct gatccttcgg agttccgggt tgcaaagtgg ggtcccatca | 180 |
| cgtttcagtg gcagtggatc tgggacagat ttcactctca ccatcagcag tctgcaacct | 240 |
| gaagattttg ctacgtacta ctgtcatcag ggtcattctg ctcctggtac gttcggccaa | 300 |
| gggaccaagg tggaaatcaa acgggc | 326 |

<210> SEQ ID NO 215
<211> LENGTH: 326
<212> TYPE: DNA
<213> ORGANISM: Homo sapiens

<400> SEQUENCE: 215

| gacatccaga tgacccagtc tccatcctcc ctgtctgcat ctgtaggaga ccgtgtcacc | 60 |
| atcacttgcc gggcaagtcg gtatattggg gtgtctttag attggtacca gcagaaacca | 120 |
| gggaaagccc ctaagctcct gatcatgtgg ggttccgcgt tgcaaagtgg ggtcccatca | 180 |
| cgtttcagtg gcagtggatc tgggacagat ttcactctca ccatcagcag tctgcaacct | 240 |
| gaagattttg ctacgtacta ctgtttgcag tctgcggcgc cgcctgcgac gttcggccaa | 300 |
| gggaccaagg tggaaatcaa acgggc | 326 |

<210> SEQ ID NO 216
<211> LENGTH: 326
<212> TYPE: DNA
<213> ORGANISM: Homo sapiens

<400> SEQUENCE: 216

| gacatccaga tgacccagtc tccatcctcc ctgtctgcat ctgtaggaga ccgtgtcacc | 60 |
| atcacttgcc gggcaagtca ggagattggt gtgagtttaa gttggtacca gcagaaacca | 120 |
| gggaaagccc ctaagctcct gatctattgg gcgtccgcgt tgcaaagtgg ggtcccatca | 180 |
| cgtttcagtg gcagtggatc tgggacagat ttcactctca ccatcagcag tctgcaacct | 240 |
| gaagattttg ctacgtacta ctgtcaacag tcttatttgc ctcctgatac gttcggccaa | 300 |
| gggaccaagg tggaaatcaa acgggc | 326 |

<210> SEQ ID NO 217
<211> LENGTH: 326
<212> TYPE: DNA
<213> ORGANISM: Homo sapiens

<400> SEQUENCE: 217

| gacatccaga tgacccagtc tccatcctcc ctgtctgcat ctgtaggaga ccgtgtcacc | 60 |
| atcacttgcc gggcaagtca ggagattgct agtgatttac tttggtatca gcagaaacca | 120 |
| gggaaagccc ctaagctcct gatctataat gggtcctcgt tgcaaagtgg ggtcccatca | 180 |
| cgtttcagtg gcagtggatc tgggacagat ttcactctca ccatcagcag actgcaacct | 240 |
| gaagattttg ctacgtacta ctgtcaatgg ttgtggagtg agcctttgac gttcggccaa | 300 |
| gggaccaagg tggaaatcaa acgggc | 326 |

<210> SEQ ID NO 218
<211> LENGTH: 326
<212> TYPE: DNA
<213> ORGANISM: Homo sapiens

<400> SEQUENCE: 218

| gacatccaga tgacccagtc tccatcctcc ctgtctgcat ctgtaggaga ccgtgtcacc | 60 |
| atcacttgcc gggcaagtca gcatattggt gatgcgttat ggtggtatca gcagaaacca | 120 |

```
gggaaagccc ctaagctcct gatctattgg acttccaatt tgcaaagtgg ggtcccatca      180
cgtttcagtg gcagtggatc tgggacagat ttcactctca ccatcagcag tctgcaacct      240
gaagattttg ctacgtacta ctgtcaacag actattcgtc ggccttatac gttcggccaa      300
gggaccaagg tgaaaatcaa acgggc                                          326

<210> SEQ ID NO 219
<211> LENGTH: 326
<212> TYPE: DNA
<213> ORGANISM: Homo sapiens

<400> SEQUENCE: 219
gacatccaga tgacccagtc tccatcctcc ctgtctgcat ctgtaggaga ccgtgtcacc       60
atcacttgcc gggcaagtca gtggattggt attttgttag attggtacca gcagaaacca      120
ggggaagccc ctaagctcct gatctattat gcttcctttt tgcaaagtgg ggtcccatca      180
cgtttcagtg gcagtggatc tgggacagat ttcactctca ccatcagcag tctgcaacct      240
gaagattttg ctacgtacta ctgtcaacag gctaatccgg cgcctctgac gttcggccaa      300
gggaccaagg tggaaatcaa acgggc                                          326

<210> SEQ ID NO 220
<211> LENGTH: 326
<212> TYPE: DNA
<213> ORGANISM: Homo sapiens

<400> SEQUENCE: 220
gacatccaga tgacccagtc tccatcctcc ctgtctgcat ctgtaggaga ccgtgtcacc       60
atcacttgcc gggcaagtca gaatattggt attaatttgc agtggtatca gcagaaacca      120
aggaaagccc ctaagctcct gatctattat gcttccattt tgcaaagtgg ggtcccatca      180
cgtttcagtg gcagtggatc tgggacagat ttcactctca ccatcagcag tctgcaacct      240
gaagattttg ctacgtacta ctgtcaacag tcttatgatt tgcctaagac gttcggccaa      300
gggaccaagg tggaaatcaa acgggc                                          326

<210> SEQ ID NO 221
<211> LENGTH: 326
<212> TYPE: DNA
<213> ORGANISM: Homo sapiens

<400> SEQUENCE: 221
gacatccaga tgatccagtc tccatcctcc ctgtctgcat ctgtaggaga ccgtgtcacc       60
atcacttgcc gggcaagtca ggagattggt gttagtttat cgtggtacca gcagaaacca      120 ggga aagccc ctaagctcct gatctattgg ggttccgagt tgcaaagtgg ggtcccatca      180
cgtttcagtg gcagtggatc tgggacagat ttcactctca ccatcagcag tctgcaacct      240
gaagattttg ctacgtacta ctgtcaacag tggtatggtt ggcctgatac gttcggccaa      300
gggaccaagg taggaatcaa acgggc                                          326

<210> SEQ ID NO 222
<211> LENGTH: 326
<212> TYPE: DNA
<213> ORGANISM: Homo sapiens

<400> SEQUENCE: 222
gacatccaga tgacccagtc tccatcttcc ctgtctgcat ctgtaggaga ccgtgtcacc       60
```

| | |
|---|---|
| atcacttgcc gggcaagtca gcatattggg attgagttaa attggtatca gcagaaacca | 120 |
| gggaaagccc ctaagctcct gatctattgg gcttccgttt tgcaaagtgg ggtcccatca | 180 |
| cgtttcagtg gcagtggatc tgggacagat ttcactctca ccatcagcag tctgcaacct | 240 |
| gaagatttcg ctacgtacta ctgtcaacag agtgtttatg ttcctactac gttcggccaa | 300 |
| gggaccaagg tggaaatcaa acgggc | 326 |

<210> SEQ ID NO 223
<211> LENGTH: 326
<212> TYPE: DNA
<213> ORGANISM: Homo sapiens

<400> SEQUENCE: 223

| | |
|---|---|
| gacatccaga tgacccagtc tccatcctcc ctgtctgcat ctgtaggaga ccgtgtcacc | 60 |
| atcacttgcc gggcaagtca gtggattggt gcggagttag tgtggtatca gcagaaacca | 120 |
| gggaaagccc ctaagctcct gatctattgg agttccgttt tgcaaagtgg ggtcccatca | 180 |
| cgtttcagtg gcagtggatc tgggacagat ttcactctca ccatcagcag tctgcaacct | 240 |
| gaagattttg ctacgtacta ctgtcagcag gctgctcata gtcctcctac gttcggccaa | 300 |
| gggaccaagg tggaaatcaa acgggc | 326 |

<210> SEQ ID NO 224
<211> LENGTH: 326
<212> TYPE: DNA
<213> ORGANISM: Homo sapiens

<400> SEQUENCE: 224

| | |
|---|---|
| gacatccaga tgacccagtc tccatcctcc ctgtctgcat ctgtaggaga ccgtgtcacc | 60 |
| atcacttgcc gggcaagtca ggatattagt cgtagtttag cttggtacca gcggaaacca | 120 |
| gggaaagccc ctaggcttct gatctatatg tcttccactt tgcaaagtgg ggtcccatca | 180 |
| cgtttcagtg gcagtggatc tgggacagat ttcactctca ccatcagcag tctgcaacct | 240 |
| gaagattttg ctacgtacta ctgtcaacag tatgattctt atccttcgac gttcggccaa | 300 |
| gggaccaagg tggaaatcaa acgggc | 326 |

<210> SEQ ID NO 225
<211> LENGTH: 326
<212> TYPE: DNA
<213> ORGANISM: Homo sapiens

<400> SEQUENCE: 225

| | |
|---|---|
| gacatccaga tgacccagtc tccatcctcc ctgtctgcat ctgtaggaga ccgtgtcacc | 60 |
| atcacttgcc gggcaagtag gatgattggg ggtatgttac tttggtacca gcagaaacca | 120 |
| gggaaagccc ctaagctcct gatcacgtat gggtccgtgt tgcaaagtgg ggtcccatca | 180 |
| cgtttcagtg gcagtggatc tgggacagat ttcactctca ccatcagcag tctgcaacct | 240 |
| gaagattttg ctacgtacta ctgtgctcag gagttttggt ggcctcatac gttcggccaa | 300 |
| gggaccaagg tggaaatcaa acgggc | 326 |

<210> SEQ ID NO 226
<211> LENGTH: 326
<212> TYPE: DNA
<213> ORGANISM: Homo sapiens

<400> SEQUENCE: 226

| | |
|---|---|
| gacatccaga tgacccagtc tccatcctcc ctgtctgcat ctgtaggaga ccgtgtcacc | 60 |

| | |
|---|---|
| atcacttgcc gggcaagtcg gcctattggg gataggttaa cgtggtacca gcagaaacca | 120 |
| gggaaagccc ctaagctcct gatctcgtgg gtttccgttt tgcaaagtgg ggtcccatca | 180 |
| cgtttcagtg gcagtggatc tgggacagat ttcactctca ccatcagcag tctgcaacct | 240 |
| gaagattttg ctacgtacta ctgtcgtcag cttgggggtg ggccttttac gttcggccaa | 300 |
| gggaccaagg tggaaatcaa acgggc | 326 |

<210> SEQ ID NO 227
<211> LENGTH: 326
<212> TYPE: DNA
<213> ORGANISM: Homo sapiens

<400> SEQUENCE: 227

| | |
|---|---|
| gacatccaga tgacccagtc tccatcctcc ctgtctgcat ctgtaggaga ccgtgtcacc | 60 |
| atcacttgcc gggcaagtca gtatattggg gtgtcgttaa gttggtacca gcagaaacca | 120 |
| gggaaagccc ctaagctcct gatctatttt gcttccgcgt tgcaaagtgg ggtcccatca | 180 |
| cgtttcagtg gcagtggatc tgggacagat ttcactctca ccatcagcag tctgcaacct | 240 |
| gaagattttg ctacgtacta ctgtcaacag gatcgtgatt ggcctgcgac gttcggccaa | 300 |
| gggaccaagg tggaaatcaa acgggc | 326 |

<210> SEQ ID NO 228
<211> LENGTH: 326
<212> TYPE: DNA
<213> ORGANISM: Homo sapiens

<400> SEQUENCE: 228

| | |
|---|---|
| gacatccaga tgacccagtc tccatcctcc ctgtctgcat ctgtaggaga ccgtgtcacc | 60 |
| atcacttgcc gggcaagtgg tgctattggg gatcgtttaa agtggtacca gcagaaacca | 120 |
| gggaaagccc ctaagctcct gatctcttgg gcgtccgttt tgcaaagtgg ggtcccatca | 180 |
| cgtttcagtg gcagtggatc tgggacagat ttcactctca ccatcagcag tctgcaacct | 240 |
| gaagattttg ctacgtacta ctgtgtgcag gggccggggg tgcctctgac gttcggccaa | 300 |
| gggaccaagg tggaaatcaa acgggc | 326 |

<210> SEQ ID NO 229
<211> LENGTH: 326
<212> TYPE: DNA
<213> ORGANISM: Homo sapiens

<400> SEQUENCE: 229

| | |
|---|---|
| gacatccaga tgactcagtc tccatcctcc ctgtccgcat ctgtaggaga ccgtgtcacc | 60 |
| atcacttgcc gggcaagtca gccgattgct cgttggttag cttggtacca gcagaaacca | 120 |
| gggaaagccc ctaagctcct gatctatggt tcttccgttt tgcaaagtgg ggtcccatca | 180 |
| cgtttcagtg gcagtggatc tgggacagat ttcactctca ccatcagcag tctgcaacct | 240 |
| gaagattttg ctacgtacta ctgtcaacag gatttgaggt tgcctccgac gttcggccaa | 300 |
| gggaccaagg tggaaatcaa acgggc | 326 |

<210> SEQ ID NO 230
<211> LENGTH: 326
<212> TYPE: DNA
<213> ORGANISM: Homo sapiens

<400> SEQUENCE: 230

```
gacatccaga tgacccagtc tccatcctcc ctgtctgcat ctgtaggaga ccgtgtcacc      60
atcacttgcc gggcaagtca gaatattggt gtgtcgttat cgtggtacca gcagaaacca    120
gggaaagccc ctaggctcct gatctattat gggtccaatt tgctaagtgg ggtcccatca    180
cgtttcagtg gcagtggatc tgggacagat ttcactctca ccatcagcag tctgcaacct    240
gaagattttg ctacgtacta ctgtcaacag gagttttcgt ggcctgtgac gttcggccaa    300
gggaccaagg tggaaatcaa acgggc                                          326

<210> SEQ ID NO 231
<211> LENGTH: 326
<212> TYPE: DNA
<213> ORGANISM: Homo sapiens

<400> SEQUENCE: 231
gacatccaga tgacccagtc tccatcctcc ctgtctgcat ctgtaggaga ccgtgtcacc      60
atcacttgcc gggcaagtct tccgattgat gatggtttag gttggtacca gcagaaacca    120
gggaaagccc ctaagctcct gatctgtggg gtgtccggtt tgcaaagtgg ggtcccatta    180
cgtttcagtg gcagtggatc tgggacagat ttcactctca ccatcagcag tctgcaacct    240
gaagattttg ctacgtacta ctgtggtcag ggcaggttc agcctagtac gttcggccaa     300
gggaccaagg tggaaatcaa acggc                                           326

<210> SEQ ID NO 232
<211> LENGTH: 326
<212> TYPE: DNA
<213> ORGANISM: Homo sapiens

<400> SEQUENCE: 232
gacatccaga tgacccagtc tccatcctcc ctgtctgcat ctgtaggaga ccgtgtcacc      60
atcacttgcc gggcaagtca gaatattggt attaatttgc agtggtatca gcagaaacca    120
aggaaagccc ctaagctcct gatctattat gcttccattt tgcaaagtgg ggtcccatca    180
cgtttcagtg gcagtggatc tgggacagat ttcactctca ccatcagcag tctgcaacct    240
gaagattttg ctacgtacta ctgtcaacag tcgtatgatg cgcctactac gttcggccaa    300
gggaccaagg tggaaatcaa acgggc                                          326

<210> SEQ ID NO 233
<211> LENGTH: 326
<212> TYPE: DNA
<213> ORGANISM: Homo sapiens

<400> SEQUENCE: 233
gacatccaga tgacccagtc tccatcctcc ctgtctgcat ctgtaggaga ccgtgtcacc      60
atcacttgcc gggcaagtca gtctattggg gttaatttaa tgtggtacca gcagaaacca    120
gggaaagccc ctaagctcct gatctatttt gcttccattt tgcaaagtgg ggtcccatca    180
cgtttcagtg gcagtggatc tgggacagat ttcactctca ccatcagcag tctgcaacct    240
gaagactttg ctacgtacta ctgtcaacag aattatgata ttcctaagac gttcggccaa    300
gggaccaagg tggaaatcaa acgggc                                          326

<210> SEQ ID NO 234
<211> LENGTH: 326
<212> TYPE: DNA
<213> ORGANISM: Homo sapiens

<400> SEQUENCE: 234
```

```
gacatccaga tgacccagtc tccatcctcc ctgtctgcat ctgtaggaga ccgtgtcacc      60
atcacttgcc gggcaagtca gtggattggt atttctttat cttggtatca gcagaaacca     120
gggaaagccc ctaagctcct aatctattat gggtccgtgt tgcaaagtgg ggtcccatcc     180
cgtttcagtg gcagtggatc tgggacagat ttcactctca ccatcagcag tctgcaacct     240
gaagattttg ctacgtacta ctgtcaacag tctcatgatc ttcctgtgac gtttggccaa     300
gggaccaagg tggaaatcaa acgggc                                          326

<210> SEQ ID NO 235
<211> LENGTH: 326
<212> TYPE: DNA
<213> ORGANISM: Homo sapiens

<400> SEQUENCE: 235
gacatccaga tgacccagtc tccatcctcc ctgtctgcat ctgtaggaga ccgtgtcacc      60
atcacttgcc gggcaagtca gtggattggt gttagttat cttggtatca gcagaaacca     120
gggaaagccc ctaagctcct gatctattat gcgtccattt tgcaaagtgg ggtcccatca     180
cgtttcagtg gcagtggatc tgggacagat ttcactctca ccatcagcag tctgcaacct     240
gaagattttg ctacgtacta ctgtcaacag gagatgtcgt atcctcctac gttcggccaa     300
gggaccaagg tggaaatcaa acgggc                                          326

<210> SEQ ID NO 236
<211> LENGTH: 326
<212> TYPE: DNA
<213> ORGANISM: Homo sapiens

<400> SEQUENCE: 236
gacatccaga tgacccagtc tccatcctcc ctgtctgcat ctgtaggaga ccgtgtcacc      60
atcacttgcc gggcaagcca ggatattggt gttagtttag agtggtatca gcagaaacca     120
gggaaagccc ctaagctcct gatctattgg agttccgctt tgcaaagtgg ggtcccatca     180
cgtttcagtg gcagtggatc tgggacagat ttcactctca ccatcagcag tctgcaacct     240
gaagatttgg ctacgtacta ctgtcaacag gggcatacgt atcctagtac gttcggccaa     300
gggaccaagg tggaaatcaa acgggc                                          326

<210> SEQ ID NO 237
<211> LENGTH: 326
<212> TYPE: DNA
<213> ORGANISM: Homo sapiens

<400> SEQUENCE: 237
gacatccaga tgacccagtc tccatcctcc ctgtctgcat ctgtaggaga ccgtgtcacc      60
atcacttgcc gggcaagtca gtatattggt gtttatttaa gttggtatca gcagaaacca     120
gggaaagccc ctaagctcct gatctattgg gcgtcccttt tgcaaagtgg ggtcccatca     180
cgtttcagtg gcagtggatc tgggacagat ttcactctca ccatcagcag tctgcaacct     240
gaagattttg ctacgtacta ctgtcaacag actgttaggg atcctattac gttcggccaa     300
gggaccaagg tggaaatcaa acgggc                                          326

<210> SEQ ID NO 238
<211> LENGTH: 326
<212> TYPE: DNA
<213> ORGANISM: Homo sapiens
```

<400> SEQUENCE: 238

```
gacatccaga tgacccagtc tccatccttc ctgtctgcat ctgtaggaga ccgtgtcacc    60
atcacttgcc gggcaagtca gtctatttat actatgttaa attggtatca gcagaaacca   120
gggaaagccc ctaagctcct gatctatcgt gcttcctatt tgcaaagtgg ggtcccatca   180
cgtttcagtg gcagtggatc tgggacagat ttcactctca ccatcagcag tctgctacct   240
gaagattctg ctacgtacta ctgtcaacag gattttcgt atcctagtac gttcggccaa    300
gggaccaagg tggaaatcaa acgggc                                        326
```

<210> SEQ ID NO 239
<211> LENGTH: 326
<212> TYPE: DNA
<213> ORGANISM: Homo sapiens

<400> SEQUENCE: 239

```
gacatccaga tgacccagtc tccatcctcc ctgtctgcat ctgtaggaga ccgtgtcacc    60
atcacttgcc gggcaagtca gtatattggg gcgaatttaa gttggtatca gcagaaacca   120
gggaaagccc ctaagctcct gatctattat atttccgttt tgcaaagtgg ggtcccatca   180
cgtttcagtg gcagtggatc tgggacagat ttcactctca ccatcagcag tctgcaacct   240
gaagattttg ctacgtacta ctgtcaacag gagctttata ctcctcatac gttcggccaa   300
gggaccaagg tggaaatcaa acgggc                                        326
```

<210> SEQ ID NO 240
<211> LENGTH: 326
<212> TYPE: DNA
<213> ORGANISM: Homo sapiens

<400> SEQUENCE: 240

```
gacatccagt tgacccagtc tccatcctcc ctgtctgcat ctgtaggaga ccgtgtcacc    60
atcacttgcc gggcaagtca gtatattggt gtgactttaa tgtggtatca gcagaaacca   120
gggaaagccc ctaagctcct gatctattat gcttcccagt tgcaaagtgg ggtcccatca   180
cgtttcagtg gcagtggatc tgggacagat ttcactctca ccatcagcag tctgcaacct   240
gaagattttg ctacgtacta ctgtcaacag gaggttagtt atccttatac gttcggccaa   300
gggaccaagg tggaaatcaa acgggc                                        326
```

<210> SEQ ID NO 241
<211> LENGTH: 326
<212> TYPE: DNA
<213> ORGANISM: Homo sapiens

<400> SEQUENCE: 241

```
gacatccaga tgacccagtc tccatcctct ctgtctgcat ctgtaggaga ccgtgtcacc    60
atcacttgcc gggcaagtca gcatattggt gtgagtttaa cttggtacca gcagaaacca   120
gggaaagccc ctaagctcct gatctatttt gcttccattt tgcaaagtgg ggtcccatca   180
cgtttcagtg gcagtggatc tgggacagat ttcactctca ccatcagcag tctgcaacct   240
gaagattatg ctacgtacta ctgtcaacag gatatgtctt atcctcctac gttcggccaa   300
gggaccaagg tggaaatcaa acgggc                                        326
```

<210> SEQ ID NO 242
<211> LENGTH: 326
<212> TYPE: DNA
<213> ORGANISM: Homo sapiens

<400> SEQUENCE: 242
gacatccaga tgacccagtc tccatcctcc ctgtctgcat ctgtaggaga ccgtgtcacc    60
atcacttgcc gggcaagtca ggatattggt atcagtttag agtggtatca gcagaaacca   120
gggaaagccc ctaagctcct gatctatttt gcttccagt tgcaaagtgg ggtcccatca    180
cgtttcagtg gcagtggatc tgggacagat ttcactctca ccatcagcag tctgcaacct   240
gaagattttg ctacgtacta ctgtcaacag gtgtatgatt ttcctaatac gttcggccaa   300
gggaccaagg tggaaatcaa acgggc                                        326

<210> SEQ ID NO 243
<211> LENGTH: 326
<212> TYPE: DNA
<213> ORGANISM: Homo sapiens

<400> SEQUENCE: 243
gacatccaga tgacccagtc tccatcctcc ctgtctgcat ctgtaggaga ccgtgtcacc    60
atcacttgcc gggcaagtca gcatattggt gtgagtttaa attggtatca gcagaaacca   120
gggaaagtcc ctaagctcct gatctattgg gcttccattt tgcaaagtgg ggtcccatca   180
cgtttcagtg gcagtggatc tgggacagat ttcactctca ccatcagcag tctgcaacct   240
gaagattttg ctacgtacta ctgtcaacag gagcatacta ttccttctac gttcggccaa   300
gggaccaagg tggaaatcaa acgggc                                        326

<210> SEQ ID NO 244
<211> LENGTH: 326
<212> TYPE: DNA
<213> ORGANISM: Homo sapiens

<400> SEQUENCE: 244
gacatccaga tgacccagtc tccatcctcc ctgtctgcat ctgtaggaga ccgtgtcacc    60
atcacttgcc gggcaagtca gcatattggg gtttcgttag attggtacca gcagaaacca   120
gggaaagccc ctaagctcct gatctattat ggttccgagt tgcaaagtgg ggtcccatca   180
cgtttcagtg gcagtggatc tgggacagat ttcactctca ccatcagcag tctgcaacct   240
gaagattttg ctacgtacta ctgtcaacag tatgttactc atcctacgac gttcggccaa   300
gggaccaagg tggaaatcaa acgggc                                        326

<210> SEQ ID NO 245
<211> LENGTH: 326
<212> TYPE: DNA
<213> ORGANISM: Homo sapiens

<400> SEQUENCE: 245
gacatccaga tgacccagtc tccatcctcc ctgtctgcat ctgtaggaga ccgtgtcacc    60
atcacttgcc gggcaagtca gaggattggt atgatgttag attggtatca gcagaaacca   120
gggaaagccc ctaagctcct gatctatggg ggttccaagt tgcaaagtgg ggtcccatca   180
cgtttcagtg gcagtggatc tgggacagat ttcactctca ccatcagcag tctgcaacct   240
gaagattttg ctacgtacta ctgtcaacac cggggttggt atcctctgac gttcggccaa   300
gggaccaagg tggaaatcaa acgggc                                        326

<210> SEQ ID NO 246
<211> LENGTH: 326
<212> TYPE: DNA

<213> ORGANISM: Homo sapiens

<400> SEQUENCE: 246

```
gacatccaga tgacccagtc tccatcctcc ctgtctgcat ctgtaggaga ccgtgtcacc      60
atcacttgcc gggcaagtca gcctattggt gatcgtttaa gttggtacca gcagaaacca     120
gggaaagccc ctaagctcct gatctatttt tcttccgttt tgcaaagtgg ggtcccatca     180
cgtttcagtg gcagtggatc tgggacagat ttcactctca ccatcagcag tctgcaacct    240
gaagattttg ctacgtacta ctgtcaacag catggtttgc ggcctgatac gttcggccaa    300
gggaccaagg tggaaatcaa acgggc                                         326
```

<210> SEQ ID NO 247
<211> LENGTH: 326
<212> TYPE: DNA
<213> ORGANISM: Homo sapiens

<400> SEQUENCE: 247

```
gacatccaga tgacccagtc tccatcctcc ctgtctgcat cagtaggaga ccgtgtcacc      60
atcacttgcc gggcaagtca gtggattggt agtagtttaa tgtggtatca gcagaaacca    120
gggaaagccc ctaagctcct gatctattgg gcttccgagt tgcaaagtgg ggtcccatcg    180
cgtttcagtg gcagtggatc tgggacagat ttcactctca ccatcagcag tctgcaacct    240
gaagattttg ctacgtacta ctgtcaacag gagtatagtt atcctagtac gttcggccaa    300
gggaccaaag tggaaatcaa acgggc                                         326
```

<210> SEQ ID NO 248
<211> LENGTH: 326
<212> TYPE: DNA
<213> ORGANISM: Homo sapiens

<400> SEQUENCE: 248

```
gacatccaga tgacccagtc tccatcctcc ctgtctgcat ctgtaggaga ccgtgtcacc      60
atcacttgcc gggcaagtca ggatattggt gtttcgttag cttggtacca gcagaaaccg    120
gggaaagccc ctaagctcct gatctatttt ggttccgtgt cgctaagtgg ggtcccatca    180
cgtttcagtg gcagtggatc tgggacagat ttcactctca ccatcagcag tctgcaacct    240
gaagattttg ctacgtacta ctgtcaacag tctcatcttc ctcctactac gttcggccaa    300
gggaccaagg tggaaatcaa acgggc                                         326
```

<210> SEQ ID NO 249
<211> LENGTH: 326
<212> TYPE: DNA
<213> ORGANISM: Homo sapiens

<400> SEQUENCE: 249

```
gacatccaga tgacccagtc tccatcctcc ctgtctgcat ctgtaggaga ccgtgtcacc      60
atcacttgcc gggcaagtca gtggattggg gtggagttaa attggtatca gcagaaacca    120
gggaaagccc ctaagctcct gatctattgg acgtccattt tgcaaagtgg ggtcccatca    180
cgtttcagtg gcagtggatc tgggacagat ttcactctca ccatcagcag tctgcaacct    240
gaagattttg ctacgtacta ctgtcaacag gttattaata gtccctatac gttcggccaa    300
gggaccaagg tggaaatcaa acgggc                                         326
```

<210> SEQ ID NO 250
<211> LENGTH: 326

<212> TYPE: DNA
<213> ORGANISM: Homo sapiens

<400> SEQUENCE: 250

```
gacatccaga tgacccagtc tccatcctcc ctgtctgcat ctgtaggaga ccgtgtcacc    60
atcacttgcc gggcaagtca ggatattggt aagtggttag agtggtacca gcagaaacca   120
gggaaagccc ctaagctcct gatcggggcg acgtcctggt tgcaaagtgg ggtcccatca   180
cgtttcagtg gcagtggatc tgggacagat ttcactctca ccatcagcag tctgcaacct   240
gaagattttg ctacgtacta ctgtgttcag caggggaggc gtcctgggac gttcggccaa   300
gggaccaagg tggaaatcaa acgggc                                        326
```

<210> SEQ ID NO 251
<211> LENGTH: 326
<212> TYPE: DNA
<213> ORGANISM: Homo sapiens

<400> SEQUENCE: 251

```
gacatccaga tgacccagtc tccatcctcc ctgtctgcat ctgtaggaga ccgtgtcacc    60
atcacttgcc gggcaagtca gtggattggt attttgttag attggtacca gcagaaacca   120
ggggaagccc ctaagctcct gatctattat gcttcctttt tgcaaagtgg ggtcccatca   180
cgtttcagtg gcagtggatc tgggacagat ttcactctca ccatcagcag tctgcaacct   240
gaagattttg ctacgtacta ctgtcaacgg tcggatctgt ctcctctgac gttcggccaa   300
gggaccaagg tggaaatcaa acgggc                                        326
```

<210> SEQ ID NO 252
<211> LENGTH: 326
<212> TYPE: DNA
<213> ORGANISM: Homo sapiens

<400> SEQUENCE: 252

```
gacatccaga tgacccagtc tccatcctcc ctgtctgcat ctgtaggaga ccgtgtcacc    60
atcacttgcc gggcaagtca gaatatttat atgaatttag agtggtacca gcagaaacca   120
gggaaagccc ctaagctcct gatcgttttt ggttcctggt tgcaaagtgg ggtcccatca   180
cgtttcagtg gcagtggatc tgggacagat ttcactctca ccatcagcag tctgcaacct   240
gaagattttg ctacgtacta ctgtcggcag actgaggcgc cgccttctac gttcggccaa   300
gggaccaagg tggaaatcaa acgggc                                        326
```

<210> SEQ ID NO 253
<211> LENGTH: 326
<212> TYPE: DNA
<213> ORGANISM: Homo sapiens

<400> SEQUENCE: 253

```
gacatccgga tgacccagtc tccatcctcc ctgtctgcat ctgtaggaga ccgtgtcacc    60
atcacttgcc gggcaagtca gcatattggg tcgtcgttat cttggtacca gcagaaacca   120
gggaaagccc ctaagctcct gatctattat gcctccgttt tgcaaagtgg ggtcccatca   180
cgtttcagtg gcagtggatc tgggacagat ttcactctca ccatcagcag tctgcaacct   240
gaagattttg ctacgtacta ctgtcaacag gagtattctt ggcctcctac gctcggccaa   300
gggaccaagg tggaaatcaa acgggc                                        326
```

<210> SEQ ID NO 254

<211> LENGTH: 326
<212> TYPE: DNA
<213> ORGANISM: Homo sapiens

<400> SEQUENCE: 254

```
gacatccaga tgacccagtc tccatcctcc ctgtctgcat ctgtaggaga ccgtgtcacc    60
atcacttgcc gggcaagtca ggatattcgg acgctgttac ggtggtacca gcagaaacca   120
gggaaagccc ctaagctcct gatctattgg tcttccgagt tgcaaagtgg ggtcccatca   180
cgtttcagtg gcagtggatc tgggacagat ttcactctca ccatcagcag tctgcaacct   240
gaagattttg ctacgtacta ctgtcaacag acgtttcatg cgcctaatac gttcggccaa   300
gggaccaagg tggaaatcaa acgggc                                        326
```

<210> SEQ ID NO 255
<211> LENGTH: 326
<212> TYPE: DNA
<213> ORGANISM: Homo sapiens

<400> SEQUENCE: 255

```
gacatccgga tgacccagtc tccatcctcc ctgtctgcat ctgtaggaga ccgtgtcacc    60
atcacttgcc gggcaagtca gtatattggg aagtatttaa gttggtacca gcagaaacca   120
gggaaagccc ctaagctcct gatctatttg tcgtccacgt tgcaaagtgg ggtcccatca   180
cgtttcagtg gcagtggatc tgggacagat ttcactctca ccatcagcag tctgcaacct   240
gaagattttg ctacgtacta ctgtcaacag aatgatcgtt acctcttac gctcggccaa    300
gggaccaagg tggaaatcaa acgggc                                        326
```

<210> SEQ ID NO 256
<211> LENGTH: 326
<212> TYPE: DNA
<213> ORGANISM: Homo sapiens

<400> SEQUENCE: 256

```
gacatccaga tgacccagtc tccatcctcc ctgtctgcat ctgtaggaga ccgtgtcacc    60
atcacttgcc aggcaagtca gctgattggg aatatgttat cttggtacca gcagaaacca   120
gggaaagccc ctacgctcct gatctatatt ggttcctctt tgcaaagtgg ggtcccatca   180
cgtttcagtg gcagtggatc tgggacagat ttcactctca ccatcagcag tctgcaacct   240
gaagattttg ctacgtacta ctgtcaacag acgtattttg atcctcctac gttcggccaa   300
gggaccaagg tggaaatcaa acgggc                                        326
```

<210> SEQ ID NO 257
<211> LENGTH: 326
<212> TYPE: DNA
<213> ORGANISM: Homo sapiens

<400> SEQUENCE: 257

```
gacatccaga tgacccagtc tccatcctcc ctgtctgcat ctgtaggaga ccgtgtcacc    60
atcacttgcc gggcaagtca gtatattggt attaatttaa ggtggtacca gcagaaacca   120
gggaaagccc ctaagctcct gatctattat agttccactt tgctaagtgg ggtcccatca   180
cgtttcagtg gcagtggatc tgggacagat ttcactctca ccatcagcag tctgcaacct   240
gaagattttg ctacgtacta ctgtcaacag tcttatgatt ctcctgttac gttcggccaa   300
gggaccaagg tggaaatcaa acgggc                                        326
```

```
<210> SEQ ID NO 258
<211> LENGTH: 326
<212> TYPE: DNA
<213> ORGANISM: Homo sapiens

<400> SEQUENCE: 258
gacatccaga tgacccagtc tccatcctcc ctgtctgcat ctgtaggaga ccgtgtcacc      60
atcacttgcc gggcaagttg ggctattggt gatcgtttag agtggtacca gcagaaacca     120
gggaaagccc ctaagctcct gatcgcgtgg gggtccgtgt tgcaaagtgg ggtcccatca     180
cgtttcagtg gcagtggatc tgggacagat ttcactctca ccatcagcag tctgcaacct     240
gaagattttg ctacgtacta ctgttctcag ctgggttcgc ggcctcgtac gttcggccaa     300
gggaccaagg tggaaatcaa acgggc                                          326

<210> SEQ ID NO 259
<211> LENGTH: 326
<212> TYPE: DNA
<213> ORGANISM: Homo sapiens

<400> SEQUENCE: 259
gacatccaga tgacccagtc tccatcctcc ctgtctgcat ctgtaggaga ccgtgtcacc      60
atcacttgcc gggcaagtca gtcgattgat aattggttag cgtggtacca gcagaaacca     120
ggggaagccc ctaagctcct gatctatggt acgtcccggt tgcaaagtgg ggtcccatcg     180
cgtttcagtg gcagtggatc tgggacagat tttactctca ccatcagcag tctgcaacct     240
gaagattttg ctacgtacta ctgtcaacag tataattttt ttccttctac gttcggccaa     300
gggaccaagg tggaaatcaa acgggc                                          326

<210> SEQ ID NO 260
<211> LENGTH: 326
<212> TYPE: DNA
<213> ORGANISM: Homo sapiens

<400> SEQUENCE: 260
gacatccaga tgacccagtc tccatcctcc ctgtctgcat ctgtaggaga ccgtgtcacc      60
atcacttgcc gggcaagtac ttttattggt aatgtgttaa attggtacca gcagaaacca     120
gggaaagccc ctaagctcct gatctcttat gtgtccatgt tgcaaagtgg ggtcccatca     180
cgtttcagtg gcagtggatc tgggacagat ttcactctca ccatcagcag tctgcaacct     240
gaagattttg ctacgtacta ctgttgtcag tcgtatgatg tgccttttac gttcggccaa     300
gggacccagg tggaaatcaa acgggc                                          326

<210> SEQ ID NO 261
<211> LENGTH: 326
<212> TYPE: DNA
<213> ORGANISM: Homo sapiens

<400> SEQUENCE: 261
gacatccaga tgacccagtc tccatcctcc ctgtctgcat ctgtaggaga ccgtgtcacc      60
atcacttgcc gggcaagtca gtggattggg gttagtttag tttggtatca gcagaaacca     120
gggaaagccc ctaagctcct gatctattgg gcttccgttt tgcaaagtgg agtcccatca     180
cgtttcagtg gcagtggatc tgggacagat ttcactctca ccatcagcag tctgcaacct     240
gaggattttg ctacgtacta ctgtcaacag acgcatgcag ggcctcatac gttcggccaa     300
gggaccaagg tggaaatcaa acgggc                                          326
```

<210> SEQ ID NO 262
<211> LENGTH: 326
<212> TYPE: DNA
<213> ORGANISM: Homo sapiens

<400> SEQUENCE: 262

```
gacatccaga tgacccagtc tccatcctcc ctgtctgcat ctgtaggaga ccgtgtcacc      60
atcacttgcc gggcaagtca gtggattggt attttgttag attggtacca gcagaaacca     120
ggggaagccc ctaagctcct gatctattat gcttcctttt tgcaaagtgg ggtcccatca     180
cgtttcagtg gcagtggatc tgggacagat ttcactctca ccatcagcag tctgcaacct     240
gaagattttg ctacgtacta ctgtcaacag tcttctgtgg atcctcttac gttcggccaa     300
gggaccaagg tggaaatcaa acgggc                                          326
```

<210> SEQ ID NO 263
<211> LENGTH: 326
<212> TYPE: DNA
<213> ORGANISM: Homo sapiens

<400> SEQUENCE: 263

```
gacatccaga tgacccagtc tccatcctcc ctgtctgcat ctgtaggaga ccgtgtcacc      60
atcacttgcc gggcaagtca ggatattggt gtgtcgttaa ggtggtatca gcagaaacca     120
gggaaagccc ctaagctcct gatctattgg gcttccgagt tgcaaagtgg ggtcccatca     180
cgtttcagtg gcagtggatc tgggacagat ttcactctca ccatcagcag tctgcaacct     240
gaagattttg ctacgtacta ctgtcaacag ctttatgatt atcctccgac gttcggccaa     300
gggaccaagg tggaaatcaa acgggc                                          326
```

<210> SEQ ID NO 264
<211> LENGTH: 326
<212> TYPE: DNA
<213> ORGANISM: Homo sapiens

<400> SEQUENCE: 264

```
gacatccaga tgacccagtc tccatcctcc ctgtctgcat ctgtaggaga ccgtgtcacc      60
atcacttgcc gggcaagtcg ttttattgct tctggtttag attggtacca gcagaaacca     120
gggaaagccc ctaagctcct gatctcgcgg ttttccgggt tgcaaagtgg ggtcccatca     180
cgtttcagtg gcagtggatc tgggacagat ttcactctca ccatcagcag tctgcaacct     240
gaagattttg ctacgtacta ctgtaagcag gggtttgggg ctcctgcgac gttcggccaa     300
gggaccaagg tggaaatcaa acgggc                                          326
```

<210> SEQ ID NO 265
<211> LENGTH: 329
<212> TYPE: DNA
<213> ORGANISM: Homo sapiens

<400> SEQUENCE: 265

```
gacatccaga tgacccagtc tccatcctcc ctgtctgcat ctgtaggaga ccgtgtcacc      60
atcacttgcc gggcaagtca gtatatttct acggagttag agtggtatca gcagaaacca     120
gggaaagccc ctaagctcct gatctattcg agttccatgt tgcaaagtgg ggtcccatca     180
cgtttcagtg gcagtggatc tgggacagat ttcactctca ccatcagcag tctgcaacct     240
gaagattttg ctacgtacta ctgtcaacag agtgcttcgg cgcttcctct gacgttcggc     300
caagggacca aggtggaaat caaacgggc                                       329
```

<210> SEQ ID NO 266
<211> LENGTH: 326
<212> TYPE: DNA
<213> ORGANISM: Homo sapiens

<400> SEQUENCE: 266

```
gacatccaga tgacccagtc tccatcctcc ctgtctgcat ctgtaggaga ccgtgtcacc    60
atcacttgcc gggcaagtca gtggattggt gcgtctttac agtggtacca gcagaaacca   120
gggcaagccc ctaagctcct gatctattat atgtccgtgt tgcaaagtgg ggtcccatca   180
cgtttcagtg gcagtggatc tgggacagat ttcactctca ccatcagcag tctgcaacct   240
gaagattttg ctacgtacta ctgtcaacag acggctttga ctcctgctac gttcggccaa   300
gggaccaagg tggaaatcaa acgggc                                        326
```

<210> SEQ ID NO 267
<211> LENGTH: 326
<212> TYPE: DNA
<213> ORGANISM: Homo sapiens

<400> SEQUENCE: 267

```
gacatccaga tgacccagtc tccatcctcc ctgtctgcat ctgtaggaga ccgtgtcacc    60
atcacttgcc gggcaagtca ggttattggg gattatttat cttggtacca gcagaaacca   120
gggaaagccc ctaagctcct gatctatttt cgttccgttt tgcaaagtgg ggtcccatca   180
cgtttcagtg gcagtggatc tgggacagat ttcactctca ccatcagcag tctgcaacct   240
gaagattttg ctacgtacta ctgtcaacag aattggaatt tgcctgttac gttcggccaa   300
gggaccaagg tggaaatcaa acgggc                                        326
```

<210> SEQ ID NO 268
<211> LENGTH: 326
<212> TYPE: DNA
<213> ORGANISM: Homo sapiens

<400> SEQUENCE: 268

```
gacatccaga tgacccagtc tccatcctcc ctgtctgcat ctgtaggaga ccgtgtcacc    60
atcacttgcc gggcaagtca gtatattggt gtgaatttat cgtggtacca gcagaaacca   120
gggaaagccc ctaagctcct gatctattat gtttccgttt tgcaaagtgg ggtcccatca   180
cgtttcagtg gcagtggatc tgggacagat ttcactctca ccatcagcag tctgcaacct   240
gaagattttg ctacgtacta ctgtcaacag acttatgata ttccttctac gttcggccaa   300
gggaccaagg tggaaattaa acgggc                                        326
```

<210> SEQ ID NO 269
<211> LENGTH: 326
<212> TYPE: DNA
<213> ORGANISM: Homo sapiens

<400> SEQUENCE: 269

```
gacatccaga tgacccagtc tccatccacc ctgtctgcat ctgtaggaga ccgtgtcacc    60
atcacttgcc gggcaagtca gtggattggt gtgtctttat cgtggtacca gcagaaacca   120
gggaaagccc ctaagctcct gatctattat acgtccgtat tgcaaagtgg ggtcccatca   180
cgtttcagtg gcagtggatc tgggacagat ttcactctca ccatcagcag tctgcaacct   240
gaagattttg ctacatacta ctgtcaacag gagacgacgt ggccttatac gttcggccaa   300
```

| | |
|---|---:|
| gggaccaagg tggaaatcaa acgggc | 326 |

<210> SEQ ID NO 270
<211> LENGTH: 326
<212> TYPE: DNA
<213> ORGANISM: Homo sapiens

<400> SEQUENCE: 270

| | |
|---|---:|
| gacatccaga tgacccagtc tccatcctcc ttgtctgcat ctgtaggaga ccgtgtcacc | 60 |
| atcacttgcc gggcaagtca gtatattggg gcggagttaa attggtacca gcagaaacca | 120 |
| gggaaagccc ctaagctcct gatctattgg acttccgtgt tgcaaagtgg ggtcccatca | 180 |
| cgtttcagtg gcagtggatc tgggacagat ttcactctca ccatcagcag tctgcaacct | 240 |
| gaagattttg ctacgtacta ctgtcaacag gcgattctgg cgcctcttac gttcggccaa | 300 |
| gggaccaagg tggaaatcaa acgggc | 326 |

<210> SEQ ID NO 271
<211> LENGTH: 326
<212> TYPE: DNA
<213> ORGANISM: Homo sapiens

<400> SEQUENCE: 271

| | |
|---|---:|
| gacatccaga tgacccagtc tccatcctcc ctgtctgcat ctgtaggaga ccgtgtcacc | 60 |
| atcacttgcc gggcaagtca gtggattggt gttagtttaa attggtatca gcagaaacca | 120 |
| gggaaagccc ctaagctcct gatctacttt gcgtccgtgt tgcagagtgg ggtcccatca | 180 |
| cgtttcagtg gcagtggatc tgggacagat ttcactctca ccatcagcag tctgcaacct | 240 |
| gaagattttg ctacgtacta ctgtcaacag aatgcgtttt atcctgatac gttcggccaa | 300 |
| gggaccaagg tggaaatcaa acgggc | 326 |

<210> SEQ ID NO 272
<211> LENGTH: 326
<212> TYPE: DNA
<213> ORGANISM: Homo sapiens

<400> SEQUENCE: 272

| | |
|---|---:|
| gacatccaga tgacccagtc tccatcctcc ctgtctgcat ctgtaggaga ccgtgtcacc | 60 |
| atcacttgcc gggcaagtca gtggattggt gcggagttaa attggtatca gcagaaacca | 120 |
| gggaaagccc ctaagctcct gatctattgg atgtccgtgt tgcaaagtgg ggtcccatca | 180 |
| cgtttcagtg gcagtggatc tgggacagat ttcactctca ccatcagcag tctgcaacct | 240 |
| gaagattttg ctacgtacta ctgtcaacag acttcttttt ttcctattac gttcggccaa | 300 |
| gggaccaagg tggaaatcaa acgggc | 326 |

<210> SEQ ID NO 273
<211> LENGTH: 326
<212> TYPE: DNA
<213> ORGANISM: Homo sapiens

<400> SEQUENCE: 273

| | |
|---|---:|
| gacatccaga tgacccagtc tccatcctcc ctgtctgcct ctgtaggaga ccgtgtcgcc | 60 |
| atcacttgcc gggcaagtca ggatattcgg acgcttttag cttggtacca gcagaaacca | 120 |
| gggaaagccc ctatgctcct gatctattgg gcttccgagt tgcaaagtgg ggtcccatca | 180 |
| cgtttcagtg gcagtggatc tgggacagat ttcactctca ccatcagcag tctgcaacct | 240 |
| gaagattttg ctacgtacta ctgtcaacag tctctttctt ggccttcgac gttcggccaa | 300 |

```
gggaccaagg tggaaatcaa acgggc                                          326

<210> SEQ ID NO 274
<211> LENGTH: 325
<212> TYPE: DNA
<213> ORGANISM: Homo sapiens

<400> SEQUENCE: 274
acatccagat gacccagtct ccatcctccc tgtctgcatc tgtaggagac cgtgtcacca      60
tcacttgccg ggcaagtcag tatattgggg tgagtttaga ttggtaccag cagaaaccag    120
ggaaagcccc taagctcctg atctattata gttccatgtt gcaaagtggg gtcccatcac    180
gtttcagtgg cagtggatct gggacagatt tcactctcac catcagcagt ctgcaacctg    240
aagattttgc tacgtactac tgtcaacagt attatactgt tcctgatacg ttcggccaag    300
ggaccaaggt ggaaatcaaa cgggc                                          325

<210> SEQ ID NO 275
<211> LENGTH: 326
<212> TYPE: DNA
<213> ORGANISM: Homo sapiens

<400> SEQUENCE: 275
gacatccaga tgacccagtc tccatcctcc ctgtctgcat ctgtaggaga ccgtgtcacc      60
atcacttgcc gggcaagttg gccgattggt gatcgtttaa attggtacca gcagaaacca    120
gggaaagccc ctaagctcct gatcgcttgg gtttccgttt gcaaagtggg ggtcccatca    180
cgtttcagtg gcagtggatc tgggacagat tcactctca ccatcagcag tctgcaacct    240
gaagattttg ctacgtacta ctgtgggcag ttggggggtg ggcctcggac gttcggccaa    300
gggaccaagg tggaaatcaa acgggc                                          326

<210> SEQ ID NO 276
<211> LENGTH: 326
<212> TYPE: DNA
<213> ORGANISM: Homo sapiens

<400> SEQUENCE: 276
gacatccaga tgacccagtc tccatcctcc ctgtctgcat ctgtaggaga ccgtgtctcc      60
atcacttgcc gggcaagtca gtttattggg tgggagttag cttggtacca gcagaaacca    120
gggaaagccc ctatgctcct gatctatccg tattccacgt tgcaaagtgg ggtcccatca    180
cgtttcagtg gcagtggatc tgggacagat tcactctca ccatcagcag tctgcaacct    240
gaagattttg ctacgtacta ctgtcaacag ctggctggtt ttccttatac gttcggccaa    300
gggaccaagg tggaaatcaa acgggc                                          326

<210> SEQ ID NO 277
<211> LENGTH: 326
<212> TYPE: DNA
<213> ORGANISM: Homo sapiens

<400> SEQUENCE: 277
gacatccaga tgacccagtc tccatcctcc ctgtctgcat ctgtaggaga ccgtgtcacc      60
atcacttgcc gggcaagtca gcctattggt gatcgtttat cttggtacca gcagaaacca    120
gggaaagccc ctaagctcct gatctatttt gtgtcccagt tgcaaagtgg ggtcccatca    180
cgtttcagtg gcagtggatc tgggacagat tcactctca ccatcagcag tctgcaacct    240
```

```
gaagattttg ctacgtacta ctgtcaacag agtcatccta atcctaagac gtttggccaa    300
gggaccaagg tggaaatcaa acgggc                                         326

<210> SEQ ID NO 278
<211> LENGTH: 326
<212> TYPE: DNA
<213> ORGANISM: Homo sapiens

<400> SEQUENCE: 278
gacatccaga tgacccagtc tccatcctcc ctgtctgcat ctgtaggaga cggtgtcacc     60
atcacttgcc gggcaagtca gtggattggg gtggagttaa gttggtatca gcagaaacca    120
gggaaagccc ctaagctcct gatctattgg ggttccgagt tgcaaagtgg ggtcccatca    180
cgtttcagtg gcagtggatc tgggacagat ttcactctca ccatcagcag tctgcaacct    240
gaagattttg ctacgtacta ctgtcaacag ttggcgttac ctccttttac gttcggccaa    300
gggaccaagg tggaaatcaa acgggc                                         326

<210> SEQ ID NO 279
<211> LENGTH: 326
<212> TYPE: DNA
<213> ORGANISM: Homo sapiens

<400> SEQUENCE: 279
gacatccaga tgacccagtc tccatcctcc ctgtctgcat ctgtaggaga ccgtgtcacc     60
atcacttgcc gggcaagtca ggagatcggg gctagtttag agtggtacca gcagaaacca    120
gggaaagccc ctaagctcct gatctattgg gcttccgtgt tgcaaagtgg ggtcccatca    180
cgtttcagtg gcagtggatc tgggacagat ttcactctca ccatcagcag tctgcaacct    240
gaagattttg ctacgtacta ctgtcaacag atgcatcata ctccttttac gttcggccaa    300
gggaccaagg tggaaatcaa acgggc                                         326

<210> SEQ ID NO 280
<211> LENGTH: 326
<212> TYPE: DNA
<213> ORGANISM: Homo sapiens

<400> SEQUENCE: 280
gacatccaga tgacccaatc tccatcctcc ctgtccgcat ctgtaggaga ccgtgtcacc     60
atcacttgcc gggcaagtca gcatattggg cagttttaa gttggtacca gcagaagcca    120
gggaaagccc ctaagctcct gatctatttg gcttccaggt tgcaaagtgg ggtcccatca    180
cgtttcagtg gtagtggatc tgggacagat ttcactctca ccatcagcag tctgcaacct    240
gaagattttg ctacgtacta ctgtcaacag gttgatagga ttcctgttac gttcggccaa    300
gggaccaagg tggaaatcaa acgggc                                         326

<210> SEQ ID NO 281
<211> LENGTH: 326
<212> TYPE: DNA
<213> ORGANISM: Homo sapiens

<400> SEQUENCE: 281
gacatccaga tgacccagtc tccatcctcc ctgtctgcat ctgtaggaga ccgtgtcacc     60
atcacttgcc gggcaagtca ggggattgat cattttttat cgtggtacca gcagaaacca    120
gggaaagccc ctaagctcct gatctatttt gcgtccacgt tgcaaagtgg ggtcccatca    180
cgtttcagtg gcagtggatc tgggacagat ttcactctca ccatcagcag tctgcaacct    240
```

```
gaagattttg ctacgtacta ctgtcaacag aatgcgagta ttcctattac gttcggccaa    300
gggaccaagg tggaaatcaa acgggc                                         326

<210> SEQ ID NO 282
<211> LENGTH: 326
<212> TYPE: DNA
<213> ORGANISM: Homo sapiens

<400> SEQUENCE: 282
gacatccaga tgacccagtc tccatcctcc ctgtctgcat ctgtaggaga ccgtgtcacc     60
atcacttgcc gggcaagtca gaatattggt actaatttaa agtggtatca gcagaaacca    120
gagaaagccc ctaagctcct gatctattat gggtcccttt tgcaaagtgg ggtcccatca    180
cgtttcagtg gcagtggatc tgggacagat ttcactctca ccatcagcag tctgcaacct    240
gaagattttg ctacgtacta ctgtcaacag gattatgatt ttccttatac gttcggccaa    300
gggaccaagg tggaaatcaa acgggc                                         326

<210> SEQ ID NO 283
<211> LENGTH: 326
<212> TYPE: DNA
<213> ORGANISM: Homo sapiens

<400> SEQUENCE: 283
gacatccaga tgacccagtc tccatcttcc ctgtctgcat ctgtaggaga ccgtgtctcc     60
atcacttgcc gggcaagtca gtggattggg ggagagttaa attggtacca gcagaaacca    120
gggaaagccc ctaagctcct gatctattgg gtttccacgt tgcaaagtgg ggtcccatca    180
cgtttcagtg gcagtggatc tgggacagat ttcactctca ccatcagcag tctgcaacca    240
gaagattttg ctacgtacta ctgtcaacag attgcgcggt atcctgcgac gttcggccaa    300
gggaccaagg tggaaatcaa acgggc                                         326

<210> SEQ ID NO 284
<211> LENGTH: 326
<212> TYPE: DNA
<213> ORGANISM: Homo sapiens

<400> SEQUENCE: 284
gacatccaga tgacccagtc tccatcctcc ctgtctgcat ctgtaggaga ccgtgtcacc     60
atcacttgcc gggcaagtca gaatattggt gtgaatttaa tttggtacca gcagaaacca    120
gggaaagccc ctaggctcct gatctatttt tcttcccttt tgcaaagtgg ggtcccatca    180
cgtttcagtg gcagtggatc tgggacagat ttcactctca ccatcagcag tctgcaacct    240
gaagattttg ctacgtacta ctgtcaacag gattatgatg ttcctcagac gttcggccaa    300
gggaccaagg tggaaatcaa acgggc                                         326

<210> SEQ ID NO 285
<211> LENGTH: 326
<212> TYPE: DNA
<213> ORGANISM: Homo sapiens

<400> SEQUENCE: 285
gacatccaga tgacccagtc tccatcctcc ctgtctgcat ctgtaggaga ccgtgtcacc     60
atcacttgcc gggcaagtca gaatattggg agtgggttac attggtacca gcagaaacca    120
gggaaagccc ctaagctcct gatcgtttct tggtccggtt tgcaaagtgg ggtcccatca    180
```

```
cgtttcagtg gcagtggatc tgggacagat ttcactctca ccatcagcag tctgcaacct      240
gaagattttg ctacgtacta ctgtggtcag gatgtgttgg gtcctcctac gttcggccaa      300
gggaccaagg tggaaatcaa acgggc                                           326
```

<210> SEQ ID NO 286
<211> LENGTH: 326
<212> TYPE: DNA
<213> ORGANISM: Homo sapiens

<400> SEQUENCE: 286

```
gacatccaga tgacccagtc tccatcctcc ctgtctgcat ctgtaggaga ccgtgtcacc      60
atcacttgcc gggcaagtca gtggattggg gcgtcgttag cttggtacca gcagaaacca     120
gggaaagccc ctaagctcct gatctatttt atgtccgagt tgcaaagtgg ggtcccatca     180
cgttttagtg gcagtggatc tgggacagat ttcactctca ccatcagcag tctgcaacct     240
gaagattttg ctacgtacta ctgtcaacag gattatggtt atcctactac gttcggccaa     300
gggaccaagg tggaaatcaa acgggc                                           326
```

<210> SEQ ID NO 287
<211> LENGTH: 326
<212> TYPE: DNA
<213> ORGANISM: Homo sapiens

<400> SEQUENCE: 287

```
gacatccaga tgacccagtc tccatcctcc ctgtctgcat ctgtaggaga ccgtgtcacc      60
atcacttgcc gggcaagtca gtggattggt gttaatttat tgtggtacca gcagaaacca     120
gggaaagccc ctaagctcct gatctattat ggttccattt tgcaaagtgg ggtcccatca     180
cgtttcagtg gcagtggatc tgggacagat ttcactctca ccatcagcag tctgcaacct     240
gaagattttg ctacgtacta ctgtcaacag gattatcatg ggccttatac gttcggccaa     300
gggaccaagg tggaaatcaa acgggc                                           326
```

<210> SEQ ID NO 288
<211> LENGTH: 326
<212> TYPE: DNA
<213> ORGANISM: Homo sapiens

<400> SEQUENCE: 288

```
gacatccaga tgacccagtc tccatcctcc ctgtctgcat ctgtaggaga ccgtgtcacc      60
atcacttgcc ggacaagtca ggatattggg tctctgttat cgtggtacca gcagaaacca     120
gggaaagccc ctaagctcct gatctatatg gtttccatgt tgcaaagtgg ggtcccatca     180
cgtttcagtg gcagtggatc tgggacagat ttcactctca ccatcagcag tctgcaacct     240
gaagattttg ctacgtacta ctgtcaacat aattcgtggt atcctattac gttcggccaa     300
gggaccaagg tggaaatcaa acgggc                                           326
```

<210> SEQ ID NO 289
<211> LENGTH: 325
<212> TYPE: DNA
<213> ORGANISM: Homo sapiens

<400> SEQUENCE: 289

```
acatccagat gacccagtct ccatcctccc tgtctgcatc tgtaggagac cgtgtcacca      60
tcacttgccg ggcaagtcag tttatttata ctatgttaaa ttggtaccag cagaaaccag     120
ggaaagcccc taagctcctg atctatagga cgtcctggtt gcaaagtggg gtcccatcac     180
```

```
gtttcagtgg cagtggatct gggacagatt tcactctcac catcagcagt ctgcaacctg      240
aagattttgc tacgtactac tgtcaacagg attatgcgtc gccttttacg ttcggccaag      300
ggaccaaggt ggaaatcaaa cgggc                                            325
```

<210> SEQ ID NO 290
<211> LENGTH: 326
<212> TYPE: DNA
<213> ORGANISM: Homo sapiens

<400> SEQUENCE: 290

```
gacatccaga tgacccagtc tccatcctcc ctgtctgcat ctgttggaga ccgtgtcacc      60
atcacttgcc gggcaagtca gtggattggt attttgttag attggtacca gcagaaacca      120
ggggaagccc ctaagctcct gatctattat gcttcctttt tgcaaagcgg ggtcccatca      180
cgtttcagtg gcagtggatt tgggacagat ttcactctca ccatcagcag tctgcaacct      240
gaagattttg ctacgtacta ctgtcaacag gctaatccgg cgcctctgac gttcggccaa      300
gggaccaagg tggaaatcaa acgggc                                           326
```

<210> SEQ ID NO 291
<211> LENGTH: 326
<212> TYPE: DNA
<213> ORGANISM: Homo sapiens

<400> SEQUENCE: 291

```
gacatccaga tgacccagtc tccatcctcc ctgtctgcat ctgtaggaga ccgtgtcacc      60
atcacttgcc gggcaagtca gtggattggt attttgatag attggtacca gcagaaacca      120
ggggaagccc ctaagctcct gatctattat gcttcctttt tgcaaagtgg ggtcccatca      180
cgtttcagtg gcagtggatc tgggacagat ttcactctca ccatcagcag tctgcaacct      240
gaagattctg ctacgtacta ctgtcaacag gctaatccgg cgcctctgac gttcggccaa      300
gggaccaagg tggaaatcaa acgggc                                           326
```

<210> SEQ ID NO 292
<211> LENGTH: 326
<212> TYPE: DNA
<213> ORGANISM: Homo sapiens

<400> SEQUENCE: 292

```
gacatccagt tgacccagtc tccatcctcc ctgtctgcat ctgtaggaga ccgagtcacc      60
atcacttgcc gggcaagtca gtggattggt attttgttag attggtacca gcagaaacca      120
ggggaagccc ctaagctcct gatctattat gcttcctttt tgcaaagtgg ggtcccatca      180
cgtttcagtg gcagtggatc tgggacagat ttcactctca ccatcaacag tctgcaacct      240
gaagattttg ctacgtacta ctgtcaacag gctaatccgg cgcctctgac gttcggccaa      300
gggaccaagg tggaaatcaa acgggc                                           326
```

<210> SEQ ID NO 293
<211> LENGTH: 326
<212> TYPE: DNA
<213> ORGANISM: Homo sapiens

<400> SEQUENCE: 293

```
gacatccaga tgacccagtc tccatccttc ctgtctgcat ctgtaggaga ccgtgtcacc      60
atcacttgcc gggcaagtca gtggattggt attttgttag attggtacca gcagaaacca      120
```

| ggggaagccc ctaagctcct gatctattat gcttcctttt tgcaaagtgg ggtcccatca | 180 |
| cgtttcagtg gcagtggatc tgggacagat ttcactctca ccatcagcag tctgcaacct | 240 |
| gaagattttg ctacgtacta ctgtcaacag gctaatccgg cgcctctgac gttaggccaa | 300 |
| gggaccaagg tggaaatcaa acgggc | 326 |

<210> SEQ ID NO 294
<211> LENGTH: 326
<212> TYPE: DNA
<213> ORGANISM: Homo sapiens

<400> SEQUENCE: 294

| gacatccaga tgacccagtc tccatcctcc ctgtctgcat ctgtaggaga ccgtgtcacc | 60 |
| atcacttgcc gggcaagtca gtggattggt attttggtag attggtacca gcagaaacca | 120 |
| ggggaagccc ctaagctcct gatctattat gcttcctttt tgcaaagtgg ggtcccatca | 180 |
| cgtttcagtg gcagtggatc tgggacagat ttcactctca ccatcagcag tctgcaacct | 240 |
| gaagattttg ctacgtacta ctgtcaacag gctaatccgg cgcctctgag gttcggccaa | 300 |
| gggaccaagg tggaaatcaa acgggc | 326 |

<210> SEQ ID NO 295
<211> LENGTH: 326
<212> TYPE: DNA
<213> ORGANISM: Homo sapiens

<400> SEQUENCE: 295

| gacatccaga tgacccagtc tccatcctcc ctgtctgcat ctgtaggaga ccgtgtcacc | 60 |
| atcacttgcc gggcaagtca gtggattggt attttgttag attggtacca gcagaaacca | 120 |
| ggggaagccc ctaagctcct gatctattat gcttcctttt tgcaaaatgg ggtcccatca | 180 |
| cgtttcagtg gcagtggatc tgggacagat ttcactctca ccatcagcag tctgcaacct | 240 |
| gaagattttg ctacgtacta ctgtcaacag gctaatccgg cgcctctgac gttcggccaa | 300 |
| gggaccaagg tggaaatcaa acgggc | 326 |

<210> SEQ ID NO 296
<211> LENGTH: 326
<212> TYPE: DNA
<213> ORGANISM: Homo sapiens

<400> SEQUENCE: 296

| gacatccaga tgatccagtc tccatcctcc ctgtctgcat ctgtaggaga ccgtgtcacc | 60 |
| atcacttgcc gggcaagtca gtggattggt attttgttag attggtacca gcagaaacca | 120 |
| ggggaagccc ctaagctcct gatctattat gcttcctttt tgcaaagtgg ggtcccatca | 180 |
| cgtttcagtg gcagtggatc tgggacagat ttcactctca ccatcagtaa tctgcaacct | 240 |
| gaagattttg ctacgtacta ctgtcaacag gctaatccgg cgcctctgac gttcggccaa | 300 |
| gggaccaagg tggaaatcaa acgggc | 326 |

<210> SEQ ID NO 297
<211> LENGTH: 326
<212> TYPE: DNA
<213> ORGANISM: Homo sapiens

<400> SEQUENCE: 297

| gacatccaga tgacccagtc tccatcctcc ctgtctgcat ctgtgggaga ccgtgtcacc | 60 |
| atcacttgcc gggcaagtca gtggattggt attttggtag attggtacca gcagaaacca | 120 |

```
ggggaagccc ctaagctcct gatctattat gcttcctttt tgcaaagtgg ggtcccatca    180
cgtttcagcg gcagtggatt tgggacagat ttcactctca ccatcagcag tctgcatcct    240
gaagattttg ctacgtacta ctgtcaacag gctaatccgg cgcctctgac gttcggccaa    300
gggaccaagg tggaaatcaa acgggc                                         326

<210> SEQ ID NO 298
<211> LENGTH: 326
<212> TYPE: DNA
<213> ORGANISM: Homo sapiens

<400> SEQUENCE: 298
gacatccaga tgacccagtc tccatcctcc ctgtctgcat ctgtaggaga ccgtgtcacc     60
atcacttgcc gggcaagtca gtggattggt attttgttag attggtacca gcagaaacca    120
ggggaagccc ctaagctcct gatctattat gcttcctttt tgcaaagtgg ggtcccatca    180
cgtttcagtg gcagtggatc tgggacagat ttcactctca ccatcagcaa tctgcaacct    240
gaagattttg ctacgtacta ctgtcaacag gctgatccgg cgcctctgac gttcggccaa    300
gggaccaagg tggaaatcaa acgggc                                         326

<210> SEQ ID NO 299
<211> LENGTH: 326
<212> TYPE: DNA
<213> ORGANISM: Homo sapiens

<400> SEQUENCE: 299
gacatccaga tgacccagtc tccatcttcc ctgtctgcat ctgtaggaga cagtgtcacc     60
atcacttgcc gggcaagtca gtggattggt attttgttag attggtacca gcagaaacca    120
ggggaagccc ctaagctcct gatctattat gcttcctttt tgcaaagtgg ggtcccatca    180
cgtttcagtg gcagtggatc tgggacagat ttcactctca ccatcagcag tctgcaacct    240
gaagattttg ctacgtacta ctgtcaacag gctaatccgg cgcctctgac gttcggccaa    300
gggacaaagg tggaaatcaa acgggc                                         326

<210> SEQ ID NO 300
<211> LENGTH: 326
<212> TYPE: DNA
<213> ORGANISM: Homo sapiens

<400> SEQUENCE: 300
gacatccaga tgacccagta tccatcctcc ctgtctgcat ctgtaggaga ccgtgtcacc     60
atcacttgcc gggcaagtca gtggattggt attttgttag attggtacca gcagaaacca    120
ggggaagccc ctaagctcct gatctattat gcctcctttt tgcagagtgg ggtcccatca    180
cgtttcagtg gcagtggatc tgggacagat ttcactctca ccatcagcag tctgcaacct    240
gaagattttg gtacgtacta ctgtcaacag gctaatccgg cgcctctgac gttcggccaa    300
gggaccaagg tggaaatcaa acgggc                                         326

<210> SEQ ID NO 301
<211> LENGTH: 326
<212> TYPE: DNA
<213> ORGANISM: Homo sapiens

<400> SEQUENCE: 301
gacatccaga tgacccagtc tccatcctcc ctgtatgcat ctgtaggaga ccgtgtcacc     60
```

```
atcacttgcc gggcaagtca gtggattggt attttgttag attggtacca gcagaaacca    120
ggggaagccc ctaagctcct gatctattat gcttcctttt tgcaaagtgg ggtcccatca    180
cgtttcagtg gcagtggatc tgggacagat ttcactctca ccatcagcag tctgcaacct    240
gaagattttg ctacgtacta ctgtcaacag gctaatccgg cgcctctgac gttcggccaa    300
gggaccaagg tggaaatcaa acgggc                                         326
```

<210> SEQ ID NO 302
<211> LENGTH: 326
<212> TYPE: DNA
<213> ORGANISM: Homo sapiens

<400> SEQUENCE: 302

```
gacatccaga tgacccagtc tccatcctcc ctgtctgcat ctgtaggaga ccgtgtcacc     60
atcacttgcc gggcaagtca gtggattggt attttgttag attggtacca gcagaaacca    120
ggggaagccc ctaagctcct gatctattat gcttcctttt tgcaaagtgg ggtcccatca    180
cgtttcagtg gcagtggatc tgggacagat ttcactctca ccatcagcag tctgcaacct    240
gaagattttg ctacgtacta ctgtcaaccg gctaatccgg cacctctgac gttcggccaa    300
gggaccaagg tggaaatcaa acgggc                                         326
```

<210> SEQ ID NO 303
<211> LENGTH: 326
<212> TYPE: DNA
<213> ORGANISM: Homo sapiens

<400> SEQUENCE: 303

```
gacatccaga tgacccagtc tccatcctcc ctgtctgcat ctgtaggaga ccgtgtcacc     60
atcacttgcc ggtcaagtcg gtggattggt attttgttag attggtacca gcagaaacca    120
ggggaagccc ctaagctcct gatctattat gcttcctttt tgcaaagtgg ggtcccctca    180
cgtttcagtg gcagtgggtc tgggacagat ttcactctca ccatcagcag tctgcaacct    240
gaagatgttg ctacgtacta ctgtcaacag gctaatccgg cgcctctgac gttcggccaa    300
gggaccaagg tggaaatcaa acgggc                                         326
```

<210> SEQ ID NO 304
<211> LENGTH: 326
<212> TYPE: DNA
<213> ORGANISM: Homo sapiens

<400> SEQUENCE: 304

```
gacatccaga tgacccagtc tccatcctcc ctgtctgcat ctgtaggaga ccgtgtcacc     60
atcacttgcc gggcaagtca gtggatcggt attttggtag attggtacca gcagaaacca    120
ggggaagccc ctaagctcct gatctattat gcttcctttt tgcaaagtgg ggtcccatca    180
cgtttcagtg gcagtggatc aggacagat ttcactctca ccatcagcag tctgcaacct     240
gaagattttg ctacgtacta ctgtcaacag gctaatccgg cgcctctgac gttcggccaa    300
gggaccaagg tggaaatcaa acgggc                                         326
```

<210> SEQ ID NO 305
<211> LENGTH: 326
<212> TYPE: DNA
<213> ORGANISM: Homo sapiens

<400> SEQUENCE: 305

```
gacatccagt tgacccagtc tccatcctcc ctgtctgcat ctgtaggaga ccgtgtcacc     60
```

```
atcacttgcc gggcaagtca gtggattggt attttgttag attggtacca gcagaaacca    120
ggggaagccc ctaagctcct gatctattat gcttcctttt tgcaaagtgg ggtcccatca    180
cgtttcagtg gcagtggatc tgggacagat ttcactctca ccatcagcag tctgcaacct    240
gaagattttg ctacgtacta ttgtcaacag gctaatccgg cgcctctgac gttcggccaa    300
gggaccaagg tggaaatcaa acgggc                                         326
```

<210> SEQ ID NO 306
<211> LENGTH: 326
<212> TYPE: DNA
<213> ORGANISM: Homo sapiens

<400> SEQUENCE: 306

```
gacatccaga tgacccagtc tccaacctcc ctgtctgcat ctgtaggaga ccgtgtcacc     60
atcacttgcc gggcaagtca gtggattggt aatttgttag attggtacca gcagaaacca    120
ggggaagccc ctaagctcct gatctattat gcttcctttt tgcaaagtgg ggtcccatca    180
cgtttcagtg gcggtggatt tgggacagat ttcactctca ccatcagcag tctgcaacct    240
gaagattttg ctacgtacta ctgtcaacag gctaatccgg cgcctctgac gttcggccaa    300
gggaccaagg tggaaatcaa acgggc                                         326
```

<210> SEQ ID NO 307
<211> LENGTH: 326
<212> TYPE: DNA
<213> ORGANISM: Homo sapiens

<400> SEQUENCE: 307

```
gacatccaga tgacccagtc tccatcctcc ctgtctgcat ctgtaggaga ccgtgtcacc     60
atcacttgcc gggcaagtca gtggattggt attttgttag attggtacca gcagaaacca    120
ggggaagccc ctaagctcct gatctattat gcttcctttt tgcaaagtgg ggtcccatca    180
cgtttcagtg gcagtggatc tgggacagat ttcactctca ccatcagcag tctgcaacct    240
gaagattttg ctacgtacta ctgtcaacag gctaatccgg cgcctccgac gttcggccaa    300
gggaccaagg tggaaatcaa acgggc                                         326
```

<210> SEQ ID NO 308
<211> LENGTH: 326
<212> TYPE: DNA
<213> ORGANISM: Homo sapiens

<400> SEQUENCE: 308

```
gacatccaga tgacccagtc tccatcctcc ctgtctgcat ctgtaggaga ccgtgtcacc     60
atcacttgcc gggcaagtca gtggattggt attttgttag attggtacca gcagaaacca    120
ggggaagacc ctaagctcct gatctattat gcttcctttt tgcaaagtgg ggtcccatca    180
cgtttcagtg gcagtggatc tgggacagat ttcactctca ccatcagcag tctgcaacct    240
gaagattttg ctacgtacta ctgccaacag gctaatccgg cgcctctgac gttcggccaa    300
gggaccaagg tggaaatcaa acgggc                                         326
```

<210> SEQ ID NO 309
<211> LENGTH: 326
<212> TYPE: DNA
<213> ORGANISM: Homo sapiens

<400> SEQUENCE: 309

```
gacatccaga tgacccagtc tccaacctcc ctgtctgcat ctgtaggaga ccgtgtcacc        60
atcacctgca gggcaagtca gtggattggt attttgttag attggtacca gcagaaacca      120
ggggaagccc ctaagctcct gatctattat gcttcctttt tgcaaagtgg ggtcccatca      180
cgtttcagtg gcagtggatc tgggacagat ttcactctca ccatcagcag tctgcaacct      240
gaagattttg ctacgtacta ctgtcaacag gctaatccgg cgcctctgac gttcggccaa      300
gggaccaagg tggaaatcaa acgggc                                           326
```

<210> SEQ ID NO 310
<211> LENGTH: 326
<212> TYPE: DNA
<213> ORGANISM: Homo sapiens

<400> SEQUENCE: 310

```
gacatccaga tgacccagtc tccatcctcc ctgtctgcat ctgtaggaga ccgtgtcacc        60
atcacttgcc gggcaagtca gtggattggt attttggtag attggtacca gcagaaacca      120
ggggaagccc ctaagctcct gatctattat ggttcctttt tgcaaagtgg ggtcccatca      180
cgtttcagtg gcagtggatc tgggacagat ttcactctca ccatcagcag tctgcaacct      240
gaagattttg ctacgtacta ctgtcaacag gctaatccgg cgcctctgac gttcggccaa      300
gggaccaagg tggaaatcaa acgggc                                           326
```

<210> SEQ ID NO 311
<211> LENGTH: 326
<212> TYPE: DNA
<213> ORGANISM: Homo sapiens

<400> SEQUENCE: 311

```
gacatccaga tgacccagtc tccatcctcc ctgtctgcat ctgtaggaga ccgtgtcacc        60
atcacttgcc gggcaagtca gtggattggt attttgttag attggtacca gcagaaacca      120
ggggaagccc ctaagctcct gatctattat gcttcctttt tgcaaagtgg ggtcccatca      180
cgtttcagtg gcagtggatc tgggacagat ttcactctca ccatcagcag tctgcaacct      240
gaagattttg ctacgtacta ctgtcaacag gctaatccgg cgcctctgac gttcggccaa      300
gggaccaagg tggaaatcag acgggc                                           326
```

<210> SEQ ID NO 312
<211> LENGTH: 326
<212> TYPE: DNA
<213> ORGANISM: Homo sapiens

<400> SEQUENCE: 312

```
gacatccaga tgacccagtc tccatcctcc ctgtctgcat ctgtaggaga ccgtgtcacc        60
atcacttgcc gggcaagtca gtggattggt attttgttag attggtacca gcagaaacca      120
ggggaagccc ctaagctcct gatctattat gcttcctttt tgcaaagtgg ggtcccatca      180
cgtttcagtg gcagtggata tgggacagat ttcactctca ccatcagcag tttgcaacct      240
gaagattttg ctacgtacta ctgccaacag gctaatccgg cgcctctgac gttcggccaa      300
gggaccaagg tggaaatcaa acgggc                                           326
```

<210> SEQ ID NO 313
<211> LENGTH: 326
<212> TYPE: DNA
<213> ORGANISM: Homo sapiens

<400> SEQUENCE: 313

```
gacatccaga tgacccagtc tccatcctcc ctgtctgcat ctgtaggaga ccgtgtcacc      60
atcacttgcc gggcaagtca gtggattggt attttgttag attggtatca gcagaaacca    120
ggggaagccc ctaagctcct gatctattat gcttcctttt tgcaaagtgg ggtcccatca    180
cgtttcagtg gcagtggatc tgggacagat ttcactctca ccatcagcag tctgcaacct    240
gaagattttg ctacgtacta ctgtcaacag gctaatccgg cgcctctgac gttcggccaa    300
gggaccaagg tggaaatgaa acgggc                                         326

<210> SEQ ID NO 314
<211> LENGTH: 326
<212> TYPE: DNA
<213> ORGANISM: Homo sapiens

<400> SEQUENCE: 314
gacatccaga tgacccagtc tccatcctcc ctgtctgcat ctgtaggaga ccgtgtcacc      60
atcacttgcc gggcaagtca gtggattggt attttgttag attggtacca gcagaaacca    120
ggggaagacc ctaagctcct gatctattat gcttcctttt tgcaaagtgg ggtcccatca    180
cgtttcagtg gcagcggatc tgggacagat ttcactctca ccatcagcag tctgcaacct    240
gaagattttg ctacgtacta ctgtcaacag gctaatccgg cgcctctgat gttcggccaa    300
gggaccaagg tggaaatcaa acgggc                                         326

<210> SEQ ID NO 315
<211> LENGTH: 326
<212> TYPE: DNA
<213> ORGANISM: Homo sapiens

<400> SEQUENCE: 315
gacatccaga tgacccagtc tccatcctcc ctgtctgcat ctgtaggaga ccgtgtcacc      60
atcacttgcc gggcaagtca gtggattggt attttgttag attggtacca gcagaaacca    120
gggaaagccc ctaagctcct gatctattat gcttcctttt tgcaaagtgg ggtcccatca    180
cgtttcagtg gcagtggatc tgggacagat ttcactctca ccatcagcag tctgcaacct    240
gaagattttg ctacgtacta ctgtcaacag gctaatccgg cgcctctgac gttcggccaa    300
gggaccaagg tggaaatcaa acgggc                                         326

<210> SEQ ID NO 316
<211> LENGTH: 326
<212> TYPE: DNA
<213> ORGANISM: Homo sapiens

<400> SEQUENCE: 316
gacatccaga tgacccagtc tccatcctcc ctgtctgcat ctgtaggaga ccgtgtcacc      60
atcacttgcc gggcaagtca gtggattggt attttggtag attggtacca gcagaaacca    120
gggaaagccc ctaagctcct gatctattat gcttcctttt tgcaaagtgg ggtcccatca    180
cgtttcagtg gcagtggatc tgggacagat ttcactctca ccatcagcag tctgcaacct    240
gaagattttg ctacgtacta ctgtcaacag gctaatccgg cgcctctgac gttcggccaa    300
gggaccaagg tggaaatcaa acgggc                                         326

<210> SEQ ID NO 317
<211> LENGTH: 326
<212> TYPE: DNA
<213> ORGANISM: Homo sapiens
```

<400> SEQUENCE: 317

```
gacatccaga tgacccagtc tccatcctcc ctgtctgcat ctgtaggaga ccgtgtcacc      60
atcacttgcc gggcaagtca gtggattggt attttgttag attggtacca gcagaaacca     120
gggaaagccc ctaagctcct gatctattat gcttcctttt tgcaaagtgg ggtcccatca     180
cgtttcagtg gcagtggatc tgggacagat ttcactctca ccatcagcag tctgcaacct     240
gaagattttg ctacgtacta ctgtcaacag gctaatccgg cgcctctgag gttcggccaa     300
gggaccaagg tggaaatcaa acgggc                                          326
```

<210> SEQ ID NO 318
<211> LENGTH: 326
<212> TYPE: DNA
<213> ORGANISM: Homo sapiens

<400> SEQUENCE: 318

```
gacatccaga tgacccagtc tccatcctcc ctgtctgcat ctgtaggaga ccgtgtcacc      60
atcacttgcc gggcaagtca gtggattggt attttgatag attggtacca gcagaaacca     120
gggaaagccc ctaagctcct gatctattat gcttcctttt tgcaaagtgg ggtcccatca     180
cgtttcagtg gcagtggatc tgggacagat ttcactctca ccatcagcag tctgcaacct     240
gaagattttg ctacgtacta ctgtcaacag gctaatccgg cgcctctgac gttcggccaa     300
gggaccaagg tggaaatcaa acgggc                                          326
```

<210> SEQ ID NO 319
<211> LENGTH: 326
<212> TYPE: DNA
<213> ORGANISM: Homo sapiens

<400> SEQUENCE: 319

```
gacatccaga tgacccagtc tccatcctcc ctgtctgcat ctgtaggaga ccgtgtcacc      60
atcacttgcc gggcaagtca gtggattggt aatttggtag attggtacca gcagaaacca     120
gggaaagccc ctaagctcct gatctattat gcttcctttt tgcaaagtgg ggtcccatca     180
cgtttcagtg gcagtggatc tgggacagat ttcactctca ccatcagcag tctgcaacct     240
gaagattttg ctacgtacta ctgtcaacag gctaatccgg cgcctctgac gttcggccaa     300
gggaccaagg tggaaatcaa acgggc                                          326
```

<210> SEQ ID NO 320
<211> LENGTH: 326
<212> TYPE: DNA
<213> ORGANISM: Homo sapiens

<400> SEQUENCE: 320

```
gacatccaga tgacccagtc tccatcctcc ctgtctgcat ctgtaggaga ccgtgtcacc      60
atcacttgcc gggcaagtca gtggattggt aatttggtag attggtacca gcagaaacca     120
gggaaagccc ctaagctcct gatctattat gcttcctttt tgcaaagtgg ggtcccatca     180
cgtttcagtg gcagtggatc tgggacagat ttcactctca ccatcagcag tctgcaacct     240
gaagattttg ctacgtacta ctgtcaacag gctaatccgg cgcctccgac gttcggccaa     300
gggaccaagg tggaaatcaa acgggc                                          326
```

<210> SEQ ID NO 321
<211> LENGTH: 326
<212> TYPE: DNA
<213> ORGANISM: Homo sapiens

<400> SEQUENCE: 321

| gacatccaga tgacccagtc tccatcctcc ctgtctgcat ctgtaggaga ccgtgtcacc | 60 |
| atcacttgcc gggcaagtca gtggattggt atcaacttag actggtacca gcagaaacca | 120 |
| gggaaagccc ctaagctcct gatctattat gcttcctttt tgcaaagtgg ggtcccatca | 180 |
| cgtttcagtg gcagtggatc tgggacagat ttcactctca ccatcagcag tctgcaaccg | 240 |
| gaagattttg ctacgtacta ctgtcaacag gctaatccgg cgcctctgac gttcggccaa | 300 |
| gggaccaagg tggaaatcaa acgggc | 326 |

<210> SEQ ID NO 322
<211> LENGTH: 326
<212> TYPE: DNA
<213> ORGANISM: Homo sapiens

<400> SEQUENCE: 322

| gacatccaga tgacccagtc tccatcctcc ctgtctgcat ctgtaggaga ccgtgtcacc | 60 |
| atcacttgcc gggcaagtca gaacattggc aacttgttag attggtacca gcagaaacca | 120 |
| gggaaagccc ctaagctcct gatctattat gcttcctttt tgcaaagtgg ggtcccatca | 180 |
| cgtttcagtg gcagtggatt tgggacagat ttcactctca ccatcagcag tctgcaacct | 240 |
| gaagattttg ctacgtacta ctgtcaacag gctaatccgg cgcctctgac gttcggccaa | 300 |
| gggaccaagg tggaaatcaa acgggc | 326 |

<210> SEQ ID NO 323
<211> LENGTH: 326
<212> TYPE: DNA
<213> ORGANISM: Homo sapiens

<400> SEQUENCE: 323

| gacatccaga tgacccagtc tccatcctcc ctgtctgcat ctgtaggaga ccgtgtcacc | 60 |
| atcacttgcc gggcaagtca gtggattggt atcaacttag actggtacca gcagaaacca | 120 |
| gggaaagccc ctaggctcct gatctattat gcttcctttt tgcaaagtgg ggtcccatca | 180 |
| cgtttcagtg gcagtggatc tgggacagat ttcactctca ccatcagcag tctgcaacct | 240 |
| gaagattttg ctacgtacta ctgtcaacag gctaatccgg cgcctctgac gttcggccaa | 300 |
| gggaccaagg tggaaatcaa acgggc | 326 |

<210> SEQ ID NO 324
<211> LENGTH: 357
<212> TYPE: DNA
<213> ORGANISM: Homo sapiens

<400> SEQUENCE: 324

| gaggtgcagc tgttggagtc tggggggaggc ttggtacagc ctggggggtc cctgcgtctc | 60 |
| tcctgtgctg cctccggatt cacctttgct gagcagccga tgacttgggc cgccaggct | 120 |
| ccagggaagg gtctagagtg gtctcaagt atttctagtt ttggtgatct tacatactac | 180 |
| gcagactccg tgaagggccg gttcaccatc tcccgcgaca attccaagaa cacgctgtat | 240 |
| ctgcaaatga acagcctgcg tgccgaggac accgcggtat attactgtgc gaaaggtgtg | 300 |
| tatcggatta gtcggtttga ctactggggt cagggaaccc tggtcaccgt ctcgagc | 357 |

<210> SEQ ID NO 325
<211> LENGTH: 108
<212> TYPE: PRT

<213> ORGANISM: Homo sapiens

<400> SEQUENCE: 325

```
Asp Ile Gln Met Thr Gln Ser Pro Ser Ser Leu Ser Ala Ser Val Gly
1               5                   10                  15
Asp Arg Val Thr Ile Thr Cys Arg Ala Ser Gln Tyr Ile Gly Ala Glu
            20                  25                  30
Leu Ser Trp Tyr Gln Gln Lys Pro Gly Lys Ala Pro Lys Leu Leu Ile
        35                  40                  45
Tyr Trp Ile Ser Glu Leu Gln Ser Gly Val Pro Ser Arg Phe Ser Gly
    50                  55                  60
Ser Gly Ser Gly Thr Asp Phe Thr Leu Thr Ile Ser Ser Leu Gln Pro
65                  70                  75                  80
Glu Asp Phe Ala Thr Tyr Tyr Cys Gln Gln Ser Ser Asn Thr Pro Tyr
                85                  90                  95
Thr Phe Gly Gln Gly Thr Lys Val Glu Ile Lys Arg
            100                 105
```

<210> SEQ ID NO 326
<211> LENGTH: 108
<212> TYPE: PRT
<213> ORGANISM: Homo sapiens

<400> SEQUENCE: 326

```
Asp Ile Gln Met Thr Gln Ser Pro Ser Ser Leu Ser Ala Ser Val Gly
1               5                   10                  15
Asp Arg Val Thr Ile Thr Cys Arg Ala Ser Gln Tyr Ile Gly Ile Asn
            20                  25                  30
Leu Ile Trp Tyr Gln Gln Lys Pro Gly Lys Ala Pro Lys Leu Leu Ile
        35                  40                  45
Tyr Trp Ala Ser Val Leu Gln Ser Gly Val Pro Ser Arg Phe Ser Gly
    50                  55                  60
Ser Gly Ser Gly Thr Asp Phe Thr Leu Thr Ile Ser Ser Leu Gln Pro
65                  70                  75                  80
Glu Asp Phe Ala Thr Tyr Tyr Cys Gln Gln Ser Val Tyr Asp Pro Pro
                85                  90                  95
Thr Tyr Gly Gln Gly Thr Lys Val Glu Ile Lys Arg
            100                 105
```

<210> SEQ ID NO 327
<211> LENGTH: 108
<212> TYPE: PRT
<213> ORGANISM: Homo sapiens

<400> SEQUENCE: 327

```
Asp Ile Gln Met Thr Gln Ser Pro Ser Ser Leu Ser Ala Ser Val Gly
1               5                   10                  15
Asp Arg Val Thr Ile Thr Cys Arg Ala Ser Gln Asp Ile Phe Trp Leu
            20                  25                  30
Leu Ser Trp Tyr Gln Gln Lys Pro Gly Lys Ala Pro Thr Leu Leu Ile
        35                  40                  45
Tyr Ser Thr Ser Ile Leu Gln Ser Gly Val Pro Ser Arg Phe Ser Gly
    50                  55                  60
Ser Gly Ser Gly Thr Asp Phe Thr Leu Thr Ile Ser Ser Leu Gln Pro
65                  70                  75                  80
Glu Asp Phe Ala Thr Tyr Tyr Cys Gln Gln Tyr Tyr Leu Asp Pro Pro
                85                  90                  95
```

```
Thr Phe Ser Gln Gly Thr Lys Val Glu Ile Lys Arg
            100                 105

<210> SEQ ID NO 328
<211> LENGTH: 108
<212> TYPE: PRT
<213> ORGANISM: Homo sapiens

<400> SEQUENCE: 328

Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Phe Ile Gly Val Asn
             20                  25                  30

Leu Asn Trp Tyr Gln Gln Lys Pro Gly Lys Ala Pro Arg Leu Leu Ile
         35                  40                  45

Tyr Leu Ser Ser Ile Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Thr Tyr Asp Ile Pro Thr
                 85                  90                  95

Thr Phe Gly Gln Gly Thr Lys Val Glu Ile Lys Arg
            100                 105

<210> SEQ ID NO 329
<211> LENGTH: 108
<212> TYPE: PRT
<213> ORGANISM: Homo sapiens

<400> SEQUENCE: 329

Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Asn Ile Gly Ile Asn
             20                  25                  30

Leu Gln Trp Tyr Gln Gln Lys Pro Arg Lys Ala Pro Lys Leu Leu Ile
         35                  40                  45

Tyr Tyr Ala Ser Ile Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Asp Tyr Asp Thr Pro Phe
                 85                  90                  95

Thr Phe Gly Gln Gly Thr Lys Val Glu Ile Lys Arg
            100                 105

<210> SEQ ID NO 330
<211> LENGTH: 108
<212> TYPE: PRT
<213> ORGANISM: Homo sapiens

<400> SEQUENCE: 330

Asp Ile Gln Met Thr Gln Phe Pro Ser Ser Leu Ser Ala Ser Val Gly
  1               5                  10                  15

Asp Arg Val Thr Ile Thr Cys Arg Ala Ser Gln His Ile Glu Arg Trp
             20                  25                  30

Leu Asn Trp Tyr Gln Gln Lys Pro Gly Lys Ala Pro Lys Leu Leu Ile
         35                  40                  45
```

```
Tyr Arg Ser Ser Tyr Leu Gln Ser Gly Val Pro Ser Arg Phe Ser Gly
         50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Asp Ala Ile Leu Pro His
                 85                  90                  95

Thr Phe Gly Gln Gly Thr Lys Val Glu Ile Lys Arg
            100                 105
```

<210> SEQ ID NO 331
<211> LENGTH: 108
<212> TYPE: PRT
<213> ORGANISM: Homo sapiens

<400> SEQUENCE: 331

```
Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Gly Ile Gly Val Asn
                 20                  25                  30

Leu Gln Trp Tyr Gln Gln Lys Pro Gly Lys Ala Pro Lys Leu Leu Ile
             35                  40                  45

Tyr Phe Ser Ser Val Leu Gln Ser Gly Val Pro Ser Arg Phe Ser Gly
         50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Asp Phe Asp Phe Pro Gln
                 85                  90                  95

Thr Phe Gly Gln Gly Thr Lys Val Glu Ile Lys Arg
            100                 105
```

<210> SEQ ID NO 332
<211> LENGTH: 108
<212> TYPE: PRT
<213> ORGANISM: Homo sapiens

<400> SEQUENCE: 332

```
Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Asn Ile Gly Ile Asn
                 20                  25                  30

Leu Gln Trp Tyr Gln Gln Lys Pro Arg Lys Ala Pro Lys Leu Leu Ile
             35                  40                  45

Tyr Tyr Ala Ser Ile Leu Gln Ser Gly Val Pro Ser Arg Phe Ser Gly
         50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Glu Tyr Asp Tyr Pro Asn
                 85                  90                  95

Thr Phe Gly Gln Gly Thr Lys Val Glu Ile Lys Arg
            100                 105
```

<210> SEQ ID NO 333
<211> LENGTH: 108
<212> TYPE: PRT
<213> ORGANISM: Homo sapiens

<400> SEQUENCE: 333

```
Asp Ile Gln Met Thr Gln Ser Pro Ser Ser Leu Ser Ala Ser Val Gly
```

```
  1               5                   10                  15
Asp Arg Val Thr Ile Thr Cys Arg Ala Ser Ser Ser Ile Gly Ser Gly
            20                  25                  30

Leu Glu Trp Tyr Gln Gln Lys Pro Gly Lys Ala Pro Lys Leu Leu Ile
            35                  40                  45

Val Gly Trp Ser Gly Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Arg Gln Cys Val Gly Leu Pro Cys
                85                  90                  95

Thr Phe Gly Gln Gly Thr Lys Val Glu Ile Lys Arg
                100                 105
```

<210> SEQ ID NO 334
<211> LENGTH: 108
<212> TYPE: PRT
<213> ORGANISM: Homo sapiens

<400> SEQUENCE: 334

```
Asp Ile Gln Met Thr Gln Ser Pro Ser Ser Leu Ser Ala Ser Val Gly
 1               5                   10                  15

Asp Arg Val Thr Ile Thr Cys Arg Ala Ser Gln Trp Ile Gly Val Glu
            20                  25                  30

Leu Ser Trp Tyr Gln Gln Lys Pro Gly Lys Ala Pro Lys Leu Leu Ile
            35                  40                  45

Tyr Trp Gly Ser Glu Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Leu Ala Leu Pro Pro Phe
                85                  90                  95

Thr Phe Gly Gln Gly Thr Lys Val Glu Ile Lys Arg
                100                 105
```

<210> SEQ ID NO 335
<211> LENGTH: 108
<212> TYPE: PRT
<213> ORGANISM: Homo sapiens

<400> SEQUENCE: 335

```
Asp Ile Gln Met Thr Gln Ser Pro Ser Ser Leu Ser Ala Ser Val Gly
 1               5                   10                  15

Asp Arg Val Thr Ile Thr Cys Arg Ala Ser His Asp Ile Gly Val Ser
            20                  25                  30

Leu Asp Trp Tyr Gln Gln Lys Pro Gly Lys Ala Pro Lys Leu Leu Ile
            35                  40                  45

Val Trp Ala Ser Val Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Leu Gln Val Gly Ala Gly Pro Met
                85                  90                  95

Thr Phe Gly Gln Gly Thr Lys Val Glu Ile Lys Arg
                100                 105
```

<210> SEQ ID NO 336
<211> LENGTH: 108
<212> TYPE: PRT
<213> ORGANISM: Homo sapiens

<400> SEQUENCE: 336

```
Asp Ile Gln Met Thr Gln Ser Pro Ser Ser Leu Ser Ala Ser Val Gly
1               5                   10                  15
Asp Gly Val Thr Ile Thr Cys Arg Ala Ser Gln Tyr Ile Gly Ile Asp
            20                  25                  30
Leu Ala Trp Tyr Gln Arg Lys Pro Gly Lys Ala Pro Arg Leu Leu Ile
        35                  40                  45
Tyr Lys Ala Ser Ala Leu Gln Ser Gly Val Pro Ser Arg Phe Ser Gly
    50                  55                  60
Ser Gly Ser Gly Thr Asp Phe Thr Leu Thr Ile Ser Ser Leu Gln Pro
65                  70                  75                  80
Glu Asp Phe Ala Thr Tyr Tyr Cys Gln Gln Tyr Ala Asp Tyr Pro Ala
                85                  90                  95
Thr Phe Gly Gln Gly Thr Lys Val Glu Ile Lys Arg
            100                 105
```

<210> SEQ ID NO 337
<211> LENGTH: 108
<212> TYPE: PRT
<213> ORGANISM: Homo sapiens

<400> SEQUENCE: 337

```
Asp Ile Gln Met Thr Gln Ser Pro Ser Ser Leu Ser Ala Ser Val Gly
1               5                   10                  15
Asp Arg Val Thr Ile Thr Cys Arg Ala Ser Gln Glu Ile Glu His Tyr
            20                  25                  30
Leu Ser Trp Tyr Gln Gln Lys Pro Gly Lys Ala Pro Lys Leu Leu Ile
        35                  40                  45
Tyr Leu Ser Ser Arg Leu Gln Ser Gly Val Pro Ser Arg Phe Ser Gly
    50                  55                  60
Ser Gly Ser Gly Thr Asp Phe Thr Leu Thr Ile Ser Ser Leu Gln Pro
65                  70                  75                  80
Glu Asp Phe Ala Thr Tyr Tyr Cys Gln Gln Asn Val Gln Leu Pro Ile
                85                  90                  95
Thr Phe Gly Gln Gly Thr Lys Val Glu Ile Lys Arg
            100                 105
```

<210> SEQ ID NO 338
<211> LENGTH: 108
<212> TYPE: PRT
<213> ORGANISM: Homo sapiens

<400> SEQUENCE: 338

```
Asp Ile Gln Met Thr Gln Ser Pro Ser Ser Leu Ser Ala Ser Val Gly
1               5                   10                  15
Asp Arg Val Thr Ile Thr Cys Arg Ala Ser Gln Glu Ile Gly Val Ser
            20                  25                  30
Leu Ser Trp Tyr Gln Gln Lys Pro Gly Lys Ala Pro Lys Leu Leu Ile
        35                  40                  45
Tyr Trp Gly Ser Glu Leu Gln Ser Gly Val Pro Ser Arg Phe Ser Gly
    50                  55                  60
Ser Gly Ser Gly Thr Asp Phe Thr Leu Thr Ile Ser Ser Leu Gln Pro
65                  70                  75                  80
```

```
Glu Asp Phe Ala Thr Tyr Tyr Cys Gln Gln Asp His Asn Trp Pro Met
                85                  90                  95

Thr Phe Gly Gln Gly Thr Lys Val Glu Ile Lys Arg
            100                 105
```

<210> SEQ ID NO 339
<211> LENGTH: 108
<212> TYPE: PRT
<213> ORGANISM: Homo sapiens

<400> SEQUENCE: 339

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Ala Leu Ile Met Gly Asp
            20                  25                  30

Leu Asp Trp Tyr Gln Gln Lys Pro Gly Lys Ala Pro Lys Leu Leu Ile
            35                  40                  45

Ala Gly Val Ser Phe Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Ala Gln Ser Arg Ser Trp Pro Tyr
                85                  90                  95

Thr Phe Gly Gln Gly Thr Lys Val Glu Ile Lys Arg
            100                 105
```

<210> SEQ ID NO 340
<211> LENGTH: 108
<212> TYPE: PRT
<213> ORGANISM: Homo sapiens

<400> SEQUENCE: 340

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Lys Met Ile Asp Glu Asn
            20                  25                  30

Leu Ala Trp Tyr Gln Gln Lys Pro Gly Lys Ala Pro Lys Leu Leu Ile
            35                  40                  45

Leu Arg Ser Ser Gly Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys His Gln Gly His Ser Ala Pro Gly
                85                  90                  95

Thr Phe Gly Gln Gly Thr Lys Val Glu Ile Lys Arg
            100                 105
```

<210> SEQ ID NO 341
<211> LENGTH: 108
<212> TYPE: PRT
<213> ORGANISM: Homo sapiens

<400> SEQUENCE: 341

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Arg Tyr Ile Gly Val Ser
            20                  25                  30
```

Leu Asp Trp Tyr Gln Gln Lys Pro Gly Lys Ala Pro Lys Leu Leu Ile
            35                  40                  45

Met Trp Gly Ser Ala Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Leu Gln Ser Ala Ala Pro Pro Ala
                85                  90                  95

Thr Phe Gly Gln Gly Thr Lys Val Glu Ile Lys Arg
            100                 105

<210> SEQ ID NO 342
<211> LENGTH: 108
<212> TYPE: PRT
<213> ORGANISM: Homo sapiens

<400> SEQUENCE: 342

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Glu Ile Gly Val Ser
            20                  25                  30

Leu Ser Trp Tyr Gln Gln Lys Pro Gly Lys Ala Pro Lys Leu Leu Ile
            35                  40                  45

Tyr Trp Ala Ser Ala Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Tyr Leu Pro Pro Asp
                85                  90                  95

Thr Phe Gly Gln Gly Thr Lys Val Glu Ile Lys Arg
            100                 105

<210> SEQ ID NO 343
<211> LENGTH: 108
<212> TYPE: PRT
<213> ORGANISM: Homo sapiens

<400> SEQUENCE: 343

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Glu Ile Ala Ser Asp
            20                  25                  30

Leu Leu Trp Tyr Gln Gln Lys Pro Gly Lys Ala Pro Lys Leu Leu Ile
            35                  40                  45

Tyr Asn Gly Ser Ser Leu Gln Ser Gly Val Pro Ser Arg Phe Ser Gly
 50                  55                  60

Ser Gly Ser Gly Thr Asp Phe Thr Leu Thr Ile Ser Arg Leu Gln Pro
 65                  70                  75                  80

Glu Asp Phe Ala Thr Tyr Tyr Cys Gln Trp Leu Trp Ser Glu Pro Leu
                85                  90                  95

Thr Phe Gly Gln Gly Thr Lys Val Glu Ile Lys Arg
            100                 105

<210> SEQ ID NO 344
<211> LENGTH: 108
<212> TYPE: PRT
<213> ORGANISM: Homo sapiens

<400> SEQUENCE: 344

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln His Ile Gly Asp Ala
            20                  25                  30

Leu Trp Trp Tyr Gln Gln Lys Pro Gly Lys Ala Pro Lys Leu Leu Ile
        35                  40                  45

Tyr Trp Thr Ser Asn Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Thr Ile Arg Arg Pro Tyr
                85                  90                  95

Thr Phe Gly Gln Gly Thr Lys Val Lys Ile Lys Arg
            100                 105

<210> SEQ ID NO 345
<211> LENGTH: 108
<212> TYPE: PRT
<213> ORGANISM: Homo sapiens

<400> SEQUENCE: 345

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Trp Ile Gly Ile Leu
            20                  25                  30

Leu Asp Trp Tyr Gln Gln Lys Pro Gly Glu Ala Pro Lys Leu Leu Ile
        35                  40                  45

Tyr Tyr Ala Ser Phe Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Pro Ala Pro Leu
                85                  90                  95

Thr Phe Gly Gln Gly Thr Lys Val Glu Ile Lys Arg
            100                 105

<210> SEQ ID NO 346
<211> LENGTH: 108
<212> TYPE: PRT
<213> ORGANISM: Homo sapiens

<400> SEQUENCE: 346

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asn Ile Gly Ile Asn
            20                  25                  30

Leu Gln Trp Tyr Gln Gln Lys Pro Arg Lys Ala Pro Lys Leu Leu Ile
        35                  40                  45

Tyr Tyr Ala Ser Ile Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Asp Leu Pro Lys
                85                  90                  95

Thr Phe Gly Gln Gly Thr Lys Val Glu Ile Lys Arg

-continued

```
                100                 105

<210> SEQ ID NO 347
<211> LENGTH: 108
<212> TYPE: PRT
<213> ORGANISM: Homo sapiens

<400> SEQUENCE: 347

Asp Ile Gln Met Ile Gln Ser Pro Ser Ser Leu Ser Ala Ser Val Gly
 1               5                  10                  15

Asp Arg Val Thr Ile Thr Cys Arg Ala Ser Gln Glu Ile Gly Val Ser
            20                  25                  30

Leu Ser Trp Tyr Gln Gln Lys Pro Gly Lys Ala Pro Lys Leu Leu Ile
        35                  40                  45

Tyr Trp Gly Ser Glu Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Trp Tyr Gly Trp Pro Asp
                85                  90                  95

Thr Phe Gly Gln Gly Thr Lys Val Gly Ile Lys Arg
            100                 105

<210> SEQ ID NO 348
<211> LENGTH: 108
<212> TYPE: PRT
<213> ORGANISM: Homo sapiens

<400> SEQUENCE: 348

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln His Ile Gly Ile Glu
            20                  25                  30

Leu Asn Trp Tyr Gln Gln Lys Pro Gly Lys Ala Pro Lys Leu Leu Ile
        35                  40                  45

Tyr Trp Ala Ser Val Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Val Tyr Val Pro Thr
                85                  90                  95

Thr Phe Gly Gln Gly Thr Lys Val Glu Ile Lys Arg
            100                 105

<210> SEQ ID NO 349
<211> LENGTH: 108
<212> TYPE: PRT
<213> ORGANISM: Homo sapiens

<400> SEQUENCE: 349

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Trp Ile Gly Ala Glu
            20                  25                  30

Leu Val Trp Tyr Gln Gln Lys Pro Gly Lys Ala Pro Lys Leu Leu Ile
        35                  40                  45

Tyr Trp Ser Ser Val Leu Gln Ser Gly Val Pro Ser Arg Phe Ser Gly
    50                  55                  60
```

```
Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ala Ala His Ser Pro Pro
                 85                  90                  95

Thr Phe Gly Gln Gly Thr Lys Val Glu Ile Lys Arg
            100                 105

<210> SEQ ID NO 350
<211> LENGTH: 108
<212> TYPE: PRT
<213> ORGANISM: Homo sapiens

<400> SEQUENCE: 350

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Asp Ile Ser Arg Ser
             20                  25                  30

Leu Ala Trp Tyr Gln Arg Lys Pro Gly Lys Ala Pro Arg Leu Leu Ile
         35                  40                  45

Tyr Met Ser Ser Thr Leu Gln Ser Gly Val Pro Ser Arg Phe Ser Gly
     50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Asp Ser Tyr Pro Ser
                 85                  90                  95

Thr Phe Gly Gln Gly Thr Lys Val Glu Ile Lys Arg
            100                 105

<210> SEQ ID NO 351
<211> LENGTH: 108
<212> TYPE: PRT
<213> ORGANISM: Homo sapiens

<400> SEQUENCE: 351

Asp Ile Gln Met Thr Gln Ser Pro Ser Ser Leu Ser Ala Ser Val Gly
 1               5                  10                  15

Asp Arg Val Thr Ile Thr Cys Arg Ala Ser Arg Met Ile Gly Gly Met
             20                  25                  30

Leu Leu Trp Tyr Gln Gln Lys Pro Gly Lys Ala Pro Lys Leu Leu Ile
         35                  40                  45

Thr Tyr Gly Ser Val Leu Gln Ser Gly Val Pro Ser Arg Phe Ser Gly
     50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Ala Gln Glu Phe Trp Trp Pro His
                 85                  90                  95

Thr Phe Gly Gln Gly Thr Lys Val Glu Ile Lys Arg
            100                 105

<210> SEQ ID NO 352
<211> LENGTH: 108
<212> TYPE: PRT
<213> ORGANISM: Homo sapiens

<400> SEQUENCE: 352

Asp Ile Gln Met Thr Gln Ser Pro Ser Ser Leu Ser Ala Ser Val Gly
 1               5                  10                  15
```

-continued

Asp Arg Val Thr Ile Thr Cys Arg Ala Ser Arg Pro Ile Gly Asp Arg
            20                  25                  30

Leu Thr Trp Tyr Gln Gln Lys Pro Gly Lys Ala Pro Lys Leu Leu Ile
        35                  40                  45

Ser Trp Val Ser Val Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Arg Gln Leu Gly Gly Pro Phe
                85                  90                  95

Thr Phe Gly Gln Gly Thr Lys Val Glu Ile Lys Arg
            100                 105

<210> SEQ ID NO 353
<211> LENGTH: 108
<212> TYPE: PRT
<213> ORGANISM: Homo sapiens

<400> SEQUENCE: 353

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Tyr Ile Gly Val Ser
            20                  25                  30

Leu Ser Trp Tyr Gln Gln Lys Pro Gly Lys Ala Pro Lys Leu Leu Ile
        35                  40                  45

Tyr Phe Ala Ser Ala Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Asp Arg Asp Trp Pro Ala
                85                  90                  95

Thr Phe Gly Gln Gly Thr Lys Val Glu Ile Lys Arg
            100                 105

<210> SEQ ID NO 354
<211> LENGTH: 108
<212> TYPE: PRT
<213> ORGANISM: Homo sapiens

<400> SEQUENCE: 354

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gly Ala Ile Gly Asp Arg
            20                  25                  30

Leu Lys Trp Tyr Gln Gln Lys Pro Gly Lys Ala Pro Lys Leu Leu Ile
        35                  40                  45

Ser Trp Ala Ser Val Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Val Gln Gly Pro Gly Val Pro Leu
                85                  90                  95

Thr Phe Gly Gln Gly Thr Lys Val Glu Ile Lys Arg
            100                 105

<210> SEQ ID NO 355
<211> LENGTH: 108

```
<212> TYPE: PRT
<213> ORGANISM: Homo sapiens

<400> SEQUENCE: 355

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Pro Ile Ala Arg Trp
            20                  25                  30

Leu Ala Trp Tyr Gln Gln Lys Pro Gly Lys Ala Pro Lys Leu Leu Ile
        35                  40                  45

Tyr Gly Ser Ser Val Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Asp Leu Arg Leu Pro Pro
                85                  90                  95

Thr Phe Gly Gln Gly Thr Lys Val Glu Ile Lys Arg
            100                 105

<210> SEQ ID NO 356
<211> LENGTH: 108
<212> TYPE: PRT
<213> ORGANISM: Homo sapiens

<400> SEQUENCE: 356

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asn Ile Gly Val Ser
            20                  25                  30

Leu Ser Trp Tyr Gln Gln Lys Pro Gly Lys Ala Pro Arg Leu Leu Ile
        35                  40                  45

Tyr Tyr Gly Ser Asn Leu Leu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Glu Phe Ser Trp Pro Val
                85                  90                  95

Thr Phe Gly Gln Gly Thr Lys Val Glu Ile Lys Arg
            100                 105

<210> SEQ ID NO 357
<211> LENGTH: 108
<212> TYPE: PRT
<213> ORGANISM: Homo sapiens

<400> SEQUENCE: 357

Asp Ile Gln Met Thr Gln Ser Pro Ser Ser Leu Ser Ala Ser Val Gly
1               5                   10                  15

Asp Arg Val Thr Ile Thr Cys Arg Ala Ser Leu Pro Ile Asp Asp Gly
            20                  25                  30

Leu Gly Trp Tyr Gln Gln Lys Pro Gly Lys Ala Pro Lys Leu Leu Ile
        35                  40                  45

Cys Gly Val Ser Gly Leu Gln Ser Gly Val Pro Leu Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gly Gln Gly Gln Val Gln Pro Ser
```

```
                85                  90                  95

Thr Phe Gly Gln Gly Thr Lys Val Glu Ile Lys Arg
            100                 105

<210> SEQ ID NO 358
<211> LENGTH: 108
<212> TYPE: PRT
<213> ORGANISM: Homo sapiens

<400> SEQUENCE: 358

Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Asn Ile Gly Ile Asn
             20                  25                  30

Leu Gln Trp Tyr Gln Gln Lys Pro Arg Lys Ala Pro Lys Leu Leu Ile
         35                  40                  45

Tyr Tyr Ala Ser Ile Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Tyr Asp Ala Pro Thr
                 85                  90                  95

Thr Phe Gly Gln Gly Thr Lys Val Glu Ile Lys Arg
            100                 105

<210> SEQ ID NO 359
<211> LENGTH: 108
<212> TYPE: PRT
<213> ORGANISM: Homo sapiens

<400> SEQUENCE: 359

Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Ser Ile Gly Val Asn
             20                  25                  30

Leu Met Trp Tyr Gln Gln Lys Pro Gly Lys Ala Pro Lys Leu Leu Ile
         35                  40                  45

Tyr Phe Ala Ser Ile Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Asn Tyr Asp Ile Pro Lys
                 85                  90                  95

Thr Phe Gly Gln Gly Thr Lys Val Glu Ile Lys Arg
            100                 105

<210> SEQ ID NO 360
<211> LENGTH: 108
<212> TYPE: PRT
<213> ORGANISM: Homo sapiens

<400> SEQUENCE: 360

Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Trp Ile Gly Ile Ser
             20                  25                  30

Leu Ser Trp Tyr Gln Gln Lys Pro Gly Lys Ala Pro Lys Leu Leu Ile
         35                  40                  45
```

```
Tyr Tyr Gly Ser Val Leu Gln Ser Gly Val Pro Ser Arg Phe Ser Gly
     50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser His Asp Leu Pro Val
                 85                  90                  95

Thr Phe Gly Gln Gly Thr Lys Val Glu Ile Lys Arg
            100                 105

<210> SEQ ID NO 361
<211> LENGTH: 108
<212> TYPE: PRT
<213> ORGANISM: Homo sapiens

<400> SEQUENCE: 361

Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Trp Ile Gly Val Ser
                 20                  25                  30

Leu Ser Trp Tyr Gln Gln Lys Pro Gly Lys Ala Pro Lys Leu Leu Ile
             35                  40                  45

Tyr Tyr Ala Ser Ile Leu Gln Ser Gly Val Pro Ser Arg Phe Ser Gly
     50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Glu Met Ser Tyr Pro Pro
                 85                  90                  95

Thr Phe Gly Gln Gly Thr Lys Val Glu Ile Lys Arg
            100                 105

<210> SEQ ID NO 362
<211> LENGTH: 108
<212> TYPE: PRT
<213> ORGANISM: Homo sapiens

<400> SEQUENCE: 362

Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Asp Ile Gly Val Ser
                 20                  25                  30

Leu Glu Trp Tyr Gln Gln Lys Pro Gly Lys Ala Pro Lys Leu Leu Ile
             35                  40                  45

Tyr Trp Ser Ser Ala Leu Gln Ser Gly Val Pro Ser Arg Phe Ser Gly
     50                  55                  60

Ser Gly Ser Gly Thr Asp Phe Thr Leu Thr Ile Ser Ser Leu Gln Pro
 65                  70                  75                  80

Glu Asp Leu Ala Thr Tyr Tyr Cys Gln Gln Gly His Thr Tyr Pro Ser
                 85                  90                  95

Thr Phe Gly Gln Gly Thr Lys Val Glu Ile Lys Arg
            100                 105

<210> SEQ ID NO 363
<211> LENGTH: 108
<212> TYPE: PRT
<213> ORGANISM: Homo sapiens

<400> SEQUENCE: 363
```

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Tyr Ile Gly Val Tyr
            20                  25                  30

Leu Ser Trp Tyr Gln Gln Lys Pro Gly Lys Ala Pro Lys Leu Leu Ile
        35                  40                  45

Tyr Trp Ala Ser Leu Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Thr Val Arg Asp Pro Ile
                85                  90                  95

Thr Phe Gly Gln Gly Thr Lys Val Glu Ile Lys Arg
            100                 105
```

<210> SEQ ID NO 364
<211> LENGTH: 108
<212> TYPE: PRT
<213> ORGANISM: Homo sapiens

<400> SEQUENCE: 364

```
Asp Ile Gln Met Thr Gln Ser Pro Ser Phe Leu Ser Ala Ser Val Gly
1               5                   10                  15

Asp Arg Val Thr Ile Thr Cys Arg Ala Ser Gln Ser Ile Tyr Thr Met
            20                  25                  30

Leu Asn Trp Tyr Gln Gln Lys Pro Gly Lys Ala Pro Lys Leu Leu Ile
        35                  40                  45

Tyr Arg Ala Ser Tyr Leu Gln Ser Gly Val Pro Ser Arg Phe Ser Gly
50                  55                  60

Ser Gly Ser Gly Thr Asp Phe Thr Leu Thr Ile Ser Ser Leu Leu Pro
65                  70                  75                  80

Glu Asp Ser Ala Thr Tyr Tyr Cys Gln Gln Asp Phe Ser Tyr Pro Ser
                85                  90                  95

Thr Phe Gly Gln Gly Thr Lys Val Glu Ile Lys Arg
            100                 105
```

<210> SEQ ID NO 365
<211> LENGTH: 108
<212> TYPE: PRT
<213> ORGANISM: Homo sapiens

<400> SEQUENCE: 365

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Tyr Ile Gly Ala Asn
            20                  25                  30

Leu Ser Trp Tyr Gln Gln Lys Pro Gly Lys Ala Pro Lys Leu Leu Ile
        35                  40                  45

Tyr Tyr Ile Ser Val Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Glu Leu Tyr Thr Pro His
                85                  90                  95

Thr Phe Gly Gln Gly Thr Lys Val Glu Ile Lys Arg
            100                 105
```

<210> SEQ ID NO 366
<211> LENGTH: 108
<212> TYPE: PRT
<213> ORGANISM: Homo sapiens

<400> SEQUENCE: 366

Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Tyr Ile Gly Val Thr
            20                  25                  30

Leu Met Trp Tyr Gln Gln Lys Pro Gly Lys Ala Pro Lys Leu Leu Ile
        35                  40                  45

Tyr Tyr Ala Ser Gln Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Glu Val Ser Tyr Pro Tyr
                85                  90                  95

Thr Phe Gly Gln Gly Thr Lys Val Glu Ile Lys Arg
            100                 105

<210> SEQ ID NO 367
<211> LENGTH: 108
<212> TYPE: PRT
<213> ORGANISM: Homo sapiens

<400> SEQUENCE: 367

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln His Ile Gly Val Ser
            20                  25                  30

Leu Thr Trp Tyr Gln Gln Lys Pro Gly Lys Ala Pro Lys Leu Leu Ile
        35                  40                  45

Tyr Phe Ala Ser Ile Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Tyr Ala Thr Tyr Tyr Cys Gln Gln Asp Met Ser Tyr Pro Pro
                85                  90                  95

Thr Phe Gly Gln Gly Thr Lys Val Gly Ile Lys Arg
            100                 105

<210> SEQ ID NO 368
<211> LENGTH: 108
<212> TYPE: PRT
<213> ORGANISM: Homo sapiens

<400> SEQUENCE: 368

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Gly Ile Ser
            20                  25                  30

Leu Glu Trp Tyr Gln Gln Lys Pro Gly Lys Ala Pro Lys Leu Leu Ile
        35                  40                  45

Tyr Phe Ala Ser Gln Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro

```
                65                  70                  75                  80
Glu Asp Phe Ala Thr Tyr Tyr Cys Gln Gln Val Tyr Asp Phe Pro Asn
                85                  90                  95

Thr Phe Gly Gln Gly Thr Lys Val Glu Ile Lys Arg
            100                 105
```

<210> SEQ ID NO 369
<211> LENGTH: 108
<212> TYPE: PRT
<213> ORGANISM: Homo sapiens

<400> SEQUENCE: 369

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln His Ile Gly Val Ser
            20                  25                  30

Leu Asn Trp Tyr Gln Gln Lys Pro Gly Lys Val Pro Lys Leu Leu Ile
            35                  40                  45

Tyr Trp Ala Ser Ile Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Glu His Thr Ile Pro Ser
                85                  90                  95

Thr Phe Gly Gln Gly Thr Lys Val Glu Ile Lys Arg
            100                 105
```

<210> SEQ ID NO 370
<211> LENGTH: 108
<212> TYPE: PRT
<213> ORGANISM: Homo sapiens

<400> SEQUENCE: 370

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln His Ile Gly Val Ser
            20                  25                  30

Leu Asp Trp Tyr Gln Gln Lys Pro Gly Lys Ala Pro Lys Leu Leu Ile
            35                  40                  45

Tyr Tyr Gly Ser Glu Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Val Thr His Pro Thr
                85                  90                  95

Thr Phe Gly Gln Gly Thr Lys Val Glu Ile Lys Arg
            100                 105
```

<210> SEQ ID NO 371
<211> LENGTH: 108
<212> TYPE: PRT
<213> ORGANISM: Homo sapiens

<400> SEQUENCE: 371

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Arg Ile Gly Met Met
            20                  25                  30
```

```
Leu Asp Trp Tyr Gln Gln Lys Pro Gly Lys Ala Pro Lys Leu Leu Ile
            35                  40                  45

Tyr Gly Gly Ser Lys Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln His Arg Gly Trp Tyr Pro Leu
                 85                  90                  95

Thr Phe Gly Gln Gly Thr Lys Val Glu Ile Lys Arg
            100                 105

<210> SEQ ID NO 372
<211> LENGTH: 108
<212> TYPE: PRT
<213> ORGANISM: Homo sapiens

<400> SEQUENCE: 372

Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Pro Ile Gly Asp Arg
             20                  25                  30

Leu Ser Trp Tyr Gln Gln Lys Pro Gly Lys Ala Pro Lys Leu Leu Ile
            35                  40                  45

Tyr Phe Ser Ser Val Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln His Gly Leu Arg Pro Asp
                 85                  90                  95

Thr Phe Gly Gln Gly Thr Lys Val Glu Ile Lys Arg
            100                 105

<210> SEQ ID NO 373
<211> LENGTH: 108
<212> TYPE: PRT
<213> ORGANISM: Homo sapiens

<400> SEQUENCE: 373

Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Trp Ile Gly Ser Ser
             20                  25                  30

Leu Met Trp Tyr Gln Gln Lys Pro Gly Lys Ala Pro Lys Leu Leu Ile
            35                  40                  45

Tyr Trp Ala Ser Glu Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Glu Tyr Ser Tyr Pro Ser
                 85                  90                  95

Thr Phe Gly Gln Gly Thr Lys Val Glu Ile Lys Arg
            100                 105

<210> SEQ ID NO 374
<211> LENGTH: 108
<212> TYPE: PRT
<213> ORGANISM: Homo sapiens
```

<400> SEQUENCE: 374

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Gly Val Ser
            20                  25                  30

Leu Ala Trp Tyr Gln Gln Lys Pro Gly Lys Ala Pro Lys Leu Leu Ile
        35                  40                  45

Tyr Phe Gly Ser Val Ser Leu Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser His Leu Pro Pro Thr
                85                  90                  95

Thr Phe Gly Gln Gly Thr Lys Val Glu Ile Lys Arg
            100                 105

<210> SEQ ID NO 375
<211> LENGTH: 108
<212> TYPE: PRT
<213> ORGANISM: Homo sapiens

<400> SEQUENCE: 375

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Trp Ile Gly Val Glu
            20                  25                  30

Leu Asn Trp Tyr Gln Gln Lys Pro Gly Lys Ala Pro Lys Leu Leu Ile
        35                  40                  45

Tyr Trp Thr Ser Ile Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Val Ile Asn Ser Pro Tyr
                85                  90                  95

Thr Phe Gly Gln Gly Thr Lys Val Glu Ile Lys Arg
            100                 105

<210> SEQ ID NO 376
<211> LENGTH: 108
<212> TYPE: PRT
<213> ORGANISM: Homo sapiens

<400> SEQUENCE: 376

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Gly Lys Trp
            20                  25                  30

Leu Glu Trp Tyr Gln Gln Lys Pro Gly Lys Ala Pro Lys Leu Leu Ile
        35                  40                  45

Gly Ala Thr Ser Trp Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Val Gln Gln Gly Arg Arg Pro Gly
                85                  90                  95

```
Thr Phe Gly Gln Gly Thr Lys Val Glu Ile Lys Arg
            100                 105

<210> SEQ ID NO 377
<211> LENGTH: 108
<212> TYPE: PRT
<213> ORGANISM: Homo sapiens

<400> SEQUENCE: 377

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Trp Ile Gly Ile Leu
            20                  25                  30

Leu Asp Trp Tyr Gln Gln Lys Pro Gly Glu Ala Pro Lys Leu Leu Ile
        35                  40                  45

Tyr Tyr Ala Ser Phe Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Arg Ser Asp Leu Ser Pro Leu
                85                  90                  95

Thr Phe Gly Gln Gly Thr Lys Val Glu Ile Lys Arg
            100                 105

<210> SEQ ID NO 378
<211> LENGTH: 108
<212> TYPE: PRT
<213> ORGANISM: Homo sapiens

<400> SEQUENCE: 378

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asn Ile Tyr Met Asn
            20                  25                  30

Leu Glu Trp Tyr Gln Gln Lys Pro Gly Lys Ala Pro Lys Leu Leu Ile
        35                  40                  45

Val Phe Gly Ser Trp Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Arg Gln Thr Glu Ala Pro Pro Ser
                85                  90                  95

Thr Phe Gly Gln Gly Thr Lys Val Glu Ile Lys Arg
            100                 105

<210> SEQ ID NO 379
<211> LENGTH: 108
<212> TYPE: PRT
<213> ORGANISM: Homo sapiens

<400> SEQUENCE: 379

Asp Ile Arg Met Thr Gln Ser Pro Ser Ser Leu Ser Ala Ser Val Gly
1               5                   10                  15

Asp Arg Val Thr Ile Thr Cys Arg Ala Ser Gln His Ile Gly Ser Ser
            20                  25                  30

Leu Ser Trp Tyr Gln Gln Lys Pro Gly Lys Ala Pro Lys Leu Leu Ile
        35                  40                  45

Tyr Tyr Ala Ser Val Leu Gln Ser Gly Val Pro Ser Arg Phe Ser Gly
```

```
                    50                  55                  60
Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Glu Tyr Ser Trp Pro Pro
                 85                  90                  95

Thr Leu Gly Gln Gly Thr Lys Val Glu Ile Lys Arg
            100                 105

<210> SEQ ID NO 380
<211> LENGTH: 108
<212> TYPE: PRT
<213> ORGANISM: Homo sapiens

<400> SEQUENCE: 380

Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Asp Ile Arg Thr Leu
                 20                  25                  30

Leu Arg Trp Tyr Gln Gln Lys Pro Gly Lys Ala Pro Lys Leu Leu Ile
             35                  40                  45

Tyr Trp Ser Ser Glu Leu Gln Ser Gly Val Pro Ser Arg Phe Ser Gly
         50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Thr Phe His Ala Pro Asn
                 85                  90                  95

Thr Phe Gly Gln Gly Thr Lys Val Glu Ile Lys Arg
            100                 105

<210> SEQ ID NO 381
<211> LENGTH: 108
<212> TYPE: PRT
<213> ORGANISM: Homo sapiens

<400> SEQUENCE: 381

Asp Ile Arg Met Thr Gln Ser Pro Ser Ser Leu Ser Ala Ser Val Gly
  1               5                  10                  15

Asp Arg Val Thr Ile Thr Cys Arg Ala Ser Gln Tyr Ile Gly Lys Tyr
                 20                  25                  30

Leu Ser Trp Tyr Gln Gln Lys Pro Gly Lys Ala Pro Lys Leu Leu Ile
             35                  40                  45

Tyr Leu Ser Ser Thr Leu Gln Ser Gly Val Pro Ser Arg Phe Ser Gly
         50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Asn Asp Arg Leu Pro Leu
                 85                  90                  95

Thr Leu Gly Gln Gly Thr Lys Val Glu Ile Lys Arg
            100                 105

<210> SEQ ID NO 382
<211> LENGTH: 108
<212> TYPE: PRT
<213> ORGANISM: Homo sapiens

<400> SEQUENCE: 382

Asp Ile Gln Met Thr Gln Ser Pro Ser Ser Leu Ser Ala Ser Val Gly
  1               5                  10                  15
```

```
Asp Arg Val Thr Ile Thr Cys Gln Ala Ser Gln Leu Ile Gly Asn Met
            20                  25                  30

Leu Ser Trp Tyr Gln Gln Lys Pro Gly Lys Ala Pro Thr Leu Leu Ile
            35                  40                  45

Tyr Ile Gly Ser Ser Leu Gln Ser Gly Val Pro Ser Arg Phe Ser Gly
            50                  55                  60

Ser Gly Ser Gly Thr Asp Phe Thr Leu Thr Ile Ser Ser Leu Gln Pro
 65                 70                  75                  80

Glu Asp Phe Ala Thr Tyr Tyr Cys Gln Gln Thr Tyr Phe Asp Pro Pro
                85                  90                  95

Thr Phe Gly Gln Gly Thr Lys Val Glu Ile Lys Arg
            100                 105
```

<210> SEQ ID NO 383
<211> LENGTH: 108
<212> TYPE: PRT
<213> ORGANISM: Homo sapiens

<400> SEQUENCE: 383

```
Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Tyr Ile Gly Ile Asn
            20                  25                  30

Leu Arg Trp Tyr Gln Gln Lys Pro Gly Lys Ala Pro Lys Leu Leu Ile
            35                  40                  45

Tyr Tyr Ser Ser Thr Leu Leu Ser Gly Val Pro Ser Arg Phe Ser Gly
            50                  55                  60

Ser Gly Ser Gly Thr Asp Phe Thr Leu Thr Ile Ser Ser Leu Gln Pro
 65                 70                  75                  80

Glu Asp Phe Ala Thr Tyr Tyr Cys Gln Gln Ser Tyr Asp Ser Pro Val
                85                  90                  95

Thr Phe Gly Gln Gly Thr Lys Val Glu Ile Lys Arg
            100                 105
```

<210> SEQ ID NO 384
<211> LENGTH: 108
<212> TYPE: PRT
<213> ORGANISM: Homo sapiens

<400> SEQUENCE: 384

```
Asp Ile Gln Met Thr Gln Ser Pro Ser Ser Leu Ser Ala Ser Val Gly
 1               5                  10                  15

Asp Arg Val Thr Ile Thr Cys Arg Ala Ser Trp Ala Ile Gly Asp Arg
            20                  25                  30

Leu Glu Trp Tyr Gln Gln Lys Pro Gly Lys Ala Pro Lys Leu Leu Ile
            35                  40                  45

Ala Trp Gly Ser Val Leu Gln Ser Gly Val Pro Ser Arg Phe Ser Gly
            50                  55                  60

Ser Gly Ser Gly Thr Asp Phe Thr Leu Thr Ile Ser Ser Leu Gln Pro
 65                 70                  75                  80

Glu Asp Phe Ala Thr Tyr Tyr Cys Ser Gln Leu Gly Ser Arg Pro Arg
                85                  90                  95

Thr Phe Gly Gln Gly Thr Lys Val Glu Ile Lys Arg
            100                 105
```

<210> SEQ ID NO 385

-continued

```
<211> LENGTH: 108
<212> TYPE: PRT
<213> ORGANISM: Homo sapiens

<400> SEQUENCE: 385

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Asp Asn Trp
            20                  25                  30

Leu Ala Trp Tyr Gln Gln Lys Pro Gly Glu Ala Pro Lys Leu Leu Ile
        35                  40                  45

Tyr Gly Thr Ser Arg Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Phe Phe Pro Ser
                85                  90                  95

Thr Phe Gly Gln Gly Thr Lys Val Glu Ile Lys Arg
            100                 105

<210> SEQ ID NO 386
<211> LENGTH: 108
<212> TYPE: PRT
<213> ORGANISM: Homo sapiens

<400> SEQUENCE: 386

Asp Ile Gln Met Thr Gln Ser Pro Ser Ser Leu Ser Ala Ser Val Gly
1               5                   10                  15

Asp Arg Val Thr Ile Thr Cys Arg Ala Ser Thr Phe Ile Gly Asn Val
            20                  25                  30

Leu Asn Trp Tyr Gln Gln Lys Pro Gly Lys Ala Pro Lys Leu Leu Ile
        35                  40                  45

Ser Tyr Val Ser Met Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Cys Gln Ser Tyr Asp Val Pro Phe
                85                  90                  95

Thr Phe Gly Gln Gly Thr Gln Val Glu Ile Lys Arg
            100                 105

<210> SEQ ID NO 387
<211> LENGTH: 108
<212> TYPE: PRT
<213> ORGANISM: Homo sapiens

<400> SEQUENCE: 387

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Trp Ile Gly Val Ser
            20                  25                  30

Leu Val Trp Tyr Gln Gln Lys Pro Gly Lys Ala Pro Lys Leu Leu Ile
        35                  40                  45

Tyr Trp Ala Ser Val Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80
```

-continued

Glu Asp Phe Ala Thr Tyr Tyr Cys Gln Gln Thr His Ala Gly Pro His
                85                  90                  95

Thr Phe Gly Gln Gly Thr Lys Val Glu Ile Lys Arg
            100                 105

<210> SEQ ID NO 388
<211> LENGTH: 108
<212> TYPE: PRT
<213> ORGANISM: Homo sapiens

<400> SEQUENCE: 388

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Trp Ile Gly Ile Leu
            20                  25                  30

Leu Asp Trp Tyr Gln Gln Lys Pro Gly Glu Ala Pro Lys Leu Leu Ile
        35                  40                  45

Tyr Tyr Ala Ser Phe Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Ser Val Asp Pro Leu
                85                  90                  95

Thr Phe Gly Gln Gly Thr Lys Val Glu Ile Lys Arg
            100                 105

<210> SEQ ID NO 389
<211> LENGTH: 108
<212> TYPE: PRT
<213> ORGANISM: Homo sapiens

<400> SEQUENCE: 389

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Gly Val Ser
            20                  25                  30

Leu Arg Trp Tyr Gln Gln Lys Pro Gly Lys Ala Pro Lys Leu Leu Ile
        35                  40                  45

Tyr Trp Ala Ser Glu Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Leu Tyr Asp Tyr Pro Pro
                85                  90                  95

Thr Phe Gly Gln Gly Thr Lys Val Glu Ile Lys Arg
            100                 105

<210> SEQ ID NO 390
<211> LENGTH: 108
<212> TYPE: PRT
<213> ORGANISM: Homo sapiens

<400> SEQUENCE: 390

Asp Ile Gln Met Thr Gln Ser Pro Ser Ser Leu Ser Ala Ser Val Gly
1               5                   10                  15

Asp Arg Val Thr Ile Thr Cys Arg Ala Ser Arg Phe Ile Ala Ser Gly
            20                  25                  30

Leu Asp Trp Tyr Gln Gln Lys Pro Gly Lys Ala Pro Lys Leu Leu Ile

-continued

```
                35                  40                  45
Ser Arg Phe Ser Gly Leu Gln Ser Gly Val Pro Ser Arg Phe Ser Gly
         50                  55                  60
Ser Gly Ser Gly Thr Asp Phe Thr Leu Thr Ile Ser Ser Leu Gln Pro
 65                  70                  75                  80
Glu Asp Phe Ala Thr Tyr Tyr Cys Lys Gln Gly Phe Gly Ala Pro Ala
                 85                  90                  95
Thr Phe Gly Gln Gly Thr Lys Val Glu Ile Lys Arg
                100                 105
```

<210> SEQ ID NO 391
<211> LENGTH: 109
<212> TYPE: PRT
<213> ORGANISM: Homo sapiens

<400> SEQUENCE: 391

```
Asp Ile Gln Met Thr Gln Ser Pro Ser Ser Leu Ser Ala Ser Val Gly
  1               5                  10                  15
Asp Arg Val Thr Ile Thr Cys Arg Ala Ser Gln Tyr Ile Ser Thr Glu
                 20                  25                  30
Leu Glu Trp Tyr Gln Gln Lys Pro Gly Lys Ala Pro Lys Leu Leu Ile
             35                  40                  45
Tyr Ser Ser Ser Met Leu Gln Ser Gly Val Pro Ser Arg Phe Ser Gly
         50                  55                  60
Ser Gly Ser Gly Thr Asp Phe Thr Leu Thr Ile Ser Ser Leu Gln Pro
 65                  70                  75                  80
Glu Asp Phe Ala Thr Tyr Tyr Cys Gln Gln Ser Ala Ser Ala Leu Pro
                 85                  90                  95
Leu Thr Phe Gly Gln Gly Thr Lys Val Glu Ile Lys Arg
                100                 105
```

<210> SEQ ID NO 392
<211> LENGTH: 108
<212> TYPE: PRT
<213> ORGANISM: Homo sapiens

<400> SEQUENCE: 392

```
Asp Ile Gln Met Thr Gln Ser Pro Ser Ser Leu Ser Ala Ser Val Gly
  1               5                  10                  15
Asp Arg Val Thr Ile Thr Cys Arg Ala Ser Gln Trp Ile Gly Ala Ser
                 20                  25                  30
Leu Gln Trp Tyr Gln Gln Lys Pro Gly Gln Ala Pro Lys Leu Leu Ile
             35                  40                  45
Tyr Tyr Met Ser Val Leu Gln Ser Gly Val Pro Ser Arg Phe Ser Gly
         50                  55                  60
Ser Gly Ser Gly Thr Asp Phe Thr Leu Thr Ile Ser Ser Leu Gln Pro
 65                  70                  75                  80
Glu Asp Phe Ala Thr Tyr Tyr Cys Gln Gln Thr Ala Leu Thr Pro Ala
                 85                  90                  95
Thr Phe Gly Gln Gly Thr Lys Val Glu Ile Lys Arg
                100                 105
```

<210> SEQ ID NO 393
<211> LENGTH: 108
<212> TYPE: PRT
<213> ORGANISM: Homo sapiens

<400> SEQUENCE: 393

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Val Ile Gly Asp Tyr
            20                  25                  30

Leu Ser Trp Tyr Gln Gln Lys Pro Gly Lys Ala Pro Lys Leu Leu Ile
        35                  40                  45

Tyr Phe Arg Ser Val Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Asn Trp Asn Leu Pro Val
                85                  90                  95

Thr Phe Gly Gln Gly Thr Lys Val Glu Ile Lys Arg
            100                 105

<210> SEQ ID NO 394
<211> LENGTH: 108
<212> TYPE: PRT
<213> ORGANISM: Homo sapiens

<400> SEQUENCE: 394

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Tyr Ile Gly Val Asn
            20                  25                  30

Leu Ser Trp Tyr Gln Gln Lys Pro Gly Lys Ala Pro Lys Leu Leu Ile
        35                  40                  45

Tyr Tyr Val Ser Val Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Thr Tyr Asp Ile Pro Ser
                85                  90                  95

Thr Phe Gly Gln Gly Thr Lys Val Glu Ile Lys Arg
            100                 105

<210> SEQ ID NO 395
<211> LENGTH: 108
<212> TYPE: PRT
<213> ORGANISM: Homo sapiens

<400> SEQUENCE: 395

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Trp Ile Gly Val Ser
            20                  25                  30

Leu Ser Trp Tyr Gln Gln Lys Pro Gly Lys Ala Pro Lys Leu Leu Ile
        35                  40                  45

Tyr Tyr Thr Ser Tyr Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Glu Thr Trp Pro Tyr
                85                  90                  95

Thr Phe Gly Gln Gly Thr Lys Val Glu Ile Lys Arg
            100                 105

<210> SEQ ID NO 396
<211> LENGTH: 108
<212> TYPE: PRT
<213> ORGANISM: Homo sapiens

<400> SEQUENCE: 396

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Tyr Ile Gly Ala Glu
            20                  25                  30

Leu Asn Trp Tyr Gln Gln Lys Pro Gly Lys Ala Pro Lys Leu Leu Ile
        35                  40                  45

Tyr Trp Thr Ser Val Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Ile Leu Ala Pro Leu
                85                  90                  95

Thr Phe Gly Gln Gly Thr Lys Val Glu Ile Lys Arg
            100                 105

<210> SEQ ID NO 397
<211> LENGTH: 108
<212> TYPE: PRT
<213> ORGANISM: Homo sapiens

<400> SEQUENCE: 397

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Trp Ile Gly Val Ser
            20                  25                  30

Leu Asn Trp Tyr Gln Gln Lys Pro Gly Lys Ala Pro Lys Leu Leu Ile
        35                  40                  45

Tyr Phe Ala Ser Val Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Asn Ala Phe Tyr Pro Asp
                85                  90                  95

Thr Phe Gly Gln Gly Thr Lys Val Glu Ile Lys Arg
            100                 105

<210> SEQ ID NO 398
<211> LENGTH: 108
<212> TYPE: PRT
<213> ORGANISM: Homo sapiens

<400> SEQUENCE: 398

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Trp Ile Gly Ala Glu
            20                  25                  30

Leu Asn Trp Tyr Gln Gln Lys Pro Gly Lys Ala Pro Lys Leu Leu Ile
        35                  40                  45

Tyr Trp Met Ser Val Leu Gln Ser Gly Val Pro Ser Arg Phe Ser Gly
    50                  55                  60

```
Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Thr Ser Phe Phe Pro Ile
                 85                  90                  95

Thr Phe Gly Gln Gly Thr Lys Val Glu Ile Lys Arg
            100                 105

<210> SEQ ID NO 399
<211> LENGTH: 108
<212> TYPE: PRT
<213> ORGANISM: Homo sapiens

<400> SEQUENCE: 399

Asp Ile Gln Met Thr Gln Ser Pro Ser Ser Leu Ser Ala Ser Val Gly
  1               5                  10                  15

Asp Arg Val Ala Ile Thr Cys Arg Ala Ser Gln Asp Ile Arg Thr Leu
                 20                  25                  30

Leu Ala Trp Tyr Gln Gln Lys Pro Gly Lys Ala Pro Met Leu Leu Ile
             35                  40                  45

Tyr Trp Ala Ser Glu Leu Gln Ser Gly Val Pro Ser Arg Phe Ser Gly
         50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Leu Ser Trp Pro Ser
                 85                  90                  95

Thr Phe Gly Gln Gly Thr Lys Val Glu Ile Lys Arg
            100                 105

<210> SEQ ID NO 400
<211> LENGTH: 108
<212> TYPE: PRT
<213> ORGANISM: Homo sapiens

<400> SEQUENCE: 400

Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Tyr Ile Gly Val Ser
                 20                  25                  30

Leu Asp Trp Tyr Gln Gln Lys Pro Gly Lys Ala Pro Lys Leu Leu Ile
             35                  40                  45

Tyr Tyr Ser Ser Met Leu Gln Ser Gly Val Pro Ser Arg Phe Ser Gly
         50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Tyr Thr Val Pro Asp
                 85                  90                  95

Thr Phe Gly Gln Gly Thr Lys Val Glu Ile Lys Arg
            100                 105

<210> SEQ ID NO 401
<211> LENGTH: 108
<212> TYPE: PRT
<213> ORGANISM: Homo sapiens

<400> SEQUENCE: 401

Asp Ile Gln Met Thr Gln Ser Pro Ser Ser Leu Ser Ala Ser Val Gly
  1               5                  10                  15

Asp Arg Val Thr Ile Thr Cys Arg Ala Ser Trp Pro Ile Gly Asp Arg
```

```
                    20                  25                  30

Leu Asn Trp Tyr Gln Gln Lys Pro Gly Lys Ala Pro Lys Leu Leu Ile
        35                  40                  45

Ala Trp Val Ser Val Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gly Gln Leu Gly Gly Gly Pro Arg
                85                  90                  95

Thr Phe Gly Gln Gly Thr Lys Val Glu Ile Lys Arg
            100                 105

<210> SEQ ID NO 402
<211> LENGTH: 108
<212> TYPE: PRT
<213> ORGANISM: Homo sapiens

<400> SEQUENCE: 402

Asp Ile Gln Met Thr Gln Ser Pro Ser Ser Leu Ser Ala Ser Val Gly
1               5                   10                  15

Asp Arg Val Ser Ile Thr Cys Arg Ala Ser Gln Phe Ile Gly Trp Glu
                20                  25                  30

Leu Ala Trp Tyr Gln Gln Lys Pro Gly Lys Ala Pro Met Leu Leu Ile
        35                  40                  45

Tyr Pro Tyr Ser Thr Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Leu Ala Gly Phe Pro Tyr
                85                  90                  95

Thr Phe Gly Gln Gly Thr Lys Val Glu Ile Lys Arg
            100                 105

<210> SEQ ID NO 403
<211> LENGTH: 108
<212> TYPE: PRT
<213> ORGANISM: Homo sapiens

<400> SEQUENCE: 403

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Pro Ile Gly Asp Arg
                20                  25                  30

Leu Ser Trp Tyr Gln Gln Lys Pro Gly Lys Ala Pro Lys Leu Leu Ile
        35                  40                  45

Tyr Phe Val Ser Gln Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser His Pro Asn Pro Lys
                85                  90                  95

Thr Phe Gly Gln Gly Thr Lys Val Glu Ile Lys Arg
            100                 105

<210> SEQ ID NO 404
<211> LENGTH: 108
<212> TYPE: PRT
```

<213> ORGANISM: Homo sapiens

<400> SEQUENCE: 404

Asp Ile Gln Met Thr Gln Ser Pro Ser Ser Leu Ser Ala Ser Val Gly
1               5                   10                  15

Asp Gly Val Thr Ile Thr Cys Arg Ala Ser Gln Trp Ile Gly Val Glu
            20                  25                  30

Leu Ser Trp Tyr Gln Gln Lys Pro Gly Lys Ala Pro Lys Leu Leu Ile
        35                  40                  45

Tyr Trp Gly Ser Glu Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Leu Ala Leu Pro Pro Phe
                85                  90                  95

Thr Phe Gly Gln Gly Thr Lys Val Glu Ile Lys Arg
            100                 105

<210> SEQ ID NO 405
<211> LENGTH: 108
<212> TYPE: PRT
<213> ORGANISM: Homo sapiens

<400> SEQUENCE: 405

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Glu Ile Gly Ala Ser
            20                  25                  30

Leu Glu Trp Tyr Gln Gln Lys Pro Gly Lys Ala Pro Lys Leu Leu Ile
        35                  40                  45

Tyr Trp Ala Ser Val Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Met His His Thr Pro Phe
                85                  90                  95

Thr Phe Gly Gln Gly Thr Lys Val Glu Ile Lys Arg
            100                 105

<210> SEQ ID NO 406
<211> LENGTH: 108
<212> TYPE: PRT
<213> ORGANISM: Homo sapiens

<400> SEQUENCE: 406

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln His Ile Gly Gln Phe
            20                  25                  30

Leu Ser Trp Tyr Gln Gln Lys Pro Gly Lys Ala Pro Lys Leu Leu Ile
        35                  40                  45

Tyr Leu Ala Ser Arg Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Val Asp Arg Ile Pro Val
                85                  90                  95

Thr Phe Gly Gln Gly Thr Lys Val Glu Ile Lys Arg
            100                 105

<210> SEQ ID NO 407
<211> LENGTH: 108
<212> TYPE: PRT
<213> ORGANISM: Homo sapiens

<400> SEQUENCE: 407

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Asp His Phe
            20                  25                  30

Leu Ser Trp Tyr Gln Gln Lys Pro Gly Lys Ala Pro Lys Leu Leu Ile
        35                  40                  45

Tyr Phe Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Asn Ala Ser Ile Pro Ile
                85                  90                  95

Thr Phe Gly Gln Gly Thr Lys Val Glu Ile Lys Arg
            100                 105

<210> SEQ ID NO 408
<211> LENGTH: 108
<212> TYPE: PRT
<213> ORGANISM: Homo sapiens

<400> SEQUENCE: 408

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asn Ile Gly Thr Asn
            20                  25                  30

Leu Lys Trp Tyr Gln Gln Lys Pro Glu Lys Ala Pro Lys Leu Leu Ile
        35                  40                  45

Tyr Tyr Gly Ser Leu Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Asp Tyr Asp Phe Pro Tyr
                85                  90                  95

Thr Phe Gly Gln Gly Thr Lys Val Glu Ile Lys Arg
            100                 105

<210> SEQ ID NO 409
<211> LENGTH: 108
<212> TYPE: PRT
<213> ORGANISM: Homo sapiens

<400> SEQUENCE: 409

Asp Ile Gln Met Thr Gln Ser Pro Ser Ser Leu Ser Ala Ser Val Gly
1               5                   10                  15

Asp Arg Val Ser Ile Thr Cys Arg Ala Ser Gln Trp Ile Gly Gly Glu
            20                  25                  30

Leu Asn Trp Tyr Gln Gln Lys Pro Gly Lys Ala Pro Lys Leu Leu Ile
        35                  40                  45

```
Tyr Trp Val Ser Thr Leu Gln Ser Gly Val Pro Ser Arg Phe Ser Gly
         50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ile Ala Arg Tyr Pro Ala
                 85                  90                  95

Thr Phe Gly Gln Gly Thr Lys Val Glu Ile Lys Arg
            100                 105
```

<210> SEQ ID NO 410
<211> LENGTH: 108
<212> TYPE: PRT
<213> ORGANISM: Homo sapiens

<400> SEQUENCE: 410

```
Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Asn Ile Gly Val Asn
                 20                  25                  30

Leu Ile Trp Tyr Gln Gln Lys Pro Gly Lys Ala Pro Arg Leu Leu Ile
             35                  40                  45

Tyr Phe Ser Ser Leu Leu Gln Ser Gly Val Pro Ser Arg Phe Ser Gly
         50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Asp Tyr Asp Val Pro Gln
                 85                  90                  95

Thr Phe Gly Gln Gly Thr Lys Val Glu Ile Lys Arg
            100                 105
```

<210> SEQ ID NO 411
<211> LENGTH: 108
<212> TYPE: PRT
<213> ORGANISM: Homo sapiens

<400> SEQUENCE: 411

```
Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Asn Ile Gly Ser Gly
                 20                  25                  30

Leu His Trp Tyr Gln Gln Lys Pro Gly Lys Ala Pro Lys Leu Leu Ile
             35                  40                  45

Val Ser Trp Ser Gly Leu Gln Ser Gly Val Pro Ser Arg Phe Ser Gly
         50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gly Gln Asp Val Leu Gly Pro Pro
                 85                  90                  95

Thr Phe Gly Gln Gly Thr Lys Val Glu Ile Lys Arg
            100                 105
```

<210> SEQ ID NO 412
<211> LENGTH: 108
<212> TYPE: PRT
<213> ORGANISM: Homo sapiens

<400> SEQUENCE: 412

```
Asp Ile Gln Met Thr Gln Ser Pro Ser Ser Leu Ser Ala Ser Val Gly
```

```
1               5                   10                  15
Asp Arg Val Thr Ile Thr Cys Arg Ala Ser Gln Trp Ile Gly Ala Ser
                20                  25                  30

Leu Ala Trp Tyr Gln Gln Lys Pro Gly Lys Ala Pro Lys Leu Leu Ile
            35                  40                  45

Tyr Phe Met Ser Glu Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Asp Tyr Gly Tyr Pro Thr
                85                  90                  95

Thr Phe Gly Gln Gly Thr Lys Val Glu Ile Lys Arg
            100                 105
```

<210> SEQ ID NO 413
<211> LENGTH: 108
<212> TYPE: PRT
<213> ORGANISM: Homo sapiens

<400> SEQUENCE: 413

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Trp Ile Gly Val Asn
                20                  25                  30

Leu Leu Trp Tyr Gln Gln Lys Pro Gly Lys Ala Pro Lys Leu Leu Ile
            35                  40                  45

Tyr Tyr Gly Ser Ile Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Asp Tyr His Gly Pro Tyr
                85                  90                  95

Thr Phe Gly Gln Gly Thr Lys Val Glu Ile Lys Arg
            100                 105
```

<210> SEQ ID NO 414
<211> LENGTH: 108
<212> TYPE: PRT
<213> ORGANISM: Homo sapiens

<400> SEQUENCE: 414

```
Asp Ile Gln Met Thr Gln Ser Pro Ser Ser Leu Ser Ala Ser Val Gly
1               5                   10                  15

Asp Arg Val Thr Ile Thr Cys Arg Thr Ser Gln Asp Ile Gly Ser Leu
                20                  25                  30

Leu Ser Trp Tyr Gln Gln Lys Pro Gly Lys Ala Pro Lys Leu Leu Ile
            35                  40                  45

Tyr Met Val Ser Met Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln His Asn Ser Trp Tyr Pro Ile
                85                  90                  95

Thr Phe Gly Gln Gly Thr Lys Val Glu Ile Lys Arg
            100                 105
```

<210> SEQ ID NO 415
<211> LENGTH: 108
<212> TYPE: PRT
<213> ORGANISM: Homo sapiens

<400> SEQUENCE: 415

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Phe Ile Tyr Thr Met
            20                  25                  30

Leu Asn Trp Tyr Gln Gln Lys Pro Gly Lys Ala Pro Lys Leu Leu Ile
        35                  40                  45

Tyr Arg Thr Ser Trp Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Asp Tyr Ala Ser Pro Phe
                85                  90                  95

Thr Phe Gly Gln Gly Thr Lys Val Glu Ile Lys Arg
            100                 105

<210> SEQ ID NO 416
<211> LENGTH: 108
<212> TYPE: PRT
<213> ORGANISM: Homo sapiens

<400> SEQUENCE: 416

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Trp Ile Gly Ile Leu
            20                  25                  30

Leu Asp Trp Tyr Gln Gln Lys Pro Gly Glu Ala Pro Lys Leu Leu Ile
        35                  40                  45

Tyr Tyr Ala Ser Phe Leu Gln Ser Gly Val Pro Ser Arg Phe Ser Gly
    50                  55                  60

Ser Gly Phe Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Pro Ala Pro Leu
                85                  90                  95

Thr Phe Gly Gln Gly Thr Lys Val Glu Ile Lys Arg
            100                 105

<210> SEQ ID NO 417
<211> LENGTH: 108
<212> TYPE: PRT
<213> ORGANISM: Homo sapiens

<400> SEQUENCE: 417

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Trp Ile Gly Ile Leu
            20                  25                  30

Ile Asp Trp Tyr Gln Gln Lys Pro Gly Glu Ala Pro Lys Leu Leu Ile
        35                  40                  45

Tyr Tyr Ala Ser Phe Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Ser Ala Thr Tyr Tyr Cys Gln Gln Ala Asn Pro Ala Pro Leu
            85                  90                  95

Thr Phe Gly Gln Gly Thr Lys Val Glu Ile Lys Arg
            100                 105

<210> SEQ ID NO 418
<211> LENGTH: 108
<212> TYPE: PRT
<213> ORGANISM: Homo sapiens

<400> SEQUENCE: 418

Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Trp Ile Gly Ile Leu
            20                  25                  30

Leu Asp Trp Tyr Gln Gln Lys Pro Gly Glu Ala Pro Lys Leu Leu Ile
        35                  40                  45

Tyr Tyr Ala Ser Phe Leu Gln Ser Gly Val Pro Ser Arg Phe Ser Gly
    50                  55                  60

Ser Gly Ser Gly Thr Asp Phe Thr Leu Thr Ile Asn Ser Leu Gln Pro
65                  70                  75                  80

Glu Asp Phe Ala Thr Tyr Tyr Cys Gln Gln Ala Asn Pro Ala Pro Leu
            85                  90                  95

Thr Phe Gly Gln Gly Thr Lys Val Glu Ile Lys Arg
            100                 105

<210> SEQ ID NO 419
<211> LENGTH: 108
<212> TYPE: PRT
<213> ORGANISM: Homo sapiens

<400> SEQUENCE: 419

Asp Ile Gln Met Thr Gln Ser Pro Ser Phe Leu Ser Ala Ser Val Gly
1               5                   10                  15

Asp Arg Val Thr Ile Thr Cys Arg Ala Ser Gln Trp Ile Gly Ile Leu
            20                  25                  30

Leu Asp Trp Tyr Gln Gln Lys Pro Gly Glu Ala Pro Lys Leu Leu Ile
        35                  40                  45

Tyr Tyr Ala Ser Phe Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Pro Ala Pro Leu
            85                  90                  95

Thr Leu Gly Gln Gly Thr Lys Val Glu Ile Lys Arg
            100                 105

<210> SEQ ID NO 420
<211> LENGTH: 108
<212> TYPE: PRT
<213> ORGANISM: Homo sapiens

<400> SEQUENCE: 420

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Trp Ile Gly Ile Leu
            20                  25                  30

-continued

Val Asp Trp Tyr Gln Gln Lys Pro Gly Glu Ala Pro Lys Leu Leu Ile
            35                  40                  45

Tyr Tyr Ala Ser Phe Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Pro Ala Pro Leu
                85                  90                  95

Arg Phe Gly Gln Gly Thr Lys Val Glu Ile Lys Arg
            100                 105

<210> SEQ ID NO 421
<211> LENGTH: 108
<212> TYPE: PRT
<213> ORGANISM: Homo sapiens

<400> SEQUENCE: 421

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Trp Ile Gly Ile Leu
            20                  25                  30

Leu Asp Trp Tyr Gln Gln Lys Pro Gly Glu Ala Pro Lys Leu Leu Ile
            35                  40                  45

Tyr Tyr Ala Ser Phe Leu Gln Asn Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Pro Ala Pro Leu
                85                  90                  95

Thr Phe Gly Gln Gly Thr Lys Val Glu Ile Lys Arg
            100                 105

<210> SEQ ID NO 422
<211> LENGTH: 108
<212> TYPE: PRT
<213> ORGANISM: Homo sapiens

<400> SEQUENCE: 422

Asp Ile Gln Met Ile Gln Ser Pro Ser Ser Leu Ser Ala Ser Val Gly
1               5                   10                  15

Asp Arg Val Thr Ile Thr Cys Arg Ala Ser Gln Trp Ile Gly Ile Leu
            20                  25                  30

Leu Asp Trp Tyr Gln Gln Lys Pro Gly Glu Ala Pro Lys Leu Leu Ile
            35                  40                  45

Tyr Tyr Ala Ser Phe Leu Gln Ser Gly Val Pro Ser Arg Phe Ser Gly
        50                  55                  60

Ser Gly Ser Gly Thr Asp Phe Thr Leu Thr Ile Ser Asn Leu Gln Pro
65                  70                  75                  80

Glu Asp Phe Ala Thr Tyr Tyr Cys Gln Gln Ala Asn Pro Ala Pro Leu
                85                  90                  95

Thr Phe Gly Gln Gly Thr Lys Val Glu Ile Lys Arg
            100                 105

<210> SEQ ID NO 423
<211> LENGTH: 108
<212> TYPE: PRT
<213> ORGANISM: Homo sapiens

```
<400> SEQUENCE: 423

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Trp Ile Gly Ile Leu
            20                  25                  30

Val Asp Trp Tyr Gln Gln Lys Pro Gly Glu Ala Pro Lys Leu Leu Ile
        35                  40                  45

Tyr Tyr Ala Ser Phe Leu Gln Ser Gly Val Pro Ser Arg Phe Ser Gly
    50                  55                  60

Ser Gly Phe Gly Thr Asp Phe Thr Leu Thr Ile Ser Ser Leu His Pro
65                  70                  75                  80

Glu Asp Phe Ala Thr Tyr Tyr Cys Gln Gln Ala Asn Pro Ala Pro Leu
                85                  90                  95

Thr Phe Gly Gln Gly Thr Lys Val Glu Ile Lys Arg
            100                 105

<210> SEQ ID NO 424
<211> LENGTH: 108
<212> TYPE: PRT
<213> ORGANISM: Homo sapiens

<400> SEQUENCE: 424

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Trp Ile Gly Ile Leu
            20                  25                  30

Leu Asp Trp Tyr Gln Gln Lys Pro Gly Glu Ala Pro Lys Leu Leu Ile
        35                  40                  45

Tyr Tyr Ala Ser Phe Leu Gln Ser Gly Val Pro Ser Arg Phe Ser Gly
    50                  55                  60

Ser Gly Ser Gly Thr Asp Phe Thr Leu Thr Ile Ser Asn Leu Gln Pro
65                  70                  75                  80

Glu Asp Phe Ala Thr Tyr Tyr Cys Gln Gln Ala Asp Pro Ala Pro Leu
                85                  90                  95

Thr Phe Gly Gln Gly Thr Lys Val Glu Ile Lys Arg
            100                 105

<210> SEQ ID NO 425
<211> LENGTH: 108
<212> TYPE: PRT
<213> ORGANISM: Homo sapiens

<400> SEQUENCE: 425

Asp Ile Gln Met Thr Gln Ser Pro Ser Ser Leu Ser Ala Ser Val Gly
1               5                   10                  15

Asp Ser Val Thr Ile Thr Cys Arg Ala Ser Gln Trp Ile Gly Ile Leu
            20                  25                  30

Leu Asp Trp Tyr Gln Gln Lys Pro Gly Glu Ala Pro Lys Leu Leu Ile
        35                  40                  45

Tyr Tyr Ala Ser Phe Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Pro Ala Pro Leu
                85                  90                  95

Thr Phe Gly Gln Gly Thr Lys Val Glu Ile Lys Arg
```

<210> SEQ ID NO 426
<211> LENGTH: 108
<212> TYPE: PRT
<213> ORGANISM: Homo sapiens

<400> SEQUENCE: 426

Asp Ile Gln Met Thr Gln Tyr Pro Ser Ser Leu Ser Ala Ser Val Gly
1               5                   10                  15

Asp Arg Val Thr Ile Thr Cys Arg Ala Ser Gln Trp Ile Gly Ile Leu
            20                  25                  30

Leu Asp Trp Tyr Gln Gln Lys Pro Gly Glu Ala Pro Lys Leu Leu Ile
        35                  40                  45

Tyr Tyr Ala Ser Phe Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Gly Thr Tyr Tyr Cys Gln Gln Ala Asn Pro Ala Pro Leu
                85                  90                  95

Thr Phe Gly Gln Gly Thr Lys Val Glu Ile Lys Arg
            100                 105

<210> SEQ ID NO 427
<211> LENGTH: 108
<212> TYPE: PRT
<213> ORGANISM: Homo sapiens

<400> SEQUENCE: 427

Asp Ile Gln Met Thr Gln Ser Pro Ser Ser Leu Tyr Ala Ser Val Gly
1               5                   10                  15

Asp Arg Val Thr Ile Thr Cys Arg Ala Ser Gln Trp Ile Gly Ile Leu
            20                  25                  30

Leu Asp Trp Tyr Gln Gln Lys Pro Gly Glu Ala Pro Lys Leu Leu Ile
        35                  40                  45

Tyr Tyr Ala Ser Phe Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Pro Ala Pro Leu
                85                  90                  95

Thr Phe Gly Gln Gly Thr Lys Val Glu Ile Lys Arg
            100                 105

<210> SEQ ID NO 428
<211> LENGTH: 108
<212> TYPE: PRT
<213> ORGANISM: Homo sapiens

<400> SEQUENCE: 428

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Trp Ile Gly Ile Leu
            20                  25                  30

Leu Asp Trp Tyr Gln Gln Lys Pro Gly Glu Ala Pro Lys Leu Leu Ile
        35                  40                  45

Tyr Tyr Ala Ser Phe Leu Gln Ser Gly Val Pro Ser Arg Phe Ser Gly
    50                  55                  60

-continued

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Pro Ala Asn Pro Ala Pro Leu
                85                  90                  95

Thr Phe Gly Gln Gly Thr Lys Val Glu Ile Lys Arg
            100                 105

<210> SEQ ID NO 429
<211> LENGTH: 108
<212> TYPE: PRT
<213> ORGANISM: Homo sapiens

<400> SEQUENCE: 429

Asp Ile Gln Met Thr Gln Ser Pro Ser Ser Leu Ser Ala Ser Val Gly
1               5                   10                  15

Asp Arg Val Thr Ile Thr Cys Arg Ser Ser Arg Trp Ile Gly Ile Leu
            20                  25                  30

Leu Asp Trp Tyr Gln Gln Lys Pro Gly Glu Ala Pro Lys Leu Leu Ile
        35                  40                  45

Tyr Tyr Ala Ser Phe Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Gln Ala Asn Pro Ala Pro Leu
                85                  90                  95

Thr Phe Gly Gln Gly Thr Lys Val Glu Ile Lys Arg
            100                 105

<210> SEQ ID NO 430
<211> LENGTH: 108
<212> TYPE: PRT
<213> ORGANISM: Homo sapiens

<400> SEQUENCE: 430

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Trp Ile Gly Ile Leu
            20                  25                  30

Val Asp Trp Tyr Gln Gln Lys Pro Gly Glu Ala Pro Lys Leu Leu Ile
        35                  40                  45

Tyr Tyr Ala Ser Phe Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Pro Ala Pro Leu
                85                  90                  95

Thr Phe Gly Gln Gly Thr Lys Val Glu Ile Lys Arg
            100                 105

<210> SEQ ID NO 431
<211> LENGTH: 108
<212> TYPE: PRT
<213> ORGANISM: Homo sapiens

<400> SEQUENCE: 431

Asp Ile Gln Leu Thr Gln Ser Pro Ser Ser Leu Ser Ala Ser Val Gly
1               5                   10                  15

```
Asp Arg Val Thr Ile Thr Cys Arg Ala Ser Gln Trp Ile Gly Ile Leu
            20                  25                  30

Leu Asp Trp Tyr Gln Gln Lys Pro Gly Glu Ala Pro Lys Leu Leu Ile
        35                  40                  45

Tyr Tyr Ala Ser Phe Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Pro Ala Pro Leu
                85                  90                  95

Thr Phe Gly Gln Gly Thr Lys Val Glu Ile Lys Arg
            100                 105
```

<210> SEQ ID NO 432
<211> LENGTH: 108
<212> TYPE: PRT
<213> ORGANISM: Homo sapiens

<400> SEQUENCE: 432

```
Asp Ile Gln Met Thr Gln Ser Pro Thr Ser Leu Ser Ala Ser Val Gly
1               5                   10                  15

Asp Arg Val Thr Ile Thr Cys Arg Ala Ser Gln Trp Ile Gly Asn Leu
            20                  25                  30

Leu Asp Trp Tyr Gln Gln Lys Pro Gly Glu Ala Pro Lys Leu Leu Ile
        35                  40                  45

Tyr Tyr Ala Ser Phe Leu Gln Ser Gly Val Pro Ser Arg Phe Ser Gly
    50                  55                  60

Gly Gly Phe Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Pro Ala Pro Leu
                85                  90                  95

Thr Phe Gly Gln Gly Thr Lys Val Glu Ile Lys Arg
            100                 105
```

<210> SEQ ID NO 433
<211> LENGTH: 108
<212> TYPE: PRT
<213> ORGANISM: Homo sapiens

<400> SEQUENCE: 433

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Trp Ile Gly Ile Leu
            20                  25                  30

Leu Asp Trp Tyr Gln Gln Lys Pro Gly Glu Ala Pro Lys Leu Leu Ile
        35                  40                  45

Tyr Tyr Ala Ser Phe Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Pro Ala Pro Pro
                85                  90                  95

Thr Phe Gly Gln Gly Thr Lys Val Glu Ile Lys Arg
            100                 105
```

<210> SEQ ID NO 434
<211> LENGTH: 108

```
<212> TYPE: PRT
<213> ORGANISM: Homo sapiens

<400> SEQUENCE: 434

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Trp Ile Gly Ile Leu
            20                  25                  30

Leu Asp Trp Tyr Gln Gln Lys Pro Gly Glu Asp Pro Lys Leu Leu Ile
        35                  40                  45

Tyr Tyr Ala Ser Phe Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Pro Ala Pro Leu
                85                  90                  95

Thr Phe Gly Gln Gly Thr Lys Val Glu Ile Lys Arg
            100                 105

<210> SEQ ID NO 435
<211> LENGTH: 108
<212> TYPE: PRT
<213> ORGANISM: Homo sapiens

<400> SEQUENCE: 435

Asp Ile Gln Met Thr Gln Ser Pro Thr Ser Leu Ser Ala Ser Val Gly
1               5                   10                  15

Asp Arg Val Thr Ile Thr Cys Arg Ala Ser Gln Trp Ile Gly Ile Leu
            20                  25                  30

Leu Asp Trp Tyr Gln Gln Lys Pro Gly Glu Ala Pro Lys Leu Leu Ile
        35                  40                  45

Tyr Tyr Ala Ser Phe Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Pro Ala Pro Leu
                85                  90                  95

Thr Phe Gly Gln Gly Thr Lys Val Glu Ile Lys Arg
            100                 105

<210> SEQ ID NO 436
<211> LENGTH: 108
<212> TYPE: PRT
<213> ORGANISM: Homo sapiens

<400> SEQUENCE: 436

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Trp Ile Gly Ile Leu
            20                  25                  30

Val Asp Trp Tyr Gln Gln Lys Pro Gly Glu Ala Pro Lys Leu Leu Ile
        35                  40                  45

Tyr Tyr Gly Ser Phe Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Pro Ala Pro Leu
```

```
                    85                  90                  95

Thr Phe Gly Gln Gly Thr Lys Val Glu Ile Lys Arg
                100                 105

<210> SEQ ID NO 437
<211> LENGTH: 108
<212> TYPE: PRT
<213> ORGANISM: Homo sapiens

<400> SEQUENCE: 437

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Trp Ile Gly Ile Leu
            20                  25                  30

Leu Asp Trp Tyr Gln Gln Lys Pro Gly Glu Ala Pro Lys Leu Leu Ile
        35                  40                  45

Tyr Tyr Ala Ser Phe Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Pro Ala Pro Leu
                85                  90                  95

Thr Phe Gly Gln Gly Thr Lys Val Glu Ile Arg Arg
                100                 105

<210> SEQ ID NO 438
<211> LENGTH: 108
<212> TYPE: PRT
<213> ORGANISM: Homo sapiens

<400> SEQUENCE: 438

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Trp Ile Gly Ile Leu
            20                  25                  30

Leu Asp Trp Tyr Gln Gln Lys Pro Gly Glu Ala Pro Lys Leu Leu Ile
        35                  40                  45

Tyr Tyr Ala Ser Phe Leu Gln Ser Gly Val Pro Ser Arg Phe Ser Gly
    50                  55                  60

Ser Gly Tyr Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Pro Ala Pro Leu
                85                  90                  95

Thr Phe Gly Gln Gly Thr Lys Val Glu Ile Lys Arg
                100                 105

<210> SEQ ID NO 439
<211> LENGTH: 108
<212> TYPE: PRT
<213> ORGANISM: Homo sapiens

<400> SEQUENCE: 439

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Trp Ile Gly Ile Leu
            20                  25                  30

Leu Asp Trp Tyr Gln Gln Lys Pro Gly Glu Ala Pro Lys Leu Leu Ile
        35                  40                  45
```

```
Tyr Tyr Ala Ser Phe Leu Gln Ser Gly Val Pro Ser Arg Phe Ser Gly
         50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ala Asn Pro Ala Pro Leu
                 85                  90                  95

Thr Phe Gly Gln Gly Thr Lys Val Glu Met Lys Arg
            100                 105

<210> SEQ ID NO 440
<211> LENGTH: 108
<212> TYPE: PRT
<213> ORGANISM: Homo sapiens

<400> SEQUENCE: 440

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Trp Ile Gly Ile Leu
                 20                  25                  30

Leu Asp Trp Tyr Gln Gln Lys Pro Gly Glu Asp Pro Lys Leu Leu Ile
             35                  40                  45

Tyr Tyr Ala Ser Phe Leu Gln Ser Gly Val Pro Ser Arg Phe Ser Gly
         50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ala Asn Pro Ala Pro Leu
                 85                  90                  95

Met Phe Gly Gln Gly Thr Lys Val Glu Ile Lys Arg
            100                 105

<210> SEQ ID NO 441
<211> LENGTH: 108
<212> TYPE: PRT
<213> ORGANISM: Homo sapiens

<400> SEQUENCE: 441

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Trp Ile Gly Ile Leu
                 20                  25                  30

Leu Asp Trp Tyr Gln Gln Lys Pro Gly Lys Ala Pro Lys Leu Leu Ile
             35                  40                  45

Tyr Tyr Ala Ser Phe Leu Gln Ser Gly Val Pro Ser Arg Phe Ser Gly
         50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ala Asn Pro Ala Pro Leu
                 85                  90                  95

Thr Phe Gly Gln Gly Thr Lys Val Glu Ile Lys Arg
            100                 105

<210> SEQ ID NO 442
<211> LENGTH: 108
<212> TYPE: PRT
<213> ORGANISM: Homo sapiens

<400> SEQUENCE: 442
```

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Trp Ile Gly Ile Leu
            20                  25                  30

Val Asp Trp Tyr Gln Gln Lys Pro Gly Lys Ala Pro Lys Leu Leu Ile
            35                  40                  45

Tyr Tyr Ala Ser Phe Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Pro Ala Pro Leu
            85                  90                  95

Thr Phe Gly Gln Gly Thr Lys Val Glu Ile Lys Arg
            100                 105

<210> SEQ ID NO 443
<211> LENGTH: 108
<212> TYPE: PRT
<213> ORGANISM: Homo sapiens

<400> SEQUENCE: 443

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Trp Ile Gly Ile Leu
            20                  25                  30

Leu Asp Trp Tyr Gln Gln Lys Pro Gly Lys Ala Pro Lys Leu Leu Ile
            35                  40                  45

Tyr Tyr Ala Ser Phe Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Pro Ala Pro Leu
            85                  90                  95

Arg Phe Gly Gln Gly Thr Lys Val Glu Ile Lys Arg
            100                 105

<210> SEQ ID NO 444
<211> LENGTH: 108
<212> TYPE: PRT
<213> ORGANISM: Homo sapiens

<400> SEQUENCE: 444

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Trp Ile Gly Ile Leu
            20                  25                  30

Ile Asp Trp Tyr Gln Gln Lys Pro Gly Lys Ala Pro Lys Leu Leu Ile
            35                  40                  45

Tyr Tyr Ala Ser Phe Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Pro Ala Pro Leu
            85                  90                  95

Thr Phe Gly Gln Gly Thr Lys Val Glu Ile Lys Arg
            100                 105

```
<210> SEQ ID NO 445
<211> LENGTH: 108
<212> TYPE: PRT
<213> ORGANISM: Homo sapiens

<400> SEQUENCE: 445

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Trp Ile Gly Asn Leu
            20                  25                  30

Val Asp Trp Tyr Gln Gln Lys Pro Gly Lys Ala Pro Lys Leu Leu Ile
        35                  40                  45

Tyr Tyr Ala Ser Phe Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Pro Ala Pro Leu
                85                  90                  95

Thr Phe Gly Gln Gly Thr Lys Val Glu Ile Lys Arg
            100                 105

<210> SEQ ID NO 446
<211> LENGTH: 108
<212> TYPE: PRT
<213> ORGANISM: Homo sapiens

<400> SEQUENCE: 446

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Trp Ile Gly Asn Leu
            20                  25                  30

Val Asp Trp Tyr Gln Gln Lys Pro Gly Lys Ala Pro Lys Leu Leu Ile
        35                  40                  45

Tyr Tyr Ala Ser Phe Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Pro Ala Pro Pro
                85                  90                  95

Thr Phe Gly Gln Gly Thr Lys Val Glu Ile Lys Arg
            100                 105

<210> SEQ ID NO 447
<211> LENGTH: 108
<212> TYPE: PRT
<213> ORGANISM: Homo sapiens

<400> SEQUENCE: 447

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Trp Ile Gly Ile Asn
            20                  25                  30

Leu Asp Trp Tyr Gln Gln Lys Pro Gly Lys Ala Pro Lys Leu Leu Ile
            35                  40                  45

Tyr Tyr Ala Ser Phe Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
```

-continued

```
                65                  70                  75                  80
Glu Asp Phe Ala Thr Tyr Tyr Cys Gln Gln Ala Asn Pro Ala Pro Leu
                    85                  90                  95

Thr Phe Gly Gln Gly Thr Lys Val Glu Ile Lys Arg
                100                 105
```

<210> SEQ ID NO 448
<211> LENGTH: 108
<212> TYPE: PRT
<213> ORGANISM: Homo sapiens

<400> SEQUENCE: 448

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asn Ile Gly Asn Leu
                20                  25                  30

Leu Asp Trp Tyr Gln Gln Lys Pro Gly Lys Ala Pro Lys Leu Leu Ile
            35                  40                  45

Tyr Tyr Ala Ser Phe Leu Gln Ser Gly Val Pro Ser Arg Phe Ser Gly
    50                  55                  60

Ser Gly Phe Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Pro Ala Pro Leu
                    85                  90                  95

Thr Phe Gly Gln Gly Thr Lys Val Glu Ile Lys Arg
                100                 105
```

<210> SEQ ID NO 449
<211> LENGTH: 108
<212> TYPE: PRT
<213> ORGANISM: Homo sapiens

<400> SEQUENCE: 449

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Trp Ile Gly Ile Asn
                20                  25                  30

Leu Asp Trp Tyr Gln Gln Lys Pro Gly Lys Ala Pro Arg Leu Leu Ile
            35                  40                  45

Tyr Tyr Ala Ser Phe Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Pro Ala Pro Leu
                    85                  90                  95

Thr Phe Gly Gln Gly Thr Lys Val Glu Ile Lys Arg
                100                 105
```

<210> SEQ ID NO 450
<211> LENGTH: 119
<212> TYPE: PRT
<213> ORGANISM: Homo sapiens

<400> SEQUENCE: 450

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ala Glu Gln
                20                  25                  30
```

```
Pro Met Thr Trp Ala Arg Gln Ala Pro Gly Lys Gly Leu Glu Trp Val
        35                  40                  45

Ser Ser Ile Ser Ser Phe Gly Asp Leu Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Gly Val Tyr Arg Ile Ser Arg Phe Asp Tyr Trp Gly Gln Gly
            100                 105                 110

Thr Leu Val Thr Val Ser Ser
            115

<210> SEQ ID NO 451
<211> LENGTH: 127
<212> TYPE: PRT
<213> ORGANISM: Unknown
<220> FEATURE:
<223> OTHER INFORMATION: Camelid

<400> SEQUENCE: 451

Glu Val Gln Leu Val Glu Ser Gly Gly Gly Leu Val Gln Ala Gly Gly
 1               5                  10                  15

Ser Leu Arg Leu Ser Cys Ala Ala Ser Gly Arg Thr Phe Ser Asn Tyr
             20                  25                  30

Val Met Gly Trp Phe Arg Gln Ala Pro Gly Lys Glu Arg Asp Phe Val
         35                  40                  45

Val Gly Ile Gly Arg Ser Gly Gly Asp Asn Thr Tyr Tyr Ala Asp Ser
 50                  55                  60

Val Lys Gly Arg Phe Thr Ile Ser Trp Asp Asn Ala Lys Asn Thr Met
 65                  70                  75                  80

Tyr Leu Gln Met Asn Ser Leu Lys Pro Glu Asp Thr Ala Val Tyr Tyr
                 85                  90                  95

Cys Ala Ala Ser Thr Tyr Ser Arg Asp Thr Ile Phe Thr Lys Trp Ala
            100                 105                 110

Asn Tyr Asn Tyr Trp Gly Gln Gly Thr Gln Val Thr Val Ser Ser
        115                 120                 125

<210> SEQ ID NO 452
<211> LENGTH: 127
<212> TYPE: PRT
<213> ORGANISM: Unknown
<220> FEATURE:
<223> OTHER INFORMATION: Camelid

<400> SEQUENCE: 452

Gln Val Gln Leu Gln Glu Ser Gly Gly Gly Leu Val Lys Ala Gly Gly
 1               5                  10                  15

Ser Leu Arg Leu Ser Cys Ala Ala Ser Gly Arg Thr Phe Ser Ser Tyr
             20                  25                  30

Val Met Gly Trp Phe Arg Gln Ala Pro Gly Lys Glu Arg Glu Phe Val
         35                  40                  45

Gly Ala Ile His Trp Ser Gly Arg Thr Tyr Tyr Ala Asp Ser Val
 50                  55                  60

Lys Gly Arg Phe Thr Ile Ser Ser Asp Asn Ala Lys Asn Thr Leu Tyr
 65                  70                  75                  80

Leu Gln Met Asn Ser Leu Lys Pro Glu Asp Thr Ala Val Tyr Tyr Cys
```

85                  90                  95
Ala Ala Ser Arg Ile Ile Tyr Ser Tyr Val Asn Tyr Val Asn Pro Gly
                100                 105                 110

Glu Tyr Asp Tyr Trp Gly Gln Gly Thr Gln Val Thr Val Ser Ser
        115                 120                 125

<210> SEQ ID NO 453
<211> LENGTH: 122
<212> TYPE: PRT
<213> ORGANISM: Unknown
<220> FEATURE:
<223> OTHER INFORMATION: Camelid

<400> SEQUENCE: 453

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser His
            20                  25                  30

Tyr Met Ser Trp Phe Arg Gln Ala Pro Gly Lys Glu Arg Glu Phe Val
        35                  40                  45

Ala Ala Ile Thr Ser Ser Arg Thr Tyr Tyr Thr Glu Ser Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Ser Glu Asp Thr Ala Val Tyr Tyr Cys Ala
                85                  90                  95

Ala Asp Arg Thr Phe Tyr Gly Ser Thr Trp Ser Lys Tyr Asp Tyr Arg
            100                 105                 110

Gly Gln Gly Thr Gln Val Thr Val Ser Ser
        115                 120

<210> SEQ ID NO 454
<211> LENGTH: 129
<212> TYPE: PRT
<213> ORGANISM: Unknown
<220> FEATURE:
<223> OTHER INFORMATION: Camelid

<400> SEQUENCE: 454

Gln Val Gln Leu Gln Glu Ser Gly Gly Gly Leu Val Gln Ala Gly Gly
1               5                   10                  15

Ser Leu Arg Leu Ser Cys Ala Ala Ser Gly Arg Thr Phe Ser Lys Tyr
            20                  25                  30

Ala Met Gly Trp Phe Arg Gln Ala Pro Gly Lys Glu Arg Glu Phe Val
        35                  40                  45

Ser Ala Ile Ser Trp Ser Asp Gly Ser Thr Tyr Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Val Asn Ser Leu Lys Pro Glu Asp Thr Ala Val Tyr Tyr Cys
                85                  90                  95

Ala Ala Thr Tyr Leu Val Asp Val Trp Ala Val His Val Pro Ile Arg
            100                 105                 110

Pro Tyr Glu Tyr Asp Tyr Trp Gly Gln Gly Thr Gln Val Thr Val Ser
        115                 120                 125

Ser

<210> SEQ ID NO 455
<211> LENGTH: 125
<212> TYPE: PRT
<213> ORGANISM: Unknown
<220> FEATURE:
<223> OTHER INFORMATION: Camelid

<400> SEQUENCE: 455

Gln Val Gln Leu Gln Asp Ser Gly Gly Gly Leu Val Gln Ala Gly Asp
1               5                   10                  15

Ser Leu Arg Leu Ser Cys Ala Ala Ser Gly Arg Ser Phe Gly Gly Tyr
            20                  25                  30

Ala Met Gly Trp Phe Arg Gln Ala Pro Gly Lys Glu Arg Glu Phe Val
        35                  40                  45

Ala Ala Ile Ser Trp Ser Gly Gly Ser Thr Tyr Tyr Ala Asp Ser Leu
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Leu Tyr Tyr Cys
                85                  90                  95

Ala Ala Gly Leu Arg Pro Ser Pro Asn Tyr Asn His Glu Arg Ser Tyr
            100                 105                 110

Asp Tyr Trp Gly Gln Gly Thr Gln Val Thr Val Ser Ser
        115                 120                 125

<210> SEQ ID NO 456
<211> LENGTH: 129
<212> TYPE: PRT
<213> ORGANISM: Unknown
<220> FEATURE:
<223> OTHER INFORMATION: Camelid

<400> SEQUENCE: 456

Gln Val Gln Leu Gln Glu Ser Gly Gly Gly Leu Val Gln Ala Gly Gly
1               5                   10                  15

Ser Leu Leu Leu Ser Cys Ala Ala Ser Gly Arg Thr Phe Ser Ser Tyr
            20                  25                  30

Ala Met Gly Trp Phe Arg Gln Ala Pro Gly Lys Glu Arg Glu Phe Val
        35                  40                  45

Ala Ala Ile Asn Trp Ser Gly Ser Thr Ser Tyr Ala Asp Ser Val
    50                  55                  60

Lys Gly Arg Phe Thr Ile Ser Arg Asp Asn Thr Lys Asn Thr Val Tyr
65                  70                  75                  80

Leu Gln Met Asn Ser Leu Lys Pro Glu Asp Thr Ala Ala Phe Tyr Cys
                85                  90                  95

Ala Ala Thr Tyr Asn Pro Tyr Ser Arg Asp His Tyr Phe Pro Arg Met
            100                 105                 110

Thr Thr Glu Tyr Asp Tyr Trp Gly Gln Gly Thr Gln Val Thr Val Ser
        115                 120                 125

Ser

<210> SEQ ID NO 457
<211> LENGTH: 122
<212> TYPE: PRT
<213> ORGANISM: Unknown
<220> FEATURE:
<223> OTHER INFORMATION: Camelid

<400> SEQUENCE: 457

```
Gln Val Gln Leu Gln Glu Ser Gly Gly Arg Leu Val Gln Thr Gly Gly
1               5                   10                  15

Ser Leu Arg Leu Ser Cys Ala Ala Ser Gly Gly Thr Phe Gly Thr Tyr
            20                  25                  30

Ala Leu Gly Trp Phe Arg Gln Ala Pro Gly Lys Glu Arg Glu Phe Val
            35                  40                  45

Ala Ala Ile Ser Arg Phe Gly Ser Thr Tyr Tyr Ala Asp Ser Val Lys
        50                  55                  60

Gly Arg Phe Thr Ile Ser Arg Asp Asn Ala Asn Asn Thr Val Tyr Leu
65                  70                  75                  80

Glu Met Asn Ser Leu Lys Pro Glu Asp Thr Ala Val Tyr Tyr Cys Ala
                85                  90                  95

Ala Arg Glu Gly Val Ala Leu Gly Leu Arg Asn Asp Ala Asn Tyr Trp
            100                 105                 110

Gly Gln Gly Thr Gln Val Thr Val Ser Ser
            115                 120
```

<210> SEQ ID NO 458
<211> LENGTH: 121
<212> TYPE: PRT
<213> ORGANISM: Unknown
<220> FEATURE:
<223> OTHER INFORMATION: Camelid

<400> SEQUENCE: 458

```
Gln Val Gln Leu Gln Asp Ser Gly Gly Gly Leu Val Gln Ala Gly Gly
1               5                   10                  15

Ser Leu Arg Leu Ser Cys Ala Ala Ser Gly Gly Thr Phe Ser Ser Tyr
            20                  25                  30

Ala Met Gly Trp Phe Arg Gln Ala Pro Gly Lys Glu Arg Glu Phe Val
            35                  40                  45

Ala Ala Ile Gly Leu Asn Thr Tyr Tyr Ala Asp Ser Val Lys Gly Arg
        50                  55                  60

Phe Thr Ile Ser Arg Asp Asn Ala Lys Asn Thr Val Tyr Leu Gln Met
65                  70                  75                  80

Asn Ser Leu Lys Pro Glu Asp Thr Ala Val Tyr Tyr Cys Ala Ala Arg
                85                  90                  95

Thr Ser Gly Val Val Gly Gly Thr Pro Lys Arg Tyr Asp Tyr Trp Gly
            100                 105                 110

Gln Gly Thr Gln Val Thr Val Ser Ser
            115                 120
```

<210> SEQ ID NO 459
<211> LENGTH: 122
<212> TYPE: PRT
<213> ORGANISM: Unknown
<220> FEATURE:
<223> OTHER INFORMATION: Camelid

<400> SEQUENCE: 459

```
Gln Val Gln Leu Gln Glu Ser Gly Gly Gly Ser Val Gln Ala Gly Gly
1               5                   10                  15

Ser Leu Lys Leu Ser Cys Ala Ala Ser Gly Arg Gly Phe Ser Arg Tyr
            20                  25                  30

Ala Met Gly Trp Phe Arg Gln Ala Pro Gly Gln Asp Arg Glu Phe Val
            35                  40                  45

Ala Thr Ile Ser Trp Thr Asn Ser Thr Asp Tyr Ala Asp Ser Val Lys
        50                  55                  60
```

```
Gly Arg Phe Ala Ile Ser Arg Asp Asn Ala Lys Asn Thr Ala Tyr Leu
 65                  70                  75                  80

Gln Met Asn Ser Leu Lys Pro Glu Asp Thr Ala Val Tyr Tyr Cys Ala
                 85                  90                  95

Ala Asp Lys Trp Ala Ser Ser Thr Arg Ser Ile Asp Tyr Asp Tyr Trp
            100                 105                 110

Gly Gln Gly Ile Gln Val Thr Val Ser Ser
        115                 120
```

<210> SEQ ID NO 460
<211> LENGTH: 123
<212> TYPE: PRT
<213> ORGANISM: Unknown
<220> FEATURE:
<223> OTHER INFORMATION: Camelid

<400> SEQUENCE: 460

```
Gln Val Gln Leu Gln Glu Ser Gly Gly Gly Leu Val Gln Ala Gly Gly
  1               5                  10                  15

Ser Leu Arg Leu Ser Cys Ala Ala Ser Gly Arg Thr Phe Ser Asn Tyr
             20                  25                  30

Ala Met Gly Trp Phe Arg Gln Ala Pro Gly Lys Glu Arg Glu Phe Val
         35                  40                  45

Ala Ala Ile Asn Trp Gly Gly Gly Asn Thr Tyr Tyr Ala Asp Ser Val
     50                  55                  60

Lys Gly Arg Phe Thr Ile Ser Arg Asp Asn Ala Lys Asn Thr Val Tyr
 65                  70                  75                  80

Leu Gln Met Asn Ser Leu Lys Pro Glu Asp Thr Ala Val Tyr Tyr Cys
                 85                  90                  95

Ala Ala Ser Glu Trp Gly Gly Ser Asp Tyr Asp His Asp Tyr Asp Tyr
            100                 105                 110

Trp Gly Gln Gly Thr Gln Val Thr Val Ser Ser
        115                 120
```

<210> SEQ ID NO 461
<211> LENGTH: 123
<212> TYPE: PRT
<213> ORGANISM: Unknown
<220> FEATURE:
<223> OTHER INFORMATION: Camelid

<400> SEQUENCE: 461

```
Glu Val Gln Leu Val Glu Ser Gly Gly Gly Leu Val Gln Ala Gly Gly
  1               5                  10                  15

Ser Leu Arg Leu Ser Cys Ala Ala Ser Gly Arg Ser Phe Ser Ser Tyr
             20                  25                  30

Ala Met Ala Trp Phe Arg Gln Ala Pro Gly Lys Glu Arg Glu Phe Val
         35                  40                  45

Ala Ala Ile Ser Trp Gly Gly Gly Ser Thr Tyr Tyr Ala Val Ser Val
     50                  55                  60

Lys Gly Arg Phe Thr Ile Ser Arg Asp Asn Ala Lys Asn Thr Val Tyr
 65                  70                  75                  80

Leu Gln Met Asn Ser Leu Lys Pro Glu Asp Thr Ala Arg Tyr Tyr Cys
                 85                  90                  95

Ala Ala Asp Glu Thr Phe His Ser Ser Ala Tyr Gly Glu Tyr Glu Tyr
            100                 105                 110

Trp Gly Gln Gly Thr Gln Val Thr Val Ser Ser
```

```
                115                 120

<210> SEQ ID NO 462
<211> LENGTH: 133
<212> TYPE: PRT
<213> ORGANISM: Unknown
<220> FEATURE:
<223> OTHER INFORMATION: Camelid

<400> SEQUENCE: 462

Glu Val Gln Leu Val Glu Ser Gly Gly Gly Leu Val Gln Ala Gly Gly
 1               5                  10                  15

Ser Leu Arg Leu Ser Cys Thr Ala Ser Gly Arg Thr Phe Ser Ser Tyr
            20                  25                  30

Ala Met Gly Trp Phe Arg Gln Thr Pro Gly Lys Glu Arg Glu Phe Val
        35                  40                  45

Ala Ala Ile Thr Ser Ser Gly Gly Ser Thr Tyr Tyr Ala Asp Ser Val
    50                  55                  60

Lys Gly Arg Phe Thr Ile Ser Arg Asp Asn Ala Lys Ser Thr Met Tyr
65                  70                  75                  80

Leu Gln Met Asp Ser Leu Met Leu Asp Asp Thr Ser Val Tyr Tyr Cys
                85                  90                  95

Ala Ala Asp Ser Ser Arg Pro Gln Tyr Ser Asp Ser Ala Leu Arg Arg
            100                 105                 110

Ile Leu Ser Leu Ser Asn Ser Tyr Pro Tyr Trp Gly Gln Gly Thr Gln
        115                 120                 125

Val Thr Val Ser Ser
    130

<210> SEQ ID NO 463
<211> LENGTH: 120
<212> TYPE: PRT
<213> ORGANISM: Unknown
<220> FEATURE:
<223> OTHER INFORMATION: Camelid
<221> NAME/KEY: VARIANT
<222> LOCATION: 3, 13
<223> OTHER INFORMATION: Xaa=Orn

<400> SEQUENCE: 463

Glu Val Xaa Leu Val Glu Ser Gly Gly Gly Leu Val Xaa Pro Gly Gly
 1               5                  10                  15

Ser Leu Arg Leu Ser Cys Val Ala Ser Gly Phe Thr Phe Ala Asp Tyr
            20                  25                  30

Ala Met Ser Trp Val Arg Gln Ala Pro Gly Lys Gly Leu Gln Trp Val
        35                  40                  45

Ser Ser Ile Ser Tyr Asn Gly Asp Thr Thr Tyr Tyr Ala Glu Ser Met
    50                  55                  60

Lys Asp Arg Phe Thr Ile Ser Arg Asp Asn Ala Lys Asn Thr Leu Tyr
65                  70                  75                  80

Leu Gln Met Asn Ser Leu Lys Ser Glu Asp Thr Ala Val Tyr Tyr Cys
                85                  90                  95

Ala Ser Ser Gly Ser Tyr Tyr Pro Gly His Phe Glu Ser Trp Gly Gln
            100                 105                 110

Gly Thr Gln Val Thr Val Ser Ser
        115                 120

<210> SEQ ID NO 464
<211> LENGTH: 121
```

```
<212> TYPE: PRT
<213> ORGANISM: Unknown
<220> FEATURE:
<223> OTHER INFORMATION: Camelid

<400> SEQUENCE: 464

Gln Val Gln Leu Gln Glu Ser Gly Gly Gly Leu Val Gln Ala Gly Gly
1               5                   10                  15

Ser Leu Arg Leu Ser Cys Ala Ala Ser Gly Arg Thr Phe Ser Gly Tyr
            20                  25                  30

Ala Met Gly Trp Phe Arg Gln Ala Pro Gly Glu Glu Arg Glu Phe Val
        35                  40                  45

Ala Ala Ile Ser Trp Arg Gly Thr Ser Thr Tyr Tyr Gly Asp Ser Ala
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Ala Gly Ser His Ser Asp Tyr Ala Pro Asp Tyr Asp Tyr Trp Gly
            100                 105                 110

Gln Gly Thr Gln Val Thr Val Ser Ser
        115                 120

<210> SEQ ID NO 465
<211> LENGTH: 123
<212> TYPE: PRT
<213> ORGANISM: Unknown
<220> FEATURE:
<223> OTHER INFORMATION: Camelid

<400> SEQUENCE: 465

Gln Val Gln Leu Gln Glu Ser Gly Gly Gly Leu Val Gln Ala Gly Gly
1               5                   10                  15

Ser Leu Arg Leu Ser Cys Ala Ala Ser Gly Arg Thr Phe Ser Ser Tyr
            20                  25                  30

Ala Ile Gly Trp Phe Arg Gln Ala Pro Gly Lys Glu Arg Glu Phe Val
        35                  40                  45

Ala Ala Ile Ser Trp Gly Gly Ser Asn Thr Tyr Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Ala Gly Glu Val Ser Asn Ser Asp Tyr Ala Tyr Glu Tyr Asp Tyr
            100                 105                 110

Trp Gly Gln Gly Thr Gln Val Thr Val Ser Ser
        115                 120

<210> SEQ ID NO 466
<211> LENGTH: 122
<212> TYPE: PRT
<213> ORGANISM: Unknown
<220> FEATURE:
<223> OTHER INFORMATION: Camelid

<400> SEQUENCE: 466

Gln Val Gln Leu Gln Glu Ser Gly Gly Gly Leu Val Gln Thr Gly Gly
1               5                   10                  15

Ser Leu Arg Leu Ser Cys Ala Ala Ser Gly Arg Tyr Ile Met Gly Trp
```

-continued

```
                20                  25                  30
Phe Arg Gln Ala Pro Gly Lys Glu Arg Glu Phe Val Ala Gly Ile Ser
        35                  40                  45

Arg Ser Gly Ala Ser Thr Ala Tyr Ala Asp Ser Val Lys Asp Arg Phe
 50                  55                  60

Thr Ile Ser Arg Asp Ser Ala Leu Asn Thr Val Tyr Leu Gln Met Asn
 65                  70                  75                  80

Ser Leu Lys Ala Glu Asp Thr Ala Val Tyr Phe Cys Ala Ala Ala Leu
                85                  90                  95

Ala Ile Arg Leu Gly Ile Pro Arg Gly Glu Thr Glu Tyr Glu Tyr Trp
            100                 105                 110

Gly Gln Gly Thr Gln Val Thr Val Ser Ser
        115                 120

<210> SEQ ID NO 467
<211> LENGTH: 121
<212> TYPE: PRT
<213> ORGANISM: Unknown
<220> FEATURE:
<223> OTHER INFORMATION: Camelid

<400> SEQUENCE: 467

Gln Val Lys Leu Glu Glu Ser Gly Gly Gly Leu Val Gln Ala Gly Gly
  1               5                  10                  15

Ser Leu Arg Leu Ser Cys Ser Ala Ser Gly Leu Thr Phe Ser Asn Tyr
                20                  25                  30

Ala Met Ala Trp Phe Arg Gln Ala Pro Gly Lys Glu Arg Glu Phe Val
        35                  40                  45

Ala Thr Ile Ser Gln Arg Gly Gly Met Arg His Tyr Leu Asp Ser Val
 50                  55                  60

Lys Asp Arg Phe Thr Ile Ser Arg Asp Asn Ala Lys Asn Thr Val Tyr
 65                  70                  75                  80

Leu Gln Met Asn Ser Leu Lys Pro Asp Asp Thr Ala Val Tyr Tyr Cys
                85                  90                  95

Ala Ala Asp Leu Met Tyr Gly Val Asp Arg Arg Tyr Asp Tyr Trp Gly
            100                 105                 110

Arg Gly Thr Gln Val Thr Val Ser Ser
        115                 120

<210> SEQ ID NO 468
<211> LENGTH: 127
<212> TYPE: PRT
<213> ORGANISM: Unknown
<220> FEATURE:
<223> OTHER INFORMATION: Camelid

<400> SEQUENCE: 468

Gln Val Lys Leu Glu Glu Ser Gly Gly Gly Leu Val Gln Ala Gly Asp
  1               5                  10                  15

Ser Leu Arg Leu Ser Cys Ala Ala Ser Gly Arg Ser Phe Ser Ser Ile
                20                  25                  30

Thr Met Gly Trp Phe Arg Gln Ala Pro Gly Lys Glu Arg Gln Phe Val
        35                  40                  45

Ser Ala Ile Asn Ser Asn Gly Asn Arg Tyr Tyr Ala Asp Ser Val Lys
 50                  55                  60

Gly Arg Phe Thr Ile Ser Arg Asp Asn Ala Lys Asn Thr Val Tyr Leu
 65                  70                  75                  80
```

```
Gln Met Asn Ser Leu Lys Pro Glu Asp Thr Ala Val Tyr Tyr Cys Ala
                85                  90                  95

Ala Val Gln Ala Tyr Ser Ser Ser Asp Tyr Tyr Ser Gln Glu Gly
            100                 105                 110

Ala Tyr Asp Tyr Trp Gly Gln Gly Thr Gln Val Thr Val Ser Ser
        115                 120                 125
```

<210> SEQ ID NO 469
<211> LENGTH: 126
<212> TYPE: PRT
<213> ORGANISM: Unknown
<220> FEATURE:
<223> OTHER INFORMATION: Camelid

<400> SEQUENCE: 469

```
Glu Val Gln Leu Val Glu Ser Gly Gly Gly Leu Val Gln Ala Gly Gly
  1               5                  10                  15

Ser Leu Arg Leu Ser Cys Ala Val Ser Gly Arg Thr Phe Ser Ser Met
            20                  25                  30

Gly Trp Phe Arg Gln Ala Pro Gly Lys Glu Arg Glu Phe Val Ala Thr
        35                  40                  45

Ile Asn Leu Ser Gly Asp Arg Thr Asp Tyr Ala Asp Ser Val Lys Gly
    50                  55                  60

Arg Phe Thr Ile Ser Arg Asp Asn Pro Lys Asn Thr Val Tyr Leu Gln
65                  70                  75                  80

Met Asp Ser Leu Glu Pro Glu Asp Ser Ala Val Tyr Tyr Cys Ala Gly
                85                  90                  95

Thr Ser Leu Tyr Pro Ser Asn Leu Arg Tyr Tyr Thr Leu Pro Gly Thr
            100                 105                 110

Tyr Ala Asp Trp Gly Gln Gly Thr Gln Val Thr Val Ser Ser
        115                 120                 125
```

<210> SEQ ID NO 470
<211> LENGTH: 126
<212> TYPE: PRT
<213> ORGANISM: Unknown
<220> FEATURE:
<223> OTHER INFORMATION: Camelid

<400> SEQUENCE: 470

```
Gln Val Lys Leu Glu Glu Ser Gly Gly Gly Leu Val Gln Ala Gly Gly
  1               5                  10                  15

Ser Leu Arg Leu Ser Cys Ala Ala Ser Gly Ser Ile Phe Ser Ile Asn
            20                  25                  30

Ala Met Gly Trp Tyr Arg Gln Ala Pro Gly Lys Gln Arg Glu Leu Val
        35                  40                  45

Ala Arg Ile Thr Gly Thr Gly Thr Gly Ile Thr Gly Ala Val Ser Thr
    50                  55                  60

Asn Tyr Ala Asp Ser Val Lys Gly Arg Phe Thr Ile Ser Arg Asp Asn
65                  70                  75                  80

Ala Arg Asn Thr Val Tyr Leu Gln Met Asn Ser Leu Lys Pro Glu Asp
                85                  90                  95

Thr Ala Val Tyr Tyr Cys Ala Ala Asp Arg Ser Arg Thr Ile Val Val
            100                 105                 110

Pro Asp Tyr Trp Gly Gln Gly Thr Gln Val Thr Val Ser Ser
        115                 120                 125
```

<210> SEQ ID NO 471

```
<211> LENGTH: 126
<212> TYPE: PRT
<213> ORGANISM: Unknown
<220> FEATURE:
<223> OTHER INFORMATION: Camelid

<400> SEQUENCE: 471

Gln Val Gln Leu Gln Asp Ser Gly Gly Gly Leu Val Gln Ala Gly Gly
  1               5                  10                  15

Ser Leu Arg Leu Ser Cys Ala Ala Ser Arg Phe Ser Ser Ala Gln Tyr
             20                  25                  30

Ala Ile Gly Trp Phe Arg Gln Ala Pro Gly Lys Glu Arg Glu Gly Val
         35                  40                  45

Ser Tyr Ile Thr Phe Ser Gly Gly Pro Thr Gly Tyr Ala Asp Ser Val
 50                  55                  60

Lys Gly Arg Phe Thr Val Ser Arg Asp Asn Ala Lys Asn Thr Val Tyr
 65                  70                  75                  80

Leu Gln Met Asn Ser Leu Lys Pro Glu Asp Thr Ala Val Tyr Tyr Cys
                 85                  90                  95

Ala Ala Arg Pro Tyr Thr Arg Pro Gly Ser Met Trp Val Ser Ser Leu
            100                 105                 110

Tyr Asp Asn Trp Gly Gln Gly Thr Gln Val Thr Val Ser Ser
            115                 120                 125

<210> SEQ ID NO 472
<211> LENGTH: 123
<212> TYPE: PRT
<213> ORGANISM: Unknown
<220> FEATURE:
<223> OTHER INFORMATION: Camelid

<400> SEQUENCE: 472

Gln Val Gln Leu Gln Glu Ser Gly Gly Arg Leu Val Gln Ala Gly Gly
  1               5                  10                  15

Ser Leu Arg Leu Ser Cys Ala Ala Ser Glu His Thr Phe Arg Gly Tyr
             20                  25                  30

Ala Ile Gly Trp Phe Arg Gln Ala Pro Gly Lys Glu Arg Glu Phe Val
         35                  40                  45

Ser Ser Ile Thr Tyr Asp Gly Thr Leu Thr Asn Tyr Ala Asp Ser Val
 50                  55                  60

Thr Gly Arg Phe Thr Ile Ser Arg Asp Asn Ala Lys Asn Thr Val Tyr
 65                  70                  75                  80

Leu Gln Met Asn Ser Leu Lys Pro Glu Asp Thr Ala Val Tyr Val Cys
                 85                  90                  95

Ala Ala Gly Tyr Ser Tyr Arg Tyr Thr Thr Leu Asn Gln Tyr Asp Ser
            100                 105                 110

Trp Gly Gln Gly Thr Gln Val Thr Val Ser Ser
            115                 120

<210> SEQ ID NO 473
<211> LENGTH: 108
<212> TYPE: PRT
<213> ORGANISM: Homo sapiens

<400> SEQUENCE: 473

Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Ser Ile Ile Lys His
             20                  25                  30
```

```
Leu Lys Trp Tyr Gln Gln Lys Pro Gly Lys Ala Pro Lys Leu Leu Ile
         35                  40                  45

Tyr Gly Ala Ser Arg Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Gly Ala Arg Trp Pro Gln
                 85                  90                  95

Thr Phe Gly Gln Gly Thr Lys Val Glu Ile Lys Arg
            100                 105
```

<210> SEQ ID NO 474
<211> LENGTH: 108
<212> TYPE: PRT
<213> ORGANISM: Homo sapiens

<400> SEQUENCE: 474

```
Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Ser Ile Phe Arg His
                 20                  25                  30

Leu Lys Trp Tyr Gln Gln Lys Pro Gly Lys Ala Pro Lys Leu Leu Ile
         35                  40                  45

Tyr Ala Ala Ser Arg Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Val Ala Leu Tyr Pro Lys
                 85                  90                  95

Thr Phe Gly Gln Gly Thr Lys Val Glu Ile Lys Arg
            100                 105
```

<210> SEQ ID NO 475
<211> LENGTH: 108
<212> TYPE: PRT
<213> ORGANISM: Homo sapiens

<400> SEQUENCE: 475

```
Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Ser Ile Tyr Tyr His
                 20                  25                  30

Leu Lys Trp Tyr Gln Gln Lys Pro Gly Lys Ala Pro Lys Leu Leu Ile
         35                  40                  45

Tyr Lys Ala Ser Thr Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Val Arg Lys Val Pro Arg
                 85                  90                  95

Thr Phe Gly Gln Gly Thr Lys Val Glu Ile Lys Arg
            100                 105
```

<210> SEQ ID NO 476
<211> LENGTH: 108
<212> TYPE: PRT
<213> ORGANISM: Homo sapiens -continued

<400> SEQUENCE: 476

Asp Ile Gln Thr Thr Gln Ser Pro Ser Ser Leu Ser Ala Ser Val Gly
1               5                   10                  15

Asp Arg Val Thr Ile Thr Cys Arg Ala Ser Gln Tyr Ile Gly Arg Tyr
            20                  25                  30

Leu Arg Trp Tyr Gln Gln Lys Pro Gly Lys Ala Pro Lys Leu Leu Ile
        35                  40                  45

Tyr Asp Ser Ser Val Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Arg Tyr Arg Met Pro Tyr
                85                  90                  95

Thr Phe Gly Gln Gly Thr Arg Val Glu Ile Lys Arg
            100                 105

<210> SEQ ID NO 477
<211> LENGTH: 108
<212> TYPE: PRT
<213> ORGANISM: Homo sapiens

<400> SEQUENCE: 477

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Tyr Ile Gly Arg Tyr
            20                  25                  30

Leu Arg Trp Tyr Gln Gln Lys Pro Gly Lys Ala Pro Lys Leu Leu Ile
        35                  40                  45

Tyr Asp Ser Ser Val Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Arg Tyr Met Gln Pro Phe
                85                  90                  95

Thr Phe Gly Gln Gly Thr Lys Val Glu Ile Lys Arg
            100                 105

<210> SEQ ID NO 478
<211> LENGTH: 108
<212> TYPE: PRT
<213> ORGANISM: Homo sapiens

<400> SEQUENCE: 478

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Trp Ile Gly Arg Tyr
            20                  25                  30

Leu Arg Trp Tyr Gln Gln Lys Pro Gly Lys Ala Pro Lys Leu Leu Ile
        35                  40                  45

Tyr Asn Gly Ser Gln Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Arg Tyr Leu Gln Pro Tyr
                85                  90                  95

```
Thr Phe Gly Gln Gly Thr Lys Val Glu Ile Lys Arg
            100                 105
```

```
<210> SEQ ID NO 479
<211> LENGTH: 108
<212> TYPE: PRT
<213> ORGANISM: Homo sapiens

<400> SEQUENCE: 479

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Tyr Ile Ser Arg Gln
            20                  25                  30

Leu Arg Trp Tyr Gln Gln Lys Pro Gly Lys Ala Pro Arg Leu Leu Ile
        35                  40                  45

Tyr Gly Ala Ser Val Leu Gln Ser Gly Ile Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Arg Tyr Ile Thr Pro Tyr
                85                  90                  95

Thr Phe Gly Gln Gly Thr Lys Val Glu Val Lys Arg
            100                 105
```

```
<210> SEQ ID NO 480
<211> LENGTH: 108
<212> TYPE: PRT
<213> ORGANISM: Homo sapiens

<400> SEQUENCE: 480

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Tyr Ile Gly Arg Tyr
            20                  25                  30

Leu Arg Trp Tyr Gln Gln Lys Pro Gly Lys Ala Pro Lys Leu Leu Ile
        35                  40                  45

Tyr Asp Ser Ser Val Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Arg Tyr Ser Ser Pro Tyr
                85                  90                  95

Thr Phe Gly Gln Gly Thr Lys Val Glu Ile Lys Arg
            100                 105
```

```
<210> SEQ ID NO 481
<211> LENGTH: 108
<212> TYPE: PRT
<213> ORGANISM: Homo sapiens

<400> SEQUENCE: 481

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Trp Ile His Arg Gln
            20                  25                  30

Leu Lys Trp Tyr Gln Gln Lys Pro Gly Lys Ala Pro Lys Leu Leu Ile
        35                  40                  45

Tyr Tyr Ala Ser Ile Leu Gln Ser Gly Val Pro Ser Arg Phe Ser Gly
```

```
                50                  55                  60
Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Thr Phe Ser Lys Pro Ser
                 85                  90                  95

Thr Phe Gly Gln Gly Thr Lys Val Glu Ile Lys Arg
            100                 105

<210> SEQ ID NO 482
<211> LENGTH: 108
<212> TYPE: PRT
<213> ORGANISM: Homo sapiens

<400> SEQUENCE: 482

Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Lys Ile Ala Thr Tyr
                 20                  25                  30

Leu Asn Trp Tyr Gln Gln Lys Pro Gly Lys Ala Pro Lys Leu Leu Ile
             35                  40                  45

Tyr Arg Ser Ser Ser Leu Gln Ser Ala Val Pro Ser Arg Phe Ser Gly
         50                  55                  60

Ser Gly Ser Gly Thr Val Phe Thr Leu Thr Ile Ser Ser Leu Gln Pro
 65                  70                  75                  80

Glu Asp Phe Ala Thr Tyr Tyr Cys Gln Gln Thr Tyr Ala Val Pro Pro
                 85                  90                  95

Thr Phe Gly Gln Gly Thr Lys Val Glu Ile Lys Arg
            100                 105

<210> SEQ ID NO 483
<211> LENGTH: 108
<212> TYPE: PRT
<213> ORGANISM: Homo sapiens

<400> SEQUENCE: 483

Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Trp Ile Asp Thr Gly
                 20                  25                  30

Leu Ala Trp Tyr Gln Gln Lys Pro Gly Lys Ala Pro Arg Leu Leu Ile
             35                  40                  45

Tyr Asn Val Ser Arg Leu Gln Ser Gly Val Pro Ser Arg Phe Ser Gly
         50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Trp Gly Ser Pro Thr
                 85                  90                  95

Thr Phe Gly Gln Gly Thr Lys Val Glu Ile Lys Arg
            100                 105

<210> SEQ ID NO 484
<211> LENGTH: 108
<212> TYPE: PRT
<213> ORGANISM: Homo sapiens

<400> SEQUENCE: 484

Asp Ile Gln Met Thr Gln Ser Pro Ser Ser Leu Ser Ala Ser Val Gly
  1               5                  10                  15
```

```
Asp Arg Val Thr Ile Thr Cys Arg Ala Ser Gln Glu Ile Tyr Ser Trp
            20                  25                  30

Leu Ala Trp Tyr Gln Gln Arg Pro Gly Lys Ala Pro Lys Leu Leu Ile
        35                  40                  45

Tyr Asn Ala Ser His Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Val Ile Gly Asp Pro Val
                85                  90                  95

Thr Phe Gly Gln Gly Thr Lys Val Glu Ile Lys Arg
            100                 105
```

<210> SEQ ID NO 485
<211> LENGTH: 108
<212> TYPE: PRT
<213> ORGANISM: Homo sapiens

<400> SEQUENCE: 485

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Thr Leu Leu Ile
        35                  40                  45

Tyr Arg Leu Ser Val Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Thr Tyr Asn Val Pro Pro
                85                  90                  95

Thr Phe Gly Gln Gly Thr Lys Val Glu Ile Lys Arg
            100                 105
```

<210> SEQ ID NO 486
<211> LENGTH: 108
<212> TYPE: PRT
<213> ORGANISM: Homo sapiens

<400> SEQUENCE: 486

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Arg Asn Ser Phe Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Thr Tyr Thr Val Pro Pro
                85                  90                  95

Thr Phe Gly Gln Gly Thr Lys Val Glu Ile Lys Gln
            100                 105
```

<210> SEQ ID NO 487

```
<211> LENGTH: 108
<212> TYPE: PRT
<213> ORGANISM: Homo sapiens

<400> SEQUENCE: 487

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Arg Asn Ser Gln Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Thr Phe Ala Val Pro Pro
                85                  90                  95

Thr Phe Gly Gln Gly Thr Lys Val Glu Ile Lys Arg
            100                 105

<210> SEQ ID NO 488
<211> LENGTH: 35
<212> TYPE: PRT
<213> ORGANISM: Homo sapiens
<220> FEATURE:
<223> OTHER INFORMATION: Consensus
<221> NAME/KEY: VARIANT
<222> LOCATION: 30, 31
<223> OTHER INFORMATION: Xaa = Any Amino Acid

<400> SEQUENCE: 488

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Xaa Xaa Tyr
            20                  25                  30

Asn Met Ser
        35

<210> SEQ ID NO 489
<211> LENGTH: 123
<212> TYPE: PRT
<213> ORGANISM: Homo sapiens

<400> SEQUENCE: 489

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Lys Tyr
            20                  25                  30

Trp Met Ser Trp Val Arg Gln Ala Pro Gly Lys Gly Leu Glu Trp Val
        35                  40                  45

Ser Ser Ile Asp Phe Met Gly Pro His Thr Tyr Tyr Ala Asp Ser Val
50                  55                  60

Lys Gly Arg Phe Thr Ile Ser Arg Asp Asn Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Arg Thr Ser Met Leu Pro Met Lys Gly Lys Phe Asp Tyr
            100                 105                 110

Trp Gly Gln Gly Thr Leu Val Thr Val Ser Ser
```

```
                115                 120

<210> SEQ ID NO 490
<211> LENGTH: 118
<212> TYPE: PRT
<213> ORGANISM: Homo sapiens

<400> SEQUENCE: 490

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Tyr Asp Tyr
            20                  25                  30

Asn Met Ser Trp Val Arg Gln Ala Pro Gly Lys Gly Leu Glu Trp Val
        35                  40                  45

Ser Thr Ile Thr His Thr Gly Val Thr Tyr Tyr Ala Asp Ser Val
    50                  55                  60

Lys Gly Arg Phe Thr Ile Ser Arg Asp Asn Ser Lys Asn Thr Leu Tyr
 65                 70                  75                  80

Leu Gln Met Asn Ser Leu Arg Ala Glu Asp Thr Ala Val Tyr Tyr Cys
                85                  90                  95

Ala Lys Gln Asn Pro Ser Tyr Gln Phe Asp Tyr Trp Gly Gln Gly Thr
            100                 105                 110

Leu Val Thr Val Ser Ser
        115

<210> SEQ ID NO 491
<211> LENGTH: 118
<212> TYPE: PRT
<213> ORGANISM: Homo sapiens

<400> SEQUENCE: 491

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe His Arg Tyr
            20                  25                  30

Ser Met Ser Trp Val Arg Gln Ala Pro Gly Lys Gly Leu Glu Trp Val
        35                  40                  45

Ser Thr Ile Leu Pro Gly Gly Asp Val Thr Tyr Tyr Ala Asp Ser Val
    50                  55                  60

Lys Gly Arg Phe Thr Ile Ser Arg Asp Asn Ser Lys Asn Thr Leu Tyr
 65                 70                  75                  80

Leu Gln Met Asn Ser Leu Arg Ala Glu Asp Thr Ala Val Tyr Tyr Cys
                85                  90                  95

Ala Lys Gln Thr Pro Asp Tyr Met Phe Asp Tyr Trp Gly Gln Gly Thr
            100                 105                 110

Leu Val Thr Val Ser Ser
        115

<210> SEQ ID NO 492
<211> LENGTH: 117
<212> TYPE: PRT
<213> ORGANISM: Homo sapiens

<400> SEQUENCE: 492

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Trp Lys Tyr
            20                  25                  30
```

```
Asn Met Ala Trp Val Arg Gln Ala Pro Gly Lys Gly Leu Glu Trp Val
            35                  40                  45

Ser Thr Ile Leu Gly Glu Gly Asn Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Thr Met Asp Tyr Lys Phe Asp Tyr Trp Gly Gln Gly Thr Leu
            100                 105                 110

Val Thr Val Ser Ser
        115

<210> SEQ ID NO 493
<211> LENGTH: 118
<212> TYPE: PRT
<213> ORGANISM: Homo sapiens

<400> SEQUENCE: 493

Glu Val Gln Leu Leu Glu Ser Gly Gly Gly Leu Val Gln Pro Gly Gly
1               5                   10                  15

Ser Leu Arg Leu Ser Cys Thr Ala Ser Gly Phe Thr Phe Asp Glu Tyr
            20                  25                  30

Asn Met Ser Trp Val Arg Gln Ala Pro Gly Lys Gly Leu Glu Trp Val
            35                  40                  45

Ser Thr Ile Leu Pro His Gly Asp Arg Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gln Asp Pro Leu Tyr Arg Phe Asp Tyr Trp Gly Gln Gly Thr
            100                 105                 110

Leu Val Thr Val Ser Ser
        115

<210> SEQ ID NO 494
<211> LENGTH: 120
<212> TYPE: PRT
<213> ORGANISM: Homo sapiens

<400> SEQUENCE: 494

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Asp Leu Tyr
            20                  25                  30

Asp Met Ser Trp Val Arg Gln Ala Pro Gly Lys Gly Leu Glu Trp Val
            35                  40                  45

Ser Ser Ile Val Asn Ser Gly Val Arg Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Leu Asn Gln Ser Tyr His Trp Asp Phe Asp Tyr Trp Gly Gln
            100                 105                 110
```

Gly Thr Leu Val Thr Val Ser Ser
        115                 120

<210> SEQ ID NO 495
<211> LENGTH: 118
<212> TYPE: PRT
<213> ORGANISM: Homo sapiens

<400> SEQUENCE: 495

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Asp Tyr
            20                  25                  30

Arg Met Ser Trp Val Arg Gln Ala Pro Gly Lys Gly Leu Glu Trp Val
        35                  40                  45

Ser Thr Ile Ile Ser Asn Gly Lys Phe Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gln Asp Trp Met Tyr Met Phe Asp Tyr Trp Gly Gln Gly Thr
            100                 105                 110

Leu Val Thr Val Ser Ser
        115

<210> SEQ ID NO 496
<211> LENGTH: 108
<212> TYPE: PRT
<213> ORGANISM: Homo sapiens

<400> SEQUENCE: 496

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Arg Asn Ser Pro Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Thr Tyr Arg Val Pro Pro
                85                  90                  95

Thr Phe Gly Gln Gly Thr Lys Val Glu Ile Lys Arg
            100                 105

<210> SEQ ID NO 497
<211> LENGTH: 108
<212> TYPE: PRT
<213> ORGANISM: Homo sapiens

<400> SEQUENCE: 497

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln His Ile His Arg Glu
            20                  25                  30

```
Leu Arg Trp Tyr Gln Gln Lys Pro Gly Lys Ala Pro Lys Leu Leu Ile
            35                  40                  45

Tyr Gln Ala Ser Arg Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Lys Tyr Leu Pro Pro Tyr
                85                  90                  95

Thr Phe Gly Gln Gly Thr Lys Val Glu Ile Lys Arg
            100                 105
```

<210> SEQ ID NO 498
<211> LENGTH: 108
<212> TYPE: PRT
<213> ORGANISM: Homo sapiens

<400> SEQUENCE: 498

```
Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln His Ile His Arg Glu
                20                  25                  30

Leu Arg Trp Tyr Gln Gln Lys Pro Gly Lys Ala Pro Lys Leu Leu Ile
            35                  40                  45

Tyr Gln Ala Ser Arg Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Arg Tyr Arg Val Pro Tyr
                85                  90                  95

Thr Phe Gly Gln Gly Thr Lys Val Glu Ile Lys Arg
            100                 105
```

<210> SEQ ID NO 499
<211> LENGTH: 108
<212> TYPE: PRT
<213> ORGANISM: Homo sapiens

<400> SEQUENCE: 499

```
Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Ser Ile Gly Arg Arg
                20                  25                  30

Leu Lys Trp Tyr Gln Gln Lys Pro Gly Ala Ala Pro Arg Leu Leu Ile
            35                  40                  45

Tyr Arg Thr Ser Trp Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Thr Ser Gln Trp Pro His
                85                  90                  95

Thr Phe Gly Gln Gly Thr Lys Val Glu Ile Lys Arg
            100                 105
```

<210> SEQ ID NO 500
<211> LENGTH: 108
<212> TYPE: PRT
<213> ORGANISM: Homo sapiens

<400> SEQUENCE: 500

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Lys Ile Tyr Lys Asn
            20                  25                  30

Leu Arg Trp Tyr Gln Gln Lys Pro Gly Lys Ala Pro Lys Leu Leu Ile
        35                  40                  45

Tyr Asn Ser Ser Ile Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Arg Tyr Leu Ser Pro Tyr
                85                  90                  95

Thr Phe Gly Gln Gly Thr Lys Val Glu Ile Lys Arg
            100                 105

<210> SEQ ID NO 501
<211> LENGTH: 108
<212> TYPE: PRT
<213> ORGANISM: Homo sapiens

<400> SEQUENCE: 501

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Lys Ile Tyr Asn Asn
            20                  25                  30

Leu Arg Trp Tyr Gln Gln Lys Pro Gly Lys Ala Pro Lys Leu Leu Ile
        35                  40                  45

Tyr Asn Thr Ser Ile Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Arg Trp Arg Ala Pro Tyr
                85                  90                  95

Thr Phe Gly Gln Gly Thr Lys Val Glu Ile Lys Arg
            100                 105

<210> SEQ ID NO 502
<211> LENGTH: 108
<212> TYPE: PRT
<213> ORGANISM: Homo sapiens

<400> SEQUENCE: 502

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Trp Ile Tyr Lys Ser
            20                  25                  30

Leu Gly Trp Tyr Gln Gln Lys Pro Gly Lys Ala Pro Lys Leu Leu Ile
        35                  40                  45

Tyr Gln Ser Ser Leu Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr His Gln Met Pro Arg
                85                  90                  95

Thr Phe Gly Gln Gly Thr Lys Val Glu Ile Lys Arg

-continued

```
                100                 105
```

<210> SEQ ID NO 503
<211> LENGTH: 108
<212> TYPE: PRT
<213> ORGANISM: Homo sapiens

<400> SEQUENCE: 503

```
Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Trp Ile Tyr Arg His
                 20                  25                  30

Leu Arg Trp Tyr Gln Gln Lys Pro Gly Lys Ala Pro Lys Leu Leu Ile
             35                  40                  45

Tyr Asp Ala Ser Arg Leu Gln Ser Gly Val Pro Thr Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Thr His Asn Pro Pro Lys
                 85                  90                  95

Thr Phe Gly Gln Gly Thr Lys Val Glu Ile Lys Arg
            100                 105
```

<210> SEQ ID NO 504
<211> LENGTH: 116
<212> TYPE: PRT
<213> ORGANISM: Homo sapiens

<400> SEQUENCE: 504

```
Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Trp Pro Tyr
                 20                  25                  30

Thr Met Ser Trp Val Arg Gln Ala Pro Gly Lys Gly Leu Glu Trp Val
             35                  40                  45

Ser Thr Ile Ser Pro Phe Gly Ser Thr Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Gly Gly Lys Asp Phe Asp Tyr Trp Gly Gln Gly Thr Leu Val
            100                 105                 110

Thr Val Ser Ser
        115
```

<210> SEQ ID NO 505
<211> LENGTH: 117
<212> TYPE: PRT
<213> ORGANISM: Homo sapiens

<400> SEQUENCE: 505

```
Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Trp Pro Tyr
                 20                  25                  30

Thr Met Ser Trp Val Arg Gln Ala Pro Gly Lys Gly Leu Glu Trp Val
             35                  40                  45
```

```
Ser Thr Ile Ser Pro Phe Gly Ser Thr Thr Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Asn Leu Glu Pro Phe Asp Tyr Trp Gly Gln Gly Thr Leu
                100                 105                 110

Val Thr Val Ser Ser
        115

<210> SEQ ID NO 506
<211> LENGTH: 117
<212> TYPE: PRT
<213> ORGANISM: Homo sapiens

<400> SEQUENCE: 506

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Trp Pro Tyr
            20                  25                  30

Thr Met Ser Trp Val Arg Gln Ala Pro Gly Lys Gly Leu Glu Trp Val
        35                  40                  45

Ser Thr Ile Ser Pro Phe Gly Ser Thr Thr Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Lys Leu Ser Asn Gly Phe Asp Tyr Trp Gly Gln Gly Thr Leu
                100                 105                 110

Val Thr Val Ser Ser
        115

<210> SEQ ID NO 507
<211> LENGTH: 118
<212> TYPE: PRT
<213> ORGANISM: Homo sapiens

<400> SEQUENCE: 507

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Trp Pro Tyr
            20                  25                  30

Thr Met Ser Trp Val Arg Gln Ala Pro Gly Lys Gly Leu Glu Trp Val
        35                  40                  45

Ser Thr Ile Ser Pro Phe Gly Ser Thr Thr Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Val Val Lys Asp Asn Thr Phe Asp Tyr Trp Gly Gln Gly Thr
                100                 105                 110

Leu Val Thr Val Ser Ser
        115
```

<210> SEQ ID NO 508
<211> LENGTH: 118
<212> TYPE: PRT
<213> ORGANISM: Homo sapiens

<400> SEQUENCE: 508

```
Glu Val Gln Leu Leu Glu Ser Gly Gly Gly Leu Val Gln Pro Gly Gly
 1               5                   10                  15

Ser Leu Arg Leu Ser Cys Ala Ala Ser Gly Phe Thr Phe Trp Pro Tyr
            20                  25                  30

Thr Met Ser Trp Val Arg Gln Ala Pro Gly Lys Gly Leu Glu Trp Val
        35                  40                  45

Ser Thr Ile Ser Pro Phe Gly Ser Thr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asn Thr Gly Gly Lys Gln Phe Asp Tyr Trp Gly Gln Gly Thr
            100                 105                 110

Leu Val Thr Val Ser Ser
        115
```

<210> SEQ ID NO 509
<211> LENGTH: 118
<212> TYPE: PRT
<213> ORGANISM: Homo sapiens

<400> SEQUENCE: 509

```
Glu Val Gln Leu Leu Glu Ser Gly Gly Gly Leu Val Gln Pro Gly Gly
 1               5                   10                  15

Ser Leu Arg Leu Ser Cys Ala Ala Ser Gly Phe Thr Phe Trp Pro Tyr
            20                  25                  30

Thr Met Ser Trp Val Arg Gln Ala Pro Gly Lys Gly Leu Glu Trp Val
        35                  40                  45

Ser Thr Ile Ser Pro Phe Gly Ser Thr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Lys Thr Gly Pro Ser Ser Phe Asp Tyr Trp Gly Gln Gly Thr
            100                 105                 110

Leu Val Thr Val Ser Ser
        115
```

<210> SEQ ID NO 510
<211> LENGTH: 120
<212> TYPE: PRT
<213> ORGANISM: Homo sapiens

<400> SEQUENCE: 510

```
Glu Val Gln Leu Leu Glu Ser Gly Gly Gly Leu Val Gln Pro Gly Gly
 1               5                   10                  15

Ser Leu Arg Leu Ser Cys Ala Ala Ser Gly Phe Thr Phe Trp Pro Tyr
            20                  25                  30
```

```
Thr Met Ser Trp Val Arg Gln Ala Pro Gly Lys Gly Leu Glu Trp Val
            35                  40                  45

Ser Thr Ile Ser Pro Phe Gly Ser Thr Thr Tyr Tyr Ala Asp Ser Val
 50                      55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Arg Thr Glu Asn Arg Gly Val Ser Phe Asp Tyr Trp Gly Gln
             100                 105                 110

Gly Thr Leu Val Thr Val Ser Ser
            115                 120
```

<210> SEQ ID NO 511
<211> LENGTH: 122
<212> TYPE: PRT
<213> ORGANISM: Homo sapiens

<400> SEQUENCE: 511

```
Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Trp Pro Tyr
             20                  25                  30

Thr Met Ser Trp Val Arg Gln Ala Pro Gly Lys Gly Leu Glu Trp Val
            35                  40                  45

Ser Thr Ile Ser Pro Phe Gly Ser Thr Thr Tyr Tyr Ala Asp Ser Val
 50                      55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Ser Asp Val Leu Lys Thr Gly Leu Asp Gly Phe Asp Tyr Trp
             100                 105                 110

Gly Gln Gly Thr Leu Val Thr Val Ser Ser
            115                 120
```

<210> SEQ ID NO 512
<211> LENGTH: 120
<212> TYPE: PRT
<213> ORGANISM: Homo sapiens

<400> SEQUENCE: 512

```
Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Met Ala Tyr
             20                  25                  30

Gln Met Ala Trp Val Arg Gln Ala Pro Gly Lys Gly Leu Glu Trp Val
            35                  40                  45

Ser Thr Ile His Gln Thr Gly Phe Ser Thr Tyr Tyr Ala Asp Ser Val
 50                      55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Val Arg Ser Met Arg Pro Tyr Lys Phe Asp Tyr Trp Gly Gln
             100                 105                 110
```

Gly Thr Leu Val Thr Val Ser Ser
        115                 120

<210> SEQ ID NO 513
<211> LENGTH: 120
<212> TYPE: PRT
<213> ORGANISM: Homo sapiens

<400> SEQUENCE: 513

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Lys Asp Tyr
            20                  25                  30

Asp Met Thr Trp Val Arg Gln Ala Pro Gly Lys Gly Leu Glu Trp Val
        35                  40                  45

Ser Met Ile Ser Ser Ser Gly Leu Trp Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Phe Arg Leu Phe Pro Arg Thr Phe Asp Tyr Trp Gly Gln
            100                 105                 110

Gly Thr Leu Val Thr Val Ser Ser
        115                 120

<210> SEQ ID NO 514
<211> LENGTH: 121
<212> TYPE: PRT
<213> ORGANISM: Homo sapiens

<400> SEQUENCE: 514

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe His Asp Tyr
            20                  25                  30

Val Met Gly Trp Ala Arg Gln Ala Pro Gly Lys Gly Leu Glu Trp Val
        35                  40                  45

Ser Leu Ile Lys Pro Asn Gly Ser Pro Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Arg Gly Arg Phe Asn Val Leu Gln Phe Asp Tyr Trp Gly
            100                 105                 110

Gln Gly Thr Leu Val Thr Val Ser Ser
        115                 120

<210> SEQ ID NO 515
<211> LENGTH: 118
<212> TYPE: PRT
<213> ORGANISM: Homo sapiens

<400> SEQUENCE: 515

Glu Val Gln Leu Leu Glu Ser Gly Gly Gly Leu Val Gln Pro Gly Gly
1               5                   10                  15

Ser Leu Arg Leu Ser Cys Thr Ala Ser Gly Phe Thr Phe Arg His Tyr

-continued

```
                20                  25                  30
Arg Met Gly Trp Val Arg Gln Ala Pro Gly Lys Gly Leu Glu Trp Val
         35                  40                  45

Ser Trp Ile Arg Pro Asp Gly Thr Phe Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Ser Tyr Met Gly Asp Arg Phe Asp Tyr Trp Gly Gln Gly Thr
            100                 105                 110

Leu Val Thr Val Ser Ser
            115

<210> SEQ ID NO 516
<211> LENGTH: 116
<212> TYPE: PRT
<213> ORGANISM: Homo sapiens

<400> SEQUENCE: 516

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Met Trp Asp
             20                  25                  30

Lys Met Gly Trp Val Arg Gln Ala Pro Gly Lys Gly Leu Glu Trp Val
         35                  40                  45

Ser Phe Ile Gly Arg Glu Gly Tyr Gly Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Ser Val Ala Ser Phe Asp Tyr Trp Gly Gln Gly Thr Leu Val
            100                 105                 110

Thr Val Ser Ser
            115

<210> SEQ ID NO 517
<211> LENGTH: 117
<212> TYPE: PRT
<213> ORGANISM: Homo sapiens

<400> SEQUENCE: 517

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Trp Ala Tyr
             20                  25                  30

Pro Met Ser Trp Val Arg Gln Ala Pro Gly Lys Gly Leu Glu Trp Val
         35                  40                  45

Ser Ser Ile Ser Ser Trp Gly Thr Gly Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Gly Gly Gln Gly Ser Phe Asp Tyr Trp Gly Gln Gly Thr Leu
```

```
                    100                 105                 110

Val Thr Val Ser Ser
        115

<210> SEQ ID NO 518
<211> LENGTH: 115
<212> TYPE: PRT
<213> ORGANISM: Unknown
<220> FEATURE:
<223> OTHER INFORMATION: Camelid

<400> SEQUENCE: 518

Gln Val Gln Leu Gln Glu Ser Gly Gly Gly Leu Val Gln Pro Gly Gly
1               5                   10                  15

Ser Leu Arg Leu Ser Cys Glu Ala Ser Gly Phe Thr Phe Ser Arg Phe
            20                  25                  30

Gly Met Thr Trp Val Arg Gln Ala Pro Gly Lys Gly Val Glu Trp Val
        35                  40                  45

Ser Gly Ile Ser Ser Leu Gly Asp Ser Thr Leu Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Lys Pro Glu Asp Thr Ala Val Tyr Tyr Cys
                85                  90                  95

Thr Ile Gly Gly Ser Leu Asn Pro Gly Gly Gln Gly Thr Gln Val Thr
            100                 105                 110

Val Ser Ser
        115

<210> SEQ ID NO 519
<211> LENGTH: 115
<212> TYPE: PRT
<213> ORGANISM: Unknown
<220> FEATURE:
<223> OTHER INFORMATION: Camelid

<400> SEQUENCE: 519

Gln Val Gln Leu Gln Glu Ser Gly Gly Gly Leu Val Gln Pro Gly Asn
1               5                   10                  15

Ser Leu Arg Leu Ser Cys Ala Ala Ser Gly Phe Thr Phe Arg Asn Phe
            20                  25                  30

Gly Met Ser Trp Val Arg Gln Ala Pro Gly Lys Glu Pro Glu Trp Val
        35                  40                  45

Ser Ser Ile Ser Gly Ser Gly Ser Asn Thr Ile Tyr Ala Asp Ser Val
    50                  55                  60

Lys Asp Arg Phe Thr Ile Ser Arg Asp Asn Ala Lys Ser Thr Leu Tyr
65                  70                  75                  80

Leu Gln Met Asn Ser Leu Lys Pro Glu Asp Thr Ala Val Tyr Tyr Cys
                85                  90                  95

Thr Ile Gly Gly Ser Leu Ser Arg Ser Ser Gln Gly Thr Gln Val Thr
            100                 105                 110

Val Ser Ser
        115

<210> SEQ ID NO 520
<211> LENGTH: 114
<212> TYPE: PRT
<213> ORGANISM: Unknown
<220> FEATURE:
```

<223> OTHER INFORMATION: Camelid

<400> SEQUENCE: 520

```
Gln Val Gln Leu Gln Glu Ser Gly Gly Gly Leu Val Gln Pro Gly Gly
 1               5                  10                  15

Ser Leu Arg Leu Thr Cys Thr Ala Ser Gly Phe Thr Phe Ser Ser Phe
            20                  25                  30

Gly Met Ser Trp Val Arg Gln Ala Pro Gly Lys Gly Leu Glu Trp Val
        35                  40                  45

Ser Ala Ile Ser Ser Asp Ser Gly Thr Lys Asn Tyr Ala Asp Ser Val
    50                  55                  60

Lys Gly Arg Phe Thr Ile Ser Arg Asp Asn Ala Lys Lys Met Leu Phe
65                  70                  75                  80

Leu Gln Met Asn Ser Leu Arg Pro Glu Asp Thr Ala Val Tyr Tyr Cys
                85                  90                  95

Val Ile Gly Arg Gly Ser Pro Ser Ser Gln Gly Thr Gln Val Thr Val
               100                 105                 110

Ser Ser
```

<210> SEQ ID NO 521
<211> LENGTH: 114
<212> TYPE: PRT
<213> ORGANISM: Unknown
<220> FEATURE:
<223> OTHER INFORMATION: Camelid

<400> SEQUENCE: 521

```
Gln Val Gln Leu Gln Glu Ser Gly Gly Gly Leu Val Gln Pro Gly Gly
 1               5                  10                  15

Ser Leu Arg Leu Thr Cys Thr Ala Ser Gly Phe Thr Phe Arg Ser Phe
            20                  25                  30

Gly Met Ser Trp Val Arg Gln Ala Pro Gly Lys Gly Leu Glu Trp Val
        35                  40                  45

Ser Ala Ile Ser Ala Asp Gly Ser Asp Lys Arg Tyr Ala Asp Ser Val
    50                  55                  60

Lys Gly Arg Phe Thr Ile Ser Arg Asp Asn Gly Lys Lys Met Leu Thr
65                  70                  75                  80

Leu Asp Met Asn Ser Leu Lys Pro Glu Asp Thr Ala Val Tyr Tyr Cys
                85                  90                  95

Val Ile Gly Arg Gly Ser Pro Ala Ser Gln Gly Thr Gln Val Thr Val
               100                 105                 110

Ser Ser
```

<210> SEQ ID NO 522
<211> LENGTH: 128
<212> TYPE: PRT
<213> ORGANISM: Unknown
<220> FEATURE:
<223> OTHER INFORMATION: Camelid

<400> SEQUENCE: 522

```
Ala Val Gln Leu Val Glu Ser Gly Gly Gly Leu Val Gln Ala Gly Asp
 1               5                  10                  15

Ser Leu Arg Leu Ser Cys Val Val Ser Gly Thr Thr Phe Ser Ser Ala
            20                  25                  30

Ala Met Gly Trp Phe Arg Gln Ala Pro Gly Lys Glu Arg Glu Phe Val
        35                  40                  45
```

```
Gly Ala Ile Lys Trp Ser Gly Thr Ser Thr Tyr Tyr Thr Asp Ser Val
    50                  55                  60

Lys Gly Arg Phe Thr Ile Ser Arg Asp Asn Val Lys Asn Thr Val Tyr
 65                  70                  75                  80

Leu Gln Met Asn Asn Leu Lys Pro Glu Asp Thr Gly Val Tyr Thr Cys
                 85                  90                  95

Ala Ala Asp Arg Asp Arg Tyr Arg Asp Arg Met Gly Pro Met Thr Thr
            100                 105                 110

Thr Asp Phe Arg Phe Trp Gly Gln Gly Thr Gln Val Thr Val Ser Ser
            115                 120                 125
```

<210> SEQ ID NO 523
<211> LENGTH: 124
<212> TYPE: PRT
<213> ORGANISM: Unknown
<220> FEATURE:
<223> OTHER INFORMATION: Camelid

<400> SEQUENCE: 523

```
Gln Val Lys Leu Glu Glu Ser Gly Gly Gly Leu Val Gln Thr Gly Gly
  1               5                  10                  15

Ser Leu Arg Leu Ser Cys Ala Ala Ser Gly Arg Thr Phe Ser Ser Phe
                 20                  25                  30

Ala Met Gly Trp Phe Arg Gln Ala Pro Gly Arg Glu Arg Glu Phe Val
            35                  40                  45

Ala Ser Ile Gly Ser Ser Gly Ile Thr Thr Asn Tyr Ala Asp Ser Val
    50                  55                  60

Lys Gly Arg Phe Thr Ile Ser Arg Asp Asn Ala Lys Asn Thr Val Tyr
 65                  70                  75                  80

Leu Gln Met Asn Ser Leu Lys Pro Glu Asp Thr Gly Leu Cys Tyr Cys
                 85                  90                  95

Ala Val Asn Arg Tyr Gly Ile Pro Tyr Arg Ser Gly Thr Gln Tyr Gln
            100                 105                 110

Asn Trp Gly Gln Gly Thr Gln Val Thr Val Ser Ser
            115                 120
```

<210> SEQ ID NO 524
<211> LENGTH: 120
<212> TYPE: PRT
<213> ORGANISM: Unknown
<220> FEATURE:
<223> OTHER INFORMATION: Camelid

<400> SEQUENCE: 524

```
Glu Val Gln Leu Glu Glu Ser Gly Gly Gly Leu Val Gln Pro Gly Gly
  1               5                  10                  15

Ser Leu Arg Leu Ser Cys Ala Ala Ser Gly Leu Thr Phe Asn Asp Tyr
                 20                  25                  30

Ala Met Gly Trp Tyr Arg Gln Ala Pro Gly Lys Glu Arg Asp Met Val
            35                  40                  45

Ala Thr Ile Ser Ile Gly Gly Arg Thr Tyr Tyr Ala Asp Ser Val Lys
    50                  55                  60

Gly Arg Phe Thr Ile Ser Arg Asp Asn Ala Lys Asn Thr Val Tyr Leu
 65                  70                  75                  80

Gln Met Asn Ser Leu Lys Pro Glu Asp Thr Ala Ile Tyr Tyr Cys Val
                 85                  90                  95

Ala His Arg Gln Thr Val Val Arg Gly Pro Tyr Leu Leu Trp Gly Gln
            100                 105                 110
```

Gly Thr Gln Val Thr Val Ser Ser
        115                 120

<210> SEQ ID NO 525
<211> LENGTH: 123
<212> TYPE: PRT
<213> ORGANISM: Unknown
<220> FEATURE:
<223> OTHER INFORMATION: Camelid

<400> SEQUENCE: 525

Gln Val Gln Leu Val Glu Ser Gly Gly Lys Leu Val Gln Ala Gly Gly
 1               5                  10                  15

Ser Leu Arg Leu Ser Cys Ala Ala Ser Gly Arg Thr Phe Ser Asn Tyr
            20                  25                  30

Ala Met Gly Trp Phe Arg Gln Ala Pro Gly Lys Glu Arg Glu Phe Val
        35                  40                  45

Ala Gly Ser Gly Arg Ser Asn Ser Tyr Asn Tyr Tyr Ser Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Ala Ser Thr Asn Leu Trp Pro Arg Asp Arg Asn Leu Tyr Ala Tyr
            100                 105                 110

Trp Gly Gln Gly Thr Gln Val Thr Val Ser Ser
        115                 120

<210> SEQ ID NO 526
<211> LENGTH: 125
<212> TYPE: PRT
<213> ORGANISM: Unknown
<220> FEATURE:
<223> OTHER INFORMATION: Camelid

<400> SEQUENCE: 526

Glu Val Gln Leu Val Glu Ser Gly Gly Gly Leu Val Gln Ala Gly Asp
 1               5                  10                  15

Ser Leu Arg Leu Ser Cys Ala Ala Ser Gly Arg Ser Leu Gly Ile Tyr
            20                  25                  30

Arg Met Gly Trp Phe Arg Gln Val Pro Gly Lys Glu Arg Glu Phe Val
        35                  40                  45

Ala Ala Ile Ser Trp Ser Gly Gly Thr Thr Arg Tyr Leu Asp Ser Val
    50                  55                  60

Lys Gly Arg Phe Thr Ile Ser Arg Asp Ser Thr Lys Asn Ala Val Tyr
65                  70                  75                  80

Leu Gln Met Asn Ser Leu Lys Pro Glu Asp Thr Ala Val Tyr Tyr Cys
                85                  90                  95

Ala Val Asp Ser Ser Gly Arg Leu Tyr Trp Thr Leu Ser Thr Ser Tyr
            100                 105                 110

Asp Tyr Trp Gly Gln Gly Thr Gln Val Thr Val Ser Ser
        115                 120                 125

<210> SEQ ID NO 527
<211> LENGTH: 125
<212> TYPE: PRT
<213> ORGANISM: Unknown
<220> FEATURE:
<223> OTHER INFORMATION: Camelid -continued

<400> SEQUENCE: 527

Gln Val Gln Leu Val Glu Phe Gly Gly Gly Leu Val Gln Ala Gly Asp
1               5                   10                  15

Ser Leu Arg Leu Ser Cys Ala Ala Ser Gly Arg Ser Leu Gly Ile Tyr
            20                  25                  30

Lys Met Ala Trp Phe Arg Gln Val Pro Gly Lys Glu Arg Glu Phe Val
        35                  40                  45

Ala Ala Ile Ser Trp Ser Gly Gly Thr Thr Arg Tyr Ile Asp Ser Val
    50                  55                  60

Lys Gly Arg Phe Thr Leu Ser Arg Asp Asn Thr Lys Asn Met Val Tyr
65                  70                  75                  80

Leu Gln Met Asn Ser Leu Lys Pro Asp Asp Thr Ala Val Tyr Tyr Cys
                85                  90                  95

Ala Val Asp Ser Ser Gly Arg Leu Tyr Trp Thr Leu Ser Thr Ser Tyr
            100                 105                 110

Asp Tyr Trp Gly Gln Gly Thr Gln Val Thr Val Ser Ser
        115                 120                 125

<210> SEQ ID NO 528
<211> LENGTH: 124
<212> TYPE: PRT
<213> ORGANISM: Unknown
<220> FEATURE:
<223> OTHER INFORMATION: Camelid

<400> SEQUENCE: 528

Glu Val Gln Leu Val Glu Ser Gly Gly Gly Leu Val Gln Ala Gly Gly
1               5                   10                  15

Ser Leu Ser Leu Ser Cys Ala Ala Ser Gly Arg Thr Phe Ser Pro Tyr
            20                  25                  30

Thr Met Gly Trp Phe Arg Gln Ala Pro Gly Lys Glu Arg Glu Phe Leu
        35                  40                  45

Ala Gly Val Thr Trp Ser Gly Ser Ser Thr Phe Tyr Gly Asp Ser Val
    50                  55                  60

Lys Gly Arg Phe Thr Ala Ser Arg Asp Ser Ala Lys Asn Thr Val Thr
65                  70                  75                  80

Leu Glu Met Asn Ser Leu Asn Pro Glu Asp Thr Ala Val Tyr Tyr Cys
                85                  90                  95

Ala Ala Ala Tyr Gly Gly Gly Leu Tyr Arg Asp Pro Arg Ser Tyr Asp
            100                 105                 110

Tyr Trp Gly Arg Gly Thr Gln Val Thr Val Ser Ser
        115                 120

<210> SEQ ID NO 529
<211> LENGTH: 131
<212> TYPE: PRT
<213> ORGANISM: Unknown
<220> FEATURE:
<223> OTHER INFORMATION: Camelid

<400> SEQUENCE: 529

Ala Val Gln Leu Val Glu Ser Gly Gly Gly Leu Val Gln Ala Gly Gly
1               5                   10                  15

Ser Leu Arg Leu Ser Cys Ala Ala Ser Gly Phe Thr Leu Asp Ala Trp
            20                  25                  30

Pro Ile Ala Trp Phe Arg Gln Ala Pro Gly Lys Glu Arg Glu Gly Val
        35                  40                  45

```
Ser Cys Ile Arg Asp Gly Thr Thr Tyr Tyr Ala Asp Ser Val Lys Gly
 50                  55                  60

Arg Phe Thr Ile Ser Ser Asp Asn Ala Asn Asn Thr Val Tyr Leu Gln
 65                  70                  75                  80

Thr Asn Ser Leu Lys Pro Glu Asp Thr Ala Val Tyr Tyr Cys Ala Ala
                 85                  90                  95

Pro Ser Gly Pro Ala Thr Gly Ser Ser His Thr Phe Gly Ile Tyr Trp
            100                 105                 110

Asn Leu Arg Asp Asp Tyr Asp Asn Trp Gly Gln Gly Thr Gln Val Thr
        115                 120                 125

Val Ser Ser
    130

<210> SEQ ID NO 530
<211> LENGTH: 126
<212> TYPE: PRT
<213> ORGANISM: Unknown
<220> FEATURE:
<223> OTHER INFORMATION: Camelid

<400> SEQUENCE: 530

Glu Val Gln Leu Val Glu Ser Gly Gly Gly Leu Val Gln Ala Gly Gly
 1               5                  10                  15

Ser Leu Arg Leu Ser Cys Ala Ala Ser Gly Phe Thr Phe Asp His Tyr
                20                  25                  30

Thr Ile Gly Trp Phe Arg Gln Val Pro Gly Lys Glu Arg Glu Gly Val
            35                  40                  45

Ser Cys Ile Ser Ser Ser Asp Gly Ser Thr Tyr Tyr Ala Asp Ser Val
        50                  55                  60

Lys Gly Arg Phe Thr Ile Ser Ser Asp Asn Ala Lys Asn Thr Val Tyr
 65                  70                  75                  80

Leu Gln Met Asn Thr Leu Glu Pro Asp Asp Thr Ala Val Tyr Tyr Cys
                 85                  90                  95

Ala Ala Gly Gly Leu Leu Leu Arg Val Glu Glu Leu Gln Ala Ser Asp
            100                 105                 110

Tyr Asp Tyr Trp Gly Gln Gly Ile Gln Val Thr Val Ser Ser
        115                 120                 125

<210> SEQ ID NO 531
<211> LENGTH: 128
<212> TYPE: PRT
<213> ORGANISM: Unknown
<220> FEATURE:
<223> OTHER INFORMATION: Camelid

<400> SEQUENCE: 531

Ala Val Gln Leu Val Asp Ser Gly Gly Gly Leu Val Gln Pro Gly Gly
 1               5                  10                  15

Ser Leu Arg Leu Ser Cys Thr Ala Ser Gly Phe Thr Leu Asp Tyr Tyr
                20                  25                  30

Ala Ile Gly Trp Phe Arg Gln Ala Pro Gly Lys Glu Arg Glu Gly Val
            35                  40                  45

Ala Cys Ile Ser Asn Ser Asp Gly Ser Thr Tyr Tyr Gly Asp Ser Val
        50                  55                  60

Lys Gly Arg Phe Thr Ile Ser Arg Asp Asn Ala Lys Thr Thr Val Tyr
 65                  70                  75                  80

Leu Gln Met Asn Ser Leu Lys Pro Glu Asp Thr Ala Val Tyr Tyr Cys
```

```
                85                  90                  95
Ala Thr Ala Asp Arg His Tyr Ser Ala Ser His His Pro Phe Ala Asp
            100                 105                 110

Phe Ala Phe Asn Ser Trp Gly Gln Gly Thr Gln Val Thr Val Ser Ser
        115                 120                 125

<210> SEQ ID NO 532
<211> LENGTH: 120
<212> TYPE: PRT
<213> ORGANISM: Unknown
<220> FEATURE:
<223> OTHER INFORMATION: Camelid

<400> SEQUENCE: 532

Glu Val Gln Leu Val Glu Ser Gly Gly Gly Leu Val Gln Ala Gly Gly
  1               5                  10                  15

Ser Leu Arg Leu Ser Cys Ala Ala Tyr Gly Leu Thr Phe Trp Arg Ala
             20                  25                  30

Ala Met Ala Trp Phe Arg Arg Ala Pro Gly Lys Glu Arg Glu Leu Val
         35                  40                  45

Val Ala Arg Asn Trp Gly Asp Gly Ser Thr Arg Tyr Ala Asp Ser Val
     50                  55                  60

Lys Gly Arg Phe Thr Ile Ser Arg Asp Asn Ala Lys Asn Thr Val Tyr
 65                  70                  75                  80

Leu Gln Met Asn Ser Leu Lys Pro Glu Asp Thr Ala Val Tyr Tyr Cys
                 85                  90                  95

Ala Ala Val Arg Thr Tyr Gly Ser Ala Thr Tyr Asp Ile Trp Gly Gln
            100                 105                 110

Gly Thr Gln Val Thr Val Ser Ser
        115                 120

<210> SEQ ID NO 533
<211> LENGTH: 123
<212> TYPE: PRT
<213> ORGANISM: Unknown
<220> FEATURE:
<223> OTHER INFORMATION: Camelid

<400> SEQUENCE: 533

Glu Val Gln Leu Val Glu Ser Gly Gly Gly Leu Val Gln Asp Gly Gly
  1               5                  10                  15

Ser Leu Arg Leu Ser Cys Ile Phe Ser Gly Arg Thr Phe Ala Asn Tyr
             20                  25                  30

Ala Met Gly Trp Phe Arg Gln Ala Pro Gly Lys Glu Arg Glu Phe Val
         35                  40                  45

Ala Ala Ile Asn Arg Asn Gly Gly Thr Thr Asn Tyr Ala Asp Ala Leu
     50                  55                  60

Lys Gly Arg Phe Thr Ile Ser Arg Asp Asn Thr Lys Asn Thr Ala Phe
 65                  70                  75                  80

Leu Gln Met Asn Ser Leu Lys Pro Asp Asp Thr Ala Val Tyr Tyr Cys
                 85                  90                  95

Ala Ala Arg Glu Trp Pro Phe Ser Thr Ile Pro Ser Gly Trp Arg Tyr
            100                 105                 110

Trp Gly Gln Gly Thr Gln Val Thr Val Ser Ser
        115                 120

<210> SEQ ID NO 534
<211> LENGTH: 125
```

<212> TYPE: PRT
<213> ORGANISM: Unknown
<220> FEATURE:
<223> OTHER INFORMATION: Camelid

<400> SEQUENCE: 534

Asp Val Gln Leu Val Glu Ser Gly Gly Gly Trp Val Gln Pro Gly Gly
1               5                   10                  15
Ser Leu Arg Leu Ser Cys Ala Ala Ser Gly Pro Thr Ala Ser Ser His
            20                  25                  30
Ala Ile Gly Trp Phe Arg Gln Ala Pro Gly Lys Glu Arg Glu Phe Val
        35                  40                  45
Val Gly Ile Asn Arg Gly Gly Val Thr Arg Asp Tyr Ala Asp Ser Val
    50                  55                  60
Lys Gly Arg Phe Ala Val Ser Arg Asp Asn Val Lys Asn Thr Val Tyr
65                  70                  75                  80
Leu Gln Met Asn Arg Leu Lys Pro Glu Asp Ser Ala Ile Tyr Ile Cys
                85                  90                  95
Ala Ala Arg Pro Glu Tyr Ser Phe Thr Ala Met Ser Lys Gly Asp Met
            100                 105                 110
Asp Tyr Trp Gly Lys Gly Thr Leu Val Thr Val Ser Ser
        115                 120                 125

<210> SEQ ID NO 535
<211> LENGTH: 324
<212> TYPE: DNA
<213> ORGANISM: Homo sapiens

<400> SEQUENCE: 535
gacatccaga tgacccagtc tccatcctcc ctgtctgcat ctgtaggaga ccgtgtcacc      60
atcacttgcc gggcaagtca gtggattggt cctgagttaa gttggtacca gcagaaacca    120
gggaaagccc ctaagctcct gatctatcat ggttccattt tgcaaagtgg ggtcccatca    180
cgtttcagtg gcagtggatc tgggacagat ttcactctca ccatcagcag tctgcaacct    240
gaagattttg ctacgtacta ctgtcaacag tatatgacgt atcctccgac gttcggccaa    300
gggaccaagg tggaaatcaa acgg                                            324

<210> SEQ ID NO 536
<211> LENGTH: 324
<212> TYPE: DNA
<213> ORGANISM: Homo sapiens

<400> SEQUENCE: 536
gacatccaga tgacccagtc tccatcctcc ctgtctgcat ccgtaggaga ccgtgtcacc      60
atcacttgcc gggcaagtca gtttattggg aaggagttac gttggtatca gcagaaacca    120
gggaaagccc ctaagctcct gatctatcat cagtccttgt tgcaaagtgg ggtcccatca    180
cgtttcagtg gcagtggatc tgggacagat ttcattctca ccatcagcag tctgcaacct    240
gaagattttg ctacgtacta ctgtcaacag catatgtata ggccttttac gttcggccaa    300
gggaccaagg tggaaatcaa acga                                            324

<210> SEQ ID NO 537
<211> LENGTH: 348
<212> TYPE: DNA
<213> ORGANISM: Homo sapiens

<400> SEQUENCE: 537

```
gaggtgcagc tgttggagtc tggggggaggc ttggtacagc ctgggggggtc cctgcgtctc    60 tcctgtgcag cctccggatt cacctttaag gcttatccga taatgtgggt ccgccaggct   120
ccagggaagg gtctagagtg ggtctcagag atttcgcctt cgggttctga gacatactac   180
gcagactccg tgaagggccg gttcaccatc tcccgcgaca attccaagaa cacgctgtat   240
ctgcaaatga acagcctgcg tgccgaggac accgcggtat attactgtgc gaaagatcct   300
cggaagtttg actactgggg tcagggaacc ctggtcaccg tctcgagc                348
```

`<210>` SEQ ID NO 538
`<211>` LENGTH: 348
`<212>` TYPE: DNA
`<213>` ORGANISM: Homo sapiens

`<400>` SEQUENCE: 538

```
gaggtgcagc tgttggagtc tggggggaggc ttggtacagc ctgggggggtc cctgcgtctc    60 tcctgcgcag cctccggatt cacctttaag gcttatccga taatgtgggt ccgccaggct   120
ccagggaagg gtctagagtg ggtctcagag atttcgcctt cgggttctcg acatactac    180 gcagactctg tgaagggccg gttcaccatc tcccgcgaca attccaagaa cacgctgtat   240
ctgcaaatga acagcctgcg tgccgaggac accgcggtat attactgtgc gaaagatcct   300
cggaagtttg actactgggg tcagggaacc ctggtcaccg tctcgagc                348
```

`<210>` SEQ ID NO 539
`<211>` LENGTH: 116
`<212>` TYPE: PRT
`<213>` ORGANISM: Homo sapiens

`<400>` SEQUENCE: 539

```
Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Lys Ala Tyr
             20                  25                  30

Pro Ile Met Trp Val Arg Gln Ala Pro Gly Lys Gly Leu Glu Trp Val
         35                  40                  45

Ser Glu Ile Ser Pro Ser Gly Ser Glu Thr Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Asp Pro Arg Lys Phe Asp Tyr Trp Gly Gln Gly Thr Leu Val
            100                 105                 110

Thr Val Ser Ser
            115
```

`<210>` SEQ ID NO 540
`<211>` LENGTH: 116
`<212>` TYPE: PRT
`<213>` ORGANISM: Homo sapiens

`<400>` SEQUENCE: 540

```
Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Lys Ala Tyr
             20                  25                  30

Pro Ile Met Trp Val Arg Gln Ala Pro Gly Lys Gly Leu Glu Trp Val
```

-continued

```
                        35                  40                  45

Ser Glu Ile Ser Pro Ser Gly Ser Arg Thr Tyr Tyr Ala Asp Ser Val
        50                  55                  60

Lys Gly Arg Phe Thr Ile Ser Arg Asp Asn Ser Lys Asn Thr Leu Tyr
65                      70                  75                  80

Leu Gln Met Asn Ser Leu Arg Ala Glu Asp Thr Ala Val Tyr Tyr Cys
                    85                  90                  95

Ala Lys Asp Pro Arg Lys Phe Asp Tyr Trp Gly Gln Gly Thr Leu Val
                100                 105                 110

Thr Val Ser Ser
            115

<210> SEQ ID NO 541
<211> LENGTH: 5
<212> TYPE: PRT
<213> ORGANISM: Artificial
<220> FEATURE:
<223> OTHER INFORMATION: linker

<400> SEQUENCE: 541

Gly Gly Gly Gly Ser
                5
```